US012797330B2

(12) United States Patent
Kirpotin et al.

(10) Patent No.: US 12,797,330 B2
(45) **Date of Patent: *Nov. 17, 2026**

(54) OXAZOLIDINONE LIPOSOME COMPOSITIONS

(71) Applicant: Akagera Medicines, Inc., Boxford, MA (US)

(72) Inventors: Dmitri B. Kirpotin, San Francisco, CA (US); Alexander Koshkaryev, Norwood, MA (US); Charles O. Noble, San Francisco, CA (US); Daryl C. Drummond, Lincoln, MA (US)

(73) Assignee: Akagera Medicines, Inc., Waltham, MA (US)

( * ) Notice: Subject to any disclaimer, the term of this patent is extended or adjusted under 35 U.S.C. 154(b) by 265 days.

This patent is subject to a terminal disclaimer.

(21) Appl. No.: 18/723,262

(22) PCT Filed: Dec. 22, 2022

(86) PCT No.: PCT/US2022/082290

§ 371 (c)(1),
(2) Date: Jun. 21, 2024

(87) PCT Pub. No.: WO2023/122759

PCT Pub. Date: Jun. 29, 2023

(65) Prior Publication Data

US 2025/0064739 A1 Feb. 27, 2025

Related U.S. Application Data

(60) Provisional application No. 63/292,899, filed on Dec. 22, 2021.

(51) Int. Cl.

| | |
|---|---|
| ***A61K 9/127*** | (2025.01) |
| ***A61K 9/1271*** | (2025.01) |
| ***A61K 9/1277*** | (2025.01) |
| ***A61K 31/4439*** | (2006.01) |
| ***A61K 47/02*** | (2006.01) |
| ***A61K 47/18*** | (2017.01) |
| ***A61P 31/04*** | (2006.01) |
| ***A61P 31/06*** | (2006.01) |

(52) U.S. Cl.

CPC .......... *A61K 9/1271* (2013.01); *A61K 9/1277* (2013.01); *A61K 31/4439* (2013.01); *A61K 47/02* (2013.01); *A61K 47/183* (2013.01); *A61P 31/04* (2018.01); *A61P 31/06* (2018.01)

(58) Field of Classification Search

CPC ...... A61K 9/0019; A61K 9/0029; A61K 9/10; A61K 9/127; A61K 9/1277

See application file for complete search history.

(56) References Cited

U.S. PATENT DOCUMENTS

| | | | | |
|---|---|---|---|---|
| 5,316,771 | A | 5/1994 | Barenholz et al. | |
| 5,800,833 | A | 9/1998 | Hope et al. | |
| 6,110,491 | A | 8/2000 | Kirpotin | |
| 6,180,134 | B1 * | 1/2001 | Zalipsky ................ | A61K 47/62 530/319 |
| 6,689,779 | B2 | 2/2004 | Lee et al. | |
| 7,498,350 | B2 | 3/2009 | Gravestock et al. | |
| 7,744,921 | B2 | 6/2010 | Tardi et al. | |
| 7,759,351 | B2 | 7/2010 | Cano et al. | |
| 7,816,379 | B2 | 10/2010 | Rhee et al. | |
| 8,147,867 | B2 | 4/2012 | Hong et al. | |
| 8,349,360 | B2 | 1/2013 | Bally et al. | |
| 8,420,676 | B2 | 4/2013 | Rhee et al. | |
| 9,549,939 | B2 | 1/2017 | Weers | |
| 11,555,033 | B2 | 1/2023 | Drummond et al. | |
| 11,566,023 | B2 | 1/2023 | Drummond et al. | |
| 12,116,361 | B2 | 10/2024 | Drummond et al. | |
| 12,145,928 | B2 | 11/2024 | Drummond et al. | |
| 2003/0224039 | A1 | 12/2003 | Boni et al. | |
| 2004/0009126 | A1 | 1/2004 | Pilkiewicz et al. | |
| 2005/0043317 | A1 | 2/2005 | Zhou et al. | |
| 2007/0110798 | A1 * | 5/2007 | Drummond .......... | A61K 9/1278 514/283 |
| 2008/0021071 | A1 | 1/2008 | Gravestock et al. | |
| 2010/0022772 | A1 | 1/2010 | Wu et al. | |
| 2015/0072970 | A1 | 3/2015 | Zhou et al. | |
| 2018/0369143 | A1 | 12/2018 | Bally et al. | |
| 2020/0078345 | A1 | 3/2020 | Rhee et al. | |
| 2021/0403463 | A1 * | 12/2021 | Drummond .......... | C07D 263/22 |
| 2022/0274975 | A1 | 9/2022 | Drummond et al. | |
| 2023/0126415 | A1 | 4/2023 | Drummond et al. | |

(Continued)

FOREIGN PATENT DOCUMENTS

| | | | |
|---|---|---|---|
| CN | 105163720 | B | 10/2019 |
| WO | WO1990001405 | | 2/1990 |

(Continued)

OTHER PUBLICATIONS

Doxil © drug information package insert, updated Aug. 2019.
International Search Report and Written Opinion in PCT International Application No. PCT/US2022/082290 mailed Jun. 23, 2023 (19 pages).
Bulbake et al., "Liposomal Formulations in Clinical Use: An Updated Review", Pharmaceutics, 9, 12, (2017), 33 pages.
Chiu et al., "Effects of phosphatidylserine on membrane incorporation and surface protection properties of exchangeable poly(ethylene glycol)-conjugated lipids", Biochimica et Biophysica Acta, vol. 1560, Issues 1-2, Feb. 18, 2002, pp. 37-50.
Danaei et al., "Impact of Particle Size and Polydispersity Index on the Clinical Applications of Lipidic Nanocarrier Systems", Pharmaceutics, 10, 57, (2018), 17 pages.
Mozafari, M.R, "Nanoliposomes: Preparation and Analysis", Methods in Molecular Biology, vol. 605, (Clifton, N.J.), Jan. 2010.

(Continued)

*Primary Examiner* — Micah Paul Young

(74) *Attorney, Agent, or Firm* — Greenberg Traurig, LLP; Natalie Salem; David J. Dykeman

(57) ABSTRACT

Aspects of the disclosure relate to various liposomal compositions of oxazolidinone compounds, and related methods of manufacturing and using the oxazolidinone liposome compositions. In some embodiments, the liposome compositions have improved storage stability with regard to component degradation.

21 Claims, 42 Drawing Sheets

(56) References Cited

U.S. PATENT DOCUMENTS

| | | | |
|---|---|---|---|
| 2023/0219941 A1 | 7/2023 | Drummond et al. |
| 2024/0425494 A1 | 12/2024 | Drummond et al. |
| 2024/0425495 A1 | 12/2024 | Drummond et al. |

FOREIGN PATENT DOCUMENTS

| | | | |
|---|---|---|---|
| WO | WO1994001110 A1 | 1/1994 |
| WO | WO1995025106 A1 | 9/1995 |
| WO | WO2002006278 A1 | 1/2002 |
| WO | WO2003007870 A2 | 1/2003 |
| WO | WO2003097059 A1 | 11/2003 |
| WO | WO2004014392 A1 | 2/2004 |
| WO | WO2004056818 A1 | 7/2004 |
| WO | WO2004099199 A1 | 11/2004 |
| WO | WO2005058886 A1 | 6/2005 |
| WO | WO2005082899 A1 | 9/2005 |
| WO | WO2005116022 A1 | 12/2005 |
| WO | WO2006035283 A1 | 4/2006 |
| WO | WO2006051408 A1 | 5/2006 |
| WO | 2007005754 A2 | 1/2007 |
| WO | WO2010036000 A2 | 4/2010 |
| WO | WO2010042887 A2 | 4/2010 |
| WO | WO2010091131 A1 | 8/2010 |
| WO | WO2010138649 A1 | 12/2010 |
| WO | WO2012033952 A1 | 3/2012 |
| WO | WO2013044845 A1 | 4/2013 |
| WO | WO2016009401 A2 | 1/2016 |
| WO | WO2016041505 A1 | 3/2016 |
| WO | WO2016041508 A1 | 3/2016 |
| WO | WO2016058467 A1 | 4/2016 |
| WO | WO2016088100 A1 | 6/2016 |
| WO | WO2016088101 A1 | 6/2016 |
| WO | WO2016088102 A1 | 6/2016 |
| WO | WO2016088103 A1 | 6/2016 |
| WO | 2017053464 A1 | 3/2017 |
| WO | WO2017044828 A1 | 3/2017 |
| WO | WO2017066726 A1 | 3/2017 |
| WO | WO2017066964 A1 | 4/2017 |
| WO | WO2017070024 A1 | 4/2017 |
| WO | WO2017076285 A1 | 5/2017 |
| WO | WO2017099530 A1 | 6/2017 |
| WO | WO2017123588 A1 | 7/2017 |
| WO | WO2017143112 A3 | 8/2017 |
| WO | WO2018170664 A1 | 9/2018 |
| WO | WO2018175185 A1 | 9/2018 |
| WO | WO2020021468 A1 | 1/2020 |
| WO | WO2020147504 A1 | 7/2020 |
| WO | WO2021188606 A1 | 9/2021 |
| WO | WO2021258013 A1 | 12/2021 |
| WO | WO2023122759 A2 | 6/2023 |

OTHER PUBLICATIONS

Richardson et al., "The Effect of the Iron(III) Chelator, Desferrioxamine, on Iron and Transferrin Uptake by the Human Malignant Melanoma Cell", Cancer Research, vol. 54, pp. 685-689, Feb. 1, 1994.

Han et al., "Profiling patent compounds in lipid nanoparticle formulations of siRNA", Molecular Therapy: Nucleic Acids, vol. 35, pp. 1-11, Dec. 2024.

Allen et al., "Pharmacokinetics and Anti-Tumor Activity of Vincristine Encapsulated in Sterically Stabilized Liposomes", Int. J. Cancer, vol. 62, No. 2, pp. 199-204, Jul. 17, 1995.

Bigelow et al., "Pharmacodynamic Correlates of Linezolid Activity and Toxicity in Murine Models of Tuberculosis", Journal of Infectious Diseases, vol. 223, pp. 1855-1864, Jun. 2021.

Cheng et al., "Multiplex PCR Amplimer Conformation Analysis for Rapid Detection of gyrA Mutations in Fluoroquinolone-Resistant *Mycobacterium tuberculosis* Clinical Isolates", Antimicrobial Agents and Chemotherapy, vol. 48, No. 2, pp. 596-601, Feb. 2004.

Collins et al., "Microplate Alamar Blue Assay versus BACTEC 460 System for High-Throughput Screening of Compounds against *Mycobacterium tuberculosis* and *Mycobacterium avium*", Antimicrobial Agents and Chemotherapy, vol. 41, No. 5, pp. 1004-1009, May 1997.

Conradie et al., "Treatment of Highly Drug-Resistant Pulmonary Tuberculosis", N Engl J Med, vol. 382, No. 10, pp. 893-902, Mar. 2020.

Driver et al., "Evaluation of a Mouse Model of Necrotic Granuloma Formation Using C3HeB/FeJ Mice for Testing of Drugs against Mycobacterium Tuberculosis", Antimicrobial Agents and Chemotherapy, vol. 56, No. 6, pp. 3181-3195, Jun. 2012.

Drummond et al. "Development of a Highly Active Nanoliposomal Irinotecan Using a Novel Intraliposomal Stabilization Strategy" Cancer Res, vol. 66, No. 6, pp. 3271-3277, Mar. 15, 2006.

Drummond et al., "Pharmacokinetics and In Vivo Dug Release Rates in Liposomal Nanocarrier Development", J. Pharm Sci, vol. 97, No. 11, pp. 4696-4740, Nov. 2008.

Drummond, et al. "Intraliposomal Trapping Agents for Improving in Vivo Liposomal Drug Formulation Stability" Liposome Technology, Third Edition (Ed. Gregoriadis, G.) vol. 2, p. 149-168, 2006.

Flanagan et al. , "Nonclinical and Pharmacokinetic Assessments to Evaluate the Potential of Tedizolid and Linezolid to Affect Mitochondrial Function", Antimicrob Agents Chemotherapy, vol. 59, No. 1, pp. 178-185, Jan. 2015.

Gregoriadis (editor), Liposome Technology, vol. 1-3, 1st edition, 1983; 2nd edition, 1993; 3rd edition, 2006; CRC Press, Boca Raton, Florida.—Book—will not be uploaded.

Gruppo et al., "Rapid Microbiologic and Pharmacologic Evaluation of Experimental Compounds against *Mycobacterium tuberculosis*", Antimicrob Agents Chemotherapy, vol. 50, No. 4, pp. 1245-1250, Apr. 2006.

Irwin et al., "Presence of Multiple Lesion Types with Vastly Different Microenvironments in C3HeB/FeJ Mice Following Aerosol Infection with *Mycobacterium tuberculosis*", Dis Model Mech, vol. 8, pp. 591-602, Mar. 2015.

Ishida et al., "Accelerated Blood Clearance of PEGylated Liposomes Following Preceding Liposome Injection: Effects of Lipid Dose and PEG Surface-Density and Chain Length of the First-Dose Liposomes", Journal of Controlled Release vol. 105, pp. 305-317, Apr. 2005.

Lanoix et al., "Heterogeneous Disease Progression and Treatment Response in a C3HeB/FeJ Mouse Model of Tuberculosis", Disease Models & Mechanisms, vol. 8, pp. 603-610, Mar. 2015.

Laverman et al., "Factors Affecting the Accelerated Blood Clearance of Polyethylene Glycol-Liposomes Upon Repeated Injection", JPET, vol. 298, No. 2, pp. 607-612, 2001.

Lenaerts et al., "Preclinical Testing of the Nitroimidazopyran PA-824 for Activity against *Mycobacterium tuberculosis* in a Series of In Vitro and In Vivo Models", AAC, vol. 49, No. 6, pp. 2294-2301, Jun. 2005.

Obregón-Henao et al. "Susceptibility of *Mycobacterium abscessus* to Antimycobacterial Drugs in Preclinical Models" Antimicrobial Agents and Chemotherapy, vol. 59, No. 11, pp. 6904-6912, Nov. 2015.

Palanisamy et al., "Disseminated Disease Severity as a Measure of Virulence of *Mycobacterium tuberculosis* in the Guinea Pig Model", Tuberculosis, vol. 88, Issue 4, pp. 295-306, Jul. 2008.

Reddy et al., "In Vitro Interactions Between New Antitubercular Drug Candidates SQ109 and TMC207", Antimicrob Agents Chemother., vol. 54, No. 7, pp. 2840-2846, Jul. 2010.

Renslo, Adam R., "Antibacterial Oxazolidinones: Emerging Structure-Toxicity Relationships", Expert Review Anti Infect Therapy, vol. 8, No. 5, pp. 565-574, 2010.

Ruiz et al., "In Vitro Activity of Tedizolid Against *Mycobacterium tuberculosis*", Antimicrobial Agents and Chemotherapy, vol. 63, Issue 4, pp. 1-3, Apr. 2019.

Santini et al. , "Linezolid-Induced Lactic Acidosis: the Thin Line Between Bacterial and Mitochondrial Ribosomes", Exp. Opinion on Drug Safety, vol. 16, No. 7, pp. 833-843, Jun. 2017.

Shirley et al., "Amikacin Liposome Inhalation Suspension: A Review in *Mycobacterium avium* Complex Lung Disease", Drugs, vol. 79, No. 5, pp. 555-562, Apr. 2019.

Torrea et al., Bedaquiline Susceptibility Testing of *Mycobacterium tuberculosis* in an Automated Liquid Culture System, J Antimicrob Chemother., vol. 70, pp. 2300-2305, Aug. 2015.

(56) References Cited

OTHER PUBLICATIONS

Tweed et al., "Bedaquiline, Moxifloxacin, Pretomanid, and Pyrazinamide During the First 8 Weeks of Treatment of Patients with Drug-Susceptible or Drug-Resistant Pulmonary Tuberculosis: a Multicentre, Open-Label, Partially Randomised, Phase 2B Trial", Lancet Respir Med, vol. 7, No. 12, pp. 1048-1058, Dec 2019.
Merchant et al., "A New Era of Pulmonary Delivery of Nano-Antimicrobial Therapeutic to Treat Chronic Pulmonary Infections", Current Pharmaceutical Design, vol. 22, pp. 1-22, May 1, 2016.

* cited by examiner

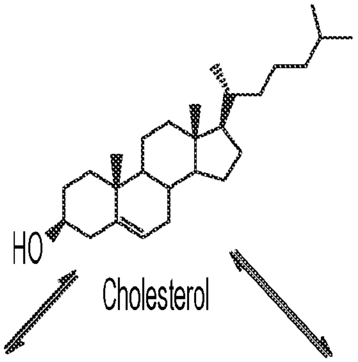
Cholesterol
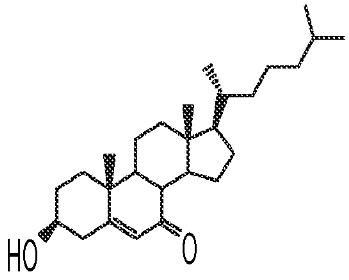
7-keto-cholesterol
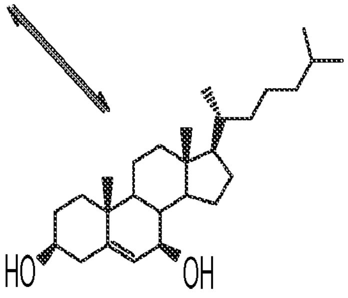
7-hydroxy-cholesterol
FIG. 17 distearoylphosphatidylcholine (DSPC)

lysophosphatidylcholine (Lyso-PC)

+ stearic acid (SA)

Scheme 1

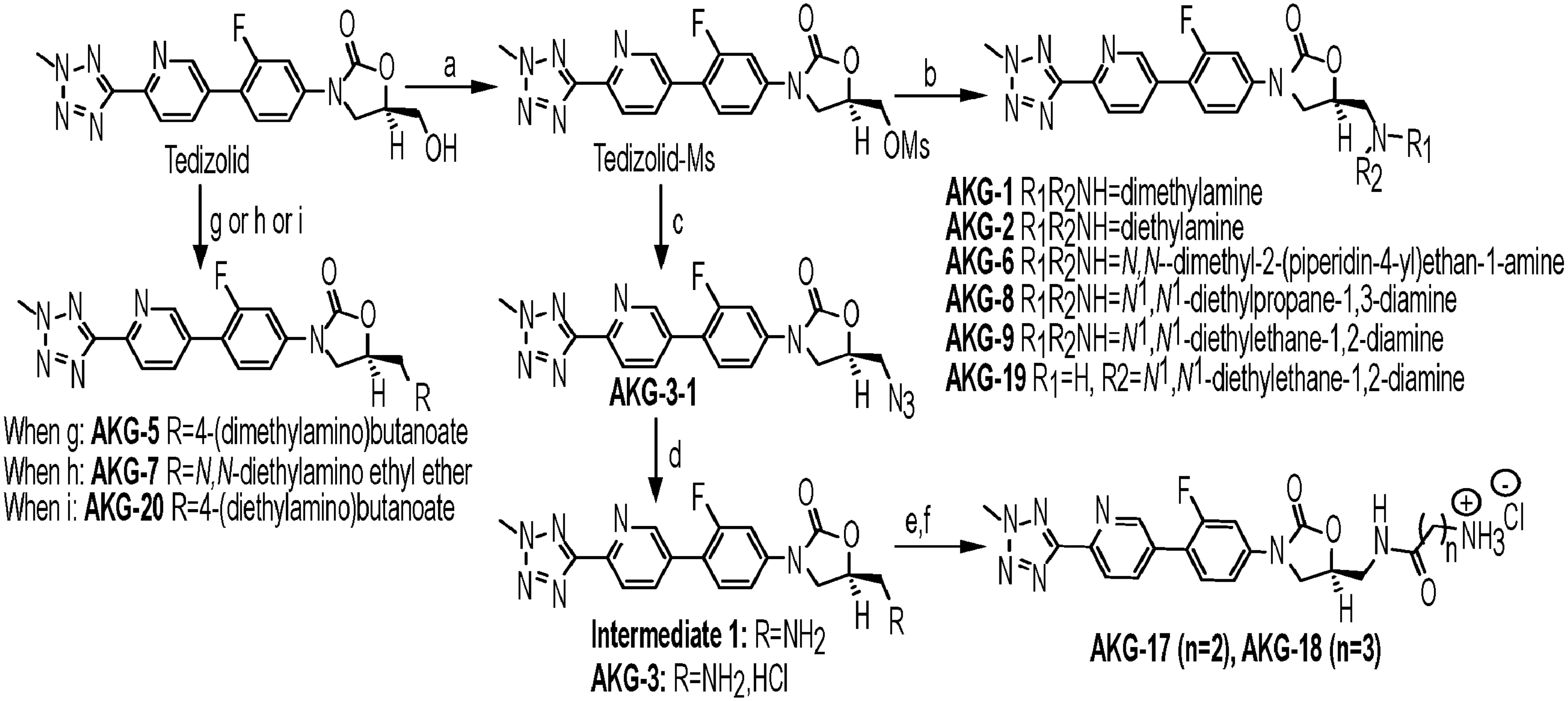

Tedizolid

Tedizolid-Ms

AKG-1 $R_1R_2NH$=dimethylamine
AKG-2 $R_1R_2NH$=diethylamine
AKG-6 $R_1R_2NH$=*N*,*N*--dimethyl-2-(piperidin-4-yl)ethan-1-amine
AKG-8 $R_1R_2NH$=*N*$^1$,*N*$^1$-diethylpropane-1,3-diamine
AKG-9 $R_1R_2NH$=*N*$^1$,*N*$^1$-diethylethane-1,2-diamine
AKG-19 $R_1$=H, R2=*N*$^1$,*N*$^1$-diethylethane-1,2-diamine When g: AKG-5 R=4-(dimethylamino)butanoate
When h: AKG-7 R=*N*,*N*-diethylamino ethyl ether
When i: AKG-20 R=4-(diethylamino)butanoate

AKG-3-1

Intermediate 1: R=$NH_2$
AKG-3: R=$NH_2$,HCl

AKG-17 (n=2), AKG-18 (n=3)

Conditions: (a) $CH_2Cl_2$, MsCl, TEA, r.t 2h; (b) $R_1R_2NH$, NMP, 60°C 16h; (c) $NaN_3$, DMF, 90 °C, 3 h; (d) $Ph_3P$, THF/$H_2O$, reflux 1 h; (e) HATU, acid, DMF; (f) HCl/EtOAc; (g) DCC, DMF, TEA, DMAP, 4-(dimethylamino)butanoic acid hydrogen chloride, r.t, 16 h; (h) NaH, DMF, 2-chloro-*N*,*N*-diethylethan-1-amine, 0°C-r.t, 3 h; (i) DCC, DMF, DMAP, 4-(diethylamino)butanoic acid hydrogen chloride, r.t, 16 h.

FIG. 24

Scheme 2

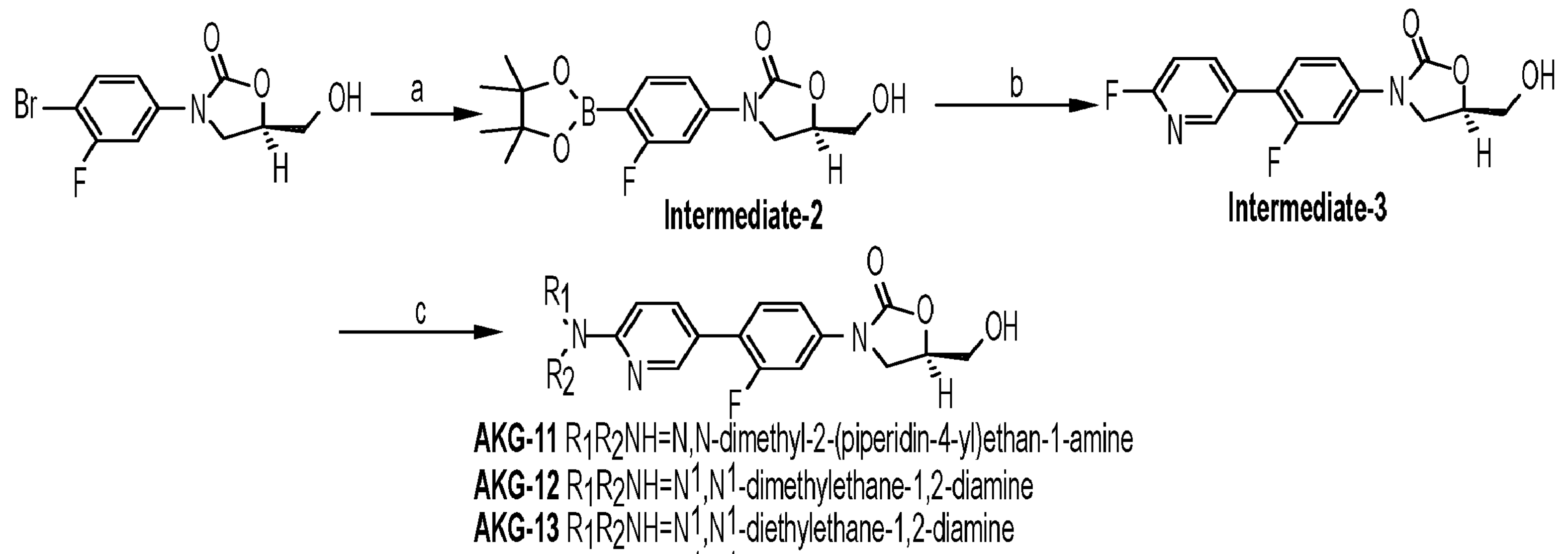

Intermediate-2

Intermediate-3

AKG-11 $R_1R_2NH$=N,N-dimethyl-2-(piperidin-4-yl)ethan-1-amine

AKG-12 $R_1R_2NH$=$N^1$,$N^1$-dimethylethane-1,2-diamine

AKG-13 $R_1R_2NH$=$N^1$,$N^1$-diethylethane-1,2-diamine

AKG-14 $R_1R_2NH$=$N^1$,$N^1$-dimethylpropane-1,3-diamine

AKG-15 $R_1R_2NH$=$N^1$,$N^1$-diethylpropane-1,3-diamine

Conditions: (a) Bis(pinacolato)diboron, KOAc, $(Ph_3P)_2PdCl_2$, dioxane, 90 °C; (b), 5-bromo-2-fluoropyridine, $K_3PO_4$, $(dppf)PdCl_2$, dioxane/$H_2O$, 90 °C, 16 h; (c), $R_1R_2NH$, DMAP, NMP, 100 °C, 16 h.

FIG. 25

Scheme 3

Intermediate-4

Intermediate-5

Intermediate-6

Intermediate-7

Intermediate-8

AKG-16

AKG-21

AKG-22-1

AKG-22

AKG-23-1

AKG-23

Conditions: (a) $NaN_3/ZnCl_2$, pyridine, 120 °C, 2 h; (b) (2-Bromoethyl)dimethylamine hydrobromide, $Ca(OH)_2$, $H_2O/DMF$, 80 °C, 24 h; (c) $NHBoc(CH_2)_2Br$, $Ca(OH)_2$, $H_2O/DMF$ 80 °C, 24 h;(d) Intermediate-2, (dppf)$PdCl_2$, $K_3PO_4$, dioxane 90 °C, 16 h; (e) HCl/Dioxane, r.t., 5 h.

Scheme 4

Intermediate-4

Intermediate-9

Intermediate-10

Intermediate-11

Intermediate-12

AKG-24

AKG-25

AKG-26

AKG-27-1

AKG-27

Conditions: (a) Amine, $Ca(OH)_2$, $H_2O$/DMF, 80 °C, 24 h; (b) Intermediate-2, (dppf)$PdCl_2$, $K_3PO_4$, dioxane, 90 °C, 16 h; (c) HCl/Dioxane, r.t., 5 h.

OXAZOLIDINONE LIPOSOME COMPOSITIONS

RELATED APPLICATION(S)

This patent application is a U.S. National Phase patent application under 35 U.S.C. 371 of International Application No. PCT/US2022/082290, Dec. 22, 2022, which claims the benefit of and priority to U.S. Provisional Patent Application No. 63/292,899, filed Dec. 22, 2021, the disclosures of each of which are incorporated herein by reference in their entireties.

FIELD

The present disclosure relates to liposome compositions comprising oxazolidinone compounds, methods of their making and use of the aminoalkyl oxazolidinone compounds in the treatment of *Mycobacterium tuberculosis* and other gram-positive bacterial infections.

BACKGROUND

Liposome compositions are useful for the delivery of therapeutic compounds. Liposome compositions can comprise liposomes encapsulating a therapeutic compound within a vesicle formed by a membrane formed by lipids. Liposomes are usually characterized by having an interior space sequestered from an outer medium by a membrane of one or more bilayers forming a microscopic sack, or vesicle.

However, liposomes encapsulating therapeutic compounds can degrade during storage and prior to therapeutic administration. For example, oxidative degradation of liposome components and changes in liposome particle size or polydispersity index (PDI) can occur during storage of liposome compositions comprising therapeutic compounds. There remains a need for liposome compositions comprising therapeutic agents with improved storage stability, demonstrating reduced liposome degradation during storage.

SUMMARY

Liposome compositions and methods of treating a methicillin resistant *Staphylococcus aureus* (MRSA) bacterial infection are provided herein.

Aspects of the disclosure relate to a liposome composition of a compound of Formula (I), or a pharmaceutically acceptable salt thereof, Formula (I)

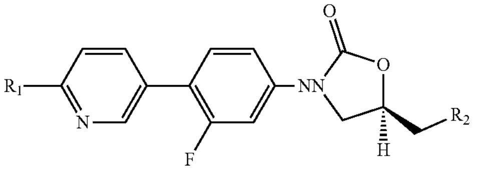

wherein $R_1$ is a tetrazole ring substituted at position 2' with an aminoalkyl; and $R_2$ is an amine or an acetamide; wherein the compound of Formula (I) or pharmaceutically acceptable salt thereof is encapsulated in liposomes in an aqueous medium having a pH greater than 6.7; and wherein the liposomes comprise a phosphatidylcholine, cholesterol and a PEG polymer-conjugated lipid with 50-65 mol % cholesterol relative to the sum of cholesterol and non-pegylated phospholipid in the liposomes.

In some embodiments, $R_2$ is an acetamide ($NHCOCH_3$). In some embodiments, $R_1$ is selected from the group consisting of:

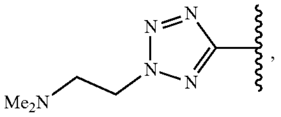

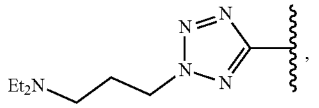

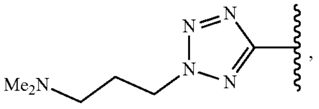

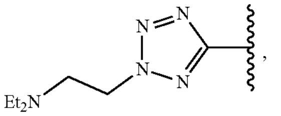

and

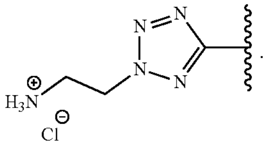

In some embodiments, the PEG polymer-conjugated lipid is in an amount of 5 mol % relative to phosphatidylcholine. In some embodiments, a sulfate salt of the compound of Formula (I) is encapsulated in the liposomes comprising the phosphatidylcholine, cholesterol and PEG polymer-conjugated lipid in a 45:55:2.25 molar ratio. In some embodiments, the phosphatidylcholine is distearoylphosphatidylcholine (DSPC) or hydrogenated soy phosphatidylcholine (HSPC). In some embodiments, the PEG polymer-conjugated lipid is PEG(Mol. weight 2,000)-distearoylglycerol (PEG-DSG) or PEG(Mol. weight 2,000)-distearoylphosphatidylethanolamine (PEG-DSPE). In some embodiments, the liposome composition further comprises a chelator selected from the group consisting of deferoxamine (DFO) and EDTA, wherein the chelator is at a concentration of 0.1-1 mM.

In some embodiments, the compound of Formula (I) is a compound selected from AKG-38, AKG-39 and AKG-40 or a pharmaceutically acceptable salt thereof:

AKG-38

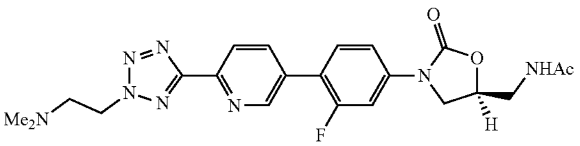

AKG-39

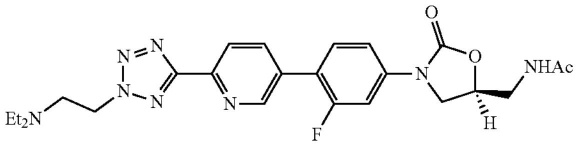

-continued

AKG-40

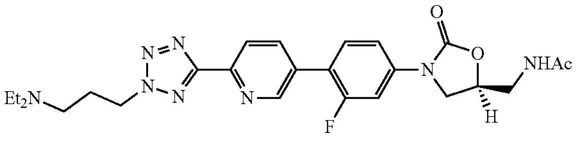

In some embodiments, the compound of Formula (I) is a sulfate salt of AKG-38.

In some embodiments, the pH of the liposome composition is over 7 and no more than 8. In some embodiments, the pH of the liposome composition is 7.3-7.7. In some embodiments, the pH of the liposome composition is 7.5.

In some embodiments, the compound of Formula (I) is a sulfate salt of AKG-38

AKG-38

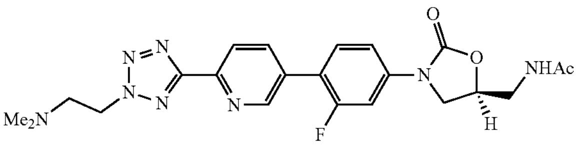

wherein the compound is encapsulated in liposomes formed from hydrogenated soy phosphatidylcholine (HSPC), cholesterol and PEG(2000)-DSPE in a 45.55.2.25 molar ratio, in an aqueous medium at a pH of 7.3-7.7. In some embodiments, the liposome composition further comprises a chelator, wherein the chelator is deferoxamine (DFO) and wherein the chelator is at a concentration of 0.1-1 mM. In some embodiments, the drug/lipid ratio of the AKG-38 to a total phospholipid (PhL) in the composition is 430-680 g/mol. In some embodiments, the drug/lipid ratio of the AKG-38 to a total phospholipid (PhL) in the composition is 600 g/mol. In some embodiments, the liposome composition comprises mono- or oligolamellar vesicles having z-average diameter of 90-130 nm; and the liposome composition has a polydispersity index of less than 0.15. In some embodiments, liposome composition has a proportion of encapsulated AKG-38 to overall AKG-38 of at least 90%. In some embodiments, the aqueous medium further comprises sodium chloride. In some embodiments, the aqueous medium has an osmolality of 270-330 mOsmol/kg; the sodium chloride is at a concentration of 130-150 mM; and the chelator is at a concentration of 0.5 mM. In some embodiments, the aqueous medium comprises an ammonium ion at a concentration of 20-60 mM, and the sodium chloride is at a concentration of 50-80 mM. In some embodiments, the liposome composition further comprises a HEPES or phosphate buffer.

Aspects of the disclosure relate to an AKG-38 liposome composition having a pH of at least 7.0 and not more than 8.0, the liposome composition comprising lipids HSPC, cholesterol, and PEG(2000)-DSPE in a molar ratio of 45:55: 2.25 or in a mass ratio of 5:3:1 and a pharmaceutically acceptable salt of AKG-38

AKG-38

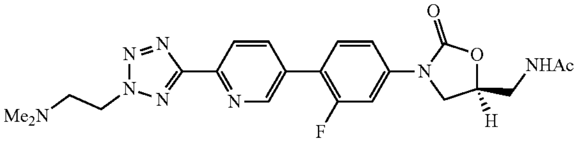

wherein the liposome composition is further characterized by any one or more of the following characteristics: (a) the liposome composition comprises mono- or oligolamellar vesicles having z-average diameter of 90-130 nm or the liposome composition comprises mono- or oligolamellar vesicles have a z-average diameter of 100-130 nm; (b) the liposome composition has a polydispersity index of less than 0.15 or the liposome composition has a polydispersity index of less than 0.10; (c) the drug/lipid ratio of the AKG-38 to the total phospholipid (PhL) in the liposome composition is 430-480 g/mol, or the drug/lipid ratio of the AKG-38 to the total phospholipid (PhL) in the liposome composition is 500-650 g/mol; or the drug/lipid ratio of the AKG-38 to the total phospholipid (PhL) in the liposome composition is 430-650 g/mol; or the drug/lipid ratio of the AKG-38 to the total phospholipid (PhL) in the liposome composition is 450 g/mol; or the drug/lipid ratio of the AKG-38 to the total phospholipid (PhL) in the liposome composition is 450 g/mol; or the drug/lipid ratio of the AKG-38 to the total phospholipid (PhL) in the liposome composition is 600 g/mol; or the drug/lipid ratio of the AKG-38 to the total phospholipid (PhL) in the liposome composition is 600 g/mol; (d) the overall concentration of AKG-38 in the liposome composition is 12-25 mg/mL, or the overall concentration of AKG-38 in the liposome composition is 13.5-16.5 mg/mL, or the overall concentration of AKG-38 in the composition is 15 mg/mL, or the overall concentration of AKG-38 in the liposome composition is 20 mg/mL (200 mg in a 10-mL vial); (e) the proportion of encapsulated AKG-38 to overall AKG-38 in the liposome composition is at least 90%, or the proportion of encapsulated AKG-38 to overall AKG-38 in the liposome composition is at least 95%, or the proportion of encapsulated AKG-38 to overall AKG-38 in the liposome composition is at least 97%, or the proportion of encapsulated AKG-38 to overall AKG-38 in the liposome composition is at least 98%; (f) the liposome composition comprises an aqueous medium comprising sodium chloride and optionally comprising an ammonium ion; (g) the aqueous medium has a osmolality of 270-330 mOsmol/kg, or the aqueous medium has a osmolality of 270-310 mOsmol/kg; (h) the aqueous medium comprises an ammonium ion at a concentration of 20-60 mM, or the aqueous medium comprises an ammonium ion at a concentration of 50-80 mM, or the aqueous medium comprises an ammonium ion at a concentration of less than 0.5 mM, or the aqueous medium comprises an ammonium ion at a concentration of less than 1 mM, or the aqueous medium comprises an ammonium ion at a concentration of 1-10 mM; (i) the aqueous medium comprises sodium chloride at a concentration of 130-150 mM; (j) the aqueous medium further comprises a buffer, wherein the buffer buffers the liposome composition at a pH of 7.3-7.7, or at a pH of 7.5; (k) the aqueous medium further comprises a HEPES or phosphate buffer, or the aqueous medium further comprises HEPES or phosphate buffer at a concentration of 5-50 mM, or the aqueous medium further comprises HEPES or phosphate buffer at a concentration of 20 mM; (1) the aqueous medium further comprises a chelator, or the aqueous medium further comprises a chelator at a concentration of 0.1-1 mM, or the aqueous medium further comprises a chelator at a concentration of 0.5 mM, or the aqueous medium further comprises deferoxamine (DFO) or EDTA, or the aqueous medium further comprises deferoxamine (DFO) or EDTA at a concentration of 0.1-1 mM, or the aqueous medium further comprises deferoxamine (DFO) or EDTA at a concentration of 0.5 mM; (m) the liposome composition is storage stable; or (n) the AKG-38 is encapsulated in the liposomes as a sulfate salt of AKG-38.

Aspects of the disclosure relate toisotonic AKG-38 liposomal dispersion formulated with (5R)-3-{3-Fluoro-4-[6-(2-(2-dimethylaminoethyl)-2H-tetrazol-5-yl)-3-pyridinyl]phenyl}-5-(methylacetamido)-1,3-oxazolidin-2-one, or a pharmaceutically acceptable salt thereof, encapsulated in liposomes comprising hydrogenated soy phosphatidylcholine (HSPC), cholesterol, and (PEG(Mol. weight 2,000)-distearoylphosphatidylethanolamine, PEG-DSPE) (PEG (2000)-DSPE), in an aqueous medium comprising a chelator selected from the group consisting of: deferoxamine (desferrioxamine, Desferal), ethylenediamine tetraacetic acid (EDTA), diethylenetriamine pentaacetic acid (DTPA), nitrilotriacetic acid (NTA), ethyleneglycol-O,O'-bis(2-aminoethyl)-N,N,N',N'-tetraacetic acid (EGTA), N-(2-hydroxyethyl)ethylenediamine-N,N',N'-triacetic acid (HEDTA), and 1,4,7,10-tetraazacyclododecane-1,4,7,10-tetraacetic acid (DOTA).

In some embodiments, the isotonic AKG-38 liposomal dispersion has a pH of greater than 6.7 and not more than 8.0. In some embodiments, the isotonic AKG-38 liposomal dispersion has a pH of 7.5. In some embodiments, the liposomes are formed from hydrogenated soy phosphatidylcholine (HSPC), cholesterol and PEG(2000)-DSPE in a molar ratio of 45:55:2.2. In some embodiments, the chelator is deferoxamine. In some embodiments, the liposomal dispersion comprises lipid vesicles formed from a composition comprising a phosphatidylcholine, 55 mol % cholesterol and 5 mol % PEG-DSG or 5 mol % or PEG-DSPE.

Aspect of the disclosure relate to a method of treating a methicillin resistant *Staphylococcus aureus* (MRSA) bacterial infection, the method comprising administering to a subject in need thereof a therapeutically effective amount of the liposomal composition.

Aspect of the disclosure relate to method of making liposome composition comprising the steps of (a) dissolving one or more phospholipid, cholesterol and a PEG-lipid derivative in ethanol to obtain a lipid solution; (b) combining the lipid solution of step (a) with a trapping agent solution to obtain a uniform lipid suspension having a desired phospholipid concentration; (c) extruding the lipid suspension of step (b) through membranes having defined pore sizes, such as polycarbonate track-etched (PCTE) membranes with the nominal pore size of 50-200 nm; (d) purifying liposomes from extraliposomal trapping agent in the extruded lipid suspension to obtain a purified extruded liposome preparation; (e) contacting the liposomes with the compound of Formula (I) in an aqueous medium to effect encapsulation of the compound in the liposomes; (f) optionally removing unencapsulated compound; and (g) providing the liposomes in a physiologically acceptable medium suitable for parenteral use; wherein the trapping agent solution of step (b) comprises aqueous ammonium sulfate at a concentration of more than 0.25M, and wherein the physiologically acceptable medium of step (g) comprises a chelator.

In some embodiments, the trapping agent solution of step (b) comprises ammonium sulfate at the concentration of 0.5M. In some embodiments, the chelator is deferoxamine. In some embodiments, the extruded liposomes in step (c) are mono- or oligolamellar vesicles having a z-average diameter of 90-130 nm.

Liposome compositions and methods of treating a mycobacterial infection are provided herein.

In some embodiments, the liposome composition comprises the compound of Formula (I) or a pharmaceutically acceptable salt thereof, wherein $R_2$ is an amine ($NH_2$). In some embodiments, $R_1$ is selected from the group consisting of:

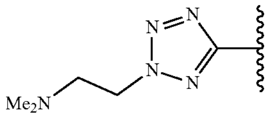
,

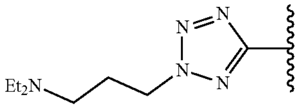
,

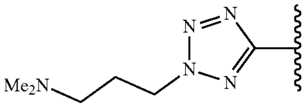
,

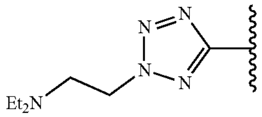
, and

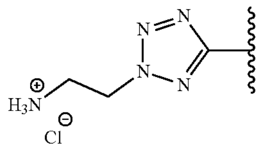
.

In some embodiments, the compound of Formula (I) or pharmaceutically acceptable salt thereof is encapsulated in liposomes in an aqueous medium having a pH greater than 6.7; and the liposomes comprise a phosphatidylcholine, cholesterol and a PEG polymer-conjugated lipid with 50-65 mol % cholesterol relative to the sum of cholesterol and non-pegylated phospholipid in the liposomes. In some embodiments, the PEG polymer-conjugated lipid is in an amount of 5 mol % relative to phosphatidylcholine. In some embodiments, a sulfate salt of the compound of Formula (I) is encapsulated in the liposomes comprising the phosphatidylcholine, cholesterol and PEG polymer-conjugated lipid in a 45:55:2.25 molar ratio. In some embodiments, the phosphatidylcholine is distearoylphosphatidylcholine (DSPC) or hydrogenated soy phosphatidylcholine (HSPC). In some embodiments, the PEG polymer-conjugated lipid is PEG(Mol. weight 2,000)-distearoylglycerol (PEG-DSG) or PEG(Mol. weight 2,000)-distearoylphosphatidylethanolamine (PEG-DSPE). In some embodiments, the liposome composition further comprises a chelator selected from the group consisting of deferoxamine (DFO) and EDTA, wherein the chelator is at a concentration of 0.1-1 mM. In some embodiments, the compound of Formula (I) is a compound selected from AKG-28, AKG-29, AKG-30, AKG-31, AKG-38 and AKG-39 or a pharmaceutically acceptable salt thereof:

AKG-28

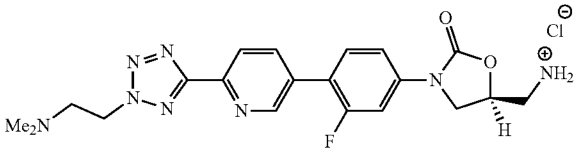

AKG-29

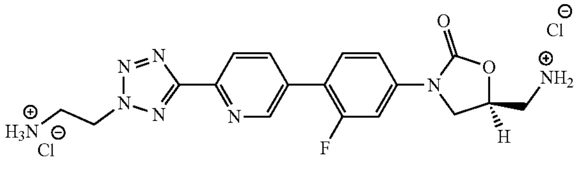

AKG-30

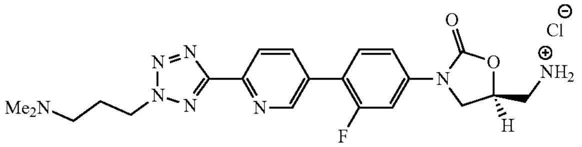

AKG-31

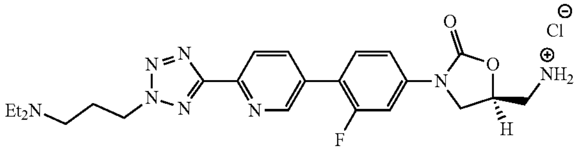

AKG-38

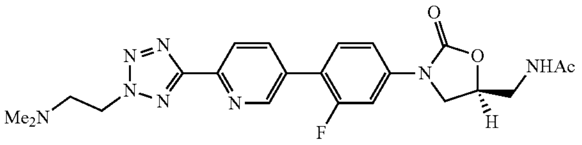

AKG-39

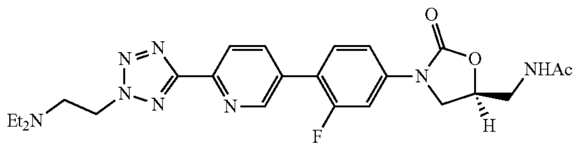

In some embodiments, the compound of Formula (I) is a sulfate salt of AKG-28

(AGK-28)

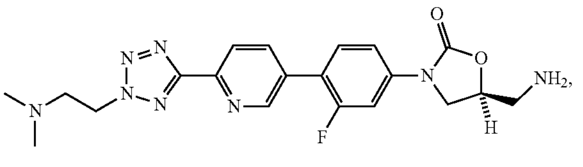

and the compound is encapsulated in liposomes formed from hydrogenated soy phosphatidylcholine (HSPC), cholesterol and PEG(2000)-DSPE in a 45:55:2.25 molar ratio, in an aqueous medium at a pH of 7.3-7.7.

Aspects of the disclosure relate to an AKG-28 liposome composition comprising liposomes, the liposomes comprising lipids HSPC, cholesterol, and PEG(2000)-DSPE in a molar ratio of 45:55:2.25 or in a mass ratio of 5:3:1, and a pharmaceutically acceptable salt of AKG-28 encapsulated into said liposomes (AGK-28)

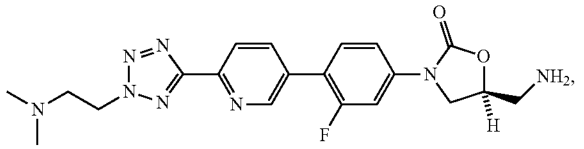

wherein the liposome composition is further characterized by any one or more of the following characteristics: (a) the liposome composition comprises mono- or oligolamellar vesicles having z-average diameter of 90-130 nm, or the liposome composition comprises mono- or oligolamellar vesicles having a z-average diameter of 100-130 nm; (b) the liposome composition has a polydispersity index of less than 0.15, or the liposome composition has a polydispersity index of less than 0.10; (c) the drug/lipid ratio of the AKG-28 to the total phospholipid (PhL) in the composition is 99-530 g/mol PhL, or 85-456 g/mol as AKG-28 free base (FB); 99-470 g/mol PhL, or 85-400 g/mol as AKG-28 free base (FB); 230-280 g/mol, or 190-240 g/mol as AKG-28 free base (FB); or the drug/lipid ratio of the AKG-28 to the total phospholipid (PhL) in the composition is 290-360 g/mol, or 245-305 g/mol as FB; or the drug/lipid ratio of the AKG-28 to the total phospholipid (PhL) in the composition is 300-340 g/mol, or 256-290 g/mol as FB; or the drug/lipid ratio of the AKG-28 to the total phospholipid (PhL) in the composition is 250 g/mol, or 215 g/mol as FB; or the drug/lipid ratio of the AKG-28 to the total phospholipid (PhL) in the composition is 330 g/mol, or 280 g/mol as FB; or the drug/lipid ratio of the AKG-28 to the total phospholipid (PhL) in the composition is 330 g/mol, or 280 g/mol as FB; (d) the overall concentration of AKG-28 in the composition is 8-15 mg/mL, or 6.8-12.8 mg/mL as FB; or the overall concentration of AKG-28 in the composition is 9-11 mg/mL, or 7.6-9.4 mg/mL as FB; or the overall concentration of AKG-28 in the composition is 10 mg/mL, or 8.5 mg/mL as FB; or the overall concentration of AKG-28 in the composition is 10 mg/mL (100 mg in a 10-ml vial), or 8.5 mg/mL (85 mg in a 10 mL vial) as FB; (e) the proportion of encapsulated AKG-28 to overall AKG-28 in the liposome composition is at least 90%; or the proportion of encapsulated AKG-28 to overall AKG-28 in the liposome composition is at least 95%; or the proportion of encapsulated AKG-28 to overall AKG-28 in the liposome composition is at least 97%; or the proportion of encapsulated AKG-28 to overall AKG-28 in the liposome composition is at least 98%; (f) the liposome composition comprises an aqueous medium comprising sodium chloride and optionally comprising an ammonium ion; (g) the aqueous medium has an osmolality of 270-330 mOsmol/kg; or the aqueous medium has an osmolality of 270-310 mOsmol/kg; or the aqueous medium is isotonic; (h) the aqueous medium comprises an ammonium ion at a concentration of 20-60 mM; or the aqueous medium comprises an ammonium ion at a concentration of 50-80 mM; or the aqueous medium comprises an ammonium ion at a concentration of less than 0.5 mM; or the aqueous medium comprises an ammonium ion at a concentration of less than 1 mM; or t the aqueous medium comprises an ammonium ion at a concentration of 1-10 mM; or the aqueous medium comprises an ammonium ion at a concentration of less than 130 mM; (i) the aqueous medium further comprises a buffer, wherein the buffer buffers the liposome composition at a pH of 7.3-7.7 or at a pH of 7.5; (j) the aqueous medium further comprising a HEPES or phosphate buffer; or the aqueous medium further comprises HEPES or phosphate buffer at a concentration of 5-50 mM; or the aqueous medium further comprises HEPES or phosphate buffer at a concentration of 20 mM; (k) the composition further comprises a chelator; or the composition further comprises a chelator at a concentration of 0.1-1 mM; or the composition further comprises a chelator at a concentration of 0.5 mM; or the composition further comprises deferoxamine (DFO) or EDTA; or the composition further comprises deferoxamine (DFO) or EDTA at a concentration of 0.1-1 mM; or the composition further comprises deferoxamine (DFO) or EDTA at a concentration of 0.5 mM; or (l) AKG-28 is encapsulated within the liposome as a sulfate salt of AKG-28.

Aspects of the disclosure relate to method of making liposome composition, the method comprising the steps of: (a) dissolving one or more phospholipid, cholesterol and a PEG-lipid derivative in ethanol to obtain a lipid solution; (b) combining the lipid solution of step (a) with a trapping agent solution to obtain a uniform lipid suspension having a desired phospholipid concentration; (c) extruding the lipid suspension of step (b) through membranes having defined pore sizes, such as polycarbonate track-etched (PCTE) membranes with the nominal pore size of 50-200 nm; (d) purifying liposomes from extraliposomal trapping agent in the extruded lipid suspension to obtain a purified extruded liposome preparation; (e) contacting the liposomes with the compound of Formula (I) in an aqueous medium to effect encapsulation of the compound in the liposomes; (f) optionally removing unencapsulated compound; and (g) providing the liposomes in a physiologically acceptable medium suitable for parenteral use, wherein the trapping agent solution of step (b) comprises aqueous ammonium sulfate at a concentration of more than 0.25M, and wherein the physiologically acceptable medium of step (g) comprises a chelator.

In some embodiments, the trapping agent solution of step (b) comprises ammonium sulfate at the concentration of 0.5M. In some embodiments, the chelator is deferoxamine. In some embodiments, the extruded liposomes in step (c) are mono- or oligolamellar vesicles having a z-average diameter of 90-130 nm. In some embodiments, the chelator is deferoxamine and the extruded liposomes in step (c) are mono- or oligolamellar vesicles having a z-average diameter of 90-130 nm.

Aspects of the disclosure relate to method of treating a mycobacterial infection, the method comprising administering to a subject in need thereof a therapeutically effective amount of the liposomal composition. In some embodiments, the mycobacterial infection is an infection with *Mycobacterium tuberculosis*, or an infection with a multi-drug resistant (MDR) strain of *Mycobacterium tuberculosis*, or an infection with an extremely drug resistant (XDR) strain of *Mycobacterium tuberculosis.*

Provided herein is the use of a liposomal composition for treating a mycobacterial infection.

Provided herein is the use of a liposomal composition for treating a methicillin resistant *Staphylococcus aureus* (MRSA) bacterial infection.

In some embodiments, liposome preparations of oxazolidinone compounds with improved storage stability are provided. In some embodiments, oxazolidinone liposome compositions comprising greater than 50 mol % cholesterol relative to sum of cholesterol and non-pegylated phospholipid in the liposome composition and having a pH of 7 or greater have surprisingly improved storage stability properties. In some embodiments, adding a chelator such as deferoxamine or EDTA reduced the oxidative degradation of cholesterol during storage of oxazolidinone liposome compositions. In some embodiments, oxazolidinone liposome compositions comprising ammonium displaced from the liposomes comprising an ammonium sulfate trapping agent during oxazolidinone drug loading (e.g., by omitting a post-loading buffer exchange) exhibited improved phosphatidylcholine storage stability.

In some embodiments, oxazolidinone liposome compositions provided herein consist of lipids consisting of HSPC, cholesterol and PEG-DSPE in a mass ratio of about 5:3:1. In some embodiments, oxazolidinone liposome compositions provided herein consist of lipids consisting of HSPC, cholesterol and PEG-DSPE in a molar ratio of 45:55:2.25. In some embodiments, oxazolidinone liposome compositions comprise an oxazolidinone consisting of AKG-28 or a pharmaceutically acceptable salt thereof. In some embodiments, oxazolidinone liposome compositions comprise an oxazolidinone consisting of AKG-38 or a pharmaceutically acceptable salt thereof.

In some embodiments, liposome compositions comprising liposome vesicles and an oxazolidinone are provided. In some embodiments, oxazolidinone liposome compositions comprise liposome vesicles encapsulating an oxazolidinone sulfate are provided. In some embodiments, the liposome vesicles are in an aqueous medium.

In some embodiments, the oxazolidinone compounds and salts thereof can be used to prepare liposome compositions. In some embodiments, an oxazolidinone liposome composition can be obtained by a process comprising the step of combining oxazolidine compounds with a purified, extruded lipid suspension under conditions effective to form the oxazolidinone liposomes. The purified, extruded lipid suspension can comprise lipid components consisting of a phospholipid, cholesterol and optionally a PEG-lipid derivative combined in an aqueous medium at a desired concentration and a trapping agent such as ammonium sulfate (AS). In some embodiments, the lipid components of the extruded lipid suspension consist of HSPC, cholesterol and PEG (2000)-DSPE. In some embodiments, the lipid components of the extruded lipid suspension comprises HSPC and cholesterol in a molar ratio of 45:55. In some embodiments, the lipid components of the extruded lipid suspension comprises HSPC and cholesterol in a weight ratio of 5:3. In some embodiments, the lipid components of the extruded lipid suspension consist of HSPC, cholesterol and PEG(2000)-DSPE in a molar ratio of 45:55:2.25. In some embodiments, the lipid components of the extruded lipid suspension consist of HSPC, cholesterol and PEG(2000)-DSPE in a weight ratio of 5:3:1.

In some embodiments, the purified, extruded lipid suspension is obtained by a process comprising the steps of: (a) dissolving one or more phospholipid, cholesterol and a PEG-lipid derivative in ethanol; (b) combining the lipid solution of step (a) with a trapping agent solution (e.g., 0.5 M ammonium sulfate) to obtain a uniform lipid suspension having a desired phospholipid concentration (e.g., 60 mM phospholipid); (c) extruding the lipid suspension of step (b) through membranes having defined pore sizes, such as polycarbonate track-etched (PCTE) membranes with the nominal pore size of 50-200 nm; and (d) purifying liposomes from extraliposomal trapping agent in the extruded lipid suspension (e.g., by tangential flow filtration on a hollow fiber cartridge) to obtain a purified extruded liposome preparation. In some embodiments, the liposomes are mono- or oligolamellar vesicles having a z-average diameter of 90-130 nm or 100-130 nm. In some embodiments, the liposomes are mono- or oligolamellar vesicles having a polydispersity index of less than 0.15 or less than 0.10.

The purified extruded liposomes can be loaded with an oxazolidinone drug in a subsequent drug loading step. A drug stock solution of an oxazolidinone drug compound or salt thereof can be combined at a desired drug to phospholipid concentration with the purified, extruded lipid suspension of step (d) to form a drug-liposome mixture under conditions effective to load the drug into the liposomes within the purified extruded liposome preparation. In some embodiments, the drug loading step comprises an exchange, across the liposome bilayer membrane, of the trapping agent ammonium cation with the oxazolidinone compound, resulting in generation of extraliposomal ammonium in the drug-liposome mixture that is displaced from within the liposomes during the drug loading process.

After the drug loading process, unencapsulated drug compound can be purified from the drug-liposome mixture (e.g., by size exclusion chromatography, SEC, dialysis, or diafiltration, such as, tangential flow filtration), and the composition comprising oxazolidinone drug liposomes can be isolated and stored.

In some embodiments, the compound is entrapped in the liposome vesicle with a trapping agent, wherein the trapping agent comprises a polyanion. In some embodiments, the trapping agent is triethylammonium sucrose octasulfate or ammonium sulfate. In some embodiments, the trapping agent is triethylammonium sucrose octasulfate. In some embodiments, the trapping agent is ammonium sulfate.

In some embodiments, the liposomal composition comprises a salt of the compound, wherein the salt is sulfate, citrate, sucrosofate, a salt with a phosphorylated or sulfated polyol, or a salt with a phosphorylated or sulfated polyanionic polymer. In some embodiments, the liposomal composition comprises a sulfate salt of the compound. For example, in some embodiments, the liposomal composition comprises a sulfate or hydrosulfate salt of an oxazolidinone compound of Formula (I). In some embodiments, the liposomal composition comprises a sulfate or hydrosulfate salt of (AKG-28). In some embodiments, the liposomal composition comprises a sulfate or hydrosulfate salt of (AKG-38).

In some embodiments, the compound in the liposome vesicle has an aqueous solubility less than 1 mg/mL. In some embodiments, the compound in the liposome vesicle has an aqueous solubility less than 0.1 mg/mL.

In some embodiments, the liposome vesicle comprises a membrane comprising phosphatidylcholine and cholesterol. In some embodiments, the liposome vesicle comprises a membrane comprising phosphatidylcholine and cholesterol, wherein the membrane separates the inside of the liposome vesicles from the aqueous medium. In some embodiments, the phosphatidylcholine is distearoylphosphatidylcholine (DSPC) or hydrogenated soy phosphatidylcholine (HSPC). In some embodiments, the phosphatidylcholine to cholesterol molar ratios is from about 60:40 to 35:65. In some embodiments, the phosphatidylcholine to cholesterol molar ratio is from about 55:45 to about 35:65. In some embodiments, the phosphatidylcholine to cholesterol molar ratio is from about 50:50 to about 40:60. In some embodiments, the phosphatidylcholine to cholesterol molar ratio is from about 50:50 to about 45:55. In some embodiments, the membrane further comprises a polymer-conjugated lipid. In some embodiments, the liposome vesicle comprises HSPC, cholesterol and polymer-conjugated lipid in about 45:55:2.75 molar ratio. In some embodiments, the liposome vesicle comprises HSPC, cholesterol and polymer-conjugated lipid in a 45:55:2.25 molar ratio. In some embodiments, the polymer-conjugated lipid is PEG(Mol. weight 2,000)-distearoylglycerol (PEG-DSG) or PEG(Mol. weight 2,000)-distearoylphosphatidylethanolamine (PEG-DSPE). In some embodiments, the liposomes in the liposome composition have Z-average particle size from about 80 to about 130 nm.

In some embodiments, the drug liposomes are provided in an aqueous medium comprising sodium chloride and optionally further comprising ammonium displaced from the liposome during the drug loading process. In some embodiments, the concentration of sodium chloride in the liposome composition is 50-80 mM. In some embodiments, the concentration of sodium chloride in the liposome aqueous composition is 130-150 mM. In some embodiments, the drug liposomes are provided in an aqueous medium comprise 20-60 mM ammonium displaced from the liposome during the drug loading process. In some embodiments, the concentration of the ammonium in the liposome aqueous medium is less than 0.5 mM. In some embodiments, the osmolality of the aqueous medium of the liposome composition is 270-330 mOsmol/kg. In some embodiments, the osmolality of the aqueous medium of the liposome composition is 270-310 mOsmol/kg.

In some embodiments, the oxazolidinone liposome composition has a pH greater than about 6.7. In some embodiments, the oxazolidinone liposome composition has a pH of 7-8. In some embodiments, the oxazolidinone liposome composition further comprises a buffer to bring the pH of the liposome aqueous medium to about 7.3-7.7. In some embodiments, the oxazolidinone liposome composition further comprises a buffer to bring the pH of the liposome aqueous medium to about 7.5. In some embodiments, oxazolidinone liposome composition comprises a buffer substance selected from the group consisting of HEPES and phosphate. In some embodiments, oxazolidinone liposome composition comprises HEPES buffer. In some embodiments, oxazolidinone liposome composition comprises phosphate buffer. In some embodiments, oxazolidinone liposome composition comprises a buffer substance selected from the group consisting of HEPES and phosphate at a concentration of 5-50 mM. In some embodiments, oxazolidinone liposome composition comprises a buffer substance selected from the group consisting of HEPES and phosphate at a concentration of 20 mM.

In some embodiments, the oxazolidinone liposome composition further comprises a chelator. In some embodiments, the oxazolidinone liposome composition further comprises a chelator selected from the group consisting of deferoxamine (DFO) and EDTA. In some embodiments, the oxazolidinone liposome composition further comprises a chelator selected from the group consisting of: deferoxamine (DFO) and EDTA at a concentration of 0.1-1 mM. In some embodiments, the oxazolidinone liposome composition further comprises a chelator selected from the group consisting of: deferoxamine (DFO) and EDTA at a concentration of 0.5 mM.

In some embodiments, oxazolidinone drug compounds were efficiently (>95%) loaded into extruded liposomes at increased drug to lipid ratios (Example 51) with blood PK characteristics close to that of liposomes with lower drug to lipid ratios (Example 53).

In some embodiments, oxazolidinone liposome preparations can be stabilized by retaining ammonium displaced from the trapping agent within the liposomes during the drug loading process (e.g., by omitting the buffer exchange step).

In some embodiments, the oxazolidinone drug compound is AKG-28, and the liposome composition comprises a sulphate salt of AKG-28 formed within the liposomes during the drug loading process. In some embodiments, the AKG-28 liposome is prepared using a drug stock solution obtained by dissolving a salt form of (5R)-3-{3-Fluoro-4-[6-(2-(2-dimethylaminoethyl)-2H-tetrazol-5-yl)-3-pyridinyl]phenyl}-5-(methylamino)-1,3-oxazolidin-2-one (AKG-28). In some embodiments, salts of AKG-28 are provided, including hydrochloride salts of AKG-28. The salts of AKG-28 are useful in preparing the drug stock solution for loading the AKG-28 liposomes. In some embodiments, the AKG-28 ion exchanges with the ammonium displaced from an ammonium sulfate trapping agent within the liposome, forming an AKG-28 salt within the AKG-28 liposome.

liposome composition has AKG-28 at a drug/lipid ratio of about 250 g/mol total phospholipid (PhL). In some embodiments, the AKG-28 liposome composition has AKG-28 at a drug/lipid ratio of about 330 g/mol total phospholipid (PhL). In some embodiments, the overall (or total) concentration of AKG-28 in a liposome composition is 8-15 mg/ml. In some embodiments, the overall concentration of AKG-28 in a liposome composition is 9-11 mg/ml. In some embodiments, the proportion of encapsulated AKG-28 to overall AKG-28 in the AKG-28 liposome composition is at least 90%, at least 95%, at least 97% or at least 98%.

In some embodiments, the oxazolidinone drug compound is AKG-38, and the liposome composition comprises a sulphate salt of AKG-38 formed within the liposomes during the drug loading process. In some embodiments, the AKG-38 liposome is prepared using a drug stock solution obtained by dissolving a salt form of (5R)-3-{3-Fluoro-4-[6-(2-(2-

| Chemical Structure | Compound | Molecular weight |
|---|---|---|
| 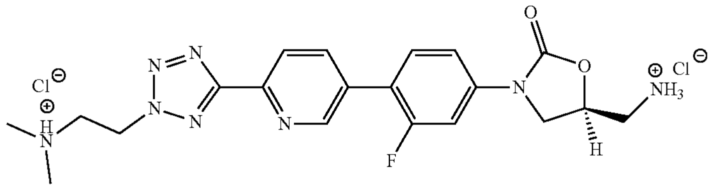 | AKG-28 | Mol. wt 499.4 |
| 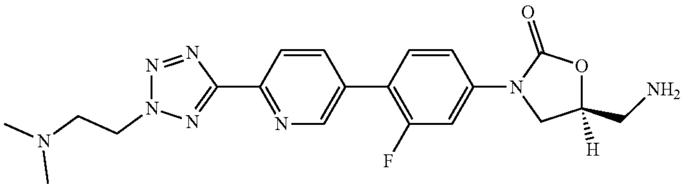 [SMILES: CN(C)CCn1nnc(-c2ccc(-c3ccc(N4C[C@H](CN)OC4=O)cc3F)cn2)n1] | AKG-28 free base | Mol. wt 426.5 |
| 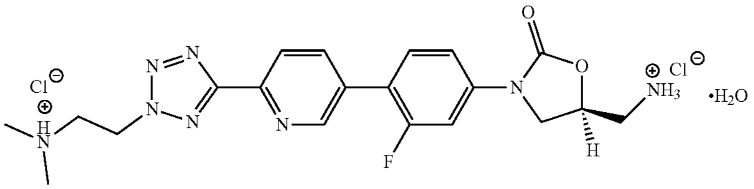 | AKG-28 dihydrochloride monohydrate | Mol. wt 517.4 |

In some embodiments, the AKG-28 liposome composition has AKG-28 at a drug/lipid ratio of 230-380 g/mol total phospholipid (PhL). In some embodiments, the AKG-28 liposome composition has AKG-28 at a drug/lipid ratio of 230-290 g/mol total phospholipid (PhL). In some embodiments, the AKG-28 liposome composition has AKG-28 at a drug/lipid ratio of 290-360 g/mol total phospholipid (PhL). In some embodiments, the AKG-28 liposome composition has AKG-28 at a drug/lipid ratio of 300-340 g/mol total phospholipid (PhL). In some embodiments, the AKG-28 dimethylaminoethyl)-2H-tetrazol-5-yl)-3-pyridinyl]phenyl}-5-(methylacetamido)-1,3-oxazolidin-2-one (AKG-38). In some embodiments, salts of AKG-38 are provided, including hydrochloride salts of AKG-38. The salts of AKG-38 are useful in preparing the drug stock solution for loading the AKG-38 liposomes. In some embodiments, the AKG-38 ion exchanges with the ammonium displaced from an ammonium sulfate trapping agent within the liposome, forming an AKG-38 salt within the AKG-38 liposome.

| Chemical Structure | Compound | Molecular weight |
|---|---|---|
| 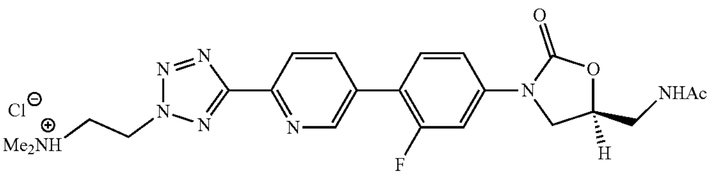 | AKG-38 hydrochloride | Mol. wt 505.0 |

-continued

| Chemical Structure | Compound | Molecular weight |
|---|---|---|
| 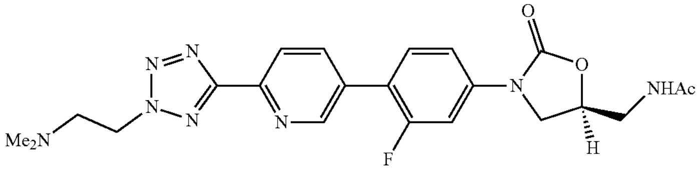 [SMILES: CC(=O)NC[C@H]1CN(c2ccc(-c3ccc(-c4nnn(CCN(C)C)n4)nc3)c(F)c2)C(=O)O1] | AKG-38 free base | Mol. wt 468.5 |

In some embodiments, the AKG-38 liposome composition has AKG-38 at a drug/lipid ratio of 430-680 g/mol total phospholipid (PhL). In some embodiments, the AKG-38 liposome composition has AKG-38 at a drug/lipid ratio of 500-650 g/mol total phospholipid (PhL). In some embodiments, the AKG-28 liposome composition has AKG-38 at a drug/lipid ratio of 550-650 g/mol total phospholipid (PhL). In some embodiments, the AKG-38 liposome composition has AKG-38 at a drug/lipid ratio of about 450 g/mol total phospholipid (PhL). In some embodiments, the AKG-38 liposome composition has AKG-38 at a drug/lipid ratio of about 600 g/mol total phospholipid (PhL). In some embodiments, the overall concentration of AKG-38 in a liposome composition is 12-25 mg/ml. In some embodiments, the overall concentration of AKG-38 in a liposome composition is 13.5-16.5 mg/ml. In some embodiments, the overall concentration of AKG-38 in a liposome composition is about 15 mg/ml. In some embodiments, the overall concentration of AKG-38 in a liposome composition is about 20 mg/ml. In some embodiments, the proportion of encapsulated AKG-38 to overall AKG-38 in the AKG-38 liposome composition is at least 90%, at least 95%, at least 97% or at least 98%.

Cholesterol and HSPC degradation was observed in certain AKG-28 and AKG-38 liposome compositions during accelerated stability testing of oxazolidinone liposome preparations (Examples 54, 65). FIG. 17 is a scheme showing the two major cholesterol oxidation degradation products, 7-hydroxy-cholesterol (alpha- and beta-isomers), and 7-ketocholesterol. FIG. 18 is a scheme showing breakdown of distearoylphosphatidylcholine (DSPC) to lysophosphatidylcholine (lyso-PC) and stearic acid. Hydrogenated soy phosphatidylcholine (HSPC) is a 1,2-diacyl-sn-glycero-phosphocholine, where the 1 and 2 acyl chain positions are saturated fatty acids C16 to C22, being primarily stearic (C18) and palmitic (C16) acid. Distearoylphosphatidylcholine is the largest component of HSPC.

However, in an accelerated stability study, in certain unpurified, buffered liposome formulations of AKG-28 prepared without the buffer exchange step formation of HSPC degradation products lyso-PC, stearic acid and palmitic acid was undetectable at the point when post-buffer exchange formulations already showed HSPC degradation (Example 54). The liposome external medium in these formulations had increased levels of ammonium displaced from the ammonium sulfate trapping agent contained within the liposome interior prior to the drug loading step (displaced ammonium), In some embodiments, AKG-28 liposomes can comprise displaced ammonium in an amount equal to or greater than the molar equivalent of AKG-28 drug loaded into the liposomes. Similarly, the degradation of HSPC was minimized during accelerated stability testing in AKG-38 liposomes without post-drug loading buffer exchange (Example 55).

The addition of a deferoxamine chelator to the liposome excipient buffer of AKG-28 and AKG-38 liposome compositions comprising over 50 mol % cholesterol relative to the sum of cholesterol and non-pegylated phospholipid surprisingly prevented the degradation of cholesterol through at least 3 months at 37° C. accelerated stability testing (Example 56). However, the addition of DFO, EDTA and DTPA chelators to drug stocks prior to drug loading did not protect against lipid degradation in AKG-28 and AKG-38 liposomes comprising HSPC and over 50 mol % cholesterol relative to the sum of cholesterol and non-pegylated phospholipid (Example 57). Without chelators (DFO or EDTA), oxidative degradation of cholesterol was observed in AKG-28 and AKG-38 liposome formulations (Examples 58, 67).

In some embodiments, the liposome composition is stable against degradation of the liposome lipid components and has pH>7.0. It was discovered that the rate of lipid degradation, in particular, degradation of cholesterol depends on the liposome formulation pH and is lower at pH above 7.0 (Example 65). In some embodiments, the liposome composition has the pH of at least 7.1, at least 7.2, or at least 7.3, and no more than pH 8.0, no more than pH 7.7, or no more than pH 7.6. In some embodiments, the degree of cholesterol degradation after 3 months at 37° C. is less than 10%, less than 5%, or less than 1% of the total cholesterol. In some embodiments, the degree of phospholipid degradation after 6 weeks at 37° C. is less than 10%, less than 5%, or less than 1% of the total phospholipid. In some embodiments, the phospholipid is phosphatidylcholine. In some embodiments, the phospholipid is HSPC, and the pH is between pH 7.3-7.6.

In some embodiments, the liposome composition comprises cholesterol and is stable against degradation of cholesterol, the degree of cholesterol degradation after 3 months at 37° C. being less than 10%, less than 5%, or less than 1% of the total cholesterol. Avoiding degradation of cholesterol is important because the products of cholesterol degradation are toxic and may cause vascular endothelial injury (Rong et al., Arteriosclerosis, Thrombosis, and Vascular Biology, 1998, vol. 18, p. 1885-1894; Sevanian et al., J Lipid Res, 1995, vol. 36, p. 1971-1986). In some embodiments, the liposome composition comprises a chelator. In some embodiments, the chelator is a chelator known to be tolerated in humans. In some embodiments, the chelator is deferoxamine (Desferal, DFO), ethylenediamine tetraacetic acid (EDTA), diethylenetriamine pentaacetic acid (DTPA), nitrilotriacetic acid (NTA), ethyleneglycol-O, O'-bis(2-aminoethyl)-N, N, N', N'-tetraacetic acid (EGTA), N-(2-hydroxyethyl)ethylenediamine-N,N',N'-triacetic acid (HEDTA), 1,4,7,10-tetraazacyclododecane-1,4,7,10-tetraacetic acid (DOTA), including their pharmaceutically acceptable salts. In some embodiments, the chelator is present in the composition at the concentration of at least 0.01 mM, at least 0.05 mM, at least 0.1 mM, at least 0.2 mM, or at least 0.5 mM, and not more than 1 mM, nor more than 2 mM, not more than 5 mM, or not more than 10 mM. In some embodiments, the chelator is deferoxamine or deferoxamine mesylate, and the chelator concentration is about 0.5 mM.

In some embodiments the external medium of the liposome composition has less than 0.5 mEq/L(milligram-equivalents per liter) of ammonium or substituted ammonium. In some embodiments the liposome composition contains in the liposome external medium an ammonium or substituted ammonium in the concentration of at least 10 mEq/L, at least 15 mEq/L, or at least 20 mEq/l, and no more than 200 mEq/L, no more than 150 mEq/L, no more than 100 mEq/L, no more than 80 mEq/L, or no more than 60 mEq/L. In some embodiments, the liposome composition contains in the liposome external medium an ammonium or substituted ammonium in the concentration of at least 10 mEq/L, at least 15 mEq/L, or at least 20 mEq/l, and no more than 200 mEq/L, no more than 150 mEq/L, no more than 100 mEq/L, no more than 80 mEq/L, or no more than 60 mEq/L, and is stable against phospholipid degradation, the degree of phospholipid degradation after 6 weeks at 37° C. being less than 10%, less than 5%, or less than 1% of the total phospholipid. In some embodiments, the phospholipid is phosphatidylcholine. In some embodiments, the phospholipid is HSPC, and the ammonium salt is ammonium chloride, ammonium sulphate, or a combination thereof, at the ammonium concentration of 10-80 mM, or 15-60 mM. In some embodiments, the normality of ammonium in the external medium of the liposome composition is within 90-110% of the normality of encapsulated drug at the drug loading step, normality being the concentration expressed in gram-equivalents/L (eq/L).

In some embodiments, the liposome composition comprises encapsulated compound of Formula 1b at the drug/lipid (DL)ratio of 300-350 g/mol PhL. In some embodiments, the liposome composition comprises encapsulated compound of Formula 1b at the DL ratio of 300-350 g/mol PhL and is characterized by the in vivo drug release half-life in the blood of a CD-1 mouse of more than 80 hours, more than 200 hours, or more than 300 hours.

In some embodiments, the liposome composition comprises encapsulated compound of Formula 1c at the DL ratio of 500-650 g/mol PhL.

In some embodiments, the liposome composition comprises liposomes in an aqueous medium, the liposomes composed of HSPC, cholesterol, and PEG(2000)-DSPE in the molar ratio of 45:55:2.25 or in the mass ratio of 5:3:1, the liposomes being mono- or oligolamellar vesicles having z-average diameter of 90-130 nm or 100-130 nm, and polydispersity index of less than 0.15 or less than 0.10, the liposomes containing encapsulated compound AKG-28 at the drug/lipid (DL) ratio of 230-280 g/mol phospholipid (PhL), 290-360 g/mol PhL, 300-340 g/mol PhL, about 250 g/mol PhL, or about 330 g/mol PhL, the overall concentration of AKG-28 in the composition being 8-15 mg/ml or 9-11 mg/ml, and the proportion of encapsulated AKG-28 to overall AKG-28 in the composition is at least 90%, at least 95%, at least 97%, or at least 98%. In some embodiments, the aqueous medium comprises sodium chloride and optionally an ammonium ion. In some embodiments, the osmolality of the aqueous medium is 270-330 mOsmol/kg or 270-310 mOsmol/kg. In some embodiments, the ammonium concentration in the aqueous medium is 20-60 mM, and the concentration of sodium chloride is 50-80 mM. In some embodiments the concentration of ammonium in the aqueous medium is less than 0.5 mM, and the concentration of sodium chloride is 130-150 mM. In some embodiments the composition also contains a buffer substance to bring the pH of the aqueous medium to about 7.3-7.7, or about pH 7.5. In some embodiments, the buffer substance is HEPES or phosphate, at the concentration of 5-50 mM, or of about 20 mM. The composition can also contain a chelator, the chelator being deferoxamine (DFO) or EDTA, at the concentration of 0.1-1 mM, or about 0.5 mM. In some embodiments, the liposome composition is storage-stable.

In some embodiments, the liposome composition comprises liposomes in an aqueous medium, the liposomes composed of HSPC, cholesterol, and PEG(2000)-DSPE in the molar ratio of 45:55:2.25 or in the mass ratio of 5:3:1, the liposomes being mono- or oligolamellar vesicles having z-average diameter of 90-130 nm or 100-130 nm and polydispersity index of less than 0.15, or less than 0.10, the liposomes containing encapsulated compound AKG-38 at the drug/lipid ratio of 430-480 g/mol phospholipid (Phl,), 500-650 g/mol PhL, 550-650 g/mol PhL, about 450 g/mol PhL, or about 600 g/mol PhL, the overall concentration of AKG-38 in the composition being 12-25 mg/ml, 13.5-16.5 mg/ml, about 15 mg/ml, or about 20 mg/ml, and the proportion of encapsulated AKG-38 to overall AKG-38 in the composition is at least 90%, at least 95%, at least 97%, or at least 98%. In some embodiments, the aqueous medium comprises sodium chloride and optionally an ammonium ion. In some embodiments, the osmolality of the aqueous medium is 270-330 mOsmol/kg or 270-310 mOsmol/kg. In some embodiments, the ammonium concentration in the aqueous medium is 20-60 mM, and the concentration of sodium chloride is 50-80 mM, In some embodiments, the concentration of ammonium in the aqueous medium is less than 0.5 mM, and the concentration of sodium chloride is 130-150 mM. In some embodiments, the composition also contains a buffer substance to bring the pH of the medium to about 7.3-7.7, or about pH 7.5. In some embodiments, the buffer substance is HEPES or phosphate, at the concentration of 5-50 mM, or of about 20 mM. The composition can also contain a chelator, the chelator being deferoxamine (DFO) or EDTA, at the concentration of 0.1-1 mM, or about 0.5 mM. In some embodiments, the liposome composition is storage-stable.

In some embodiments, the liposome composition is stable against degradation of the encapsulated compound upon storage. In some embodiments, the degradation of the encapsulated compound upon storage under the accelerated degradation conditions (37° C.), as measured by the decrease of the compound purity, expressed in percentage points, is less than 5%, less than 4%, less than 3%, less than 2%, or about 1% or less after three months of storage. In some embodiments, the degradation of the encapsulated compound upon storage under the accelerated degradation conditions (37° C.), as measured by the decrease of the overall concentration of the intact compound in the liposome composition, is less than 20%, less than 10%, or less than 5% after three months of storage. In some embodiments, the encapsulated compounds are AKG-28 or AKG-38. Thus, a liposomal composition of AKG-38, stored at 37° C. for three months, showed remarkably low decrease of AKG-38 purity from 98.99% to 98.07% (0.92 percentage points) and the low overall decrease in the intact AKG-38 concentration from 19.9 mg/ml to 19.06 mg/ml (4.2% decrease) (Example 68).

BRIEF DESCRIPTION OF THE DRAWINGS

FIG. 2A shows the effect of the added drug-to-lipid (DL0) ratio, in grams of the drug per mole of liposome phospholipid (PhL), on the liposome payload, expressed as post-load drug-to-lipid ratio (DL). FIG. 2B shows the effect the DL0 ratio (drug-to-lipid input ratio) on liposome loading efficiency, calculated as percent of post-load DL relative to DL0.

FIG. 3A shows the effect the DL0 ratio on liposome payload for AKG-5, and AKG-16. FIG. 3B shows the effect the DL0 ratio on liposome loading efficiency for AKG-5, and AKG-16. FIG. 3C shows the effect the DL0 ratio on liposome payload for AKG-3. FIG. 3D shows the effect the DL0 ratio on liposome loading efficiency for AKG-3.

FIG. 4A shows the effect the DL0 ratio on liposome payload. FIG. 4B shows the effect the DL0 ratio on loading efficiency.

FIG. 17 is a scheme showing the two major cholesterol oxidation degradation products, 7-hydroxy-cholesterol (alpha- and beta-isomers), and 7-ketocholesterol.

FIG. 24 shows synthesis Scheme-1 according to embodiments of the disclosure.

FIG. 25 shows synthesis Scheme-2 according to embodiments of the disclosure.

DETAILED DESCRIPTION

Figure 1:
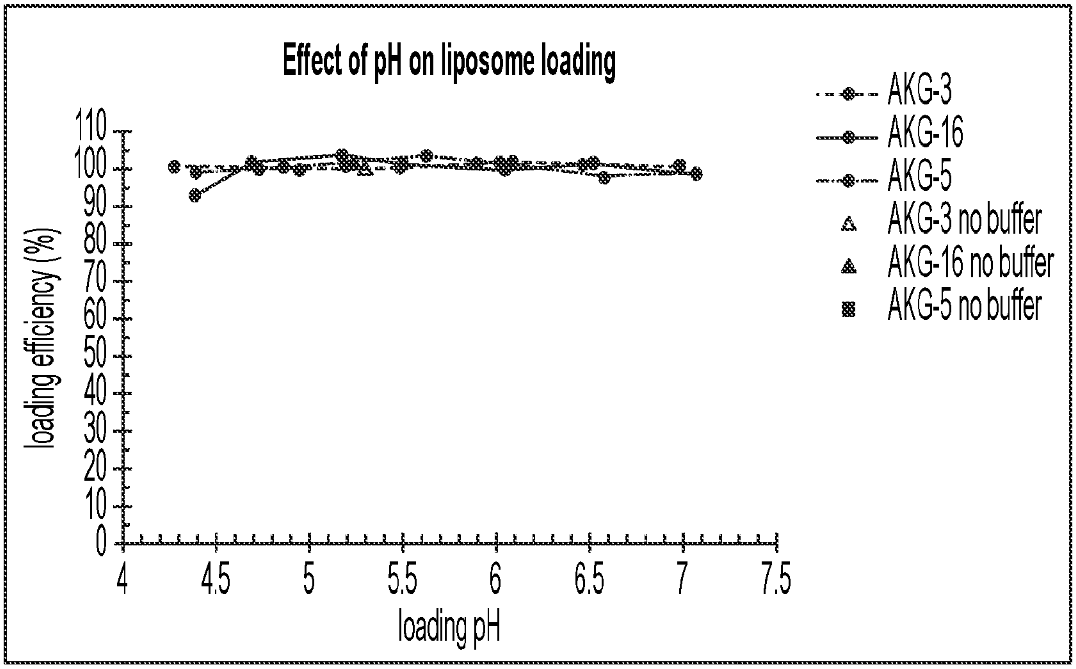
FIG. 1 is a graph showing the effect of pH on the liposome loading of compounds AKG-3, AKG-5, and AKG-16.

This disclosure describes oxazolidinone liposome compositions. In some embodiments, the liposome compositions comprise compound of Formula (I) encapsulated in lipid vesicles. In some embodiments, the liposome compositions comprise an oxazolidinone compound as a pharmaceutically acceptable salt thereof, and lipid vesicles comprising a phospholipid and cholesterol. In some embodiments, the liposome compositions comprise an oxazolidinone compound as a pharmaceutically acceptable salt thereof, and lipid vesicles comprising a phospholipid and more than 50 mol % cholesterol relative to the sum of cholesterol and non-pegylated phospholipid in the liposome composition. In some embodiments, the liposome compositions comprise an oxazolidinone compound as a pharmaceutically acceptable salt thereof, and lipid vesicles comprising a phospholipid and more than about 50 mol % cholesterol relative to the sum of cholesterol and non-pegylated phospholipid in the liposome composition. In some embodiments, the liposome compositions comprise an oxazolidinone compound as a pharmaceutically acceptable salt thereof, and lipid vesicles comprising a phospholipid and between 50-65 mol % cholesterol relative to the sum of cholesterol and non-pegylated phospholipid in the liposome composition. In some embodiments, the liposome compositions comprise an oxazolidinone compound as a pharmaceutically acceptable salt thereof, and lipid vesicles comprising a phospholipid and between 50-60 mol % cholesterol relative to the sum of cholesterol and non-pegylated phospholipid in the liposome composition. In some embodiments, the liposome compositions comprise an oxazolidinone compound as a pharmaceutically acceptable salt thereof, and lipid vesicles comprising a phospholipid and between 50-55 mol % cholesterol relative to the sum of cholesterol and non-pegylated phospholipid in the liposome composition. In some embodiments, the liposome compositions comprise an oxazolidinone compound as a pharmaceutically acceptable salt thereof, and lipid vesicles comprising a phospholipid and about 50 mol % cholesterol relative to the sum of cholesterol and non-pegylated phospholipid in the liposome composition. In some embodiments, the liposome compositions comprise an oxazolidinone compound as a pharmaceutically acceptable salt thereof, and lipid vesicles comprising a phospholipid and about 55 mol % cholesterol relative to the sum of cholesterol and non-pegylated phospholipid in the liposome composition.

In some embodiments oxazolidinone liposome compositions are provided that are characterized by reduced amounts of phospholipid or cholesterol degradation during storage. In some embodiments, oxazolidinone liposome compositions having a pH of about 7 or greater (e.g., 7-8) and comprising a phospholipid and more than 50 mol % cholesterol (e.g. 50-65 mol %, 50-60 mol %, 50-55 mol %, about 50 mol %, or about 55 mol %) relative to the sum of cholesterol and non-pegylated phospholipid in the liposome composition. In some embodiments, oxazolidinone liposome compositions further comprise a chelator such as DFO or EDTA in combination with a phospholipid and more than 50 mol % cholesterol relative to the sum of cholesterol and non-pegylated phospholipid in the liposome composition. In some embodiments, oxazolidinone liposome compositions having a pH of 7-8 (including 7-7.7, 7.1-7.7, 7.3-7.7 and about 7.5) further comprise a chelator such as DFO or EDTA in combination with a phospholipid and more than 50 mol % cholesterol relative to the sum of cholesterol and non-pegylated phospholipid in the liposome composition. In some embodiments, oxazolidinone liposome compositions further comprise extra-liposomal ammonium in combination with a vesicle comprising phospholipid and more than 50 mol % cholesterol relative to the sum of cholesterol and non-pegylated phospholipid in the liposome composition. In some embodiments, oxazolidinone liposome compositions further comprise extra-liposomal ammonium generated during the drug loading of a oxazolidinone into liposome vesicles comprising phospholipid and more than 50 mol % cholesterol relative to the sum of cholesterol and non-pegylated phospholipid in the liposome composition.

It is to be understood that both the foregoing general description and the following detailed description are exemplary and explanatory only and are not restrictive of the compositions and methods of the present disclosure.

Definitions

For convenience, certain terms employed in the specification, examples, and appended claims are collected here.

Unless defined otherwise, all technical and scientific terms used herein have the same meaning as commonly understood by one of ordinary skill in the art to which this disclosure belongs.

As used herein, the following terms and phrases are intended to have the following meanings:

The articles "a" and "an" are used herein to refer to one or to more than one (i.e., to at least one) of the grammatical object of the article. By way of example, "an element" means one element or more than one element.

As used herein the term "comprising" or "comprises" is used in reference to compositions, methods, and respective component(s) thereof, that are present in a given embodiment, yet open to the inclusion of unspecified elements.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

The term "comprising" when used in the specification includes "consisting of" and "consisting essentially of".

If it is referred to "as mentioned above" or "mentioned above", "supra" within the description it is referred to any of the disclosures made within the specification in any of the preceding pages.

If it is referred to "as mentioned herein", "described herein", "provided herein," or "as mentioned in the present text," or "stated herein" within the description it is referred to any of the disclosures made within the specification in any of the preceding or subsequent pages.

As used herein, the term "about" means acceptable variations within 20%, within 10% and within 5% of the stated value. In certain embodiments, "about" can mean a variation of +/−1%, 2%, 3%, 4%, 5%, 10% or 20%.

The term "effective amount" as used herein with respect to a compound or the composition means the amount of active compound (also referred herein as active agent or drug) sufficient to cause a bactericidal or bacteriostatic effect. In one embodiment, the effective amount is a "therapeutically effective amount" meaning the amount of active compound that is sufficient alleviate the symptoms of the bacterial infection being treated.

The term "subject" (or, alternatively, "patient") as used herein refers to an animal, preferably a mammal, most preferably a human that receives either prophylactic or therapeutic treatment.

The term "administration" or "administering" as used herein includes all means of introducing the compounds or the pharmaceutical compositions to the subject in need thereof, including but not limited to, oral, intravenous, intramuscular, intraperitoneal, subcutaneous, transdermal, inhalation, buccal, ocular, sublingual, vaginal, rectal and the like. Administration of the compound or the composition is suitably parenteral. For example, the compounds or the composition can be preferentially administered intravenously but can also be administered intraperitoneally or via inhalation like is currently used in the clinic for liposomal amikacin in the treatment of *Mycobacterium avium* (see Shirley et al., Amikacin Liposome Inhalation Suspension: A Review in *Mycobacterium avium* Complex Lung Disease. Drugs. 2019 April; 79(5):555-562)

The terms "treat," "treating," and "treatment," as used herein, refer to therapeutic or preventative measures such as those described herein.

The terms "synergy" and "synergistic" as used herein, means that the effect achieved with the compounds used together is greater than the sum of the effects that results from using the compounds separately, i.e. greater than what would be predicted based on the two active ingredients administered separately.

The term "pharmaceutically acceptable salt" refers to a relatively non-toxic, inorganic or organic acid addition salt of a compound of the present disclosure which salt possesses the desired pharmacological activity.

The term "alkyl" means saturated carbon chains which may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, and the like.

The term "aminoalkyl" means an alkyl wherein at least one carbon of an alkyl carbon chain forms the bond with an amino group, wherein said amino group is primary amino group, mono-alkyl-substituted (secondary) amino group, di-alkyl-substituted (tertiary) amino group, or an alkyl-substituted amino group where the amine nitrogen atom and the alkyl chain that substitutes for amine hydrogens form a heterocycle.

The term "liposomes" means vesicles composed of a bilayer (unilamellar) and/or a concentric series of multiple bilayers (multi-lamellar) separated by aqueous compartments formed by amphipathic molecules such as phospholipids that enclose a central aqueous compartment. In a liposome drug product, the drug substance is generally contained in liposomes. Typically, water soluble drugs are contained in the aqueous compartment(s) and hydrophobic drugs are contained in the lipid bilayer(s) of the liposomes. Release of drugs from liposome formulations, among other characteristics such as liposomal clearance and circulation half-life, can be modified by the presence of polyethylene glycol and/or cholesterol or other potential additives in the liposome.

"Unilamellar liposomes," also referred to as "unilamellar vesicles," are liposomes that include one lipid bilayer membrane which defines a single closed aqueous compartment. The bilayer membrane includes two layers of lipids; an inner layer and an outer layer (leaflet). Lipid molecules in the outer layer are oriented with their hydrophilic ("head") portions toward the external aqueous environment and their hydrophobic ("tail") portions pointed downward toward the interior of the liposome. The inner layer of the lipid lays directly beneath the outer layer, the lipids are oriented with their heads facing the aqueous interior of the liposome and their tails toward the tails of the outer layer of lipid.

"Multilamellar liposomes" also referred to as "multilamellar vesicles" or "multiple lamellar vesicles," include more than one lipid bilayer membrane, which membranes define more than one closed aqueous compartment. The membranes are concentrically arranged so that the different membranes are separated by aqueous compartments.

The terms "encapsulation" and "entrapped," as used herein, refer to the incorporation or association of the oxazolidinone pharmaceutical agent in or with a liposome.

The terms "DL", "DL ratio", "D/L", or "D/L ratio" are used interchangeably and refer to the ratio of the drug to the liposome lipid. Unless indicated otherwise, it is expressed as grams of the drug per mole of liposome phospholipid (PhL).

The term "mol %" with regard to cholesterol refers to the molar amount of cholesterol relative to the sum of the molar amounts of cholesterol and non-PEGylated phospholipid expressed in percentage points. For example, "55 mol. % cholesterol" in a liposome containing cholesterol and HSPC refers to the composition of 55 mol, parts of cholesterol per 45 mol. parts of HSPC.

The term "mol %" with regard to PEG-lipid refers to the ratio of the molar amount of PEG-lipid and non-PEGylated phospholipid expressed in percentage points. For example, "5 mol. % PEG-DSPE" in a liposome containing HSPC and PEG-DSPE refers to the composition having 5 mol, parts of PEG-DSPE per 100 mol. parts of HSPC.

The terms "sucrose octasulfate", "sucrosofate', and "sucrooctasulfate" refer the same compound, sucrose octasulfuric acid or an anion thereof, and are used herein interchangeably.

The symbols "Ac", "Me", and "Et", as found in chemical formulas, refer to acetyl group ($CH_3CO$), methyl group ($CH_3$), and ethyl group ($C_2H_5$), respectively.

The term "free base concentration" or "FB concentration" is used to express the mass concentration of a salt-forming compound in its free base form. By default, for the compounds synthesized and isolated in the salt form (e.g., a hydrochloride of dihydrochloride) the mass-based concentration or ratio (e.g., mg/ml or g/mol phospholipid) is expressed as the concentration or ratio of this salt form. However, when stated, concentration of the compounds isolated in the form of a salt (e.g., AKG-28 dihydrochloride) is also expressed as the equivalent concentration of the compound as an anhydrous free base (a FB concentration). To obtain the FB concentration, the calculated molecular weight of the compound in the free base form is divided by the calculated molecular weight of the salt form, and the concentration is multiplied by this factor. For example, the molecular weight of AKG-28 as free base is 426.46, and the dihydrochloride form (in which this compound is isolated) has molecular weight of 499.37. Accordingly, the factor for calculating the concentration of AKG-28 on the FB basis is 426.46/499.37=0.854, so that, for example, 10 mg/ml of AKG-28 dihydrochloride has the FB concentration of 8.54 mg/ml. When the compound additionally contains a known amount of water (e.g., AKG-28 dihydrochloride monohydrate) the correction is also made for a known water content. The mass concentration of compounds isolated as free bases (e.g., AKG-38) is always expressed as a FB concentration.

While the mass concentrations and ratios disclosed herein depend on the salt form of the compound, the concentrations and ratios of the compounds can be expressed in molar units independent of their salt forms. To convert the mass concentration or amount of, e.g., AKG-28, as quoted herein on the basis of its isolated synthetic product form of a dihydrochloride salt, into a molar concentration, the mass concentration or amount is divided by the AKG-28 dihydrochloride molecular weight of 499.4 g/mol. Thus, the DL ratio of AKG-28 in the liposome composition quoted herein as 330 g/mol PhL is expressed as 330/499.4=0.661 mol/mol PhL; the concentration of AKG-28 quoted as 10 mg/mL is expressed as 10/499.4=20.0 mM. When the concentration is quoted on the compound free base basis, the mass amounts and concentration are divided by the molecular weight of the compound free base. Thus, the DL ratio of AKG-38 in a liposome composition quoted herein as 600 g/mol PhL is expressed as 600/468.5=1.281 mol/mol PhL, AKG-38 being isolated from the synthesis in a free base form with molecular weight of 468.5. Accordingly, the quoted 20 mg/mL concentration of AKG-38 is expressed in molar terms as 20/468.5=42.7 mM.

Various aspects and embodiments are described in further detail in the following subsections.

Compounds

In some embodiments, liposome compositions comprising an oxazolidinone compound are provided.

Oxazolidinones are synthetic antibiotics that exert their function by inhibiting protein synthesis. Linezolid (LZD) is an oxazolidinone compound that exhibits bacteriostatic activity against *M. tuberculosis*. However, administration of LZD may cause severe side effects such as anemia, thrombocytopenia, and peripheral neuropathy. Tedizolid is an oxazolidinone compound which has been shown to inhibit gram positive bacteria. The side effects for tedizolid phosphate are similar, but generally less severe than observed for linezolid, although the experience with prolonged dosing such as that required for the treatment of tuberculosis has been limited for tedizolid phosphate compared to the extensive experience with linezolid.

Figure 6:
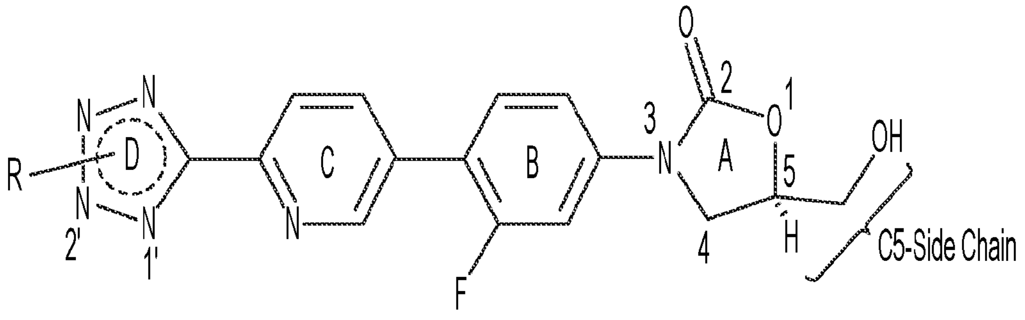
FIG. 6 represents the numbered ring structure of a compound of Formula (I).

Aspects of the disclosure relate to compounds that are aminoalkyl derivatives of oxazolidinone (see FIG. 6). In some embodiments, the compounds having the following chemical Formula (I) and pharmaceutically acceptable salts thereof:

Formula (I)

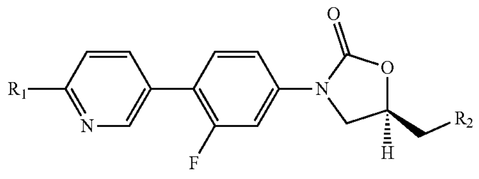

wherein $R_2$ is an amine ($NH_2$) or an acetamide ($NHCOCH_3$), wherein $R_1$ is a tetrazole ring substituted at position 2' with an aminoalkyl.

In some embodiments, the aminoalkyl is a dimethylaminoalkyl. In some embodiments, the aminoalkyl derivatives of oxazolidinone compounds include either an amine or acetamide group at the $R_2$ positions of the oxazolidinone ring and a dimethylaminoethyl group on the tetrazole ring.

In other embodiments, the compounds having the following chemical Formula (I) and pharmaceutically acceptable salts thereof:

Formula (I)

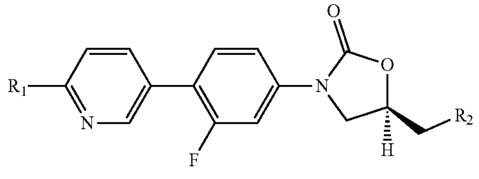

wherein $R_2$ is an amine ($NH_2$) or an acetamide ($NHCOCH_3$), and wherein $R_1$ is a tetrazole ring substituted 1' with an aminoalkyl.

The aminoalkyl derivatives of oxazolidinone compounds having the chemical structure of the Table 1 below were synthesized as described in Example 1.

The compounds of the present disclosure can exist in free form, e.g. as a free base, or as a free acid, or as a zwitterion, or can exist in the form of a salt. Said salt may be any salt, either an organic or inorganic addition salt or a cocrystal, particularly any pharmaceutically acceptable organic or inorganic addition salt or a cocrystal, customarily used in pharmacy. It is understood that the chemical formula showing a compound in a particular salt form or ionic form also discloses this compound in its non-dissociated, free base (or free acid) form.

The present disclosure encompasses all stereoisomeric forms of the compounds. In some embodiments, the compounds of Table 1 below are substantially pure (i.e. at least 60%, 70%, 80%, 90%, 91%, 92%, 93%, 94%, 95%, 96%, 97%, 98%, 99%, e.g. 100%)

TABLE 1

| Name | Structure |
|---|---|
| AKG-1 | 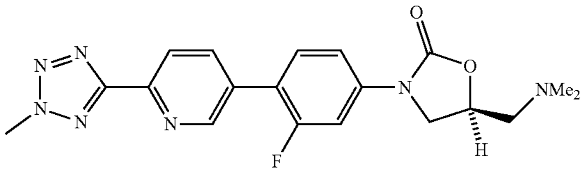 [SMILES: CN(C)C[C@H]1CN(c2ccc(-c3ccc(-c4nnn(C)n4)nc3)c(F)c2)C(=O)O1] |
| AKG-2 | 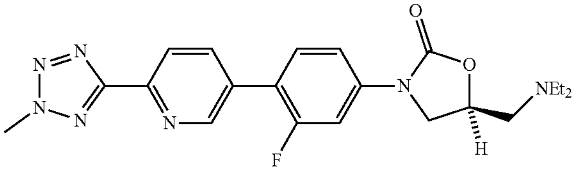 |
| AKG-3 | 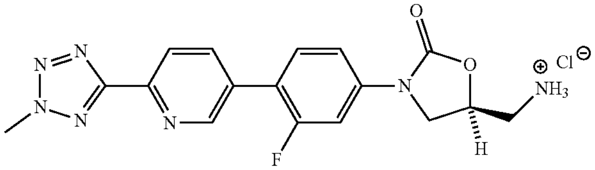 [SMILES: Cn1nnc(-c2ccc(-c3ccc(N4C[C@H](C[NH3+])OC4=O)cc3F)cn2)n1 ; [Cl-]] |
| AKG-5 | 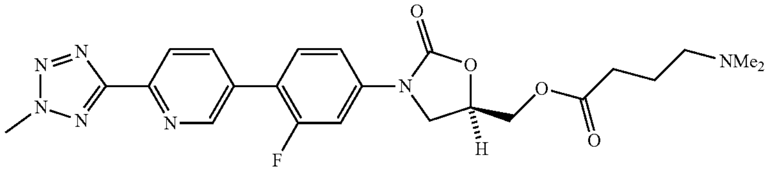 [SMILES: CN(C)CCCC(=O)OC[C@H]1CN(c2ccc(-c3ccc(-c4nnn(C)n4)nc3)c(F)c2)C(=O)O1] |
| AKG-6 | 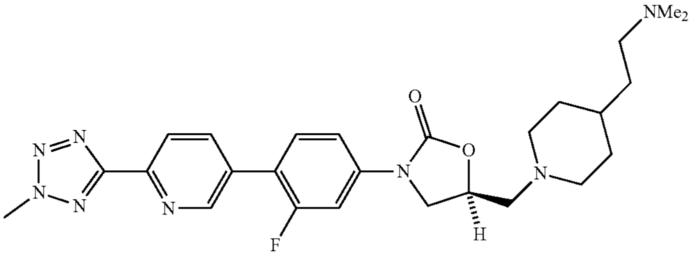 [SMILES: CN(C)CCC1CCN(C[C@H]2CN(c3ccc(-c4ccc(-c5nnn(C)n5)nc4)c(F)c3)C(=O)O2)CC1] |
| AKG-7 | 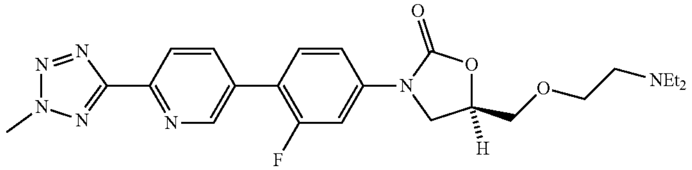 |
| AKG-8 | 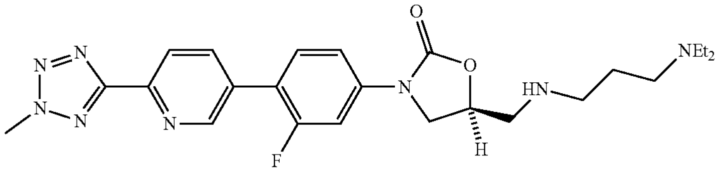 |

TABLE 1-continued
| Name | Structure |
|---|---|
| AKG-9 | 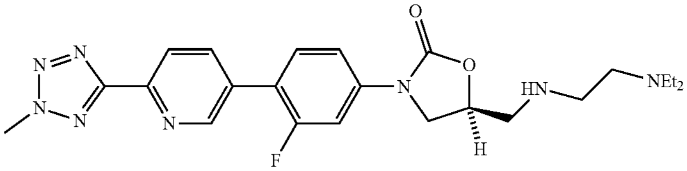 |
| AKG-11 | 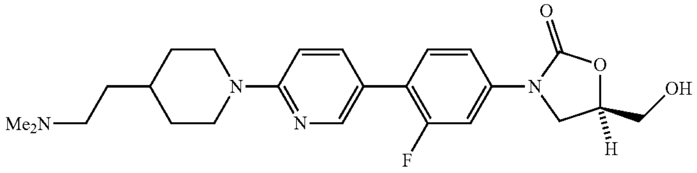 [SMILES: CN(C)CCC1CCN(c2ccc(-c3ccc(N4C[C@H](CO)OC4=O)cc3F)cn2)CC1] |
| AKG-12 | 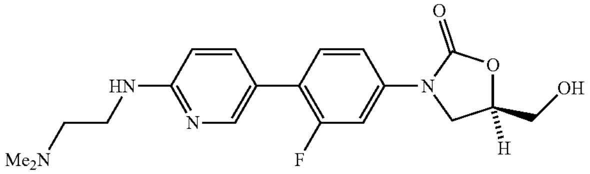 [SMILES: CN(C)CCNc1ccc(-c2ccc(N3C[C@H](CO)OC3=O)cc2F)cn1] |
| AKG-13 | 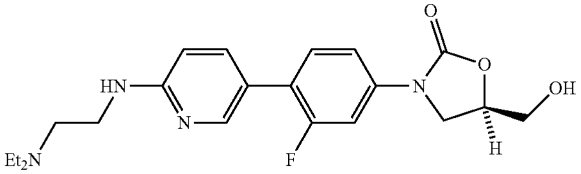 |
| AKG-14 | 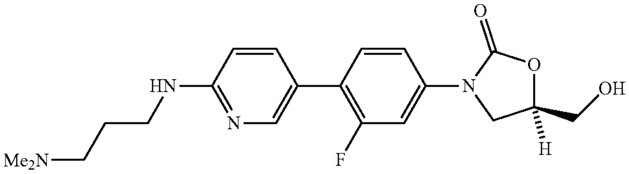 [SMILES: CN(C)CCCNc1ccc(-c2ccc(N3C[C@H](CO)OC3=O)cc2F)cn1] |
| AKG-15 | 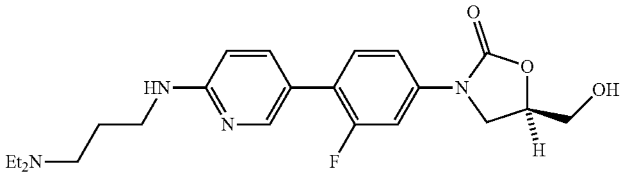 |
| AKG-16 | 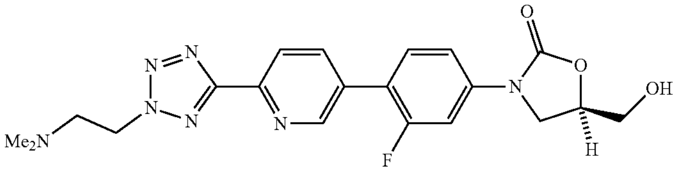 [SMILES: CN(C)CCn1nnc(-c2ccc(-c3ccc(N4C[C@H](CO)OC4=O)cc3F)cn2)n1] |
| AKG-17 | 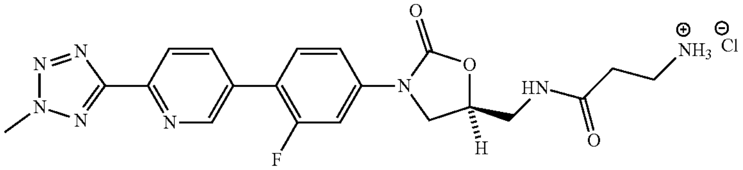 [SMILES: Cn1nnc(-c2ccc(-c3ccc(N4C[C@H](CNC(=O)CC[NH3+])OC4=O)cc3F)cn2)n1 ; [Cl-]] |

TABLE 1-continued
| Name | Structure |
|---|---|
| AKG-18 | 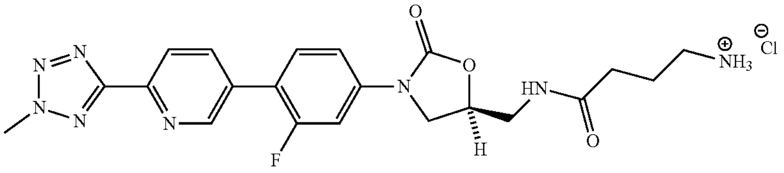 [SMILES: Cn1nnc(-c2ccc(-c3ccc(N4C[C@H](CNC(=O)CCC[NH3+])OC4=O)cc3F)cn2)n1 ; [Cl-]] |
| AKG-19 | 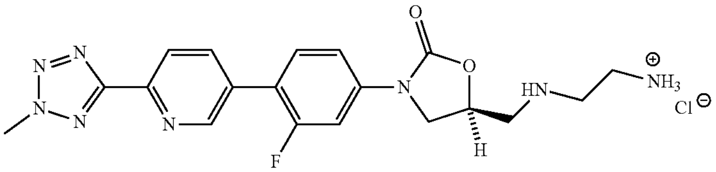 [SMILES: Cn1nnc(-c2ccc(-c3ccc(N4C[C@H](CNCC[NH3+])OC4=O)cc3F)cn2)n1 ; [Cl-]] |
| AKG-20 | 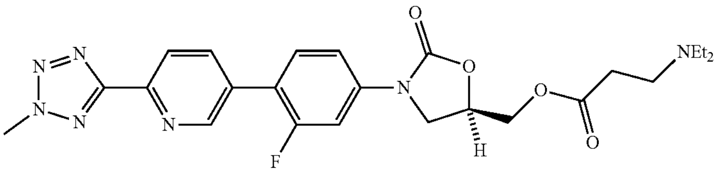 |
| AKG-21 | 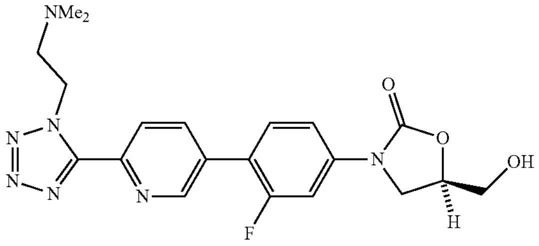 [SMILES: CN(C)CCn1nnnc1-c1ccc(-c2ccc(N3C[C@H](CO)OC3=O)cc2F)cn1] |
| AKG-22 | 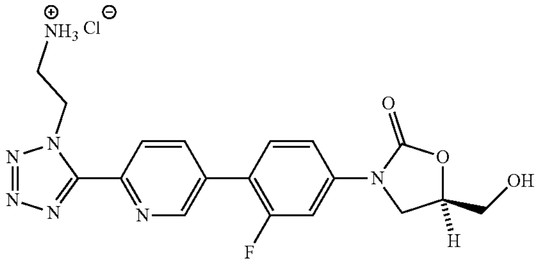 [SMILES: [Cl-] ; [NH3+]CCn1nnnc1-c1ccc(-c2ccc(N3C[C@H](CO)OC3=O)cc2F)cn1] |
| AKG-23 | 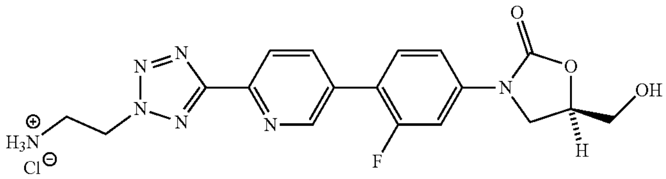 [SMILES: [NH3+]CCn1nnc(-c2ccc(-c3ccc(N4C[C@H](CO)OC4=O)cc3F)cn2)n1 ; [Cl-]] |
| AKG-24 | 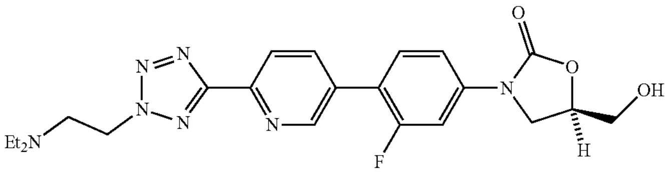 |

TABLE 1-continued
| Name | Structure |
| --- | --- |
| AKG-25 | 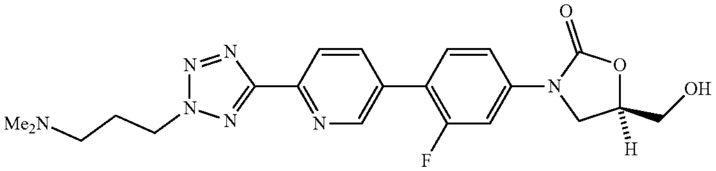 [SMILES: CN(C)CCCn1nnc(-c2ccc(-c3ccc(N4C[C@H](CO)OC4=O)cc3F)cn2)n1] |
| AKG-26 | 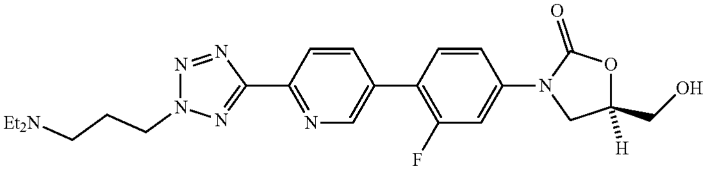 |
| AKG-27 | 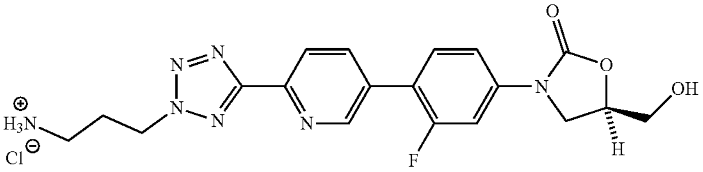 [SMILES: [Cl-] ; [NH3+]CCCn1nnc(-c2ccc(-c3ccc(N4C[C@H](CO)OC4=O)cc3F)cn2)n1] |
| AKG-28 | 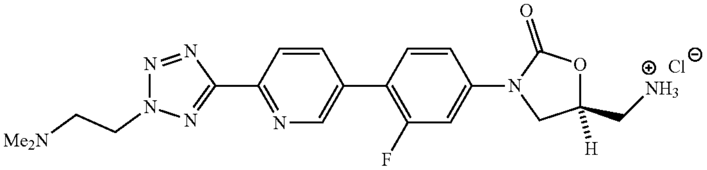 [SMILES: CN(C)CCn1nnc(-c2ccc(-c3ccc(N4C[C@H](C[NH3+])OC4=O)cc3F)cn2)n1 ; [Cl-]] |
| AKG-29 | 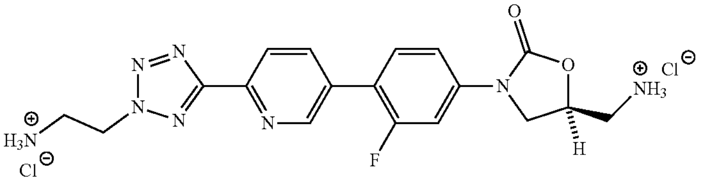 [SMILES: [NH3+]CCn1nnc(-c2ccc(-c3ccc(N4C[C@H](C[NH3+])OC4=O)cc3F)cn2)n1 ; [Cl-] ; [Cl-]] |
| AKG-30 | 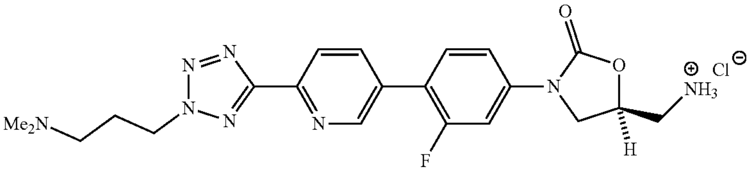 [SMILES: CN(C)CCCn1nnc(-c2ccc(-c3ccc(N4C[C@H](C[NH3+])OC4=O)cc3F)cn2)n1 ; [Cl-]] |
| AKG-31 | 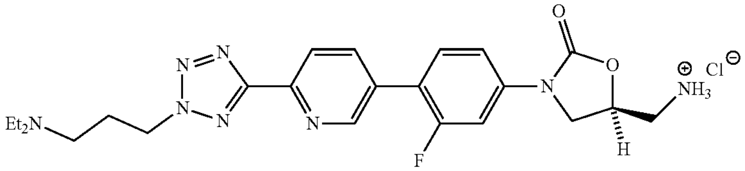 |
| AKG-38 | 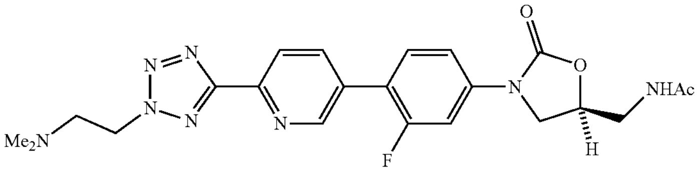 [SMILES: CC(=O)NC[C@H]1CN(c2ccc(-c3ccc(-c4nnn(CCN(C)C)n4)nc3)c(F)c2)C(=O)O1] |

TABLE 1-continued

| Name | Structure |
| --- | --- |
| AKG-39 | 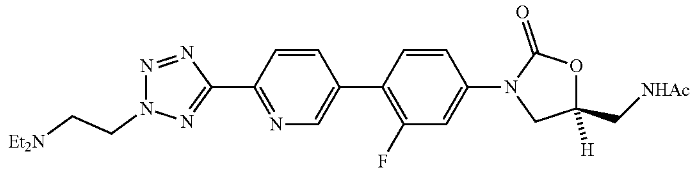 |
| AKG-40 | 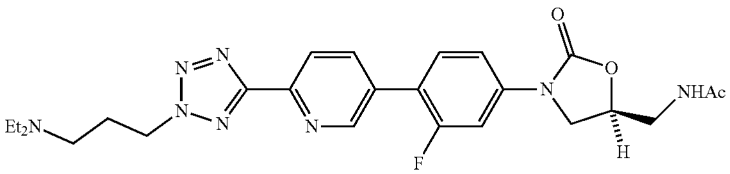 |

In some embodiments, the compound has the following chemical formula:

Formula 1a

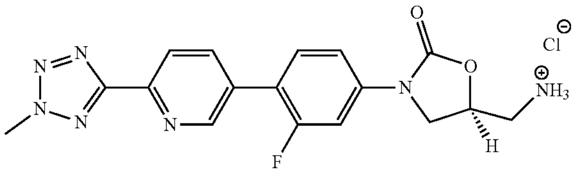

In some embodiments, the compound has the following chemical formula:

Formula 1b

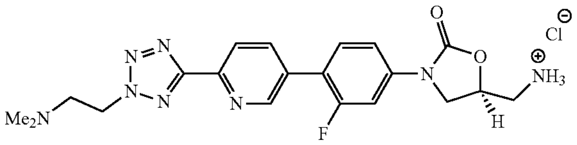

In some embodiments, the compound of the Formula 1b is crystallized from aqueous ethanol. In some embodiments the compound of the Formula 1b is the form of a dihydrochloride or dihydrochloride monohydrate In some embodiments, the compound has the following chemical formula:

Formula 1c

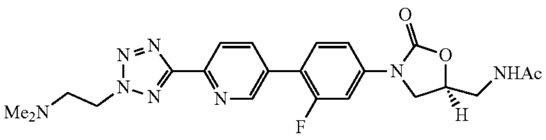

In some embodiments, the compound has the following chemical formula:

Formula 1d

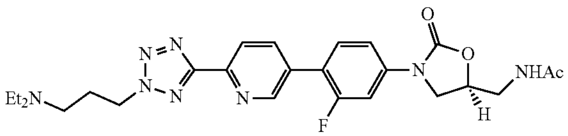

In some embodiments, the compound has the following chemical formula:

Formula 1e

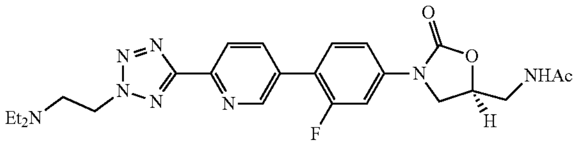

Disclosed herein are compounds of Formula (I) or pharmaceutically acceptable salts thereof that are useful for the treatment of *Mycobacterium* infections. In some embodiments, the compounds have the chemical formula 1a, 1b, 1c, 1d or 1e. In some embodiments, the compounds have the chemical formula 1b. In some embodiments, the compounds of Formula (I) have a minimum inhibitory concentration (MIC), for example against *Mycobacterium tuberculosis*, ranging from 0.1 μg/ml to 1 μg/ml, from 0.25 μg/ml to 1 μg/ml, from 0.5 μg/ml to 1 μg/ml, from 0.1 μg/ml to 0.25 μg/ml, from 0.1 μg/ml to 0.5 μg/ml, from 0.25 μg/ml to 0.5 μg/ml, from 0.01 μg/ml to 1 μg/ml, from 0.01 μg/ml to 0.25 μg/ml, from 0.01 μg/ml to 0.5 μg/ml, from 0.01 μg/ml to 0.1 μg/ml. In some embodiments, the compounds of Formula (I) have a minimum inhibitory concentration (MIC), for example against *Mycobacterium tuberculosis* of less than 1 μg/ml, less than 0.25 μg/ml, or less than 0.1 μg/ml. In some embodiments, the compounds of Formula (I) have a MIC ranging from 0.01 μg/ml to 0.25 μg/ml. In some embodiments, the compound of Formula (I) have a MIC ranging from 0.01 μg/ml to 0.1 μg/ml. It should be appreciated that the MIC values can be lower or than the ranges provided herein depending on the bacteria.

In some embodiments for the treatment of *Mycobacterium*, for example *M. tuberculosis*, the compound (AKG-28 or AKG-38) has a MIC below 0.1 μg/mL. In some embodiments for the treatment of *Mycobacterium*, for example *M. tuberculosis*, the compound has a selectivity index (SI) for killing *M. tuberculosis* vs human kidney cells (VERO) of at least 1,000. In some embodiments for the treatment of *Mycobacterium*, for example *M. tuberculosis*, the compound has a MIC below 0.1 μg/mL and a selectivity index (SI) for killing *M. tuberculosis* vs human kidney cells (VERO) of at least 1,000. In some embodiments, the compound has the structure of AKG-28 (Formula 1b) or AKG-38 (Formula 1c). In some embodiments, the MIC is less than 0.05 g/mL and the selectivity index for MIC in *M. tuberculosis* relative to mitochondrial protein synthesis inhibition (SI-MPS) is greater than 20, such as for AKG-28.

In some embodiments, the compounds described herein have a 2-to-20 fold increase (about 2, about 3, about 4, about 5, about 6, about 7, about 8, about 9, about 10, about 11, about 12, about 13, about 14, about 15, about 16, about 17, about 18, about 19, about 20) in potency adjusted dose compared to linezolid for *M. tuberculosis*.

In some embodiments for the treatment of methicillin-resistant *Staphylococcus aureus* (MRSA), the compound has a MIC against MRSA strains of less than 2 μg/mL. In some embodiments for the treatment of methicillin-resistant *Staphylococcus aureus* (MRSA), the compound has an IC50 of greater than 100 μg/mL against human VERO kidney cells. In some embodiments for the treatment of methicillin-resistant *Staphylococcus aureus* (MRSA), the compound has a MIC against MRSA strains of less than 2 μg/mL and an IC50 of greater than 100 μg/mL against human VERO kidney cells. In some embodiments, the compound has the structure of AKG-38 (Formula 1c), AKG-39 (Formula 1e), and AKG-40 (Formula 1d).

Aqueous Solubility

In some embodiments, the compounds are in the form of salts, e.g., a hydrochloride or mesylate salt and are soluble in water at greater than 1 mg/ml, and preferably greater than 10 mg/ml (and up to 1 g/ml) prior to encapsulation in liposomes. Additional salts prior to encapsulation can include, but are not limited to, besylate, bitartrate, carbonate, citrate, esylate, gluconate, glutamate, glycolate, lactate, malate, maleate, mandelate, methylsulfate, napsylate, phosphate, propionate, salicylate, succinate, tartrate, and tosylate. In some embodiments, the compounds are in the form of hydrate or solvate or a cocrystal prior to encapsulation in the liposomes.

In some embodiments, the drug is entrapped in the interior of the liposomes in a different salt form with a reduced aqueous solubility, for example less than 1 mg/mL and preferably less than 0.1 mg/mL (0.1-0.001 mg/mL). The salt of the compound once entrapped in the liposomes includes, but not limited to sulfate, citrate, phosphate, sucrosofate, or various phosphorylated or sulfated polyols or polyanionic polymers. Exemplary polyols include, but not limited to, sucrose, erythritol, mannitol, xylitol, sorbitol, inositol, and combinations thereof. Exemplary polyanionic polymers include but not limited to, polyvinylsulfonate, polyvinylsulfate, polyphosphate, copolymers of acrylic acid and vinylalcohol sulfate, and combinations thereof.

Working stocks of the compounds were prepared as follows: to an aliquot of a compound (free base) in a powder form 1-1.5 equivalents of HCl in the form of 1 N aqueous solution was added, and the mixture was vortexed until homogeneity. To the resulting cake or syrup, water was added typically to the final 10 mg/ml, and complete dissolution was observed. In some instances, 0.95 equivalents of HCl were added to the free base form of the drug, and 20 mg/ml stock solution was prepared.

Aqueous solubility of the compounds of the present disclosure is illustrated by the following observations of obtaining visually clear solutions:

| Compound | Amount, mg | Volume of 1N HCl added, ml | Volume of water added, ml | Concentration % (w/w) of free base |
|---|---|---|---|---|
| AKG-16 (free base) | 22.3 | 0.052 | — | 30.0 |
| AKG-28 (2HCl) | 32.5 | — | 0.35 | 7.3 |
| AKG-38 (free base) | 31.7 | 0.067 | 0.35 | 7.1 |

These results show that the compounds provided herein have an aqueous solubility that is higher than the known aqueous solubilities of:

linezolid (3 mg/ml) (www.drugbank.ca/drugs/DB00601)

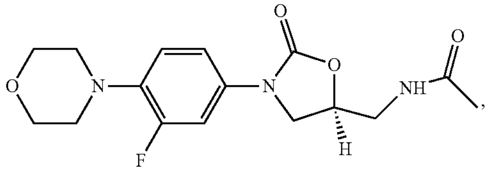 [SMILES: CC(=O)NC[C@H]1CN(c2ccc(N3CCOCC3)c(F)c2)C(=O)O1]

, sutezolid (0.237 mg/ml) (www.drugbank.ca/drugs/DB11905)

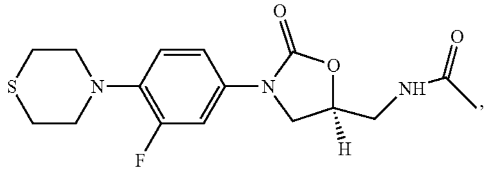 [SMILES: CC(=O)NC[C@H]1CN(c2ccc(N3CCSCC3)c(F)c2)C(=O)O1]

, tedizolid (0.382 mg/ml) (www.drugbank.ca/drugs/DB14569)

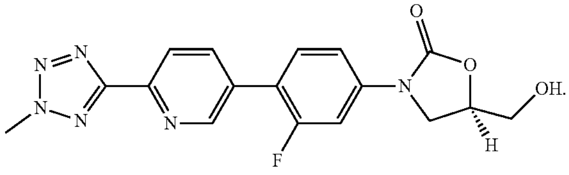 [SMILES: Cn1nnc(-c2ccc(-c3ccc(N4C[C@H](CO)OC4=O)cc3F)cn2)n1]

.

In some embodiments, the aqueous solubility of the compounds described herein, prior to encapsulation into the liposomes, is at least 5 times, at least 10 times, at least 20 times, at least 30 times, or at least 40 times of the above oxazolidinones.

The excellent aqueous solubility of the compounds of described herein and their properties of amphiphilic weak bases allows efficient use of transmembrane-gradient-based and intraliposomal complexation (active loading) approach to creating liposome-encapsulated forms of these compounds with high drug/carrier (drug/lipid) ratio and pharmacokinetic properties favorable for encapsulated drug delivery to the infected tissues after systemic administration of the drug. As used herein, an amphiphilic weak base has a pKa of between 7 and 12 and a log P between 1 and 6.

Liposome Loading Properties and Antimycobacterial Activity.

An important feature of the compounds described herein is their weak amphiphilic base property that facilitates transmembrane gradient-driven loading of these compounds into liposomes. In some embodiments, a weak base property of the compounds of the present disclosure is characterized by an electrolytic dissociation constant in the pKa range of 7.0-12.0, 7.5-11.0, 7.8-10.5, or 8.0-10.0. In some embodiments, the amphiphilic property of the compounds described herein is characterized by a log P parameter in the range of 0.5-5.0, 1.0-4.0, 1.0-3.5, or 1.0-3.0. It was unexpectedly discovered that certain embodiments having these favorable properties with regard to the liposome loading, also have superior activity against mycobacteria that matches or surpasses the activity of similar compounds in the same class of drugs whose properties are less favorable for efficient and stable liposome encapsulation.

Liposome Compositions

Compositions and use of the compositions for the treatment of tuberculosis, as well as other mycobacterial and gram positive bacterial infections are disclosed, These compositions provided herein contain a highly potent and selective oxazolidinone encapsulated with high efficiency to maximize dosing potential of low toxicity drugs, and are stable in the presence of plasma. In some embodiments, the compositions are long circulating and retain their encapsulated drug while in the circulation following intravenous dosing to allow for efficient accumulation at the site of the bacterial or mycobacterial infection. In some embodiments, high doses that can be achieved when combined with the long circulating properties and highly stable retention of the drug allow for a reduced frequency of administration when compared to daily or twice daily administrations of other drugs typically utilized to treat these infections.

Disclosed herein are pharmaceutical compositions for treating bacterial infections, in particular a *Mycobacterium tuberculosis* infection. In some embodiments, the pharmaceutical composition is a liposomal composition comprising a polyanion or a sulfate containing polyanion and an aminoalkyl oxazolidinone compound.

Other aspects of the disclosure relate to a method of treating bacterial infection, the method comprising administering to a subject in need thereof a therapeutically effective amount of the liposomal composition provided herein.

In some embodiments, the bacterial infection is *Mycobacterium tuberculosis* infection. In some embodiments, the compound in the liposome vesicle has a minimum inhibitory concentration (MIC) ranging from about 0.01 μg/ml to about 0.25 μg/ml. In some embodiments, the compound in the liposome vesicle has a minimum inhibitory concentration (MIC) ranging from about 0.01 μg/ml to about 0.1 μg/ml.

In some embodiments, the composition comprises liposomes in a medium, wherein the intraliposomal space comprises an aqueous phase with a polyanion and the compound of Formula (I). In some embodiments, the composition comprises liposomes in a medium, wherein the intraliposomal space comprises a polyanion or a sulfate containing polyanion and the compound AKG-16, AKG-28, or AKG-38. In some embodiments, the medium is an aqueous medium, where the primary composition in that media is the compound of Formula (I) and a corresponding trapping agent.

The compound of Formula (I) can be entrapped within the liposome with a suitable polyanion, such as sucrose octasulfate (e.g. derived from triethylammonium sucrose octasulfate, (TEA-SOS) gradients) or sulfate (e.g. derived from ammonium sulfate gradients). Additional polyanion trapping agents include but are not limited to inositol hexaphosphate, inositol hexasulfate, polyvinylsulfonate, dextran sulfate, citrate, polyphosphate, and suramin.

The exterior aqueous medium is typically composed of a suitable buffer and an isotonicity agent. Suitable buffers may include histidine, citrate, HEPES, MOPS, MES, TRIS, phosphate, glycine, and imidazole, borate, carbonate, and succinate. Isotonicity agents may include salts such as sodium chloride, potassium chloride, sucrose, glycerin, dextrose, or mannitol.

In some embodiments, the composition comprises a compound of Formula (I) or the Formula 1a, 1b, 1c, or 1d or pharmaceutical acceptable salt thereof, encapsulated with a polyanion in a primarily unilamellar vesicle formed from one or more phospholipid, a sterol and optionally a lipid conjugated to a hydrophilic polymer (a polymer-conjugated lipid). In some embodiments, the composition can comprise a compound of Formula (I) or the Formula 1a, 1b 1c, or 1d, or pharmaceutical acceptable salt thereof, encapsulated with a polyanion in unilamellar and multilamellar vesicles (e.g. having two or three lamella). It should be appreciated that multilamellar vesicles can be cleared more quickly from circulation than unilamellar vesicles. In some embodiments, the phospholipid is hydrogenated soy phosphatidyl choline (HSPC), distearoylphosphatidylcholine (DSPC), or egg sphingomyelin (ESM). The term "phospholipid as used herein refers to any one phospholipid or combination of phospholipids capable of forming liposomes. Neutral phospholipids can include diacylphosphatidylcholines, dialkylphosphatidylcholines, sphingomyelins, and diacylphosphatidylethanolamines. Phosphatidylcholines (PC), including those obtained from egg, soybeans or other plant sources or those that are partially or wholly synthetic, or of variable lipid chain length and unsaturation are suitable for use in the present compositions. Synthetic, semisynthetic and natural product phosphatidylcholines including, but not limited to, distearoylphosphatidylcholine (DSPC), hydrogenated soy phosphatidylcholine (HSPC), soy phosphatidylcholine (soy PC), egg phosphatidylcholine (egg PC), hydrogenated egg phosphatidylcholine (HEPC), dipalmitoylphosphatidylcholine (DPPC) and dimyristoylphosphatidylcholine (DMPC) are suitable phosphatidylcholines for use in this disclosure. Charged phospholipids can include phosphatidylserines, phosphatidic acids, phosphatidylinositols, phosphatidylglycerols, cardiolipins, or headgroup modified lipids such as N-succinyl-phosphatidylethanolamines, N-glutaryl-phosphatidylethanolamines, and PEG-derivatized phosphatidylethanolamines.

Polymer-conjugated lipids may include poly(ethylene glycol)-conjugated (pegylated)phospholipids (PEG-lipids) such as PEG(Mol. weight 2,000) methoxy-poly(ethylene glycol)-1,2-distearoyl-sn-glycerol (PEG(2000)-distearoylglycerol, PEG-DSG), PEG(Mol. weight 2,000) 1,2-dstearoyl-sn-glycero-3-phosphoethanolamine-N-[methoxy (polyethylene glycol)-2000] (PEG(Mol. weight 2,000)-distearoylphosphatidylethanolamine, PEG-DSPE), or PEG (Mol. weight 2,000) N-palmitoyl-sphingosine-1-{succinyl [methoxy(polyethylene glycol)-2000]}(PEG-ceramide). The molecular weight of the PEG portion in the PEG-lipid component can also vary from 500-10,000 g/mol, from 1,500-6000 g/mol, but is preferably about 2,000 MW. Other polymers used for conjugation to lipid anchors may include poly(2-methyl-2-oxazoline) (PMOZ), poly(2-ethyl-2-oxazoline) (PEOZ), poly-N-vinylpyrrolidone (PVP), polyglycerol, poly(hydroxyethyl L-asparagine) (PHEA), and poly (hydroxyethyl L-glutamine) (PHEG).

In some embodiments, the sterol is cholesterol. Other exemplary sterols include, but are not limited to, ergosterol, phytosterols such as β-sitosterol, and hopanoids. In some embodiments, the ratio of the phospholipid(s) and the cholesterol is selected to provide a desired amount of liposome membrane rigidity while maintaining a sufficiently reduced amount of leakage of the compound of Formula (I) from the liposome. In some embodiments, the optional polymer-conjugated lipid can be added to reduce the tendency of the liposomes to aggregate. The type and amount of polymer-conjugated lipid can be selected to provide desirable levels of protein binding, liposome stability and circulation time in the blood stream. For example, the liposome vesicle comprises phosphatidylcholine (e.g. DSPC or HSPC) and cholesterol in an about 45:55 molar ratio. Phosphatidylcholine to cholesterol molar ratios can vary from about 60:40 to 35:65, about 50:50 to 35:65, about 50:50 to about 45:55. In particular, the liposome can comprise a vesicle consisting of HSPC, cholesterol and polymer-conjugated lipid (PEG-DSG or PEG-DSPE) in a about 45:55:2.75 molar ratio, corresponding to a PEG-lipid concentration of 5 mol % relative to the concentration of phospholipid. The concentration of PEG-lipid can vary from 0.5-to-10 mol % relative to (non-PEGylated) phospholipid, with a preferred ratio of 3-10 mol %, and an even more preferred ratio of 4-8 mol %.

In some embodiments, liposomes compositions provide desirable pharmacokinetic properties such as extended plasma half-life, measured as the percentage of the injected dose (ID) (or injected amount) remaining in blood after 6 or 24 hours following injection intravenously in immunocompetent mice, and stable encapsulation of drug over 24 hours in plasma as determined by changes in the drug-to-lipid ratio (DL ratio) following iv administration in mice. In some embodiments, the percentage of drug remaining in blood is greater than 20%, preferably greater than 30%, and most preferably greater than 40% of the injected dose at 6 hours. The percent retained in blood after 24 h is preferably greater than 10%, and more preferably greater than 20% of the injected dose. The DL ratio is greater than 20% at 24 hours, preferably greater than 50%, and most preferably greater than 80% of the originally injected liposomal drug. Desirable liposome compositions also display stable encapsulation in the presence of human plasma in vitro using a burst release method, with liposomes retaining greater than 50% of the drug over 20 min, greater than 60%, greater than 70%, preferably greater than 80%, and most preferably greater than 90% of encapsulated drug over 20 min.

Liposomes of the present disclosure can be made by any method known in the art. See, for example, G. Gregoriadis (editor), Liposome Technology, vol. 1-3, 1st edition, 1983; 2nd edition, 1993; $3^{rd}$ edition, 2006; CRC Press, Boca Raton, Fla. Examples of methods suitable for making liposome composition of the present disclosure include membrane extrusion, reverse phase evaporation, sonication, solvent (e.g., ethanol) injection (including microfluidic, Y-junction and T-junction mixing), microfluidization, detergent dialysis, ether injection, and dehydration/rehydration. The size of liposomes can be controlled by controlling the pore size of membranes used for extrusions or the pressure and number of passes utilized in microfluidization or any other suitable methods. In some embodiments, the desired lipids are first hydrated by thin-film hydration or by ethanol injection and subsequently sized by extrusion through membranes of a defined pore size, such as, 50 nm, 80 nm, 100 nm, or 200 nm, or the combinations thereof, producing the liposomes with the average size in the range of 70-150 nm, or 80-130 nm, and polydispersity index of 0.1 or less. The drug compound to be encapsulated can be added to the liposome lipids prior to the liposome formation, dissolved in the aqueous medium in which the liposomes are formed by the above methods, whereby the drug is sequestered within the liposomes. In some embodiments, the drug compound is encapsulated in the liposomes using a trapping agent incorporated into the interior space of the liposomes (see Drummond, D. C., et al. (2006) in: Liposome Technology, Third Edition (Ed. Gregoriadis, G.) Volume 2, p. 149-168).

In some embodiments, the method of making liposome composition of the present disclosure comprises the steps of: (i) preparing the liposomes comprising phospholipid, cholesterol, and PEG-lipid, and having an interior space containing a trapping agent, in a medium substantially free from said trapping agent; (ii) contacting said liposomes with the compound of the present disclosure in an aqueous medium to effect encapsulation of the compound in the liposomes; (iii) removing unencapsulated compound; and (iv) providing the liposomes in a physiologically acceptable medium suitable for parenteral use. In some embodiments, where the encapsulation efficiency of the step (ii) is high enough typically >95%, >97%, or >99%, the step (iii), removing of unencapsulated compound, is omitted.

In some embodiments, the process to generate the liposomes with the compound therein includes the steps of (a) preparing a liposome containing a trapping agent composed of an ammonium or substituted ammonium salt of a polyanion, (b) subsequently removing extra-liposomal trapping agent to form an electrochemical gradients across the membrane, and (c) contacting the liposome with the compound under conditions effective for the compound to enter the liposome and to permit a corresponding amount of the ammonia or substituted ammonia to leave the liposome (thereby exhausting or reducing the pH gradient across the resulting liposome). Liposome compositions containing a trapping agent in the interior of the liposome can be made by formation of the liposomes in a solution of the trapping agent. The transmembrane concentration gradient of the trapping agent can be formed across the liposome by the removal of the trapping agent outside of the or dilution of the liposomes either following liposome formation or before loading (entrapping) of the drug.

In some embodiments, the contacting step includes incubation of the liposomes with the drug in an aqueous medium at the temperature above ambient and below the boiling point of water, preferably between 30° C. and 90° C., between 40° C. and 80° C., between 50° C. and 80° C., or between 60° C. and 75° C. In some embodiments, the incubation is carried at ionic strength of less than that equivalent to 50 mM NaCl, or more preferably, less than that equivalent to 30 mM NaCl. Following the incubation, a concentrated salt, e.g., NaCl, solution may be added to raise the ionic strength to higher than that of 50 mM NaCl, or of about 100 mM NaCl. The increase of ionic strength after the drug loading incubation step aided in reducing post-loading aggregation of the liposomes. The incubation times may range from few minutes to several hours. In some embodiments, the incubation times are from 5 to 40 min, from 10 to 30 min, or from 15-25 min. After the incubation, the liposomes are cooled down and then allowed to reach the ambient temperature. In some embodiments, the liposomes are cooled down to 2-15° C. In some embodiments, the liposomes are cooled down to 4-10° C. Following the cooling step, a concentrated salt, e.g., NaCl, solution may be added to raise the ionic strength to higher than that of 50 mM NaCl, or of about 100 mM NaCl. The increase of ionic strength after the drug loading incubation step aided in reducing post-loading aggregation of the liposomes.

In other embodiments, the loading is performed in the presence of ionic agent, such as agent NaCl, KCl, $NH_4Cl$, $Na_2SO_4$, $K_2SO_4$, or $(NH_4)_2SO_4$. at 20-350 mEq/L, 20-100 mEq/L, or 50-80 mEq/L. Contrary to the convention in the field that low ionic strength (low salt concentration), it was found that loading of the compounds of present disclosure, in particular AKG-28, into the liposomes was more efficient in the presence of relatively high ionic strength agents such as NaCl, in particular when the loading was performed at higher concentrations of the drug. Thus, at 10-12 mg/ml of AKG-28 in the liposome loading mixture, the loading at 0-20 mM NaCl resulted in the encapsulation efficiency of about 90-94%, whereas at about 80-360 mM NaCl the loading efficiency was >97% (Example 62). Accordingly, in some embodiments of the disclosure, the loading of the compounds described herein is performed at 20-350 mEq/L, 20-100 mEq/L, or 50-80 mEq/L of an ionic strength agent. In some embodiments, the ionic agent is NaCl. In some embodiments, the concentration of the added ionic strength agent is selected so that the post-loading liposomes are isotonic (have osmolality of 280-310 mOsmol/L, or osmolarity 270-310 mOsmol/kg). In some embodiments, the drug is AKG-28, the ionic strength agent is NaCl, the loading is preformed at about 12-13 mg/ml of the drug and the NaCl concentration 50-80 mM. The encapsulation efficiency of 95% or more, 97% or more, or 98% or more can be achieved.

In some embodiments, the contacting step also includes incubation of the liposomes with the drug in aqueous medium in the presence of an osmotic (tonicity) balancing agent. In some embodiments, the osmotic balancing agent (also referred herein as osmotic agent) is a non-ionic agent. Exemplary non-ionic osmotic agents include, but are not limited to, dextrose (glucose), sucrose, trehalose, lactose, mannitol, sorbitol, and polyvinylpyrrolidone. In some embodiments, the concentration of osmotic agent has osmotic concentration (expressed as osmolarity or osmolality) equal to the osmotic concentration of the trapping agent solution in the interior space of the liposomes prior to drug loading. The osmotic concentration of the trapping agent solution can be measured by method known in the art before the solution is combined with the lipids to form liposomes. In another embodiment, the concentration of osmotic agent provides osmotic concentration that is lower than the osmotic concentration of the trapping agent solution, and is less than about 90%, less than about 80%, less than about 70%, less than about 60%, less than about 50%, less than about 40%, less than about 30%, less than about 20%, or less than about 10% of the osmotic concentration of the trapping agent solution. In yet another embodiment, the concentration of osmotic agent during the drug loading process is in the range of 200-400 mmol/kg, preferably 250-350 mmol/kg. In yet another embodiment, the osmotic agent is dextrose, and the concentration is 45 g/L. In yet another embodiment, no osmotic agent is used during the incubation of the liposomes with the drug. In yet another embodiment, the incubation is performed in the presence of a ionic strength adjusting agent. A non limiting example of the ionic strength adjusting agent is sodium chloride, added to the liposome-drug solution for example at the concentration between 5 and 50 mM, between 10 and 20 mM, or about 10 mM. Contrary to the convention in the field of liposomes, the compounds of the present disclosure, for example, AKG-28 and AKG-38, are loaded into the liposomes of the present disclosure in a stable and highly efficient manner even if, during the drug-liposome contacting step, the amount of osmotic agent provides osmotic concentration that is lower than the osmotic concentration of the trapping agent solution (osmotically imbalanced liposomes), up to complete absence of the added osmotic agent.

For compounds AKG-28 and AKG-38, surprisingly, the loading was found to be very effective (>95% loading, >97% loading and >98% loading) even at the higher end of the achievable DL ratio (AKG-28, 300-350 g/mol PhL; AKG-38, 500-600 g/mol PhL) and at high concentrations of the drug in the liposome-drug loading mixture (over 16 mg/ml for AKG-38, over 12 mg/ml for AKG-28). Typically, in some embodiments, the liposome loading of AKG-28 is performed at 300-350 g/mol PhL and the drug concentration over 6 mg/ml, at least 10 mg/ml, or at least 12 mg/ml; while the liposome loading of AKG-38 is performed at 500-650 mg/ml, or 500-600 mg/ml of the drug, and the drug concentration over 8 mg/ml, at least 12 mg/ml, or at least 16 mg/ml, and the efficiency of at least 95% loading, at least 97% loading, or at least 98% loading is achieved.

In some embodiments, the compounds of the present disclosure are loaded in the liposomes in the broad range of pH, such as pH 4.5-7. For AKG-28, the optimum loading efficiency of 95% or more, or 97% or more, was achieved in the range of pH 5.5-7.0 (Example 62). The loading pH is defined by the pH of the drug aqueous stock solution (40 mg/ml) which is selected in the range pH 5.3-7.0. In some embodiments, pH of the 40 mg/ml AKG-28 stock solution is in the range pH 5.7-6.9, adjusted with NaOH.

Figure 18:
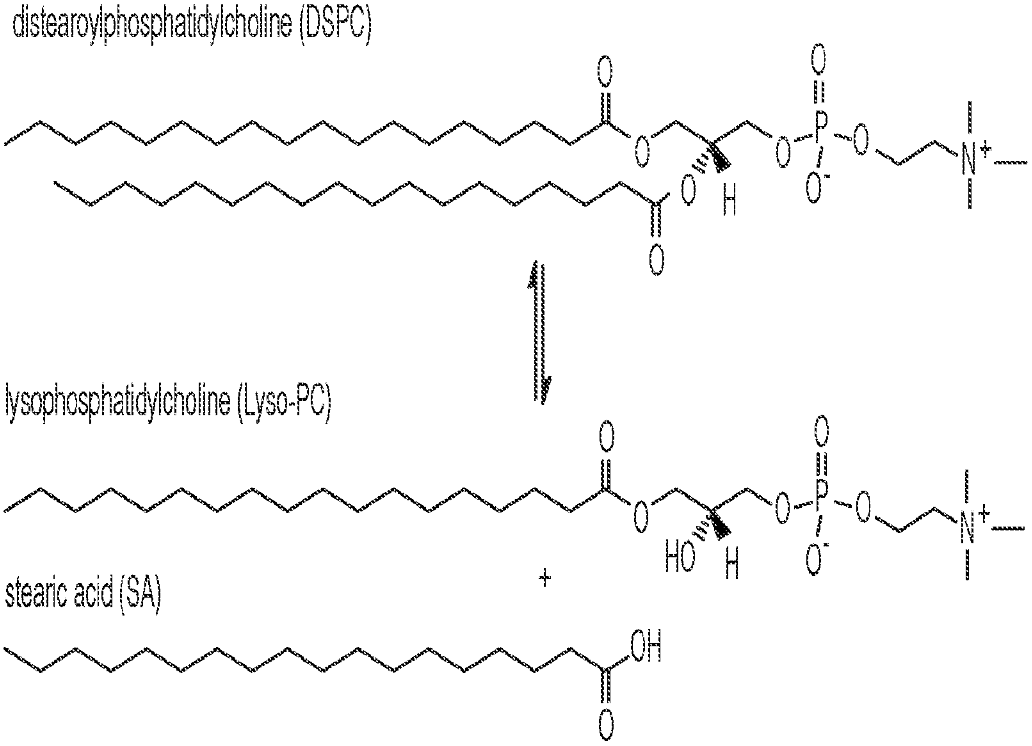
FIG. 18 is a scheme showing breakdown of distearoylphosphatidylcholine (DSPC) to lysophosphatidylcholine and stearic acid. Hydrogenated soy phosphatidylcholine (HSPC) is a 1,2-diacyl-sn-glycero-phosphocholine, where the 1 and 2 acyl chain positions are saturated fatty acids C16 to C22, being primarily stearic (C18) and palmitic (C16) acid. Distearoylphosphatidylcholine is the largest component of HSPC.

Liposomal and other lipid nanoparticle compositions are susceptible to degradation of the lipid components during storage which unfavorably effects their pharmaceutical qualities. Degradation of the lipids can be studied in accelerated stability study format where the liposome samples are stored at temperatures higher than the suggested storage temperature, so that the degradation takes place faster; generally being assumed to follow the Arrhenius law. The liposomes of present disclosure, for example, containing the compounds AKG-28 and AKG-38 in the lipid compositions of PC and cholesterol, were found to accumulate both cholesterol oxidative degradation products (FIG. 17) and the products of phosphatidylcholine hydrolytic degradation (FIG. 18). While typically oxidative degradation is observed for the lipids with unsaturated hydrocarbon chains, oxidative degradation of cholesterol is an unusual phenomenon. Stabilization of the liposomes with encapsulated compounds described herein can be achieved by incorporation of chelators. Chelators are molecules that bind metal ions by forming one or more stable heterocyclic groups that include a metal and a coordination bond. Exemplary chelators are deferoxamine (desferrioxamine, Desferal) (abbreviated herein as DFO), ethylenediamine tetraacetic acid (EDTA), diethylenetriamine pentaacetic acid (DTPA), nitrilotriacetic acid (NTA), ethyleneglycol-O,O'-bis(2-aminoethyl)-N,N,N',N'-tetraacetic acid (EGTA), N-(2-hydroxyethyl)ethylenediamine-N,N',N'-triacetic acid (HEDTA), 1,4,7,10-tetraazacyclododecane-1,4,7,10-tetraacetic acid (DOTA. In some embodiments, the liposome composition comprises cholesterol and is stable against degradation of cholesterol, the degree of cholesterol degradation after 3 months at 37° C. being less than 10%, less than 5%, or less than 1% of the total cholesterol. In some embodiments, the liposome composition comprises a chelator. In some embodiments, the chelator is deferoxamine (Desferal, DFO), ethylenediamine tetraacetic acid (EDTA), diethylenetriamine pentaacetic acid (DTPA), nitrilotriacetic acid (NTA), ethyleneglycol-O,O'-bis(2-aminoethyl)-N,N,N',N'-tetraacetic acid (EGTA), N-(2-hydroxyethyl)ethylenediamine-N,N',N'-triacetic acid (HEDTA), 1,4,7,10-tetraazacyclododecane-1,4,7,10-tetraacetic acid (DOTA), including their pharmaceutically acceptable salts. The chelator can be present in the composition at the concentration of at least 0.01 mM, at least 0.05 mM, at least 0.1 mM, at least 0.2 mM, or at least 0.5 mM, and not more than 1 mM, nor more than 2 mM, not more than 5 mM, or not more than 10 mM. In some embodiments, the chelator is deferoxamine or deferoxamine mesylate, and the chelator concentration is about 0.5 mM. Deferoxamine was found to be particularly effective in preventing degradation of cholesterol in the liposomes of present disclosure. Stability of the lipids with encapsulated compounds of present disclosure, in particular, AKG-28 and AKG-38, was influenced by the pH of the liposome external medium. While general teaching in the field is that the optimum stability of the lipids in liposomes is achieved at pH around 6.5, it was discovered that for the liposomes of the present disclosure the optimum lipid stability for both cholesterol and PC components is achieved at pH over 7.0. In some embodiments, the liposome composition has the pH of at least 7.1, at least 7.2, or at least 7.3, and no more than pH 8.0, no more than pH 7.7, or no more than pH 7.6. In some embodiments, the degree of cholesterol degradation after 3 months at 37° C. is less than 10%, less than 5%, or less than 1% of the total cholesterol. In some embodiments, the degree of phospholipid degradation after 6 weeks at 37° C. is less than 10%, less than 5%, or less than 1% of the total phospholipid content. In some embodiments, the phospholipid is phosphatidylcholine. In some embodiments, the phospholipid is HSPC, and the pH is between pH 7.3-7.6.

Another factor that had an unexpected effect on the lipid stability in the liposomes of this disclosure was the presence of ammonium or substituted ammonium in the external medium. In some embodiments, ammonium salt is used as a trapping agent to effect the loading of the compounds described herein, such as AKG-28 or AKG-38, into the liposomes. Accordingly, for each molecule of the drug entering the liposome interior, one or two molecules of ammonia leave the interior of the liposome and accumulate in the liposome external medium, which is subsequently purged from the accumulated ammonium at the post-loading buffer exchange/unencapsulated drug removal step, such as by tangential flow filtration, dialysis, or size exclusion chromatography. Surprisingly, in in accelerated storage stability studies of the post-loading liposome preparations that did not undergo buffer exchange, the phospholipids were more stable against degradation than in the buffer-exchanged preparations. Analysis of ammonium in the post-loading liposomes with and without buffer exchange showed that buffer exchanged liposomes indeed have significantly lower levels of ammonium in the liposome external medium. Thus, the presence of ammonium in the liposome external medium, in the amounts resulting from the ammonium-drug transmembrane exchange during the drug loading step ("exchanged ammonium"), is favorable for reducing storage-related degradation of the lipids. We surprisingly found that even relatively small amounts, such as 1.7 mEq/L of external (extraliposomal) ammonium have pronounced stabilizing effect of the liposome lipids (Example 71). (For convenience, we use the term "mM" to designate the concentration of $NH_4^+$ in mEq/L where the salt form of ammonium is not defined.) In some embodiments the external medium of the liposome composition has less than 0.5 mEq/L of ammonium or substituted ammonium. In some embodiments, the liposome composition contains in the liposome external medium an ammonium or substituted ammonium in the concentration of at least 1 mEq/L, at least 2 mEq/L, at least 5 mEq/L, at least 10 mEq/L, at least 15 mEq/L, or at least 20 mEq/l, and no more than 200 mEq/L, no more than 150 mEq/L, no more than 100 mEq/L, no more than 80 mEq/L, or no more than 60 mEq/L. In some embodiments, the liposome composition contains in the liposome external medium an ammonium or substituted ammonium in the concentration of at least 1 mEq/L., at least 2 mEq/L, at least 5 mEq/L, at least 10 mEq/L, at least 15 mEq/L, or at least 20 mEq/l, and no more than 200 mEq/L, no more than 150 mEq/L, no more than 100 mEq/L, no more than 80 mEq/L, or no more than 60 mEq/L, and is stable against phospholipid degradation, the degree of phospholipid degradation after 6 weeks at 37° C. being less than 10%, less than 5%, or less than 1% of the total phospholipid. In some embodiments, the liposome composition contains in the liposome external medium an ammonium or substituted ammonium in the concentration of at least 1 mEq/L., at least 2 mEq/L, at least 5 mEq/L, at least 10 mEq/L, at least 15 mEq/L, or at least 20 mEq/l, and no more than 200 mEq/L, no more than 150 mEq/L, no more than 100 mEq/L, no more than 80 mEq/L, or no more than 60 mEq/L, and is stable against phospholipid degradation, the degree of phospholipid degradation after 3 months at 37° C. being less than 10%, less than 7%, less than 5%, or less than 4% of the total phospholipid. In some embodiments, the phospholipid is phosphatidylcholine. In some embodiments, the phospholipid is HSPC, and the ammonium salt is ammonium chloride, ammonium sulphate, or a combination thereof, at the ammonium concentration of 10-80 mM, or 15-60 mM. In some embodiments, the phospholipid is HSPC, and the ammonium salt is ammonium chloride, ammonium sulphate, or a combination thereof, at the ammonium concentration of 1-10 mM, or 2-5 mM. In some embodiments, the normality of ammonium in the external medium of the liposome composition is within 90-110% of the normality of encapsulated drug at the drug loading step, normality being the concentration expressed in gram-equivalents/L (eq/L).

The desired concentration of ammonium in the liposome external medium can be achieved by accumulation of the extraliposomal ammonium during the drug loading step at the expense of ammonium (used as part of a trapping agent) escape from the liposome interior as explained above. Alternatively, the desired levels of extraliposomal ammonium are contributed by the extraliposomal ammonium that remains in the liposomes after the removal of extraliposomal ammonium prior to the drug loading, or are achieved by addition of ammonium salt, such as ammonium chloride or ammonium sulfate, to the external medium of the liposome formulation. In the latter case, if post-loading purification of liposomes from the unencapsulated material is desired ammonium salt can be added to the liposomal preparation after the post-load buffer-exchange/unencapsulated drug removal step, or added to the exchange buffer, In some embodiments, liposome compositions provided herein can further include in the liposome formulation, a lipophilic free-radical scavenger, such as .alpha.-tocopherol.

In some embodiments, oxazolidinone liposome compositions provided herein comprise HSPC, cholesterol and PEG-DSPE in a mass ratio of about 5:3:1. In some embodiments, oxazolidinone liposome compositions provided herein comprise HSPC, cholesterol and PEG-DSPE in a molar ratio of about 45:55:2.25. In some embodiments, oxazolidinone liposome compositions comprise an oxazolidinone consisting of AKG-28 or a pharmaceutically acceptable salt thereof. In some embodiments, oxazolidinone liposome compositions comprise an oxazolidinone consisting of AKG-38 or a pharmaceutically acceptable salt thereof.

Methods of Use

Disclosed herein are methods for inhibiting the growth of mycobacteria, such as *Mycobacterium tuberculosis*, or gram positive bacteria, such as methicillin-resistant *Staphylococcus aureus* (MRSA). Additional mycobacteria and gram positive bacteria include, but are not limited to, *Mycobacterium avium* complex, *Mycobacterium leprae, Mycobacterium gordonae, Mycobacterium abscessus, Mycobacterium abscessus, Mycobacterium mucogenicum*, streptococci, vancomycin-resistant enterococci (VRE), *Staphylococcus pneumoniae, Enterococcus faecium, Streptococcus agalactiae, Streptococcus pneumoniae, Streptococcus pyogenes*, the *viridans* group streptococci, *Listeria monocytogenes, Nocardia*, and *Corynebacterium*. In some embodiments, the compounds and compositions provided herein inhibit the growth of drug resistant strains of *Mycobacterium tuberculosis*. In some embodiments, methods of treating mycobacterial infections are provided. In some embodiments, the compounds and compositions provided herein can be used to treat nontuberculosis mycobacteria infections. In some embodiments, the method comprises administering a therapeutically effective amount of an aminoalkyl oxazolidinone of the disclosure and/or a pharmaceutical acceptable salt thereof to a subject in need thereof. In some embodiments, the method comprises administering a therapeutically effective amount of a liposomal composition comprising an aminoalkyl oxazolidinone compound of the disclosure and/or a pharmaceutical acceptable salt thereof to a subject in need thereof.

Mycobacteria is a genus of bacteria responsible for tuberculosis (TB). According to the World Health Organization, worldwide, TB is one of the top 10 causes of death and the leading cause of death from a single infectious agent. Rifampicin is the most effective first-line drug to treat TB. However, there is a growing number of cases infected with *Mycobacterium tuberculosis* that is resistant to rifampicin. Multidrug-resistant tuberculosis (MDR-TB) is a form of TB caused by bacteria that do not respond to isoniazid and rifampicin.

In some embodiments, the composition is a liquid pharmaceutical formulation for parenteral administration. In some embodiments, the liquid pharmaceutical formulation is a liposomal formulation containing a suitable amount of the oxazolidinone compound described herein, wherein the oxazolidinone compound is encapsulated in the interior of the liposomes. In another embodiment, that compound is in a salt form in the interior of the liposome with a polyanion such as sulfate, citrate, sucrose octasulfate, inositol hexaphosphate. In some embodiments, the compound is a precipitated or gelated salt with sulfate inside a liposome composed of multiple lipid excipients, including but not limited to, phosphatidylcholine, cholesterol, and pegylated phosphatidylethanolamine. The liposomes of the present disclosure show entrapment efficiencies of more than 85%, more than 90%, and more than 95%. In some embodiments, the residual amount of the unentrapped drug is removed from the liposome composition. This can be achieved by various means, such as size exclusion chromatography, ion exchange, dialysis, ultrafiltration, tangential flow filtration, adsorption, or precipitation. During or after the unentrapped drug removal step, the liposomes may be brought into a desired pharmaceutically acceptable carrier, for example, normal saline, isotonic dextrose, isotonic sucrose, Ringer's solution, or Hanks' solution. A buffer substance can be added to provide desired physiologically acceptable pH. The liposomal composition may be adjusted for desired drug concentration, and sterilized, e.g., by aseptic filtration through 0.2-0.22 μm filters. In some embodiments, the compound concentration in the liposomal composition is in the range of 1-50 mg/ml, 3-30 mg/ml, or 5-25 mg/ml.

In some embodiments, pharmaceutical preparations comprising the liposome composition provided herein may be sterilized by conventional, well known sterilization techniques. The aqueous solutions can then be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc. Additionally, the lipidic suspension may include lipid-protective agents which protect lipids against free-radical and lipid-peroxidative damages on storage. Lipophilic free-radical quenchers, such as .alpha.-tocopherol are suitable.

In some embodiments, the liposomes are mixed with one or more additional excipients for isotonicity or pH control. In some embodiments, the excipients include but are not limited to sodium chloride, Hepes buffer, phosphate buffer, and histidine buffer.

The liposome compositions can also contain other pharmaceutically acceptable substances as required to approximate physiological conditions, such as pH adjusting and buffering agents, tonicity adjusting agents and the like, for example, sodium acetate, sodium lactate, sodium chloride, potassium chloride, calcium chloride, and the like. Additionally, the liposome suspension may include lipid-protective agents which protect lipids against free-radical and lipid-peroxidative damages on storage. Lipophilic free-radical quenchers, such as alpha-tocopherol, are suitable.

In other embodiments, the composition is an oral formulation. In some embodiments, the composition is a liquid formulation. In some embodiments, the composition is a solid formulation (e.g. tablet, capsule, pill, dragees, caplets etc.). When used for oral use for example, tablets, troches, lozenges, aqueous or oil suspensions, dispersible powders or granules, emulsions, hard or soft capsules, syrups or elixirs may be prepared (Remington's Pharmaceutical Sciences (Mack Publishing Co., Easton, Pa.). Compositions intended for oral use may be prepared according to any method known to the art for the manufacture of pharmaceutical compositions. The compositions may contain one or more agents including antioxidants, sweetening agents, flavoring agents, coloring agents and preserving agents, in order to provide a palatable preparation. Tablets containing the active ingredient in admixture with non-toxic pharmaceutically acceptable excipient or auxiliary agents which are suitable for manufacture of tablets are acceptable. Suitable excipients or auxiliary agents include but are not limited to, for example, inert diluents, solubilizers, suspending agents, adjuvants, wetting agents, sweeteners, perfuming or flavoring substances, isotonic substances, colloidal dispersants and surfactants.

Tablets, dragees, capsules, pills, granules, suppositories, solutions, suspensions and emulsions, pastes, ointments, gels, creams, lotions, powders and sprays can be suitable pharmaceutical compositions.

The compound or the composition can be administered locally, orally, parenterally., intraperitoneally and/or rectally.

Dosage regimens are adjusted to provide the optimum desired response (e.g., a therapeutic response). For example, one or more doses may be administered over time or the dose may be proportionally reduced or increased as indicated by the exigencies of the therapeutic situation.

The dosage of the compounds and/or of their pharmaceutically acceptable salts or the liposomes comprising the compounds and/or of their pharmaceutically acceptable salts may vary within wide limits and should naturally be adjusted, in each particular case, to the individual conditions and to the pathogenic agent to be controlled.

In some embodiments, for a use in the treatment of bacterial infections, the compound or the pharmaceutical liposomal composition is administered once every 7 days (i.e., once every week), once every 14 days (i.e., once every two weeks), once every 21 days (i.e., once every three weeks), once every 28 days (i.e., once every four weeks) and once every 42 days (i.e., once every six weeks) to the subject in need thereof. In some embodiments, the average weekly dosage is from about 1 mg to about 1500 mg, about 10 to about 700 mg, about 25 to about 500 mg, or about 70 to about 250 mg. In some embodiments, the average weekly dosage is from about 1 mg to about 10 mg, from about 10 mg to about 25 mg, from about 25 mg to about 50 mg, from about 50 mg to about 100 mg, from about 100 mg to about 200 mg, from about 200 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 mg to about 900 mg, from about 900 mg to about 1000 mg, from about 1000 mg to about 1100 mg, from about 1100 mg to about 1200 mg, from about 1200 mg to about 1300 mg, from about 1300 mg to about 1400 mg, from about 1400 mg to about 1500 mg. In some embodiments, the compound or composition is administered for up to one month, up to two months, up to three months, up to four months or more. The specific therapeutically effective amount will depend on a variety of factors, including the bacterial infection being treated, the activity of the specific compound being administered, the pharmaceutical composition employed, the age, body eight, gender etc. of the subject, the route of administration, the severity of the bacterial infection, the optional drugs/active agents used in combination (sequentially or simultaneously) with the specific compound, and the like factors known to the medical doctor of ordinary skill. In some embodiments, the compounds or the composition can be used for the treatment of tuberculosis or other *Mycobacterium* infections. In some embodiments, the compound can be used as a monotherapy. In some embodiments, the treatment can include administering simultaneously and/or sequentially an effective amount of the compound described herein and an effective amount of one or more additional active agents to treat *Mycobacterium tuberculosis* and other gram-positive bacterial infections. In some embodiments, the treatment can include administering simultaneously and/or sequentially an effective amount of the compound described herein and an effective amount of two or more additional active agents (two, three, four, etc.) to treat *Mycobacterium tuberculosis* and other gram-positive bacterial infections. A synergistic antibacterial effect denotes an antibacterial effect which is greater than the predicted purely additive effects of the individual compounds of the combination. When administered simultaneously, the compound and the active agent can be contained in the same composition or in separate compositions. When administered sequentially, the composition comprising the compound and the composition comprising the additional active agent can be administered with a time separation (e.g. 20 minutes, 40 minutes, 60 minutes or more). In some embodiments, the additional active agents can be administered using a different administration route or by different injections. For example, the compounds of the disclosure can be administered intravenously and one or more additional agents can be administered orally.

In some embodiments, the administration of the compounds with one or more (e.g. one, two, three or four) additional active agents can result in a reduction of the length of the treatment duration. For example, administration of the compounds with one or more (e.g. one, two, three or four) additional active agent can result in a treatment duration at least three times, at least twice, at least 1.5 times shorter than compared to the treatment with only one active agent. In some embodiments, the additional agent(s) is an antibacterial agent. In some embodiments, the additional active agent can include, but are not limited to, fluoroquinolines, such as moxifloxacin, gatifloxacin, or levofloxacin, bedaquiline and other diaryl quinoline analogs (e.g. TBAJ-587 and TBAJ-876), delamanid, pretomanid, isoniazid, rifampicin, rifapentine, pyrazinamide, clofazimine, spectinamide, ethambutol, streptomycin, kanamycin, capreomycin, amikacin, the Leucyl-tRNA Synthetase (LeuRS) inhibitor GSK 3036656, tryptophan synthase inhibitor GSK839, DprE1 inhibitors OPC-167832 and Macozinone (PBTZ-169), Telacebec, GSK-656, TBA-7371, and amoxicillin plus clavulanate, a pharmaceutically acceptable salt of each thereof and any combinations thereof. For the treatment of gram positive bacterial infections, the additional active agent can include, but are not limited to, vancomycin, gentamycin, daptomycin, teicoplanin, ceftaroline, cefirobiprole, telavancin, dalbavancin, oritavancin, fluoroquinolines (e.g. delafloxacin), tetracyclines (e.g. eravacycline and omadacycline), sulfonamides (e.g. sulfamethoxazole), trimetrhoprim, lefamulin, and any combinations thereof. In some embodiments, the treatment can include administering simultaneously and/or sequentially an effective amount of the compound described herein and an effective amount of bedaquiline, pretomanid, pyrazinamide, moxifloxacin or a pharmaceutically acceptable salt of each thereof or a combination of the foregoing.

Actual dosage levels of the active ingredients in the pharmaceutical compositions disclosed herein may be varied so as to obtain an amount of the active ingredient which is effective to achieve the desired therapeutic response for a particular patient, composition, and mode of administration, without being toxic to the patient.

"Parenteral" as used herein in the context of administration means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The phrases "parenteral administration" and "administered parenterally" as used herein refer to modes of administration other than enteral (i.e., via the digestive tract) and topical administration, usually by injection or infusion, and includes, without limitation, intravenous, intramuscular, intraarterial, intrathecal, intracapsular, intraorbital, intracardiac, intradermal, intraperitoneal, transtracheal, subcutaneous, subcuticular, intraarticular, inhalation, subcapsular, subarachnoid, intraspinal, epidural and intrasternal injection and infusion. Intravenous injection and infusion are often (but not exclusively) used for liposomal drug administration.

In some embodiments, the liquid composition is injected intravenously. In some embodiments, the compound or the pharmaceutical composition is administered once every 7 days (i.e., once every week), once every 14 days (i.e., once every two weeks), once every 21 days (i.e., once every three weeks), once every 28 days (i.e., once every four weeks) and once every 42 days (i.e., once every six weeks) to the subject in need thereof. In some embodiments, the average weekly dosage is from about 1 mg to about 1500 mg, about 10 to about 700 mg, about 25 to about 500 mg, or about 70 to about 250 mg. In some embodiments, the average weekly dosage is from about 1 mg to about 10 mg, from about 10 mg to about 25 mg, from about 25 mg to about 50 mg, from about 50 mg to about 100 mg, from about 100 mg to about 200 mg, from about 200 mg to about 300 mg, from about 300 mg to about 400 mg, from about 400 mg to about 500 mg, from about 500 mg to about 600 mg, from about 600 mg to about 700 mg, from about 700 mg to about 800 mg, from about 800 mg to about 900 mg, from about 900 mg to about 1000 mg, from about 1000 mg to about 1100 mg, from about 1100 mg to about 1200 mg, from about 1200 mg to about 1300 mg, from about 1300 mg to about 1400 mg, from about 1400 mg to about 1500 mg. The specific therapeutically effective amount will depend on a variety of factors, including the bacterial infection being treated, the activity of the specific compound being administered, the pharmaceutical composition employed, the age, body weight, gender etc. of the subject, the route of administration, the severity of the bacterial infection, the optional drugs/active agents used in combination (sequentially or simultaneously) with the specific compound, and the like factors known to the medical doctor of ordinary skill in the art.

In some embodiments, the liposomal composition is administered parenterally.

In some embodiments, the method comprises administering simultaneously or sequentially one or more additional active agent. In some embodiments, the one or more active agents comprise bedaquiline, pretomanid, pyrazinamide, moxifloxacin, a pharmaceutically acceptable salt thereof or a combination thereof.

In some embodiments, the liposomal composition is administered once a week to once every six weeks.

In some embodiments, the percentage of compound remaining in blood is greater than 20% of the administered amount at 6 hours following administration to the subject in need thereof. In some embodiments, the percentage of compound remaining in blood is greater than 10% of the administered amount.

Aspects of the disclosure relate to method of making liposome composition comprising the steps of: (i) preparing the liposomes comprising phospholipid, cholesterol, and PEG-lipid, and having an interior space containing a trapping agent, in a medium substantially free from the trapping agent; (ii) contacting the liposomes with a compound disclosed herein in an aqueous medium to effect encapsulation of the compound in the liposomes; (iii) removing unencapsulated compound; and (iv) providing the liposomes in a physiologically acceptable medium suitable for parenteral use.

In some embodiments, for a use in the treatment of bacterial infections, the compound or the pharmaceutical oral composition is administered once or twice daily. The specific therapeutically effective amount will depend on a variety of factors, including the bacterial infection being treated, the activity of the specific compound being administered, the pharmaceutical composition employed, the age, body eight, gender etc. of the subject, the route of administration, the severity of the bacterial infection, the optional drugs/active agents used in combination (sequentially or simultaneously) with the specific compound, and the like factors known to the medical doctor of ordinary skill.

Additional Embodiments

The following additional embodiments are provided for illustrative purposes.

1. An AKG-28 liposome composition comprising lipids HSPC, cholesterol, and PEG(2000)-DSPE in a molar ratio of 45:55:2.25 or in a mass ratio of 5:3:1 and a pharmaceutically acceptable salt of AKG-28

(AKG-28)

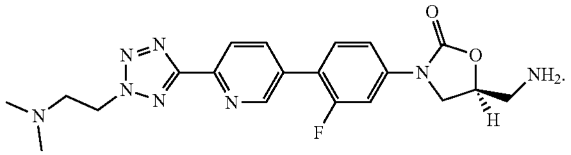

2. The composition of embodiment 1, wherein the liposome composition comprises mono- or oligolamellar vesicles having z-average diameter of 90-130 nm.
3. The composition of embodiment 2, wherein the mono- or oligolamellar vesicles have a z-average diameter of 100-130 nm.
4. The composition of embodiment 1, wherein the liposome composition has a polydispersity index of less than 0.15.
5. The composition of embodiment 4, wherein the liposome composition has a polydispersity index of less than 0.10.
6. The composition of embodiment 1, wherein the drug/lipid ratio of the AKG-28 to the total phospholipid (PhL) in the composition is 230-290 g/mol.
7. The composition of embodiment 1, wherein the drug/lipid ratio of the AKG-28 to the total phospholipid (PhL) in the composition is 290-360 g/mol.
8. The composition of embodiment 1, wherein the drug/lipid ratio of the AKG-28 to the total phospholipid (PhL) in the composition is 300-340 g/mol.
9. The composition of embodiment 1, wherein the drug/lipid ratio of the AKG-28 to the total phospholipid (PhL) in the composition is about 250 g/mol.
10. The composition of embodiment 1, wherein the drug/lipid ratio of the AKG-28 to the total phospholipid (PhL) in the composition is about 330 g/mol.
11. The composition of embodiment 1, wherein the overall concentration of AKG-28 in the composition is 8-15 mg/mL.
12. The composition of embodiment 1, wherein the overall concentration of AKG-28 in the composition is 9-11 mg/mL.
13. The composition of embodiment 1, wherein the proportion of encapsulated AKG-28 to overall AKG-28 in the composition is at least 90%.
14. The composition of embodiment 1, wherein the proportion of encapsulated AKG-28 to overall AKG-28 in the composition is at least 95%.
15. The composition of embodiment 1, wherein the proportion of encapsulated AKG-28 to overall AKG-28 in the composition is at least 97%.

16. The composition of embodiment 1, wherein the proportion of encapsulated AKG-28 to overall AKG-28 in the composition is at least 98%.
17. The composition of embodiment 1, wherein the composition comprises liposome vesicles in an aqueous medium, the aqueous medium comprising sodium chloride and optionally comprising an ammonium ion.
18. The composition of embodiment 17, wherein the osmolality of the aqueous medium is 270-330 mOsmol/kg.
19. The composition of embodiment 17, wherein the osmolality of the aqueous medium is 270-310 mOsmol/kg.
20. The composition of embodiment 17, wherein the ammonium concentration in the aqueous medium is 20-60 mM.
21. The composition of embodiment 17, wherein the ammonium concentration in the aqueous medium is 50-80 mM.
22. The composition of embodiment 17, wherein the concentration of ammonium in the aqueous medium is less than 0.5 mM.
23. The composition of embodiment 17, wherein the concentration of ammonium in the aqueous medium is less than 130-150 mM.
24. The composition of embodiment 1, further comprising a buffer, wherein the buffer buffers the composition at a pH of 7.3-7.7.
25. The composition of embodiment 1, further comprising a buffer, wherein the buffer buffers the composition at a pH of about 7.5.
26. The composition of embodiment 1, further comprising a buffer, wherein the buffer buffers the composition at a pH of 7.5.
27. The composition of embodiment 1, further comprising a HEPES or phosphate buffer.
28. The composition of embodiment 27, wherein the composition comprises HEPES or phosphate buffer at a concentration of 5-50 mM.
29. The composition of embodiment 27, wherein the composition comprises HEPES or phosphate buffer at a concentration of about 20 mM.
30. The composition of embodiment 27, wherein the composition comprises HEPES or phosphate buffer at a concentration of 20 mM.
31. The composition of embodiment 1, further comprising a chelator.
32. The composition of embodiment 1, further comprising a chelator at a concentration of 0.1-1 mM.
33. The composition of embodiment 1, further comprising a chelator at a concentration of about 0.5 mM.
34. The composition of embodiment 1, further comprising a chelator at a concentration of 0.5 mM.
35. The composition of embodiment 1, further comprising deferoxamine (DFO) or EDTA.
36. The composition of embodiment 1, further comprising deferoxamine (DFO) or EDTA at a concentration of 0.1-1 mM.
37. The composition of embodiment 1, further comprising deferoxamine (DFO) or EDTA at a concentration of about 0.5 mM.
38. The composition of embodiment 1, further comprising deferoxamine (DFO) or EDTA at a concentration of 0.5 mM.
39. The composition of embodiment 1, wherein the composition is storage stable.
40. The composition of any one of embodiments 1-39, wherein the composition comprises AKG-28 as a sulfate salt of AKG-28.
41. An AKG-38 liposome composition comprising lipids HSPC, cholesterol, and PEG(2000)-DSPE in a molar ratio of 45:55:2.25 or in a mass ratio of 5:3:1 and a pharmaceutically acceptable salt of AKG-38

(AKG-38)

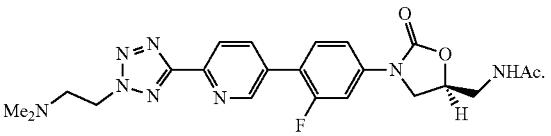

42. The composition of embodiment 41, wherein the liposome composition comprises mono- or oligolamellar vesicles having z-average diameter of 90-130 nm.
43. The composition of embodiment 42, wherein the mono- or oligolamellar vesicles have a z-average diameter of 100-130 nm.
44. The composition of embodiment 41, wherein the liposome composition has a polydispersity index of less than 0.15.
45. The composition of embodiment 44, wherein the liposome composition has a polydispersity index of less than 0.10.
46. The composition of embodiment 41, wherein the drug/lipid ratio of the AKG-38 to the total phospholipid (PhL) in the composition is 430-480 g/mol.
47. The composition of embodiment 41, wherein the drug/lipid ratio of the AKG-38 to the total phospholipid (PhL) in the composition is 500-650 g/mol.
48. The composition of embodiment 41, wherein the drug/lipid ratio of the AKG-38 to the total phospholipid (PhL) in the composition is 430-650 g/mol.
49. The composition of embodiment 41, wherein the drug/lipid ratio of the AKG-38 to the total phospholipid (PhL) in the composition is about 450 g/mol.
50. The composition of embodiment 41, wherein the drug/lipid ratio of the AKG-38 to the total phospholipid (PhL) in the composition is about 600 g/mol.
51. The composition of embodiment 41, wherein the overall concentration of AKG-38 in the composition is 12-25 mg/mL.
52. The composition of embodiment 41, wherein the overall concentration of AKG-38 in the composition is 13.5-16.5 mg/mL.
53. The composition of embodiment 41, wherein the overall concentration of AKG-38 in the composition is about 15 mg/mL.
54. The composition of embodiment 41, wherein the overall concentration of AKG-38 in the composition is about 20 mg/mL.
55. The composition of embodiment 41, wherein the proportion of encapsulated AKG-38 to overall AKG-38 in the composition is at least 90%.
56. The composition of embodiment 41, wherein the proportion of encapsulated AKG-38 to overall AKG-38 in the composition is at least 95%.
57. The composition of embodiment 41, wherein the proportion of encapsulated AKG-38 to overall AKG-38 in the composition is at least 97%.

58. The composition of embodiment 41, wherein the proportion of encapsulated AKG-38 to overall AKG-38 in the composition is at least 98%.
59. The composition of embodiment 41, wherein the composition comprises liposome vesicles in an aqueous medium, the aqueous medium comprising sodium chloride and optionally comprising an ammonium ion.
60. The composition of embodiment 59, wherein the osmolality of the aqueous medium is 270-330 mOsmol/kg.
61. The composition of embodiment 59, wherein the osmolality of the aqueous medium is 270-310 mOsmol/kg.
62. The composition of embodiment 59, wherein the ammonium concentration in the aqueous medium is 20-60 mM.
63. The composition of embodiment 59, wherein the ammonium concentration in the aqueous medium is 50-80 mM.
64. The composition of embodiment 59, wherein the concentration of ammonium in the aqueous medium is less than 0.5 mM.
65. The composition of embodiment 59, wherein the concentration of ammonium in the aqueous medium is less than about 0.5 mM
66. The composition of embodiment 59, wherein the concentration of sodium chloride is 130-150 mM.
67. The composition of embodiment 41, further comprising a buffer, wherein the buffer buffers the composition at a pH of 7.3-7.7.
68. The composition of embodiment 41, further comprising a buffer, wherein the buffer buffers the composition at a pH of about 7.5.
69. The composition of embodiment 41, further comprising a buffer, wherein the buffer buffers the composition at a pH of 7.5.
70. The composition of embodiment 41, further comprising a HEPES or phosphate buffer.
71. The composition of embodiment 70, wherein the composition comprises HEPES or phosphate buffer at a concentration of 5-50 mM.
72. The composition of embodiment 70, wherein the composition comprises HEPES or phosphate buffer at a concentration of about 20 mM.
73. The composition of embodiment 70, wherein the composition comprises HEPES or phosphate buffer at a concentration of 20 mM.
74. The composition of embodiment 41, further comprising a chelator.
75. The composition of embodiment 41, further comprising a chelator at a concentration of 0.1-1 mM.
76. The composition of embodiment 41, further comprising a chelator at a concentration of about 0.5 mM.
77. The composition of embodiment 41, further comprising a chelator at a concentration of 0.5 mM.
78. The composition of embodiment 41, further comprising deferoxamine (DFO) or EDTA.
79. The composition of embodiment 41, further comprising deferoxamine (DFO) or EDTA at a concentration of 0.1-1 mM.
80. The composition of embodiment 41, further comprising deferoxamine (DFO) or EDTA at a concentration of about 0.5 mM.
81. The composition of embodiment 41, further comprising deferoxamine (DFO) or EDTA at a concentration of 0.5 mM.
82. The composition of embodiment 41, wherein the composition is storage stable.
83. The composition of any one of embodiments 1-82, wherein the comprises AKG-28 as a sulfate salt of AKG-28.
84. An AKG-28 liposome composition comprising lipids HSPC, cholesterol, and PEG(2000)-DSPE in a molar ratio of 45:55:2.25 or in a mass ratio of 5:3:1 and a pharmaceutically acceptable salt of AKG-28

(AKG-28)

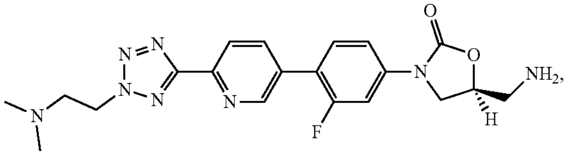

wherein the liposome composition is further characterized by any one or more of the following characteristics:
a. the liposome composition comprises mono- or oligolamellar vesicles having z-average diameter of 90-130 nm; or the liposome composition comprises mono- or oligolamellar vesicles having z-average diameter of 90-130 nm; or the liposome composition comprises mono- or oligolamellar vesicles having a z-average diameter of 100-130 nm;
b. the liposome composition has a polydispersity index of less than 0.15; or the liposome composition has a polydispersity index of less than 0.10;
c. the drug/lipid ratio of the AKG-28 to the total phospholipid (PhL) in the composition is 230-280 g/mol; or the drug/lipid ratio of the AKG-28 to the total phospholipid (PhL) in the composition is 290-360 g/mol; or the drug/lipid ratio of the AKG-28 to the total phospholipid (PhL) in the composition is 300-340 g/mol; or the drug/lipid ratio of the AKG-28 to the total phospholipid (PhL) in the composition is about 250 g/mol; or the drug/lipid ratio of the AKG-28 to the total phospholipid (PhL) in the composition is about 330 g/mol;
d. the overall concentration of AKG-28 in the composition is 8-15 mg/mL; or the overall concentration of AKG-28 in the composition is 9-11 mg/mL;
e. the proportion of encapsulated AKG-28 to overall AKG-28 in the liposome composition is at least 90%; or the proportion of encapsulated AKG-28 to overall AKG-28 in the liposome composition is at least 95%; or the proportion of encapsulated AKG-28 to overall AKG-28 in the liposome composition is at least 97%; or the proportion of encapsulated AKG-28 to overall AKG-28 in the liposome composition is at least 98%;
f. the liposome composition comprises an aqueous medium comprising sodium chloride and optionally comprising an ammonium ion;
g. the osmolality of the aqueous medium is 270-330 mOsmol/kg; or the osmolality of the aqueous medium is 270-310 mOsmol/kg;
h. the ammonium concentration in the aqueous medium is 20-60 mM; or the ammonium concentration in the aqueous medium is 50-80 mM; or the concentration of ammonium in the aqueous medium is less than 0.5 mM; or the concentration of ammonium in said aqueous medium is less than 0130-150 mM;

i. the aqueous medium further comprises a buffer, wherein the buffer buffers the liposome composition at a pH of 7.3-7.7; at a pH of about 7.5; or at a pH of 7.5;
j. the aqueous medium further comprising a HEPES or phosphate buffer; or the aqueous medium comprises HEPES or phosphate buffer at a concentration of 5-50 mM; or the aqueous medium comprises HEPES or phosphate buffer at a concentration of about 20 mM; or the aqueous medium comprises HEPES or phosphate buffer at a concentration of 20 mM;
k. the composition further comprises a chelator, or the composition further comprises a chelator at a concentration of 0.1-1 mM; or the composition further comprising a chelator at a concentration of about 0.5 mM; or the composition further comprises a chelator at a concentration of 0.5 mM; or the composition further comprises deferoxamine (DFO) or EDTA; or the composition further comprises deferoxamine (DFO) or EDTA at a concentration of 0.1-1 mM; or the composition further comprising deferoxamine (DFO) or EDTA at a concentration of about 0.5 mM or the composition further comprises deferoxamine (DFO) or EDTA at a concentration of 0.5 mM; or
l. AKG-28 is encapsulated within the liposome as a sulfate salt of AKG-28.

85. An AKG-38 liposome composition comprising lipids HSPC, cholesterol, and PEG(2000)-DSPE in a molar ratio of 45:55:2.25 or in a mass ratio of 5:3:1 and a pharmaceutically acceptable salt of AKG-38

(AKG-38)

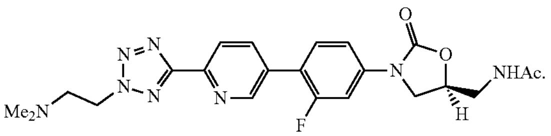

wherein the liposome composition is further characterized by any one or more of the following characteristics:
a. the liposome composition comprises mono- or oligo-lamellar vesicles having z-average diameter of 90-130 nm;
b. the liposome composition comprises mono- or oligo-lamellar vesicles have a z-average diameter of 100-130 nm;
c. the liposome composition has a polydispersity index of less than 0.15 or the liposome composition has a polydispersity index of less than 0.10;
d. the drug/lipid ratio of the AKG-38 to the total phospholipid (PhL) in the liposome composition is 430-480 g/mol, or the drug/lipid ratio of the AKG-38 to the total phospholipid (PhL) in the liposome composition is 500-650 g/mol; or the drug/lipid ratio of the AKG-38 to the total phospholipid (PhL) in the liposome composition is 430-650 g/mol; or the drug/lipid ratio of the AKG-38 to the total phospholipid (PhL) in the liposome composition is about 450 g/mol; or the drug/lipid ratio of the AKG-38 to the total phospholipid (PhL) in the liposome composition is about 600 g/mol;
e. the overall concentration of AKG-38 in the liposome composition is 12-25 mg/mL; or the overall concentration of AKG-38 in the liposome composition is 13.5-16.5 mg/mL; or the overall concentration of AKG-38 in the composition is about 15 mg/mL; or the overall concentration of AKG-38 in the liposome composition is about 20 mg/mL.
f. the proportion of encapsulated AKG-38 to overall AKG-38 in the liposome composition is at least 90%; or the proportion of encapsulated AKG-38 to overall AKG-38 in the liposome composition is at least 95%; or the proportion of encapsulated AKG-38 to overall AKG-38 in the liposome composition is at least 97%; or the proportion of encapsulated AKG-38 to overall AKG-38 in the liposome composition is at least 98%;
g. the liposome composition comprises an aqueous medium comprising sodium chloride and optionally comprising an ammonium ion;
h. the osmolality of the aqueous medium is 270-330 mOsmol/kg; or the osmolality of the aqueous medium is 270-310 mOsmol/kg;
i. the ammonium concentration in the aqueous medium is 20-60 mM; or the ammonium concentration in the aqueous medium is 50-80 mM; or the concentration of ammonium in the aqueous medium is less than 0.5 mM; or the concentration of ammonium in the aqueous medium is less than 0.5 mM;
j. the concentration of sodium chloride is 130-150 mM;
k. the aqueous medium further comprises a buffer, wherein the buffer buffers the liposome composition at a pH of 7.3-7.7, at a pH of about 7.5; or at a pH of 7.5;
l. the aqueous medium further comprises a HEPES or phosphate buffer, or the aqueous medium comprises HEPES or phosphate buffer at a concentration of 5-50 mM, or the aqueous medium comprises HEPES or phosphate buffer at a concentration of about 20 mM, or the aqueous medium comprises HEPES or phosphate buffer at a concentration of 20 mM;
m. the aqueous medium further comprises a chelator; or further comprising a chelator at a concentration of 0.1-1 mM, or further comprises a chelator at a concentration of about 0.5 mM, or further comprises a chelator at a concentration of 0.5 mM, or further comprises deferoxamine (DFO) or EDTA, or further comprises deferoxamine (DFO) or EDTA at a concentration of 0.1-1 mM, or further comprises deferoxamine (DFO) or EDTA at a concentration of about 0.5 mM, or further comprises deferoxamine (DFO) or EDTA at a concentration of 0.5 mM;
n. the liposome composition is storage stable; or
o. the AKG-38 is encapsulated in the liposomes as a sulfate salt of AKG-38.

86. An AKG-28 liposomal dispersion formulated with (5R)-3-{3-Fluoro-4-[6-(2-(2-dimethylaminoethyl)-2H-tetrazol-5-yl)-3-pyridinyl]phenyl}-5-(methylamino)-1,3-oxazolidin-2-one, or a pharmaceutically acceptable salt thereof.

87. A liposomal dispersion formulated with (5R)-3-{3-Fluoro-4-[6-(2-(2-dimethylaminoethyl)-2H-tetrazol-5-yl)-3-pyridinyl]phenyl}-5-(methylamino)-1,3-oxazolidin-2-one dihydrochloride monohydrate.

88. An isotonic liposomal dispersion of (5R)-3-{3-Fluoro-4-[6-(2-(2-dimethylaminoethyl)-2H-tetrazol-5-yl)-3-pyridinyl]phenyl}-5-(methylamino)-1,3-oxazolidin-2-one dihydrochloride monohydrate.

89. The liposomal dispersion of any one of embodiments 86-88, comprising unilamellar lipid bilayer liposome vesicles encapsulating an aqueous space containing (5R)-3-{3-Fluoro-4-[6-(2-(2-dimethylaminoethyl)-2H-tetrazol-5-yl)-3-pyridinyl]phenyl}-5-(methylamino)-1,3-oxazolidin-2-one as a sulfate salt.

90. The liposomal dispersion of embodiment 89 wherein the liposome vesicles are composed of hydrogenated soy phosphatidyl choline (HSPC), cholesterol, and (PEG(Mol. weight 2,000)-distearoylphosphatidylethanolamine, PEG-DSPE) (PEG(2000)-DSPE).
91. The liposomal dispersion of embodiment 90, comprising 45-65 mol % cholesterol relative to the sum of cholesterol and non-pegylated phospholipid in the liposome vesicles.
92. The liposomal dispersion of embodiment 90, comprising 50-60 mol % cholesterol relative to the sum of cholesterol and non-pegylated phospholipid in the liposome vesicles.
93. The liposomal dispersion of embodiment 90, comprising about 50 mol % cholesterol relative to the sum of cholesterol and non-pegylated phospholipid in the liposome vesicles.
94. The liposomal dispersion of embodiment 90, comprising about 55 mol % cholesterol relative to the sum of cholesterol and non-pegylated phospholipid in the liposome vesicles.
95. The liposomal dispersion of embodiment 90, wherein the liposomal dispersion lipid content consists of the HSPC, and PEG(2000)-DSPE.
96. The liposomal dispersion of embodiment 95, comprising HSPC and cholesterol in a weight ratio of about 5:3.
97. The liposomal dispersion of embodiment 95, comprising HSPC and cholesterol in a molar ratio of about 45:55.
98. The liposomal dispersion of embodiment 95, comprising HSPC, cholesterol and PEG(2000)-DSPE in a weight ratio of about 5:3:1.
99. The liposomal dispersion of embodiment 95, comprising HSPC, cholesterol and PEG(2000)-DSPE in a molar ratio of about 45:55:2.25.
100. The liposomal dispersion of any one of embodiments 87-99, further comprising 2-[4-(2-hydroxyethyl) piperazin-1-yl]ethanesulfonic acid (HEPES) buffer or a phosphate buffer.
101. The liposomal dispersion of embodiment 100, further comprising sodium chloride at a concentration of 50-80 mM.
102. The liposomal dispersion of any one of embodiments 99-101, further comprising ammonium displaced during drug loading process at a concentration of 20-60 mM.
103. The liposomal dispersion of any one of embodiments 99-102, wherein the liposome vesicles have a z-average diameter of 90-130 nm.
104. An AKG-38 liposomal dispersion formulated with (5R)-3-{3-Fluoro-4-[6-(2-(2-dimethylaminoethyl)-2H-tetrazol-5-yl)-3-pyridinyl]phenyl}-5-(methylacetamido)-1,3-oxazolidin-2-one, or a pharmaceutically acceptable salt thereof.
105. A liposomal dispersion formulated with (5R)-3-{3-Fluoro-4-[6-(2-(2-dimethylaminoethyl)-2H-tetrazol-5-yl)-3-pyridinyl]phenyl}-5-(methylacetamido)-1,3-oxazolidin-2-one hydrochloride.
106. An isotonic liposomal dispersion of (5R)-3-{3-Fluoro-4-[6-(2-(2-dimethylaminoethyl)-2H-tetrazol-5-yl)-3-pyridinyl]phenyl}-5-(methylacetamido)-1,3-oxazolidin-2-one hydrochloride.
107. The liposomal dispersion of any one of embodiments 104-106 comprising unilamellar lipid bilayer vesicles which encapsulate an aqueous space containing (5R)-3-{3-Fluoro-4-[6-(2-(2-dimethylaminoethyl)-2H-tetrazol-5-yl)-3-pyridinyl]phenyl}-5-(methylacetamido)-1,3-oxazolidin-2-one as a sulfate salt.
108. The liposomal dispersion of embodiment 107, wherein the liposome vesicles are composed of hydrogenated soy phosphatidyl choline (HSPC), cholesterol, and (PEG(Mol. weight 2,000)-distearoylphosphatidylethanolamine, PEG-DSPE) (PEG(2000)-DSPE).
109. The liposomal dispersion of embodiment 108, comprising 50-65 mol % cholesterol relative to the sum of cholesterol and non-pegylated phospholipid in the liposome vesicles.
110. The liposomal dispersion of embodiment 108, comprising 50-60 mol % cholesterol relative to the sum of cholesterol and non-pegylated phospholipid in the liposome vesicles.
111. The liposomal dispersion of embodiment 108, comprising about 50 mol % cholesterol relative to the sum of cholesterol and non-pegylated phospholipid in the liposome vesicles.
112. The liposomal dispersion of embodiment 108, comprising about 55 mol % cholesterol relative to the sum of cholesterol and non-pegylated phospholipid in the liposome vesicles.
113. The liposomal dispersion of embodiment 108, wherein the liposomal dispersion lipid content consists of the HSPC, and PEG(2000)-DSPE.
114. The liposomal dispersion of embodiment 113, comprising HSPC and cholesterol in a weight ratio of about 5:3.
115. The liposomal dispersion of embodiment 113, comprising HSPC and cholesterol in a molar ratio of about 45:55.
116. The liposomal dispersion of embodiment 113, comprising HSPC, cholesterol and PEG(2000)-DSPE in a weight ratio of about 5:3:1.
117. The liposomal dispersion of embodiment 113, comprising HSPC, cholesterol and PEG(2000)-DSPE in a molar ratio of about 45:55:2.25.
118. The liposomal dispersion of any one of embodiments 104-117, further comprising 2-[4-(2-hydroxyethyl) piperazin-1-yl]ethanesulfonic acid (HEPES) buffer or a phosphate buffer.
119. The liposomal dispersion of embodiment 118, further comprising sodium chloride at a concentration of 50-80 mM.
120. The liposomal dispersion of any one of embodiments 118-119, further comprising ammonium displaced during drug loading process at a concentration of 20-60 mM.
121. The liposomal dispersion of any one of embodiments 118-120, wherein the liposomes have a z-average diameter of 90-130 nm.
122. The liposomal dispersion of any one of embodiments 86-120, wherein the dispersion comprises liposome vesicles having z-average diameter of 90-130 nm.
123. The liposomal dispersion of any one of embodiments 86-121, wherein the dispersion comprises liposome vesicles having z-average diameter of 100-130 nm.
124. The liposomal dispersion of any one of embodiments 86-121, wherein the dispersion comprises liposome vesicles having z-average diameter of about 100 nm.
125. The liposomal dispersion of any one of embodiments 86-124, wherein the dispersion further comprises a chelator.
126. The liposomal dispersion of any one of embodiments 86-124, wherein the dispersion further comprises a chelator selected from the group consisting of deferoxamine (DFO) and EDTA.

127. The liposomal dispersion of any one of embodiments 86-124, wherein the dispersion further comprises a chelator selected from the group consisting of deferoxamine (DFO) and EDTA at a concentration of 0.1-1 mM.

128. The liposomal dispersion of any one of embodiments 86-124, wherein the dispersion further comprises a chelator selected from the group consisting of deferoxamine (DFO) and EDTA at a concentration of 0.5 mM.

129. The liposomal dispersion of any one of embodiments 86-128, wherein the dispersion further comprises ammonium in a concentration of 20-60 mM.

130. The liposomal dispersion of any one of embodiments 86-129, wherein the dispersion further comprises sodium chloride at a concentration of 50-80 mM.

131. An AKG-28 liposomal dispersion having a pH of 7.0-8.0, wherein the liposomal dispersion comprises a. unilamellar lipid bilayer vesicles comprising a phospholipid and over 50 mol % cholesterol; and b. (5R)-3-{3-Fluoro-4-[6-(2-(2-dimethylaminoethyl)-2H-tetrazol-5-yl)-3-pyridinyl]phenyl}-5-(methylamino)-1,3-oxazolidin-2-one as a sulfate salt formed within the liposome vesicles.

132. The liposomal dispersion of embodiment 131, formulated with (5R)-3-{3-Fluoro-4-[6-(2-(2-dimethylaminoethyl)-2H-tetrazol-5-yl)-3-pyridinyl]phenyl}-5-(methylamino)-1,3-oxazolidin-2-one hydrochloride.

133. The liposomal dispersion of embodiment 132, comprising 45-65 mol % cholesterol relative to the sum of cholesterol and non-pegylated phospholipid in the liposome vesicles.

134. The liposomal dispersion of embodiment 132, comprising 50-55 mol % cholesterol relative to the sum of cholesterol and non-pegylated phospholipid in the liposome vesicles.

135. The liposomal dispersion of embodiment 132, comprising about 50 mol % cholesterol relative to the sum of cholesterol and non-pegylated phospholipid in the liposome vesicles.

136. The liposomal dispersion of embodiment 132, comprising about 55 mol % cholesterol relative to the sum of cholesterol and non-pegylated phospholipid in the liposome vesicles.

137. The liposomal dispersion of embodiment 132, wherein the liposomal dispersion is obtained by a process comprising the step of dissolving (5R)-3-{3-Fluoro-4-[6-(2-(2-dimethylaminoethyl)-2H-tetrazol-5-yl)-3-pyridinyl]phenyl}-5-(methylamino)-1,3-oxazolidin-2-one hydrochloride in a drug loading solution and contacting the drug loading solution with extracted purified liposome vesicles comprising ammonium sulfate trapping agent to load the AKG-28 into the liposome vesicles.

138. The liposomal dispersion of any one of embodiments 131-137, wherein the unilamellar lipid bilayer vesicles comprise HSPC and cholesterol in a molar ratio of 45:55 or in a mass ratio of 5:3.

139. The liposomal dispersion of embodiment 138, wherein the unilamellar lipid bilayer vesicles consist of HSPC, cholesterol and PEG(2000)-DSPE.

140. The liposomal dispersion of embodiment 139, wherein the unilamellar lipid bilayer vesicles consist of HSPC, cholesterol and PEG(2000)-DSPE in a molar ratio of 45:55:2.25 or in a mass ratio of 5:3:1.

141. The liposomal dispersion of any one of embodiments 131-140, having a pH of 7-7.7.

142. An AKG-28 liposomal dispersion having a pH of 7.0-8.0, wherein the liposomal dispersion comprises a. unilamellar lipid bilayer vesicles comprising a phospholipid and at least 45 mol % cholesterol;

b. (5R)-3-{3-Fluoro-4-[6-(2-(2-dimethylaminoethyl)-2H-tetrazol-5-yl)-3-pyridinyl]phenyl}-5-(methylamino)-1,3-oxazolidin-2-one as a sulfate salt formed within the liposome vesicles; and c. a chelator selected from the group consisting of deferoxamine (DFO) or EDTA at the concentration of 0.1-1 mM.

143. An AKG-38 liposomal dispersion having a pH of 7.0-8.0, wherein the liposomal dispersion comprises a. unilamellar lipid bilayer liposome vesicles comprising a phospholipid and at least 50 mol % cholesterol; and b. (5R)-3-{3-Fluoro-4-[6-(2-(2-dimethylaminoethyl)-2H-tetrazol-5-yl)-3-pyridinyl]phenyl}-5-(methylacetamido)-1,3-oxazolidin-2-one as a sulfate salt formed within the liposome vesicles.

144. The liposomal dispersion of embodiment 143, formulated with (5R)-3-{3-Fluoro-4-[6-(2-(2-dimethylaminoethyl)-2H-tetrazol-5-yl)-3-pyridinyl]phenyl}-5-(methylacetamido)-1,3-oxazolidin-2-one hydrochloride.

145. The liposomal dispersion of any one of embodiment 143-144, wherein the liposomal dispersion is obtained by a process comprising a step of dissolving (5R)-3-{3-Fluoro-4-[6-(2-(2-dimethylaminoethyl)-2H-tetrazol-5-yl)-3-pyridinyl]phenyl}-5-(methylacetamido)-1,3-oxazolidin-2-one hydrochloride in a drug loading solution and contacting the drug loading solution with extracted purified liposome vesicles comprising ammonium sulfate trapping agent to load the AKG-38 into the liposome vesicles.

146. The liposomal dispersion of any one of embodiments 144-145, wherein the lipid vesicles comprise HSPC and cholesterol in a molar ratio of 45:55 or in a mass ratio of 5:3.

147. The liposomal dispersion of embodiment 146, wherein the lipid vesicles consist of HSPC, cholesterol and PEG(2000)-DSPE.

148. The liposomal dispersion of embodiment 147, wherein the lipid vesicles consist of HSPC, cholesterol and PEG(2000)-DSPE in a molar ratio of 45:55:2.25 or a mass ratio of 5:3:1.

149. The liposomal dispersion of any one of embodiments 146-148, having a pH of 7-7.7.

150. An AKG-38 liposomal dispersion having a pH of 7-8, wherein the liposomal dispersion comprises a. unilamellar lipid bilayer vesicles comprising a phospholipid and at least 50 mol % cholesterol;

b. (5R)-3-{3-Fluoro-4-[6-(2-(2-dimethylaminoethyl)-2H-tetrazol-5-yl)-3-pyridinyl]phenyl}-5-(methylacetamido)-1,3-oxazolidin-2-one as a sulfate salt formed within the liposome vesicles; and c. a chelator selected from the group consisting of deferoxamine (DFO) or EDTA at the concentration of 0.1-1 mM.

151. The liposomal dispersion of embodiment 150, formulated with a hydrochloride salt of (5R)-3-{3-Fluoro-4-[6-(2-(2-dimethylaminoethyl)-2H-tetrazol-5-yl)-3-pyridinyl]phenyl}-5-(methylacetamido)-1,3-oxazolidin-2-one.

152. The liposomal dispersion of embodiment 151, wherein the liposomal dispersion is obtained by a process comprising a step of dissolving a hydrochloride salt of (5R)-3-{3-Fluoro-4-[6-(2-(2-dimethylamino-ethyl)-2H-tetrazol-5-yl)-3-pyridinyl]phenyl}-5-(methylacetamido)-1,3-oxazolidin-2-one in a drug loading solution and contacting the drug loading solution with extracted purified liposomes comprising ammonium sulfate trapping agent to load the AKG-38 into the liposome vesicles.

153. The liposomal dispersion of any one of embodiments 150-152, wherein the lipid unilamellar lipid bilayer vesicles comprise HSPC and cholesterol in a molar ratio of 45:55 or in a mass ratio of 5:3.

154. The liposomal dispersion of embodiment 153, wherein the unilamellar lipid bilayer vesicles consist of HSPC, cholesterol and PEG(2000)-DSPE.

155. The liposomal dispersion of embodiment 154, wherein the unilamellar lipid bilayer vesicles consist of HSPC, cholesterol and PEG(2000)-DSPE in a molar ratio of 45:55:2.25 or a mass ratio of 5:3:1.

156. The liposomal dispersion of any one of embodiments 150-155, having a pH of 7-7.7.

157. The liposomal dispersion of any one of embodiments 142-145 and 150-152, comprising 50-65 mol % cholesterol relative to the sum of cholesterol and non-pegylated phospholipid in the liposome vesicles.

158. The liposomal dispersion of any one of embodiments 142-145 and 150-152, comprising 50-55 mol % cholesterol relative to the sum of cholesterol and non-pegylated phospholipid in the liposome vesicles.

159. The liposomal dispersion of any one of embodiments 142-145 and 150-152, comprising about 50 mol % cholesterol relative to the sum of cholesterol and non-pegylated phospholipid in the liposome vesicles.

160. The liposomal dispersion of any one of embodiments 142-145 and 150-152, comprising about 55 mol % cholesterol relative to the sum of cholesterol and non-pegylated phospholipid in the liposome vesicles.

161. An oxazolidinone liposomal dispersion having a pH of 7-8, wherein the liposomal dispersion comprises a. unilamellar lipid bilayer vesicles comprising a phospholipid and over 50 mol % cholesterol;

b. an oxazolidinone of Formula (I) as a sulfate salt formed within the liposome vesicles Formula (I)

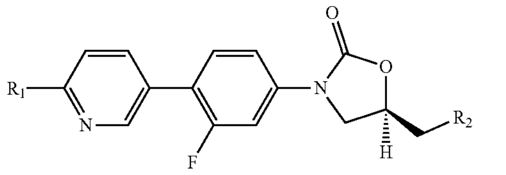

wherein $R_1$ is a tetrazole ring substituted at position 2' with an aminoalkyl;

$R_2$ is an amine ($NH_2$) or an acetamide ($NHCOCH_3$); and c. a chelator selected from the group consisting of deferoxamine (DFO) or EDTA at the concentration of 0.1-1 mM.

162. The liposomal dispersion of embodiment 161, comprising the phospholipid and the cholesterol in a mass ratio of about 5 to 3.

163. The liposomal dispersion of embodiment 161 further comprising a PEG-DSPE.

164. The liposomal dispersion of embodiment 163, wherein the liposomal composition comprises the phospholipid, cholesterol and PEG-DSPE in a mass ratio of about 5:3:2.25.

165. The liposomal dispersion of embodiment 164, wherein the liposomal composition comprises the phospholipid, cholesterol and PEG-DSPE in a molar ratio of about 45:55:2.25 mol %.

166. The liposomal dispersion of any one of embodiments 161-165, wherein the phospholipid is HSPC.

167. The liposomal dispersion of any one of embodiments 161-166, wherein the oxazolidinone is (5R)-3-{3-Fluoro-4-[6-(2-(2-dimethylaminoethyl)-2H-tetrazol-5-yl)-3-pyridinyl]phenyl}-5-(methylacetamido)-1,3-oxazolidin-2-one or a pharmaceutically acceptable salt thereof.

168. The liposomal dispersion of any one of embodiments 161-166, wherein the oxazolidinone is (5R)-3-{3-Fluoro-4-[6-(2-(2-dimethylaminoethyl)-2H-tetrazol-5-yl)-3-pyridinyl]phenyl}-5-(methylamino)-1,3-oxazolidin-2-one or a pharmaceutically acceptable salt thereof.

169. The liposomal dispersion of any one of embodiments 167-168, wherein the oxazolidinone is a sulfate salt formed within liposome vesicles comprising an ammonium sulfate (AS) trapping agent within the liposomal dispersion.

170. liposomal dispersion of any one of embodiments 161-169, wherein the unilamellar lipid bilayer vesicles comprise a total of 55 mol % cholesterol relative to the total amount of phospholipid in the liposomal dispersion.

171. The liposomal dispersion of any one of embodiments 161-170, wherein the phospholipid is present in a total of 45 mol % cholesterol relative to the total amount of phospholipid in the liposomal dispersion.

172. The liposomal dispersion of any one of embodiments 161-171, wherein the phospholipid is present in a total of 45 mol % cholesterol relative to the total amount of phospholipid in the liposomal dispersion.

173. The liposomal dispersion of any one of embodiments 161-172, wherein the oxazolidinone is a compound selected from TABLE 1, or a pharmaceutically acceptable salt thereof:

TABLE 1

| Name | Structure |
|---|---|
| AKG-1 | 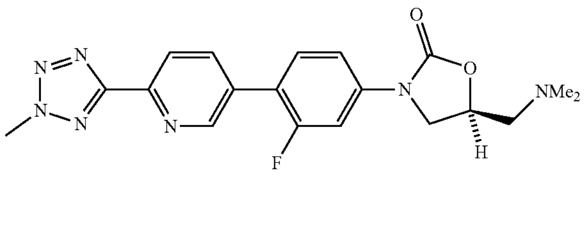 [SMILES: CN(C)C[C@H]1CN(c2ccc(-c3ccc(-c4nnn(C)n4)nc3)c(F)c2)C(=O)O1] |

TABLE 1-continued
| Name | Structure |
| --- | --- |
| AKG-2 | 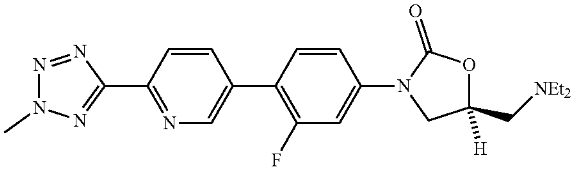 |
| AKG-3 | 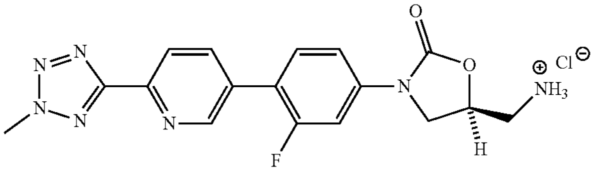 [SMILES: Cn1nnc(-c2ccc(-c3ccc(N4C[C@H](C[NH3+])OC4=O)cc3F)cn2)n1 ; [Cl-]] |
| AKG-5 | 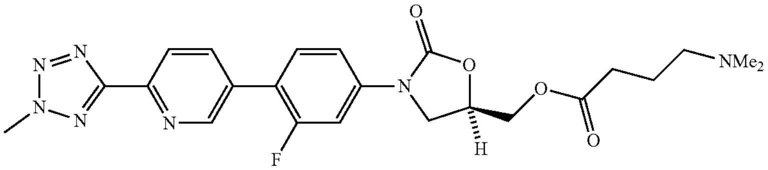 [SMILES: CN(C)CCCC(=O)OC[C@H]1CN(c2ccc(-c3ccc(-c4nnn(C)n4)nc3)c(F)c2)C(=O)O1] |
| AKG-6 | 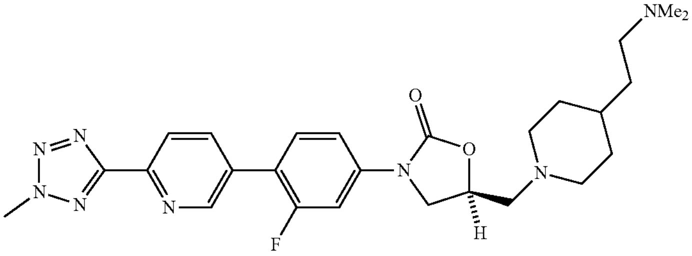 [SMILES: CN(C)CCC1CCN(C[C@H]2CN(c3ccc(-c4ccc(-c5nnn(C)n5)nc4)c(F)c3)C(=O)O2)CC1] |
| AKG-7 | 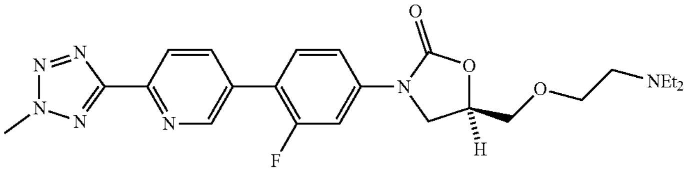 |
| AKG-8 | 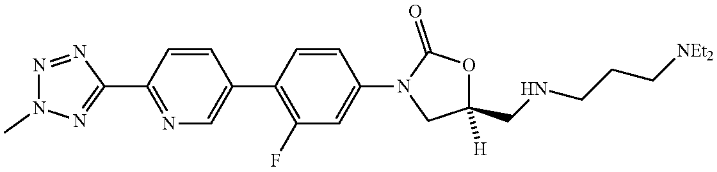 |
| AKG-9 | 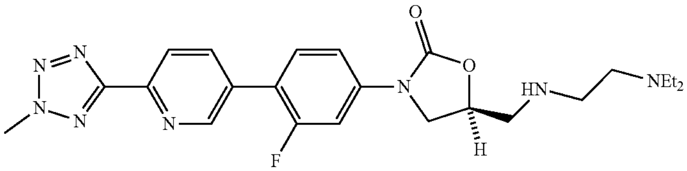 |
| AKG-11 | 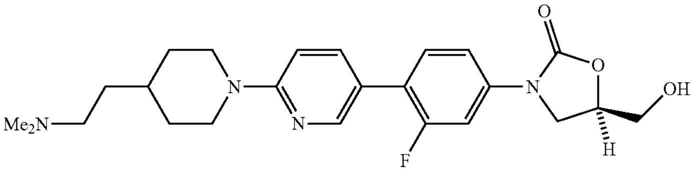 [SMILES: CN(C)CCC1CCN(c2ccc(-c3ccc(N4C[C@H](CO)OC4=O)cc3F)cn2)CC1] |

TABLE 1-continued
| Name | Structure |
|---|---|
| AKG-12 | 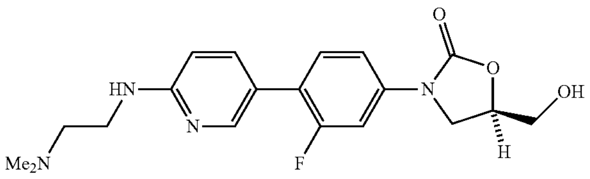 [SMILES: CN(C)CCNc1ccc(-c2ccc(N3C[C@H](CO)OC3=O)cc2F)cn1] |
| AKG-13 | 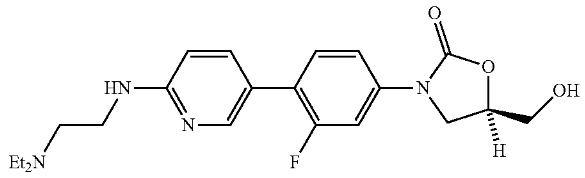 |
| AKG-14 | 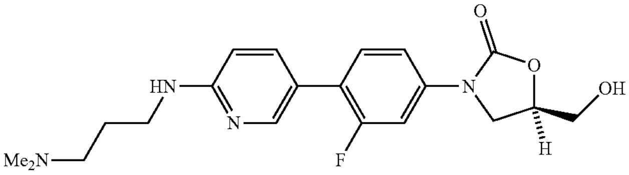 [SMILES: CN(C)CCCNc1ccc(-c2ccc(N3C[C@H](CO)OC3=O)cc2F)cn1] |
| AKG-15 | 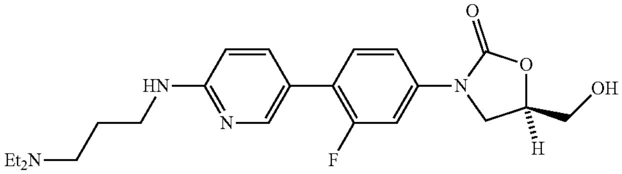 |
| AKG-16 | 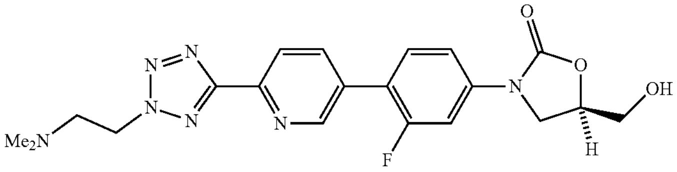 [SMILES: CN(C)CCn1nnc(-c2ccc(-c3ccc(N4C[C@H](CO)OC4=O)cc3F)cn2)n1] |
| AKG-17 | 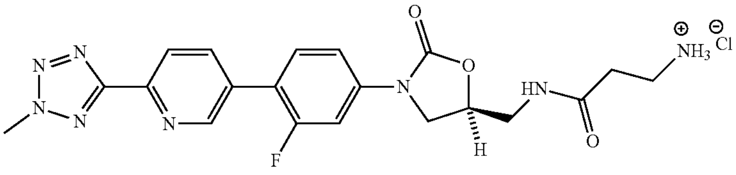 [SMILES: Cn1nnc(-c2ccc(-c3ccc(N4C[C@H](CNC(=O)CCN)OC4=O)cc3F)cn2)n1 ; [Cl-]] |
| AKG-18 | 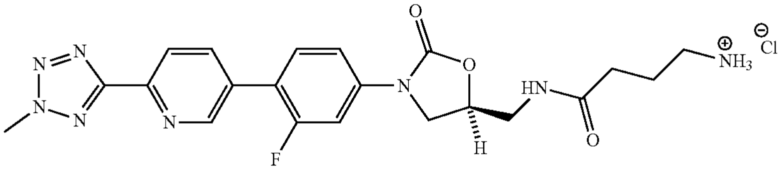 [SMILES: Cn1nnc(-c2ccc(-c3ccc(N4C[C@H](CNC(=O)CCC[NH3+])OC4=O)cc3F)cn2)n1 ; [Cl-]] |
| AKG-19 | 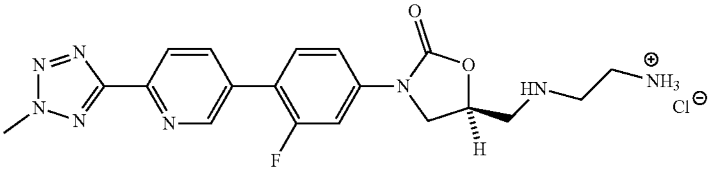 [SMILES: Cn1nnc(-c2ccc(-c3ccc(N4C[C@H](CNCC[NH3+])OC4=O)cc3F)cn2)n1 ; [Cl-]] |

TABLE 1-continued
| Name | Structure |
|---|---|
| AKG-20 | 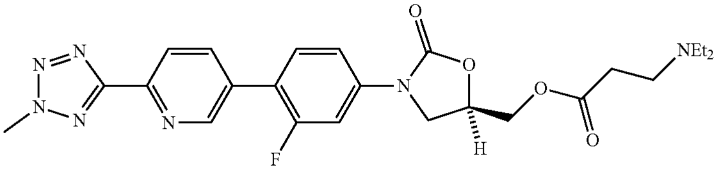 |
| AKG-21 | 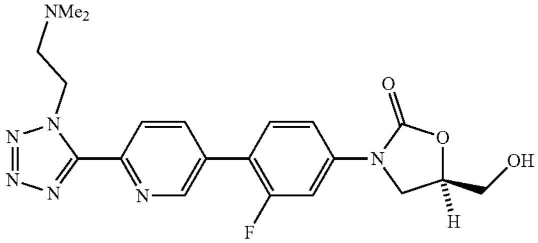 [SMILES: CN(C)CCn1nnnc1-c1ccc(-c2ccc(N3C[C@H](CO)OC3=O)cc2F)cn1] |
| AKG-22 | 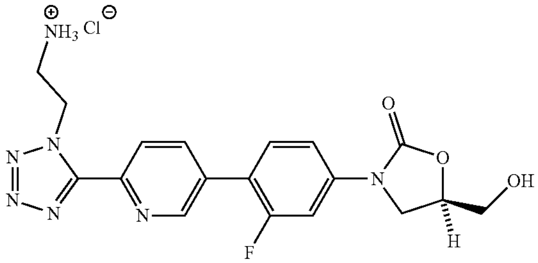 [SMILES: [Cl-] ; [NH3+]CCn1nnnc1-c1ccc(-c2ccc(N3C[C@H](CO)OC3=O)cc2F)cn1] |
| AKG-23 | 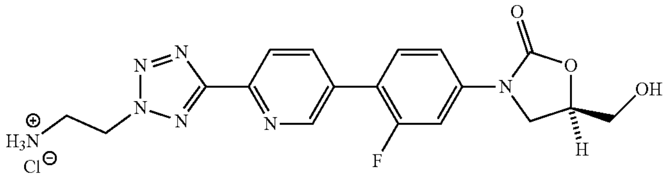 [SMILES: [NH3+]CCn1nnc(-c2ccc(-c3ccc(N4C[C@H](CO)OC4=O)cc3F)cn2)n1 ; [Cl-]] |
| AKG-24 | 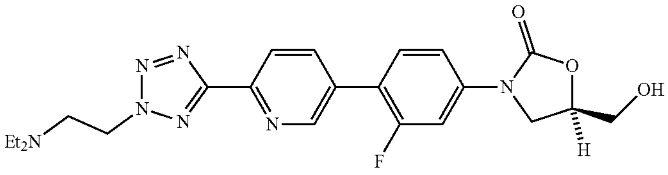 |
| AKG-25 | 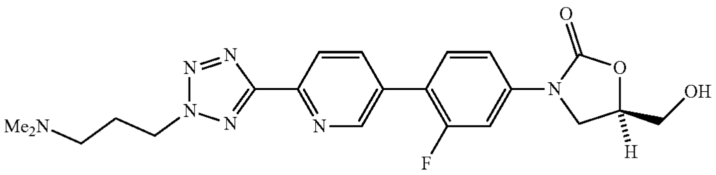 [SMILES: CN(C)CCCn1nnc(-c2ccc(-c3ccc(N4C[C@H](CO)OC4=O)cc3F)cn2)n1] |
| AKG-26 | 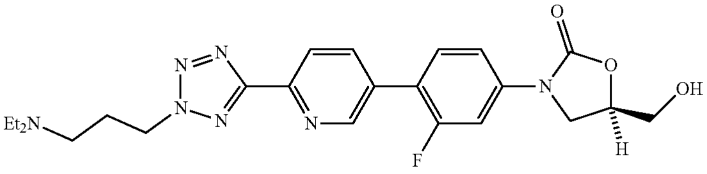 |

TABLE 1-continued
| Name | Structure |
| --- | --- |
| AKG-27 | 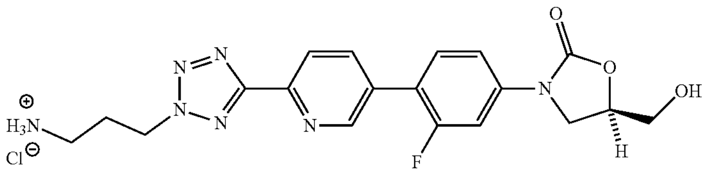 [SMILES: [Cl-] ; [NH3+]CCCn1nnc(-c2ccc(-c3ccc(N4C[C@H](CO)OC4=O)cc3F)cn2)n1] |
| AKG-28 | 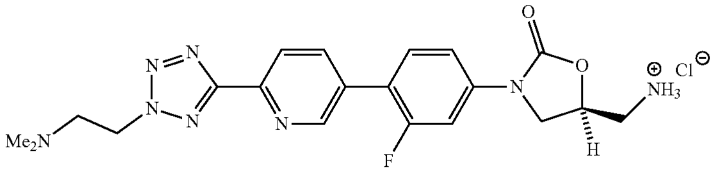 [SMILES: CN(C)CCn1nnc(-c2ccc(-c3ccc(N4C[C@H](C[NH3+])OC4=O)cc3F)cn2)n1 ; [Cl-]] |
| AKG-29 | 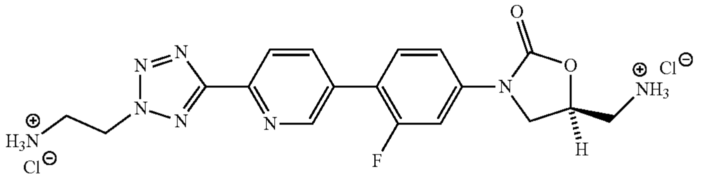 [SMILES: [NH3+]CCn1nnc(-c2ccc(-c3ccc(N4C[C@H](C[NH3+])OC4=O)cc3F)cn2)n1 ; [Cl-] ; [Cl-]] |
| AKG-30 | 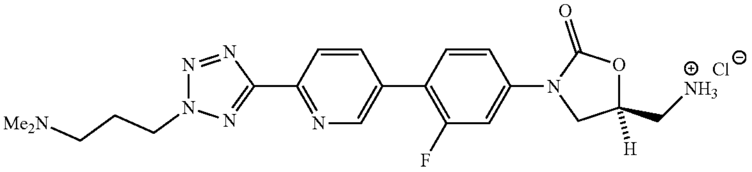 [SMILES: CN(C)CCCn1nnc(-c2ccc(-c3ccc(N4C[C@H](C[NH3+])OC4=O)cc3F)cn2)n1 ; [Cl-]] |
| AKG-31 | 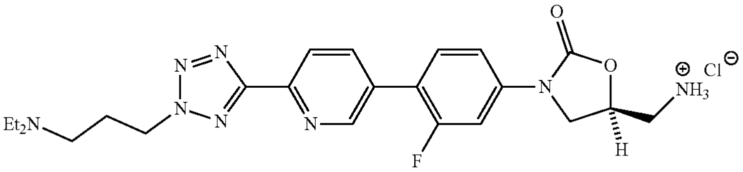 |
| AKG-38 | 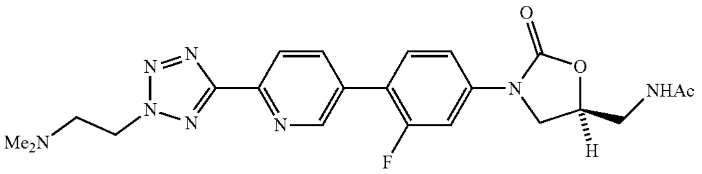 [SMILES: CC(=O)NC[C@H]1CN(c2ccc(-c3ccc(-c4nnn(CCN(C)C)n4)nc3)c(F)c2)C(=O)O1] |
| AKG-39 | 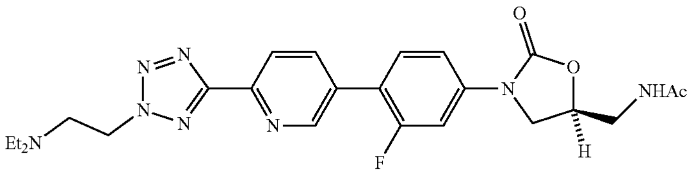 |
| AKG-40 | 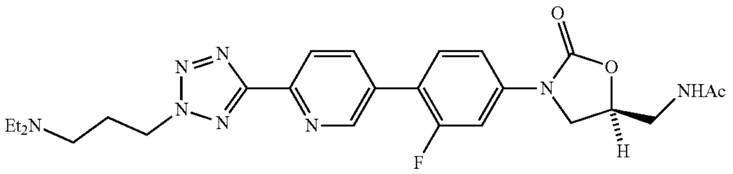 |

174. A liposomal dispersion comprising (5R)-3-{3-Fluoro-4-[6-(2-(2-dimethylaminoethyl)-2H-tetrazol-5-yl)-3-pyridinyl]phenyl}-5-(methylamino)-1,3-oxazolidin-2-one or a pharmaceutically acceptable salt thereof and lipid vesicles formed from a phospholipid, 55 mol % cholesterol and 5 mol % PEG-DSG.

175. A liposomal dispersion at a pH of 7-8, comprising (5R)-3-{3-Fluoro-4-[6-(2-(2-dimethylaminoethyl)-2H-tetrazol-5-yl)-3-pyridinyl]phenyl}-5-(methylamino)-1,3-oxazolidin-2-one or a pharmaceutically acceptable salt thereof and lipid vesicles formed from a phospholipid and 55 mol % cholesterol.

175. A liposomal dispersion comprising (5R)-3-{3-Fluoro-4-[6-(2-(2-dimethylaminoethyl)-2H-tetrazol-5-yl)-3-pyridinyl]phenyl}-5-(methylamino)-1,3-oxazolidin-2-one or a pharmaceutically acceptable salt thereof; lipid vesicles formed from a phospholipid and 55 mol % cholesterol; and a chelator.

176. The liposomal dispersion of embodiment 175, wherein the chelator is selected from the group consisting of: deferoxamine (desferrioxamine, Desferal), ethylenediamine tetraacetic acid (EDTA), diethylenetriamine pentaacetic acid (DTPA), nitrilotriacetic acid (NTA), ethyleneglycol-O,O'-bis(2-aminoethyl)-N,N,N',N'-tetraacetic acid (EGTA), N-(2-hydroxyethyl)ethylenediamine-N,N',N'-triacetic acid (HEDTA), and 1,4,7,10-tetraazacyclododecane-1,4,7,10-tetraacetic acid (DOTA).

177. A liposomal dispersion comprising (5R)-3-{3-Fluoro-4-[6-(2-(2-dimethylaminoethyl)-2H-tetrazol-5-yl)-3-pyridinyl]phenyl}-5-(methylacetamido)-1,3-oxazolidin-2-one or a pharmaceutically acceptable salt thereof and lipid vesicles formed from a phospholipid, 55 mol % cholesterol and 5 mol % PEG-DSG.

178. A liposomal dispersion at a pH of 7-8, comprising (5R)-3-{3-Fluoro-4-[6-(2-(2-dimethylaminoethyl)-2H-tetrazol-5-yl)-3-pyridinyl]phenyl}-5-(methylacetamido)-1,3-oxazolidin-2-one or a pharmaceutically acceptable salt thereof and lipid vesicles formed from a phospholipid and 55 mol % cholesterol.

179. A liposomal dispersion comprising (5R)-3-{3-Fluoro-4-[6-(2-(2-dimethylaminoethyl)-2H-tetrazol-5-yl)-3-pyridinyl]phenyl}-5-(methylacetamido)-1,3-oxazolidin-2-one or a pharmaceutically acceptable salt thereof; lipid vesicles formed from a phospholipid and 55 mol % cholesterol; and a chelator.

180. The liposomal dispersion of embodiment 179, wherein the chelator is selected from the group consisting of: deferoxamine (desferrioxamine, Desferal), ethylenediamine tetraacetic acid (EDTA), diethylenetriamine pentaacetic acid (DTPA), nitrilotriacetic acid (NTA), ethyleneglycol-O,O'-bis(2-aminoethyl)-N,N,N',N'-tetraacetic acid (EGTA), N-(2-hydroxyethyl)ethylenediamine-N,N',N'-triacetic acid (HEDTA), and 1,4,7,10-tetraazacyclododecane-1,4,7,10-tetraacetic acid (DOTA).

181. A liposomal dispersion comprising (5R)-3-{3-Fluoro-4-[6-(2-(2-dimethylaminoethyl)-2H-tetrazol-5-yl)-3-pyridinyl]phenyl}-5-(methylacetamido)-1,3-oxazolidin-2-one or a pharmaceutically acceptable salt thereof and lipid vesicles formed from a phospholipid, 55 mol % cholesterol and 5 mol % PEG-DSG.

ADDITIONAL EMBODIMENTS

Further Embodiments

The following additional embodiments are provided for illustrative purposes. Additional embodiments include the oxazolidinone liposomal compositions described in the following additional embodiments below, and other combinations of features recited thereon:

1. A liposomal pharmaceutical composition having a pH of 7.3-7.7 and comprising
   a. a chelator selected from the group consisting of DFO, EDTA and DTPA;
   b. liposomes vesicles comprising a phospholipid and greater than 40 mol % cholesterol relative to the total phospholipid in the liposomal composition, and
   c. a sulfate salt of a compound of Formula (I) encapsulated in the liposome vesicles Formula (I)

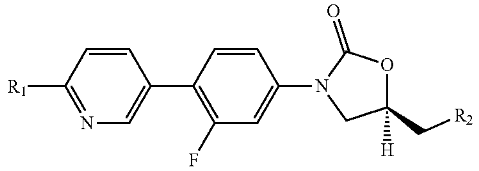

wherein $R_2$ is an amine ($NH_2$) or an acetamide ($NHCOCH_3$), and wherein $R_1$ is a tetrazole ring substituted at position 2' with an aminoalkyl.

2. The liposomal composition of embodiment 1, wherein the aminoalkyl is dimethylaminoethyl.
3. The liposomal composition of embodiment 1, the liposome vesicles comprising a compound of Formula 1b:

Formula 1b

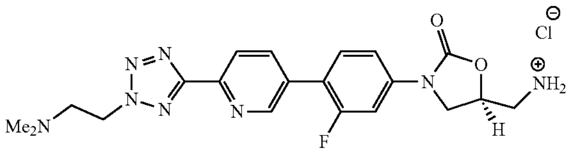

4. The liposomal composition of embodiment 1, the liposome vesicles comprising a compound of Formula 1c Formula 1c

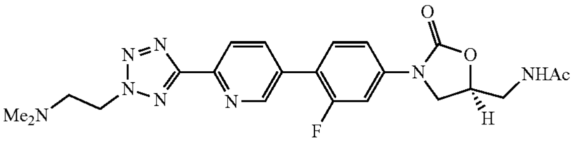

5. The liposomal composition of embodiment 1, the liposome vesicles comprising a compound of Formula 1d or Formula 1e Formula 1d

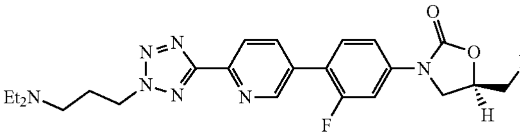

NHAc;

Formula 1e

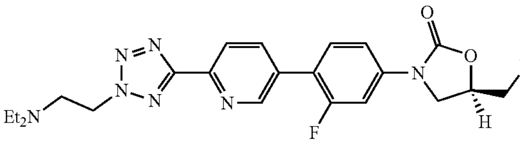

NHAc.

6. The liposomal composition of any one of embodiments 1 to 5, wherein the liposome vesicles are in an aqueous medium.
7. The liposomal composition of any one of embodiments 1 to 5, wherein the compound is entrapped in the liposome vesicles with a trapping agent, and wherein the trapping agent comprises a polyanion.
8. The liposomal composition of embodiment 7, wherein the trapping agent is triethylammonium sucrose octasulfate or ammonium sulfate.
9. The liposomal composition of embodiment 7, wherein the trapping agent is triethylammonium sucrose octasulfate.
10. The liposomal composition of embodiment 7, wherein the trapping agent is ammonium sulfate.
11. The liposomal composition of any one of embodiments 1 to 5, comprising a salt of the compound, wherein the salt is sulfate, citrate, sucrosofate, a salt with a phosphorylated or sulfated polyol, or a salt with a phosphorylated or sulfated polyanionic polymer.
12. The liposomal composition of any one of embodiments 1 to 5, comprising a salt of the compound, wherein the salt is sulfate.
13. The liposomal composition of any one of embodiments 1 to 5, wherein the compound in the liposome vesicles has an aqueous solubility less than 1 mg/mL.
14. The composition of any one of embodiments 1 to 5, wherein the compound in the liposome vesicles has an aqueous solubility less than 0.1 mg/mL.
15. The liposomal composition of any one of embodiments 1 to 5, wherein the liposome vesicles comprise a membrane comprising phosphatidylcholine and cholesterol.
16. The liposomal composition of embodiments 1 to 5, wherein the membrane separates the inside of the liposome vesicles from the aqueous medium.
17. The liposomal composition of embodiment 15, wherein the phosphatidylcholine is distearoylphosphatidylcholine (DSPC) or hydrogenated soy phosphatidylcholine (HSPC).
18. The liposomal composition of embodiment 15, wherein the phosphatidylcholine to cholesterol molar ratios is from about 60:40 to about 35:65.
19. The liposomal composition of embodiment 15, wherein the phosphatidylcholine to cholesterol molar ratio is from about 55:45 to about 35:65.
20. The liposomal composition of embodiment 15, wherein the phosphatidylcholine to cholesterol molar ratio is from about 50:50 to about 45:55.
21. The liposomal composition of embodiment 15, wherein the phosphatidylcholine to cholesterol molar ratio is from about 50:50 to about 40:60.
22. The liposomal composition of any one of embodiments 15 to 21, wherein the membrane further comprises a polymer-conjugated lipid.
23. The liposomal composition of any one of embodiments 1 to 5, wherein the liposome vesicles comprise HSPC, cholesterol and polymer-conjugated lipid in a about 45:55:2.75 molar ratio.
24. The liposomal composition of embodiment 22 or embodiment 23, wherein the polymer-conjugated lipid is PEG(Mol. weight 2,000)-distearoylglycerol (PEG-DSG) or PEG(Mol. weight 2,000)-distearoylphosphatidylethanolamine (PEG-DSPE).
25. The liposomal composition of any one of embodiments 1 to 5, wherein the composition is a liquid pharmaceutical formulation for parenteral administration.
26. The liposome composition of any of the embodiments 1 to 5 wherein the liposomes have a Z-average particle size ranging from about 80 to about 130 nm.
27. A method of treating bacterial infection, the method comprising administering to a subject in need thereof a therapeutically effective amount of the liposomal composition of any one of embodiments 1 to 5.
28. The method of embodiment 27, wherein the bacterial infection is *Mycobacterium tuberculosis* infection.
29. The method of embodiment 27 or embodiment 28, wherein the compound in the liposome vesicles has a minimum inhibitory concentration (MIC) ranging from about 0.01 μg/ml to about 0.25 μg/ml.
30. The method of embodiment 27 or embodiment 28, wherein the compound in the liposome vesicles has a MIC ranging from about 0.01 μg/ml to about 0.1 μg/ml.
31. The method of any one of embodiments 27-30, comprising administering the liposomal composition parenterally.
32. The method of embodiment 31, wherein the method comprises administering simultaneously or sequentially one or more active agents.
33. The method of embodiment 32, wherein the one or more active agents comprise bedaquiline, pretomanid, pyrazinamide, moxifloxacin, a pharmaceutically acceptable salt thereof or a combination thereof.
34. The method of embodiment 31, wherein the liposomal composition is administered once a week to once every six weeks.
35. The method of embodiment 31, wherein the percentage of compound remaining in blood following administration to the subject in need thereof is greater than 20% of the administered amount at 6 hours.
36. The method of embodiment 31, wherein the percentage of compound remaining in blood following administration to the subject in need thereof is greater than 10% of the administered amount.
37. A method of making liposome composition comprising the steps of:
(i) preparing the liposomes comprising phospholipid, cholesterol, and PEG-lipid, and having an interior space containing a trapping agent, in a medium substantially free from the trapping agent;
(ii) contacting the liposomes with a compound of any one of embodiments 1 to 8 in an aqueous medium to effect encapsulation of the compound in the liposomes;

(iii) removing unencapsulated compound; and (iv) providing the liposomes in a physiologically acceptable medium suitable for parenteral use.

EXAMPLES

The following examples, including the experiments conducted and results achieved are provided for illustrative purposes only and are not to be construed as limiting the disclosure.

Example 1—Synthesis of Oxazolidinone Derivatives

Compounds AKG-1, AKG-2, AKG-6, AKG-8, AKG-9 and AKG-19 were synthesized by reacting Tedizolid mesylate (Tedizolid-MS) with respective amines at 60° C. in N-methyl-2-pyrrolidone (NMP) as a solvent (Scheme-1). Tedizolid-MS was obtained by mesylation of the 1° hydroxyl group of Tedizolid with methanesulfonyl chloride in the presence of a base at room temperature (RT). Treatment of Tedizolid-MS with sodium azide followed by reduction of the resulting azide (AKG-3-A) gave either Intermediate-1 as a free base or AKG-3 as a hydrochloride salt depending on eluant selected for purification. Amidation of Intermediate-1 with the corresponding acid followed by hydrochloride salt formation using HCl/EtOAc resulted in compounds AKG-17 and AKG-18. Reacting Tedizolid with the corresponding dialkylamino acid under standard esterification conditions resulted in compounds AKG-5 and AKG-20. O-alkylation of Tedizolid with 2-chloro-N,N-diethylamino ethylamine using sodium hydride as a base gave compounds AKG-7.

Intermediate-2 was synthesized by boronation of commercially available aryl bromide using bis(pinocolato)diboron (Scheme-2). Suzuki coupling of Intermediate-2 with readily available 5-bromo-2-fluoropyridine resulted in Intermediate-3, which was heated in NMP in a sealed tube with the corresponding amine to give compounds AKG-11 to AKG-15.

Compounds AKG-16, AKG-21 to AKG-27 were prepared in a convergent synthesis starting from Intermediate-4 (Schemes-3 and 4). Click chemistry using sodium azide on 5-bromo-2-cyanopyridine gave Intermediate-4. N-alkylation of the tetrazole in Intermediate-4 resulted in Intermediates 5 and 6 in 3:1 ratio. The structure of these intermediates was deduced from HMBC analysis. Intermediates 7 to 12 were synthesized and the regioisomers were obtained in a similar manner (Only desired isomers are shown in Scheme-4). Suzuki coupling of Intermediates 5 to 12 with Intermediate 2 and deprotection of amine group where applicable resulted in compounds AKG-16, AKG-21 to AKG-27.

Intermediate-13 was synthesized by mesylation of readily available aryl bromide. Intermediate-15 was obtained by reducing Intermediate-14 with hydrazine (Scheme-5). Boc protection or acetylation of the primary amine in Intermediate-15 followed by boronation resulted in Intermediates-18 and 19, respectively. Suzuki (U.S. Pat. Appl. Publ. No. 20100022772, PCT Int. Appl. Publ. No. WO2013044845, which are incorporated herein by reference in their entireties) coupling of the boronate intermediates with the corresponding aryl bromide intermediates and deprotection of the amine group where applicable resulted in compounds AKG-28 to AKG-31 and AKG-38 to AKG-40.

Synthetic Schemes

See U.S. Pat. Appl. Publ. No. 20100022772, PCT Int. Appl. No. 2013044845 which are incorporated herein by reference in their entireties, for the synthesis of Intermediate-19.

FIG. 24 shows synthesis Scheme-1.

FIG. 25 shows synthesis Scheme-2.

Figure 26:
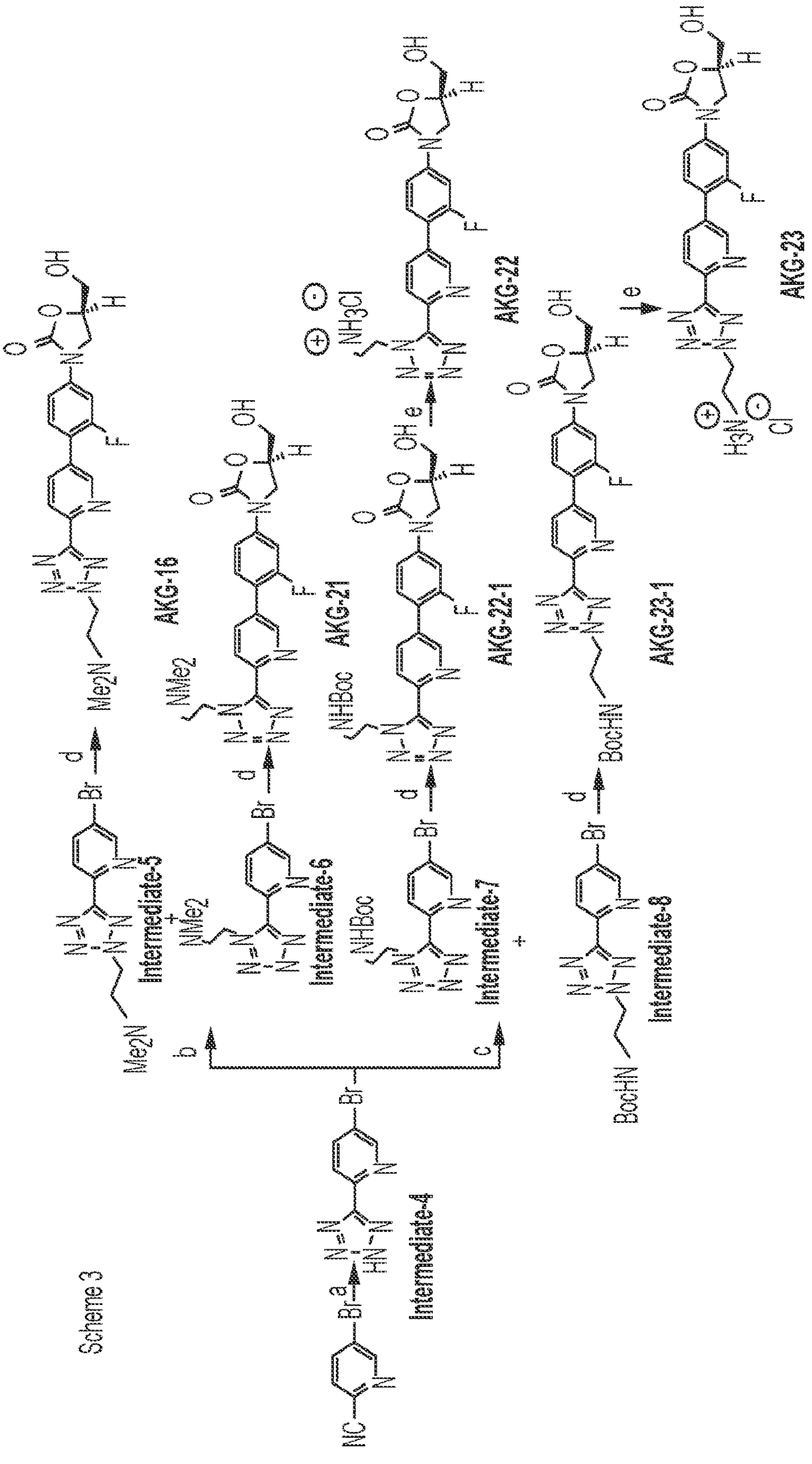
FIG. 26 shows synthesis Scheme-3 according to embodiments of the disclosure.

FIG. 26 shows synthesis Scheme-3.

Figure 27:
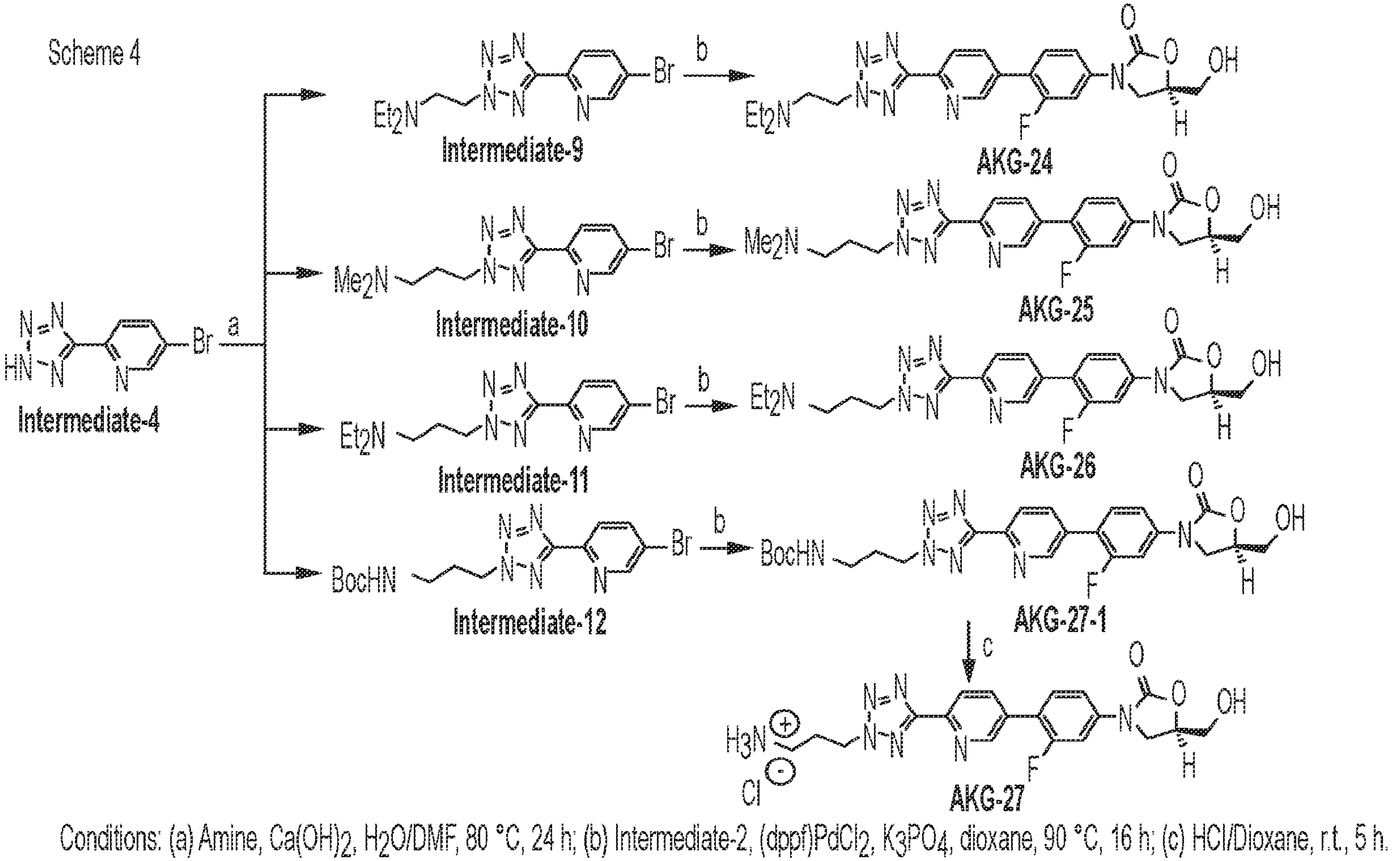
FIG. 27 shows synthesis Scheme-4 according to embodiments of the disclosure.

FIG. 27 shows synthesis Scheme-4.

Figure 28:
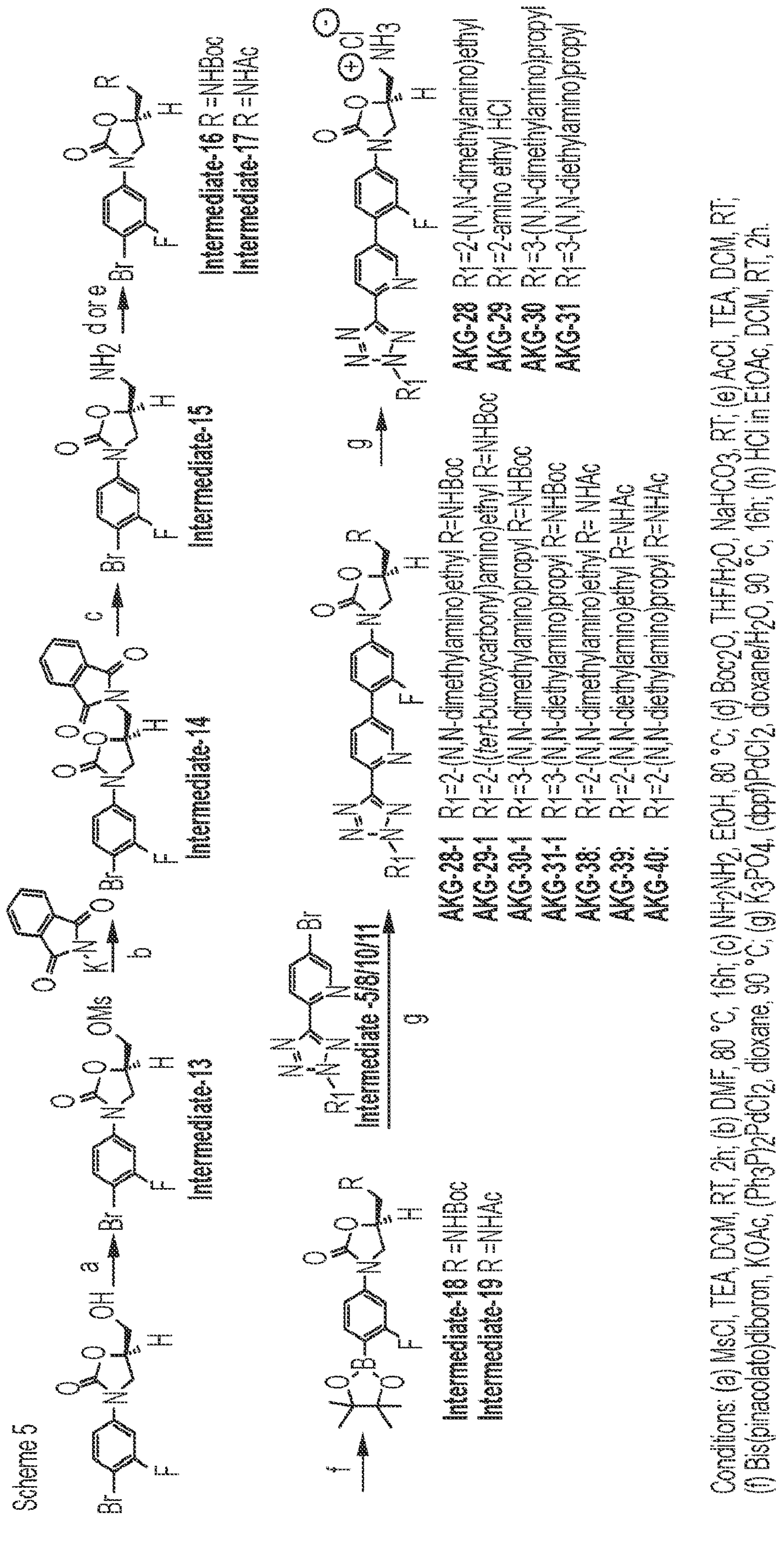
FIG. 28 shows synthesis Scheme-5 according to embodiments of the disclosure.

FIG. 28 shows synthesis Scheme-5.

Synthesis

Materials and Methods

Tedizolid, (R)-3-(4-bromo-3-fluorophenyl)-5-(hydroxymethyl)oxazolidin-2-one were purchased from Skychemical and Dimethyl-(2-piperidin-4-yl-ethyl)-amine was purchased from Enamine, the other reagents and solvents were purchased from Adams and were used as received. The chemical structures of final products were characterized by nuclear magnetic resonance spectra ($^1$H NMR, $^{13}$C NMR) determined on a Bruker NMR spectrometer (500 MHz or 400 MHz). $^{13}$C NMR spectra were fully decoupled. Chemical shifts were in parts per millions (ppm) using deuterated solvent peak or tetramethylsilane (internal) as the internal standards. Data for $^1$H NMR are recorded as follows: chemical shift (d, ppm), multiplicity (s, singlet; br s, broad singlet; d, doublet; t, triplet; m, multiplet), integration, coupling constant (Hz). Data for $^{13}$C NMR are recorded in terms of chemical shift (d, ppm). The purity of final products (≥95%) was confirmed by analytical HPLC. Analytical HPLC was performed on an Agilent analytical HPLC system using a Sunfire column, 3.5 μm (150 cm×4.6 mm) and a gradient system (water (0.01% TFA)/ACN (0.01% TFA)) and a flow rate of 1 mL/min with detection at 254 and 214 nm. Flash Chromatographic (FC) purifications were performed with Silica Gel 60 from Santai Technologies (0.04-0.063 nm; 230-400 mesh).

Procedure A. The reaction mixture of Tedizolid-Ms (1.0 eq), $R_1R_2NH$ (4.0 eq) in NMP (10 mL) was heated to 60° C. for 15 h in a sealed tube. Upon completion (LCMS), the reaction was diluted with $H_2O$ (40 mL) and extracted with EtOAc (2×50 mL). The combined extracts were washed with saturated brine dried over $Na_2SO_4$ and filtered. The solvent was removed in vacuo and the residue was purified using FC to give the product with >95% purity.

1. Synthesis of Tedizolid-Ms

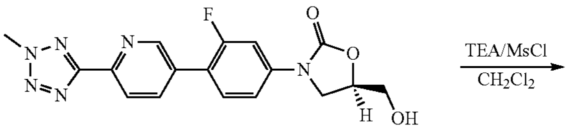

Tedizolid

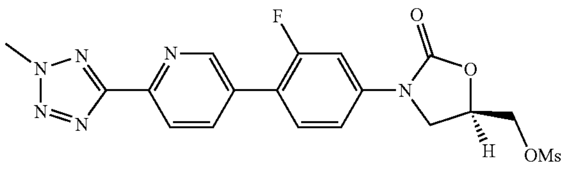

Tedizolid-Ms

To a solution of Tedizolid (7.00 g, 18.90 mmol) and triethylamine (3.83 g, 37.80 mmol) in $CH_2Cl_2$ (50 mL) at 0° C. was added dropwise methanesulfonyl chloride (3.25 g, 28.36 mmol) at 0° C. under Ar. After stirring at RT for 2 h, the reaction mixture was poured into water and extracted with $CH_2Cl_2$. The organic layer was washed with brine, dried over $Na_2SO_4$ and collected by filtration. The solvent was removed in vacuum to give the pure product Tedizolid-Ms (7.0 g, 82.6% yield) as a yellow solid. $^{1}$H NMR (400 MHz, DMSO-$d_6$) δ 8.95 (s, 1H), 8.31-8.14 (m, 2H), 7.88-7.65 (m, 2H), 7.53 (d, J=8.6 Hz, 1H), 5.14-4.96 (m, 1H), 4.59-4.39 (m, 5H), 4.28 (t, J=9.4 Hz, 1H), 3.92 (dd, J=9.2, 6.3 Hz, 1H), 3.28 (s, 3H). MS (ESI+) m/z 449.1 ([M+1]$^+$).

2. Synthesis of AKG-1, 2, 6, 8, 9 and 19

AKG-1

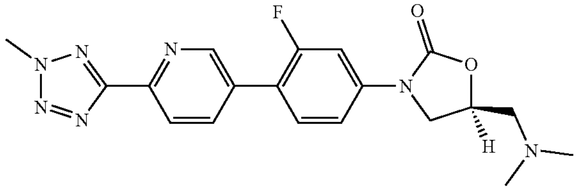

Using procedure A, AKG-1 was obtained from Tedizolid-Ms and dimethylamine as a white solid (0.5 g, 56.4% yield). $^{1}$H NMR (400 MHz, DMSO-$d_6$) δ 8.94 (s, 1H), 8.32-8.13 (m, 2H), 7.83-7.64 (m, 2H), 7.54 (d, J=7.6 Hz, 1H), 4.87 (s, 1H), 4.49 (s, 3H), 4.21 (t, J=8.6 Hz, 1H), 3.84 (t, J=7.4 Hz, 1H), 2.62 (s, 2H), 2.25 (s, 6H). $^{13}$C NMR (101 MHz, DMSO-$d_6$) δ 164.3, 161.0, 158.6, 154.6, 149.9, 145.5, 140.9, 137.6, 132.1, 131.4, 122.6, 119.1, 114.6, 106.0, 72.0, 62.1, 48.7, 46.4, 40.2. MS (ESI+) m/z 398.2 ([M+1]$^+$).

AKG-2

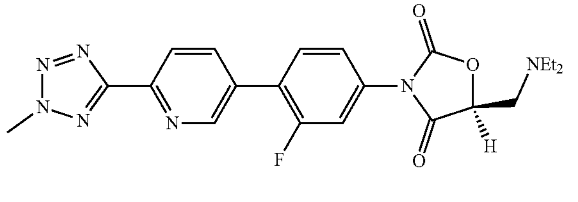

Using procedure A, AKG-2 was obtained from Tedizolid-Ms and diethylamine as a white solid (0.52 g, 54.8% yield). H NMR (400 MHz, DMSO-$d_6$) δ 8.94 (s, 1H), 8.29-8.11 (m, 2H), 7.81-7.65 (m, 2H), 7.52 (dd, J=8.6, 1.8 Hz, 1H), 4.89-4.73 (m, 1H), 4.49 (s, 3H), 4.19 (t, J=8.8 Hz, 1H), 3.82 (dd, J=8.7, 7.0 Hz, 1H), 2.75 (dd, J=5.1, 3.7 Hz, 2H), 2.57 (q, J=6.9 Hz, 4H), 0.97 (t, J=7.1 Hz, 6H). $^{1}$C NMR (101 MHz, DMSO-$d_6$) δ 164.3, 161.0, 158.6, 154.7, 149.9, 145.5, 141.0, 137.6, 132.1, 131.3, 122.5, 119.1, 114.6, 106.1, 72.6, 56.1, 48.6, 47.7, 40.3, 12.3. MS (ESI+) m/z 426.3 ([M+1]$^+$).

AKG-6

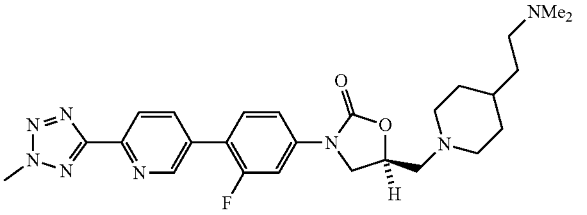

Using procedure A, AKG-6 was obtained from Tedizolid-Ms and N,N-Dimethyl-2-(piperidin-4-yl)ethan-1-amine as a white solid (0.66 g, 58.2% yield). $^{1}$H NMR (400 MHz, $CDCl_3$) δ 8.93 (s, 1H), 8.30 (dd, J=8.1, 2.4 Hz, 1H), 8.05 (d, J=7.8 Hz, 1H), 7.62 (d, J=12.9 Hz, 1H), 7.56-7.47 (m, 1H), 7.45-7.37 (m, 1H), 4.89-4.74 (m, 1H), 4.48 (s, 3H), 4.11 (t, J=8.6 Hz, 1H), 3.86 (t, J=7.8 Hz, 1H), 2.93 (dd, J=28.8, 10.9 Hz, 2H), 2.80-2.64 (m, 2H), 2.50-2.04 (m, 11H), 1.69 (d, J=10.8 Hz, 2H), 1.48 (d, J=7.1 Hz, 2H), 1.37-1.19 (m, 4H). $^{13}$C NMR (101 MHz, $CDCl_3$) δ 164.7, 161.3, 158.8, 154.3, 149.9, 145.4, 140.2, 137.0, 132.3, 130.5, 122.0, 120.0, 113.8, 106.4, 71.5, 61.4, 57.0, 55.3, 54.3, 48.9, 45.0, 39.7, 33.6, 32.4. MS (ESI+) m/z 509.2 ([M+1]$^+$).

AKH-8

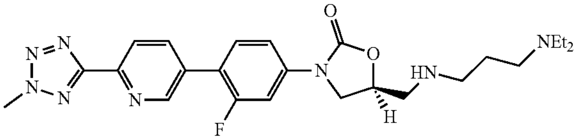

Using procedure A, AKG-8 was obtained from Tedizolid-Ms and $N^1,N^1$-diethylpropane-1,3-diamine as a white solid (0.62 g, 57.6% yield). $^{1}$H NMR (400 MHz, DMSO-$d_6$) δ 8.94 (s, 1H), 8.34-8.11 (m, 2H), 7.84-7.59 (m, 2H), 7.52 (dd, J=8.6, 2.0 Hz, 1H), 4.80 (dd, J=8.3, 5.7 Hz, 1H), 4.49 (s, 3H), 4.18 (t, J=8.9 Hz, 1H), 3.90 (dd, J=8.8, 6.5 Hz, 1H), 2.94-2.77 (m, 2H), 2.66-2.53 (m, 7H), 1.65-1.51 (m, 2H), 0.99 (t, J=7.1 Hz, 6H). $^{13}$C NMR (101 MHz, DMSO-$d_6$) δ 164.3, 161.0, 158.6, 154.6, 149.9, 145.5, 141.0, 137.6, 132.1, 131.4, 122.6, 119.1, 114.6, 106.1, 73.2, 52.1, 50.7, 48.2, 48.0, 46.7, 40.3, 26.4, 11.4. m/z 483.2 ([M+1]$^+$).

AKH-9

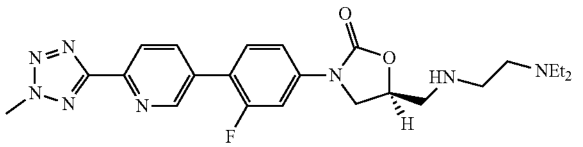

Using procedure A, AKG-9 was obtained from Tedizolid-Ms and $N^1,N^1$-diethylethane-1,2-diamine as a white solid (0.36 g, 34.4% yield). $^{1}$H NMR (500 MHz, DMSO-$d_6$) δ 8.94 (s, 1H), 8.26-8.16 (m, 2H), 7.78-7.66 (m, 2H), 7.53 (d, J=8.5 Hz, 1H), 4.85-4.73 (m, 1H), 4.49 (s, 3H), 4.18 (t, J=8.8 Hz, 1H), 3.90 (t, J=7.5 Hz, 1H), 2.88 (t, J=5.4 Hz, 2H), 2.65 (t, J=6.1 Hz, 2H), 0.95 (t, J=7.0 Hz, 6H). $^{13}$C NMR (101 MHz, DMSO-$d_6$) S 164.3, 161.0, 158.6, 154.7, 149.9, 145.5, 141.0, 137.6, 132.1, 131.4, 122.6, 119.1, 114.6, 106.1, 73.3, 52.6, 52.2, 48.1, 47.6, 47.1, 40.3, 12.0. m/z 469.3 ([M+1]$^+$).

Using procedure A, AKG-19 was obtained from Tedizolid-Ms and ethane-1,2-diamine as a white solid (0.60 g, 55% yield). $^1$H NMR (500 MHz, DMSO-$d_6$) δ 10.33 (s, 1H), 9.89 (s, 1H), 8.95 (s, 1H), 8.58 (s, 3H), 8.23 (q, J=8.3 Hz, 2H), 7.79 (t, J=8.8 Hz, 1H), 7.69 (d, J=13.5 Hz, 1H), 7.49 (d, J=8.7 Hz, 1H), 5.25-5.19 (m, 1H), 4.49 (s, 3H), 4.33 (t, J=9.2 Hz, 1H), 4.05 (dd, J=9.1, 6.7 Hz, 1H), 3.52 (s, 2H), 3.43-3.23 (m, 4H). $^{13}$C NMR (101 MHz, DMSO-$d_6$) δ 164.26, 160.94, 158.50, 153.79, 149.84, 145.51, 140.58, 137.78, 132.04, 131.42, 122.61, 119.50, 114.94, 106.46, 69.38, 49.59, 47.87, 45.16, 40.34, 35.58.

3. Synthesis of AKG-3

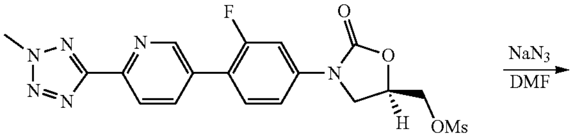

Tedizolid-Ms

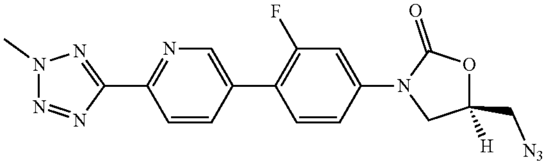

AKG-3-1

To a solution of Tedizolid-Ms (1.00 g, 2.23 mmol) in DMF (20 mL) was added $NaN_3$ (0.44 g, 6.69 mmol). After stirring at 90° C. for 3 h, the reaction mixture was poured into water and extracted with EtOAc. The organic layer was washed with brine, dried over anhydrous $MgSO_4$, filtered and concentrated in vacuo. The residue was further purified by column chromatography to obtain the title compound AKG-3-1 (0.7 g, 79.4% yield) as white solid.

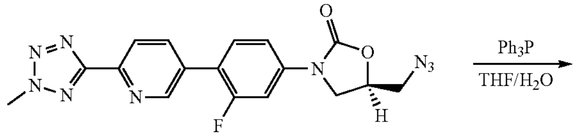

AKG-3-1

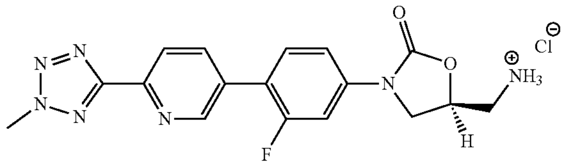

AKG-3

The reaction mixture of AKG-3-1 (0.7 g, 1.77 mmol) and $Ph_3P$ (1.39 g, 5.31 mmol) in $H_2O$ (2 mL) and THF (20 mL) was heated to reflux for 1 h. After completion of (LCMS), the reaction was concentrated in vacuo and purified using reverse phase FC. While purification using MeOH in DCM 0-10% as eluant and freeze drying gave freebase Intermediate-1 (2.5 g, 76.5% yield) as a yellow solid, FC purification with MeCN in 0.006M HCl in $H_2O$/0-30% as eluant gave hydrochloride salt AKG-3 (0.35 g, 48.8% yield) as a yellow solid after freeze drying. $^1$H NMR (400 MHz, DMSO-$d_6$) δ 8.95 (s, 1H), 8.61 (s, 3H), 8.28-8.18 (m, 2H), 7.79 (t, J=8.8 Hz, 1H), 7.69 (dd, J=13.5, 2.1 Hz, 1H), 7.48 (dd, J=8.6, 2.1 Hz, 1H), 5.13-5.00 (m, 1H), 4.49 (s, 3H), 4.29 (t, J=9.2 Hz, 1H), 4.02 (dd, J=9.3, 6.6 Hz, 1H), 3.34-3.23 (m, 2H). $^{13}$C NMR (101 MHz, DMSO-$d_6$) δ 163.8, 160.4, 158.0, 153.4, 149.4, 145.1, 140.2, 137.2, 131.5, 130.9, 122.1, 118.9, 114.3, 105.9, 69.8, 47.1, 41.4, 39.8. m/z 370.3 ([M−HCl+1]$^+$).

4. Synthesis of AKG-17

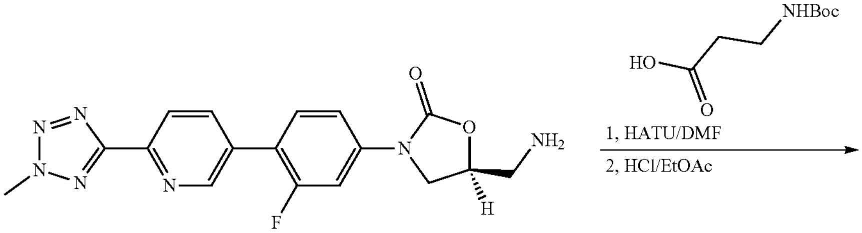

Intermediate 1

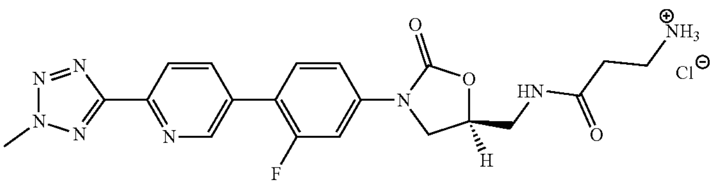

AKG-17

To a solution of 3-((tert-butoxycarbonyl)amino)propanoic acid (0.62 g, 3.25 mmol, 1.2 eq) and TEA (0.63 g, 6.25 mmol, 2.5 eq) in DMF (10 mL) was added HATU (1.44 g. 3.78 mmol, 1.4 eq) at RT under Ar. The mixture was stirred for 0.5 h and then Intermediate 1 (1.0 g, 2.70 mmol, 1.0 eq) was added. The whole mixture was stirred at RT overnight. LCMS showed the reaction was complete, it was poured into $H_2O$ and the solid was collected by filtration and washed with $H_2O$. The solid was dried in vacuo and the residue was used in the next step directly by dissolving it into EtOAc and then HCl/EtOAc (4 M, 20 mL) was added. The whole mixture was stirred for 16 h and the solvent was removed by $N_2$. The residue was purified by reverse phase FC (eluant with MeCN in 0.006M HCl in $H_2O$/0-30%) to give the product AKG-17 (0.5 g, 39.5% yield) after freeze drying as a yellow solid. $^1H$ NMR (500 MHz, DMSO-$d_6$) δ 8.95 (s, 1H), 8.67 (s, 1H), 8.23 (q, J=8.3 Hz, 2H), 8.14 (s, 3H), 7.77 (t, J=8.6 Hz, 1H), 7.69 (d, J=13.5 Hz, 1H), 7.50 (d, J=8.6 Hz, 1H), 4.87-4.78 (m, 1H), 4.49 (s, 3H), 4.22 (t, J=9.0 Hz, 1H), 3.89 (dd, J=9.0, 6.5 Hz, 1H), 3.50 (t, J=5.3 Hz, 2H), 2.98 (dd, J=12.5, 6.4 Hz, 2H), 2.58 (t, J=7.1 Hz, 2H). $^{13}C$ NMR (101 MHz, DMSO-$d_6$) δ 170.60, 164.22, 160.97, 158.53, 154.42, 149.78, 145.42, 140.89, 137.79, 132.11, 131.41, 122.61, 119.19, 114.72, 106.23, 105.95, 72.13, 47.77, 40.33, 35.58, 32.58.

5. Synthesis of AKG-18

AKG-18

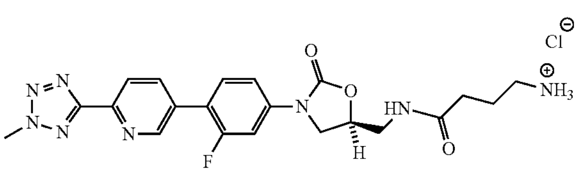

Using the procedure of AKG-17, AKG-18 was obtained from Intermediate-1 and 4-((tert-butoxycarbonyl)amino)butanoic acid as a yellow solid (0.5 g, 37.6% yield). $^1H$ NMR (500 MHz, DMSO-$d_6$) δ 8.95 (s, 1H), 8.52 (t, J=5.7 Hz, 1H), 8.29-8.08 (m, 5H), 7.77 (t, J=8.8 Hz, 1H), 7.69 (d, J=13.6 Hz, 1H), 7.50 (d, J=8.7 Hz, 1H), 4.87-4.76 (m, 1H), 4.50 (s, 3H), 4.22 (t, J=9.0 Hz, 1H), 3.93-3.83 (m, 1H), 3.49 (t, J=5.3 Hz, 2H), 2.83-2.72 (m, 2H), 2.28 (t, J=7.2 Hz, 2H), 1.88-1.75 (m, 2H). $^{13}C$ NMR (101 MHz, DMSO-$d_6$) δ 172.59, 164.23, 160.96, 158.52, 154.44, 149.00, 145.39, 140.88, 137.78, 132.10, 131.40, 122.61, 119.17, 114.70, 106.21, 72.17, 47.78, 41.88, 40.37, 38.78, 32.44, 23.60.

6. Synthesis of AKG-5

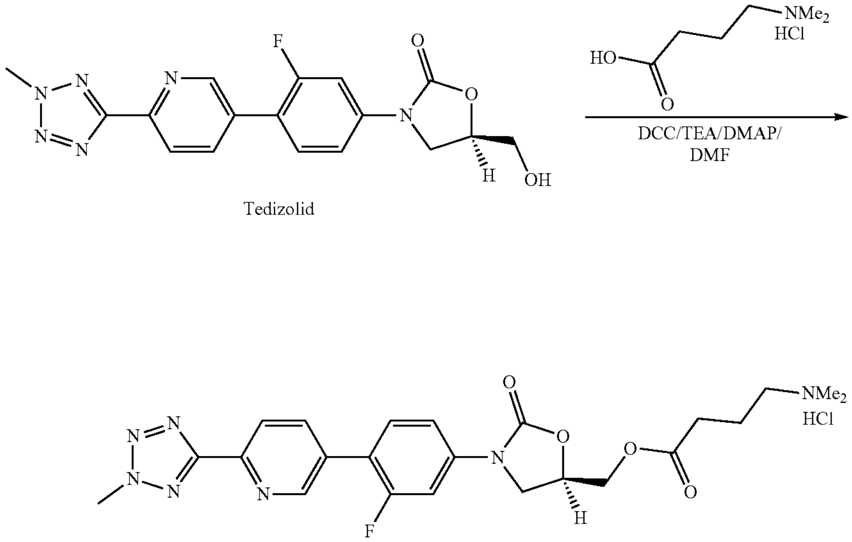

Tedizolid

AKG-5

To a mixture of Tedizolid (1.0 g, 2.70 mmol), 4-(dimethylamino)butanoic acid hydrogen chloride (0.57 g, 3.37 mmol) and TEA (0.27 g, 2.70 mmol), cat amount of DMAP in DMF (20 mL) was added DCC (0.84 g, 4.05 mmol) at under $N_2$. The mixture was stirred at RT for 16 h. Upon completion of reaction (LCMS), it was diluted with $H_2O$ (100 mL) and filtrated. The filtrate was acidified with 0.02 M HCl to pH=5-6 and then purified using RP-FC (eluant with MeCN in 0.5% formic acid/$H_2O$) to give the product AKG-5 as a formic acid salt after freeze drying. The product was re-dissolved into $H_2O$ and 1 eq of aq. HCl (0.02 M) was added. Freeze drying the product resulted in AKG-5 as a HCl salt (600 mg, 42.7% yield). $^1H$ NMR (400 MHz, DMSO-$d_6$) δ 10.40 (br, 1H), 8.95 (s, 1H), 8.23 (q, J=8.5 Hz, 2H), 7.78 (t, J=8.8 Hz, 1H), 7.71 (dd, J=13.6, 2.1 Hz, 1H), 7.53 (dd, J=8.6, 2.1 Hz, 1H), 5.03 (dd, J=5.6, 3.1 Hz, 1H), 4.48 (s, 3H), 4.36 (qd, J=12.4, 4.2 Hz, 2H), 4.26 (t, J=9.3 Hz, 1H), 3.95 (dd, J=9.2, 6.2 Hz, 1H), 2.99-2.86 (m, 2H), 2.64 (s, 6H), 2.45 (t, J=7.3 Hz, 2H), 1.87 (m, 2H). $^{13}C$ NMR (126 MHz, DMSO-$d_6$) δ 172.3, 164.3, 158.8, 154.3, 149.9, 145.6, 140.8, 137.7, 132.0, 131.5, 122.6, 119.4, 114.7, 106.2, 71.1, 64.8, 56.3, 46.7, 40.3, 30.9, 19.9. m/z 469.3 ($[M+1]^+$). m/z 484.1 ($[M-HCl+1]^+$).

7 Synthesis of AKG-7

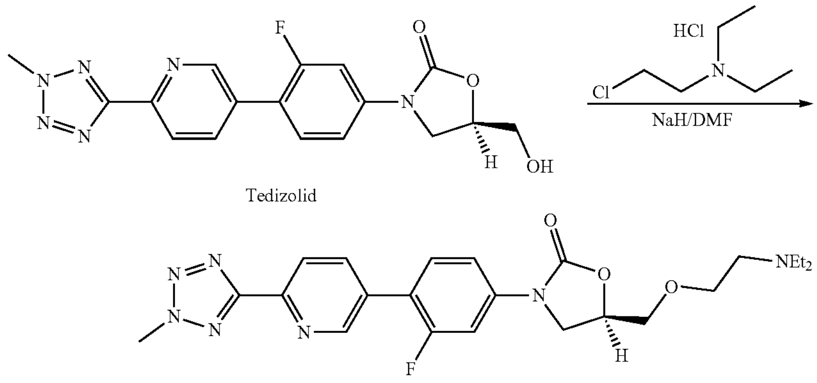

Tedizolid

AKG-7

To a mixture of Tedizolid (1.0 g, 2.70 mmol in DMF (20 mL) was added NaH (0.13 g, 60%, 5.40 mmol) at RT under $N_2$. The mixture was stirred at 0° C. for 0.5 h and then 2-Diethylaminoethylchloride hydrochloride (930 mg, 5.40 mmol) was added in one portion. The whole mixture was stirred at RT for 3 h. LCMS showed completion of the reaction. The reaction was carefully poured into ice/$H_2O$ (20 mL) and extracted with DCM (2×50 mL). The combined organic extracts were washed with saturated brine followed by the drying over $Na_2SO_4$. The solvent was removed in vacuo and the residue was purified using FC (eluant with MeOH in DCM 0-15%) to give AKG-7 as a white solid (0.5 g, 39.4% yield). $^1$H NMR (500 MHz, $CDCl_3$) δ 8.93 (s, 1H), 8.30 (d, J=8.2 Hz, 1H), 8.05 (d, J=8.2 Hz, 1H), 7.72 (d, J=12.9 Hz, 1H), 7.53 (t, J=8.5 Hz, 1H), 7.42 (d, J=8.5 Hz, 1H), 4.88 (d, J=3.5 Hz, 1H), 4.48 (s, 3H), 4.34-4.26 (m, 1H), 4.18-4.08 (m, 2H), 4.00-3.93 (m, 1H), 3.87 (qd, J=10.8, 2.9 Hz, 2H), 3.19-3.11 (m, 2H), 3.06 (q, J=7.1 Hz, 4H), 1.26 (t, J=7.2 Hz, 6H). $^{13}$C NMR (126 MHz, $CDCl_3$) δ 164.7, 161.1, 159.1, 154.3, 149.8, 145.5, 140.0, 137.0, 132.2, 130.6, 122.0, 120.1, 113.8, 106.3, 71.3, 71.3, 66.9, 51.9, 48.2, 46.6, 39.7, 8.9. m/z 470.3 ([M+1]$^+$).

8. Synthesis of AKG-20

AKG-20

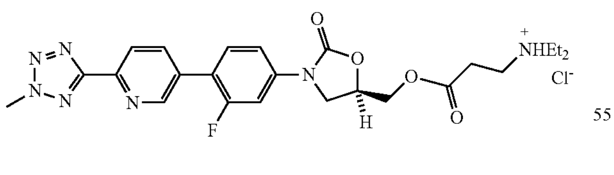

To a reaction mixture of Tedizolid (1.0 g, 2.70 mmol), 4-(diethylamino)butanoic acid hydrogen chloride (0.61 g, 3.37 mmol) and DMAP (0.05 g) in DMF (20 mL) was added DCC (0.84 g, 4.05 mmol) at RT under $N_2$. The mixture was stirred at RT for 16 h. Upon completion (LCMS), the reaction was diluted with $H_2O$ (100 mL) and filtrated. The filtrate was acidified with 0.02 M HCl to pH=5-6 and then purified using RP-FC (eluant with MeCN in 0.5% FA/$H_2O$) to give the product as a formic acid salt after freeze drying. The salt was then re-dissolved into $H_2O$ and 1 eq of HCl (0.02 M) was added, after freeze drying the product AKG-20 as a HCl salt was obtained (0.61 g, 42% yield). $^1$H NMR (400 MHz, DMSO-$d_6$) δ 8.94 (s, 1H), 8.28-8.14 (m, 2H), 7.82-7.66 (m, 2H), 7.53 (d, J=8.7 Hz, 1H), 5.11-4.97 (m, 1H), 4.49 (s, 3H), 4.43-4.33 (m, 2H), 4.27 (t, J=9.3 Hz, 1H), 4.01-3.91 (m, 1H), 3.08-2.99 (m, 2H), 2.90-2.69 (m, 6H), 1.08 (t, J=7.2 Hz, 6H). $^{13}$C NMR (101 MHz, DMSO-$d_6$) δ 171.00, 164.33, 158.55, 154.32, 149.90, 145.58, 140.71, 137.63, 132.02, 131.45, 122.58, 119.33, 114.69, 106.21, 71.01, 65.04, 46.86, 46.63, 40.31, 29.99, 9.95(s).

9. Synthesis of Intermediate-3

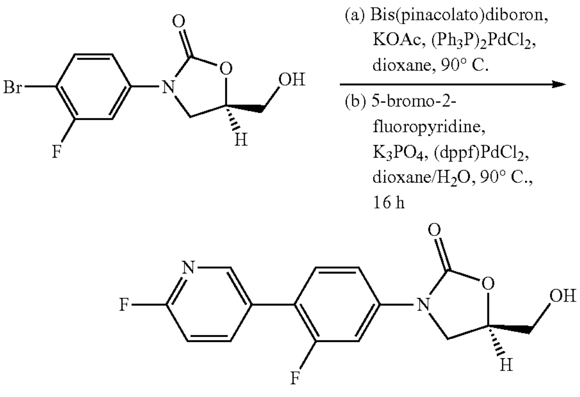

Intermediate-3

A mixture of (R)-3-(4-bromo-3-fluorophenyl)-5-(hydroxymethyl)oxazolidin-2-one (9.0 g, 31.02 mmol), Bis (pinacolato)diboron (11.88 g, 46.54 mmol) and KOAc (4.56 g, 46.54 mmol) in dioxane (200 mL) was purged with Ar for 10 min and then $(Ph_3P)_2PdCl_2$ (1.09 g, 1.55 mmol) was added. After purging the mixture with Ar again, it was heated to 90° C. for 15 h. LCMS showed completion of reaction. It was cooled to RT and filtrated over Celite to give Intermediate-2 as a filtrate. To the filtrate, 5-bromo-2-fluoropyridine (6.55 g, 37.22 mmol), $K_3PO_4$ (14.47 g, 6.80 mmol) and $H_2O$ (20 mL) were added. The mixture was purged with Ar for 10 min. and (dppf) $PdCl_2$ (2.27 g, 3.10 mmol) was added. The mixture was purged with Ar again. It was then heated to 90° C. for 15 h. Reaction was monitored by LCMS. Upon completion, it was concentrated in vacuo and the residue was diluted with $H_2O$ (200 mL) and extracted with EtOAc (2×200 mL). The combined extracts were washed with saturated brine followed by the drying over $Na_2SO_4$. Filtering and solvent removal in vacuo resulted in a residue that was purified using FC (eluant with MeOH in DCM 0-15%) to give the product Intermediate-3 (6.8 g, 71.6% yield for two steps) as a yellow solid. $^1H$ NMR (400 MHz, DMSO-$d_6$) δ 8.43 (s, 1H), 8.23-8.14 (m, 1H), 7.72-7.61 (m, 2H), 7.49 (dd, J=8.6, 2.2 Hz, 1H), 7.32 (dd, J=8.6, 2.7 Hz, 1H), 5.27 (t, J=5.6 Hz, 1H), 4.80-4.71 (m, 1H), 4.15 (t, J=9.1 Hz, 1H), 3.90 (dd, J=8.9, 6.1 Hz, 1H), 3.75-3.67 (m, 1H), 3.63-3.55 (m, 1H). MS (ESI+) m/z 307 ($[M+1]^+$).

10. Synthesis of AKG-11, 12, 13, 14, 15

Procedure B. A mixture of Intermediate-3 (1.0 eq), $R_1R_2NH$ (4.0 eq) and cat. amount of DMAP in NMP (10 mL) was heated to 100° C. for 16 h in a sealed tube. On completion of reaction (LCMS), it was diluted with $H_2O$ (50 mL) and extracted with EtOAc (2×50 mL). The combined organic extracts were washed with saturated brine followed by drying over $Na_2SO_4$ and filtering. The solvent was removed in vacuo and the residue was purified using RPFC (Eluant with MeCN in 0.1% $NH_4HCO_3/H_2O$, 0-40%, C18) to give the product.

AKG-11

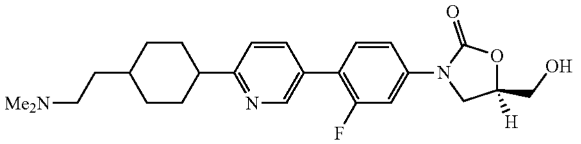

Using procedure B. AKG-11 was obtained from Intermediate-3 and N,N-Dimethyl-2-(piperidin-4-yl)ethan-1-amine as a white solid (0.40 g, 30.1% yield). $^1H$ NMR (400 MHz, DMSO-$d_6$) δ 8.28 (s, 1H), 7.73-7.65 (m, 1H), 7.60 (dd, J=13.6, 2.1 Hz, 1H), 7.54 (t, J=8.9 Hz, 1H), 7.41 (dd, J=8.6, 2.1 Hz, 1H), 6.89 (d, J=9.0 Hz, 1H), 5.25 (t, J=5.6 Hz, 1H), 4.78-4.68 (m, 1H), 4.33 (d, J=13.0 Hz, 2H), 4.12 (t, J=9.0 Hz, 1H), 3.87 (dd, J=8.9, 6.2 Hz, 1H), 3.74-3.64 (m, 1H), 3.62-3.52 (m, 1H), 2.87-2.71 (m, 2H), 2.23 (t, J=7.3 Hz, 2H), 2.11 (s, 6H), 1.72 (d, J=11.5 Hz, 2H), 1.64-1.49 (m, 1H), 1.34 (dd, J=14.3, 7.0 Hz, 2H), 1.18-1.04 (m, 2H). 13C NMR (101 MHz, DMSO-$d_6$) δ 160.68, 158.33, 154.81, 147.54, 139.15, 137.82, 130.32, 120.72, 119.11, 114.35, 106.97, 106.03, 105.74, 73.82, 62.09, 56.98, 46.45, 45.73, 45.39, 34.29, 34.15, 31.94. MS (ESI+) m/z 443.1 ($[M+1]^+$).

AKG-12

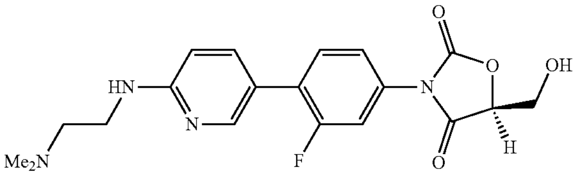

Using procedure B. AKG-12 was obtained from Intermediate-3 and $N^1$,$N^1$-dimethylethane-1,2-diamine as a white solid (0.52 g, 42.6% yield). $^1H$ NMR (400 MHz, DMSO-$d_6$) δ 8.16 (s, 1H), 7.64-7.46 (m, 3H), 7.39 (dd, J=8.6, 2.2 Hz, 1H), 6.58 (dd, J=9.9, 5.6 Hz, 2H), 5.25 (t, J=5.6 Hz, 1H), 4.80-4.66 (m, 1H), 4.11 (t, J=9.0 Hz, 1H), 3.86 (dd, J=8.9, 6.2 Hz, 1H), 3.76-3.65 (m, 1H), 3.61-3.49 (m, 1H), 3.37 (dd, J=12.3, 6.5 Hz, 2H), 2.42 (t, J=6.6 Hz, 2H), 2.18 (s, 6H). $^{13}C$ NMR (101 MHz, DMSO-$d_6$) δ 160.60, 158.48, 158.19, 154.82, 147.57, 138.92, 137.10, 130.22, 121.18, 118.53, 114.30, 108.37, 106.02, 105.74, 73.81, 62.10, 58.76, 46.45, 45.76, 39.21. MS (ESI+) m/z 375.1 ($[M+1]^+$).

AKG-13

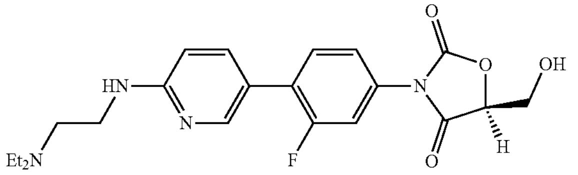

Using procedure B. AKG-13 was obtained from Intermediate-3 and $N^1$,$N^1$-diethylethane-1,2-diamine as a white solid (0.68 g, 51.9% yield). $^1H$ NMR (400 MHz, DMSO-$d_6$) δ 8.17 (s, 1H), 7.67-7.46 (m, 3H), 7.39 (dd, J=8.6, 2.1 Hz, 1H), 6.63-6.44 (m, 2H), 5.25 (s, 1H), 4.74 (dd, J=9.2, 5.8 Hz, 1H), 4.12 (t, J=9.0 Hz, 1H), 3.87 (dd, J=8.9, 6.2 Hz, 1H), 3.76-3.65 (m, 1H), 3.63-3.52 (m, 1H), 3.34 (dd, J=13.2, 6.2 Hz, 2H), 2.60-2.55 (m, 2H), 2.54-2.50 (m, 4H), 0.97 (t, J=7.1 Hz, 6H). $^{11}C$ NMR (101 MHz, DMSO-$d_6$) δ 160.60, 158.53, 158.18, 154.81, 147.62, 138.91, 137.13, 130.20, 121.16, 118.54, 114.29, 108.24, 105.87, 73.80, 62.10, 52.19, 47.13, 46.45, 39.48, 12.31. MS (ESI+) m/z 417.1 ($[M+1]^+$).

AKG-14

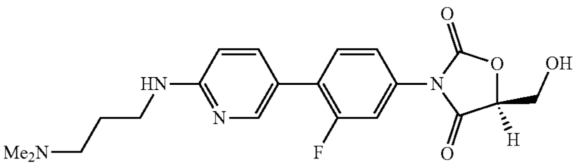

Using procedure B. AKG-14 was obtained from Intermediate-3 and $N^1$,$N^1$-dimethylpropane-1,3-diamine as a white solid (0.6 g, 47.3% yield). $^1H$ NMR (400 MHz, DMSO-$d_6$) δ 8.16 (s, 1H), 7.63-7.54 (m, 2H), 7.50 (t, J=8.9 Hz, 1H), 7.39 (dd, J=8.6, 2.2 Hz, 1H), 6.73 (t, J=5.6 Hz, 1H), 6.54 (d, J=8.7 Hz, 1H), 5.25 (t, J=5.5 Hz, 1H), 4.78-4.68 (m, 1H), 4.11 (t, J=9.0 Hz, 1H), 3.87 (dd, J=8.9, 6.2 Hz, 1H), 3.75-3.66 (m, 1H), 3.64-3.53 (m, 1H), 3.33-3.23 (m, 2H), 2.28 (t, J=7.1 Hz, 2H), 2.13 (s, 6H), 1.72-1.62 (m, 2H). $^{13}C$ NMR (101 MHz, DMSO-$d_6$) δ 160.60, 158.62, 158.18, 154.81, 147.62, 138.89, 137.08, 130.19, 121.21, 118.39, 114.29, 108.10, 106.02, 105.74, 73.81, 62.10, 57.44, 46.45, 45.72, 39.58, 27.54. MS (ESI+) m/z 389.1 ($[M+1]^+$).

AKG-15

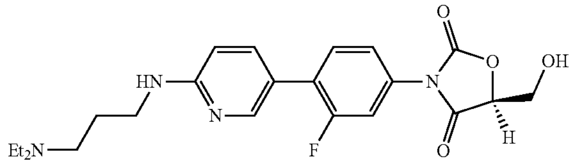

Using procedure B. AKG-15 was obtained from Intermediate-3 and $N^1$,$N^1$-diethylpropane-1,3-diamine as a white solid (0.65 g, 48.0% yield). $^{1}H$ NMR (400 MHz, DMSO-$d_6$) δ 8.16 (s, 1H), 7.63-7.54 (m, 2H), 7.50 (t, J=8.9 Hz, 1H), 7.39 (dd, J=8.6, 2.2 Hz, 1H), 6.75 (t, J=5.5 Hz, 1H), 6.54 (d, J=8.7 Hz, 1H), 5.25 (t, J=5.4 Hz, 1H), 4.79-4.68 (m, 1H), 4.12 (t, J=9.0 Hz, 1H), 3.87 (dd, J=8.9, 6.2 Hz, 1H), 3.75-3.66 (m, 1H), 3.63-3.54 (m, 1H), 3.32-3.23 (m, 2H), 2.49-2.40 (m, 6H), 1.70-1.61 (m, 2H), 0.95 (t, J=7.1 Hz, 6H). $^{11}C$ NMR (101 MHz, DMSO-$d_6$) δ 160.60, 158.65, 158.18, 154.81, 147.64, 138.89, 137.05, 130.18, 121.21, 118.37, 114.29, 108.01, 106.02, 105.74, 73.80, 62.09, 50.81, 46.80, 46.45, 40.11, 27.10, 12.23. MS (ESI+) m/z 417.1 ([M+1]$^+$).

11. Synthesis of AKG-16

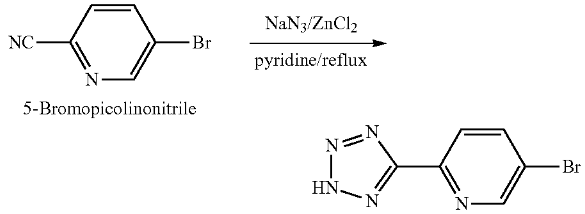

5-Bromopicolinonitrile

Intermediate-4

$ZnCl_2$ (11.2 g, 81.9 mmol) was added portion wise to pyridine (40 mL) followed by the addition of $NaN_3$ (8.90 g, 137 mmol) and 5-bromo-2-cyanopyridine (10.0 g, 54.6 mmol) at RT, and the reaction mixture was heated to reflux at 120° C. for 2 h. After the mixture was cooled to RT it was diluted with water (200 mL), stirred at RT for 1 h, filtered and washed with water (200 mL). The filtered solid was collected and suspended into HCl (200 mL, 6 M) at RT for 2 h. The product was collected by filtration and washed with $H_2O$. It was dried in vacuo to give Intermediate-4 (10.0 g, 81.3% yield) as a white solid. $^{1}H$ NMR (400 MHz, DMSO-$d_6$) δ 8.96 (s, 1H), 8.36 (dd, J=8.4, 2.2 Hz, 1H), 8.18 (d, J=8.4 Hz, 1H). MS (ESI+) m/z 225.9 227.9 ([M+1]$^+$).

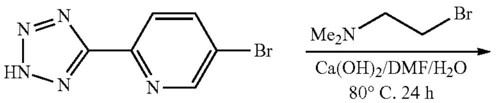

Intermediate-4

-continued

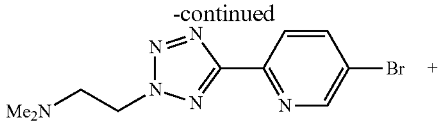

Intermediate-5

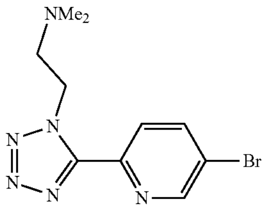

Intermediate-6

A mixture of Intermediate-4 (10.0 g, 44.25 mmol) and $Ca(OH)_2$ (7.20 g, 97.35 mmol) in $H_2O$ (150 mL) and DMF (20 mL) was stirred at r,t for 0.5 h and then (2-bromoethyl) dimethylamine hydrobromide (25.0 g, 107.3 mmol) was added. The mixture was heated at 80° C. for 24 h. LCMS showed 3:1 mixture of Intermediates 5 and 6, respectively. The mixture was diluted with $H_2O$ (40 mL) and extracted with EtOAc (2×50 mL). The combined extracts were washed with saturated brine, dried over $Na_2SO_4$ and filtered. The solvent was removed in vacuo and the residue was purified using FC (eluant with MeOH in DCM 0-15%) to give the crude product. The crude product was further purified by RPFC (MeCN in 0.1% $NH_4HCO_3/H_2O$ 0-30%, C18, Intermediate-5 eluted first followed by Intermediate-6) to give Intermediate-5 (0.74 g, 5.6% yield) as a white solid and Intermediate-6 (0.25 g as light yellow solid).

Intermediate-5: $^{1}H$ NMR (400 MHz, DMSO-$d_6$) δ 8.89 (dd, J=2.3, 0.6 Hz, 1H), 8.27 (dd, J=8.4, 2.4 Hz, 11H), 8.10 (dd, J=8.4, 0.6 Hz, 11H), 4.87 (t, J=6.1 Hz, 2H), 2.87 (t, J=6.1 Hz, 2H), 2.17 (s, 6H). $^{13}C$ NMR (101 MHz, DMSO-$d_6$) δ 163.74, 151.48, 145.51, 140.81, 124.40, 122.21, 57.73, 51.54, 45.29. MS (ESI+) m/z 297.1, 299.1 ([M+1]$^+$). Intermediate-6: $^{1}H$ NMR (400 MHz, DMSO-$d_6$) δ 8.98 (s, 1H), 8.38 (dd, J=8.4, 2 Hz, 11H), 8.20 (d, J=8.4 Hz, 1H), 5.00 (t, J=6.4 Hz, 2H), 2.75 (t, J=6 Hz, 2H), 2.10 (s, 6H), MS (ESI+) m/z 297.1, 299.1 ([M+1]$^+$).

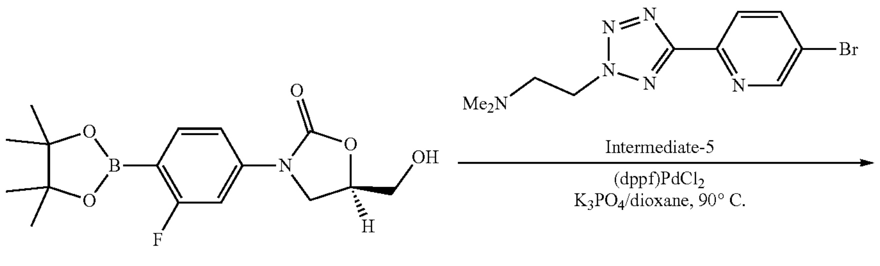

Intermediate-2

-continued

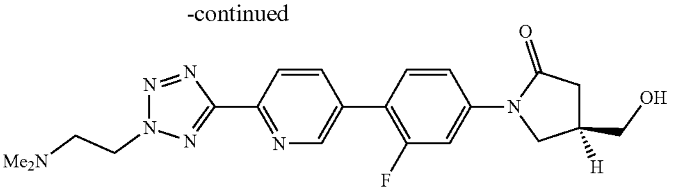

AKG-16

A mixture of freshly prepared Intermediate-2 (1.68 g, 4.98 mmol) (from 1.44 g of (R)-3-(4-bromo-3-fluorophenyl)-5-(hydroxymethyl)oxazolidin-2-one using the procedure of Intermediate-3), Intermediate-5 (740 mg, 2.49 mmol) and $K_3PO_4$ (1.16 g, 5.48 mmol) in dioxane (50 mL) and $H_2O$ (5 mL) was purged with Ar for 10 min. To this (dppf)$PdCl_2$ (182 mg, 0.25 m mol) was added. The mixture was purged with Ar again. It was then heated to 90° C. for 15 h. LCMS showed completion of reaction. It was concentrated in vacuo and the residue was diluted with $H_2O$ (200 mL) and extracted with EtOAc (2×200 mL). The combined extracts were washed with saturated brine, dried over $Na_2SO_4$ and filtered. The solvent was removed in vacuo and the residue was purified using RPFC (Eluant with MeCN in $H_2O$, 0-40%) to give the product AKG-16 (520 mg, 49.0% yield) as a white solid. $^1$H NMR (400 MHz, DMSO-$d_6$) δ 8.95 (s, 1H), 8.23 (dd, J=18.3, 8.2 Hz, 2H), 7.82-7.66 (m, 2H), 7.54 (dd, J=8.6, 2.1 Hz, 1H), 5.28 (s, 1H), 4.89 (t, J=6.1 Hz, 2H), 4.82-4.71 (m, 1H), 4.17 (t, J=9.0 Hz, 1H), 3.98-3.87 (m, 1H), 3.77-3.65 (m, 1H), 3.64-3.53 (m, 1H), 2.90 (t, J=6.1 Hz, 2H), 2.19 (s, 6H). $^{13}$C NMR (101 MHz, DMSO-$d_6$) δ 164.17, 161.02, 158.58, 154.81, 149.91, 145.59, 141.03, 137.63, 132.10, 131.39, 122.59, 119.05, 114.47, 105.97, 105.69, 73.95, 62.07, 57.72, 51.46, 46.46, 45.26. MS (ESI+) m/z 428.1 ([M+1]$^+$).

12. Synthesis of AKG-21

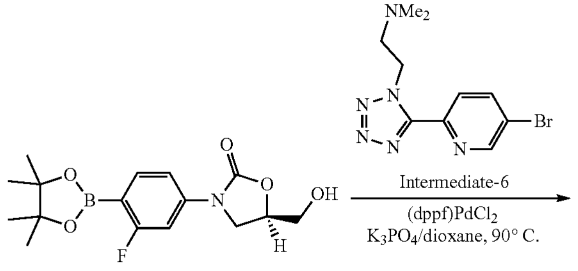

Intermediate-2

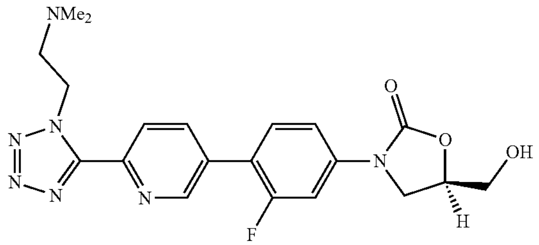

AKG-21

A solution of Intermediate-2 (1.5 g, 4.5 mmol), Intermediate-6 (0.9 g, 3 mmol), Pd(dppf)$Cl_2$ (247 mg, 0.3 mmol) and $K_3PO_4$ (1.3 g, 6 mmol) in dioxane (30 mL) and $H_2O$ (5 mL) was purged with Ar for 10 min. and heated to 100° C. for 15 h. On completion of reaction (LCMS), it was concentrated in vacuo and the residue was diluted with $H_2O$ (100 mL) and extracted with EtOAc (2×50 mL). The combined extracts were washed with saturated brine, dried over $Na_2SO_4$ and filtered. The solvent was removed in vacuo and the residue was purified using FC (eluant with MeOH in DCM (10% of $NH_4OH$) from 0 to 10%) to give AKG-21 (450 mg as white solid) in 35% yield. $^1$H NMR (400 MHz, DMSO-$d_6$) δ 9.01 (s, 1H), 8.36 (d, J=8.4 Hz, 1H), 8.30 (d, J=8.4 Hz, 1H), 7.81 (t, J=8.8 Hz, 1H), 7.74 (dd, J=13.6, 2.0 Hz, 1H), 7.55 (dd, J=8.4, 2.0 Hz, 1H), 5.26 (t, J=5.6 Hz, 1H), 5.08 (t, J=6.4 Hz, 2H), 4.79-4.75 (m, 1H), 4.18 (t, J=9.2 Hz, 1H), 3.93-3.89 (m, 1H), 3.74-3.68 (m, 1H), 3.62-3.56 (m, 1H), 2.80 (t, J=6.4 Hz, 2H), 2.13 (s, 6H). $^{13}$C NMR (101 MHz, DMSO-$d_6$): δ 161.09, 158.64, 154.80, 152.10, (149.45, 149.40), 143.46, (141.35, 141.23), (138.19, 138.15), (132.77, 132.76), (131.53, 131.48), 124.58, (118.69, 118.56), (114.51, 114.49), (105.97, 105.68), 73.96, 62.06, 58.38, 47.26, 46.47, 45.42.

13. Synthesis of AKG-22

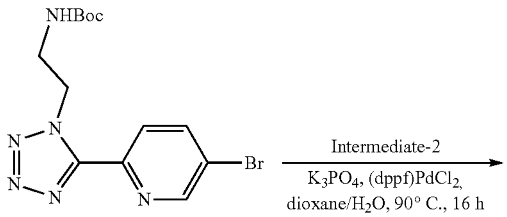

Intermediate-7

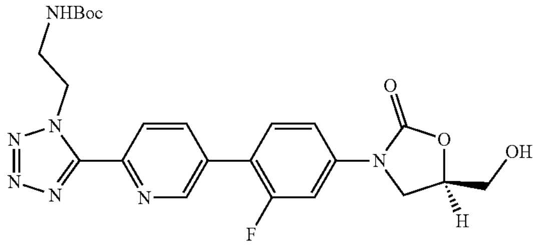

AKG-22-1

To a mixture of Intermediate-7 (500 mg, 1.354 mmol) in $H_2O$ (2 mL) and dioxane (8 mL) was added Intermediate-2 (685 mg, 2.03 mmol), $K_3PO_4$ (862 mg, 4.06 mmol) and (dppf)$PdCl_2$ (99 mg, 0.135 mmol). The flask was evacuated and backfilled with Ar. Then the mixture was stirred at 90° C. for 16 h. Water (20 mL) was added, extracted with EtOAc (2×20 mL). The organic phase was washed with brine, dried over $Na_2SO_4$, filtered and concentrated. The residue was purified by silica gel column chromatography (Biotage, 40 g silica gel column @30 mL/min, eluting with 0-100% EtOAc in Petroleum Ether) to give the desired product AKG-22-1 (450 mg, yield: 66%) as a gray solid.

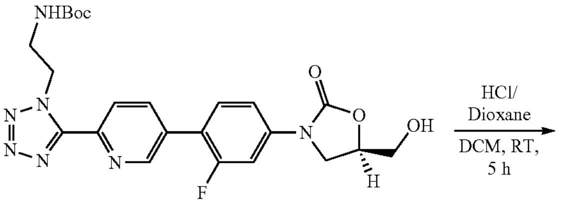

AKG-22-1

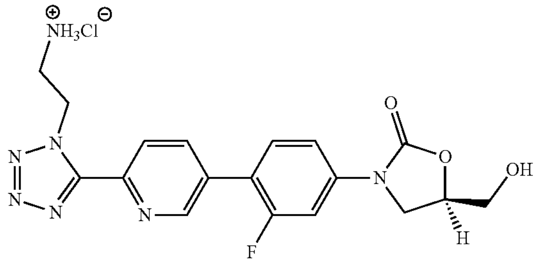

AKG-22

To a mixture of AKG-22-1 (450 mg, 0.9 mmol) in DCM (8 mL) was added 4M HCl/Dioxane (2 mL). Then the mixture was stirred at RT. for 5 h. The solvent was removed under vacuum to give the desired product AKG-22 (390 mg, yield: 99%) as a gray solid. $^1$H NMR (400 MHz, DMSO-$d_6$) δ 9.03 (s, 1H), 8.39 (d, J=8.0 Hz, 1H), 8.32 (d, J=8.0 Hz, 1H), 8.19 (brs, 3H), 7.82-7.70 (m, 2H), 7.57 (dd, J=8.8, 2.0 Hz, 1H), 5.18 (t, J=5.8 Hz, 2H), 4.81-4.74 (m, 1H), 4.17 (t, J=9.2 Hz, 1H), 3.93 (dd, J=9.2, 6.4 Hz, 1H), 3.71 (dd, J=12.4, 3.2 Hz, 1H), 3.59 (dd, J=12.4, 4.0 Hz, 1H), 3.53-3.47 (m, 2H). $^{13}$C NMR (400 MHz, DMSO-$d_6$) δ (161.07, 158.63), 154.82, 152.52, 149.54, 143.25, (141.39, 141.28), 138.24, 124.54, (118.66, 118.53), 114.60, (106.01, 105.73), 73.97, 62.02, 47.37, 46.48, 38.84.

14. Synthesis of AKG-23

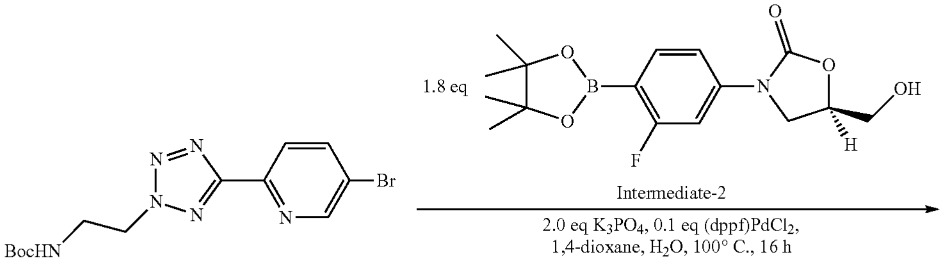

Intermediate-8

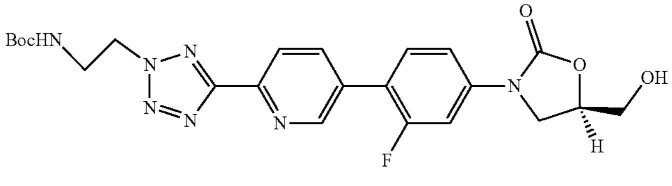

AKG-23-1

To Intermediate-8 (1.0 g, 2.71 mmol) in 20 mL 1,4-dioxane and 5 mL $H_2O$ Intermediate-2 (4.86 mmol, 1.63 g), $K_3PO_4$ (1.14 g, 5.42 mmol) and (dppf)$PdCl_2$ (0.23 g, 0.27 mmol) were added and the mixture was stirred at 100° C. for 16 h. After starting material was consumed, 100 mL sat $NaHCO_3$ was added. The aqueous phase was extracted with EtOAc (3x30 mL), combined organic extracts were washed with $H_2O$, concentrated in vacuo and purified by FC to afford desired compound AKG-23-1 (1.0 g, 70% yield).

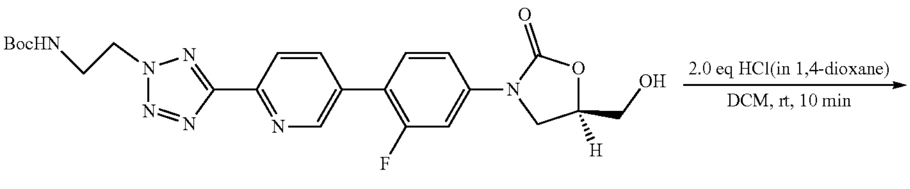

AKG-23-1

-continued

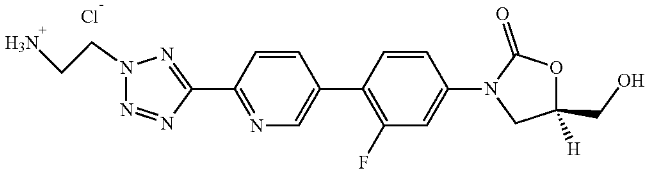

AKG-23

To AKG-23-1 (1.0 g, 2 mmol) in 30 mL DCM was added 1 mL HCl (4M in 1,4-dioxane) and the mixture was allowed to stir at for 1 h. After starting material was consumed, the mixture was flittered to afford crude product. The crude was stirred in 3 mL MeOH at for 1 h, flittered to afford desired product AKG-23 as a white solid (0.53 g, 63% yield). $^1$H NMR (400 MHz, DMSO-$d_6$) δ 8.97 (s, 1H), 8.26 (m, 5H), 7.83-7.64 (m, 2H), 7.54 (dd, J=8.6, 1.9 Hz, 1H), 5.09 (s, 2H), 4.77 (m, 1H), 4.16 (t, J=9.1 Hz, 1H), 3.92 (dd, J=8.8, 6.2 Hz, 1H), 3.71 (dd, J=12.3, 3.2 Hz, 1H), 3.61-3.57 (dd, J=12.3, 3.2 Hz, 1H), 3.53 (m, 3H). $^{13}$C NMR (125 MHz, DMSO-$d_6$) δ 38.31, 46.49, 50.86, 62.01, 73.96, [105.69, 105.97], 114.46, [118.90, 119.03], 122.73, [131.37, 131.47], 132.21, [137.66, 137.70], [140.99, 141.10], 145.42, 149.86, 154.82, [158.57, 161.02], 164.50.

15. Synthesis of AKG-24

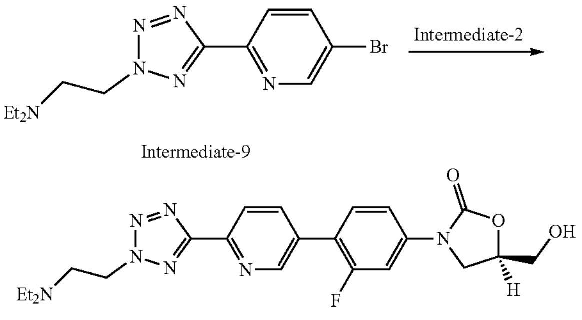

Intermediate-9

AKG-24

A mixture of Intermediate-2 (1.66 g, 4.98 mmol), Intermediate-9 (800 mg, 2.49 mmol) and $K_3PO_4$ (1.16 g, 5.48 mmol) in dioxane (50 mL) and $H_2O$ (5 mL) was purged with Ar for 10 min. and (dppf)$PdCl_2$ (182 mg, 0.25 mmol) was added. The mixture was purged again with Ar. It was then heated to 90° C. for 15 h. LCMS showed completion of the reaction; it was concentrated in vacuo and the residue was diluted with $H_2O$ (200 mL) and extracted with EtOAc (2×200 mL). The combined extracts were washed with saturated brine followed by the drying over $Na_2SO_4$ and filtered. The solvent was removed in vacuo and the residue was purified using RPFC (Eluant with MeCN in $H_2O$, 0-40%) to give the product AKG-24 (440 mg, 39.0% yield) as a white solid. $^1$H NMR (400 MHz, DMSO-$d_6$) δ 8.95 (s, 1H), 8.28-8.16 (m, 2H), 7.81-7.67 (m, 2H), 7.54 (dd, J=8.6, 2.1 Hz, 1H), 5.27 (t, J=5.6 Hz, 1H), 4.93-4.70 (m, 3H), 4.17 (t, J=9.1 Hz, 1H), 3.92 (dd, J=8.9, 6.1 Hz, 1H), 3.72 (m, 1H), 3.60 (m, 1H), 3.04 (s, 2H), 0.87 (t, J=6.9 Hz, 6H). $^{13}$C NMR (101 MHz, DMSO-$d_6$) δ 164.13, 161.03, 158.59, 154.81, 149.94, 149.90, 145.66, 141.09, 140.98, 137.66, 137.62, 132.10, 132.08, 131.41, 131.37, 122.54, 119.15, 119.02, 114.50, 114.47, 105.99, 105.71, 73.95, 62.08, 52.09, 51.60, 46.85, 46.48, 12.26. MS (ESI+) m/z 456 ([M+H]$^+$).

16. Synthesis of AKG-25

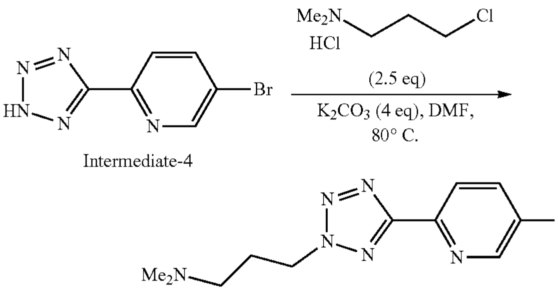

Intermediate-4

Intermediate-10

To a mixture of Intermediate-4 (2.25 g, 10 mmol) and $K_2CO_3$ (5.52 g, 40 mmol) in DMF (20 mL) 3-chloro-N, N-dimethylpropan-1-amine hydrogen chloride (3.95 g, 25 mmol) was added and the mixture was heated to 80° C. for 4 h. It was diluted with $H_2O$ (40 mL) and extracted with EtOAc (2×100 mL). The combined extracts were washed with saturated brine followed by the drying over $Na_2SO_4$ and filtered. The solvent was removed in vacuo and the residue indicated presence of two regioisomers of N-alkylation. The isomers were separated using FC (eluant with MeOH in DCM 0-15%) to give the Intermediate-10 (0.98 g, 31.6% yield) as a white solid. $^1$H NMR (400 MHz, $CDCl_3$) δ 8.83 (dd, J=2.4, 0.8 Hz, 1H), 8.16 (dd, J=8.0, 0.4 Hz, 1H), 8.01 (dd, J=8.4, 2.4 Hz, 1H), 4.78 (t, J=6.8 Hz, 2H), 2.38 (t, J=3.2 Hz, 2H), 2.27-2.22 (m, 8H). MS (ESI+) m/z 311.1, 313.1 ([M+1]$^+$).

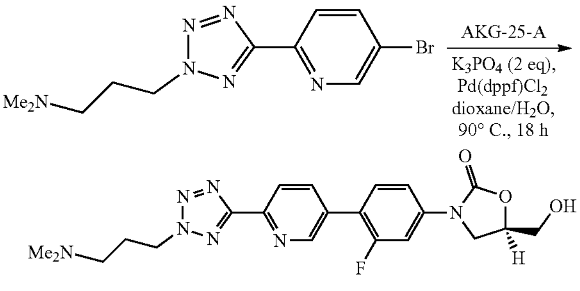

AKG-25

A mixture of Intermediate-10 (0.74 g, 2.4 mmol), Intermediate-2 (1.62 g, 4.8 mmol) and $K_3PO_4$ (1 g, 4.8 mmol) in dioxane (30 mL) and $H_2O$ (5 mL) was purged with Ar for 10 min. and Pd(dppf)$Cl_2$ (175 mg, 0.24 mmol) was added. The mixture was purged with Ar again and heated to 90° C. for 15 h. It was concentrated in vacuo and the residue was diluted with $H_2O$ (80 mL) and extracted with EtOAc (2×100 mL). The combined extracts were washed with saturated brine followed by the drying over $Na_2SO_4$ and filtered. The solvent was removed in vacuo and the residue was purified using FC (eluant with MeOH in DCM 0-15%) to give the product AKG-25 (0.73 g, 69.5% yield) as a grey solid. $^1$H NMR (400 MHz, DMSO-$d_6$) δ 8.94 (s, 1H), 8.24-8.26 (m, 1H), 8.19-8.21 (m, 1H), 7.78-7.70 (m, 2H), 7.54 (dd, J=8.4, 2.0 Hz, 1H), 5.27 (t, J=5.6 Hz, 1H), 4.80 (t, J=6.8 Hz, 2H), 4.77-4.75 (m, 1H), 4.16 (t, J=9.2 Hz, 1H), 3.92 (dd, J=8.8 Hz, 6.0 Hz, 1H), 3.74-3.69 (m, 1H), 3.63-3.58 (m, 1H), 2.28 (t, J=7.2 Hz, 2H), 2.10-2.17 (m, 8H). $^{13}$C NMR (101 MHz, DMSO-$d_6$) δ 164.26, 161.03, 158.58, 154.81, 149.92, 145.58, 141.09, 137.65, 132.10, 131.37, 122.60, 119.12, 118.99, 114.46, 105.98, 105.70, 73.95, 62.07, 55.96, 51.65, 46.47, 45.53, 27.21. MS (ESI+) m/z 442.1 ([M+1]$^+$).

17. Synthesis of AKG-26

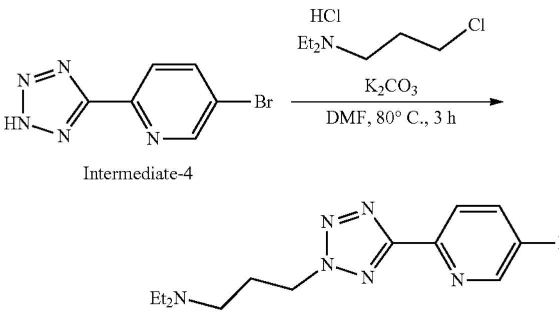

Intermediate-4

Intermediate-11

To a solution of Intermediate-4 (5.0 g, 22.12 mmol) in DMF (30 mL) was added (3-chloropropyl)diethylamine hydrochloride (8.23 g, 55.30 mmol) and $K_2CO_3$ (9.17 g, 66.36 mmol) at 80° C. for 3 h. The reaction was cooled down and poured into an ice-water bath and extracted with EA (2×200 mL). Combined organic phases was washed with brine (2×50 mL), dried over $Na_2SO_4$. Upon removal of solvent, the crude product with N-alkylation regioisomers was purified by FC (PE/EA=1:10) to give Intermediate-11 (1.70 g, 22.65%) as a white solid. $^1$H NMR (500 MHz, $CDCl_3$) δ 8.34 (d, J=2.0 Hz, 1H), 8.15 (d, J=8.0 Hz, 1H), 8.00 (dd, J=8.0, 2.0 Hz, 2H), 4.77 (t, J=7.0 Hz, 2H), 2.53-2.49 (m, 6H), 2.26-2.20 (m, 2H), 0.99 (t, J=7.5 Hz, 6H). MS (ESI$^+$) m/z 339.1, 341.1 ([M+1]$^+$).

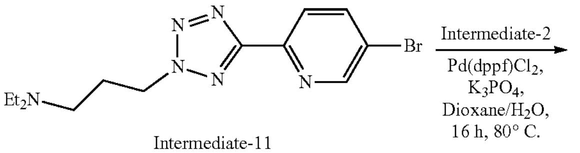

Intermediate-11

-continued

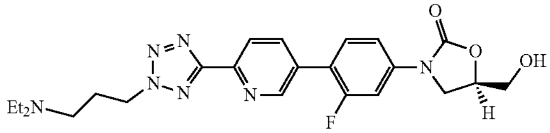

AKG-26

A mixture of Intermediate-11 (0.68 g, 2.00 mmol), Intermediate-2 (1.07 g, 3.99 mmol), tripotassium phosphate (0.85 g, 3.985 mmol) and Pd(dppf)$Cl_2$ (0.15 g, 0.20 mmol) were suspended in 1,4-dioxane:water (12 mL, 6:1). The reaction was stirred at reflux for 16 h. The mixture was partitioned between EtOAc (2×100 mL) and water, washed with brine, dried over $Na_2SO_4$ and filtered. Up to removal of solvent, the residue containing regioisomers was purified using FC eluting with (DCM/MeOH=20/1) to afford AKG-26 (0.54 g, 56.04%) as a grey solid. $^1$H NMR (500 MHz, DMSO-$d_6$) δ 8.95 (s, 1H), 8.26-8.19 (m, 2H), 7.78-7.70 (m, 2H), 7.53 (dd, J=10.5, 2.5 Hz, 1H), 5.27 (d, J=7.5 Hz, 1H), 4.83-4.75 (m, 2H), 4.17 (t, J=11.5 Hz, 1H), 3.92 (dd, J=11.0, 7.5 Hz, 1H), 3.74-3.69 (m, 1H), 3.62-3.58 (m, 1H), 3.51-3.28 (m, 8H), 2.14 (t, J=8.0 Hz, 2H), 0.93 (t, J=8.5 Hz, 6H). $^{13}$C NMR (101 MHz, DMSO-$d_6$) δ 164.24, 161.03, 158.59, 154.52, 149.91, (d, J=3.2 Hz), 145.59, 141.03 (d, J=11.8 Hz), 137.64 (d, J=3.2 Hz), 132.12, 131.40 (d, J=4.5 Hz), 122.57, 119.06 (d, J=12.8 Hz), 114.47 (d, J=2.8 Hz), 105.97, 105.70, 73.96, 62.07, 51.70, 49.19, 46.75, 46.48. MS (ESI$^+$) m/z 470.1 ([M+1]$^+$).

18. Synthesis of AKG-27

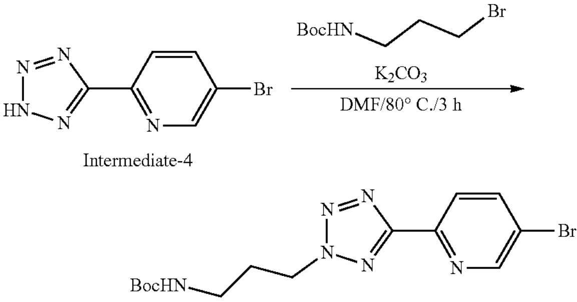

Intermediate-4

Intermediate-12

To a solution of Intermediate-4 (6.3 g, 27.87 mmol) in DMF (42 mL) was added BocNH$(CH_2)_3$Br (16.6 g, 69.71 mmol) and $K_2CO_3$ (11.1 g, 80.02 mmol) at 80° C. for 3 hours. The reaction was cooled down and poured into an ice-water bath and extracted with EtOAc (2×200 mL). The organic phase was washed with brine (2×50 mL), dried over $Na_2SO_4$ and filtered, evaporating the solvent under reduced pressure. The crude product with regioisomers of N-alkylation was purified by FC (PE/EA=2:1) to give Intermediate-12 (14 g, 13.1%) as a yellow solid. $^1$H NMR (400 MHz, DMSO-$d_6$) δ 8.89 (d, J=2.4 Hz, 1H), 8.28 (dd, J=8.4 Hz, 1H), 8.11 (d, J=8.4 Hz, 1H), 6.97 (s, 1H), 4.77 (t, J=6.8 Hz, 2H), 3.03 (q, J=12.4 Hz, 2H), 2.15-2.08 (m, 2H), 1.37 (s, 9H) ppm. MS (ESI+) m/z 383.0 ([M+1]$^+$).

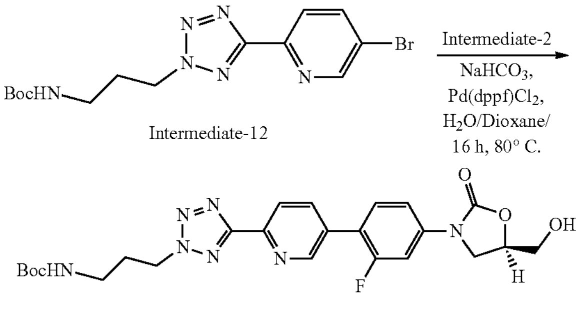

Intermediate-12

AKG-27-1

To a solution of Intermediate-12 (0.83 g, 2.15 mmol), $NaHCO_3$ (0.36 g, 4.31 mmol) and Intermediate-2 (1.24 g, 3.68 mmol) were suspended in 1.4-dioxane (32 mL) and water (8 mL). The mixture was bubbled with $N_2$ for 5 minutes then charged with Pd(dppf)$Cl_2$ (0.078 g, 0.095 mmol). The mixture was stirred at 90° C. for 15 h and then cooled to RT. The mixture was partitioned between EtOAc (2×100 mL) and water. The organic layer was dried on $Na_2SO_4$, filtered, and concentrated. The filtrate was concentrated and purified by silica gel column chromatography on silica gel (DCM/MeOH=20/1) to give AKG-27-1 (0.75 g; 66.9%) as a white solid. $^1$H NMR (400 MHz, DMSO-$d_6$) δ 8.95 (s, 1H), 8.25 (d, J=8.5 Hz, 1H), 8.21 (d, J=8.4 Hz, 1H), 7.78-7.70 (m, 2H), 7.54 (d, J=8.5 Hz, 1H), 6.93 (s, 1H), 5.26 (t, J=5.0 Hz, 1H), 4.80-4.75 (m, 3H), 4.17 (t, J=9.0 Hz, 1H), 3.91 (t, J=8.5 Hz, 1H), 3.71-3.69 (m, 1H), 3.60-3.59 (m, 1H), 3.06-3.03 (m, 2H), 2.15-2.12 (m, 2H), 1.37 (s, 9H) ppm. MS (ESI+) m/z 514.0 ([M+1]$^+$).

19. Synthesis of AKG-28 to 31

To a solution of (R)-3-(4-bromo-3-fluorophenyl)-5-(hydroxymethyl)oxazolidin-2-one (9 g, 31 mmol) in DCM (100 mL) was added (3.92 g, 34 mmol) and TEA (3.76 g, 37 mmol). The mixture was stirred at RT for 2 h. The mixture was washed with water (2×30 mL) and brine (2×30 mL), dried over $Na_2SO_4$, filtered and concentrated to give Intermediate-13 (11.4 g, yield 99%). MS (ESI+) m/z 368 ([M+1]$^+$).

To a solution of Intermediate-13 (11.4 g, 31 mmol) in DMF (200 mL) was added potassium 1,3-dioxoisoindolin-2-ide (6.02 g, 32 mmol). The mixture was stirred at 90° C. overnight. The mixture was cooled to and poured into water (1000 mL) and stirred for 0.5 h. The precipitate was collected and dried in vacuo to give Intermediate-14 (11 g, yield 85%). MS (ESI+) m/z 419 ([M+1]$^+$).

To a solution of Intermediate-14 (11 g, 26.3 mmol) in EtOH (150 mL) was added $NH_2NH_2$—$H_2O$ (85%, 7.7 g, 131 mmol). The mixture was stirred at 90° C. overnight. The mixture was filtered and rinsed with EtOH (2×50 mL). The filtrate was concentrated to give Intermediate-15 (7.6 g, yield 100%). MS (ESI+) m/z 289 ([M+1]$^+$).

To a solution of Intermediate-15 (7.6 g, 26.4 mmol) in THF (50 mL) and water (50 mL), $(Boc)_2O$ (6.9 g, 32 mmol) and $K_2CO_3$ (7.29 g, 52.8 mmol) were added and the mixture was stirred at for 2 h. The mixture was diluted with water (100 mL), extracted with EtOAc (3×50 mL). The combined organic extract was washed with brine (2×50 mL), dried over $Na_2SO_4$, filtered and concentrated. The residue was purified by FC (Biotage, 80 g silica gel column @65 mL/min, eluting with 0-60% EtOAc in petroleum ether for 30 min) to give Intermediate-16 (7.8 g, yield 75%). MS (ESI+) m/z 411 ([M+23]$^+$).

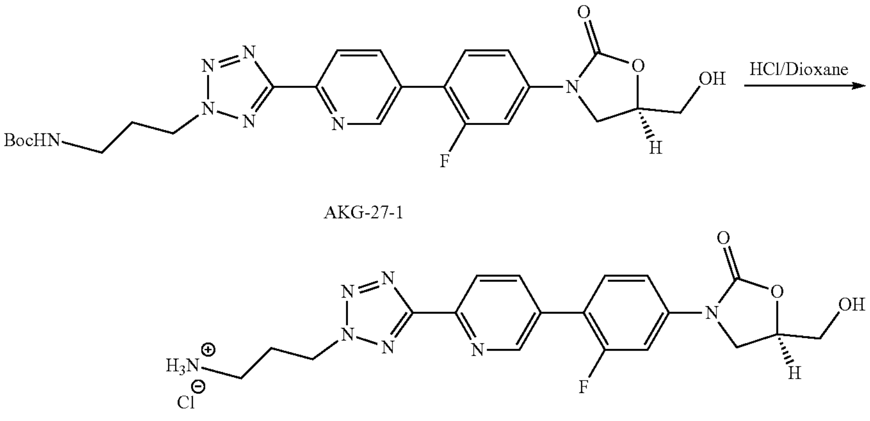

AKG-27-1

AKG-27

A solution AKG-27-1 (0.9 g, 1.75 mmol) in dry DCM (16 mL) was added HCl in dioxane (4.0 mL) under $N_2$ atmosphere at RT. The reaction mixture was stirred at the same temperature for 6 hours and cooled down RT. The mixture reaction was evaporating the solvent under reduced pressure, gave AKG-27 (0.65 g, 82.5%) as a pale yellow solid. $^1$H NMR (400 MHz, DMSO-$d_6$) δ 8.95 (s, 1H), 8.26-8.20 (m, 5H), 7.77-7.70 (m, 2H), 7.53 (d, J=7.6 Hz, 1H), 4.94 (d, J=6.4 Hz, 2H), 4.77 (s, 1H), 4.51 (s, 2H), 4.16 (t, J=8.8 Hz, 1H), 3.93 (t, J=7.0 Hz, 1H), 3.71 (d, J=12.4 Hz, 1H), 3.60 (d, J=12.4 Hz, 1H), 2.94 (s, 2H), 2.34 (t, J=6.8 Hz, 2H) ppm. MS (ESI+) m/z 414.0 ([M+1]$^+$).

The mixture of Intermediate-16 (7.8 g, 20 mmol), bis (pinacolato)diboron (6.54 g, 30 mmol) and KOAc (2.94 g, 30 mmol) in dioxane (100 mL) was purged with Ar for 10 min and then $(Ph_3P)_2PdCl_2$ (1.06 g, 1.5 mmol) was added. The mixture was purged with Ar again and stirred at 90° C. overnight. The mixture was cooled to and diluted with water (300 mL), extracted with EtOAc (3×100 mL). The combined extract was washed with brine (2×50 mL), dried over $Na_2SO_4$, filtered and concentrated. The residue was purified by FC (Biotage, 80 g silica gel column @65 mL/min, eluting with 0-60% EtOAc in petroleum ether for 30 min) to give Intermediate-18 (6.2 g, yield 70%). MS (ESI+) m/z 459 ([M+23]$^+$).

Procedure C: A mixture of one of Intermediates-5/8/9/10/11 (1.0 eq), one of Intermediates-18/19 (1.5 eq), Pd(dppf)$Cl_2$ DCM (0.1 eq), and $K_3PO_4$ (2.0 eq) in dioxane/$H_2O$ (10:1, 0.06M) was purged with $N_2$ and stirred at 90° C. overnight. The mixture was diluted with EtOAc, washed with water and brine, dried over anhydrous magnesium sulfate, filtered and concentrated. The residue was purified by FC to give one of the compounds AKG-28-1/AKG-29-1/AKG-30-1/AKG-31-1/AKG-38/AKG-39/AKG-40.

To a solution of one of the compounds AKG-28-1/AKG-29-1/AKG-30-1/AKG-31-1 in DCM (1 mL/100 mg) was added 3N HCl in EtOAc (20 eq). The mixture was stirred at for 2 h and then filtered. The solid was dried in vacuo or lyophilized to give one of the final compounds AKG-28/AKG-29/AKG-30/AKG-31 (yield 35-44% for two steps).

AKG-28

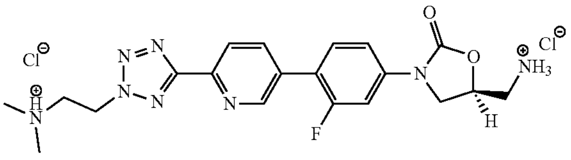

Using procedure C. This product was obtained from Intermediate-5 and Intermediate-18 as a white solid (0.35 g, 35% yield). $^1H$ NMR (500 MHz, DMSO-$d_6$) δ 10.53 (s, 1H), 8.97 (s, 1H), 8.37 (s, 3H), 8.29 (d, J=8.5 Hz, 1H), 8.24 (d, J=8.5 Hz, 1H), 7.80 (t, J=8.5 Hz, 1H), 7.69 (dd, J=13.5, 2.0 Hz, 1H), 7.50 (dd, J=8.5, 2.0 Hz, 1H), 5.31 (t, J=6.0 Hz, 2H), 5.04-4.99 (m, 1H), 4.28 (t, J=9.0 Hz, 1H), 3.96 (dd, J=9.0, 6.5 Hz, 1H), 3.84 (s, 2H), 3.28 (s, 2H), 2.87 (s, 6H) ppm. $^{13}C$ NMR (126 MHz, $D_2O$) δ 163.90 (s), 160.30 (s), 158.33 (s), 154.86 (s), 148.55 (s), 142.64 (s), 138.93 (d, J=11.0 Hz), 137.74 (s), 132.43 (s), 130.39 (s), 122.46 (s), 119.03 (s), 114.36 (s), 106.41 (s), 106.18 (s), 70.31 (s), 55.23 (s), 48.07 (s), 47.69 (s), 43.29 (s), 42.19 (s) ppm. MS (ESI+) m/z 427.1 ($[M+1]^+$).

AKG-29

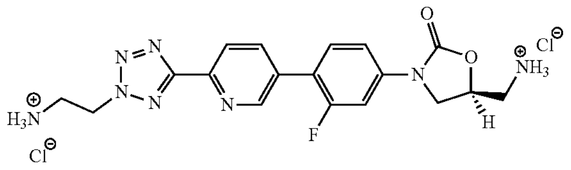

Using procedure C. This product was obtained from Intermediate-8 and Intermediate-18 as a white solid (0.4 g, 44% yield). $^1H$ NMR (400 MHz, DMSO-$d_6$) δ 8.97 (s, 1H), 8.57-8.41 m, 6H), 8.29-8.13 (m, 2H), 7.80 (t, J=9.0 Hz, 1H), 7.69 (dd, J=13.5, 2.5 Hz, 1H), 7.49 (dd, J=8.5, 2.0 Hz, 1H), 5.12-5.03 (m, 3H), 4.28 (t, J=9.0 Hz, 1H), 4.02-3.98 (m, 1H), 3.54-3.51 (m, 2H), 3.33-3.26 (m, 2H). 8.28 (s, 1H), 7.73-7.65 (m, 1H), 7.60 (dd, J=13.6, 2.1 Hz, 1H), 7.54 (t, J=8.9 Hz, 11H), 7.41 (dd, J=8.6, 2.1 Hz, 1H), 6.89 (d, J=9.0 Hz, 1H), 5.25 (t, J=5.6 Hz, 1H), 4.78-4.68 (m, 1H), 4.33 (d, J=13.0 Hz, 2H), 4.12 (t, J=9.0 Hz, 1H), 3.87 (dd, J=8.9, 6.2 Hz, 1H), 3.74-3.64 (m, 1H), 3.62-3.52 (m, 1H), 2.87-2.71 (m, 2H), 2.23 (t, J=7.3 Hz, 2H), 2.11 (s, 6H), 1.72 (d, J=11.5 Hz, 2H), 1.64-1.49 (m, 1H), 1.34 (dd, J=14.3, 7.0 Hz, 2H), 1.18-1.04 (m, 2H) ppm. $^{13}C$ NMR (101 MHz, $D_2O$) δ 161.52, 160.59, 158.12, 154.86, 145.70, 141.05, 140.16, 139.65, 133.57, 130.44, 123.64, 117.70, 114.54, 106.50, 106.22, 70.34, 50.81, 47.68 ppm. MS (ESI+) m/z 399.2 ($[M+1]^+$).

AKG-30

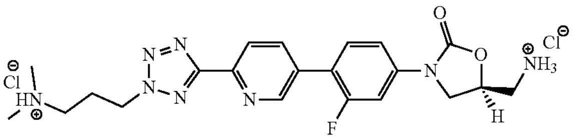

Using procedure C. This product was obtained from Intermediate-10 and Intermediate-18 as a white solid (0.36 g, 40% yield). $^1H$ NMR (400 MHz, DMSO-$d_6$) δ 10.94 (s, 1H), 8.96 (s, 1H), 8.52 (s, 3H), 8.28-8.22 (m, 2H), 7.79 (t, J=8.8 Hz, 1H), 7.69 (dd, J=13.6, 2.0 Hz, 1H), 7.49 (dd, J=8.8, 2.0 Hz, 1H), 5.08-5.01 (m, 1H), 4.93 (t, J=6.8 Hz, 2H), 4.28 (t, J=9.2 Hz, 1H), 4.00 (dd, J=9.2, 6.8 Hz, 1H), 3.29-3.26 (m, 2H), 3.21-3.16 (m, 2H), 2.75 (d, J=4.8 Hz, 6H), 2.49-2.43 (m, 2H) ppm. $^{13}C$ NMR (101 MHz, $D_2O$) δ 162.39 (s), 160.58 (s), 158.11 (s), 154.88 (s), 147.20 (s), 141.66 (s), 139.28 (d, J=11.3 Hz), 132.86 (s), 130.45 (s), 122.90 (s), 118.44 (d, J=12.0 Hz), 114.44 (s), 106.46 (s), 106.17 (s), 70.30 (s), 54.56 (s), 50.62 (s), 47.68 (s), 42.89 (s), 42.16 (s), 23.74 (s) ppm. MS (ESI+) m/z 441 ($[M+1]^+$).

AKG-31

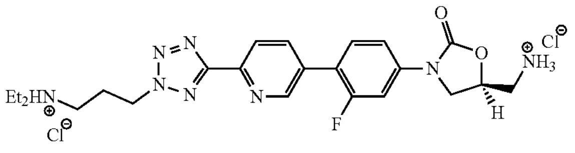

Using procedure C. This product was obtained from Intermediate-11 and Intermediate-18 as a white solid (0.36 g, 42% yield). $^1H$ NMR (400 MHz, DMSO-$d_6$) δ 10.10 (s, 1H), 8.96 (s, 1H), 8.390-8.21 (m, 5H), 7.80 (t, J=8.8 Hz, 1H), 7.69 (dd, J=13.6, 2.0 Hz, 1H), 7.50 (dd, J=8.8, 2.0 Hz, 1H), 5.04-4.97 (m, 1H), 4.94 (t, J=6.8 Hz, 2H), 4.28 (t, J=9.2 Hz, 1H), 3.94 (dd, J=9.6, 6.4 Hz, 1H), 3.31-3.26 (m, 2H), 3.21-3.17 (m, 2H), 3.15-3.12 (m, 4H), 2.46-2.42 (m, 2H), 1.21 (t, J=7.2 Hz, 6H) ppm. $^{13}C$ NMR (101 MHz, $D_2O$) δ 163.04 (s), 160.53 (s), 158.07 (s), 154.84 (s), 147.95 (d, J=5.4 Hz), 142.36 (s), 139.05 (d, J=11.3 Hz), 138.32 (s), 132.44 (s), 130.38 (d, J=4.0 Hz), 122.50 (s), 118.72 (d, J=12.8 Hz), 114.35 (s), 106.37 (s), 106.09 (s), 70.29 (s), 50.65 (s), 48.55 (s), 47.64 (d, J=7.4 Hz), 42.17 (s), 23.05 (s), 8.24 (s) ppm. MS (ESI+) m/z 469 ($[M+1]^+$).

To a solution of Intermediate-15 (7.6 g, 26.4 mmol) in DCM (150 mL) was added triethylamine (TEA, 4.57 g, 6.27 mL, 52.77 mmol, 2.0 equiv) followed by acetyl chloride (AcCl, 2.6 g, 2.74 mL, 39.58 mmol, 1.5 equiv) and 4-N,N-dimethylaminopyridine (DMAP, 0.028 g, 2.64 mmol, 0.01 equiv) at 0-5° C. under $N_2$. The resulting reaction mixture was subsequently stirred at 0-5° C. for 2 h. When TLC and LCMS showed that the reaction was complete, the reaction mixture was quenched with $H_2O$ (100 mL). The two layers were separated, and the aqueous layer was then extracted with $CH_2Cl_2$ (2×50 mL), and the combined organic extracts were washed with $H_2O$ (2×100 mL) and saturated NaCl aqueous solution (100 mL), dried over $MgSO_4$, and concentrated in vacuo. The residue was purified by FC (Biotage, 80 g silica gel column @65 mL/min, eluting with 0-60% EtOAc in petroleum ether for 30 min) to give Intermediate-17 (6.5 g, yield 75%). MS (ESI+) m/z 332 ([M+1]$^+$).

To a solution of Intermediate-17 (6.5 g, 19.7 mmol) in 1,4-dioxane (100 mL) was added 1,1'-Bis(diphenylphosphino)ferrocene-palladium(II)dichloride dichloromethane complex (1.61 g, 1.97 mmol), Bis(pinacolato)diboron (10 g, 39.39 mmol) and KOAc (4.83 g, 49.24 mmol). The resulting reaction stirred at 90° C. for 4 h. When TLC and LCMS showed that the reaction was complete, the reaction mixture was cooled to RT before being treated with water (100 mL) and EtOAc (100 mL). The two layers were separated, and the aqueous layer was extracted with EtOAc (2×50 mL). The combined organic extracts were washed with water (2×50 mL) and saturated aqueous NaCl (50 mL), dried over $MgSO_4$, and concentrated in vacuo. The residual brown oil was purified by FC (Biotage, 80 g silica gel column @60 mL/min, eluting with 0-100% EtOAc in petroleum ether for 30 min) give Intermediate-19 (6.6 g, yield 88.7%). MS (ESI+) m/z 379 ([M+1]$^+$).

20. Synthesis of AKG-38 to 40

AKG-38

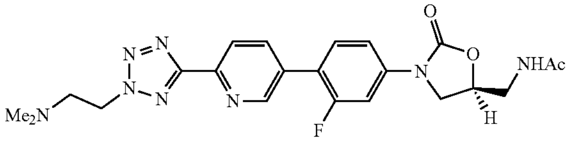

Using procedure C. This product was obtained from Intermediate-5 and Intermediate-19 as a white solid (0.48 g, 60% yield). $^1$H NMR (400 MHz, DMSO) δ 8.95 (s, 1H), 8.29-8.19 (m, 3H), 7.77 (t, J=8.8 Hz, 1H), 7.69 (dd, J=13.6, 2.0 Hz, 1H), 7.50 (dd, J=8.8, 2.0 Hz, 1H), 4.89 (t, J=6.0 Hz, 2H), 4.81-4.76 (m, 1H), 4.20 (t, J=9.2 Hz, 1H), 3.82 (dd, J=9.2, 6.8 Hz, 1H), 3.45 (t, J=5.6 Hz, 2H), 2.90 (t, J=6.0 Hz, 2H), 2.19 (s, 6H), 1.85 (s, 3H) ppm. $^{13}$C NMR (101 MHz, DMSO-$d_6$) δ 170.51, 164.17, 154.46, 149.94, 145.62, 140.90, 137.63, 132.07, 131.39, 122.59, 119.25, 114.66, 106.18, 105.90, 72.34, 57.71, 51.45, 47.67, 45.25, 41.87, 22.92 ppm. MS (ESI+) m/z 469.2 ([M+1]$^+$).

AKG-39

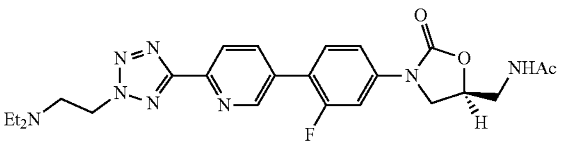

Using procedure C. This product was obtained from Intermediate-9 and Intermediate-19 as a white solid (0.35 g, 40% yield). H NMR (400 MHz, DMSO) δ 8.95 (s, 1H), 8.29-8.19 (m, 3H), 7.76 (t, J=8.8 Hz, 1H), 7.69 (dd, J=13.6, 2.0 Hz, 1H), 7.50 (dd, J=8.8, 2.0 Hz, 1H), 4.84-4.76 (m, 3H), 4.21 (t, J=9.2 Hz, 1H), 3.82 (dd, J=9.2, 6.4 Hz, 1H), 3.46 (t, J=5.6 Hz, 2H), 3.04 (t, J=5.6 Hz, 2H), 2.50-2.47 (m, 4H), 1.85 (s, 3H), 0.87 (t, J=7.2 Hz, 6H) ppm. $^{13}$C NMR (101 MHz, DMSO-$d_6$) δ 170.50, 164.11, 154.46, 149.91, 145.68, 137.68, 132.04, 131.40, 122.53, 119.27 (d, J=13.3 Hz), 114.65, 106.18, 105.90, 72.34, 52.11, 51.61, 47.67, 46.83, 41.87, 40.63, 40.42, 40.22, 40.01, 39.80, 39.59, 39.38, 22.92, 12.28 ppm. MS (ESI+) m/z 497 ([M+1]$^+$).

AKG-40

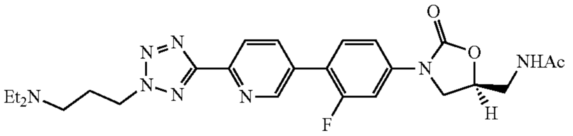

Using procedure C. This product was obtained from Intermediate-11 and Intermediate-19 as a white solid (0.36 g, 50% yield). $^1$H NMR (400 MHz, DMSO-$d_6$) δ 8.95 (s, 1H), 8.31-8.18 (m, 3H), 7.77 (t, J=8.8 Hz, 1H), 7.69 (dd, J=13.6, 2.0 Hz, 1H), 7.50 (dd, J=8.8, 2.0 Hz, 1H), 4.88-4.71 (m, 3H), 4.20 (t, J=9.2 Hz, 1H), 3.81 (dd, J=9.2, 6.4 Hz, 1H), 3.45 (t, J=5.6 Hz, 2H), 2.45 (s, 6H), 2.14 (s, 2H), 1.85 (s, 3H), 0.93 (s, 6H) ppm. $^{13}$C NMR (101 MHz, DMSO-$d_6$) δ 137.70, 131.45, 114.69, 46.79, 41.86, 40.64, 40.43, 40.22, 40.01, 39.80, 39.59, 39.38 ppm. MS (ESI+) m/z 511 ([M+1]$^+$).

Example 2. Assay for In Vitro Activity in *Mycobacterium tuberculosis*

The broth microdilution MIC method used is described in Collins et al., 1997 and Gruppo et al., 2006. MIC or the minimum inhibitory concentration of the chemical compound which prevents visible growth of a bacteria after overnight incubation.

Briefly, MICs were determined by broth microdilution assay with an Alamar blue endpoint (MABA), as described by Collins et al., 1997 (Collins L, Franzblau S G (1997). Microplate alamar blue assay versus BACTEC 460 system for high-throughput screening of compounds against *Mycobacterium tuberculosis* and *Mycobacterium avium*. AAC. 41(5):1004-1009) and Gruppo et al., 2006 (Gruppo V, Johnson C M, Marietta K S, Scherman H, Zink E E, Crick D C, Adams L B, Orme I M, Lenaerts A J. (2006) Rapid microbiologic and pharmacologic evaluation of experimental compounds against *Mycobacterium tuberculosis*. AAC 50:1245-1250). MABA is a 96-well colorimetric assay in which the redox indicator Alamar blue turns from blue to pink in the presence of mycobacterial growth activity in the broth medium.

Briefly, 7H9 complete media was prepared by adding Middlebrook 4.7 g of 7H9 broth powder (Millipore Sigma Cat #M0178), 2 mL glycerol, and 898 purified water in 1 L flask with mixing until dissolved, and subsequently adding 100 mL of ADC solution (6 g bovine serum albumin, 2 g dextrose, and 3 mg catalase dissolved in 100 mL water) to the same 1 L flask. Compounds were made to a concentration of 10 mg/mL in DMSO and then diluted with DMSO further to 80 μg/mL, or forty times the desired starting concentration of 2 μg/mL. A series of nine 1:2 dilutions was prepared by adding 50 μl of drug solution in the first well to 50 μl of DMSO in the subsequent well and the carrying forward this process to the next eight wells in a drug preparation plate. Stocks of *M. tuberculosis* (M.tb) H34Rv and M.tb Erdman strains were diluted from their initial concentration of 3-4×$10^7$ CFU/mL with media to a final concentration of 5×$10^5$ CFU/mL, mixed thoroughly by pipetting up and down with a multi-channel pipettor.

Assay plates were prepared by transferring 100 μl of the 5×$10^5$ CFU/mL inoculated media into all wells. Subsequently, 2.5 μL of each drug dilution from the drug preparation plate was transferred to the corresponding well in the assay plate. Assay plates were subsequently placed in ziplock bags and placed inside an incubator where they were incubated at 37° C. The plates were subsequently read at OD 600 nm on a plate reader on days 3 and 10. After the day ten OD600 reading, 10 μl of Alamar Blue dye was added to each analytical well. On day 12, all assay plates were scanned on a flatbed color scanner. The lowest consecutive antimicrobial concentration (typically two-fold serial dilutions) that does not produce visible color change from blue to pink with Alamar Blue, and/or shows a ≥80% reduction in OD600 relative to drug-free control wells, was regarded as the MIC for these compounds.

Assays were conducted using two unique drug sensitive strains (M.tb Erdman and M.tb H37Rv). MIC assays can also be performed in presence of 4% (w/v) human serum albumin (huSA) (Sigma #A1653) in order to assess potential protein binding (serum shift assay). Generally, a shift in MIC of two wells (4-fold shift in MIC) is considered to be significant. For PA-824 (positive control), a 4-fold shift in MIC is to be expected.

MICs were measured by the Alamar Blue (MABA) readout or by optical density readout (OD600) agreed or differed only by one 2-fold dilution, which is within the limits of the assay. All compounds tested showed consistency in MIC values against both Mtb Erdman and H37Rv, or were within one 2-fold dilution, with the exception of one compound AKG-40; which showed a higher MIC value of 1-2 ug/mL vs Erdman, and an MIC of 0.5 vs H37Rv. This discrepancy could be due to slower growth (lower OD readings) on the Erdman plate.

Linezolid showed an expected MIC value of 2 μg/mL, Tedizolid at 0.25 μg/mL and Bedaquiline at 0.125 μg/mL. These values are consistent with past MIC data and published values (Ruiz et al. Antimicrob. Agents Chemother. 2019 Mar. 27; 63(4), pii: e01939-18, Reddy et al. Antimicrob Agents Chemother. 2010 July; 54(7):2840-6, Torrea et al. J Antimicrob Chemother. 2015 August; 70(8):2300-5). AKG-28 showed an MIC of 0.03-0.015 μg/mL, significantly more active than Tedizolid. Of the oxazolidinone analogues containing an acetamide group, AKG-39 showed an MIC of 0.5 μg/mL, and AKG-40 an MIC of 1-0.5 μg/mL. AKG-38 with an MIC of 0.06 μg/mL also showed several folds greater activity than Tedizolid.

Molecules with an amine group or acetamide group at the C5 position of oxazolidinone were more active (AKG-3 vs Tedizolid, AKG-28 or AKG-38 vs AKG-16, AKG-39 vs AKG-24, AKG-40 vs AKG-26), and compounds with aminoalkyl side chain on the tetrazole showed favorable activity. Substitution of t-butoxycarbonylamino (Boc-NH) group at oxazolidinone position C5 for primary amine (AKG-28-1 vs. AKG-28) or acetamide (AKG-28-1 vs AKG-38) led to the decrease of activity. Compounds containing a dimethylaminoalkyl side chain were particularly superior when compared to aminoethyl or diethylaminoethyl analogs (AKG-16 vs AKG-24, AKG-28 vs AKG-29, AKG-30 vs AKG-31). Likewise, shorter dialkylaminoalkyl side chains (such as ethylene versus propylene) on the tetrazole ring showed greater activity (AKG-16 vs AKG-25, AKG-24 vs AKG-26, AKG-28 vs AKG-30). Analogs with substitutions on the 2' position of the tetrazole were more active than those with substitutions at the 1' position (AKG-16 vs AKG-21, AKG-23 vs AKG-22).

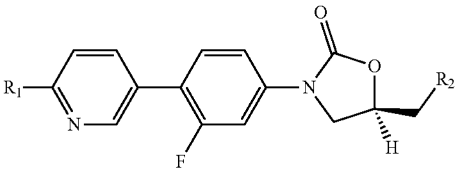

A

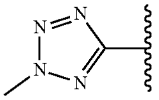

B

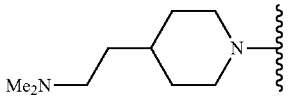

C

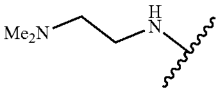

D

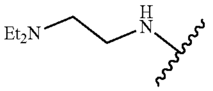

E

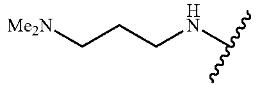

F

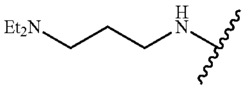

G

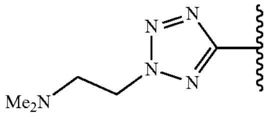

H

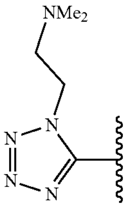

I

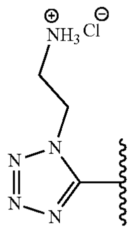

J

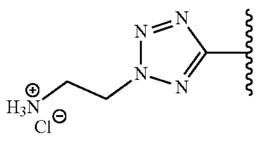

-continued

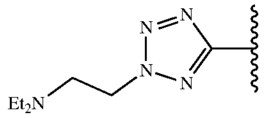

K

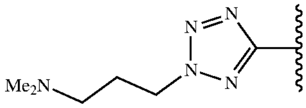

L

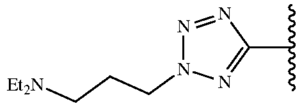

M

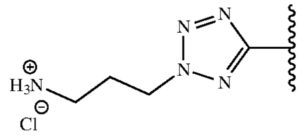

N

TABLE 2

| Compound | | | *Mycobacterium tuberculosis* MIC (μg/ml) | |
|---|---|---|---|---|
| ID | $R_1$ | $R_2$ | Erdman | H37Rv |
| Linezolid | | —NHCOMe | 1 | 1 |
| Sutezolid | | —NHCOMe | 0.5 | 0.5 |
| Tedizolid | | —OH | 0.25 | 0.25 |
| AKG-1 | A | —$NMe_2$ | >8 | >8 |
| AKG-2 | A | —$NEt_2$ | >8 | >8 |
| AKG-3 | A | —$NH_2$•HCl | 0.125 | 0.06 |
| AKG-5 | A | —$OCO(CH_2)_3NMe_2$ | 1 | 1 |
| AKG-6 | A | B | >8 | >8 |
| AKG-7 | A | —O $(CH_2)_2NEt_2$ | >8 | >8 |
| AKG-8 | A | —N $(CH_2)_3NEt_2$ | >8 | >8 |
| AKG-9 | A | D | >8 | >8 |
| AKG-11 | B | —OH | 4 | 4 |
| AKG-12 | C | —OH | 4 | 4 |
| AKG-13 | D | —OH | >8 | >8 |
| AKG-14 | E | —OH | 8 | 8 |
| AKG-15 | F | —OH | >8 | >8 |
| AKG-16 | G | —OH | 0.25 | 0.25 |
| AKG-17 | A | —$NHCO(CH_2)_2NH_2$•HCl | 2 | 2 |
| AKG-18 | A | —$NHCO(CH_2)_3NH_2$•HCl | 2 | 2 |
| AKG-19 | A | —$NH(CH_2)_2NH_2$.HCl | >8 | >8 |
| AKG-20 | A | —$OCO(CH_2)_2NEt_2$ | 0.5 | 0.5 |
| AKG-21 | H | —OH | >8 | >8 |
| AKG-22 | I | —OH | 1 | 0.5 |
| AKG-23 | J | —OH | 0.25 | 0.25 |
| AKG-24 | K | —OH | 1 | 1 |
| AKG-25 | L | —OH | 1 | 1 |
| AKG-26 | M | —OH | 2 | 2 |
| AKG-27 | N | —OH | 0.5 | 0.5 |
| AKG-28 | G | —$NH_2$•HCl | 0.03 | 0.015 |
| AKG-28-1 | G | —$NHCOOCMe_3$ | 0.25 | 0.125 |
| AKG-29 | J | —$NH_2$•HCl | 0.25 | 0.125 |
| AKG-30 | L | —$NH_2$•HCl | 0.125 | 0.125 |
| AKG-31 | M | —$NH_2$•HCl | 0.5 | 0.5 |
| AKG-38 | G | —NHCOMe | 0.06 | 0.06 |
| AKG-39 | K | —NHCOMe | 0.5 | 0.5 |
| AKG-40 | M | —NHCOMe | 1 | 0.5 |

Example 3. Assay for In Vitro Cytotoxicity to Human Kidney and Human Hepatocyte Cells Compounds were tested in vitro over a series of 10 dilutions to determine IC50 in African green monkey kidney (Vero; ATCC #CCL81) or human hepatocyte/liver (HepG2; ATCC #HB8065) cells. As these molecules are generally expected to be nontoxic, a positive control of doxorubicin is included in all studies. Data is reported out as the full cell viability curve, as well as a calculation of the actual IC50 value for each compound.

Adherent cells were grown to ~80% confluency. The cells were trypsinized by adding 0.25% trypsin-EDTA (Gibco #25200-072) and the cells subsequently spun down, and 5 ml of growth medium (MEM media; Corning #10010 CM) added to disperse the cells. The cell density was determined using a hemocytometer. Growth medium (MEM media containing 10% FBS; Corning #35015 CV) was added to the cells to adjust to an appropriate concentration of cells. Then, 200 μl of the cells (5,000 cells/well) were added to a 96-well clear flat-bottom plate (Costar #9804) and incubated in the plate at 37° C. in a humidified incubator with 5% $CO_2$ for 24 h.

Prepare serial dilutions of testing compounds using growth medium as solvent (Table 2). These compounds were provided as sterile aqueous solutions of HCl salts with a concentration of 5 mg/ml. For making dilutions, each drug stock was warmed to room temperature, vortexed and was visually inspected for precipitation. If solid drug was present, the stock was heated on a 60° C. water bath and then allowed to cool to near room temperature. Based on the treatment concentrations, 20× working stocks were made by serial dilution. These were further diluted to 1× in the growth media to the highest drug concentration tested of 250 μg/ml.

Compounds were added to the wells at a series of 1:2 dilutions from the initial 250 μg/ml concentration for each compound by aspirating out the old media and replacing it with 200 μl of the drug containing media. The plates were incubated at 37° C. in a humidified incubator with 5% $CO_2$ for 72 h. At the end of the compound incubation period, replace the media in each well with 100 μl of 1× PrestoBlue Cell Viability Reagent (ThermoFisher Cat #A13261). Incubate the plate at 37° C. in a humidified incubator with 5% $CO_2$ 30 min to 2 h. Take readings at 30, 60, and 120 min. Read fluorescence with 560 nm excitation and 590 nm emission using SpectraMax M5 plate reader (Molecular Devices). Correct background by subtracting the RFU of the control containing only the culture medium (background control well) from all sample readings. Calculate the percentage of cytotoxicity using the formula below:

$$\%\ \text{Cytotoxicity} = \left[(RFU_{\cdot Medium} - RFU_{Treatment})/RFU_{\cdot Medium}\right] \times 100\%$$

The IC50 was determined using GraphPad Prism using the following formula:

$$Y = 100/(1 + 10\hat{\ }((\text{Log}IC50 - X) * HillSlope))$$

TABLE 3

| Compound ID | Cell viability IC50 (μg/ml) | |
|---|---|---|
| Cell line | VERO | HepG2 |
| AKG-1 | 112.6 | 116.0 |
| AKG-2 | 67.9 | 24.5 |
| AKG-3 | 17.8 | 21.2 |
| AKG-5 | 32.5 | 30.8 |

TABLE 3-continued

| Compound ID | Cell viability IC50 (μg/ml) | |
|---|---|---|
| Cell line | VERO | HepG2 |
| AKG-6 | 27.4 | 15.5 |
| AKG-7 | 103.6 | 11.2 |
| AKG-9 | 139.3 | 28.1 |
| AKG-11 | 31.9 | 42.8 |
| AKG-12 | 89.1 | 67.6 |
| AKG-13 | 93.9 | 31.8 |
| AKG-14 | 155.8 | 45.6 |
| AKG-15 | 156.2 | 35.6 |
| AKG-16 | 97 | 91 |
| AKG-17 | >250 | 37.3 |
| AKG-18 | >250 | 9.5 |
| AKG-19 | >250 | 42.2 |
| AKG-20 | >250 | 15.1 |
| AKG-21 | >250 | 156.3 |
| AKG-22 | 57.7 | 17.2 |
| AKG-23 | >250 | 7.3 |
| AKG-24 | 31.3 | 11.4 |
| AKG-25 | 182 | 9.4 |
| AKG-26 | 128.5 | 9.0 |
| AKG-27 | 5.6 | 9.0 |
| AKG-28 | 83.0 | 13.4 |
| AKG-29 | 109.9 | 74.4 |
| AKG-30 | 110.5 | 18.9 |
| AKG-31 | 111.5 | 13.2 |
| AKG-38 | 395 | 97 |
| AKG-39 | 201 | 70 |
| AKG-40 | >250 | 113 |

Surprisingly, most of the analogs containing a hydroxyl group on the C5 side chain of the oxazolidinone ring, which mimics the substituent of the active metabolite tedizolid for tedizolid phosphate, were the most hepatotoxic showing single digit IC50 for the HepG2 hepatocyte cell line. Tedizolid is the most active oxazolidinone currently approved for the treatment of MRSA, and has structural similarities to the compounds described here in the tetrazole D-ring, pyridyl C-ring, and the aryl B-ring (See FIG. 6). Here, however, the increased toxicity to hepatocytes results in a comparatively low Selectivity Index for theoxazolidinones with a hydroxyl on the C5 side chain (AKG-23, AKG-25, AKG-26, and AKG-27) when compared to those with an amino or acetamide group at the same position on the C5 side chain (AKG28-31, AKG38-40, and AKG-3).

Example 4. Determination of Selectivity Index

A Selectivity Index (SI) was calculated to determine the relative inhibitory activities of the compounds on the two *Mycobacterium tuberculosis* strains, Erdman and H37Rv, compared to that on mammalian cells, namely, African green monkey kidney (VERO) or human hepatocyte-derived (HepG2) cells, as described in Experimental Examples 2 and 3, respectively. A high SI is preferable as it indicates preferred killing of the bacteria of tuberculosis strains at concentrations of the drug that are less harmful to normal cells in the body. The selectivity index was calculated using the formula below:

$$SI = IC_{50,mammalian}/MIC_{bacteria}$$

where bacteria are *M. tuberculosis* of either Erdman or H37Rv strains, and mammalian cells are VERO or HepG2 cell lines.

If the IC50 was greater than the highest value tested for the VERO or HepG2 cells, the SI is shown as greater than (>) the ratio calculated using that highest concentration. Likewise, if the MIC for Erdman or H37Rv strains is greater than the highest concentration of drug tested (8 μg/ml), then the SI is shown as less than (<) the ratio calculated using that highest concentration. Calculations where both numbers are above the highest concentrations tested are shown as not determined (nd). The results are shown in TABLE 4. The SI did not correlate directly to the activity of the molecules in either mycobacterial strains or mammalian cell lines, and increased potency in mycobacterial strains did not correlate directly to increased toxicity against the mammalian cell lines. For example, AKG-38 demonstrated nanomolar MIC against both strains of *Mycobacterium tuberculosis*, whereas it was relatively inactive against both VERO and HepG2 cell lines compared to other molecules in the panel, giving it a high SI. This was similarly seen for AKG-28. It is notable that both molecules, AKG-28 and AKG-38, had a dimethylaminoethyl substituent at the 2' position of the tetrazole ring.

TABLE 4

| Compound | Selectivity Index (SI) | | | |
|---|---|---|---|---|
| ID | Erd/VERO | Erd/HepG2 | H37Rv/VERO | H37Rv/HepG2 |
| AKG-1 | <14.1 | <14.5 | <14.1 | 14.5 |
| AKG-2 | <8.5 | <3.1 | <8.5 | 3.1 |
| AKG-3 | 142.4 | 169.6 | 296.7 | 353.3 |
| AKG-5 | 32.5 | 30.8 | 32.5 | 30.8 |
| AKG-6 | 3.4 | <1.9 | <3.4 | 1.9 |
| AKG-7 | 13.0 | <1.4 | <13.0 | 1.4 |
| AKG-9 | <17.4 | <3.5 | <17.4 | 3.5 |
| AKG-11 | 8.0 | 10.7 | 8.0 | 10.7 |
| AKG-12 | 22.3 | 16.9 | 22.3 | 16.9 |
| AKG-13 | <11.7 | <4.0 | <11.7 | <4.0 |
| AKG-14 | 19.5 | 5.7 | 19.5 | 5.7 |
| AKG-15 | <19.5 | <4.5 | <19.5 | <4.5 |
| AKG-16 | 388.0 | 364.0 | 388.0 | 364.0 |
| AKG-17 | >125 | 18.7 | >125 | 18.7 |
| AKG-18 | >125 | 4.8 | >125 | 4.8 |
| AKG-19 | >31.3 | 5.3 | >31.3 | 5.3 |
| AKG-20 | >500 | 30.2 | >500 | 30.2 |
| AKG-21 | nd | <19.5 | Nd | <19.5 |
| AKG-22 | 57.7 | 17.2 | 115.4 | 34.4 |
| AKG-23 | >1000 | 29.2 | >1000 | 29.2 |
| AKG-24 | 31.3 | 11.4 | 31.3 | 11.4 |
| AKG-25 | 182.0 | 9.4 | 182.0 | 9.4 |
| AKG-26 | 64.3 | 4.5 | 64.3 | 4.5 |
| AKG-27 | 11.2 | 18.0 | 11.2 | 18.0 |
| AKG-28 | 2766.7 | 446.7 | 5533.3 | 893.3 |
| AKG-29 | 439.6 | 297.6 | 879.2 | 595.2 |
| AKG-30 | 884.0 | 151.2 | 884.0 | 151.2 |
| AKG-31 | 223.0 | 26.4 | 223.0 | 26.4 |
| AKG-38 | 6583.3 | 1616.7 | 6583.3 | 1616.7 |
| AKG-39 | 402.0 | 140.0 | 402.0 | 140.0 |
| AKG-40 | >250.0 | 113.0 | >500.0 | 226.0 |

In some embodiments, the compounds of interest have a SI index for Erd/HepG2 and H37Rv/HepG2 higher than 100, higher than 200, higher 300, higher than 400, higher than 500, higher than 1000, higher than 1500, higher than 2000, higher than 2500, higher than 3000, higher than 3500, higher than 4000, higher than 4500, higher than 5000, higher than 5500, higher than 6000, higher than 6500, between 100 and 7000, between 100 and 6000, between 100 and 5000, between 100 and 4000, between 100 and 3000, between 100 and 2000, between 100 and 1000, between 100 and 900, between 100 and 800, between 100 and 700, between 100 and 600, between 100 and 500, between 100 and 400, between 100 and 300, between 100 and 200, between 200 and 7000, between 200 and 6000, between 200 and 5000, between 200 and 4000, between 200 and 3000, between 200 and 2000, between 200 and 1000, between 200 and 900, between 200 and 800, between 200 and 700, between 200 and 600, between 200 and 500, between 200 and 400, between 200 and 300, between 300 and 7000, between 300 and 6000, between 300 and 5000, between 300 and 4000, between 300 and 3000, between 300 and 2000, between 300 and 1000, between 300 and 900, between 300 and 800, between 300 and 700, between 300 and 600, between 300 and 500, between 300 and 400. In some embodiments, the compounds of interest have a SI index for Erd/HepG2 and H37Rv/HepG2 ranges from 100 to 1700, 200 to 1700, 300 to 1700.

Compounds with an amino or acetamide groups on the C5 side chain of the oxazolidinone ring and an aminoalkyl group at the 2' position of the tetrazole ring displayed a comparatively higher SI compared to those with a hydroxyl group on the C5 side chain. In addition, the specific tetrazole substitution further improved the SI with a dimethylamino-ethyl substitution at the 2' position of the tetrazole ring being preferred (AKG-28 and AKG-38) over methyl, diethylami-noethyl, aminoethyl, or dimethylaminopropyl substitutions at this same position. Moving a dimethyaminoethyl group to position 1' of the tetrazole ring (compound AKG-21 vs. AKG-28) unexpectedly resulted in dramatic loss of activity against *Mycobacterium tuberculosis.*

Example 5. Assay for In Vitro Activity Against Methicillin Resistant *Staphylococcus aureus* (MRSA)

The activity of the lead oxazolidinone inhibitors was measured to demonstrate sufficient potency against the gram positive bacterium methicillin resistant *Staphylococcus aureus* (MRSA) to justify their subsequent delivery in the form of liposomes for the treatment of the same. In some embodiments, the MIC in two of the three evaluated strains of less than 6 μg/mL. In some embodiments, the MIC in two of the three evaluated strains of less than 2 μg/mL less than 2 μg/mL is more preferred.

Three *S. aureus* strains were grown overnight at 37° C. in an ambient atmosphere on trypticase soy agar plates supplemented with 5% sheep blood cells. The cultures were aseptically swabbed and transferred to tubes of sterile water, and the optical density was adjusted to 0.5 at 600 nm. The cultures were then diluted 1:100 to deliver approximately $5\times10^5$ cells per well in 120 μL. Following incubation, the MIC of the test article was determined by presence/absence of growth in each well. MIC analyses were performed in triplicate.

Tedizolid showed an MIC of 0.206-0.617 μg/ml, similar to the 0.5 μg/ml described in U.S. Pat. No. 7,816,379. Interestingly, all of the molecules (AKG-3, AKG-28, AKG-29, and AKG-30) with a primary amine modification at $R_2$ of the oxazolidinone ring showed negligible activity against all three MRSA strains (>50 μg/ml). The molecules with an acetamide group at the same position (AKG-38, AKG-39, and AKG-40) were between 3 and 9-fold less active than tedizolid itself against the three MRSA strains.

TABLE 5

| Compound | methicillin resistant *Staphylococcus aureus* (MRSA) MIC (μg/ml) | | |
|---|---|---|---|
| ID strain | ATCC BAA-1556 | ATCC 43300 | 880 NR-49120 |
| Tedizolid | 0.617 | 0.617 | 0.206 |
| AKG-3 | 50 | 50 | 50 |
| AKG-16 | 1.85 | 1.85 | 1.85 |
| AKG-22 | 1.85-5.55 | 16.67 | 5.55 |
| AKG-28 | >50 | >50 | >50 |
| AKG-29 | 50 | >50 | 50 |
| AKG-30 | >50 | >50 | >50 |
| AKG-38 | 1.85 | 1.85 | 0.617 |
| AKG-39 | 1.85 | 1.85 | 1.85 |
| AKG-40 | 1.85 | 5.55 | 1.85 |

Example 6: Liposome Compositions

General Protocols

1. The lipid components (phospholipid (PhL), cholesterol, and optionally—a PEG-lipid derivative and/or a lipid fluorescent label were combined in an amount of 100% ethanol equal to one-tenth of a volume (V) calculated to obtain lipid suspension with about 60 mM phospholipid and stirred at the temperature of 65-68° C. until complete dissolution of the lipids.

Neutral phospholipids can include diacylphosphatidyl-cholines, dialkylphosphatidylcholines, sphingomyelins, and diacylphosphatidylethanolamines. Hydrogenated soyphos-phatidylcholine, distearoylphosphatidylcholine, and egg sphingomyelin are some of the preferred phospholipids.

PEG-lipid components may include PEG(Mol. weight 2,000)-distearoylglycerol (PEG-DSG), 1,2-distearoyl-sn-glycero-3-phosphoethanolamine-N-[methoxy(polyethylene glycol)-2000](PEG-DSPE) or N-palmitoyl-sphingosine-1-{succinyl[methoxy(polyethylene glycol)2000]} (PEG-cer-amide). The molecular weight of the PEG-lipid component can also vary from 1,500-6,000 g/mol, but is preferably around 2,000 MW.

Lipid fluorescent labels can include 1,1'-Dioctadecyl-3,3,3',3'-Tetramethylindocarbocyanine-5,5'-Disulfonic Acid (DiIC18(3)-DS), 1,1'-Dioctadecyl-3,3,3',3'-Tetramethylin-dodicarbocyanine-5,5'-Disulfonic Acid (DiIC8(5)-DS), 1,2-distearoyl-sn-glycero-3-phosphoethanolamine-N-(Cyanine 7) (18:0 Cy7 PE), 1,2-distearoyl-sn-glycero-3-phosphoetha-nolamine-N-[amino(polyethylene glycol)-2000]-N-(Cya-nine 7) (DSPE PEG(2000)-N-Cy7), 1,2-distearoyl-sn-glyc-ero-3-phosphoethanolamine-N-(Cyanine 5) (18:0 Cy5 PE), 1,2-distearoyl-sn-glycero-3-phosphoethanolamine-N-[amino(polyethylene glycol)-2000]-N-(Cyanine 5) (DSPE PEG(2000)-N-Cy5), 1-Oleoyl-2-[12-[(7-nitro-2-1,3-benzo-xadiazol-4-yl)amino]dodecanoyl]-sn-Glycero-3-Phospho-choline (18:1-12:0NBDPC).

2. The ethanolic lipid solution was combined with volume V of the trapping agent solution (0.25-0.5 M ammonium sulfate or 1 N triethylammonium sucrose octa-sulfate) upon stirring at 65-68° C. until a uniform suspension was obtained.

Potential trapping agents may include but are not limited to diethylammonium or triethylammonium salts of sucrose octasulfate, ammonium sulfate, ammonium citrate, citric acid, dextran sulfate, polyvinylsulfonate, or ammonium salts of inositol hexaphosphate, in the concentrations of 0.1-2 g-equivalents/L (0.1-2 N), preferably 0.2-1.5 N. Ammonium salts are typically employed and may include ammonium itself, monoalkyl-, dialkyl-, or trialkyl-ammonium salts.

3. The lipid suspension was extruded at least three times through a stack of track-etched polycarbonate membranes, typically, two or four membranes with the nominal pore size of 100 nm and one with the nominal pore size 200 nm (Whatman Nuclepore, USA), using a thermobarrel extruder (Lipex, Canada) at 65-68° C., at the pressure of 400-450 psi. When two 100-nm membranes were used in a 100-ml Lipex extruder, the extrusion pressure was typically 260-300 psi. The resulting liposomes have Z-average particle size (diameter) Xz between about 80 and about 130 nm, and PDI less than 0.1.
4. The extruded lipid suspension (known to contain unilamellar and/or oligolamellar liposomes) was chilled in refrigerator (2-8° C.) and filtered through a 0.2-micron Polyethersulfone (PES) membrane filter under positive pressure.
5. An aliquot of the extruded, filtered liposome suspension so made was chromatographed on a gravity-fed Sepharose CL-4B size exclusion column (eluent—Type 1 water), to purify the liposomes from extraliposomal trapping agent. The purified liposomes were collected near the void volume fraction of the column. For a scale-up studies, this step was performed using a tangential flow filtration (TFF) on a hollow fiber cartridge (Repligen Spectrum MicroKros PS or mPES membrane with MWCO of 500 KDa) effecting 8-10 volume exchanges (or until the conductivity of the liposome suspension dropped below 200 μS/cm) with Type 1 or USP "Water for injection" endotoxin-free water.
6. The lipid concentration in a purified extruded liposome preparation was determined using HPLC with UV detection, by measuring the concentration of cholesterol and correcting for the known phospholipid/cholesterol molar ratio Alternatively, a spectrophotometric blue phosphomolybdate method was used to directly quantify the phospholipid content
7. The drug was dissolved in Type 1 or endotoxin-free pure water in the form of a hydrochloric acid salt (e.g., AKG-3 and AKG-5 were used as monohydrochloride, AKG-28 and AKG-29 were used as dihydrochloride) at the concentration of 5-20 mg/ml of the drug. To the drug prepared in free base form (e.g., AKG-16, AKG-38), an equivalent amount of HCl was added. If necessary, pH of the solution was brought between pH 2.5-5.5, using 1 N NaOH, HCl, or tris(hydroxymethyl) aminomethane (Tris)-base solution, and the solution was filtered through a 0.2-micron PES filter under positive pressure. When necessary, the drug concentration in the stock solution so made was verified by HPLC with UV detection at 305 nm.
8. Purified liposomes of step 5 and the drug stock solution were combined in the presence of an osmotic agent (typically dextrose) and water in the amounts necessary to provide a desired drug-to-phospholipid (DL) ratio, the drug concentration in the range 1.5-3.3 mg/ml, at the osmolality equal to the measured osmolality of the trapping agent solution of step 2. Optionally, a buffer at a desired pH (typically pH 4 to pH 7) was added. In some instances, the amount of added osmotic agent (e.g., dextrose at about 45 g/L) provided osmolality less that the measured osmolality of the trapping agent solution, and the loading was effected at 6-8 mg/ml of the drug.
9. The drug-liposome mixture was incubated with constant agitation at 65-68° C. for about 15-20 min and quickly chilled on ice. After 5-10 min, the mixture was allowed to reach ambient temperature an adjusted to 0.1M NaCl by adding a calculated amount of 3 M NaCl stock solution.
10. The drug-loaded liposomes were purified from the unencapsulated drug by size exclusion chromatography (SEC) on a gravity-feed Sepharose CL-4B column, eluent—10 mM HEPES-buffer pH 7.0 in 140-144 mM NaCl (HBS-7). The liposome fractions were collected near the column void volume. For scale-up studies, the purification and buffer exchange were performed using TFF as described under item 5 above, using 10 volume exchanges with the HBS-7 buffer. In a scaled-up process, about 8 volume exchanges were typically used. Optionally, the purified liposomes were concentrated by continuing the TFF process without buffer feed. The purified, drug-loaded liposomes were aseptically filtered using 0.2-micron sterile PES filter under positive pressure and stored in refrigerator (2-8° C.).
11. The drug and lipid concentrations in the purified drug-loaded liposome preparations were determined by HPLC. Alternatively, a spectrophotometric (blue phosphomolybdate) method was used for phospholipid quantification, and the drug was quantified by UV absorption (302-305 nm) in a liposome sample solubilized in 70% isopropanol-0.1N HCl in the presence of 6.5 mg/ml efficiency was determined as:

$$EE, \% = DL/DL0 * 100\%$$

where DL0 is drug-to-phospholipid ratio in the liposome loading mixture before SEC or TFF purification, and DL is the drug-to-phospholipid ratio in the drug-loaded liposomes after purification (step 10).

12. The average liposome size (Z-average diameter, Xz) and polydispersity index (PDI) were determined using dynamic laser scattering by a method of cumulants on a Zetasizer mu-V, Zetasizer Nano, or Zetasizer Pro (Malvern Panalytical, US).

Example 7. In Vivo Stability and Blood Clearance of the Liposomes

The stability of drug encapsulation and the blood clearance rates of the liposomes that encapsulate the compounds of the present disclosure was studied in mice according to the following general protocol. Mice of a given laboratory strain (C3H female or CD-1 male) in groups of three were injected with the drug-loaded liposomes via tail vein at the dose of 9 mg of the drug per kg of the body weight. At timepoints 1 and 2, the blood was sampled from the retroorbital sinus, and the animals were sacrificed. Typically, the blood sampling timepoints included 5 min, 1 hour, 6 hours, and 24 hours post injection. The plasma was separated by centrifugation, extracted with acidified isopropanol, optionally containing a solubilizing agent (sodium octanesulfonate), and analyzed for the drug and the lipid (when a liposome the incorporated a lipid label, DiIC18(3)-DS) by HPLC. Blood clearance of the liposomal drug was expressed at percent of injected dose remaining at a given timepoint. In vivo stability of the drug encapsulation was assessed by the percent change (decrease) of DL ratio in the plasma at a given timepoint compared to the pre-injection DL value.

Example 8. Loading of AKG-3, AKG-5, and AKG-16 into Liposomes at Different pH

Trimethylammonium sucrose octasulfate trapping agent solution was prepared by passing a solution of commercial potassium sucrose octasulfate heptahydrate (40.2 g in 145 ml of water) through a 500-ml ion exchange column of Dowex 50W×8 100-200 mesh in a hydrogen form and titration of the resulting free acid form of sucrose octasulfate with neat triethylamine to pH 6.2. The concentration of triethylammonium sucrose octasulfate (TEA-SOS) (1 N, corresponding to 0.125 M sucrose octasulfate) was estimated from the amount of triethylamine consumed in titration. Residual potassium was estimated using Horiba LAQUATwin K-11 potassium analyzer by the method of additions and was less than 0.1% of the initial potassium amount.

Liposomes composed of hydrogenated soy phosphatidylcholine (HSPC) (Lipoid, Germany), cholesterol (3:2 molar ratio), and methoxypoly(ethyleneglycol) ether of 1, 2-distearoylglycerol (PEG-DSG, PEG mol·weight 2000, NOF, Japan)(0.5 mol. % of HSPC) with 1 N trimethylammonium sucrose octasulfate (TEA-SOS) as a trapping agent were prepared essentially as described in the General protocol above. The drug loading step was performed at the DL ratio (DL0) of 500 g/mol PhL in the presence of 16 mM morpholinoethanesulfonic acid (MES) −4 mM sodium citrate buffer having pH in the range of 4.3-7.1, as well as without addition of any buffer substance (pH 5.2-5.9). All drugs were encapsulated into the liposomes with high efficiency (over 98%, except for AKG-16 at pH 4.38, that was loaded with the efficiency of 93.3%) in the whole studied range of pH (FIG. 1). Addition of a buffer substance was not required for efficient encapsulation.

Figure 2A:
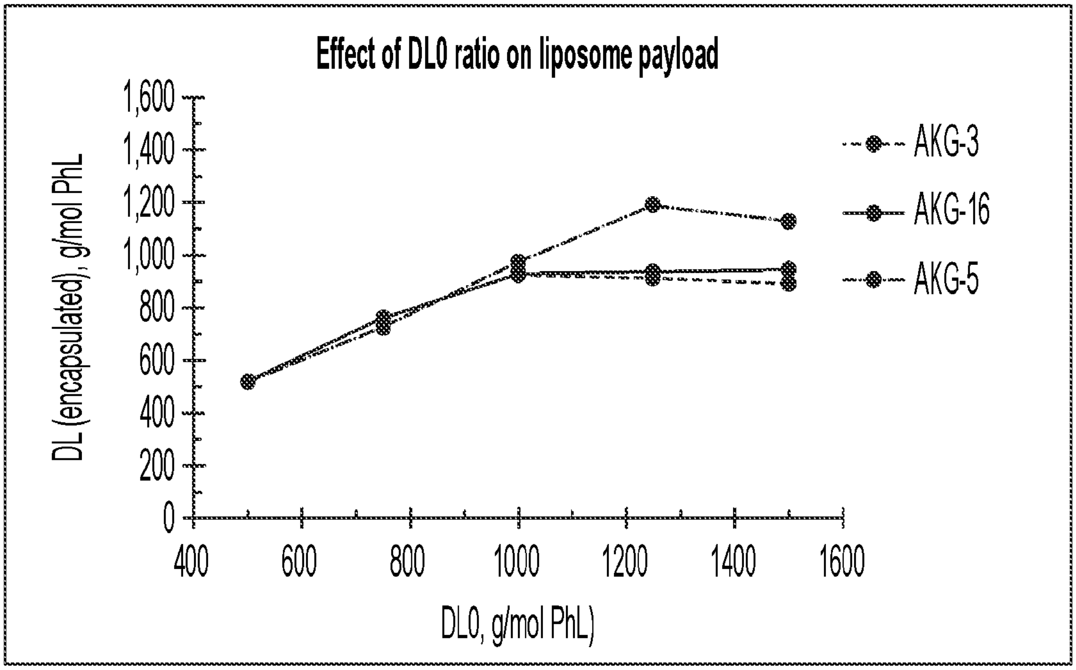
FIG. 2A and FIG. 2B are graphs showing the encapsulation of compounds AKG-3, AKG-5, and AKG-16 into liposomes with TEA-SOS trapping agent at different drug-to-lipid (DL) ratios
Figure 2B:
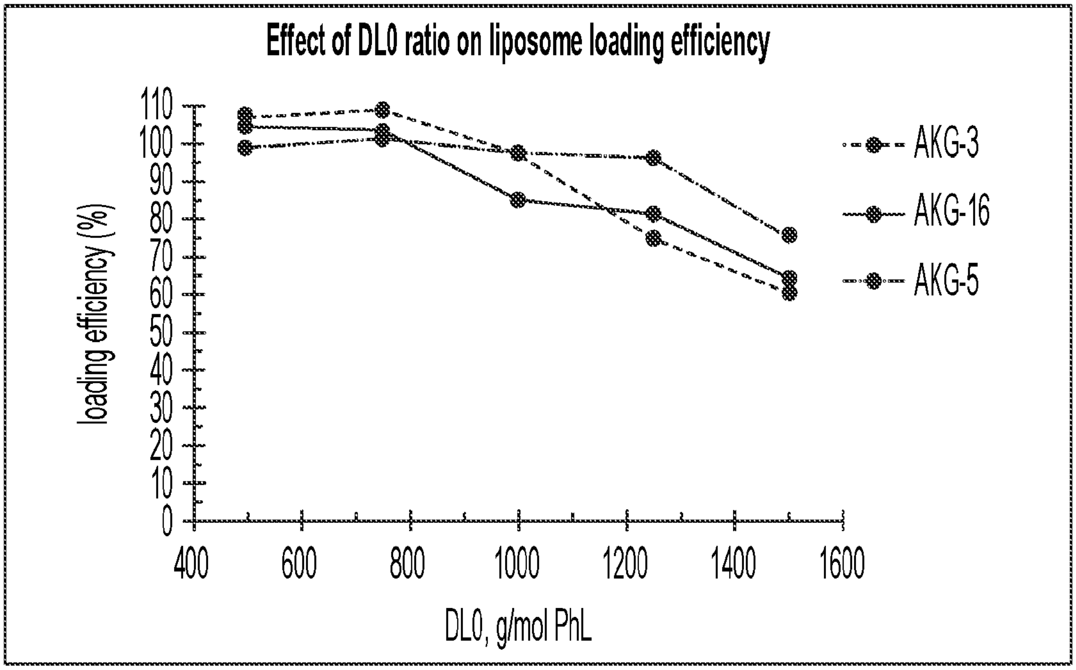
Figure 3A:
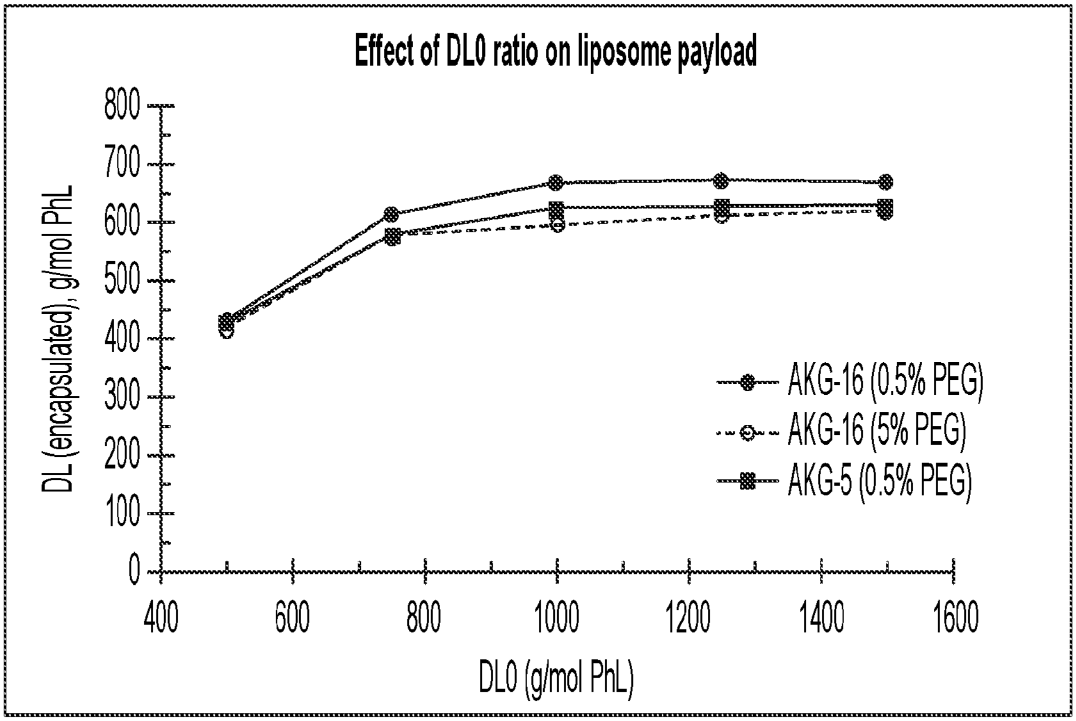
FIG. 3A, FIG. 3B FIG. 3C, and FIG. 3D are graphs showing the encapsulation of compounds AKG-3, AKG-5, and AKG-16 into liposomes with 0.5M ammonium sulfate as a trapping agent at different DL ratios.
Figure 3B:
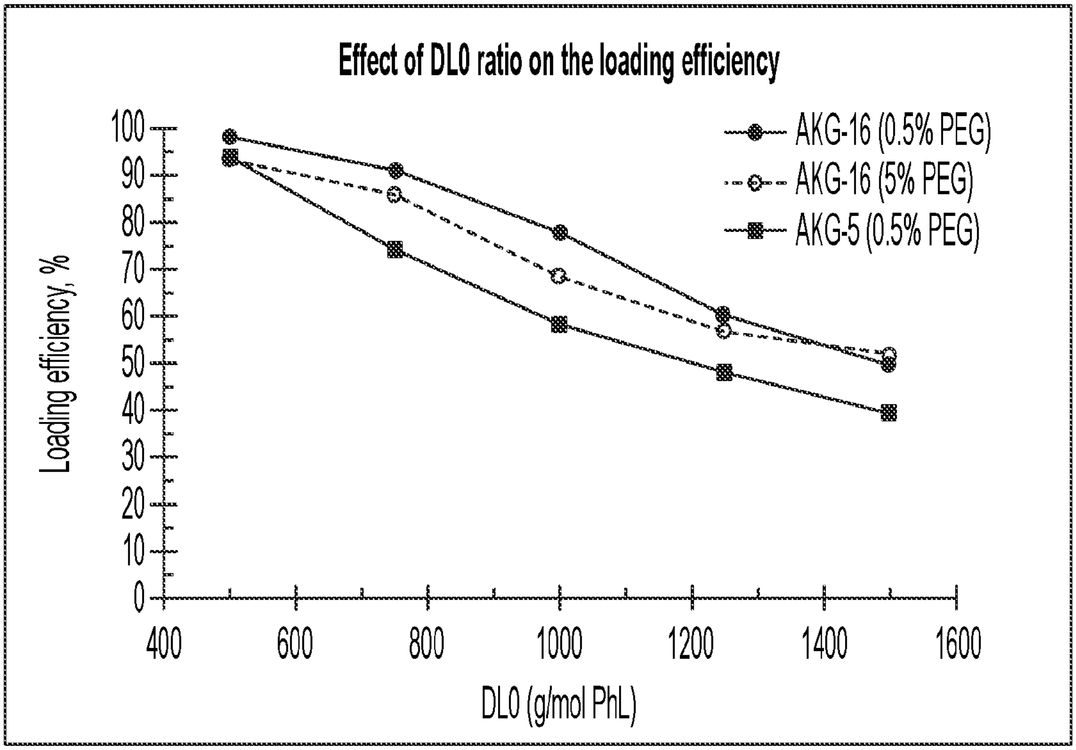
Figure 3C:
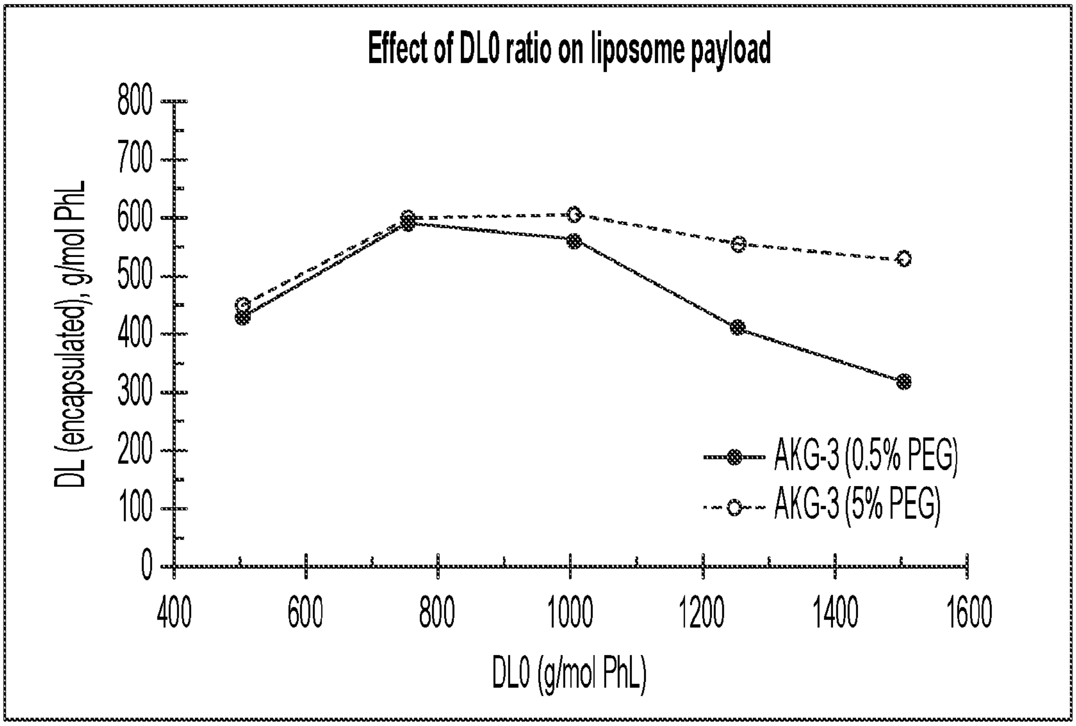
Figure 3D:
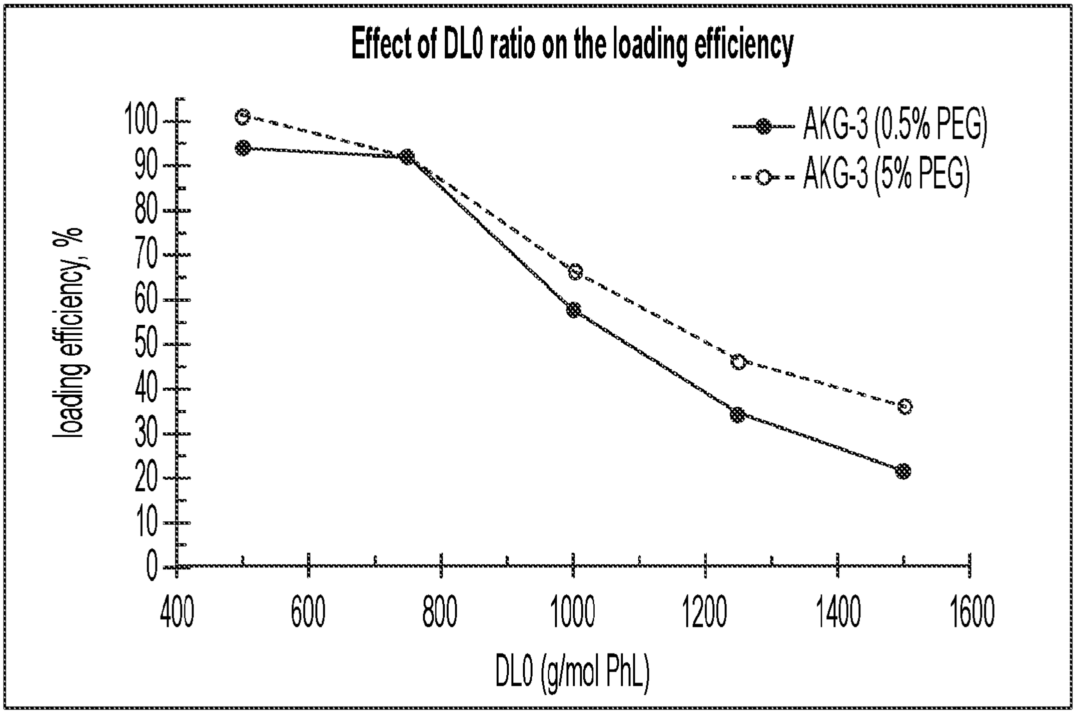

Example 9. Encapsulation of AKG-3, AKG-5, and AKG-16 into Liposomes with TEA-SOS Trapping Agent at Different DL Ratios Liposomes composed of HSPC, cholesterol (3:2 molar ratio), and PEG-DSG (0.5 mol. % of HSPC) with 1 N TEA-SOS as a trapping agent were prepared essentially as described in the General protocol (Example 6). The drug loading step was performed at the DL0 ratios in the range of 750-1500 g/mol PhL without addition of a buffer substance (pH 4.98-6.22). Maximum drug loads for compounds 3, 5, and 16 were observed in the range 900-930 g/mol PhL, 982-1197 g/mol PhL, and 938-951 g/mol PhL, respectively, and the loading efficiencies at or near the maximum drug loads were at least 97.6%, 96.0/6, or 85.2%, respectively (FIG. 2A and FIG. 2B).

Example 10. Encapsulation of AKG-3, AKG-5, and AKG-16 into Liposomes with Higher Degree of PEGylation or with 0.25 M Ammonium Sulfate (AS) as a Trapping Agent Liposomes composed of HSPC and cholesterol (3:2 molar ratio) having various PEG-DSG content and trapping agents were prepared according to the General protocol and loaded with compounds AKG-3, AKG-5, and AKG-16, as in Example 9, at DL0 ratios of 250 or 500 g/mol PhL. All three compounds were loaded into the liposomes with high efficiency as shown in the Table 6 below:

TABLE 6

| PEG-DSG, mol % of PhL | Trapping agent | DL0 ratio g/mol PhL | Drug loading efficiency AKG-3 | AKG-5 | AKG-16 |
|---|---|---|---|---|---|
| 0.5* | 1N TEA-SOS | 500 | 100.8 | 101.3 | 102.6 |
| 5 | 1N TEA-SOS | 500 | 107.4 | 99.3 | 104.8 |
| 0.5 | 0.25 M AS | 250 | 100.4 | 98.5 | 90.6 |
| 0.5 | 0.25 M AS | 500 | 80.3 | 97.7 | 82.9 |

*The data for this line are from Example 8, "no added buffer" loading.

Thus, compounds AKG-3, AKG-5, and AKG-16 were effectively loaded into phospholipid-cholesterol liposomes with increased level of PEGylation and with ammonium sulfate as an intraliposomal drug trapping agent. However, the efficiency of loading was reduced with two of the three oxazolidinones (AKG-3 and AKG-16) when loaded at the higher drug-to-lipid ratio of 500 g drug/mol PhL using 0.25 M ammonium sulfate as the trapping agent.

Example 11. Loading of Compounds AKG-3, AKG-5, and AKG-16 into the Liposomes Using 0.5 M AS as a Trapping Agent Liposomes composed of HSPC and cholesterol (3:2 molar ratio) having 0.5 mol % or 5 mol % PEG-DSG (relative to PhL) and 0.5 M ammonium sulfate (AS) as a trapping agent were prepared according to the General protocol and loaded with compounds AKG-3, AKG-5, and AKG-16, as in Example 8, at DL0 ratios in the range of 500-1500 g/mol PhL. The results are shown on FIG. 3A, FIG. 3B, FIG. 3C and FIG. 3D. All three compounds were loaded in both liposomes to the DL ratio of 420-450 g/mol PhL with encapsulation efficiency of 93-100%; maximum drug payloads were as follows:

TABLE 7

| Drug | Maximum encapsulated drug payload, g/mol PhL 0.5 mol % PEG | 5 mol % PEG |
|---|---|---|
| AKG-3 | 590 | 600-606 |
| AKG-5 | 627 | Nd |
| AKG-16 | 668-675 | 614-619 |

All three compounds tested were loadable into 0.5 M ammonium sulfate liposomes at greater than 500 g drug/mol PhL in preparations with 0.5 mol % PEG-DSG and for compounds AKG-3 and AKG-16, for formulations containing 5 mol % PEG-DSG. These high levels of loading are important in being able to reach sufficient doses of administered drug for the treatment of disease. The loading was significantly improved over Example 10, where the loading efficiency was lower using 0.25 M ammonium sulfate, demonstrating that the higher ammonium sulfate concentration of 0.5 M, despite the higher osmolarity and potential for osmotic burst, is improved with respect to the amount of drug that can be loaded per mol of phospholipid, and preferable for anti-infectives where low toxicity and high dosing can lead to improved outcomes.

Example 12. Loading of Compounds AKG-3, AKG-5, AKG-16, and AKG-28 into Liposomes of Various Compositions Including a Fluorescent Lipid Label Liposomes composed of HSPC and cholesterol (60:40 molar ratio) having 0.5 mol % PEG-DSG (relative to PhL), 0.15 mol. % lipid fluorescent label DiIC18(3)-DS (ThermoFisher, USA), and 0.5 M ammonium sulfate (AS) or 1 N TEA-SOS as trapping agents were prepared according to the General protocol and loaded with compounds AKG-3, AKG-5, and AKG-16, as in Example 11, at pH 4.7-5.8 (no added buffer substance). The liposomes had the following characteristics:

TABLE 8

| Batch ID | Compound | Trapping agent | DL0, g/mol PhL | Encapsulated drug, g/mol PhL | Liposome z-average size, nm | Liposome PDI |
|---|---|---|---|---|---|---|
| 76 | AKG-3 | 1N TEA-SOS | 500 | 497.0 | 112.7 | 0.008 |
| 85 | AKG-3 | 1N TEA-SOS | 1000 | 830.7 | 104.3 | 0.111 |
| 78 | AKG-3 | 0.5M AS | 693 | 632.9 | 104.9 | 0.013 |
| 79 | AKG-5 | 1N TEA-SOS | 500 | 515.6 | 114.3 | 0.124 |
| 80 | AKG-5 | 1N TEA-SOS | 1000 | 1003.2 | 110.5 | 0.071 |
| 81 | AKG-5 | 0.5M AS | 693 | 709.3 | 111.4 | 0.060 |
| 82 | AKG-16 | 1N TEA-SOS | 500 | 489.2 | 114.8 | 0.046 |
| 86 | AKG-16 | 1N TEA-SOS | 1000 | 854.2 | 107.6 | 0.097 |
| 84 | AKG-16 | 0.5M AS | 693 | 708.0 | 112.6 | 0.092 |

All three drugs were efficiently loaded into the liposomes. Degradation of AKG-5 during the liposome loading was detected as an appearance of a second peak on HPLC.

Liposomes composed of various phospholipids (HSPC, distearoylphosphatidylcholine (DSPC, Avanti Polar Lipids, USA), or egg sphingomyelin (ESM., Lipoid, Germany) and cholesterol (60:40 molar ratio), containing various amounts of PEG-DSG or N-methoxypoly(ethyleneglycol)oxycarbonyl-1,2-distearoylphosphatidylethanolamine (PEG-DSPE, PEG mol. weight 2000, Lipoid, Germany), and a lipid fluorescent label DiIC18(3)-DS (0.15 mol. % related to PhL) were prepared with different trapping according to the same General protocol, and loaded with AKG-16 in a similar way. When indicated, the liposome extrusion step of the General protocol was supplemented with extrusion through two stacked polycarbonate membranes with 50 nm pore size. The liposomes had the following characteristics:

TABLE 9

| Batch ID | Phospholipid | 50 nm extrusion | PEG-lipid (mol. %) | Trapping agent | DL0 ratio g/mol PhL | Drug load, g/mol PhL | Liposome z-average size, nm | PDI |
|---|---|---|---|---|---|---|---|---|
| 88 | HSPC | no | PEG-DSG (0.5) | 1N TEA-SOS | 500 | 547.0 | | |
| 90 | DSPC | yes | PEG-DSG (0.5) | 1N TEA-SOS | 500 | 514.0 | 83.3 | 0.182 |
| 91 | DSPC | yes | PEG-DSG (0.5) | 1N TEA-SOS | 1000 | 599 | | |
| 93 | HSPC | no | PEG-DSG (5) | 1N TEA-SOS | 500 | 490.2 | 108.6 | 0.046 |
| 94 | DSPC | no | PEG-DSG (0.5) | 1N TEA-SOS | 500 | 504.0 | 112.7 | 0.081 |
| 95 | ESM | no | PEG-DSG (0.5) | 1N TEA-SOS | 500 | 539.9 | 101.3 | 0.074 |
| 97 | HSPC | yes | PEG-DSPE (9.2) | 0.25M AS | 150 | 128.2 | 81.5 | 0.073 |

Liposomes composed of HSPC and cholesterol (3:2 molar ratio) having 9.2 mol % PEG-DSPE (relative to PhL), 0.15 mol. % lipid label DiIC18(3)-DS, and 0.25 M ammonium sulfate (AS) as a trapping agent were prepared according to the General protocol and Example 12 with additional 50-nm extrusion, and loaded with AKG-28 at the drug-lipid ratio (DL0) 150 g/mol PhL. The liposomes (Batch ID 98) has DL ratio of 73.8 g/mol PhL, Z-average liposome size 77.8 nm, and size polydispersity index (PDI) 0.090.

These studies demonstrate that AKG-3, AKG-5 and AKG-16 could be efficiently loaded into liposomes with range of lipid compositions, including HSPC, DSPC, or ESM as the neutral phospholipid component, or low (0.5 mol %) or high (5 mol %) PEG-lipid content. However, the efficiency was reduced significantly from about 500 g AKG-16/mol PhL to 128 g AKG-16/mol PhL when using 0.25 M AS, as compared to 1 N TEA-SOS. A similar low loading efficiency (i.e. 73.8 g/mol PhL) was observed when loading AKG-28 with 0.25 M AS. This suggests that either TEA-SOS or higher concentrations of AS may be preferable for loading high concentrations of the compounds into liposomes.

Example 13. Blood Persistence and In Vivo Encapsulation Stability of the Liposomes of Example 12 in Mice The study was performed on male CD-1 mice as described in General protocol above.

TABLE 10

| Liposome batch | % ID in plasma (Liposome lipid) | | % initial DL ratio | |
|---|---|---|---|---|
| ID | 5 min | 6 hours | 5 min | 6 hours |
| 88 | 82.4 ± 9.8 | 30.6 ± 7.0 | 89.2 ± 0.6 | 75.6 ± 2.7 |
| 90 | 84.7 ± 1.2 | 35.2 ± 5.1 | 95.9 ± 0.2 | 81.0 ± 2.5 |

TABLE 10-continued

| Liposome batch | % ID in plasma (Liposome lipid) | | % initial DL ratio | |
|---|---|---|---|---|
| ID | 5 min | 6 hours | 5 min | 6 hours |
| 93 | 85.4 ± 3.5 | 38.2 ± 1.4 | 94.5 ± 0.5 | 82.9 ± 1.1 |
| 94 | 83.1 ± 6.1 | 23.9 ± 1.2 | 97.7 ± 0.5 | 89.2 ± 0.0 |
| 95 | 79.3 ± 3.5 | 36.7 ± 2.0 | 97.9 ± 0.8 | 101.9 ± 8.8 |
| 96 | 80.2 ± 4.3 | 39.7 ± 7.0 | 102.8 ± 1.7 | 99.2 ± 2.8 |
| 97 | 83.5 ± 6.9 | 34.4 ± 2.8 | 88.7 ± 10.8 | 3.7 ± 0.3 |
| 98 | 80.3 ± 6.6 | 43.7 ± 4.7 | 100.2 ± 2.8 | 86.7 ± 1.1 |

These studies demonstrate that liposomes composed of varying neutral phospholipid components (HSPC, DSPC, or SM) and loaded with AKG-16 using the TEA-SOS trapping agent were cleared slowly with more than 30% Injected Dose remaining in plasma at 6 h for most formulation. In addition, most formulations showed good retention of drug, except for Liposome batch ID 97, which include AKG-16 loaded using 0.25 M AS, suggesting that loading of the drug using 0.25 M ammonium sulfate results not only in low loading efficiency as shown in Table 9, but also a low DL ratio (3.7%) at 6 hours due to significant leakage from the liposomes in this formulation.

Figure 4A:
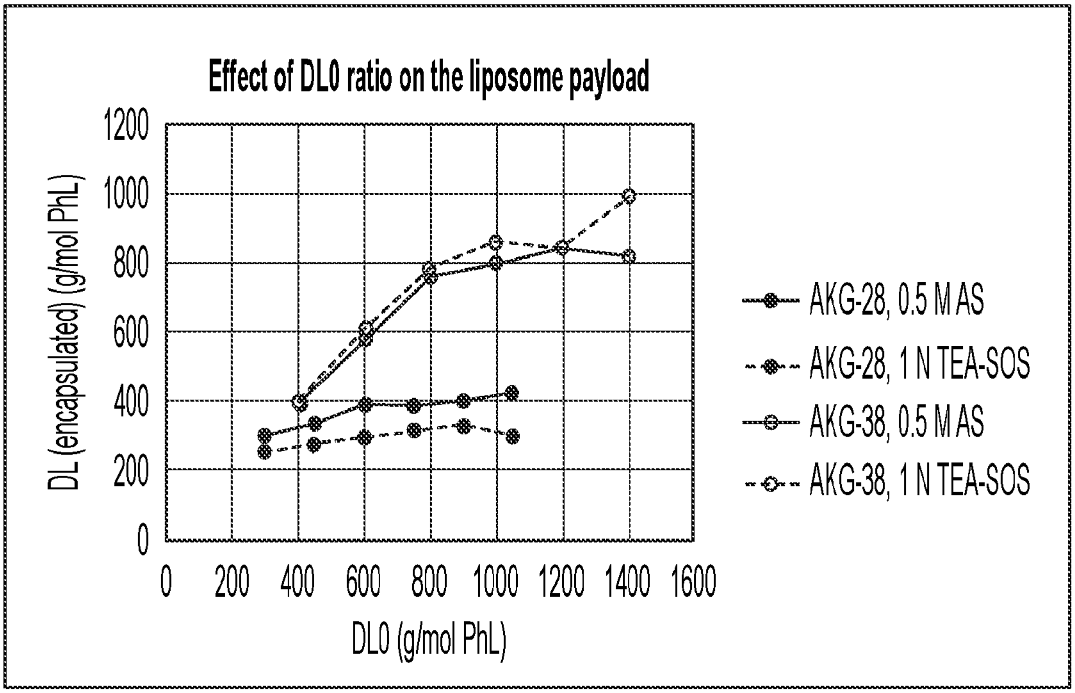
FIG. 4A and FIG. 4B are graphs showing the encapsulation of AKG-28 and AKG-38 with TEA-SOS and ammonium sulfate as trapping agents at different DL0 ratio.
Figure 4B:
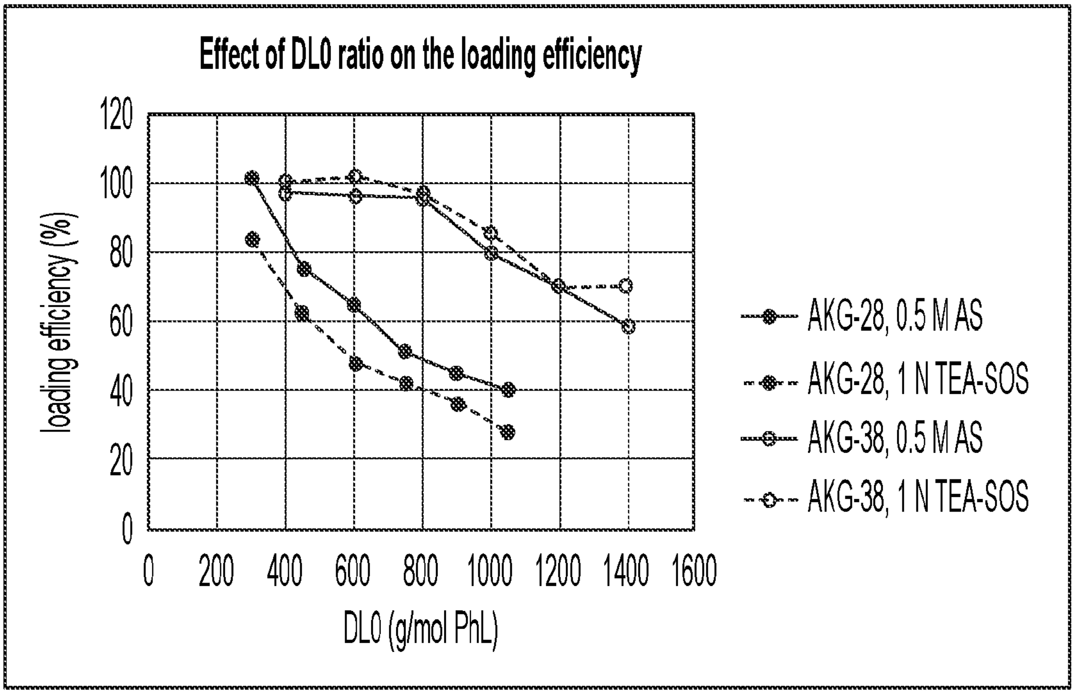
Figure 5A:
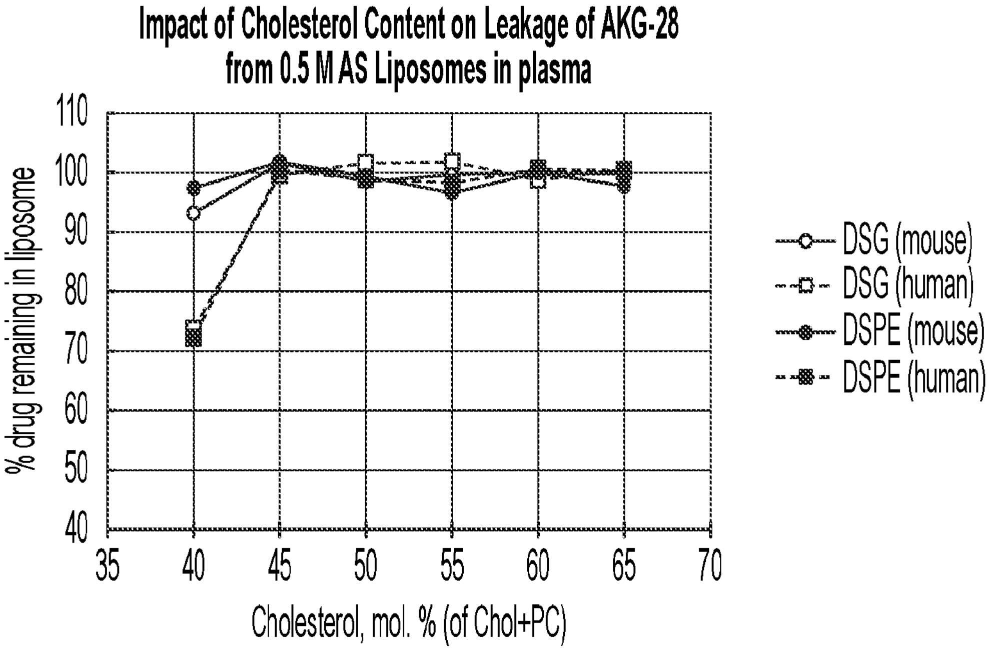
FIG. 5A, FIG. 5B, FIG. 5C, and FIG. 5D are graphs showing the dependence of fast drug leakage from the liposomes encapsulating compounds AKG-28 (FIG. 5A, FIG. 5C) and AKG-38 (FIG. 5B, FIG. 5D) upon in vitro contact with blood plasma of a mouse (denoted "mouse") or a human (denoted "human") as described in Example 19 below. Liposomes contained 5 mol % of PEG(2000)-DSPE (denoted "DSPE") or PEG-DSG (denoted "DSG"). Trapping agents: 0.5M ammonium sulfate (AS) (FIG. 5A, FIG. 5B), 1N triethylammonium sucrose octasulfate (TEA-SOS) (FIG. 5C, FIG. 5D).
Figure 5B:
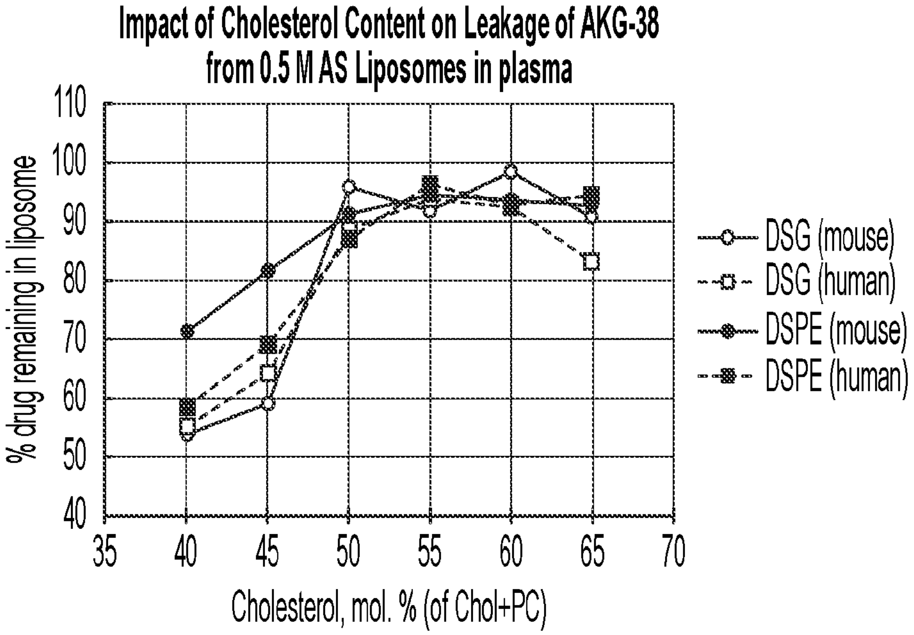
Figure 5C:
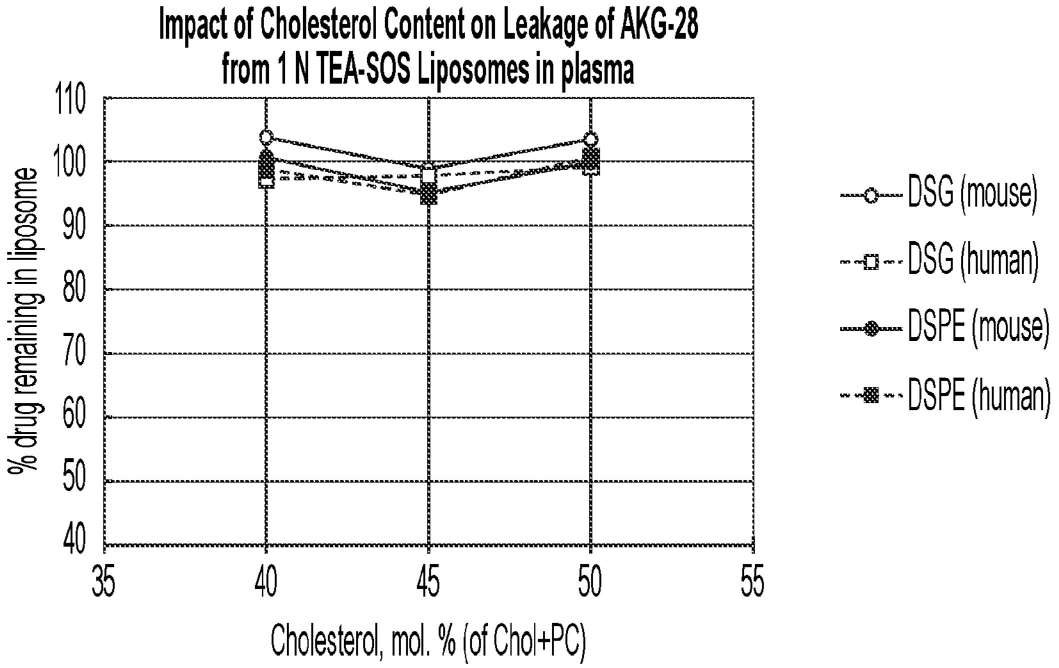
Figure 5D:
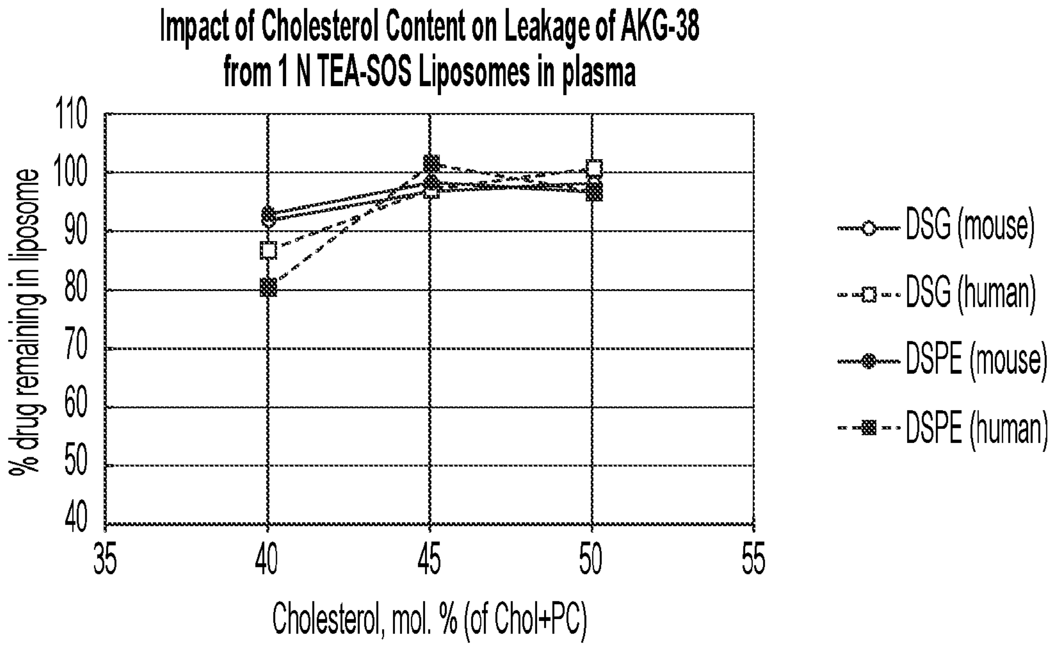

Example 14. Encapsulation of Compounds AKG-28 and AKG-38 into Liposomes with Various Trapping Agents, at Different DL Ratios Liposomes composed of HSPC and cholesterol (3:2 molar ratio) having 0.5 mol % PEG-DSG (relative to PhL), 0.15 mol. % lipid label DiIC18(3)-DS, and 0.5 M ammonium sulfate (AS) or 1 N TEA-SOS as trapping agents were prepared according to the General protocol and loaded with compounds AKG-28 and AKG-38, as in Example 8, at pH 4.95-5.17 (no added buffer substance) and DL0 ratios in the range of 300-1050 g/mol PhL (AKG-28) or 400-1400 g/mol PhL (AKG-38). Using 0.5 M AS, maximum drug loads for compounds AKG-28 and AKG-38 were in the range 404-424 g/mol PhL, and 818-842 g/mol PhL, respectively, and the loading efficiencies of more than 95% were at drug loads of 302 g/mol PhL (quantitative loading) and 387-764 g/mol PhL (95.5-96.7% loading), respectively. Using 1 N TEA-SOS, maximum drug loads for compounds AKG-28 and AKG-38 were in the range 315-328 g/mol PhL, and 989 g/mol PhL, respectively, and the maximum loading efficiencies were 83.5% at the drug load of 250 g/mol PhL, and 400-777 g/mol PhL (more than 97.2% loading), respectively (FIG. 4A and FIG. 4B).

AKG-38 showed nearly quantitative loading between 400 and 800 g AKG-38/mol PhL, while the resulting drug-to-lipid ratio remained flat for AKG-28 over the range of 250-1000 g AKG-28/mol PhL suggesting a lower maximum drug load for AKG-28 than for AKG-38. It should be appreciated that the higher potency previously demonstrated for AKG-28 would allow liposome formulations of AKG-28 to be effective for treating infectious diseases like tuberculosis.

Example 15. Encapsulation of Compounds AKG-28 and AKG-38 into Liposomes with Various Phospholipid Composition, Degree of PEGylation, and Trapping Agents Liposomes composed of a phospholipid (PhL) and cholesterol (3:2 molar ratio), PEG-DSG, and DiIC18(3)-DS (0.15 mol. % of PhL) with 0.5 M AS or 1 N TEA-SOS as trapping agents were prepared according to the General protocol and loaded with compounds AKG-28 and AKG-38 (in the absence of added buffer substance) at DL0 ratios chosen to optimize the drug load and the encapsulation efficiency (EE). The results are in the Tables 10 and 11 below.

TABLE 11

Encapsulation of compound AKG-28.

| Batch ID | PhL | PEG-DSG, mol % of PhL | Trapping agent | DL0 ratio g/mol PhL | Drug load, g/mol PhL | EE, % | Liposome z-average size, nm | Liposome PDI |
|---|---|---|---|---|---|---|---|---|
| 128 | HSPC | 0.5 | 0.5M AS | 300 | 265.9 | 88.6 | 116.7 | 0.031 |
| 129 | HSPC | 0.5 | 1N TEA-SOS | 300 | 273.9 | 91.3 | 115.2 | 0.038 |
| 130 | HSPC | 5 | 1N TEA-SOS | 300 | 260.4 | 86.8 | 109.2 | 0.031 |
| 131 | ESM | 0.5 | 1N TEA-SOS | 300 | 109.4 | 36.5 | 109.8 | 0.054 |
| 138 | HSPC | 0.5 | 0.5M AS | 400 | 260.4 | 65.1 | | |
| 139 | HSPC | 0.5 | 0.5M AS | 400 | 232.2 | 58.1 | | |

TABLE 12

Encapsulation of compound AKG-38.

| Batch ID | PhL | PEG-DSG, mol % of PhL | Trapping agent | DL0 ratio g/mol PhL | Drug load, g/mol PhL | EE, % | Liposome z-average size, nm | Liposome PDI |
|---|---|---|---|---|---|---|---|---|
| 132 | HSPC | 0.5 | 0.5M AS | 600 | 532.1 | 88.7 | 127 | 0.023 |
| 133 | HSPC | 0.5 | 1N TEA-SOS | 600 | 590.7 | 98.5 | 115.1 | 0.019 |
| 134 | HSPC | 5 | 1N TEA-SOS | 600 | 565.6 | 94.3 | 110.6 | 0.074 |
| 135 | ESM | 0.5 | 1N TEA-SOS | 600 | 529.3 | 88.2 | 106.7 | 0.049 |
| 140 | HSPC | 0.5 | 0.5M AS | 800 | 739.5 | 92.4 | | |
| 141 | HSPC | 0.5 | 1N TEA-SOS | 800 | 864.0 | 108.0 | | |

This example shows that AKG-28 can be efficiently loaded into liposomes composed of HSPC using either 0.5 M AS or 1 N TEA-SOS as the trapping agent with a maximum drug load between 230-275 g AKG-28/mol PhL. However, formulations containing sphingomyelin as the neutral phospholipid for this compound showed comparably lower loading, with a maximum of only about 1108 g AKG-28/mol PhL.

Compound AKG-38 was loaded to significantly higher D/L ratios, between 525-600 g/mol using 0.5 M AS or 1 N TEA-SOS when drug was added at 600 g AKG-38/mol PhL, or more than 735 g/mol when added at 8008 g AKG-38/mol PhL. Loading for compound AKG-38 was less sensitive to the presence of sphingomyelin than was AKG-28.

Example 16. Encapsulation of Compounds AKG-16, AKG-28, AKG-29, and AKG-38 into Liposomes with Increased PEGylation and 0.5 M Ammonium Sulfate as Trapping Agent Liposomes composed of HSPC and cholesterol (3:2 molar ratio), PEG-DSG (5 mol. %), and DiIC18(3)-DS (0.15 mol. %) with 0.5 M ammonium sulfate as trapping agent were prepared according to the General protocol and loaded with compounds AKG-16, AKG-28, AKG-29, or AKG-38 (in the absence of added buffer substance) at DL0 ratios chosen to optimize the drug load and the encapsulation efficiency (EE). The results are in the Table 13 below.

TABLE 13

| Batch ID | Compound | DL0 ratio, g/mol PhL | Drug load, g/mol PhL | EE, % |
|---|---|---|---|---|
| 145 | AKG-16 | 600 | 598.9 | 99.8 |
| 142 | AKG-28 | 300 | 292.3 | 97.4 |
| 143 | AKG-29 | 300 | 43.6 | 14.5 |
| 144 | AKG-38 | 600 | 506.2 | 84.4 |

This data shows that all compounds containing a dimethylaminoethyl substituent at the 2 position of the tetrazole ring were efficiently loaded into liposomes at greater than 80%, while AKG-29 with an aminoethyl substituent at the same position was only poorly loaded into liposomes with an efficiency of 14.5% and a final drug load of 43.6 g AKG-29/mol PhL. This illustrates that, despite the presence of titratable amines in all of the compounds tested, compounds with a substituted ammonium (for example, N,N-dimethylaminoethyl group) at the tetrazole ring unexpectedly allowed more efficient drug loading than those with a primary amine (aminoethyl group) at the same position.

Example 17. Blood Persistence and In Vivo Encapsulation Stability of the Liposomes of Examples 15 and 16 in Mice The study was performed on male CD-1 mice as described in General protocol above.

TABLE 14

| Liposome batch ID | % ID in plasma (Liposome lipid) 5 min | 6 hours | % initial DL ratio 5 min | 6 hours |
|---|---|---|---|---|
| 128 | 80.6 ± 1.3 | 34.9 ± 0.8 | 75.2 ± 1.1 | 67.9 ± 4.0 |
| 129 | 83.6 ± 0.6 | 42.2 ± 3.4 | 95.7 ± 0.9 | 88.7 ± 3.1 |
| 130 | 83.4 ± 11.9 | 54.6 ± 3.8 | 94.4 ± 4.0 | 93.2 ± 1.1 |
| 132 | 83.2 ± 8.3 | 42.4 ± 1.7 | 48.6 ± 0.2 | 29.5 ± 0.5 |
| 133 | 71.3 ± 6.0 | 21.9 ± 8.1 | 97.3 ± 2.6 | 93.2 ± 4.3 |
| 134 | 78.8 ± 2.3 | 46.5 ± 3.2 | 93.8 ± 2.6 | 83.3 ± 4.7 |
| 135 | 77.9 ± 3.6 | 38.7 ± 2.9 | 102.6 ± 2.5 | 102.3 ± 1.8 |
| 142 | 80.9 ± 2.9 | 48.9 ± 2.8 | 52.9 ± 1.1 | 40.0 ± 0.3 |
| 144 | 83.3 ± 5.6 | 42.0 ± 4.4 | 50.4 ± 1.1 | 24.0 ± 0.5 |
| 145 | 80.6 ± 1.3 | 40.3 ± 0.1 | 41.4 ± 1.7 | 13.1 ± 0.0 |

The data showed that the drug in liposome Batch ID 128, 132, 142, 144, and 145, all having 0.5 M AS as a trapping agent, lost 25-60% of the encapsulated drug almost immediately upon contact with blood as shown by the low DL ratio at 5 min, and further decrease of the DL ratio at 6 hours, especially pronounced for AKG-38 and AKG-16-loaded liposomes. Thus, the formulation of 0.5 mol % or 5 mol % PEG-DSG and 40 mol % cholesterol, 0.5 M AS (as a trapping agent) was not able to retain drug as efficiently as the formulations employing 1N TEA-SOS (Liposome Batch ID 129, 130, 133-135), where the % of initial DL ratio at both 5 min and 6 hour time points was greater than 80%.

Example 18. Preparation and Loading of AKG-28 and AKG-38 into Pegylated Liposomes with Varying Ratios of Phospholipid-to-Cholesterol Liposomes containing 5 mol % PEG-DSG or PEG-DSPE (relative to PhL), 0.15 mol. % lipid label DiIC18(3)-DS, and 0.5 M ammonium sulfate (AS) or 1 N TEA-SOS as trapping agents, were prepared according to the General protocol and loaded with compounds AKG-28 and AKG-38, as in Example 8, at pH 5.07-5.82 (no added buffer substance).

In an attempt to stabilize the liposomes having 0.5 M AS at a trapping agent against fast drug release upon contact with blood (as described in Example 17), the liposomes using DSPC (generally known to produce more drug leakage-stable liposomes compared to HSPC) and decreasing proportion of cholesterol (Chol) were prepared and loaded with AKG-28 at DL0 250 g/mol PhL, or with AKG-38 at 600 g/mol PhL (Table 15). Contrary to expectations, decreasing cholesterol content from 40 mol % down to 10 mol % cholesterol resulted in a dramatically reduced encapsulation efficiency for both AKG-28 and AKG-38. Lower cholesterol also destabilized the liposomes against aggregation. At 30 mol. % cholesterol (PhL-cholesterol molar ratio 70:30), AKG-28-containing liposomes made using 1 N TEA-SOS and 5 mol % of either PEG-DSG or PEG-DSPE irreversibly aggregated during the drug loading, as did 30 mol % cholesterol, 5 mol % PEG-DSPE containing formulation of AKG-38, while the 5 mol % PEG-DSG formulation of AKG-38 at 30 mol % cholesterol showed reduced loading efficiency of 77.1%, or 462.4 g/mol PhL

TABLE 15

| Batch ID | Compound | PEG-lipid (lipid portion) | Trapping Agent | Chol (mol %) | Drug load, (g/mol PhL) | EE, (%) |
|---|---|---|---|---|---|---|
| 158 | AKG-28 | DSG | 0.5M AS | 40 | 231.2 | 92.5 |
| 159 | AKG-28 | DSG | 0.5M AS | 30 | 173.5 | 69.4 |
| 160 | AKG-28 | DSG | 0.5M AS | 20 | 116.4 | 46.6 |
| 161 | AKG-28 | DSG | 0.5M AS | 10 | 92.4 | 36.9 |
| 162 | AKG-28 | DSPE | 0.5M AS | 30 | 130.5 | 52.2 |
| 166 | AKG-38 | DSG | 0.5M AS | 40 | 462.8 | 77.1 |
| 167 | AKG-38 | DSG | 0.5M AS | 30 | 280.2 | 46.7 |
| 168 | AKG-38 | DSG | 0.5M AS | 20 | 120.0 | 20.0 |
| 169 | AKG-38 | DSG | 0.5M AS | 10 | 69.8 | 11.6 |
| 170 | AKG-38 | DSPE | 0.5M AS | 30 | 114.9 | 19.1 |

In contrast, liposomes prepared using HPSC and containing 40 mol % or more of cholesterol, up to 65 mol % of cholesterol (maximum studied), showed excellent encapsulation efficiency over 87% and no liposome aggregation for both AKG-28 (DL0 250 g/mol PhL) and AKG-38 (DL0 500 g/mol PhL), PEG-lipids (PEG-DSG and PEG-DSPE), and trapping agents (AS or TEA-SOS) (Table 16).

In addition, the potential of the optimized formulation to load the current standard of care drug from this class, linezolid, in both 0.5 M AS and 1 N TEA-SOS formulations was evaluated. Tedizolid was not soluble enough in water to perform a transmembrane gradient-assisted loading into liposomes following the general protocol of Example 6. In both cases with linezolid, the encapsulation efficiency was less than 5%, demonstrating that these liposomal formulations of AKG-28 and AKG-38 were dramatically superior in their ability to stably encapsulate drug, when compared to linezolid.

Z-average size ($x_z$) and polydispersity index (PDI) of the liposomes were determined by dynamic light scattering (DLS) cumulants method using Malvern Zetasizer Pro (Malvern Panalytical) at 173° measurement angle.

TABLE 16

| Batch ID | Compound | PEG-lipid (lipid portion) | Trapping Agent | Chol (mol %) | Drug load, (g/mol PhL) | Liposome average size $x_z$, nm | Poly-dispersity index | EE, (%) |
|---|---|---|---|---|---|---|---|---|
| 174 | AKG-28 | DSG | 0.5M AS | 40 | 249.8 | | | 99.9 |
| 175 | AKG-28 | DSG | 0.5M AS | 45 | 253.9 | | | 101.6 |
| 176 | AKG-28 | DSG | 0.5M AS | 50 | 252.6 | | | 101.0 |
| 201 | AKG-28 | DSG | 0.5M AS | 55 | 228.2 | 107.2 | 0.0495 | 91.3 |
| 202 | AKG-28 | DSG | 0.5M AS | 60 | 233.0 | 109.4 | 0.0333 | 93.2 |
| 203 | AKG-28 | DSG | 0.5M AS | 65 | 235.3 | 111.0 | 0.0359 | 94.1 |
| 177 | AKG-28 | DSG | 1N TEA-SOS | 40 | 223.5 | | | 89.4 |
| 178 | AKG-28 | DSG | 1N TEA-SOS | 45 | 258.7 | | | 103.5 |
| 179 | AKG-28 | DSG | 1N TEA-SOS | 50 | 259.5 | | | 103.8 |
| 180 | AKG-38 | DSG | 0.5M AS | 40 | 440.4 | | | 88.1 |
| 181 | AKG-38 | DSG | 0.5M AS | 45 | 488.7 | | | 97.7 |
| 182 | AKG-38 | DSG | 0.5M AS | 50 | 468.4 | | | 93.7 |
| 207 | AKG-38 | DSG | 0.5M AS | 55 | 460.7 | 109.2 | 0.0034 | 92.1 |
| 208 | AKG-38 | DSG | 0.5M AS | 60 | 475.1 | 111.3 | 0.0201 | 95.0 |
| 209 | AKG-38 | DSG | 0.5M AS | 65 | 475.3 | 111.9 | 0.0118 | 95.1 |
| 183 | AKG-38 | DSG | 1N TEA-SOS | 40 | 505.4 | | | 101.1 |
| 184 | AKG-38 | DSG | 1N TEA-SOS | 45 | 495.8 | | | 99.2 |
| 185 | AKG-38 | DSG | 1N TEA-SOS | 50 | 489.4 | | | 97.9 |
| 186 | AKG-28 | DSPE | 0.5M AS | 40 | 244.4 | 108.9 | 0.0250 | 97.8 |
| 187 | AKG-28 | DSPE | 0.5M AS | 45 | 241.6 | 107.8 | 0.002 | 96.6 |
| 188 | AKG-28 | DSPE | 0.5M AS | 50 | 250.4 | 109.1 | 0.0076 | 100.1 |
| 204 | AKG-28 | DSPE | 0.5M AS | 55 | 223.5 | 117.0 | 0.0037 | 89.4 |
| 205 | AKG-28 | DSPE | 0.5M AS | 60 | 237.8 | 114.8 | 0.0113 | 95.1 |
| 206 | AKG-28 | DSPE | 0.5M AS | 65 | 233.0 | 115.1 | 0.0266 | 93.2 |
| 189 | AKG-28 | DSPE | 1N TEA-SOS | 40 | 244.6 | 109.3 | 0.0480 | 97.8 |
| 190 | AKG-28 | DSPE | 1N TEA-SOS | 45 | 245.6 | 107.7 | 0.0165 | 98.2 |
| 191 | AKG-28 | DSPE | 1N TEA-SOS | 50 | 245.0 | 107.9 | 0.0221 | 98.0 |
| 192 | AKG-38 | DSPE | 0.5M AS | 40 | 434.8 | 115.1 | 0.0040 | 87.0 |
| 193 | AKG-38 | DSPE | 0.5M AS | 45 | 462.7 | 112.9 | 0.0202 | 92.5 |
| 194 | AKG-38 | DSPE | 0.5M AS | 50 | 467.0 | 109.4 | 0.0323 | 93.4 |
| 210 | AKG-38 | DSPE | 0.5M AS | 55 | 463.3 | 114.5 | 0.0183 | 92.7 |
| 211 | AKG-38 | DSPE | 0.5M AS | 60 | 479.6 | 114.9 | 0.0020 | 95.9 |
| 212 | AKG-38 | DSPE | 0.5M AS | 65 | 475.0 | 114.2 | 0.0511 | 95.0 |
| 195 | AKG-38 | DSPE | 1N TEA-SOS | 40 | 503.6 | 109.1 | 0.002 | 100.7 |
| 196 | AKG-38 | DSPE | 1N TEA-SOS | 45 | 489.8 | 108.5 | 0.0298 | 98.0 |
| 197 | AKG-38 | DSPE | 1N TEA-SOS | 50 | 481.4 | 107.3 | 0.0395 | 96.3 |
| 229 | Linezolid | DSPE | 0.5M AS | 55 | 21.0 | | | 4.2 |
| 230 | Linezolid | DSPE | 1N TEA-SOS | 55 | 19.7 | | | 3.9 |

Example 19. In Vitro Burst Release of Pegylated Liposomes Containing AKG-28 or AKG-38 and Varying Ratios of Phospholipid-to-Cholesterol in the Presence of Plasma The in vitro stability of liposomal formulations of AKG-28 and AKG-38 containing 5 mol % PEG-DSPE or PEG-DSG and varying ratios of HSPC-to-Chol (40-65 mol % Chol) were evaluated for stability in the presence of Mouse CD-1 or human pooled plasma (Lithium-Heparin-stabilized from Innovative Research). The plasma was thawed, if necessary, adjusted to pH 7.4 with 1 N HCl, and sequentially filtered through glass microfiber filters (GF/C), 1 µm polyethersulfone (PES), and 0.22 µm PES filters. Plasma (80 µl) was mixed with liposomal drug formulations (20 µl) in a 0.5 ml Eppendorf tube. The mixture was subsequently incubated for 20 min at 37° C. and then put into chilled water. The mixture (0.1 mL) was chromatographed without delay on a 2 mL Sepharose CL-4B column, eluted with Hepes-buffered saline (pH 7.0) and 0.25 mL of liposomal drug was collected in the void volume fraction. The drug and DiI(3)-DS lipid label were then analyzed by HPLC as described in Example 7, and the % drug remaining encapsulated determined using the following formula:

$$(A_d/A_l/(A_{d,0}/A_{l,0})*100=\%\text{ drug remaining encapsulated}$$

Where $A_d$—are of the drug peak, $A_l$—area of the lipid label peak, $A_{d,0}$—area of the drug peak pre-incubation with plasma, and $A_{l,0}$—are of the lipid label peak pre-incubation.

The results are shown on FIG. 5A, FIG. 5B, FIG. 5C and FIG. 5D. For the liposomes with encapsulated AKG-28 (FIG. 5A), burst release phenomenon (a rapid drop of the DL ratio signifying the drug release from the liposomes) was observed in human plasma for the formulations containing 40 mol. % cholesterol, but not for the formulations with 45 mol. % or more of cholesterol. For the liposomes with encapsulated AKG-38 (FIG. 5B), burst release phenomenon was observed in both human and mouse plasma for the formulations with cholesterol content of 40 mol. % and 45 mol. %, but not at cholesterol content of 50 mol. % or more.

Example 20. In Vitro Plasma Release and In Vivo Pharmacokinetics of 5 Mol % PEG-Lipid Liposomes Containing AKG-38 and 40 or 55 Mol % Cholesterol Three of the liposome formulations of Example 18 using the 0.5 M AS trapping agent were evaluated in a two time point pharmacokinetic study in female CD-1 mice as described in Example 7, measuring percent of the injected dose (% ID) of the liposome lipid remaining in the blood at both 5 min and 6 h, and measuring drug release from the liposomes through determination of the drug-to-lipid ratio (DL). While the liposomes having either 5 mol % PEG-DSG or 5 mol % PEG-DSPE and containing 55 mol % Chol showed more than 95% of the pre-injection D/L ratio at 5 min and >85% at 6 hours, the PEG-DSG formulation containing 40 mol % Chol showed dramatically reduced DL ratios at both 5 min and 6 hours, consistent with the drug leakage data in the presence of plasma in vitro (Table 17). This finding was in contrast with previous experience with drug-loaded liposome formulations, as a number of highly stable liposomal drugs, approved for clinical use, like pegylated liposomal doxorubicin and nanoliposomal irinotecan, contain cholesterol at a ratio of about 40 mol % (see, e.g., Doxil© drug information package insert, updated 08/2019, and Drummond, D. C., et al. (2006). "Development of a highly active nanoliposomal irinotecan using a novel intraliposomal stabilization strategy." Cancer Res. 66(6): 3271-3277)

TABLE 17

| | | | | |
|---|---|---|---|---|
| Liposome lot ID | | 180 | 207 | 210 |
| Chol, mol % (of Chol + PC) | | 40 | 55 | 55 |
| PEG-lipid | | DSG | DSG | DSPE |
| D/L ratio post load | | 440.4 ± 8.5 | 460.7 ± 16.2 | 463.3 ± 13.7 |
| Encapsulation eff-cy, % | | 88.1 ± 1.7 | 92.1 ± 3.2 | 92.7 ± 2.7 |
| Plasma stability in vitro, 20 min 37° C. | Mouse CD1 | 54.6 ± 1.6 | 92.4 ± 0.7 | 95.0 ± 0.8 |
| (% drug remaining encapsulated) | Human | 55.9 ± 3.7 | 94.3 ± 0.6 | 96.8 ± 0.9 |
| Two-point PK data (CD-1 mouse, 9 mg/kg iv): | | | | |
| Liposome lipid, | 5 min | 103.4 ± 11.7 | 114.9 ± 14.9 | 104.3 ± 5.6 |
| % ID | 6 hours | 51.1 ± 5.2 | 52.6 ± 3.6 | 50.3 ± 5.7 |
| D/L ratio, % of | 5 min | 60.8 ± 1.2 | 95.1 ± 1.2 | 96.8 ± 0.2 |
| pre-injection value | 6 hours | 30.9 ± 2.4 | 86.6 ± 5.7 | 90.0 ± 4.1 |

Example 21. Inhibition of Mitochondrial Protein Synthesis (MPS) by AKG-3, AKG-16, AKG-22, AKG-28, AKG-29, AKG-30, AKG-38, AKG-39, and AKG-40 and Selectivity for *M. tuberculosis* (H37Rv) Inhibition Over MPS Inhibition Inhibition of mitochondrial protein synthesis was determined using a colorimetric MitoBiogenesis™ in-cell ELISA kit from AbCam (Catalog #ab11021), as per the manufacturer's instructions. Mitochondrial protein synthesis inhibition has been correlated to important toxicities for linezolid and other oxazolidinones, most notably ocular and peripheral neuropathy, and lactic acidosis (Renslo (2010) Expert Reve Anti Infect Ther 8(5) 565-574; Flanagan et al. (2015) Antimicrob Agents Chemother 59(1) 178-185; Santini et al. (2017) Expert Opin Drug Saf 16(7) 833-843). The levels of two mitochondrial proteins were measured simultaneously, including the mitochondrial DNA-encoded subunit I of Complex IV (COX-1) and the nuclear DNA-encoded 70 kDa subunit of Complex II (SDH-A). The H9C2 rat BDIX heart myoblast cell line was used in these studies in a 384 well plate assay format. Cells were grown in DMEM media with 10% FBS and 1× Glutamine at 37° C. and 5% CO2. Cells were plated at a density of 1,500 cells/well in 384 well plates in 47.5 μl/well. Ten concentrations of each compound, starting at a high concentration of 200 μM and including nine 3-fold dilutions and one replicate per condition, were added to the cells in 2.5 μl and incubated with the cells for five days at 37° C. and 5% CO2. The compounds tested included tedizolid and linezolid controls, as well as AKG-3, AKG-16, AKG-22, AKG-28, AKG-29, AKG-30, AKG-38, AKG-39, and AKG-40.

The MitoBiogenesis In-Cell Elisa was then performed according to the manufacturer's instructions (Abcame Catalog #ab11021) and alkaline phosphatase (AP) developed for detection of SDH-1A at 405 nm in kinetic model for 15 min (20 sec-1 min interval) and HRP developed for detection of COX-I at 600 nm in kinetic mode for 15 min (20 sec-1 min interval) in plate reader. COX-I and SDH-A signals were plotted as a ratio of COX-1/SDH-A against concentration of each compound, and the IC50 were calculated for each of the 9 investigational compounds and two controls.

An MPS selectivity index (SI-MPS) was determined by dividing the MPS IC50 in ug/ml by the MIC in the drug sensitive H37Rv *M. tuberculosis* strain as determined in Example 2. Two of the compounds tested, AKG-28 and AKG-29, had an SI-MPS that was more than ten times higher than that determined for linezolid and more than twenty times higher than determined for tedizolid. Both of these compounds contained a primary amino group at the R2 position of the oxazolidinone ring. Due to its high potency (MIC<0.1) and high selectivity for *M. tuberculosis* compared to mitochondrial protein synthesis, AKG-28 is excellent candidate for encapsulation in liposomes and treatment of tuberculosis or other mycobacterial diseases.

TABLE 18

| Compound | Tetrazole ring position, $R_1$ (Formula (I)) | $R_2$ (Formula (I)) | MIC (H37Rv) (μg/ml) | MPS IC50 (μg/ml) | SI-MPS MPS/ H37 |
|---|---|---|---|---|---|
| Linezolid | Not applicable | $—NHCOCH_3$ | 1.00 | 2.157 | 2.16 |
| Tedizolid | 2', $CH_3—$ | —OH | 0.25 | 0.143 | 0.57 |
| AKG-3 | 2', $CH_3—$ | $—NH_2$ | 0.06 | 0.115 | 1.91 |
| AKG-16 | 2', $(CH_3)_2N(CH_2)_2—$ | —OH | 0.25 | 0.244 | 0.98 |
| AKG-22 | 1', $NH_2$ $(CH_2)_2—$ | —OH | 0.5 | 1.184 | 2.37 |
| AKG-28 | 2', $(CH_3)_2N(CH_2)_2—$ | $—NH_2$ | 0.015 | 0.411 | 27.41 |
| AKG-29 | 2', $NH_2(CH_2)_2—$ | $—NH_2$ | 0.125 | 4.11 | 32.80 |
| AKG-30 | 2', $(C_2H_5)_2N(CH_2)_3—$ | $—NH_2$ | 0.125 | 0.252 | 2.02 |
| AKG-38 | 2', $(CH_3)_2N(CH_2)_2—$ | $—NHCOCH_3$ | 0.06 | 0.041 | 0.69 |
| AKG-39 | 2', $(C_2H_5)_2N(CH_2)_2—$ | $—NHCOCH_3$ | 0.5 | 0.060 | 0.12 |
| AKG-40 | 2', $(C_2H_5)_2N(CH_2)_3—$ | $—NHCOCH_3$ | 0.5 | 0.064 | 0.13 |

Example 22. Scaled-Up Preparation of Liposomal AKG-28 Lot 275

Lot 267. The general procedure of Example 6 was followed. HSPC (Lipoid AG) 4.95 g (6.30 mmol), cholesterol (Dishman, High purity) 2.98 g (7.71 mmol), and PEG-DSPE (Lipoid AG) 850 mg (0.315 mmol) (HSPC:Chol:PEG-DSPE 45:55:2.25 molar ratio) were combined with 9 ml of absolute ethanol (Sigma, E-7023) and heated with stirring on a 68° C. bath until all lipids dissolved. In a separate container 93.3 g of 0.5 M aqueous ammonium sulfate (0.2-micron filtered) was preheated on a 68° C. bath and poured with stirring into the hot lipid ethanolic solution. The obtained suspension was stirred on a 68° C. bath for 20 min. and extruded eight times at 260-300 psi through the stack of two 47-mm 100-nm pore size and one 200-nm pore size polycarbonate track-etched membranes (Whatman Nucleopore) using Lipex 100-ml thermobarrel liposome extruder (Northern Lipids, Inc.) heated with circulating 68° C. water. The resulting extruded liposomes were kept overnight in a refrigerator (2-8° C.) and filtered through 0.2-μm polyethersulfone (PES) filter under positive pressure. Extraliposomal trapping agent (ammonium sulfate) was removed by TFF buffer exchange for endotoxin-free water on a KrosFlo TFF system using polysulfone hollow fiber cartridge with MW cut-off 500 KDa (Spectrum Laboratories) until residual conductivity dropped to less than 200 μS/cm (143 μS/cm after 5.2 volume exchanges). The phospholipid concentration in the post-TFF liposome suspension was determined by blue phosphomolybdate method to be 57.4 mM.

720 mg of AKG-28 (as dihydrochloride salt) in the form of 20 mg/ml aqueous stock solution (adjusted to pH 5.03 with NaOH) were combined with post-TFF liposome suspension to form the loading mixture at drug-to-phospholipid (DL) ratio of 250 g/mol in the presence of 45 mg/ml dextrose and AKG-28 concentration of 6 mg/ml. The mixture was quickly heated to 60-63° C. by external heating under constant stirring, and the incubation continued with stirring on the 65° C. bath. After 20 min. incubation, the mixture was quickly chilled in an ice-water to less than 10° C., and kept at this temperature for about 10 min. After reaching the ambient temperature and adjustment to 0.1 M NaCl, the drug-loaded liposomes were purified by TFF using polysulfone hollow fiber cartridge with molecular weight cutoff 500 KD. The liposomes were pre-concentrated by diafiltration to about 12 mg/ml of AKG-28 and purified from any extraliposomal drug by TFF exchange into 10 mM HEPES-Na buffer pH 7.0, containing 0.144 M NaCl made with endotoxin-free water (HBS-7 buffer) for the total of about 8 volume exchanges. The proportion of unencapsulated drug prior to purification was estimated spectrophotometrically at 305 nm in the pre-concentration diafiltrate and found to be about 0.9% (corresponds to 99.1% loading efficiency). The concentrated, purified liposomes were aseptically passed through 0.2-μm sterile filter and analyzed for the particle size by DLS, and for the drug and phospholipid concentration by spectrophotometry. This procedure was repeated three more times (lots 269, 271, 273). Obtained liposomes had the characteristics shown in TABLE 19.

TABLE 19

| Lot ID | Scale, mg of AKG-28 | DL ratio g AKG-28/mol PhL | Average particle size Xz, nm | PDI |
|---|---|---|---|---|
| 267 | 720 | 251.9 | 115.4 | 0.0248 |
| 269 | 750 | 248.7 | 112.6 | 0.0282 |
| 271 | 750 | 268.0 | 114.0 | 0.0482 |
| 273 | 766 | 244.9 | 114.7 | 0.0153 |

These lots were combined to obtain lot 275 having 12.0 mg/ml AKG-28 in the liposomal form, particle size Xz 113.7 nm, PDI 0.0417.

Example 23. Scaled-Up Preparation of Liposomal AKG-38 Lot 276

Lot 268. The protocol of Example 22 was used with the following differences: the stock aqueous solution of AKG-38 (as free base) was prepared by dissolving the drug in the equivalent amount of 1 N HCl and adjusting the volume to obtain 20 mg/ml of AG-38 (as free base), pH 5.08. The loading mixture contained 1300 mg of AKG-38 and was prepared at 8 mg/ml of AKG-38 and DL ratio of 450 g/mol phospholipid, and additionally contained 10 mM NaCl. The post-loading liposomes were pre-concentrated to about 22 mg/ml of the drug; the proportion of unencapsulated drug prior to purification was estimated spectrophotometrically at 305 nm in the pre-concentration diafiltrate and found to be about 3.2% (corresponds to 96.8% loading efficiency). The process was repeated three more times (lots 270, 272, 274). Obtained liposomes had the characteristics shown in TABLE 20.

TABLE 20

| Lot ID | Scale mg of AKG-38 | DL ratio g AKG-38/mol PhL | Average particle size Xz, nm | PDI |
|---|---|---|---|---|
| 268 | 1300 | 445.9 | 114.6 | 0.0419 |
| 270 | 1360 | 444.9 | 114.2 | 0.0456 |
| 272 | 1350 | 463.7 | 115.3 | 0.0245 |
| 274 | 1375 | 437.3 | 115.0 | 0.0349 |

These lots were combined to obtain lot 276 having 22.3 mg/ml AKG-38 in the liposomal form, particle size Xz 113.1 nm, PDI 0.0454.

Example 24. Preparation of "Empty Liposome" Lot 277

2 mmol HSPC, 2.444 mmol cholesterol and 0.1 mmol PEG-DSPE (HSPC:Chol:PEG-DSPE 45:55:2.25 molar ratio) were dissolved in ethanol, formed into liposome suspension and extruded through polycarbonate membranes as described in Example 22, except that instead of 0.5M ammonium sulfate a sulfate salt of non-exchanging cation, 0.13 M sodium sulfate, was taken. The extruded liposomes were purified from extraliposomal sodium sulfate and brought into HBS-7 buffer by TFF buffer exchange using polysulfone hollow fiber cartridge with MWCO 500 KDa for the total of 10 volume exchanges. The purified liposomes had 42.9 mM phospholipid, the particle size Xz 113.7 nm, and PDI 0.0612. They were aseptically passed through 0.2-μm sterile filter and adjusted to 20 mM phospholipid with sterile HBS-7.

Example 25. Liposomal AKG-38 Lot 279

The general procedure of Example 6 was followed. HSPC (Lipoid AG) 13.102 g (16.67 mmol), cholesterol (Dishman, High purity) 7.877 g (20.37 mmol), and PEG-DSPE (Lipoid AG) 2.250 g (0.833 mmol) (HSPC:Chol:PEG-DSPE 45:55:2.25 molar ratio) were combined with 25 ml of absolute ethanol (Sigma, E-7023) and heated with stirring on a 68° C. bath until all lipids dissolved. In a separate container 259.1 g (250 ml) of 0.5 M aqueous ammonium sulfate (0.2-micron filtered) was preheated on a 70° C. bath and poured with stirring into the hot lipid ethanolic solution. The obtained suspension was stirred on a 70° C. bath for at least 20 min. and divided into four portions. Each portion was extruded five times at 280 psi through the stack of two 47-mm 100-nm pore size and one 200-nm pore size polycarbonate track-etched membranes (Whatman Nucleopore) using Lipex 100-ml thermobarrel liposome extruder (Northern Lipids, Inc.) heated with circulating 70° C. water. These partially extruded liposome portions were combined (Xz 129.7 nm) and extruded together through the same membrane stack five more times, resulting in the liposomes of the size Xz 115.9 nm, PDI 0.0212. The liposomes kept overnight in a refrigerator (2-8° C.) and filtered through 0.2-μm polyethersulfone (PES) filter under positive pressure. Phospholipid concentration was found 60.22±0.34 mM. Extraliposomal trapping agent (ammonium sulfate) was removed by TFF buffer exchange for endotoxin-free water on a KrosFlo TFF system using polysulfone hollow fiber cartridge with MW cut-off 500 KDa (Spectrum Laboratories) until residual conductivity dropped to 180 μS/cm after 5.1 volume exchanges). The phospholipid concentration in the post-TFF liposome suspension was determined by blue phosphomolybdate method to be 54.97±0.32 mM.

AKG-38 (free base) was mixed with 0.95 equivalents of 1 N HCl and made up with endotoxin-free water to obtain 20 mg/ml aqueous stock solution (pH 5.16). The solution was passed through 0.2-μm filter, and the amount of filtrate containing 3958 mg of the drug was combined with the post-TFF liposome suspension to form the loading mixture at drug-to-phospholipid (DL) ratio of 450 g/mol in the presence of 44.5 mg/ml dextrose, 10 mM NaCl, and AKG-38 concentration of 8 mg/ml, pH 5.54. The mixture was heated to 61° C. by external heating under constant stirring over the period of 5 min, and the incubation continued with stirring on the 65° C. bath for another 22 min. Then the mixture was transferred into ice-water bath, stirred for 7 minutes to let the temperature drop to 10° C., and kept in the ice-water bath for another 8 min. After being taken out of the ice bath, having reached the ambient temperature, and adjustment to 0.1 M NaCl by addition of 3 M NaCl stock, the drug-loaded liposomes (pH 6.53) were purified by TFF using polysulfone hollow fiber cartridge with molecular weight cutoff 500 KD. The liposomes were pre-concentrated by diafiltration to about 22 mg/ml of AKG-38 and purified from any extraliposomal drug by TFF exchange into HBS-7 buffer for the total of 8 volume exchanges. The concentrated, purified liposomes were aseptically passed through 0.2-μm PES high-flow sterile filter and analyzed for the particle size by DLS, and for the drug and phospholipid concentration by spectrophotometry. The liposomes had the following characteristics: AKG-38 21.1±0.19 mg/ml, DL ratio 454±4.7 g/mol phospholipid, Xz 116.4 nm, PDI 0.0231. Yield of the formulated drug 3834 mg (96.9%).

Example 26. Liposomal AKG-28 Lot 281

The general procedure of Example 6 was followed. Extruded liposomes composed of HSPC, cholesterol, and PEG-DSPE in the molar ratio of 45:55:2.25 containing 0.5 M ammonium sulfate were prepared as described in Example 25. Extraliposomal trapping agent (ammonium sulfate) was removed by TFF exchange for endotoxin-free water on a KrosFlo TFF system using polyethersulfone hollow fiber cartridge with MW cut-off 500 KDa (Spectrum Laboratories) until residual conductivity dropped to 150 μS/cm (4.1 volume exchanges). The phospholipid concentration in the post-TFF liposome suspension was determined by blue phosphomolybdate method to be 55.4 mM.

969.5 mg of AKG-28 (as dihydrochloride salt) in the form of 20 mg/ml aqueous stock solution (adjusted to pH 5.24 with NaOH) were combined with post-TFF liposome suspension to form the loading mixture at drug-to-phospholipid (DL) ratio of 250 g/mol in the presence of 44.5 mg/ml dextrose and AKG-28 concentration of 6 mg/ml. The mixture was heated to 65.4° C. in 2.5 min by external heating under constant stirring, and the incubation continued with stirring on the 65° C. bath. After 20 min. incubation, the mixture was chilled in ice-water to 9.3° C. in 2.75 min, and kept in the ice-water bath for about 10 min. Then the mixture was allowed to reach the ambient temperature and adjusted to 0.1 M NaCl; pH 6.43. 133.4 g of the loading mixture was subjected to purification by TFF using polysulfone hollow fiber cartridge with molecular weight cutoff 500 KD. The liposomes were pre-concentrated by diafiltration to about 12 mg/ml of AKG-28 and purified from any extraliposomal drug by TFF exchange into HBS-7 buffer for the total of 8.1 volume exchanges. The proportion of unencapsulated drug prior to purification was estimated spectrophotometrically at 302 nm in the pre-concentration diafiltrate and found to be about 0.7% (corresponds to 99.3% loading efficiency). The concentrated, purified liposomes were aseptically passed through 0.2-μm sterile filter and analyzed for the particle size by DLS, and for the drug and phospholipid concentration by spectrophotometry. The liposomes had the following characteristics: AKG-28 13.26±0.21 mg/ml, DL ratio 258.2±3.7 g/mol phospholipid, Xz 117.3 nm, PDI 0.0421.

Example 27. Liposomal AKG-38 Lot 285

The general procedure of Example 6 was followed. Extruded liposomes composed of HSPC, cholesterol, and PEG-DSPE in the molar ratio of 45:55:2.25 containing 0.5 M ammonium sulfate were prepared essentially as described in Example 25. Extraliposomal trapping agent (ammonium sulfate) was removed by TFF exchange for endotoxin-free water on a KrosFlo TFF system using polyethersulfone hollow fiber cartridge with MW cut-off 500 KDa (Spectrum Laboratories) until residual conductivity dropped to 138 μS/cm (5.6 volume exchanges). The phospholipid concentration in the post-TFF liposome suspension was determined by blue phosphomolybdate method to be 53.1 mM.

AKG-38 (free base) was mixed with 0.95 equivalents of 1 N HCl and made up with endotoxin-free water to obtain 19.9 mg/ml aqueous stock solution (pH 5.13). The solution was passed through 0.2-μm filter, and the amount of filtrate containing 1400 mg of the drug was combined with the post-TFF liposome suspension to form the loading mixture at drug-to-phospholipid (DL) ratio of 450 g/mol in the presence of 44.5 mg/ml dextrose, 10 mM NaCl, and AKG-38 concentration of 8 mg/ml, pH 5.58. The mixture was heated to 63° C. by external heating under constant stirring over the period of 2.25 min, and the incubation continued with stirring on the 65° C. bath for the total of 21 min. Then the mixture was transferred into ice-water bath, stirred for 3 minutes to let the temperature drop to 10.3° C., and kept in the ice-water bath for another 7 min. After being taken out of the ice bath, having reached the ambient temperature, and adjustment to 0.1 M NaCl by addition of 3 M NaCl stock, the drug-loaded liposomes (pH 6.70) were purified by TFF using polysulfone hollow fiber cartridge with molecular weight cutoff 500 KD. The liposomes were pre-concentrated by diafiltration to about 22 mg/ml of AKG-38 and purified from any extraliposomal drug by TFF exchange into HBS-7 buffer for the total of 7.7 volume exchanges. The concentrated, purified liposomes had AKG-38 concentration of 23.1 mg/ml. The drug concentration was adjusted to 20 mg/ml with HBS-7 buffer, the liposomes were aseptically passed through 0.2-μm PES high-flow sterile filter and analyzed for the particle size by DLS, and for the drug and phospholipid concentration by spectrophotometry. The liposomes had the following characteristics: AKG-38 20.35±0.26 mg/ml, DL ratio 437.8±6.5 g/mol phospholipid, Xz 121.1 nm, PDI 0.0200. Yield of the formulated drug 1355 mg (96.8%).

Example 28. Liposomal AKG-28 Lot 286

Extruded liposomes (HSPC:Chol:PEG-DSPE 45:55:2.25 molar ratio) containing 0.5M ammonium sulfate, free from extraliposomal trapping agent, were obtained as in Example 27.

600 mg of AKG-28 (as dihydrochloride salt) in the form of 20 mg/ml aqueous stock solution (adjusted to pH 5.18 with NaOH) were combined with post-TFF liposome suspension to form the loading mixture at drug-to-phospholipid (DL) ratio of 250 g/mol in the presence of 44.5 mg/ml dextrose and AKG-28 concentration of 6 mg/ml. The mixture was placed on a 65° C. water bath with stirring and reached 60° C. in 4.5 min. The incubation continued with stirring for the total of 20 min, the mixture was chilled in ice-water to 10.0° C. in 2 min, and kept in the ice-water bath for about 10 min. Then the mixture was allowed to reach the ambient temperature and adjusted to 0.1 M NaCl; pH 6.23. 104.6 g of the loading mixture was subjected to purification by TFF using polysulfone hollow fiber cartridge with molecular weight cutoff 500 KD. The liposomes were pre-concentrated by diafiltration to about 12 mg/ml of AKG-28 and purified from any extraliposomal drug by TFF exchange into HBS-7 buffer for the total of 8.3 volume exchanges. The concentrated, purified liposomes were aseptically passed through 0.2-μm sterile filter (chased with HBS-7 buffer) and analyzed for the particle size by DLS, and for the drug and phospholipid concentration by spectrophotometry. The liposomes had the following characteristics: AKG-28 12.05±0.13 mg/ml, DL ratio 239.4 g/mol phospholipid, Xz 120.1 nm, PDI 0.0294. Yield of the formulated drug 555.5 mg (92.6%).

Example 29. Liposomal AKG-38 Lot 292

Lot 288. The general procedure of Example 6 was followed. HSPC (Lipoid AG) 9.17 g (11.67 mmol), cholesterol (Dishman, High purity) 5.51 g (14.26 mmol), and PEG-DSPE (Lipoid AG) 1.575 g (0.583 mmol) were combined with 17.5 ml of absolute ethanol (Sigma, E-7023) and heated with stirring on a 69-70° C. bath until all lipids dissolved. In a separate container 181.4 g (175 ml) of 0.5 M aqueous ammonium sulfate (0.2-micron filtered) was preheated on a 70° C. bath and poured with stirring into the hot lipid ethanolic solution. The obtained suspension was stirred on a 70° C. bath for at least 20 min. and divided into three portions. Each portion was extruded five times at 280 psi through the stack of two 47-mm 100-nm pore size and one 200-nm pore size polycarbonate track-etched membranes (Whatman Nucleopore) using Lipex 100-ml thermobarrel liposome extruder (Northern Lipids, Inc.) heated with circulating 70° C. water. These partially extruded liposome portions were combined (Xz 126.7 nm) and extruded together through the same membrane stack four more times, resulting in the liposomes of the size Xz 119.2 nm, PDI 0.0385. The liposomes kept overnight in a refrigerator (2-8° C.) and filtered through 0.2-μm polyethersulfone (PES) filter under positive pressure. Phospholipid concentration was found 59.08±0.44 mM. Extraliposomal trapping agent (ammonium sulfate) was removed by TFF buffer exchange for endotoxin-free water on a KrosFlo TFF system using polysulfone hollow fiber cartridge with MW cut-off 500 KDa (Spectrum Laboratories) until residual conductivity dropped to 152 μS/cm after 5.4 volume exchanges). The phospholipid concentration in the post-TFF liposome suspension was determined by blue phosphomolybdate method to be 57.76±0.53 mM.

AKG-38 (free base) was mixed with 0.95 equivalents of 1 N HCl and made up with endotoxin-free water to obtain 19.7 mg/ml aqueous stock solution (pH 5.11). The solution was passed through 0.2-μm filter, and the amount of filtrate containing 3509 mg of the drug was combined with the post-TFF liposome suspension to form the loading mixture at drug-to-phospholipid (DL) ratio of 450 g/mol in the presence of 44.5 mg/ml dextrose, 10 mM NaCl, and AKG-38 concentration of 8 mg/ml, pH 5.50. The mixture was heated to 61.6° C. by external heating under constant stirring over the period of 5 min, and the incubation continued with stirring on the 65° C. bath for another 20 min. Then the mixture was transferred into ice-water bath, stirred for 7 minutes to let the temperature drop to 10° C., and kept in the ice-water bath for another 8 min. After being taken out of the ice bath, having reached the ambient temperature, and adjustment to 0.1 M NaCl by addition of 3 M NaCl stock, the drug-loaded liposomes were purified by TFF using polysulfone hollow fiber cartridge with molecular weight cutoff 500 KD. The liposomes were pre-concentrated by diafiltration to about 22 mg/ml of AKG-38 and purified from any extraliposomal drug by TFF exchange into HBS-7 buffer for the total of 7.8 volume exchanges. The concentrated, purified liposomes were aseptically passed through 0.2-μm PES high-flow sterile filter and analyzed for the particle size by DLS, and for the drug and phospholipid concentration by spectrophotometry. The liposomes had the following characteristics: AKG-38 22.47±0.38 mg/ml, DL ratio 441.6 g/mol phospholipid, Xz 121.3 nm, PDI 0.0465. Yield of the formulated drug 3375 mg (96.2%).

Lot 289. The process of Ls-288 was repeated using 1506 mg of AKG-38 (as similarly prepared 20.0 mg/ml aqueous stock solution, pH 5.15). The solution was combined with the same post-TFF extruded liposome suspension to form the loading mixture at drug-to-phospholipid (DL) ratio of 450 g/mol in the presence of 44.5 mg/ml dextrose, 10 mM NaCl, and AKG-38 concentration of 8 mg/ml, pH 5.53. The mixture was heated to 64.3° C. by external heating under constant stirring over the period of 2 min, and the incubation continued with stirring on the 65° C. bath for another 20 min. Then the mixture was transferred into ice-water bath, stirred for 2.75 minutes to let the temperature drop to 9.6° C., and kept in the ice-water bath for another 14 min. After being taken out of the ice bath, the loading mixture was allowed to reach the ambient temperature and adjusted to 0.1 M NaCl with 3 M NaCl stock; pH 6.54. The drug-loaded liposomes were purified by TFF using polysulfone hollow fiber cartridge with molecular weight cutoff 500 KD. The liposomes were pre-concentrated by diafiltration to about 22 mg/ml of AKG-38 and purified from any extraliposomal drug by TFF exchange into HBS-7 buffer for the total of 8.1 volume exchanges. The concentrated, purified liposomes were aseptically passed through 0.2-μm PES high-flow sterile filter and analyzed for the particle size by DLS, and for the drug and phospholipid concentration by spectrophotometry. The liposomes had the following characteristics: AKG-38 22.84±0.41 mg/ml, DL ratio 452.7 g/mol phospholipid, Xz 120.3 nm, PDI 0.0522. Yield of the formulated drug 1407 mg (93.4%).

Lot 290. The general procedure of Example 6 was followed. HSPC (Lipoid AG) 7.86 g (10.00 mmol), cholesterol (Dishman, High purity) 4.73 g (12.22 mmol), and PEG-DSPE (Lipoid AG) 1.35 g (0.50 mmol)(HSPC:Chol:PEG-DSPE 45:55:2.25 molar ratio) were combined with 15 ml of absolute ethanol (Sigma, E-7023) and heated with stirring on a 69-70° C. bath until all lipids dissolved. In a separate container 155.5 g (150 ml) of 0.5 M aqueous ammonium sulfate (0.2-micron filtered) were preheated on a 70° C. bath and poured with stirring into the hot lipid ethanolic solution. The obtained suspension was stirred on a 70° C. bath for at least 20 min. and divided into two portions. Each portion was extruded four times at 280 psi through the stack of two 47-mm 100-nm pore size and one 200-nm pore size polycarbonate track-etched membranes (Whatman Nucleopore) using Lipex 100-ml thermobarrel liposome extruder (Northern Lipids, Inc.) heated with circulating 70° C. water. These partially extruded liposome portions were combined (Xz 131.5 nm) and extruded together through the same membrane stack four more times, resulting in the liposomes of the size Xz 122.7 nm, PDI 0.0215. The liposomes were kept overnight in a refrigerator (2-8° C.) and filtered through 0.2-μm polyethersulfone (PES) filter under positive pressure. Phospholipid concentration was found 58.99±0.22 mM. Extraliposomal trapping agent (ammonium sulfate) was removed by TFF buffer exchange for endotoxin-free water on a KrosFlo TFF system using polysulfone hollow fiber cartridge with MW cut-off 500 KDa (Spectrum Laboratories) until residual conductivity dropped to 146 μS/cm after 5.5 volume exchanges. The phospholipid concentration in the post-TFF liposome suspension was determined by blue phosphomolybdate method to be 56.94±0.41 mM.

AKG-38 (free base) was mixed with 0.95 equivalents of 1 N HCl and made up with endotoxin-free water to obtain 20 mg/ml aqueous stock solution (pH 5.15). The solution was passed through 0.2-μm filter, and the amount of filtrate containing 2315 mg of the drug was combined with the post-TFF liposome suspension to form the loading mixture at drug-to-phospholipid (DL) ratio of 450 g/mol in the presence of 44.5 mg/ml dextrose, 10 mM NaCl, and AKG-38 concentration of 8.02 mg/ml, pH 5.52. The mixture was heated to 64.4° C. by external heating under constant stirring over the period of 3.25 min, and the incubation continued with stirring on the 65° C. bath for another 17 min. Then the mixture was transferred into ice-water bath, stirred to let the temperature drop to below 10° C., kept in the ice-water bath for the total of 10 min, allowed to reach the ambient temperature, and adjusted to 0.1 M NaCl with 3 M NaCl stock; pH 6.63. The drug-loaded liposomes were purified by TFF using polysulfone hollow fiber cartridge with molecular weight cutoff 500 KD. The liposomes were pre-concentrated by diafiltration to about 22 mg/ml of AKG-38 and purified from any extraliposomal drug by TFF exchange into HBS-7 buffer for the total of 8.0 volume exchanges. The concentrated, purified liposomes were aseptically passed through 0.2-μm PES high-flow sterile filter and analyzed for the particle size by DLS, and for the drug and phospholipid concentration by spectrophotometry. The liposomes had the following characteristics: AKG-38 22.07±0.23 mg/ml, DL ratio 441.6 g/mol phospholipid, Xz 120.4 nm, PDI 0.0395. Yield of the formulated drug 2141 mg (92.5%).

Lot 292. Lots 288 (150.3 g), 289 (61.2 g), and 290 (19.5 g) were combined to give 278.4 g of the lot 292 at 22.5 mg/ml of liposomally formulated AKG-38. All liposomal formulations were stored at 2-8° C.

Example 30. Preparation of Liposomal AKG-28 Lot 235

The general procedure of Example 6 was followed. HSPC (Lipoid AG) 940 mg (1.20 mmol), cholesterol (Dishman, High purity) 568 mg (1.47 mmol), PEG-DSPE (Lipoid AG) 163 mg (0.06 mmol), and 0.0018 mmol of the lipophilic fluorescent label $DiIC_{18}(3)$-DS (AAT Bioquest, USA) (HSPC:Chol:PEG-DSPE:$DiIC_{18}(3)$-DS 45:55:2.25:0.0675 molar ratio, 0.15 mol % DiI3-DS relative to HSPC) were combined in 2 ml of absolute ethanol (Sigma, E-7023) and heated with stirring on a 68° C. bath until all lipids dissolved. In a separate container 20 ml of 0.5 M aqueous ammonium sulfate solution (0.2-micron filtered) was preheated on a 68° C. bath and poured with stirring into the hot lipid ethanolic solution. The obtained suspension was stirred on a 68° C. bath for 20 min. and extruded eight times at 300 psi through the stack of two 47-mm 100-nm pore size and one 200-nm pore size polycarbonate track-etched membranes (Whatman Nucleopore) using Lipex 100-ml thermobarrel liposome extruder (Northern Lipids, Inc.) heated with circulating 68° C. water. The resulting extruded liposomes were kept overnight in a refrigerator (2-8° C.) and filtered through 0.2-μm polyethersulfone (PES) filter under positive pressure. Extraliposomal trapping agent (ammonium sulfate) was removed by TFF buffer exchange for endotoxin-free water on a KrosFlo TFF system using polysulfone hollow fiber cartridge with MW cut-off 500 KDa (Spectrum Laboratories) until the conductivity of the retentate drops to 60 μS/cm (10 volume exchanges). The phospholipid concentration in the post-TFF liposome suspension was determined by blue phosphomolybdate method to be 37.56±0.62 mM.

50 mg of AKG-28 (as dihydrochloride salt) in the form of 20 mg/ml aqueous stock solution (adjusted to pH 4.99 with NaOH) were combined with post-TFF liposome suspension to form the loading mixture at drug-to-phospholipid (DL) ratio of 250 g/mol in the presence of 140 mg/ml dextrose and AKG-28 concentration of 3 mg/ml. The mixture (pH 5.53) was incubated with stirring on a 65° C. bath for 20 min, quickly chilled in ice-water and kept in the ice-water bath for about 10 min. After reaching the ambient temperature and adjustment to 0.1 M NaCl with 3 M NaCl stock solution, the pH was 5.80. Drug-loaded liposomes were purified by TFF using polysulfone hollow fiber cartridge with molecular weight cutoff 500 KD. The liposomes were pre-concentrated by diafiltration to about 5 mg/ml of AKG-28 and purified from any extraliposomal drug by TFF exchange into HBS-7 buffer for the total of about 10 volume exchanges. The purified liposomes were further concentrated two-fold by TFF using syringe-operated small 500 KD hollow fiber cartridge (MicroKros, Spectrum). The concentrated, purified liposomes were aseptically passed through 0.2-μm sterile filter and analyzed for the particle size by DLS, and for the drug and phospholipid concentration by spectrophotometry. The liposomes had the following characteristics: AKG-28 8.22±0.16 mg/ml, DL ratio 257.3±10.3 g/mol phospholipid, liposome size Xz 118.2 nm, PDI 0.0188. Yield of the formulated drug 41.4 mg (82.8%).

Example 31. Preparation of Liposomal AKG-38 Lot 236

Post-TFF extruded liposomes containing 0.5 M ammonium sulfate of Example 30 were used. AKG-38 (free base) was mixed with 0.95 equivalents of 1 N HCl and made up with endotoxin-free water to obtain 20 mg/ml aqueous stock solution (pH 5.11). The solution was passed through 0.2-μm filter, and the amount of filtrate containing 70 mg of the drug was combined with the post-TFF liposome suspension (Example 30) to form the loading mixture at drug-to-phospholipid (DL) ratio of 450 g/mol in the presence of 140 mg/ml dextrose and AKG-38 concentration of 3 mg/ml. The mixture was incubated with stirring on a 65° C. bath for 20 min, quickly chilled in ice-water and kept in the ice-water bath for about 10 min. After reaching the ambient temperature and adjustment to 0.1 M NaCl with 3 M NaCl stock solution, the pH was 6.33. Drug-loaded liposomes were purified by TFF using polysulfone hollow fiber cartridge with molecular weight cutoff 500 KD. The liposomes were pre-concentrated by diafiltration to about 6 mg/ml of AKG-38 and purified from any extraliposomal drug by TFF exchange into HBS-7 buffer for the total of about 10 volume exchanges. The purified liposomes were further concentrated two-fold by TFF using syringe-operated small 500 KD hollow fiber cartridge (MicroKros, Spectrum). The concentrated, purified liposomes were aseptically passed through 0.2-μm sterile filter and analyzed for the particle size by DLS, and for the drug and phospholipid concentration by spectrophotometry.

The liposomes had the following characteristics: AKG-38 9.04±0.16 mg/ml, DL ratio 463.9±19.8 g/mol phospholipid, liposome size Xz 119.3 nm, PDI 0.0267. Yield of the formulated drug 56 mg (80%).

Example 32. Retention of Encapsulated Drugs in the Liposomes of the Lots 235 and 236 In Vitro in the Presence of Plasma Retention of the encapsulated drug in the liposomes in the presence of 80% mouse of human blood plasma at 37° C. was determined as described in Example 19 herein. Incubation time was 20 min.

TABLE 21

| Liposome lot ID | 235 | 236 |
|---|---|---|
| Mouse plasma | 100.2 ± 4.3 | 91.0 ± 2.5 |
| Human plasma | 99.6 ± 3.9 | 94.8 ± 2.6 |

These liposomes were stable against burst-release of the drug in contact with blood plasma.

Example 33. Preparation of Liposomal AKG-28 and AKG-38 Lots 231, 232 (HSPC:Cholesterol:PEG-DSPE 45:55:2.25 Molar Ratio, Trapping Agent 0.5 M Ammonium Sulfate)

The general procedure of Example 6 was followed. HSPC (Lipoid AG) 4.255 g (5.41 mmol), cholesterol (Dishman, High purity) 2.56 g (6.62 mmol), and PEG-DSPE (Lipoid AG) 729 mg (0.27 mmol) (HSPC:Cholsterol:PEG-DSPE 45:55:2.25 molar ratio) were combined in 9 ml of absolute ethanol (Sigma, E-7023) and heated with stirring on a 70° C. bath until all lipids dissolved. In a separate container 90 ml of 0.5 M aqueous ammonium sulfate solution (0.2-micron filtered) were preheated on a 70° C. bath and poured with stirring into the hot lipid ethanolic solution. The obtained suspension was stirred on a 70° C. bath for 25 min. and extruded eight times at 260 psi through the stack of two 47-mm 100-nm pore size and one 200-nm pore size polycarbonate track-etched membranes (Whatman Nucleopore) using Lipex 100-ml thermobarrel liposome extruder (Northern Lipids, Inc.) heated with circulating 70° C. water. The resulting extruded liposomes were kept overnight in a refrigerator (2-8° C.) and filtered through 0.2-μm polyethersulfone (PES) filter under positive pressure. Extraliposomal trapping agent (ammonium sulfate) was removed by TFF buffer exchange for endotoxin-free water on a KrosFlo TFF system using polysulfone hollow fiber cartridge with MW cut-off 500 KDa (Spectrum Laboratories) until the conductivity of the retentate drops to 60 μS/cm (10 volume exchanges). The phospholipid concentration in the post-TFF liposome suspension was determined by blue phosphomolybdate spectrophotometric method to be 46.97±0.80 mM.

Lot 231. 350 mg of AKG-28 (as dihydrochloride salt) in the form of 20 mg/ml aqueous stock solution (adjusted to pH 5.02 with NaOH) were combined with post-TFF liposome suspension to form the loading mixture at drug-to-phospholipid (DL) ratio of 250 g/mol in the presence of 137.6 mg/ml dextrose and AKG-28 concentration of 2.53 mg/ml. The mixture (pH 5.60) was incubated with stirring on a 65° C. bath for 20 min, quickly chilled in ice-water and kept in the ice-water bath for about 10 min. After reaching the ambient temperature and adjustment to 0.1 M NaCl with 3 M NaCl stock solution, the pH was 5.68. Drug-loaded liposomes were purified by TFF using polysulfone hollow fiber cartridge with molecular weight cutoff 500 KD. The liposomes were pre-concentrated by diafiltration to about 9 mg/ml of AKG-28 and purified from any extraliposomal drug by TFF exchange into HBS-7 buffer for the total of 10.9 volume exchanges. The purified liposomes were further concentrated to about 12 mg/ml of the drug by continuing TFF diafiltration without buffer feed. The concentrated, purified liposomes were aseptically passed through 0.2-μm sterile filter and analyzed for the particle size by DLS, and for the drug and phospholipid concentration by spectrophotometry. The liposomes had the following characteristics: AKG-28 11.42±0.09 mg/ml, DL ratio 247.7±7.1 g/mol phospholipid, liposome size Xz 116.5 nm, PDI 0.0511. Yield of the formulated drug 322.7 mg (92.2%).

Lot 232. AKG-38 (free base) was mixed with 0.95 equivalents of 1 N HCl and made up with endotoxin-free water to obtain 20 mg/ml aqueous stock solution (pH 5.09). The solution was passed through 0.2-μm filter, and the amount of filtrate containing 580 mg of the drug was combined with the post-TFF liposome suspension of this Example to form the loading mixture at drug-to-phospholipid (DL) ratio of 500 g/mol in the presence of 137.6 mg/ml dextrose, AKG-38 concentration of 2.53 mg/ml, pH 5.72. The mixture was incubated with stirring on a 65° C. bath for 20 min, quickly chilled in ice-water and kept in the ice-water bath for about 10 min. After reaching the ambient temperature and adjustment to 0.1 M NaCl with 3 M NaCl stock solution, the pH was 6.40. Drug-loaded liposomes were purified by TFF using polysulfone hollow fiber cartridge with molecular weight cutoff 500 KD. The liposomes were pre-concentrated by diafiltration to about 12 mg/ml of AKG-38 and purified from any extraliposomal drug by TFF exchange into HBS-7 buffer for the total of 8.5 volume exchanges. The purified liposomes were further concentrated two-fold by continuing TFF diafiltration without buffer feed. The concentrated, purified liposomes were aseptically passed through 0.2-μm sterile filter and analyzed for the particle size by DLS, and for the drug and phospholipid concentration by spectrophotometry. The liposomes had the following characteristics: AKG-38 16.03±0.07 mg/ml, DL ratio 487.3±13.9 g/mol phospholipid, liposome size Xz 120.0 nm, PDI 0.0069. Yield of the formulated drug 538.9 mg (92.9%).

Example 34. Preparation of Liposomal AKG-28 Lot 233 (HSPC:Cholesterol:PEG-DSG 60:40:3 Molar Ratio, Trapping Agent 1 N Triethylammonium Sucrooctasulfate)

The general procedure of Example 6 was followed. HSPC (Lipoid AG) 1.88 g (2.4 mmol), cholesterol (Dishman, High purity) 619 mg (1.6 mmol), and PEG-DSG (Sunbright GS-020, NOF, Japan) 312 mg (0.12 mmol) were combined in 3 ml of absolute ethanol and heated with stirring on a 67° C. bath until all lipids dissolved. In a separate container 31.5 g (30 ml) of 1 N aqueous triethylammonium sucrooctasulfate solution (0.2-micron filtered, pH 6.20, see Example 8) were preheated on a 65° C. bath and poured with stirring into the hot lipid ethanolic solution. The obtained suspension was stirred on a 65° C. bath for 5 min, and extruded three times at 400 psi through the stack of four 47-mm 100-nm pore size and one 200-nm pore size polycarbonate track-etched membranes (Whatman Nucleopore) using Lipex 100-ml thermobarrel liposome extruder (Northern Lipids, Inc.) heated with circulating 65° C. water. The resulting extruded liposomes were kept overnight in a refrigerator (2-8° C.) and filtered through 0.2-μm polyethersulfone (PES) filter under positive pressure. 9.2 g of the extruded liposomes were purified from the extraliposomal trapping agent (TEA-SOS) by TFF buffer exchange for endotoxin-free water on a KrosFlo TFF system using polysulfone hollow fiber cartridge with MW cut-off 500 KDa (Spectrum Laboratories) until the conductivity of the retentate drops to 21 μS/cm (14.5 volume exchanges). The phospholipid concentration in the post-TFF liposome suspension was determined by blue phosphomolybdate spectrophotometric method to be 31.32±0.85 mM.

140 mg of AKG-28 (as dihydrochloride salt) in the form of 20 mg/ml aqueous stock solution (adjusted to pH 5.02 with NaOH) were combined with post-TFF liposome suspension to form the loading mixture at drug-to-phospholipid (DL) ratio of 250 g/mol in the presence of 116.1 mg/ml dextrose and AKG-28 concentration of 2.52 mg/ml. The mixture (pH 5.43) was incubated with stirring on a 65° C. bath for 20 min, quickly chilled in ice-water and kept in the ice-water bath for about 10 min. After reaching the ambient temperature and adjustment to 0.1 M NaCl with 3 M NaCl stock solution, the pH was 5.80. Drug-loaded liposomes were purified by TFF using polysulfone hollow fiber cartridge with molecular weight cutoff 500 KD. The liposomes were pre-concentrated by diafiltration to about 9 mg/ml of AKG-28 and purified from any extraliposomal drug by TFF exchange into HBS-7 buffer for the total of 10.9 volume exchanges. The purified liposomes were further concentrated to about 12 mg/ml of the drug by continuing TFF diafiltration without buffer feed. The concentrated, purified liposomes were aseptically passed through 0.2-μm sterile filter (chased with HBS-7 buffer) and analyzed for the particle size by DLS, and for the drug and phospholipid concentration by spectrophotometry. The liposomes had the following characteristics: AKG-28 10.64±0.20 mg/ml, DL ratio 246.8±11.7 g/mol phospholipid, liposome size Xz 116.3 nm, PDI 0.0022. Yield of the formulated drug 118.2 mg (84.4%).

Example 35. Preparation of Liposomal AKG-38 Lot 234 (HSPC:Cholesterol:PEG-DSPE 45:55:2.25 Molar Ratio, Trapping Agent 1 N Triethylammonium Sucrooctasulfate)

The general procedure of Example 6 was followed. HSPC (Lipoid AG) 3.30 g (4.20 mmol), cholesterol (Dishman, High purity) 1.985 g (5.13 mmol), and PEG-DSPE (Lipoid AG) 567 mg (0.21 mmol) (HSPC:Cholsterol:PEG-DSPE 45:55:2.25 molar ratio) were combined in 7 ml of absolute ethanol (Sigma, E-7023) and heated with stirring on a 70° C. bath until all lipids dissolved. In a separate container 10 ml of 1 N aqueous triethylammonium sucrooctasulfate (TEA-SOS) solution (0.2-micron filtered) were preheated on a 70° C. bath and poured with stirring into the hot lipid ethanolic solution. The obtained suspension was stirred on a 70° C. bath for 10 min. and extruded eight times at 260 psi through the stack of two 47-mm 100-nm pore size and one 200-nm pore size polycarbonate track-etched membranes (Whatman Nucleopore) using Lipex 100-ml thermobarrel liposome extruder (Northern Lipids, Inc.) heated with circulating 70° C. water. The resulting extruded liposomes were kept overnight in a refrigerator (2-8° C.) and filtered through 0.2-μm polyethersulfone (PES) filter under positive pressure. Phospholipid concentration was 54.6 mM. 11.33 g of the extruded liposomes were purified from the extraliposomal trapping agent (TEA-SOS) by TFF buffer exchange for endotoxin-free water on a KrosFlo TFF system using polysulfone hollow fiber cartridge with MW cut-off 500 KDa (Spectrum Laboratories) until the conductivity of the retentate drops to 64 μS/cm (13.8 volume exchanges). The phospholipid concentration in the post-TFF liposome suspension was determined by blue phosphomolybdate spectrophotometric method to be 28.67±1.01 mM.

AKG-38 (free base) was mixed with 0.95 equivalents of 1 N HCl and made up with endotoxin-free water to obtain 20 mg/ml aqueous stock solution (pH 5.09). The solution was passed through 0.2-μm filter, and the amount of filtrate containing 250 mg of the drug was combined with the post-TFF liposome suspension of this Example to form the loading mixture at drug-to-phospholipid (DL) ratio of 500 g/mol in the presence of 116.4 mg/ml dextrose, AKG-38 concentration of 2.53 mg/ml, pH 5.24. The mixture was incubated with stirring on a 65° C. bath for 20 min, quickly chilled in ice-water and kept in the ice-water bath for about 10 min. After reaching the ambient temperature and adjustment to 0.1 M NaCl with 3 M NaCl stock solution, the pH was 6.60. Drug-loaded liposomes were purified by TFF using polysulfone hollow fiber cartridge with molecular weight cutoff 500 KD. The liposomes were pre-concentrated by diafiltration to about 10 mg/ml of AKG-38 and purified from any extraliposomal drug by TFF exchange into HBS-7 buffer for the total of 8.0 volume exchanges. The purified liposomes were further concentrated approximately two-fold by continuing TFF diafiltration without buffer feed. The concentrated, purified liposomes were aseptically passed through 0.2-μm sterile filter and analyzed for the particle size by DLS, and for the drug and phospholipid concentration by spectrophotometry. The liposomes had the following characteristics: AKG-38 15.71±0.33 mg/ml, DL ratio 518.6±18.4 g/mol phospholipid, liposome size Xz 114.3 nm, PDI 0.0284. Yield of the formulated drug 235.7 mg (94.3%).

Example 36. Effect of Osmotic Agent Concentration on the Loading Efficiency of AKG-28 and AKG-38 into the Liposomes and Drug Retention by the Liposomes in Plasma The general protocol of Example 6 was followed. Extruded liposomes containing 0.5 M ammonium sulfate and the lipid composition of HPSC, cholesterol, PEG-DSPE, and DiIC18(3)-DS (fluorescent lipid label) in the molar ratio of 45:55:2.25:0.0675 were prepared as described in Example 30. The liposomes were purified from the extraliposomal ammonium sulfate by TFF exchange for endotoxin-free "water for injection" (WFI)-quality water (Hyclone) using syringe-operated MicroKros polysulfone hollow fiber cartridge (MWCO 500 KDa, Spectrum Laboratories) (13.8 volume exchanges, residual conductivity 88 μS/cm, phospholipid concentration 55.4 mM). The liposomes were loaded with AKG-28 or AKG-38 by incubation of the drugs (prepared as aqueous 20 mg/ml stocks as described in Examples 30 and 31) with the purified extruded liposomes in aqueous solution in a 65° C. water bath for 20 min in the presence of various concentrations of osmotic agent (dextrose), at the drug concentration 2.22 mg/ml and DL ratio of 250 g/mol phospholipid (AKG-28) or 450 g/mol phospholipid (AKG-38). Unencapsulated drug was removed by size-exclusion chromatography on Sepharose CL-4B, eluent HBS-7 buffer, and the loading (encapsulation) efficiency was determined from the results of drug and phospholipid analysis. The osmotic agent concentration was expressed both in absolute terms and as percent of the 168 mg/ml dextrose concentration determined to be isoosmotic to the 0.5 M ammonium sulfate solution used to form the liposomes. Contrary to expectations from the general consensus in the liposome field, the drugs were effectively loaded into the liposomes of the disclosure (encapsulation efficiency more than 85%, and mostly more than 90%) even under hypoosmotic conditions (i.e., at the osmolality of the extra-liposomal solution lower than that of the intraliposomal trapping agent solution), down to complete absence of the added osmotic balance agent (dextrose) (Table 22). Moreover, upon exposure to blood plasma under the conditions of in vitro plasma release assay described in Example 19, the drug encapsulation in the liposomes loaded at the lowest concentrations of the osmotic agent was at least as stable as in those loaded at nearly complete (86.3%) osmotic balance.

The results show that liposomes with 55 mol % Chol, 45 mol % PC, PEG-DSPE at 5 mol % of HSPC, and 0.5 M AS trapping agent load both AKG-28 (TABLE 22) and AKG-38 (TABLE 23) at 250 or 500 g/mol PhL with efficiency >85%, mostly >90%, under hypoosmotic conditions up to zero percent dextrose, and the liposomes loaded under hypoosmotic conditions efficiently retain the drug in the presence of blood plasma.

TABLE 22

| Lot ID | Dextrose, g/L | % Osmotic balance with 0.5M AS | Output DL ratio, g/mol PhL | Encapsulation efficiency, % | % drug retained in liposomes, 80% plasma, 20 min, 37° C. Mouse | Human |
|---|---|---|---|---|---|---|
| 237 | 144.9 | 86.3 | 243.1 ± 7.5 | 97.2 ± 3.0 | 98.8 ± 4.6 | 98.0 ± 4.0 |
| 238 | 130.4 | 77.6 | 243.1 ± 4.9 | 97.2 ± 2.0 | | |
| 239 | 115.9 | 69.0 | 253.1 ± 5.2 | 101.2 ± 2.1 | | |
| 240 | 86.9 | 51.8 | 246.1 ± 3.5 | 98.4 ± 1.4 | | |
| 241 | 58.0 | 34.5 | 253.7 ± 8.1 | 101.5 ± 3.3 | | |
| 242 | 29.0 | 17.3 | 246.5 ± 5.4 | 98.6 ± 2.2 | 99.4 ± 4.3 | 100.3 ± 4.9 |
| 243 | 0 | 0 | 249.2 ± 5.4 | 99.7 ± 2.2 | 100.6 ± 4.3 | 102.2 ± 4.8 |

TABLE 23

| Lot ID | Dextrose, g/L | % Osmotic balance relative to 0.5M AS | Output DL ratio, g/mol PhL | Encapsulation efficiency, % | % drug retained in liposomes, 80% plasma, 20 min, 37° C. Mouse | Human |
|---|---|---|---|---|---|---|
| 244 | 144.9 | 86.3 | 464.9 ± 14.6 | 93.0 ± 2.9 | 82.0 ± 2.4 | 86.8 ± 2.8 |
| 245 | 130.4 | 77.6 | 463.5 ± 18.2 | 92.7 ± 3.6 | | |
| 246 | 115.9 | 69.0 | 453.2 ± 8.7 | 90.6 ± 1.7 | | |
| 247 | 86.9 | 51.8 | 459.8 ± 13.8 | 92.0 ± 2.8 | | |
| 248 | 58.0 | 34.5 | 466.1 ± 14.5 | 93.2 ± 2.9 | 85.0 ± 3.3 | 89.6 ± 3.7 |
| 249 | 29.0 | 17.3 | 455.8 ± 12.9 | 91.2 ± 2.6 | 89.7 ± 3.1 | 92.8 ± 3.0 |
| 250 | 0 | 0 | 433.1 ± 17.7 | 86.6 ± 3.5 | 93.8 ± 3.5 | 91.2 ± 3.2 |

Example 37. Single Dose Pharmacokinetic Studies of the Total Form (Encapsulated+Released Drug) of Ls-AKG28 & Ls-AKG38 in Rats This study was performed to evaluate the PK of AKG28 and AKG 38 administered as a single dose Ls-AKG28 and Ls-AKG38 in rats. The study was performed on male Sprague-Dawley rats using IV administration of liposomal AKG-38 (Ls-AKG38) at 20, 40, or 80 mg per kg of the body weight or liposomal AKG-28 (Ls-AKG28) at 10, 20, and 40 mg per kg of the body weight. Ls-AKG28 (Lot 275) and Ls-AKG38 (Lot 276) were prepared as described in Examples 22 and 23, respectively. For comparison, Linezolid at 50 mg/kg of the body weight was administered orally as a gavage formulated with 0.5% methyl cellulose and acidified to pH 3-4 (Sigma M0430) at a concentration of 20 mg/mL. For plasma drug measurements, 0.5 ml blood was collected in lithium heparin tubes at 5 min, 15 min, 1 h, 3 h, 6 h, 24 h, 48 h, and 72 h. The samples were centrifuged and the resultant plasma was separated and transferred to duplicate clear polypropylene tubes, frozen immediately over dry ice, and stored at −80° C. until analysis. The plasma concentration in rats was determined by HPLC. Non-compartment PK analyses were performed using Phoenix WinNonlin (Version 7.0). For Ls-AKG28 and Ls-AKG38, this PK software was used to estimate the plasma maximum concentration ($C_{max}$), plasma maximum concentration divided by dose ($C_{max}$/dose), time of Cmax ($T_{max}$), last measured concentration ($C_{last}$), time of last measured concentration ($T_{last}$), area-under the plasma concentration versus time curve from 0 h to last time point ($AUC_{0\text{-}last}$) and 0 h to infinity ($AUC_{0\text{-}inf}$), $AUC_{0\text{-}last}$ divided by dose ($AUC_{0\text{-}last}$/dose), clearance (CL), volume of distribution (Vd), and elimination half-life (T½). For linezolid, this PK software was used to estimate the same PK parameters except for apparent clearance (CL/F) and apparent volume of distribution (Vd/F).

Figure 7:
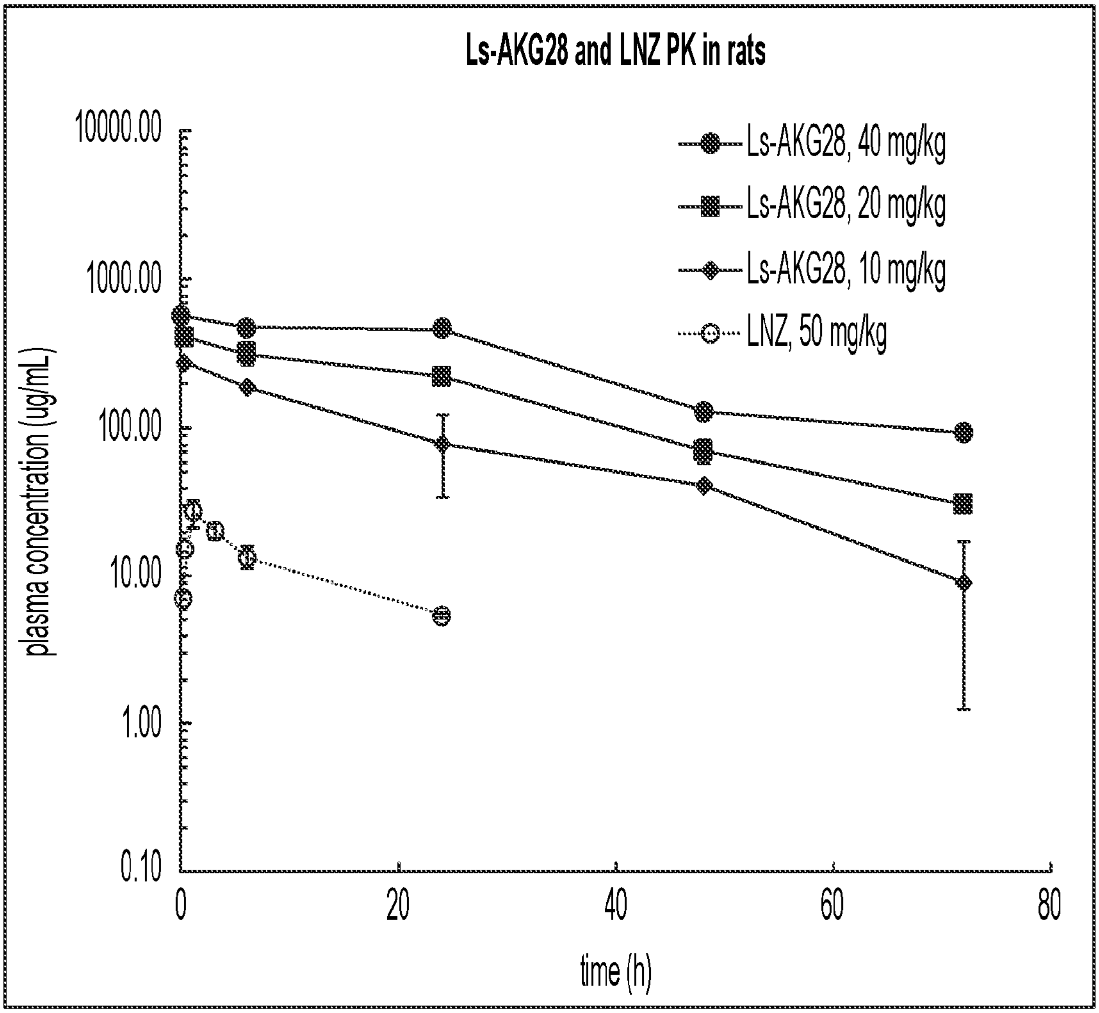
FIG. 7 is a graph showing the plasma concentration versus time profiles for total drug in Sprague-Dawley rats after administration of a single intravenous dose (IV×1) of Ls-AKG28 at 10 mg/kg (diamonds), 20 mg/kg (squares), and 40 mg/kg (circles). Plasma concentration versus time profiles of linezolid at 50 mg/kg (single oral dose, PO×1) in 5% methyl cellulose (pH 3-4) was also included for comparison. The mean and SD concentration are presented at each time point.

The plasma concentration versus time profiles for total drug after administration of Ls-AKG28 at 10, 20, and 40 mg/kg single IV dose (IV×1) are presented in FIG. 7. The summary of plasma PK parameters for total drug after administration of Ls-AKG28 at 10, 20, and 40 mg/kg IV×1 are presented in TABLE 24.

At all doses the plasma concentration versus time profiles for Ls-AKG28 were detectable from 5 min to 72 h. Based on the results of Cmax/dose and AUC/dose, the plasma PK of Ls-AKG28 is linear (dose proportional) after administration of 10, 20, and 40 mg/kg. At all doses the plasma clearance (CL) of Ls-AKG38 (~2.59 mL/h/kg) was greater than Ls- AKG28 (~1.67 mL/h/kg). At the same dose (20 or 40 mg/kg), the Vd of Ls-AKG28 was greater than for Ls-AKG38.

TABLE 24

Summary of plasma PK parameters for total drug after administration of Ls-AKG28 at 10, 20, and 40 mg/kg IV.

| PK Parameter | Linezolid | Ls-AKG28 | | |
|---|---|---|---|---|
| Total AKG28 | 50 mg/kg | 10 mg/kg | 20 mg/kg | 40 mg/kg |
| $C_{max}$ [μg/mL] | 26.73 | 272.23 | 413.83 | 577.70 |
| $C_{max}$/Dose [μg/mL]/[mg/kg] | 0.53 | 27.22 | 20.69 | 14.44 |
| $T_{max}$ [hr] | 1.0 | 0.083 | 0.083 | 0.083 |
| $C_{last}$ [μg/mL] | 5.35 | 8.95 | 31.05 | 94.89 |
| $T_{last}$ [hr] | 24.0 | 72 | 72 | 72 |
| $AUC_{0\text{-}last}$ [hr*μg/mL] | 282.01 | 5,565.17 | 11,287.31 | 20,712.25 |
| $AUC_{0\text{-}last}$/Dose [hr*μg/mL]/[mg/kg] | 5.64 | 556.52 | 564.37 | 517.81 |
| $AUC_{0\text{-}inf}$ [hr*μg/mL] | 373.53 | 5,764.67 | 12,143.11 | 24,218.25 |
| Clearance [mL/hr/kg] | 133.86 | 1.73 | 1.64 | 1.65 |
| Vd [mL/kg] | 2,291.26 | 38.66 | 45.40 | 61.03 |
| $T_{1/2}$ [hr] | 11.86 | 15.45 | 19.11 | 25.61 |

Figure 8:
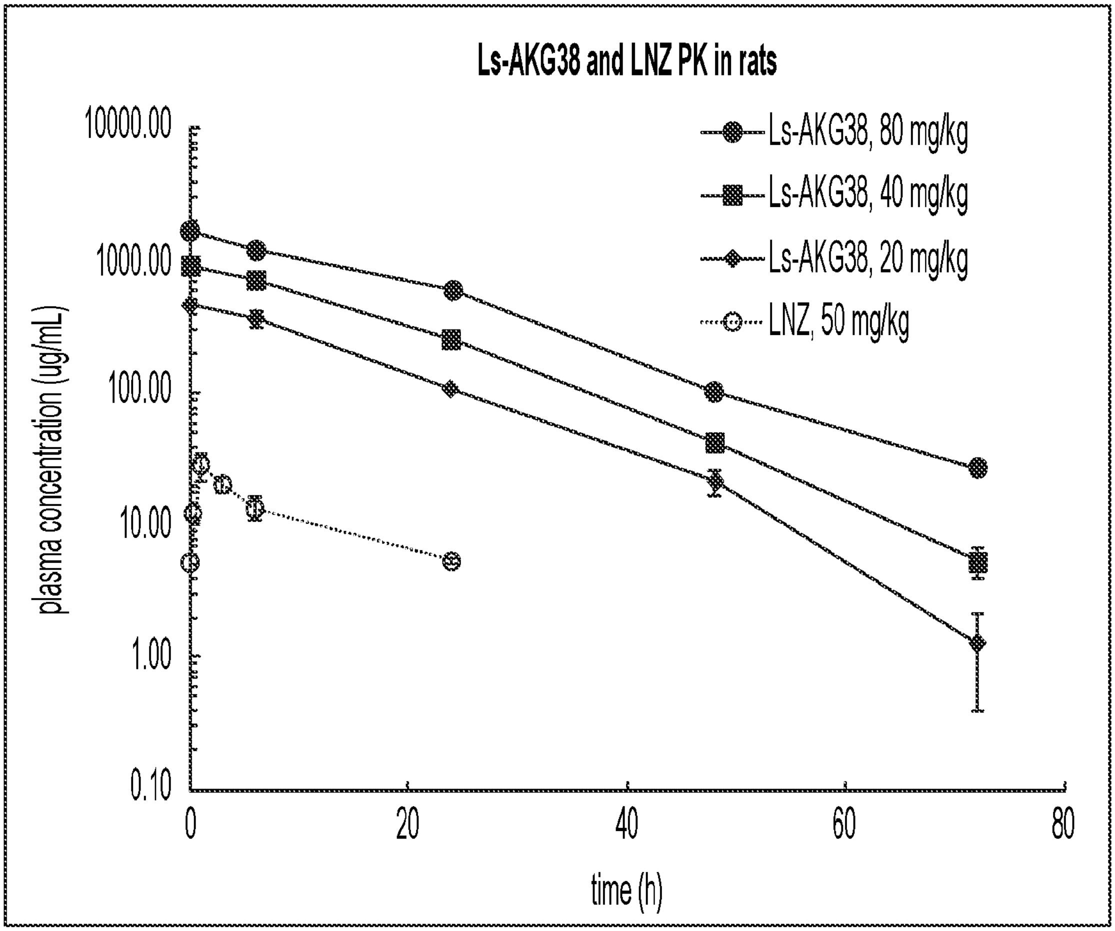
FIG. 8 is a graph showing the plasma concentration versus time profiles for total drug in Sprague-Dawley rats after administration of a single intravenous dose (IV×1) of Ls-AKG38 at 20 mg/kg (diamonds), 40 mg/kg (squares), and 80 mg/kg (diamonds). Plasma concentration versus time profiles of linezolid at 50 mg/kg (single oral dose, PO×1) in 5% methyl cellulose (pH 3-4) was also included for comparison. The mean and SD concentration are presented at each time point.

The plasma concentration versus time profiles for total drug after administration of Ls-AKG38 at 20, 40, and 80 mg/kg IV×1 are presented in FIG. 8.

The summary of plasma PK parameters for total drug after administration of Ls-AKG38 at 20, 40, and 80 mg/kg IV×1 are presented in TABLE 25.

At all doses the plasma concentration versus time profiles for Ls-AKG38 were detectable from 5 min to 72 h. Based on the results of Cmax/dose and AUC/dose, the plasma PK of Ls-AKG38 is linear (dose proportional) after administration of 20, 40, and 80 mg/kg. At all doses the plasma clearance (CL) of Ls-AKG38 (~2.59 mli/h/kg) was greater than Ls-AKG28 (~1.67 mL/h/kg). At the same dose (20 or 40 mg/kg), the Vd of Ls-AKG28 was greater than for Ls-AKG38.

TABLE 25

Summary of plasma PK parameters for total drug after administration of Ls-AKG38 at 20, 40, and 80 mg/kg IV.

| PK Parameter | Linezolid | Ls-AKG38 Dose | | |
|---|---|---|---|---|
| Total AKG38 | 50 mg/kg | 20 mg/kg | 40 mg/kg | 80 mg/kg |
| $C_{max}$ [μg/mL] | 26.73 | 452.84 | 856.42 | 1,555.85 |
| $C_{max}$/Dose [μg/mL]/[mg/kg] | 0.53 | 22.64 | 21.41 | 19.44 |
| $T_{max}$ [hr] | 1.0 | 0.083 | 0.083 | 0.083 |
| $C_{last}$ [μg/mL] | 5.35 | 1.29 | 5.29 | 27.14 |
| $T_{last}$ [hr] | 24.0 | 72 | 72 | 72 |
| $AUC_{0\text{-}last}$ [hr*μg/mL] | 282.01 | 7,532.62 | 15,402.45 | 31,313.26 |
| $AUC_{0\text{-}last}$/Dose [hr*μg/mL]/[mg/kg] | 5.64 | 376.63 | 385.06 | 391.42 |
| $AUC_{0\text{-}inf}$ [hr*μg/mL] | 373.53 | 7,548.80 | 15,468.95 | 31,784.91 |
| Clearance [mL/hr/kg] | 133.86 | 2.65 | 2.59 | 2.52 |
| Vd [mL/kg] | 2,291.26 | 33.26 | 32.48 | 43.74 |
| $T_{1/2}$ [hr] | 11.86 | 8.70 | 8.71 | 12.05 |

The plasma concentration versus time profiles for total drug after administration of Ls-AKG28 at 10, 20, and 40 mg/kg IV×1 and Ls-AKG38 at 20, 40, and 80 mg/kg IV×1 are presented in FIG. 7 and FIG. 8, respectively. In the single IV dose studies, at all doses the plasma conc vs time profiles for Ls-AKG28 and Ls-AKG38 were detectable from 5 min to 72 h. The plasma PK of Ls-AKG28 is linear (dose proportional) after administration of 10, 20, and 40 mg/kg. The plasma PK of Ls-AKG38 is linear (dose proportional) after administration of 20, 40, and 80 mg/kg. At all doses the plasma clearance (CL) of Ls-AKG38 (~2.59 mL/h/kg) was greater than Ls-AKG28 (~1.67 mL/h/kg). At the same dose (20 or 40 mg/kg), the Vd of Ls-AKG28 was greater than for Ls-AKG38. The total plasma PK exposure of Ls-AKG28 at 40 mg/kg and Ls-AKG38 were ~73-fold and ~110-fold higher than plasma PK of linezolid (using AUC from 0 to last).

The plasma AUC and the drug persistence in circulation were much greater for both liposome formulations compared to linezolid. The PK of both liposome formulations has a linear dose dependence as seen by the values for AUC/dose are very similar each for Ls-AKG28 and Ls-AKG38.

Figure 9A:
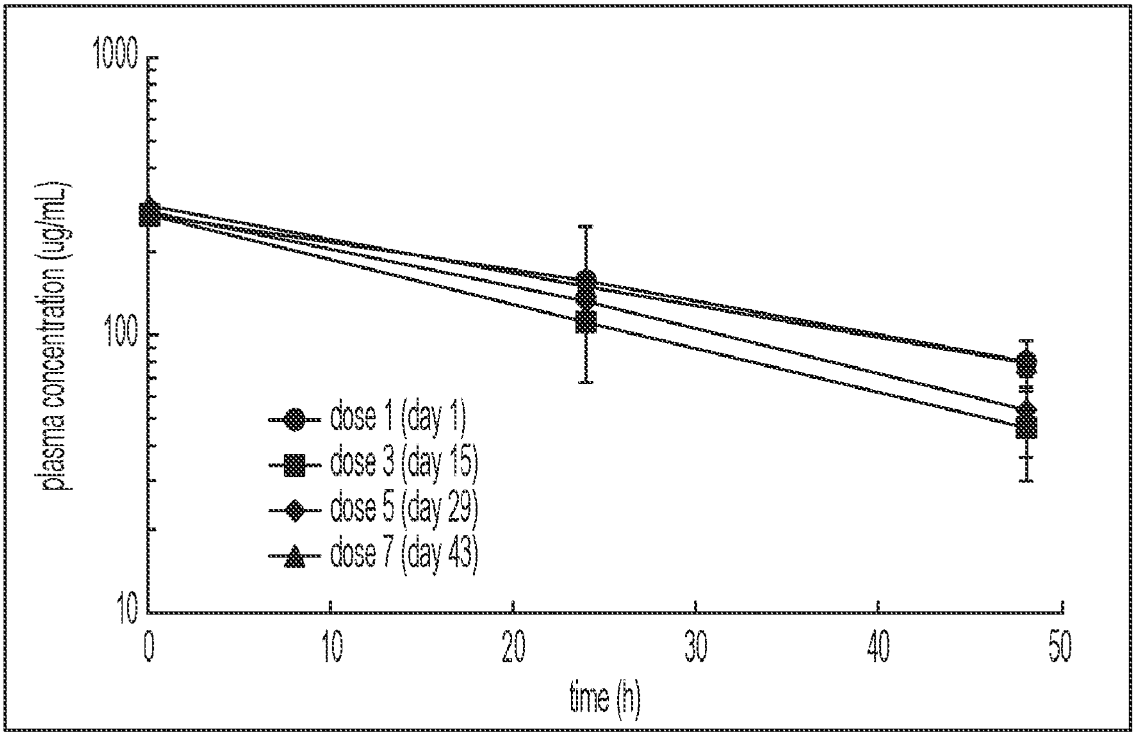
FIG. 9A, FIG. 9B, and FIG. 9C are graphs showing the plasma concentration versus time profiles for total drug in Sprague-Dawley rats after administration of Ls-AKG28 at 10 mg/kg (FIG. 9A), 20 mg/kg (FIG. 9B), and 40 mg/kg (FIG. 9C), IV×1, on day 1 (circles), day 15 (squares), day 29 (diamonds), and day 43 (triangles). The mean and SD concentration are presented at each time point.
Figure 9B:
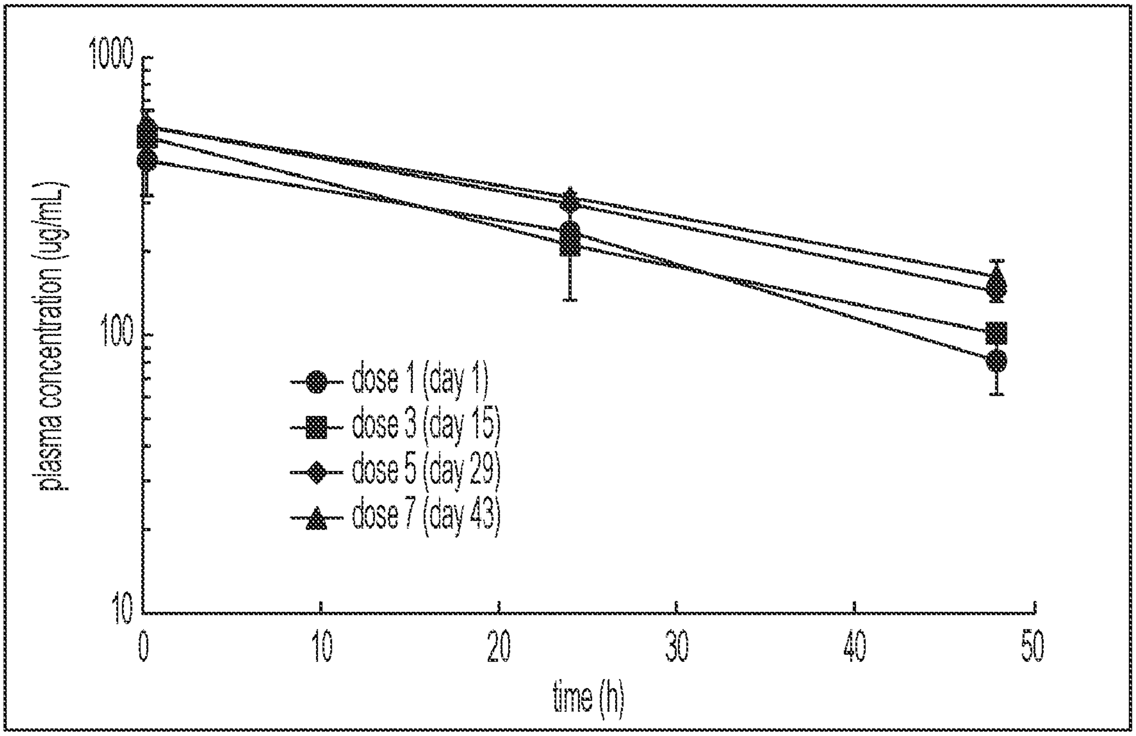
Figure 9C:
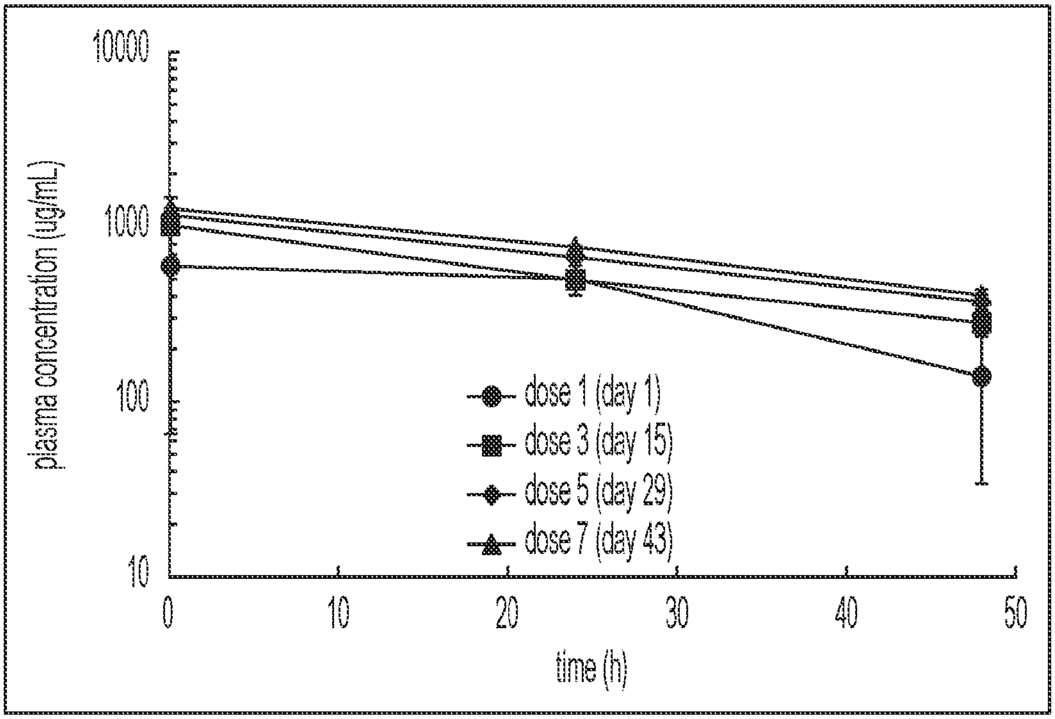

Example 38. Plasma Pharmacokinetics (PK) of the Total Form of (Encapsulated+Released Drug) Ls-AKG28 and Ls-AKG38 after Multiple IV Doses in Sprague-Dawley Rats This study was performed to evaluate the PK of AKG28 and AKG 38 administered at escalating doses of Ls-AKG28 and Ls-AKG38, weekly for a total of eight weeks in rats. The study was performed on Sprague-Dawley rats using IV administration. Ls-AKG28 (Lot 275) and Ls-AKG38 (Lot 276) were prepared as described in Examples 22 and 23, respectively The plasma concentration in rats was determined by HPLC. The plasma concentration versus time profiles for total drug after administration of Ls-AKG28 at 10, 20, and 40 mg/kg IV×1 on days 1, 15, 29, and 43 are presented in TABLE 26 and FIG. 9A, FIG. 9B, and FIG. 9C. The summary of plasma PK parameters for total drug after administration of Ls-AKG28 at 10, 20, and 40 mg/kg IV×1 on days 1, 15, 29, and 43 are presented in TABLE 26. All of the data in FIG. 9A, FIG. 9B, and FIG. 9C was used to generate the PK parameter results in TABLE 26.

In the single and multi-dose PK studies, the plasma disposition of Ls-AKG28 were similar after the first dose. For Ls-AKG28 at 10 mg/kg, the plasma Cmax and AUC were similar on days 1, 15, 29, and 43. For Ls-AKG28 at 20 mg/kg, the plasma Cmax and AUC increase on days 29 and 43. For Ls-AKG28 at 40 mg/kg, the plasma Cmax and AUC increase after doses on days 1 to 43.

Figure 10A:
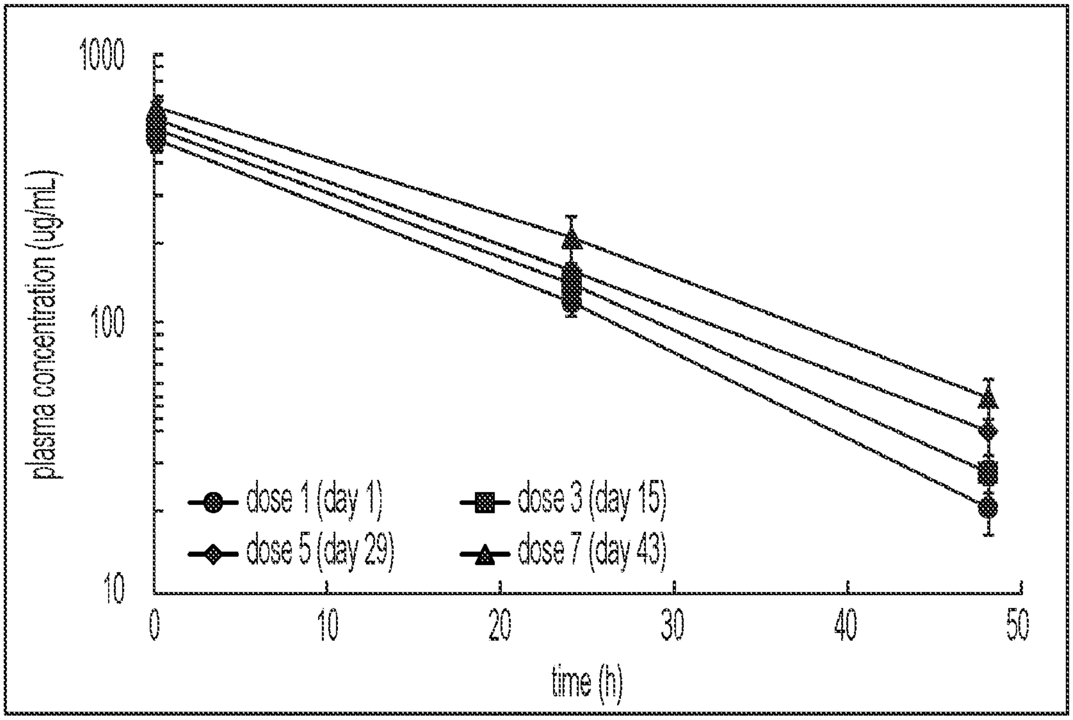
FIG. 10A, FIG. 10B, and FIG. 10C are graphs showing the plasma concentration versus time profiles for total drug in Sprague-Dawley rats after administration of Ls-AKG38 at 20 mg/kg (FIG. 10A), 40 mg/kg (FIG. 10B), and 80 mg/kg (FIG. 10C), IV×1, on day 1 (circles), day 15 (squares), day 29 (diamonds), and day 43 (triangles). The mean and SD concentration are presented at each time point.
Figure 10B:
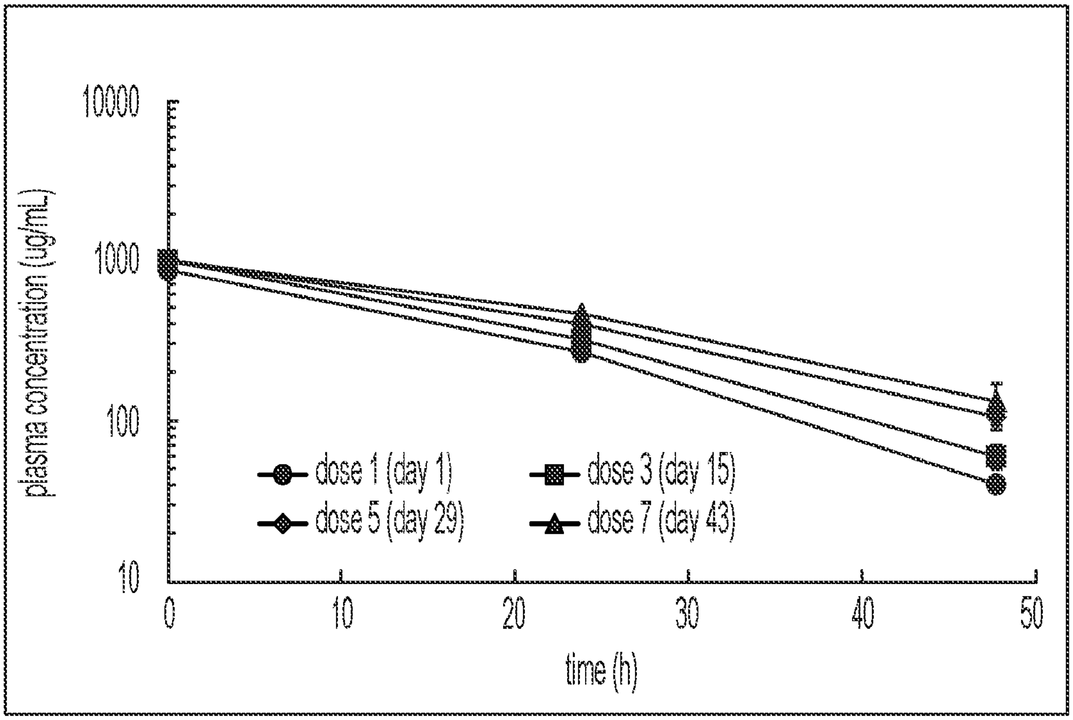
Figure 10C:
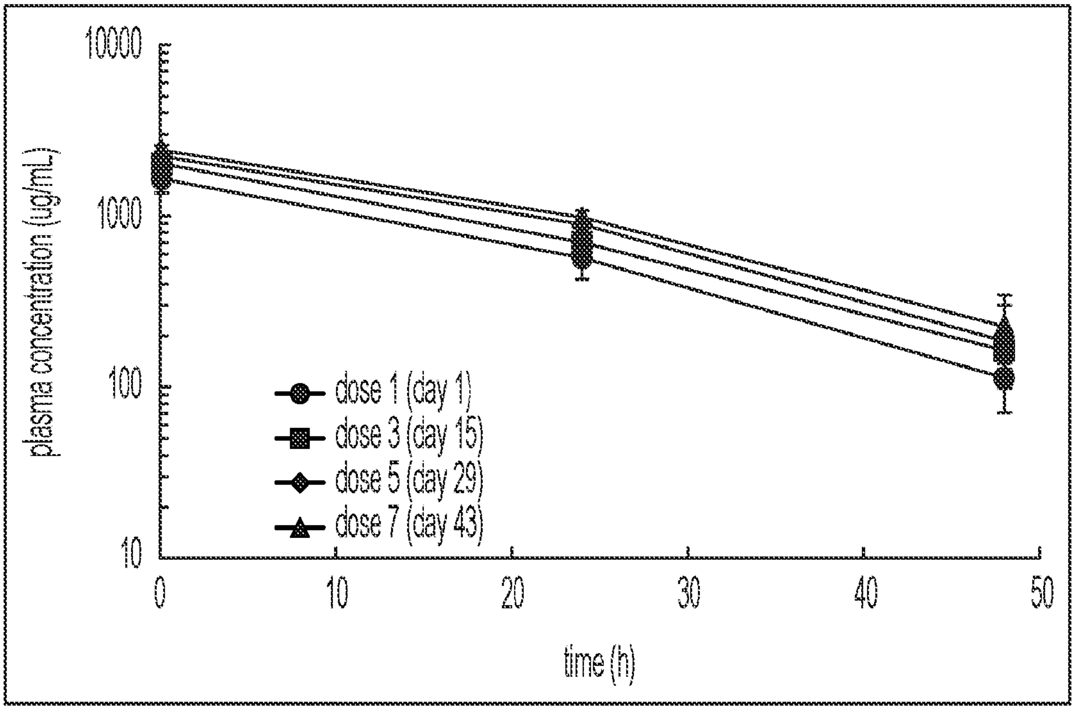

The plasma concentration versus time profiles for total drug after administration of Ls-AKG38 at 20, 40, and 80 mg/kg IV×1 on days 1, 15, 29, and 43 are presented in TABLE 27 and FIG. 10A, FIG. 10B, and FIG. 10C. The summary of plasma PK parameters for total drug after administration of Ls-AKG38 at 20, 40, and 80 mg/kg IV×1 on days 1, 15, 29, and 43 are presented in TABLE 27. In the single and multi-dose PK studies, the plasma disposition of Ls-AKG38 were similar after the first dose. For Ls-AKG38 at 20, 40, and 80 mg/kg, the plasma Cmax and AUC increase from days 1 to 43. Given the concern for accelerated blood clearance (ABC) for pegylated liposomes containing non-cytotoxic drug payloads, the lack of increased clearance at later cycles was surprising, and suggests liposomes containing AKG-28 or AKG-38 can be chronically dosed in mammals.

TABLE 26

Summary of plasma PK parameters for total drug after administration of Ls-AKG28 at 10, 20, and 40 mg/kg IV × 1 on days 1, 15, 29, and 43.

| | $C_{max}$ [μg/mL] | $AUC_{0\text{-}last}$ [hr*μg/mL] | Clearance [mL/hr/kg] | Vd [mL/kg] | $T_{1/2}$ [hr] |
|---|---|---|---|---|---|
| Ls-AKG28 (10 mg/kg)-d1 | 271.28 | 7,766.70 | 0.92 | 36.01 | 27.27 |
| Ls-AKG28 (10 mg/kg)-d15 | 270.78 | 6,093.17 | 1.36 | 36.94 | 18.83 |
| Ls-AKG28 (10 mg/kg)-d29 | 277.67 | 6,807.48 | 1.19 | 34.84 | 20.23 |
| Ls-AKG28 (10 mg/kg)-d43 | 292.14 | 7,780.12 | 0.93 | 34.37 | 25.48 |
| Ls-AKG28 (20 mg/kg)-d1 | 423.81 | 11,133.88 | 1.49 | 42.87 | 19.99 |
| Ls-AKG28 (20 mg/kg)-d15 | 514.07 | 11,757.75 | 1.36 | 39.97 | 20.41 |
| Ls-AKG28 (20 mg/kg)-d29 | 560.15 | 14,997.08 | 1.00 | 35.06 | 24.31 |
| Ls-AKG28 (20 mg/kg)-d43 | 561.51 | 15,702.04 | 0.91 | 35.13 | 26.73 |
| Ls-AKG28 (40 mg/kg)-d1 | 596.89 | 19,970.35 | 1.63 | 53.70 | 22.88 |
| Ls-AKG28 (40 mg/kg)-d15 | 1,018.25 | 26,606.26 | 1.07 | 40.29 | 26.02 |
| Ls-AKG28 (40 mg/kg)-d29 | 1,163.03 | 33,635.70 | 0.81 | 34.14 | 29.19 |
| Ls-AKG28 (40 mg/kg)-d43 | 1,269.07 | 37,580.42 | 0.73 | 30.78 | 29.17 |

TABLE 27

Summary of plasma PK parameters for total drug after administration of Ls-AKG38 at 20, 40, and 80 mg/kg IV × 1 on days 1, 15, 29, and 43.

| | $C_{max}$ [μg/mL] | $AUC_{0\text{-}last}$ [hr*μg/mL] | Clearance [mL/hr/kg] | Vd [mL/kg] | $T_{1/2}$ [hr] |
|---|---|---|---|---|---|
| Ls-AKG38 (10 mg/kg)-d1 | 485.39 | 7,702.72 | 2.49 | 38.12 | 10.61 |
| Ls-AKG38 (10 mg/kg)-d15 | 529.93 | 8,792.21 | 2.16 | 35.41 | 11.36 |
| Ls-AKG38 (10 mg/kg)-d29 | 576.14 | 9,875.80 | 1.89 | 34.05 | 12.52 |
| Ls-AKG38 (10 mg/kg)-d43 | 639.70 | 12,053.96 | 1.53 | 29.59 | 13.43 |
| Ls-AKG38 (20 mg/kg)-d1 | 880.03 | 15,364.53 | 2.50 | 38.91 | 10.78 |
| Ls-AKG38 (20 mg/kg)-d15 | 1,011.05 | 18,314.30 | 2.07 | 35.16 | 11.78 |
| Ls-AKG38 (20 mg/kg)-d29 | 1,017.30 | 21,373.77 | 1.69 | 35.96 | 14.74 |
| Ls-AKG38 (20 mg/kg)-d43 | 1,013.54 | 23,414.28 | 1.51 | 35.57 | 16.38 |
| Ls-AKG38 (40 mg/kg)-d1 | 1,648.38 | 31,180.74 | 2.41 | 43.10 | 12.40 |
| Ls-AKG38 (40 mg/kg)-d15 | 2,025.67 | 38,874.97 | 1.90 | 36.31 | 13.21 |
| Ls-AKG38 (40 mg/kg)-d29 | 2,231.92 | 45,921.63 | 1.62 | 31.15 | 13.36 |
| Ls-AKG38 (40 mg/kg)-d43 | 2,428.35 | 50,694.28 | 1.45 | 29.22 | 13.99 |

Example 39. Pharmacokinetic Studies of Drug and Liposome Lipid of Ls-AKG28 and Ls-AKG38 in CD-1 Mice This study was designed to determine the blood pharmacokinetic parameters for both drug and liposome lipid and the stability of drug retention in the liposomes of the liposome formulations of AKG-28 and AKG-38 in the blood plasma in vivo. The study was performed on male CD-1 (20-22 g) mice as described in General protocol above in Example 7, (5 mice per time point). Ls-AKG28 (Lot 235) and Ls-AKG38 (Lot 236) were prepared as described in Examples 30 and 31, respectively. The liposomes at the dose of 50 mg/kg (Ls-AKG28) or 90 mg/kg (Ls-AKG38) were injected in the lateral tail vein at time 0 and the blood was sampled at 0.083, 1, 3, 6, 24, and 48 hours post injection. The plasma concentration of AKG-28, AKG-38, and a fluorescent liposome lipid label ($DiIC_{18}$(3)-DS) was determined by HPLC. Plasma concentration of the liposome phospholipid was calculated from the fluorescent label quantification using liposome lots 235 and 236 as standards. Because the tissue affinity of non-encapsulated oxazolidinone drugs is expected to be many times higher than that of the liposome-encapsulated ones (as supported, for example, by the Vd of 2,291.26 mL/kg of non-encapsulated oxazolidinone, linezolid, in comparison with the Vd of 33.27-43.74 mL/kg for liposome-encapsulated AKG-28 in rats, see Example 37), the plasma drug concentration could be attributed predominantly to liposome-associated drug, and the plasma drug-liposome lipid (DL) ratio normalized to the original (pre-injection) DL value was taken as the measure of drug retention by the liposomes. Non-compartment PK analyses were performed using Summit Research Services, PK Solutions 2.0. For Ls-AKG28 and Ls-AKG38, this PK software was used to estimate the plasma maximum concentration ($C_{max}$), plasma maximum concentration divided by dose ($C_{max}$/dose), time of Cmax ($T_{max}$), last measured concentration ($C_{last}$), time of last measured concentration ($T_{last}$), area-under the plasma concentration versus time curve from 0 h to last time point ($AUC_{0\text{-}last}$) and 0 h to infinity ($AUC_{0\text{-}inf}$), $AUC_{0\text{-}last}$ divided by dose ($AUC_{0\text{-}last}$/dose), clearance (CL), volume of distribution (Vd), and elimination half-life.

Figure 11A:
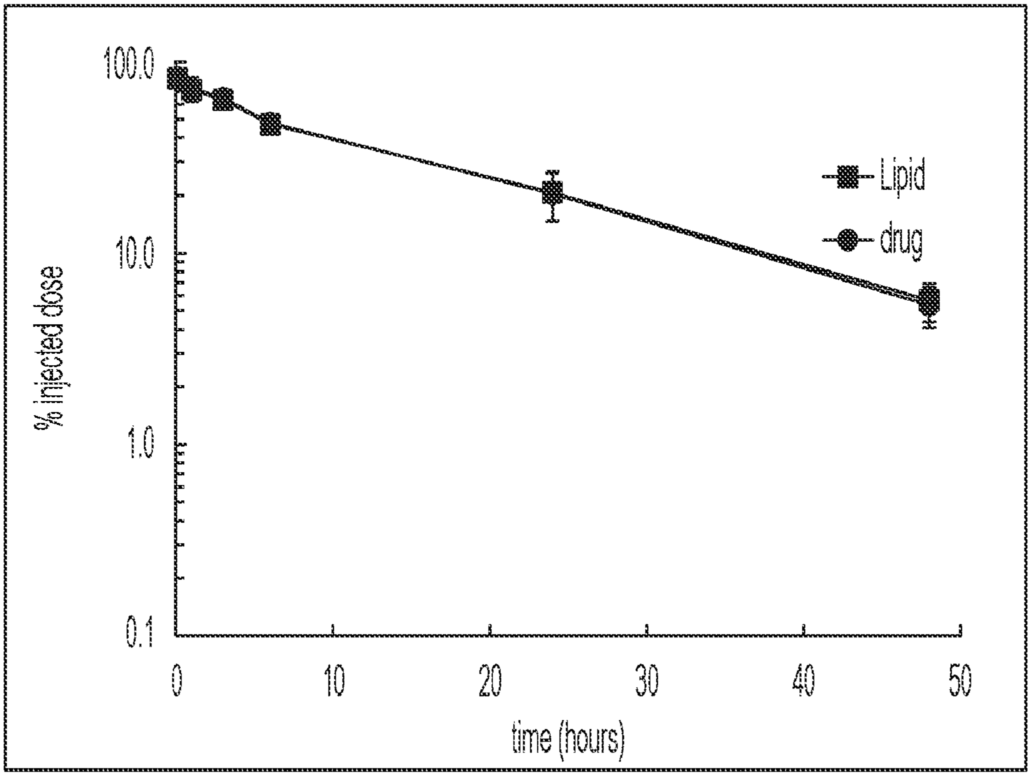
FIG. 11A, FIG. 11B, and FIG. 11C are graphs showing the plasma concentration versus time profiles of both lipid (using nonexchangeable DiIC18(3)-DS label), drug for liposomal AKG-28 (FIG. 11A) and liposomal AKG-38 (FIG. 11B), and the change in plasma drug-to-lipid ratio, a measure of drug release rate from the liposomes, for both Ls-AKG28 and Ls-AKG38 (FIG. 11C) in CD-1 mice after single intravenous injection in CD-1 mice. The mean and SD are presented at each time point.
Figure 11B:
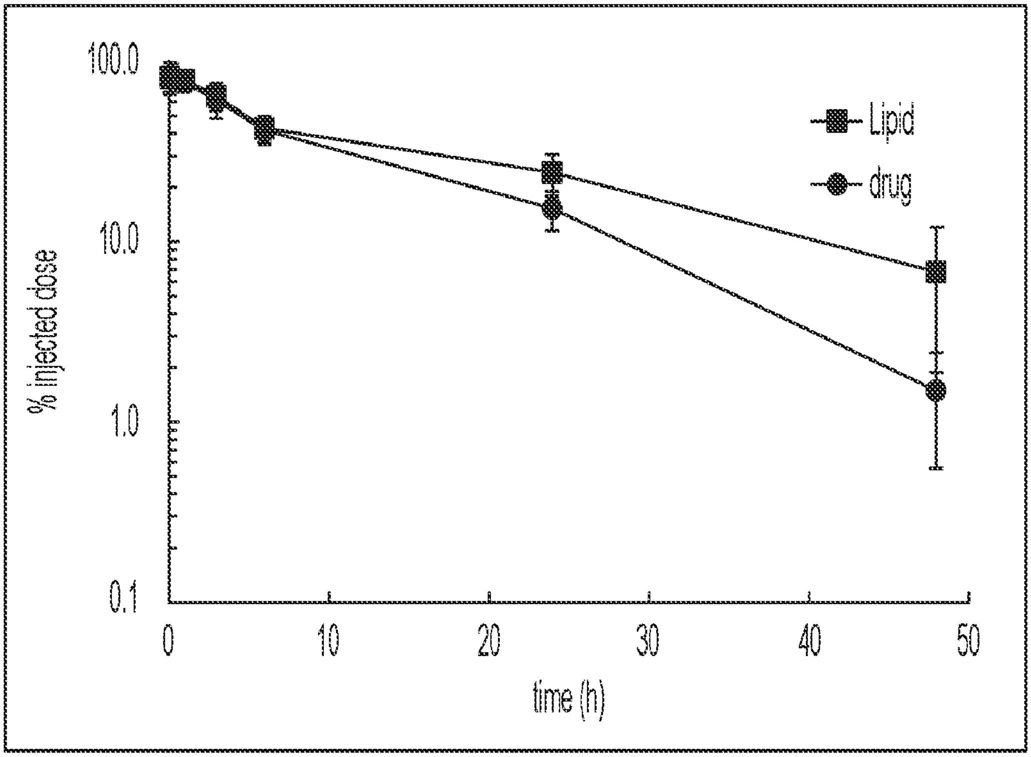
Figure 11C:
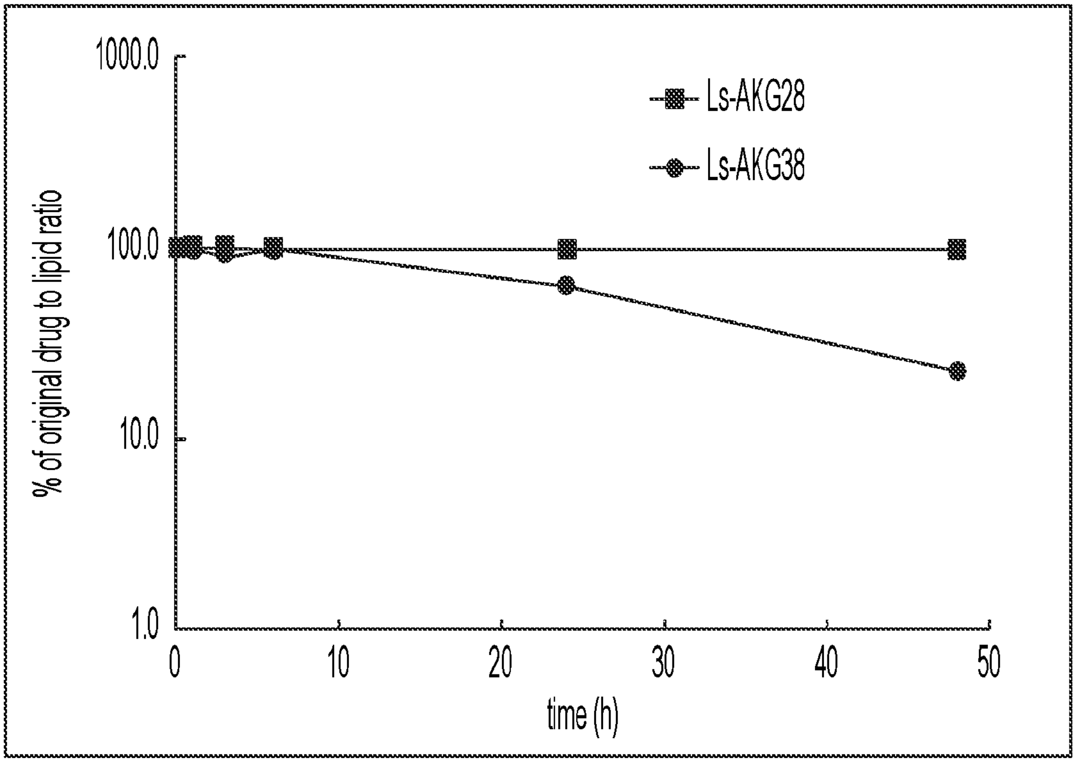

The plasma concentration versus time profiles for drug after administration of Ls-AKG28 (FIG. 11A) and Ls-AKG38 (FIG. 11B) are presented. The summary of plasma PK parameters for Ls-AKG28 and Ls-AKG38 drug in plasma are presented in TABLE 28 and of the liposomal phospholipid is presented in TABLE 29. Dynamics of the DL ratio indicative of the stability of the drug encapsulation in vivo is presented in FIG. 11C and TABLE 30.

Ls-AKG28 has a near perfect in vivo stability with an undetectable loss of drug up to 48 hours after IV injection in mice. The half-life of drug release for Ls-AKG28 is 866.3 h using a monoexponential equation ($R^2$=0.822). Ls-AKG28 has a faster drug release rate. The half-life of drug release for Ls-AKG38 is 22.9 h using a monoexponential equation ($R^2$=0.950).

TABLE 28

Summary of plasma PK parameters for the drug after administration of Ls-AKG28 and Ls-AKG38.

| PK Parameter | Ls-AKG28 | Ls-AKG38 |
|---|---|---|
| $C_{max}$ [mg/L] | 1261.1 | 2320.3 |
| $C_{max}$/Dose [mg/L]/[mg/kg] | 25.22 | 25.78 |
| $T_{max}$ [hr] | 0.083 | 0.083 |
| $C_{last}$ [mg/L] | 81.17 | 41.48 |
| $T_{last}$ [hr] | 48 | 48 |
| $AUC_{0-last}$ [hr*mg/L] | 19,820 | 30,346 |
| $AUC_{0-last}$/Dose [hr*mg/L]/[mg/kg] | 396.4 | 337.2 |
| $AUC_{0-inf}$ [hr*mg/L] | 21,156 | 45,114 |
| Clearance [mL/hr/kg] | 2.35 | 2.93 |
| Vd [mL/kg] | 42.13 | 30.12 |
| $T_{1/2}$ [hr] | 12.42 | 7.14 |

TABLE 29

Summary of plasma PK parameters for liposomal phospholipid after administration of Ls-AKG28 and Ls-AKG38.

| PK Parameter | Ls-AKG28 | Ls-AKG38 |
|---|---|---|
| $C_{max}$ [mol/L] | 0.00485 | 0.00493 |
| $C_{max}$/Dose [mol/L]/[mg/kg] | 24.87 | 25.54 |
| $T_{max}$ [hr] | 0.083 | 0.083 |
| $C_{last}$ [mol/L] | 0.00033 | 0.00041 |
| $T_{last}$ [hr] | 48 | 48 |
| $AUC_{0-last}$ [hr*mol/L] | 0.0769 | 0.0817 |
| $AUC_{0-last}$/Dose [hr*mol/L]/[mol/kg] | 394.3 | 421.1 |
| $AUC_{0-inf}$ [hr*mol/L] | 0.0826 | 0.0979 |
| Clearance [mL/hr/kg] | 2.34 | 2.17 |
| Vd [mL/kg] | 43.3 | 41.0 |
| $T_{1/2}$ [hr] | 12.82 | 13.09 |

TABLE 30

Plasma drug to liposomal phospholipid ratio of Ls-AKG28 and Ls-AKG38 after IV administration in mice.

| | Ls-AKG28 drug to phospholipid ratio | | Ls-AKG38 drug to phospholipid ratio | |
|---|---|---|---|---|
| Time (h) | (%) of original | Standard deviation | (%) of original | Standard deviation |
| 0.083 | 101.1 | 1.75 | 101.7 | 4.29 |
| 1 | 102.4 | 2.10 | 97.6 | 1.56 |
| 3 | 101.9 | 1.27 | 94.2 | 4.20 |
| 6 | 101.2 | 0.89 | 97.4 | 2.08 |
| 24 | 98.7 | 1.92 | 63.3 | 2.36 |
| 48 | 98.4 | 2.54 | 22.7 | 1.75 |

Figure 12:
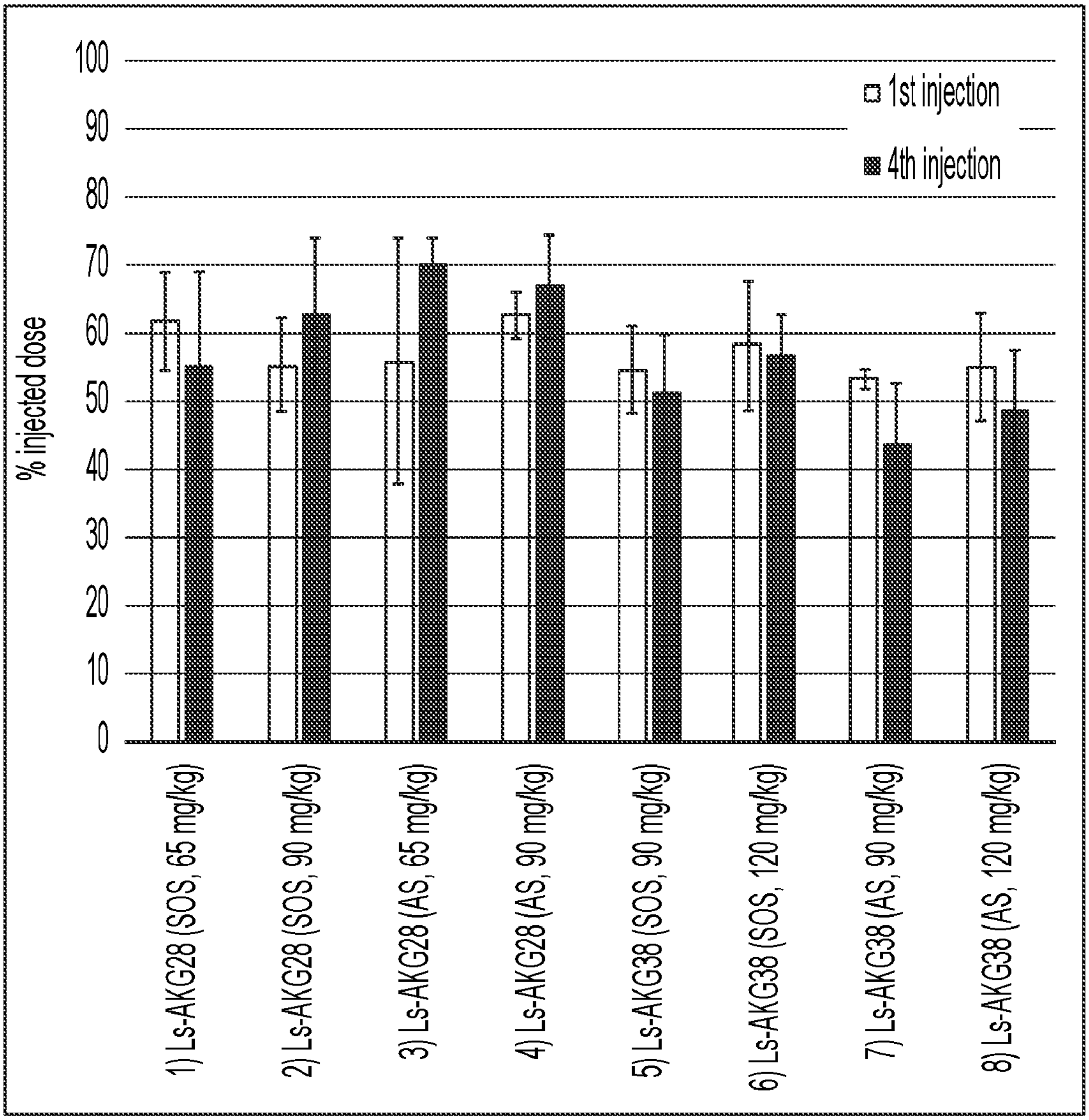
FIG. 12 is a graph showing the plasma drug concentration presented as % injected dose for Ls-AKG28 and Ls-AKG38 were compared were multiple formulations of liposomal AKG-28 and liposomal AKG-38 after the first and fourth weekly doses. Mice were injected with the indicated dose and formulation once per week for a total of 4 injections.

Example 40. Pharmacokinetic Studies of Ls-AKG28 & Ls-AKG38 Drug in Mice after Multiple Doses of the Liposomes the Presence of ABC Effect The generation of anti-PEG antibodies has been shown to cause faster clearance of the liposomes containing PEG-lipid conjugates (pegylated liposomes) after repeated multiple injections (Ishida et al. Journal of Controlled Release 105 (2005) 305-317; Laverman et al. JPET 298 (2001) 607-612), a phenomenon known as accelerated blood clearance (ABC) effect. This study was performed to determine if there is an ABC effect after multiple repeated administration of various doses of Ls-AKG28 and Ls-AKG38 having various compositions. The liposomes were prepared according to Examples 33-35, lots 231, 232, 233, and 234. This study was performed on male CD-1 mice as generally described in Example 7. Five mice were used per group. The plasma concentration of AKG-28 and AKG-38 in mice was determined by HPLC. Mice were injected with the indicated dose and formulation once per week for a total of 4 injections. The drug was measured in the plasma at the 6 h time point after the 1$^{st}$ and 4$^{th}$ doses (FIG. 12). None of the groups tested had a significant accelerated clearance of the 4$^{th}$ injection (2-tailed, unequal variance t-test all p values >0.05). This data confirms that these liposomal oxazolidinones can be dosed chronically for multiple weekly cycles with no significant negative impact on drug exposure.

TABLE 31

Plasma drug concentration for Ls-AKG28 and Ls-AKG38 for liposomal phospholipid after administration of Ls-AKG28 and Ls-AKG38.

| | | trapping | Chol | DL | Injected dose | 1$^{st}$ dose | | 4$^{th}$ dose | |
|---|---|---|---|---|---|---|---|---|---|
| group | drug | agent | (mol %) | ratio | (mg/kg) | % ID | SD | % ID | SD |
| 1 | AKG-28 | SOS | 40 | 266.9 | 65 | 61.99 | 7.20 | 55.71 | 13.88 |
| 2 | AKG-28 | SOS | 40 | 266.9 | 90 | 55.74 | 6.73 | 63.23 | 11.07 |
| 3 | AKG-28 | AS | 55 | 252.5 | 65 | 56.15 | 18.3 | 70.17 | 3.91 |
| 4 | AKG-28 | AS | 55 | 252.5 | 90 | 62.90 | 3.41 | 67.11 | 7.67 |
| 5 | AKG-38 | SOS | 55 | 538.1 | 90 | 54.67 | 6.49 | 51.57 | 8.55 |
| 6 | AKG-38 | SOS | 55 | 538.1 | 120 | 58.53 | 9.52 | 56.79 | 6.29 |
| 7 | AKG-38 | AS | 55 | 524.5 | 90 | 53.57 | 1.20 | 44.25 | 8.66 |
| 8 | AKG-38 | AS | 55 | 524.5 | 120 | 55.39 | 7.99 | 48.95 | 8.66 |

Abbreviations: SOS, 1N TEA-SOS; AS, 0.5M ammonium sulfate; Chol, cholesterol content as mol % of the sum of cholesterol and HSPC; DL, drug-to-lipid ratio, g/mol liposome phospholipid; % ID—percent of injected dose, average per group; SD—standard deviation.

This data shows that after four cycles of treatment, the blood clearance rate of liposomal AKG-28 or liposomal AKG-38 of the disclosure did not increase, in contrast to what has been previously reported for other pegylated liposomes not containing a cytotoxic drug associated with the liposome.

Example 41. Dose-Dependent Tolerability of Liposomal AKG-28 and Liposomal AKG-38 in CD-1 Mice The aim of this studies was to evaluate tolerability of Ls-AKG28 and Ls-AKG38 injected as a single agent at different doses in mice. Female CD-1 mice of 20-22 grams (5 per each group) were administered with Ls-AKG28 (50, 65, 90 or 100 mg/kg/dose) or Ls-AKG38 (50, 90, 120 or 200 mg/kg/dose) by intravenous injection (tail vein) once weekly for 4 weeks. The liposomal formulations (Ls-AKG28 lot231 and Ls-AKG38 lot 232) were prepared as described previously in Example 33. The control group was injected once weekly for 4 weeks with an equal volume of HEPES buffered saline (HBS, pH 7). The body weights were measured 3 times a week throughout the study and data were presented as a percentage of body weight change relative to the body weight measured at day zero.

The animals were humanely euthanized at the end of the study (72 hours post last treatment) using $CO_2$ inhalation. Blood samples were collected by a cardiac puncture and transferred to EDTA prefilled microtainers for hematology analysis (Homological ADVIA 120/2120i Analyzer) and to microtainers prefilled with lithium heparin for plasma separation. Plasma was separated from the cell fraction by centrifugation at 10000 rpm for 5 min and used for the biochemistry analysis (Cobas 6000 Analyzer). Tissue samples (liver, spleen, kidney, ling, heart, small intestine, and column) were collected in 50 ml tubes prefilled with 10% buffered formalin, which was replaced with 70% ethanol after 24 hrs. The tissues were embedded in paraffin, sectioned, stained with hematoxylin and eosin (H&E) and evaluated for histopathology by a board-certified veterinary pathologist.

Figure 13A:
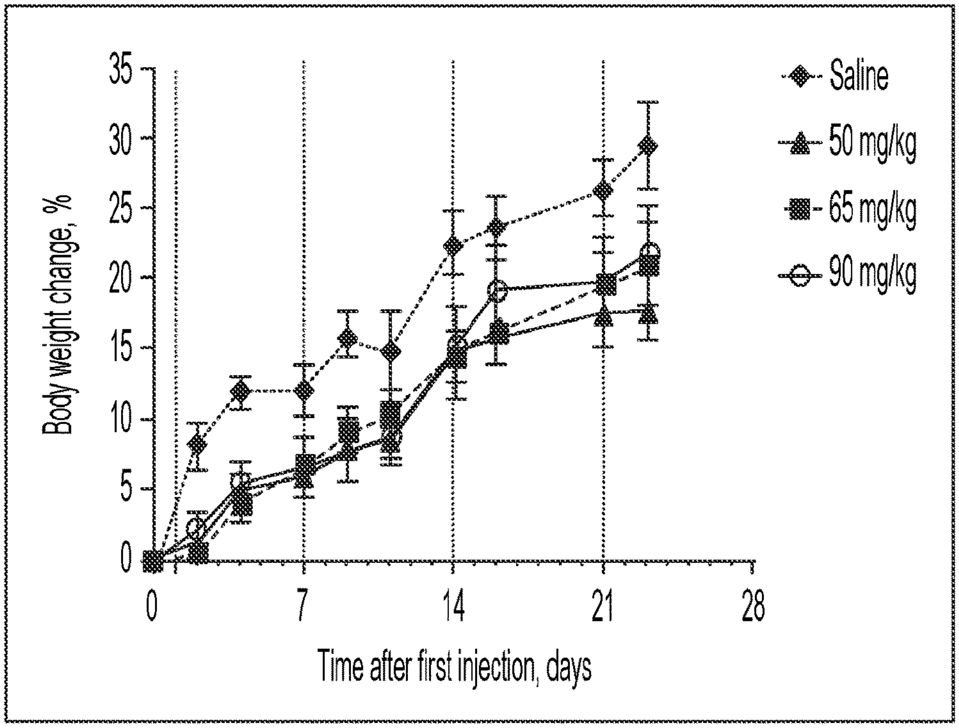
FIG. 13A is a graph showing the effect of Ls-AKG28 dose escalation on female CD-1 mice body weight over time.
Figure 13B:
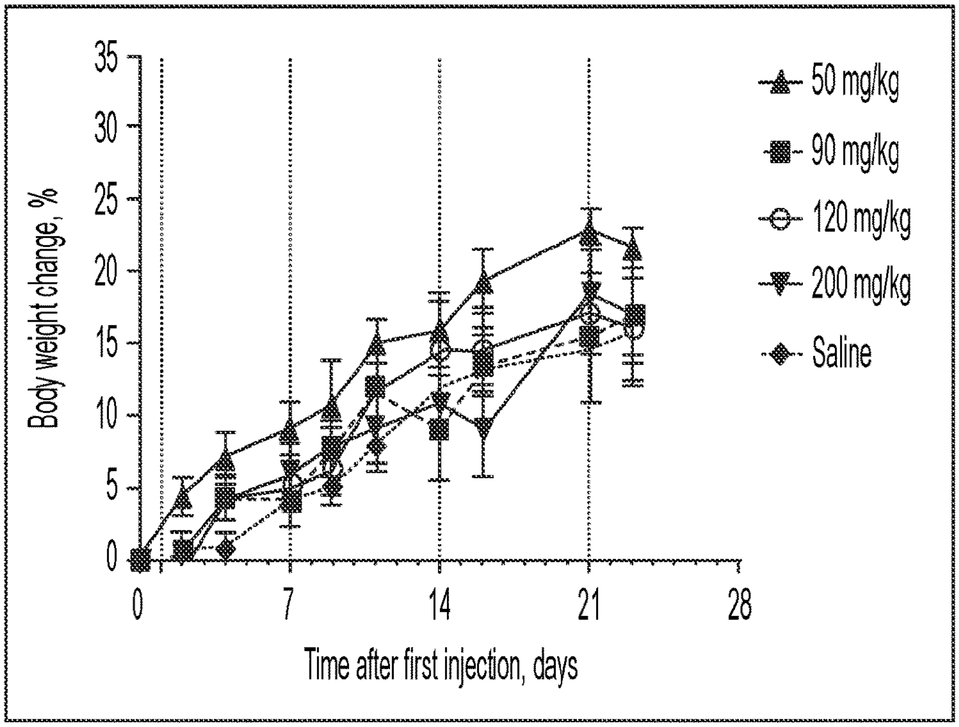
FIG. 13B is a graph showing the effect of Ls-AKG38 dose escalation on female CD-1 body weight in mice over time.

As shown in FIG. 13A and FIG. 13B, there was no significant impact on the mice body weight observed for both Ls-AKG28 and Ls-AKG38 when treating for a total of four weekly doses at doses up to 90 mg/kg for Ls-AKG28, and 200 mg/kg for Ls-AKG38 relative to the saline control group.

Figure 13C:
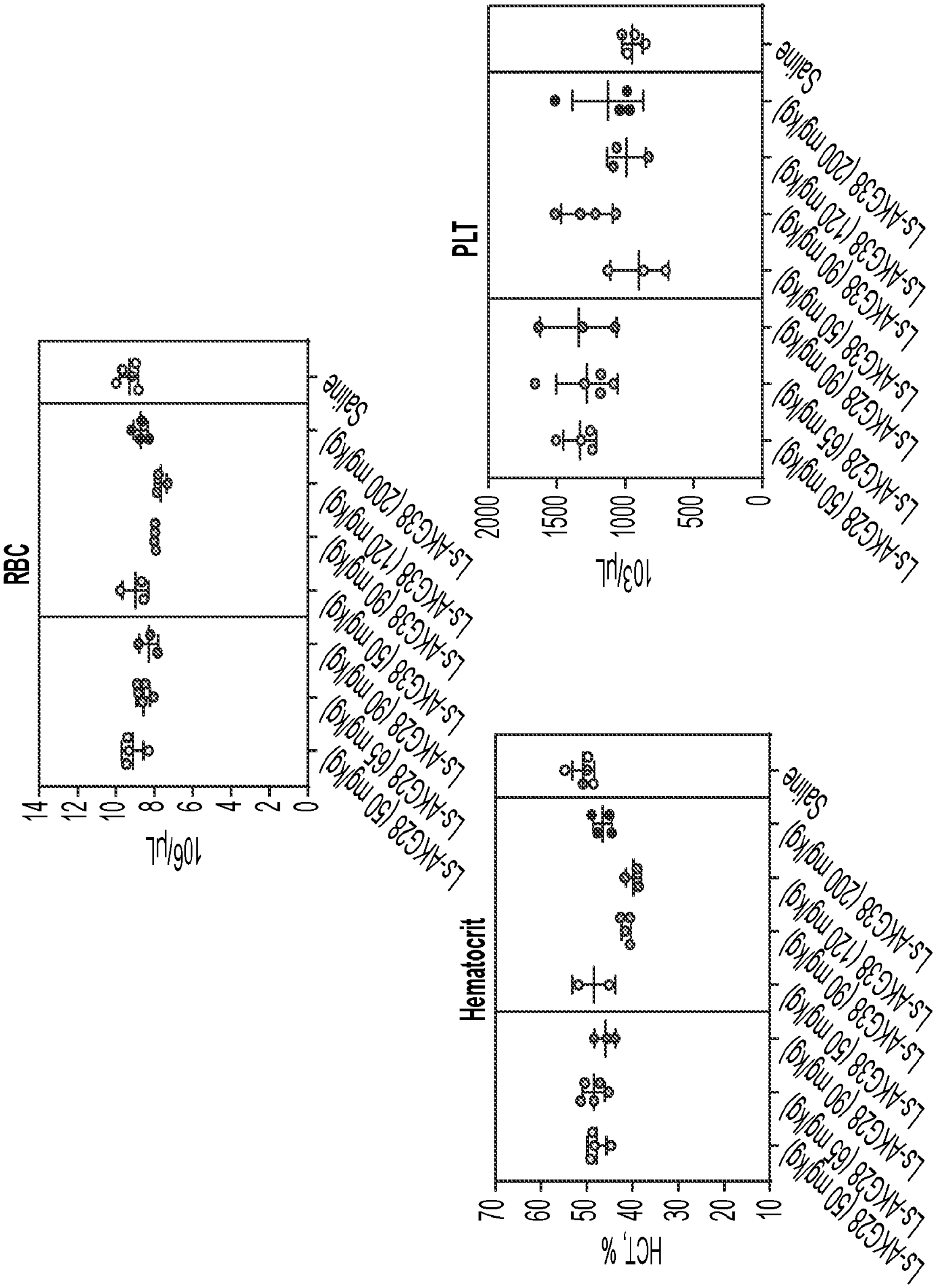
FIG. 13C are graphs showing the effects of Ls-AKG28 and Ls-AKG38 in combination with BP or BPM on hematology (RBC, HTC, PLT, WBC) and blood biochemistry (ALT, AST) parameters in female CD-1 mice.
Figure 13C:
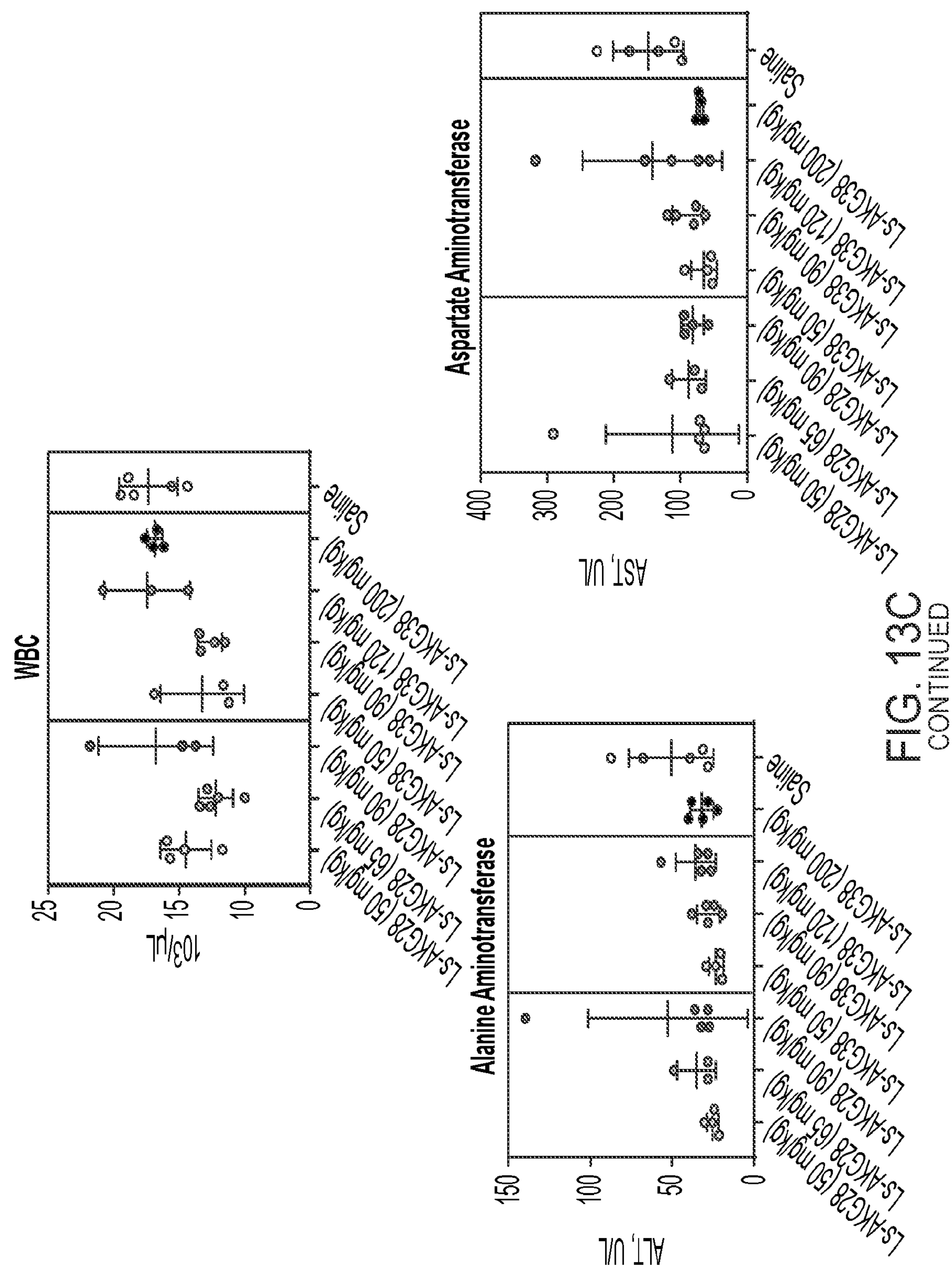

Relative to the control group, there was no significant decrease in red blood cells count and hematocrit (FIG. 13C) in the mice treated with high doses of Ls-AKG38 (90, 120 and 200 mg/kg) relative to the saline control group. No such effect was observed in mice treated with Ls-AKG28. A significant decrease in the platelet count relative to the control group was found in the mice treated with Ls-AKG28 at the highest dose of 90 mg/kg (FIG. 13C), but still less than 25% reduction compared to saline controls. Treatment with either Ls-AKG28 or Ls-AKG38 did not significantly affect the white blood cell (WBC) count or that of blood liver enzymes (ALT and AST).

Figure 13D:
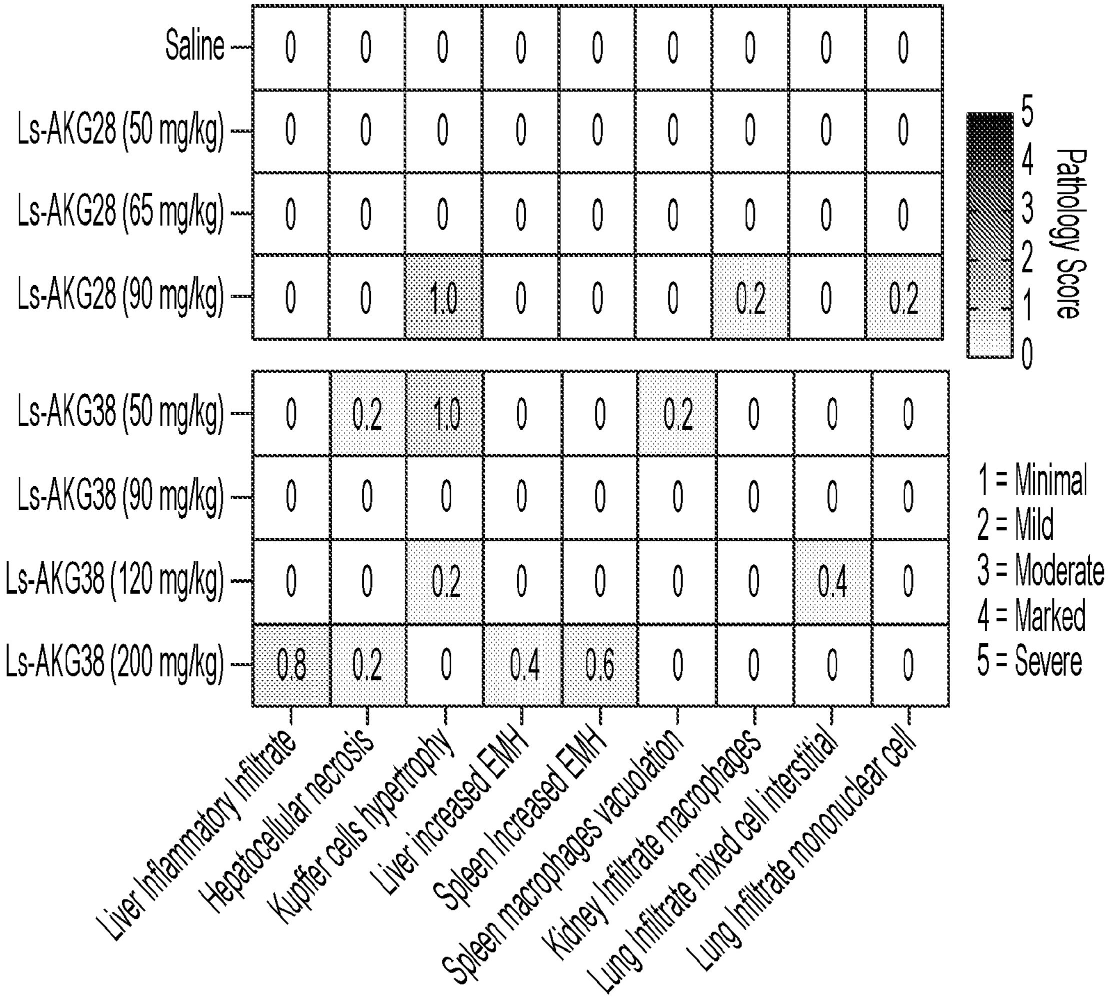
FIG. 13D is a heat map showing the effect of monotherapy Ls-AKG28 or Ls-AKG38 on tissue pathological findings in female CD-1 mice.

The histopathology analysis showed no test article-related findings in animals that received 50 and 65 mg/kg Ls-AKG28 (FIG. 13D). There were test article-related findings, that consisted of minimal vacuolization of macrophages (including Kupffer cells), in the liver, spleen, and kidney of animals that received 90 mg/kg LS-AKG28. Treatment with Ls-AKG38 was associated with test article-related findings in the liver and spleen at doses of 90 mg/kg and 120 mg/kg. In the liver, there was minimal to mild vacuolation and hypertrophy of Kupffer cells at 50 and 90 mg/kg, moderate vacuolation and hypertrophy of Kupffer cells at 50 and 120 mg/kg, and minimal multifocal aggregation of vacuolated macrophages at 90 mg/kg and 120 mg/kg.

Treatment at the highest does of Ls-AKG38 (200 mg/kg) was associated with minimally increased extramedullary hematopoiesis (EMH) in the liver and spleen, minimal to mild multifocal mixed cell infiltrates and minimal individual hepatocellular necrosis in the liver and minimal focal hepatocellular necrosis (FIG. 13D). These microscopic findings were not considered test article-related due to their common occurrence as a background finding in this species.

Overall, both Ls-AKG28 and Ls-AKG38 monotherapy show good in vivo tolerability in mice even when the liposomal drugs were injected at the highest evaluated dose for each, 90 and 200 mg/kg for Ls-AKG28 and Ls-AKG38, respectively.

Example 42. In Vivo Tolerability of Ls-AKG28 and Ls-AKG38 Combined with BDQ/PMD or BDQ/PMD/MOX in Mice In this example in vivo tolerability of liposomal oxazolidinones was evaluated in combination with therapeutically relevant anti-TB drugs. The three drug regimens of bedaquiline, pretomanid, and linezolid (BDQ/PMD/LNZ or BPL) or bedaquiline, pretomanid, and moxifloxacin (BDQ/PMD/MOXI or BPM) have shown strong activity in the clinic when treating multidrug resistant tuberculosis (Conradie et al (2020) N Engl J Med 382(10) 893-902 and Tweed et al. (2019) Lancet Respir Med 7(12) 1048-1058), although the BPL regimen has been limited by toxicities primarily related to the addition of linezolid (Conradie et al (2020) N Engl J Med 382(10) 893-902). Here, we evaluated the safety and tolerability of two liposomal oxazolidinones, Ls-AKG28 and Ls-AKG38, when used as a part of both regimens, either by replacing linezolid in the BPL regimen, or through addition to the BPM regimen. CD-1 mice (5 per each group) were treated with either Ls-AKG28 (lot 231) or LsAKG38 (lot 232) alone or together with bedaquiline (BDQ) and pretomanid (PMD) combination. Ls-AKG28 (Lot 231) and Ls-AKG38 (Lot 232) were prepared as described in Example 33. Additionally, mice were co-treated with a triple combination of BDQ, PMD and moxifloxacin (MOXI) and liposomal oxazolidinones.

Ls-AKG28 (50 mg/kg/dose) and LsAKG38 (90 mg/kg/dose) were administered by intravenous injection via a tail vein once weekly for 4 weeks. Combination of BDQ, PMD and MOXI (25/100/100 mg/kg/dose respectively) was given by oral gavage daily, five times a week for 4 weeks. As an additional control, mice were treated with only BDQ/PMD/MOX or BDQ/PMD (25/100 mg/kg/dose respectively) plus linezolid (LNZ) given orally at 100 mg/kg/dose daily, five times a week for 4 weeks. The body weight measurements, tissue collection and analysis were conducted as described previously in Example 41.

Figure 14A:
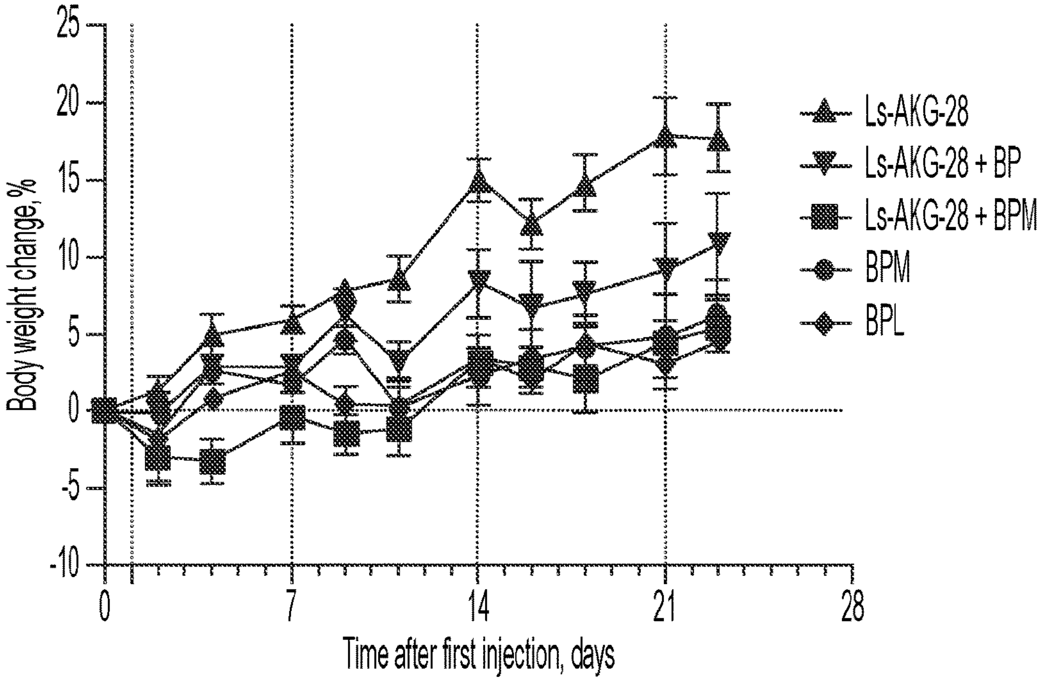
FIG. 14A is a graph showing the effect of Ls-AKG28 in combination with bedaquiline and pretomanid (BP) or bedaquiline, pretomanid, and moxifloxacin (BPM) on female CD-1 mice body weight over time.
Figure 14B:
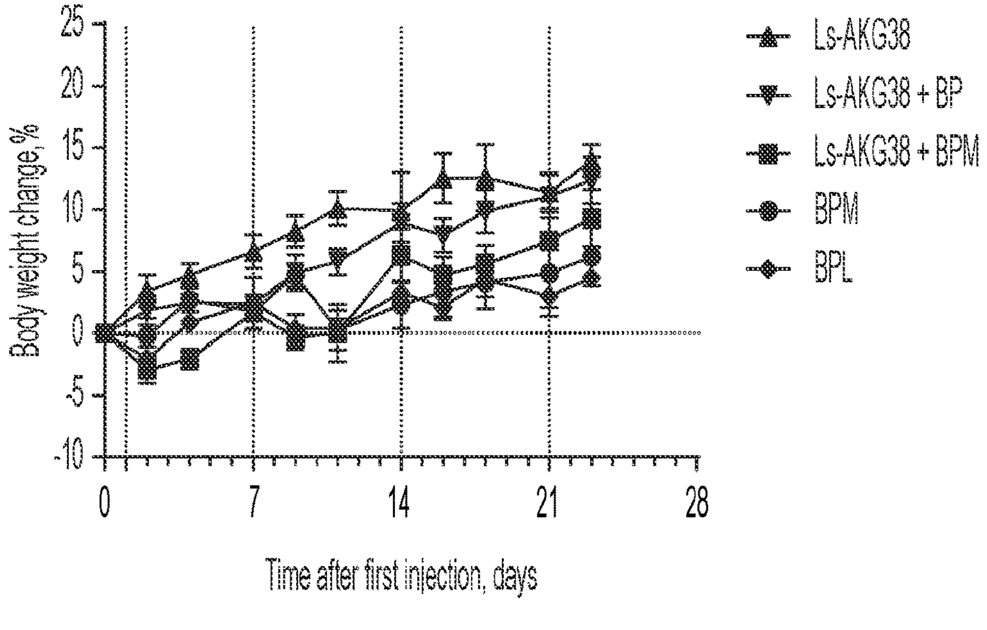
FIG. 14B is a graph showing the effect of Ls-AKG38 in combination with BP or BPM on female CD-1 mice body weight over time.
Figure 14C:
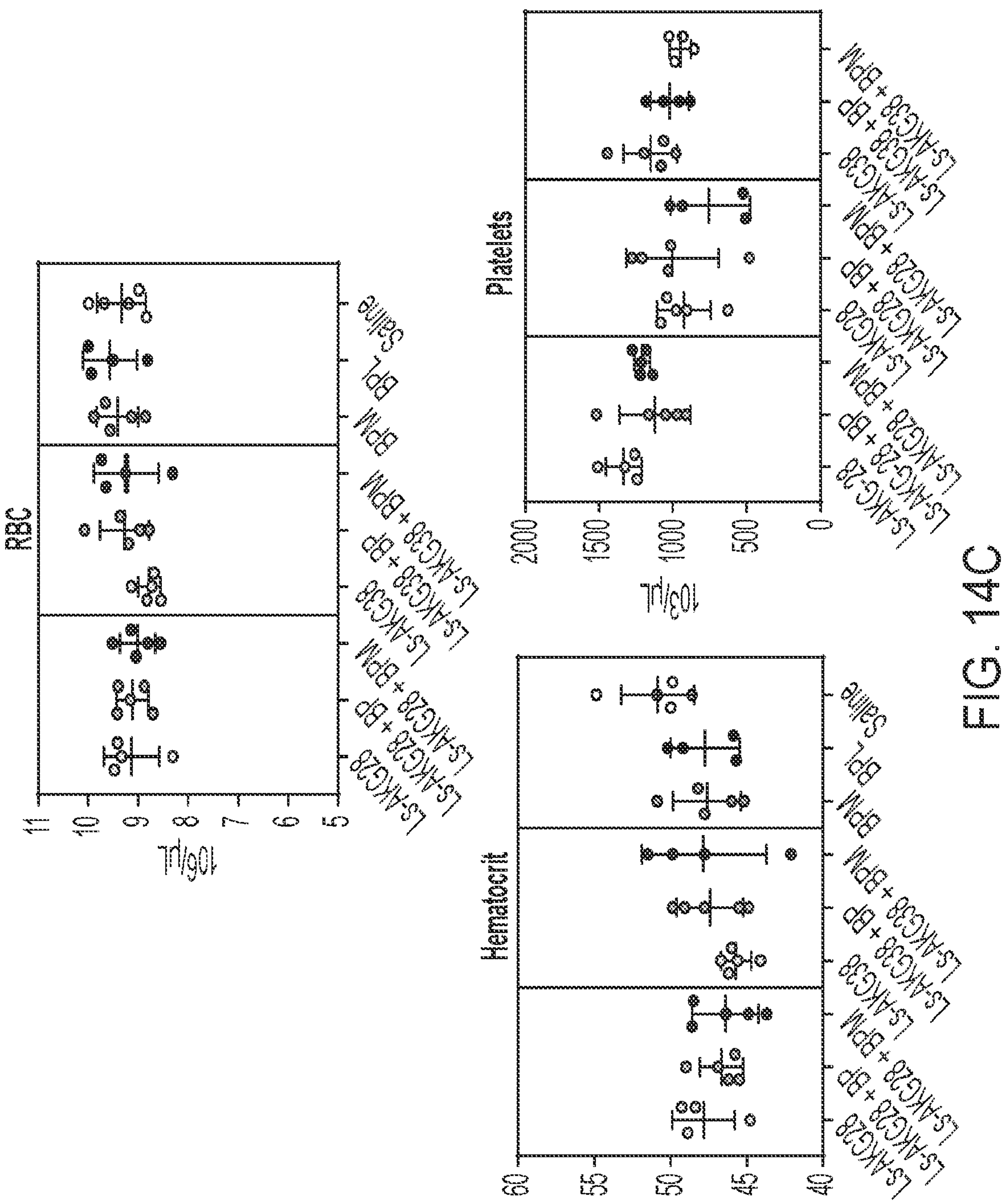
FIG. 14C are graphs showing the effect of Ls-AKG28 and Ls-AKG38 in combination with BP or BPM on hematology (RBC, HTC, PLT, WBC) and blood biochemistry (ALT, AST) parameters in female CD-1 mice.
Figure 14C:
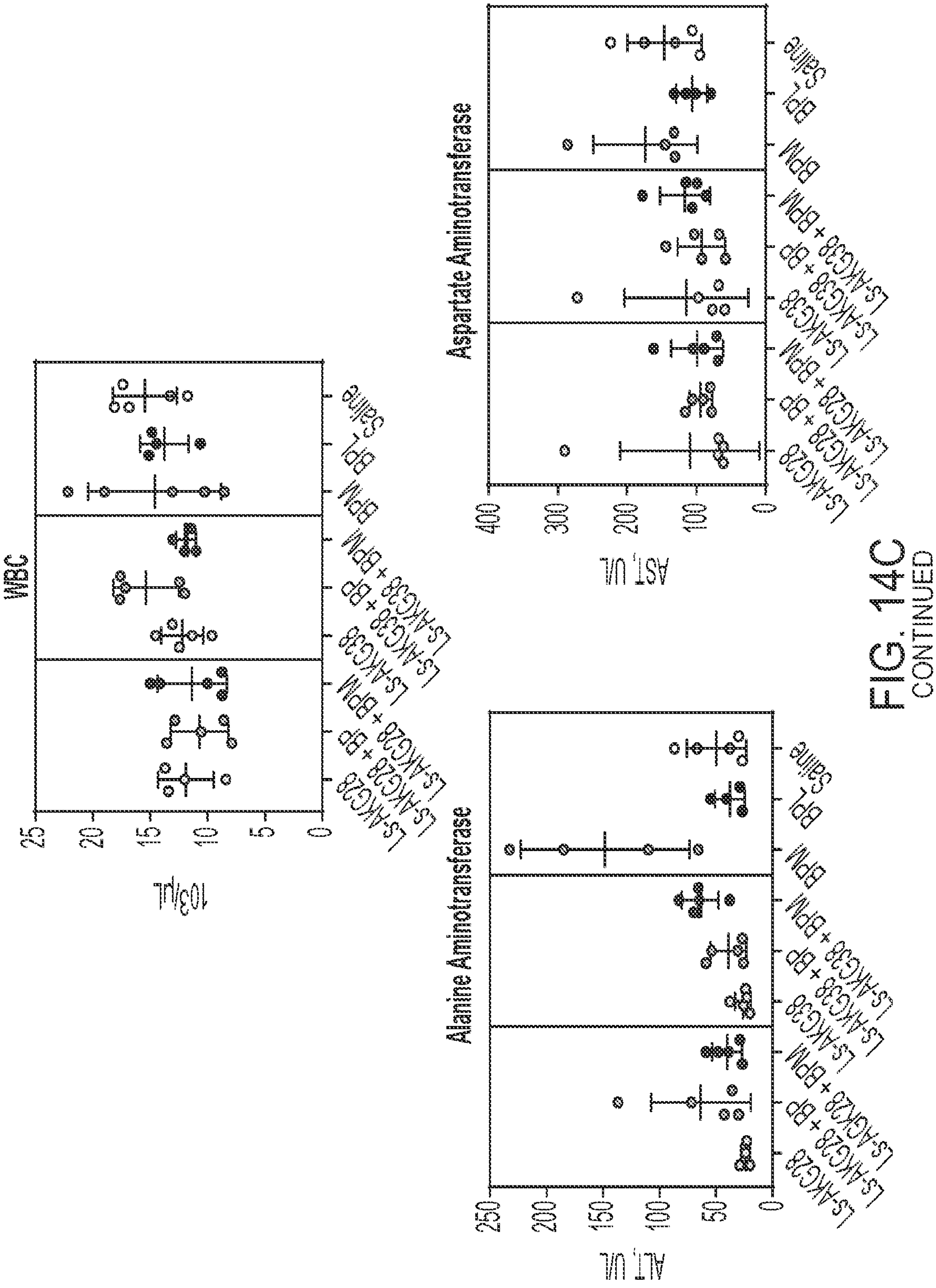

As demonstrated in FIG. 14A and FIG. 14B, no significant effect of either Ls-AKG28 or Ls-AKG38 co-treated in combination with BDQ/PMD (BP) or BDQ/PMD/MOX (BPM) on the mice body weight was observed during the study. Both Ls-AKG28 and LsAKG38 show good tolerability in combination with BDQ/PMD or BDQ/PMD/MOX and did not affect hematology or blood biochemistry in the treated mice (FIG. 14C).

Figure 14D:
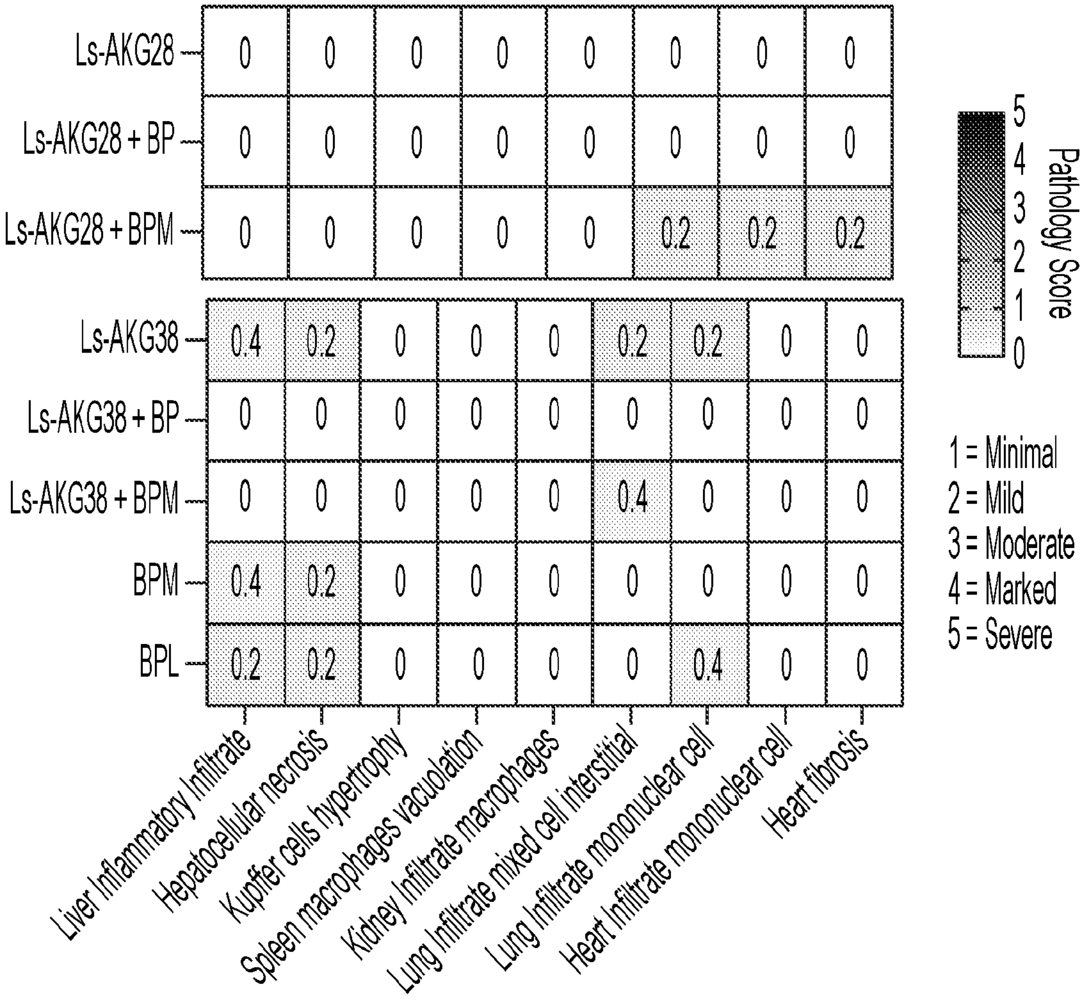
FIG. 14D is a heat map showing the effect of Ls-AKG28 and Ls-AKG38 in combination with BP or BPM on tissue pathology findings in female CD-1 mice.

The histopathology data (FIG. 14D) showed no treatment related changes in case of Ls-AKG28 combined with BDQ/

PMD. Ls-AKG28+BDQ/PMD/MOX combination has minimal events associated with mixed cell and mononuclear cell infiltration in lung and heart. Treatment with Ls-AKG38 as a monotherapy was associated with minimal test article-related findings in the liver (inflammatory infiltration and hepatocellular necrosis). Administration of Ls-AKG38+BDQ/PMD did not show any treatment related findings and combination of Ls-AKG38+BDQ/PMD/MOX was associated with minimal mixed cell infiltration in lung. Animals treated with BDQ/PMD/LNZ combination were associated with the treated-related finding of inflammatory infiltration in the liver, minimal hepatocellular necrosis and infiltration of vacuolated macrophages in the lung. Therefore, both Ls-AKG28 (50 mg/kg/dose) and Ls-AKG38 (90 mg/kg/dose) administered once weekly for 4 weeks showed good tolerability in mice in combination with BDQ/PMD or BDQ/PMD/MOX.

Example 43. Effect of Dose Scheduling on Tolerability of Ls-AKG28 and Ls-AKG38 Combined with BDQ/PMD in Mice In this study in vivo tolerability of Ls-AKG28 (50 mg/kg/dose) or Ls-AKG38 (100 mg/kg/dose) administrated twice a week was compared with Ls-AKG28 (100 mg/kg/dose) or Ls-AKG38 (200 mg/kg/dose) given once a week. The liposomes were prepared according to Example 25 (Ls-AKG38, lot 279) and Example 26 (Ls-AKG28, lot 281). Both liposomal drugs were injected into CD-1 female mice (5 per each group) alone or in combination with BDQ/PMD (BP). BDQ/PMD (25 and 100 mg/kg/dose respectively) was given by oral gavage daily, five times a week for 4 weeks. The control group was injected once weekly for 4 weeks with HEPES buffered saline (HBS, pH 7). Blood and tissue samples were collected and analyzed as described above in Examples 41 and 42.

Figure 15A:
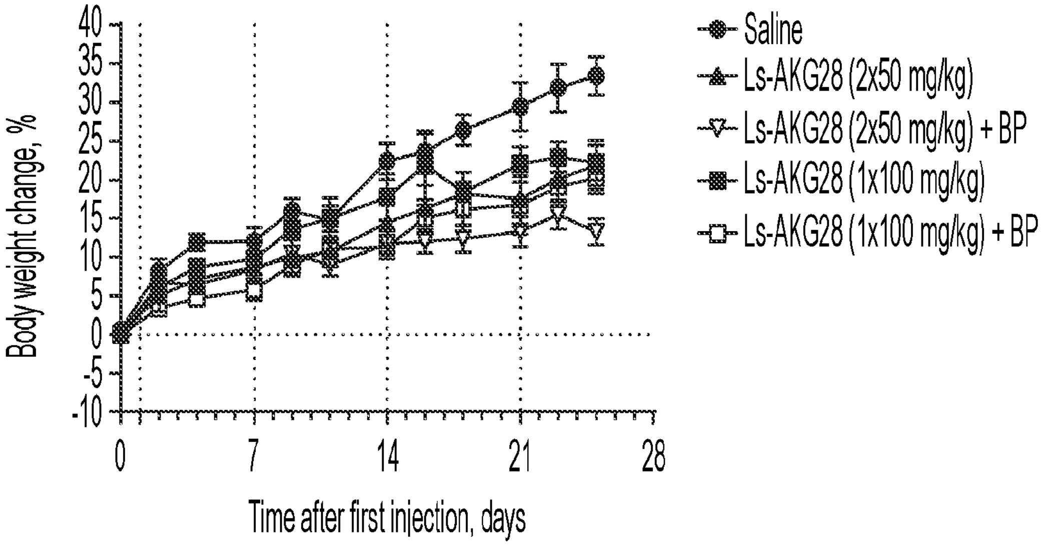
FIG. 15A is a graph showing the body weight change in female CD-1 mice treated with Ls-AKG28 injected twice a week (2 qw) at 50 mg/kg or once a week (1 qw) at 100 mg/kg alone or in in combination with BP over time.
Figure 15B:
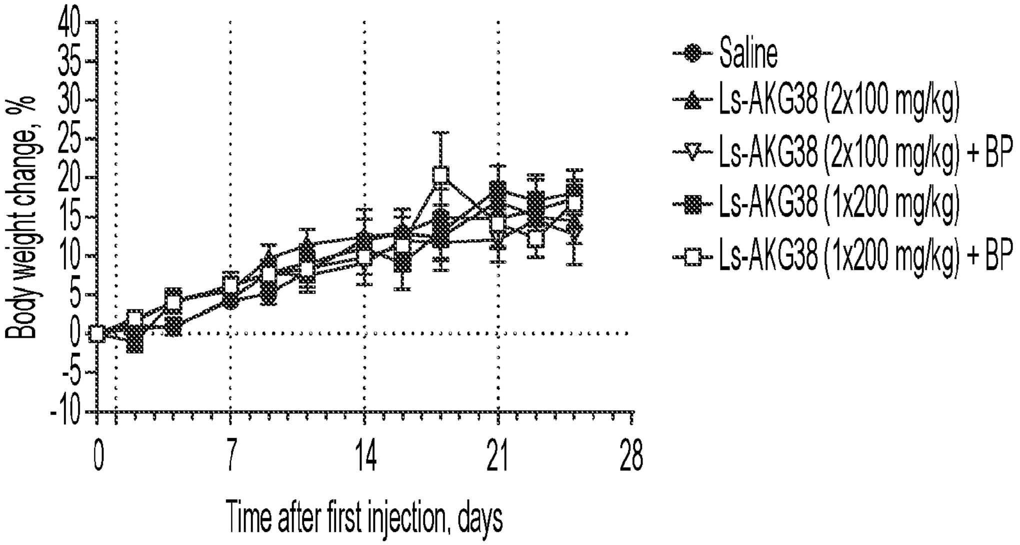
FIG. 15B is a graph showing the body weight change in female CD-1 mice treated with Ls-AKG38 injected 2 qw at 100 mg/kg or 1 qw at 200 mg/kg alone or in combination with BP.
Figure 15C:
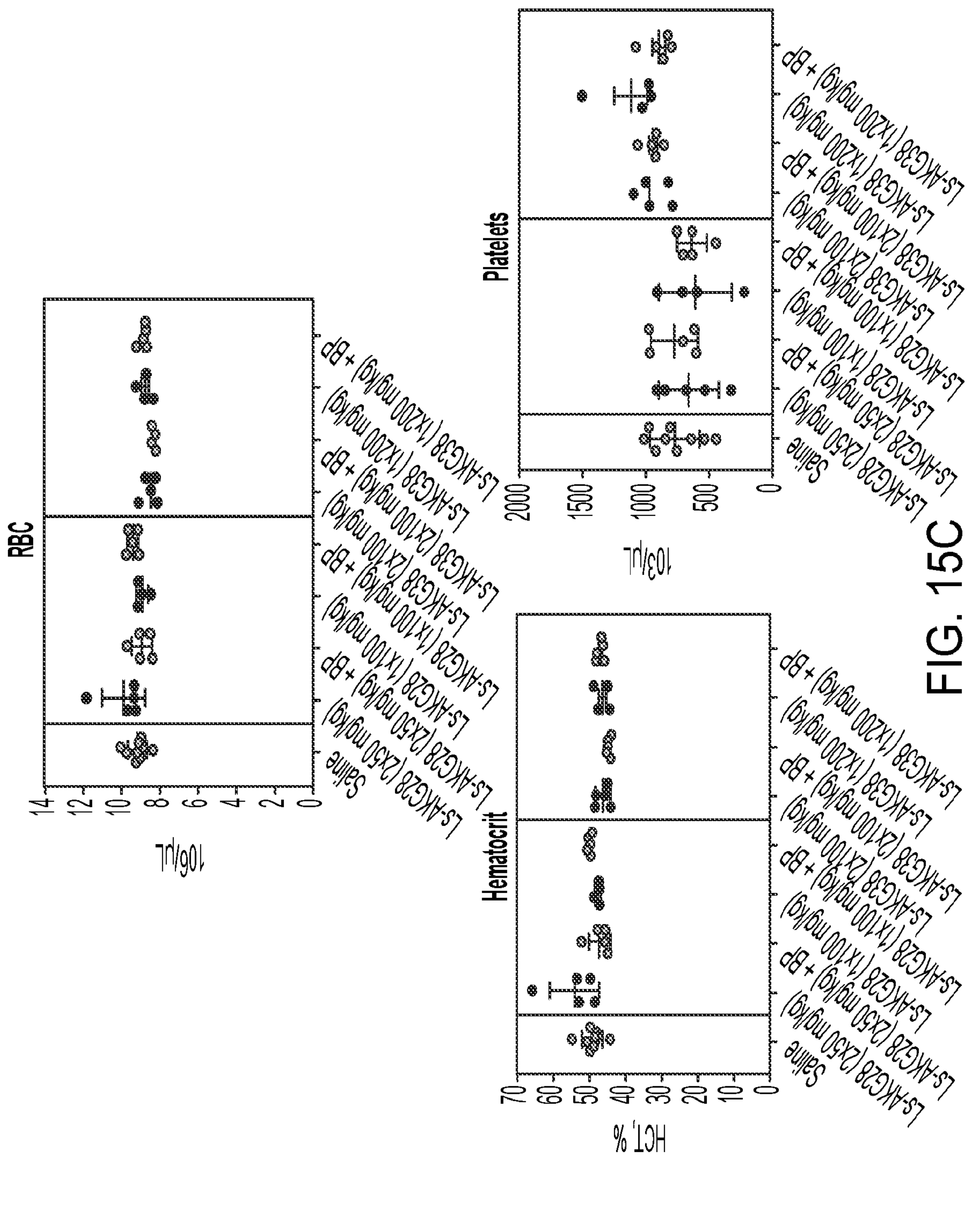
FIG. 15C are graphs showing the hematology and blood biochemistry parameters in female CD-1 mice treated with Ls-AKG28 (2 qw at 50 mg/kg or 1 qw at 100 mg/kg) or Ls-AKG28 (2 qw at 100 mg/kg or 1 qw at 200 mg/kg) alone or in combination with BP.
Figure 15C:
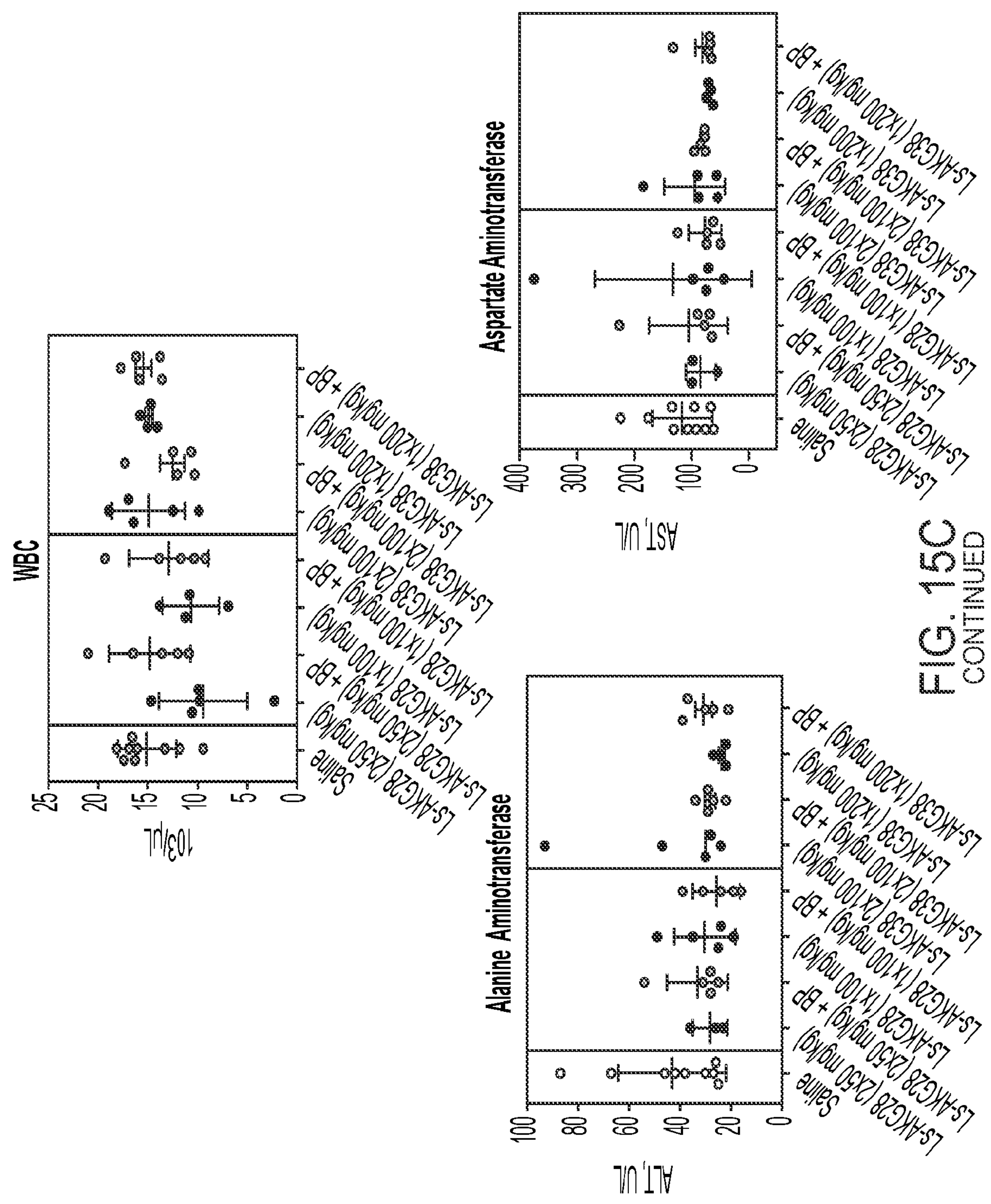

Both monotherapy and combination treatment of mice with Ls-AKG28 or Ls-AKG38 administered twice a week or once a week at higher dose did not affect neither body weight (FIG. 15A and FIG. 15B) or blood cell count and biochemistry (FIG. 15C).

Figure 15D:
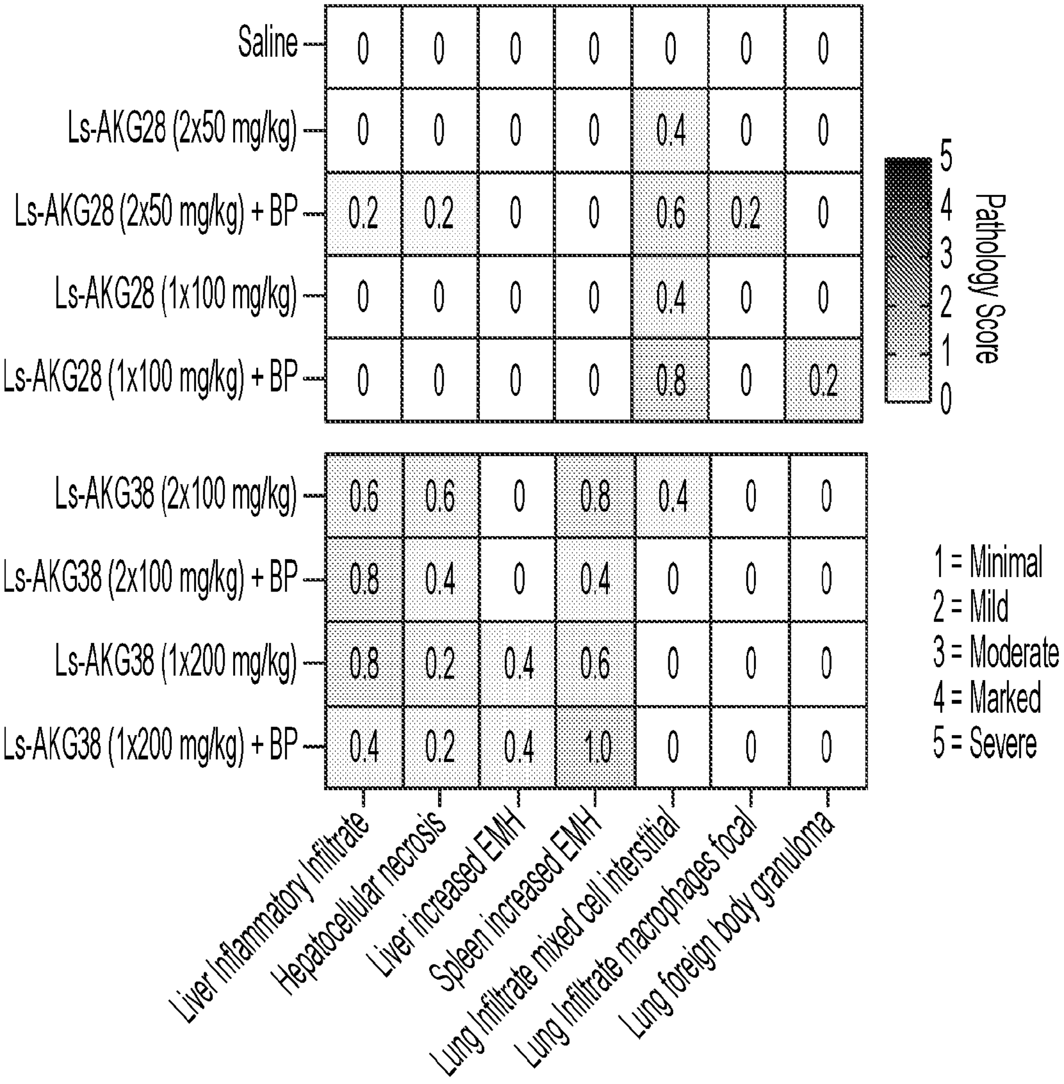
FIG. 15D is a heat map showing the histopathology results of female CD-1 mice treated with Ls-AKG28 (2 qw at 50 mg/kg or 1 qw at 100 mg/kg) or Ls-AKG28 (2 qw at 100 mg/kg or 1 qw at 200 mg/kg) alone, or in combination with BP.

Histopathology analysis of collected tissues (FIG. 15D) showed minimal interstitial mixed cell infiltrates composed of macrophages and neutrophils in 2 out of 5 mice that received Ls-AKG28 at 50 mg/kg (2 qw) and mild interstitial mixed cell infiltrates in 1 out of 5 animals that received Ls-AKG28 at 100 mg/kg (1 qw).

In the lungs of mice that received Ls-AKG28+BP at 50 mg/kg (1 qw) there were minimal interstitial infiltrates composed of macrophages (1 out of 5 animals) or mixed (macrophages and neutrophils) inflammatory cells (3 out of 5 mice). In mice that received Ls-AKG28+BP at 100 mg/kg (1 qw) there were minimal interstitial mixed cell infiltrates in 4 out of 5 animals. In addition, there were minimal multifocal foreign body granulomas associated with pale basophilic foreign material in the lungs of 2 out of 5 animals that received Ls-AKG28+BP at 100 mg/kg (1 qw). These microscopic findings were not considered test article-related due to their common occurrence as a background finding in this species included minimal multifocal mixed cell infiltrates and minimal individual hepatocellular necrosis in the liver of 1 out of 5 animals that received Ls-AKG28+BP at 50 mg/kg (2 qw).

The similar microscopic findings associated with Ls-AKG38 treatment (alone or in combination) were not considered to be test article related included minimally increased extramedullary hematopoiesis (EMH) in the liver and spleen, minimal to mild multifocal mixed cell infiltrates and minimal individual hepatocellular necrosis in the liver, minimal focal hepatocellular necrosis, minimal focal foreign body granuloma (associated with pale basophilic foreign material) in the lung, and minimal mixed cell infiltrates in the lung. Due to their minimal to mild nature, sporadic incidence, presence in the saline control group, and occurrence as common background findings in this species, these findings were not considered treatment related.

Therefore, both Ls-AKG28 and Ls-AKG38 (alone or in combination with BDQ/PMD) administrated twice a week at doses 50 mg/kg and 100 mg/kg respectively or at doubled doses of 100 mg/kg and 200 mg/kg once a week were well tolerated in mice and did not affect body weight, hematology, or histopathology of the treated animals.

Example 44. In Vivo Tolerability of Ls-AKG28 and Ls-AKG38 in Rats

The objectives of this study were to determine the potential toxicity of Ls-AKG28 (lot 275) and Ls-AKG38 (lot 276) in rats. Ls-AKG28 (Lot 275) and Ls-AKG38 (Lot 276) were prepared as described in Examples 22 and 23, respectively. Male Sprague-Dawley rats were administered with Ls-AKG28 (10, 20 or 40 mg/kg/dose) or LsAKG-38 (20, 40 or 80 mg/kg/dose) by intravenous injection (tail vein) once weekly for 8 weeks. The control group was injected once weekly for 8 weeks with an equal volume of HEPES buffered saline (HBS, pH 7). Before the endpoint of the study animals were humanely euthanized by exsanguination from the abdominal aorta following isoflurane anesthesia. Blood and tissue samples were collected for evaluation of clinical pathology parameters. Representative samples of tissues were collected and preserved in 10% neutral buffered, embedded in paraffin, sectioned, mounted on glass slides, stained with hematoxylin and eosin, and evaluated for histopathology by a board-certified veterinary pathologist. Blood hematology analysis was performed using Homological ADVIA 120/2120i Analyzer and blood biochemistry was analyzed using Cobas 6000 Analyzer.

The following parameters and end points were also evaluated: mortality and moribundity check, clinical observations, body weights, food consumption, nerve conduction velocity (NCV) and muscle action potential (MAP), functional observation battery (FOB).

Nerve Conduction Velocity (NCV) and Muscle Action Potential (MAP) were conducted on week 8. During the recording sessions, the animals were anesthetized with isoflurane. Caudal nerve NCV measures the speed of conduction in the caudal nerve, which runs along the central bone of the tail. This nerve is approximately 50% longer than any other nerve in the rat and it is especially vulnerable to a length-dependent distal axonopathy. NCV was measured over a distance of 50 mm and is sensitive to nodal and transmembrane currents, the structure and mean cross-sectional diameter of the responding axons and the integrity of the associated myelin sheaths. The amplitude of the evoked response reflects the number and synchrony of the activated fibers. Data were recorded with the active recording electrode positioned approximately 10 mm below the hair line on the tail (determined visually) and the stimulating cathode 50 mm further distal. The amplitude and the onset latency of the signal were recorded, and velocity was calculated by dividing the distance between the stimulating cathode and the active electrode by the absolute onset latency of the initial depolarizing current.

Digital nerve NCV measures the speed of conduction in the sensory digital nerve. The digital nerve is the distal extreme of the sciatic nerve innervating the dorsal surface of the hind paw. Nerve conduction velocity is sensitive to the nodal and transmembrane currents, structure and mean cross-sectional diameter of the responding axons and the integrity of the associated myelin sheaths. Data were recorded with the active recording electrode positioned at the ankle behind the lateral malleolus and the stimulating cathode at the base of the second digit of the hind paw. The amplitude and the onset latency of the signal were recorded, and velocity was calculated by dividing the distance between the stimulating cathode and the active electrode by the absolute onset latency of the initial depolarizing current.

Tibial motor conduction (onset latency) measures the response properties of the intrinsic muscles of the rat hind paw following stimulation of the motor fibers at the distal portion of the tibial nerve. Data were recorded with the active electrode positioned in a lateral dorsal muscle of the hind paw (equivalent to the extensor digitorum *brevis* muscle in humans) and the stimulating cathode positioned proximal to the ankle, behind the lateral malleolus. The speed of nerve conduction in the motor axons was estimated from the onset latency of the induced compound muscle action potential (CMAP). The amplitude of the CMAP was determined at the peak of the response following supramaximal stimulation of the associated nerve.

Figure 16A:
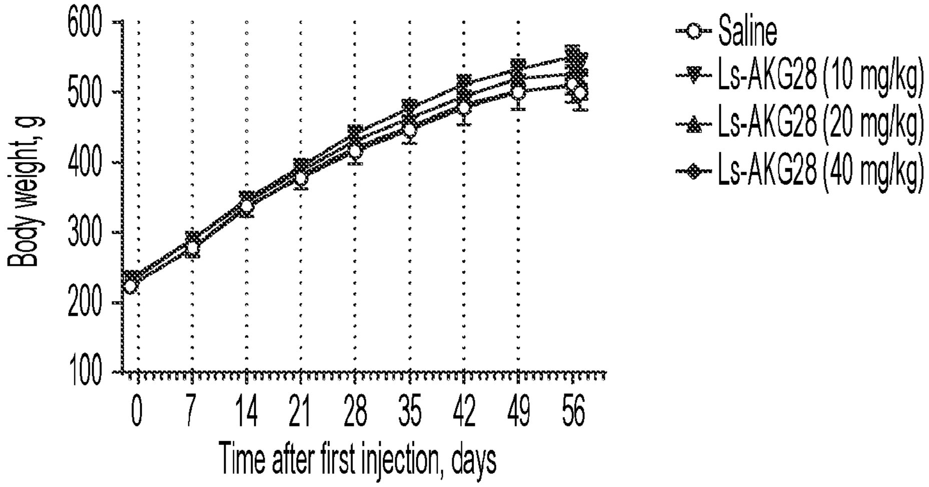
FIG. 16A is a graph showing the effect of Ls-AKG28 on body weight in male Sprague-Dawley rats treated chronically for a total of eight weeks over time.
Figure 16B:
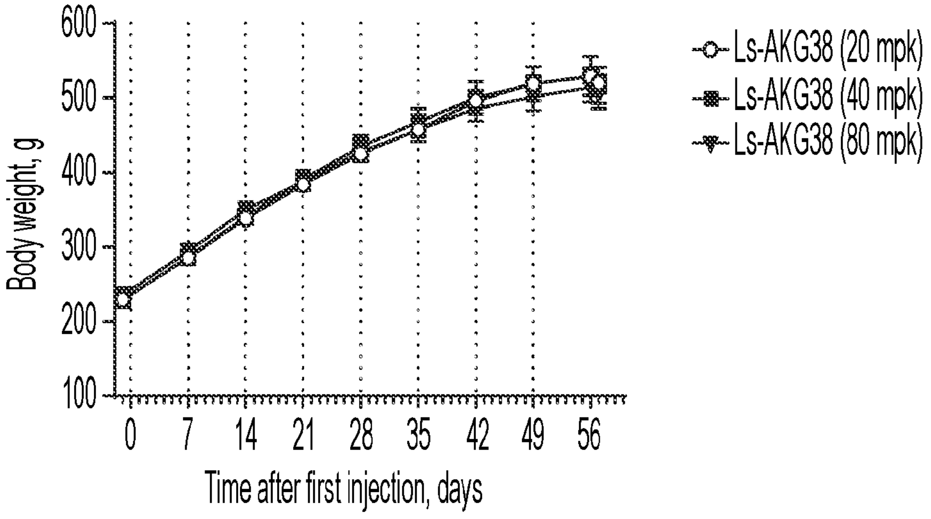
FIG. 16B is a graph showing the effect of Ls-AKG38 on body weight in male Sprague-Dawley rats treated chronically for a total of eight weeks over time.

There were no Ls-AKG28, Ls-AKG38-related unscheduled deaths, clinical observations, or effects on body weights (FIG. 16A and FIG. 16B), NCV and MAP (TABLE 34), FOB (TABLE 35), food consumption, coagulation parameters, organ weights or macroscopic findings (data is not shown). The greatest decline nerve conductance velocity for the caudal or left digital nerves in any liposomal treatment group was less than 5%, despite a 16.5-fold increase in potency adjusted dose (based on free drug potency against *M. tuberculosis* Erdmann strain in Example 2) for Ls-AKG28 or Ls-AKG38 compared to linezolid.

Administration of Ls-AKG28 and Ls-AKG38 at doses ≥20 mg/kg resulted in a statistically significant decrease of platelet count (difference up to 20% compared to control group). No additional effects on the other hematological and blood biochemistry parameters were observed (TABLE 32, TABLE 33)

Administration of Ls-AKG28 by intravenous injection to male Sprague-Dawley rats once weekly for 8 weeks at doses ≥10 mg/kg/dose resulted in spleen, kidney, and liver microscopic findings (Table 36). The spleen had minimal to moderate macrophage vacuolation with basophilic granules and minimal to mild accumulation of basophilic material in rats given 20 or 40 mg/kg/dose. The kidneys of rats given 40 mg/kg/dose had minimal glomerular mesangial cell vacuolation. The liver had minimal centrilobular single cell necrosis and minimal to mild centrilobular hepatocellular degeneration at all doses.

TABLE 32

Impact of liposomal AKG-28 and AKG-38 on level of liver enzymes in blood following treatment for eight weekly doses in male Sprague Dawley rats.

| Group | ALT (U/L) | AST (U/L) |
|---|---|---|
| saline | 105.7 ± 23.0 | 52.2 ± 9.2 |
| Ls-AKG28 (10 mg/kg) | 89.5 ± 16.5 | 37.7 ± 9.4 |
| Ls-AKG28 (20 mg/kg) | 97.5 ± 20.3 | 38.0 ± 8.1 |
| Ls-AKG28 (40 mg/kg) | 98.5 ± 10.5 | 56.3 ± 16.8 |
| Ls-AKG38 (10 mg/kg) | 98.7 ± 14.0 | 38.8 ± 10.2 |
| Ls-AKG38 (20 mg/kg) | 92.0 ± 23.6 | 38.2 ± 8.1 |
| Ls-AKG38 (40 mg/kg) | 93.3 ± 9.4 | 45.8 ± 10.1 |

TABLE 33

Impact of liposomal AKG-28 and AKG-38 on blood cell counts and hematocrit (HCT) following treatment for eight weekly doses in male Sprague Dawley rats.

| Group | RBC ($10^6$/μl) | HCT (%) | WBC ($10^3$/μl) | PLT ($10^3$/μl) |
|---|---|---|---|---|
| saline | 52.2 ± 9.2 | 8.11 ± 0.48 | 9.92 ± 3.13 | 1234 ± 113 |
| Ls-AKG28 (10 mg/kg) | 37.7 ± 9.4 | 8.13 ± 0.26 | 9.26 ± 1.10 | 1143 ± 88 |
| Ls-AKG28 (20 mg/kg) | 38.0 ± 8.1 | 8.26 ± 0.35 | 8.83 ± 1.30 | 1089 ± 118 |
| Ls-AKG28 (40 mg/kg) | 56.3 ± 16.8 | 8.15 ± 0.34 | 8.79 ± 2.44 | 973 ± 66 |
| Ls-AKG38 (10 mg/kg) | 38.8 ± 10.2 | 7.74 ± 0.41 | 10.46 ± 1.62 | 1090 ± 50 |
| Ls-AKG38 (20 mg/kg) | 38.2 ± 8.1 | 7.90 ± 0.39 | 7.23 ± 1.18 | 1039 ± 75 |
| Ls-AKG38 (40 mg/kg) | 45.8 ± 10.1 | 7.65 ± 0.43 | 9.37 ± 3.56 | 984 ± 74 |

TABLE 34

Impact of liposomal AKG-28 and AKG-38 on nerve conductance following treatment for eight weekly doses in male Sprague Dawley rats.

| Group | Caudal NCV (m/sec) | Left Digital NCV (m/sec) | Left Tibial MAP (msec) |
|---|---|---|---|
| saline | 48.7 ± 2.7 | 31.5 ± 1.8 | 1.675 ± 0.099 |
| Ls-AKG28 (10 mg/kg) | 49.6 ± 1.9 | 32.6 ± 2.3 | 1.678 ± 0.092 |
| Ls-AKG28 (20 mg/kg) | 49.1 ± 2.3 | 32.3 ± 4.6 | 1.707 ± 0.124 |
| Ls-AKG28 (40 mg/kg) | 46.8 ± 3.4 | 33.9 ± 2.2 | 1.667 ± 0.078 |
| Ls-AKG38 (10 mg/kg) | 47.6 ± 1.8 | 32.7 ± 1.8 | 1.680 ± 0.055 |
| Ls-AKG38 (20 mg/kg) | 45.6 ± 2.6 | 32.9 ± 3.2 | 1.752 ± 0.084 |
| Ls-AKG38 (40 mg/kg) | 48.6 ± 4.8 | 31.0 ± 1.7 | 1.717 ± 0.153 |

TABLE 35

Impact of liposomal AKG-28 and AKG-38 on nerve functional observational battery following treatment for eight weekly doses in male Sprague Dawley rats.

| Group | Hindlind Splay (cm) | Hindlimb Grip Mean (g) | Forelimb Grip Mean (g) |
|---|---|---|---|
| saline | 11.10 ± 1.50 | 670.2 ± 68.9 | 1274.8 ± 132.9 |
| Ls-AKG28 (10 mg/kg) | 11.20 ± 2.00 | 715.9 ± 50.9 | 1335.2 ± 153.0 |
| Ls-AKG28 (20 mg/kg) | 12.20 ± 1.50 | 695.7 ± 125.9 | 1331.9 ± 117.1 |
| Ls-AKG28 (40 mg/kg) | 11.50 ± 1.60 | 709.9 ± 61.9 | 1140.2 ± 169.9 |

TABLE 35-continued

Impact of liposomal AKG-28 and AKG-38 on nerve functional observational battery following treatment for eight weekly doses in male Sprague Dawley rats.

| Group | Hindlind Splay (cm) | Hindlimb Grip Mean (g) | Forelimb Grip Mean (g) |
|---|---|---|---|
| Ls-AKG38 (10 mg/kg) | 12.10 ± 1.30 | 741.5 ± 92.9 | 1373.6 ± 107.2 |
| Ls-AKG38 (20 mg/kg) | 11.70 ± 2.70 | 740.9 ± 74.6 | 1281.6 ± 114.8 |
| Ls-AKG38 (40 mg/kg) | 11.40 ± 2.60 | 737.6 ± 75.7 | 1350.1 ± 147.7 |

TABLE 36

Summary of microscopic findings in tissues following treatment for eight weekly doses with liposomal AKG-28 and AKG-38 in male Sprague Dawley rats.

| | Group | | | | | | | |
|---|---|---|---|---|---|---|---|---|
| | 1 | 2 | 3 | 4 | 5 | 6 | 7 | 8 |
| | Test material | | | | | | | |
| | linezolid | Ls-AKG28 | | | | Ls-AKG38 | | |
| | Dose (mg/kg/dose) | | | | | | | |
| | 0 | 50 | 10 | 20 | 40 | 20 | 40 | 80 |
| | No. Animals per Group | | | | | | | |
| | 6 | 6 | 6 | 6 | 6 | 6 | 6 | 6 |
| Liver (No. Examined) | 6 | 6 | 6 | 6 | 6 | 6 | 6 | 6 |
| Degeneration, hepatocellular, centrilobular | (0)[a] | (0) | (1) | (3) | (6) | (1) | (4) | (6) |
| Minimal | 0 | 0 | 1 | 3 | 2 | 1 | 3 | 1 |
| Mild | 0 | 0 | 0 | 0 | 4 | 0 | 1 | 5 |
| Single cell necrosis, centrilobular | (0) | (2) | (3) | (4) | (6) | (4) | (5) | (6) |
| Minimal | 0 | 2 | 3 | 4 | 6 | 4 | 5 | 6 |
| Spleen (No. Examined) | 6 | 6 | 6 | 6 | 6 | 6 | 6 | 6 |
| Vacuolation, macrophages | (0) | (0) | (0) | (6) | (6) | (0) | (0) | (0) |
| Minimal | 0 | 0 | 0 | 1 | 0 | 0 | 0 | 0 |
| Mild | 0 | 0 | 0 | 2 | 0 | 0 | 0 | 0 |
| Moderate | 0 | 0 | 0 | 3 | 6 | 0 | 0 | 0 |
| Accumulation, basophilic material | (0) | (0) | (0) | (4) | (6) | (0) | (0) | (0) |
| Minimal | 0 | 0 | 0 | 1 | 0 | 0 | 0 | 0 |
| Mild | 0 | 0 | 0 | 3 | 6 | 0 | 0 | 0 |
| Kidney (No. Examined) | 6 | 6 | 6 | 6 | 6 | 6 | 6 | 6 |
| Vacuolation, mesangial cell, glomerular | (0) | (0) | (0) | (0) | (6) | (0) | (0) | (0) |
| Minimal | 0 | 0 | 0 | 0 | 6 | 0 | 0 | 0 |

[a]Numbers in parentheses represent the number of animals with the finding.

Administration of Ls-AKG38 at doses ≥20 mg/kg/dose resulted in liver microscopic findings of minimal centrilobular single cell necrosis and minimal to mild centrilobular hepatocellular degeneration at all doses.

In comparison, the Ls-AKG28 and Ls-AKG38 dosed rats had an increased incidence of liver single cell necrosis at all doses compared to linezolid dosed rats. The liver of Ls-AKG28 and Ls-AKG38 dosed rats had a similar incidence and severity of centrilobular hepatocellular degeneration at all doses. The Ls-AKG28 dosed rats also had vacuolated macrophages and basophilic material in the spleen at 20 or 40 mg/kg/dose and glomerular mesangial cell vacuolation in the kidneys at 40 mg/kg/dose.

In conclusion, administration of Ls-AKG28 by multiple intravenous injections over 8 weeks was well tolerated in rats at levels of 10, 20 and 40 mg/kg/dose. Administration of Ls-AKG38 by multiple intravenous injections over 8 weeks was well tolerated in rats at levels of 20, 40 and 80 mg/kg/dose. Example 2 showed that AKG-28 is 33-fold more potent, and AKG-38 17-fold more potent, in killing *M. tuberculosis* in vitro (Erdmann strain) than linezolid. Thus, when corrected for potency, the rats are showing no significant neuropathy (changes to nerve conductance velocity), elevation of liver enzymes, reduced red blood cell counts or hematocrit, or reductions in body weight at linezolid-equivalent doses of 1320-1336 mg/kg, which is 16.5-fold higher than the clinically relevant dose of 80 mg/kg for linezolid.

Example 45. Efficacy of Liposomal AKG-28 and AKG-38 in Combination with Bedaquiline and Pretomanid, or with Bedaquiline (B), Pretomanid (Pa), and Moxifloxacin (M) in Kramnik (C3HeB/FeJ Mouse Mode of Pulmonary *M. tuberculosis* Infection The C3HeB/FeJ (Kramnik) mouse infection model exhibits advanced, hypoxic, caseating granulomas in lungs after TB infection (Driver E., et al., Antimicrobial Agents and Chemotherapy, 2012, vol. 56, p. 3181-3195). The lung pathology observed in C3HeB/FeJ mice resembles more closely the heterogeneity in lesion pathology and bacterial populations as seen in TB patients and was used to evaluate the efficacy of liposomal AKG-28 and AKG-38 at moderate weekly doses of 50 and 90 mg/kg. Ls-AKG28 (Lot 275) and Ls-AKG38 (Lot 276) were prepared as described in Examples 22 and 23, respectively. The lung pathology in C3HeB/FeJ mice shows three different types of lesions that were classified as caseous necrotic lesions delineated by a collagen rim (Type I), fulminant neutrophilic alveolitis (Type II), and cellular lesions (Type III) (see Irwin et al. (2015) Dis Model Mech 8, 591-602). 8-10-week-old C3HeB/FeJ female mice were infected with LDA (Low Dose Aerosol infection). A Glas-Col Inhalation Exposure System was utilized to infect the mice with a target of ~50-75 bacilli/mouse (Erdman strain). Five mice per aerosol run were sacrificed day 1 post-infection to determine bacterial uptake.

At 8 weeks post-infection, 8 mice were sacrificed to determine bacterial load in the lungs and spleens at the start of therapy. Mice were weighed prior to sacrifice. Gross pathology observations of the lungs and spleens were made. Whole lungs and spleens were extracted and frozen at −80° C. Previously frozen tissues were recovered and homogenized in 1×PBS using a Precellys homogenizer. Lung and spleen homogenates were plated on 7H11 agar quad plates. Enumeration of CFU occurred after 3-5 weeks incubation at 37° C. in a dry-air incubator. Therapy was administered via oral gavage or intraperitoneal (i.p.) injection, starting 8 weeks post-infection and continuing for 4-6 consecutive weeks (M-F for gavage, once weekly for i.p. injection). Bedaquiline (B), Pretomanid (Pa), moxifloxacin (M), and linezolid (L) were given 5 days per week for 4 or 6 weeks in total, 200 μL/dose, by gavage. Bedaquiline (25 mg/kg) was dosed first, then pretomanid (100 mg/kg), given no less than one hour later. Moxifloxacin (100 mg/kg) or linezolid (100 mg/kg) were given 4 hours later than the pretomanid dose. The liposomal formulations were given once per week for 4 or 6 weeks in total.

Daily observations of the mice were made at the time of dosing and weights were taken at least once per week. The sacrifices occurred 2 weeks after the four or six week treatment had been completed. Eight mice per treatment group were weighed prior to sacrifice. Whole lungs and spleens were aseptically harvested for all treatment groups. Gross pathology observations of the lungs and spleens were diagrammed. Lungs were photographed for gross lesion analysis. Whole lungs and spleens were frozen at −80° C. Previously frozen tissues were recovered and homogenized in either 1×PBS or 10% Bovine Serum Albumin (BSA) in 1×PBS (to avoid drug carry-over, *see below for explanation) using a Precellys homogenizer. Lung and spleen homogenates were plated on 7H11 agar or charcoal containing 7H11 quad plates, after homogenization and serially diluted in 1×PBS or 10% BSA. Enumeration of CFU occurred after 5 weeks incubation at 37° C. in a dry-air incubator.

Addition of Ls-AKG28 to BPaM treatment resulted in a further 0.64 log 10 CFU reduction vs. BPaM in lungs, while BPaM+Ls-AKG38 treatment gave a further log 10 CFU reduction of 0.25 versus BPaM after 4 weeks of treatment. The substitution of either Ls-AKG28 or Ls-AKG38 for linezolid (L) in the NIX (BPaL) regimen resulted in improved efficacy over BPaL at six weeks of treatment. At 6 weeks of treatment, the substitution of Ls-AKG38 for linezolid in the BPaL regimen did significantly improve efficacy compared the BPaL treated group. Specifically, BPaL treatment for 6 weeks resulted in a 4.18 log 10 CFU reduction, with plates for one of 8 animals having no CFU. BPa+Ls-AKG28 treatment for 6 weeks resulted in a 4.68 log 10 CFU reduction, which was not a statistically significant difference from BPaL. BPa+Ls-AKG38 treatment for 6 weeks resulted in a 5.26 log 10 CFU reduction, with plates for 2 of 8 animals having no CFU. This was a statistically significant reduction vs. BPaL (p=0.04, Dunnett's test).

In the spleen at 6 weeks of treatment, substitution of either liposomal formulation for linezolid in the NIX regimen resulted in a slight improvement in lung efficacy relative to the BPaL treated group. Treatment for 6 weeks with the NIX regimen resulted in a 3.56 log 10 CFU reduction, with plates for 3 of 8 animals showing no CFU. Treatment for 6 weeks with BPa+Ls-AKG28 resulted in a 4.18 log 10 CFU reduction, with plates for 5 of 8 mice showing no CFU. Treatment for 6 weeks with BPa+Ls-AKG38 resulted in a 4.38 log 10 CFU reduction, with plates for 6 of 8 mice showing no CFU. CFU loads in the spleens of mice on 6 weeks of drug treatment were low and approaching the lower limit of detection of 0.66 log 10 CFU.

TABLE 37

| Lung Log CFU | | | |
|---|---|---|---|
| Treatment | Doses | 4 week (Log CFU) | 6 week (Log CFU) |
| Untreated | | 7.71 ± 0.65 | |
| BPaM | 25/100/100 mg/kg | 3.05 ± 0.31 | |
| BPaM + Ls-AKG28 | 25/100/100/50 mg/kg | 2.41 ± 0.37 | |
| BPaM + Ls-AKG38 | 25/100/100/90 mg/kg | 2.80 ± 0.57 | |
| BPaL | 25/100/100 mg/kg | | 2.83 ± 1.28 |
| BPa + Ls-AKG28 | 25/100/100/50 mg/kg | | 2.33 ± 0.95 |
| BPa + Ls-AKG38 | 25/100/100/90 mg/kg | | 1.75 ± 0.59* |

*2/8 mice had no measurable CFU; all mice were listed at the detection limit of 0.96 log CFU.

TABLE 38

| Spleen Log CFU | | | |
|---|---|---|---|
| Treatment | Doses | 4 week (Log CFU) | 6 week (Log CFU) |
| Untreated | | 5.36 ± 0.48 | |
| BPaM | 25/100/100 mg/kg | 2.07 ± 0.65 | |
| BPaM + Ls-AKG28 | 25/100/100/50 mg/kg | 1.15 ± 0.45 | |
| BPaM + Ls-AKG38 | 25/100/100/90 mg/kg | 1.85 ± 0.96 | |
| BPaL | 25/100/100 mg/kg | | 1.56 ± 0.82* |

TABLE 38-continued

| Spleen Log CFU | | | |
|---|---|---|---|
| Treatment | Doses | 4 week (Log CFU) | 6 week (Log CFU) |
| BPa + Ls-AKG28 | 25/100/100/50 mg/kg | | 0.94 ± 0.45** |
| BPa + Ls-AKG38 | 25/100/100/90 mg/kg | | 0.74 ± 0.23*** |

*3/8 mice had no measurable CFU

**5/8 mice had no measurable CFU;.

***6/8 mice had no measurable CFU; all mice were listed at the detection limit of 0.66 log CFU. all mice that had no measurable CFU were listed at the detection limit of 0.66 log CFU. This shows that Ls-AKG38 and Ls-AKG28 are more active than linezolid when combined with bedaquiline and pretomanid at a moderate and highly tolerable dose of both drug after only six weeks of treatment. As Example 42 and 43 show, both Ls-AKG28 and Ls-AKG38 can be safely dosed in this combination at doses at least twice as high as those used in this study. It also shows that when Ls-AKG28 is added to a regimen of BPaM there is a further decrease in CFU in both lungs and spleen at this same highly tolerable dose.

Example 46. Efficacy of Monotherapy with Liposomal AKG-28 in Balb/c Model of Pulmonary *Mycobacterium tuberculosis* Infection The schedule and dose dependent efficacy of Ls-AKG28 was determined in comparison to free linezolid at clinically relevant doses of 50 and 100 mg/kg in a chronic Balb/c model of tuberculosis. In the chronic Balb/c mouse model, the bacterial load in lungs reaches a steady state 4-5 weeks after *M. tuberculosis* infection (Lenaerts et al. (2005) AAC 49(6) 2294-2301). Ls-AKG28 (Lot 286) was prepared as described in Example 28. 6-8 week old Balb/c female mice were obtained from Jackson Laboratories, and the mice were infected with a LDA (Low Dose Aerosol infection), using the Glas-Col Inhalation Exposure System to infect the mice with ~50-100 bacilli/mouse of *M. tuberculosis* Erdman.

Mice (n=3) were sacrificed day 1 post-infection to determine bacterial uptake. Whole lungs were aseptically harvested in Precellys tubes (Bertin cat #KT03961-1-396.7) and homogenized in 4 ml of 1×PBS using a Precellys tissue homogenizer. Undiluted homogenate was transferred to two large 7H111 agar plates (150×15 mm) and the plates were incubated in sealed zip top bags at 37° C. in a dry-air incubator for at least 21 days until colonies could be enumerated. At Day 28 post-aerosol infection, mice (n=5) were sacrificed to determine bacterial load in the lungs and spleens at the start of therapy. Mice were weighed prior to sacrifice. Gross pathology observations of the lungs and spleens were made. Lungs (divided into left lobe and upper right [cranial] lobes)+accessory lobe) and spleens were aseptically harvested and frozen at −80° C. Lower right lung lobes [caudal] were collected in 4% paraformaldehyde (PFA) for histology. Previously frozen tissues were recovered and homogenized in 1×PBS using a Precellys homogenizer. Lung and spleen homogenates were plated on 7H11 agar quad plates. Enumeration of CFU occurs after 3-5 weeks incubation at 37° C. in a dry-air incubator.

Linezolid in 5% PEG-200 (Sigma P3015, lot MKBW3119V)/95% (0.5%) methylcellulose (Sigma M0430, lot 031M0051) was administered via oral gavage‡ (200 uL per mouse) is started day 28 post-aerosol infection (Mon) and continued for 2-8 weeks 5 of 7 days per week. Ls-AKG28 was administered by injection i.p, once or twice per week at doses of 50 or 100 mg/kg. The final sacrifice occurred 3 days following the last day of dosing for mice treated with drug for 2, 4 or 8 weeks. Mice were weighed prior to sacrifice. Gross pathology observations of the lungs and spleens were made. Lungs (divided into left lobe, upper right lobes+accessory lobe) and spleens were aseptically harvested and frozen at −80° C. Lower right lung lobes were collected in 4% PFA for histology. Previously frozen tissues were recovered and homogenized in 10% Bovine Serum Albumin (BSA) in 1×PBS to avoid drug carry-over. After homogenization, lung and spleen homogenates were serially diluted in 1×PBS and 10% BSA and then plated on 7H11 agar or charcoal containing 7H11 quad plates. Enumeration of CFU occurred after 3-5 weeks incubation at 37° C. in a dry-air incubator.

The reduction in Lung CFU counts is shown in TABLE 39 and in Spleen CFU counts in TABLE 40. Treatment with Ls-AKG28 at 50 mg/kg twice weekly or once weekly at 100 mg/kg results in a 1.5 Log 10 CFU reduction after only two weeks in the lungs, compared to less than 0.15 Log 10 CFU reduction for linezolid at 100 mg/kg (q1×5). This reduction was nearly 3 Log 10 CFU in the spleen at two weeks for Ls-AKG28. At eight weeks, all of the mice treated with Ls-AKG28 were completely sterile (or below the detection limit of 1.13 in lungs and 0.66 in spleen) at eight weeks compared to 2.45 log 10 CFU in lungs and 3.15 log 10 CFU in spleen for linezolid at the higher 100 mg/kg dose of linezolid. This monotherapy activity is surprising for an oxazolidinone in the absence of an active combination partner like bedaquiline, and a relatively short period of time in only eight weeks. For example, at eight weeks of treatment, linezolid monotherapy showed log 10 CFU counts in the 4-6 range for Balb/c and C3HeB/FeJ mice (Lanoix et al. (2015) Dis Models Mech. 8, 603-610), and activity remains modest even up to 1000 mg/kg/week at schedules ranging from 3-14 doses/week (Bigelow et al (2021) J Infec. Dis. 223(11) 1855-1864).

TABLE 39

| Lung Log CFU | | | | |
|---|---|---|---|---|
| Treatment | Dose, schedule | 2 week (Log CFU) | 4 week (Log CFU) | 8 week (Log CFU) |
| Untreated | | 5.71 ± 0.15 | 5.47 ± 0.19 | |
| Linezolid | 50 mg/kg, q1x5 | | 4.61 ± 0.31 | |
| | 100 mg/kg, q1x5 | 5.58 ± 0.10 | 4.17 ± 0.21 | 2.45 ± 0.37 |
| Ls-AKG28 | 50 mg/kg, | | 3.81 ± 0.33 | |
| Ls-AKG28 | 50 mg/kg, | 4.01 ± 0.20 | 2.30 ± 0.57 | |
| Ls-AKG28 | 100 mg/kg, | 4.09 ± 0.34 | 2.65 ± 0.70 | 1.13 ± 0.00* |

*6/6 mice had no measurable CFU; all mice were listed at the detection limit of 1.13 log CFU.

TABLE 40

| Spleen Log CFU | | | | |
|---|---|---|---|---|
| Treatment | Dose, schedule | 2 week (Log CFU) | 4 week (Log CFU) | 8 week (Log CFU) |
| Untreated | | 5.08 ± 0.31 | 4.77 ± 0.21 | |
| Linezolid | 50 mg/kg, q1x5 | | 4.32 ± 0.28 | |
| | 100 mg/kg, q1x5 | 4.53 ± 0.25 | 3.90 ± 0.28 | 3.15 ± 0.27 |
| Ls-AKG28 | 50 mg/kg, | | 1.74 ± 0.65 | |
| Ls-AKG28 | 50 mg/kg, | 1.71 ± 0.59 | 0.67 ± 0.02* | |
| Ls-AKG28 | 100 mg/kg, | 2.25 ± 0.82 | 1.07 ± 0.93** | 0.66 ± 0.00*** |

*4/5 mice had no measurable CFU

**1/6 mice had no measurable CFU;.

***6/6 mice had no measurable CFU; all mice were listed at the detection limit of 0.66 log CFU.

all mice that had no measurable CFU were listed at the detection limit of 0.66 log CFU.

Example 47. Efficacy of Liposomal AKG-38 in Rabbit Endocarditis Model of Methicillin-Resistant *Staphylococcus aureus* (MRSA)

*Staphylococcus aureus* infections, especially involving the endovascular system (e.g., IE; cardiac and hemodialysis device infections, etc) are prevalent, and are associated with unacceptably high morbidity, mortality and post-therapy relapse rates. This is particularly true when such infections are caused by multi-drug-resistant strains of MRSA. Moreover, even when MRSA strains have minimal inhibitory concentrations (MICs) for vancomycin (the "workhouse" anti-MRSA agent) within the accepted Clinical Standards Laboratory Institute (CLSI) "susceptible" range (i.e., ≤2 ug/ml), clinical outcomes remain suboptimal.

A prototypical high-inoculum endovascular biofilm MRSA infection model, left-sided aortic valve rabbit IE, was employed in female New Zealand white rabbits of six months of age and 2.2-2.5 kg. Rabbits underwent general anesthesia with an intramuscular injection of xylazine and ketamine. They then had their fur clipped over the right carotid artery to expose skin. The cut-down site over the right carotid artery was locally anesthetized with 1% lidocaine. A cut-down was then performed to expose the right carotid artery. This was isolated, proximally ligated, then cannulated retrograde with a polyethylene catheter, across the aortic valve into the left ventricle, where it was then tied in-place and left indwelling for the duration of the study. For left-sided IE at 48 h after catheter placement (to induce sterile aortic valve and ventricular vegetations), animals had IE induced by an IV challenge of ~$2\times10^5$ cfu of the MW2 strain. The MRSA strain MW-2 (USA 400—clonal complex [CC] 1) used: i) is clinically-derived; ii) is genome-sequenced; iii) represents a common hospital-acquired MRSA clonotypes; iv) is virulent in the experimental IE model; and v) is daptomycin (DAP)-susceptible in vitro. Infection spreads from the heart valve infected vegetations to kidneys and spleen.

Liposomal AKG-38 (Ls-AKG38) was given, in separate animal groups, either once (in combination therapy with DAP) or twice (once in combination therapy with DAP; then a second infusion at the time of the post-DAP treatment sacrifice in a "relapse group of animals" not receiving further DAP therapy) at a dose of 40 mg/kg/dose. Ls-AKG38 (Lot 292) was prepared as described in Example 29. The first Ls-AKG38 infusions will follow the first DAP iv dose by ~1 h. The DAP was given at a sublethal dose of 2 mg/kg daily for four days, either alone or in combination with Ls-AKG38.

Animals were humanely euthanized, and key target organs sterilely removed and quantitatively cultured (blood, cardiac vegetations; kidneys and spleen for left-sided IE) on either day 6 (DAP alone or DAP+single dose of Ls-AKG38) or day 12 (DAP+two doses of Ls-AKG38 on days 1 and 6). Quantitative target tissue cultures were performed by standard preparation of sterilely removed organs by weighing, homogenization, serial dilutions and plate cultures. Serial dilution of blood and quantitative cultures were performed similarly. Data for blood cultures and each target organ for the different treatment groups were calculated as mean and median $\log_{10}$ cfu/ml or $\log_{10}$ cfu/gm of tissue (±SD), respectively.

Preliminary data from a left ventricular endocarditis model of MRSA in rabbits is shown below in Table 41. Daptomycin alone or Daptomycin plus a single dose of Ls-AKG38 showed no significant efficacy on day 6 post inoculation. Surprisingly, a second injection of Ls-AKG38 resulted in remarkably efficacy on day 12, including sterilization in 4/5 rabbits in all five tissues, and a more than 6 Log reduction in CFU in multiple organs. This data suggests that endocarditis could effectively be treated with Ls-AKG38 following discontinuation of daily daptomycin.

TABLE 41

| | Vegetations | Kidneys | Spleen | Liver | Lungs |
|---|---|---|---|---|---|
| Control (4) | 7.45 ± 0.60 | 5.93 ± 0.54 | 5.71 ± 0.85 | 5.03 ± 0.51 | 4.73 ± 0.46 |
| Daptomycin | 8.13 ± 0.17 | 6.90 ± 0.61 | 7.43 ± 0.38 | 6.77± 0.90 | 6.37 ± 0.64 |
| Daptomycin (relapse) | 9.18 ± 0.22 | 8.11 ± 0.49 | 7.91 ± 0.54 | 7.65 ± 0.26 | 8.00 ± 0.66 |
| Daptomycin + Ls-AKG38 (1 dose) | 8.26 ± 0.66 | 6.70 ± 0.83 | 5.65 ± 0.61 | 5.75 ± 0.83 | 5.97 ± 0.77 |
| Daptomycin + Ls-AKG38 (2 doses) | 1.14 ± 0.97 (4/5 sterile) | 1.05 ± 0.69 (4/5 sterile) | 0.89 ± 0.08 (5/5 sterile) | 0.93 ± 0.46 (4/5 sterile) | 1.18 ± 0.61 (4/5 sterile) |

Example 48. Activity of AKG-28 and AKG-38 in Various Species of Nontuberculosis Mycobacteria In Vitro MIC testing was performed by microbroth dilution method (Obregon-Henao et al. (2015) Antimicrobial Agents Chemother 59, 6904-6912) using Mueller Hinton (MH) broth (Cation Adjusted) to the calcium and magnesium ion concentration recommended in the CLSI standard M7-A7 (Becton Dickinson). MIC testing also was performed using the microbroth dilution method using 7H9 broth (Sigma-Aldrich)(Shang et al. (2011) PLoS One 6, e24726; Chan et al. (2010) Am J Respir Cell Mol Biol 43, 287-393). The goal was to optimize the ability to detect more compounds with activity against NTMs by using different broths in our microbroth dilution method. NTMs were grown on 7H11 agar plates (Sigma-Aldrich) for 3-25 days at 35-37° C. in ambient air (depending on bacterial strain). The CFUs were taken from the agar plates and placed in either MH broth with 0.05% tween-80 and grown at 35-37° C. in ambient air until the optical density (OD) absorbance taken after 7 days of growth is an (OD) 0.08-0.1 (0.5 McFarland Standard). The bacterial cell suspensions were then confirmed by preparing them in saline, matching the (OD) 0.08-0.1 (0.5 McFarland Standard).

The broth (MH) 180 μl was added to the first column in the 96 well plates. Then 100 μl of the broth (MH) was added to the other columns in the 96 well plate. Compounds are made using 1.28 mg/mL in DMSO and used immediately for test range 64-0.062 μg/ml and 20 μl of compound added to the first column of wells and 100 μl serially diluted. Finally, 100 μl NTM cell suspension was added in all the wells except the media only control wells. QC agents specific for each organism 1) bacteria only negative control 2) media only negative control 3) or tedizolid positive drug control 4) optional *E. coli* control.

RGMs were assayed for ODs on day 3. After that, the plate is assayed by using the Resazurin Microtiter Assay Plate method as recommended by the Clinical and Laboratories Standards Institute (Brown-Elliott et al. (2012) Clin Microbiol Rev vol. 25(3), p. 545-582). Briefly, the method used the addition of resazurin (7-Hydroxy-3H-phenoxazin-3-one 10-oxide) to the MIC 96 well plate. Resazurin is a blue dye, itself weakly fluorescent until it is irreversibly reduced to the pink colored and highly red fluorescent resorufin. It was used as an oxidation-reduction indicator in bacterial cell viability MIC assays.

The results show the both AKG-28 and AKG-38 were generally more potent than tedizolid in a range of different NTM species and strains. This included in *M. avium, M. chelonae, M. abscessus* and *M. kansasii*. Only in *M. massiliense* was tedizolid more active in all three strains evaluated.

TABLE 42

| NTM Species | Strain | AKG-28 MIC (μg/mL) | AKG-38 MIC (μg/mL) | Tedizolid MIC (μg/mL) |
|---|---|---|---|---|
| *M. avium* sbsp. *avium* | 2285 S | 0.125 | 0.125 | 0.25 |
| *M. avium* sbsp. *avium* | 3993 | 0.125 | 0.125 | 0.25 |
| *M. avium* sbsp. *avium* | 2285 R | 0.06 | 0.06 | 0.25 |
| *M. chelonae* | 49 | 0.06 | 0.06 | 0.25 |
| *M. chelonae* | 69 | 0.5 | 0.5 | 2 |
| *M. chelonae* | 35752 | 0.125 | 0.06 | 0.125 |
| *M. abscessus* sbsp. *abscessus* | 21 | 0.25 | 0.06 | 0.5 |
| *M. abscessus* sbsp. *abscessus* | 1948 | 0.125 | 0.06 | 0.5 |
| *M. abscessus* sbsp. *abscessus* | 1513 | 32 | 32 | 4 |
| *M. massiliense* | CIP 108297 | 1 | 0.5 | 0.25 |
| *M. massiliense* | CRM0019 | 0.25 | 0.25 | 0.06 |
| *M. massiliense* | M154 | 0.25 | 0.25 | 0.06 |
| *M. kansasii* | 662 | >32 | >32 | >32 |
| *M. kansasii* | 824 | 0.125 | 0.06 | 0.25 |
| *M. kansasii* | 732 | 0.125 | 0.03 | 0.25 |
| *M. kansasii* | MK13D6 | 0.125 | 0.03 | 0.25 |
| *M. kansasii* | WT171017 | 0.125 | 0.03 | 0.125 |

Example 49. Activity of Selected Compounds Against Drug Resistant Strains of *Mycobacterium tuberculosis* In Vitro Compounds of the present disclosure showing activity against drug-susceptible strains of *M. tuberculosis* were further evaluated for activity against several multidrug resistant (MDR) clinical isolate strains M70, M28, M94, M14 (Cheng A. F., et al., 2004, Antimicrob. Agents Chemother. v. 48, p. 596-601) and TN5904 (Palanisamay G. S., et al., 2008, Tuberculosis (Edinb.) vol. 88 p. 295-306). These strains are characterized by the following resistance features:

TABLE 43

Drug resistance features of the *M. tuberculosis* MDR strains used in the study.

| Strain\Drug | STR | INH | RIF | EMB | PZA |
|---|---|---|---|---|---|
| M70 | R | R | R | S | R |
| M28 | S | R | R | R | R |
| M14 | R | R | S | S | R |
| M94 | R | R | S | S | S |
| TN5904 | R | R | R | S | R |

(Abbreviations: R-resistant; S-susceptible; STR-streptomycin, INH-isoniazid; RIF-rifampin, EMB-ethambutol, PZA-pyrazinamide.

MIC of the test compounds, including comparators/resistance controls (RIF, INH, STR, moxifloxacin (MOX), and Linezolid (LNZ)) was determined using broth microdilution method with an Alamar Blue endpoint (MABA) essentially as described in Example 2, with the following modifications. Test compounds and comparators serially diluted by the factor of two in DMSO were added to the wells of a 96-well assay plate containing 100 μL of ADC-supplemented 7H9-glycerol medium. The compounds were diluted in DMSO so as to keep the compound concentration in the desired range and the final DMSO concentration in the well at 2% (M70, M28, M94) or 2.5% (M14, TN5904), except that due to low solubility in DMSO, STR was serially diluted and added as aqueous solution. Bacterial stocks of MDR strains and of the susceptible H37Rv strain (positive control) were taken from the cold storage, thawed and diluted with 7H9-ADC-glycerol medium to provide for the bacterial density of $10^6$ CFU/mL (H37Rv, TN5904), $2\times10^6$ CFU/mL (M70, M14), or $3\times10^6$ CFU/mL (M28, M94), and 50 μL of the diluted bacterial stocks were added to the compound-containing medium in the wells. The ranges of final drug concentrations in the wells are shown in the Table below. The plates were sealed in Ziplock bags, incubated at 37° C., and monitored for the bacterial growth by periodic optical density reading at 600 nm (OD600). On Day 14 (if OD600 reached or exceeded 0.40) or Day 17 15 μL of Alamar Blue solution was added to the wells, the incubation was continued, and the color of the incubation mixtures was documented three days later (seven days in the case of slow growing M28 strain). The lowest consecutive antimicrobial concentration of the two-fold serial dilutions that did not produce visible color change with Alamar Blue relative to drug-free control wells, was regarded as the MIC for these compounds. The OD600-based MIC determination (≥80/a OD600 reduction relative to the drug-free control wells) was in agreement with the MABA results. A shift in MIC of two wells (4-fold) was considered significant. The results are summarized in TABLE 44 below.

TABLE 44

Minimum inhibitory concentrations (MIC) of various compounds in drug-susceptible and drug-resistant strains of *M. tuberculosis* in vitro (MABA assay).

| Compound | Concentration range, μg/mL | MIC, μg/mL in *M. tuberculosis* strain: H37Rv | M70 | M28 | M94 | M14 | TN5904 |
|---|---|---|---|---|---|---|---|
| RIF | 8-0.03 | 0.06 | >8 | >8 | 0.125 | 0.06 | >8 |
| INH | 2-0.008 | 0.06 | >2 | >2 | >2 | >2 | 2 |
| MOX | 8-0.03 | 0.125 | 1 | 2 | 0.125 | 0.125 | 0.125 |
| STR | 8-0.03 | 0.5 | 2 | 0.125 | >8 | >8 | 1 |
| LNZ | 8-0.03 | 2 | 0.5 | 0.5 | 0.5 | 0.5 | 1 |
| AKG-3 | 4-0.015 | 0.125 | ≤0.015 | 0.06 | 0.06 | 0.03 | 0.06 |
| AKG-16 | 8-0.03 | 0.25 | 0.125 | 0.25 | 0.06 | 0.06 | 0.06 |
| AKG-28 | 1-0.004 | 0.03 | ≤0.004 | 0.015 | 0.015 | 0.015 | 0.015 |
| AKG-29 | 8-0.03 | 0.25 | ≤0.03 | 0.125 | 0.125 | 0.06 | 0.06 |
| AKG-38 | 4-0.015 | 0.03 | ≤<0.015 | 0.03 | 0.03 | 0.03 | 0.03 |
| AKG-39 | 8-0.03 | 0.5 | 0.125 | 0.5 | 1 | 0.5 | 0.25 |

The comparator/control compounds RIF, IHN, MOX, and STR showed the expected in vitro activity against the DR-TB/MDR-TB strains as well as H37Rv. Within the margin of variance of typical MIC assays, all tested compounds of the present disclosure were at least as active against the MDR-TB strains as they were against drug-susceptible strain H37Rv. The highest activity was shown by AKG-28, followed by AKG-38 and AKG-3. Compounds AKG-28 and AKG-38 stood out as the most active ones compared even to their structurally close analogs.

Example 50. Analysis of Lipids and their Degradation Products in Liposomal Preparations The purpose of this example was to develop methods that could detect lipid oxidative degradation products (FIG. 17) and phospholipid hydrolysis products (FIG. 18). Lipid components of the liposomes (HSPC, Cholesterol, and PEG-DSPE), as well as their degradation products (17-hydroxycholesterol, 7-ketocholesterol, lyso-PC, stearic acid, and palmitic acid) were quantified in the liposome samples by HPLC using Thermo Scientific Vanquish Flex UHPLC equipped with Charged Aerosol Detector (CAD) and Thermo Scientific Accucore™ C18+UHPLC column (L=50 mm, D=2.1 mm, Particle Size=1.5 μm). The UHPLC operating conditions are listed in the following table (Table 45):

TABLE 45

| Chromatographic Conditions for analysis of lipids and their degradation products | |
|---|---|
| HPLC Instrument | Thermo Scientific Vanquish Flex UHPLC |
| HPLC Column | Accucore ™ Vanquish ™ C18+ UHPLC column |
| Column Temperature | 50° C. |
| Flow Rate | 0.5 mL/min |
| Injection Volume | 2 μL |
| Absorbance detection | 230 nm |
| CAD | 10 Hz |
| Run Time | 10 min |
| Sample Temperature | 21° C. |
| Sample Solvent | MeOH/THF (85:15) |
| Mobile Phase | Mobile Phase A: 5 mM ammonium acetate in water (pH 4)<br>Mobile Phase B: Methanol |

Mobile phase program:

| Time, min | Mobile Phase A, % | Mobile Phase A, % |
|---|---|---|
| −0.5 | 15 | 85 |
| 0 | 15 | 85 |
| 2 | 10 | 90 |
| 4 | 0 | 100 |
| 8 | 0 | 100 |
| 9 | 15 | 85 |
| 10 | 15 | 85 |

To identify the peaks of individual lipids and their degradation products, 5 mg/ml lipid standards were prepared by dissolving commercially obtained individual lipids in methanol/tetrahydrofuran solution (MeOH:THF=85:15 vol: vol) and stored at −20° C. prior to use. A calibration curve for each individual lipid and their degradation products was prepared from 5 mg/ml standard prior the HPLC run (TABLE 2). 5 μl of liposomal formulations were dissolved in 495 μl MeOH/THF (dilution factor=100) by vortex at high speed for 10 sec. Chromatograms were analyzed using Chromeleon™ 7.2.10 (Thermo Scientific).

Relative content of cholesterol oxidation products was calculated using formula:

$$D\ \% = 100 * C_D/(C_{Chol} + C_{D1} + C_{D2})$$

where $C_{D1,2}$=HPLC detected concentration of oxidation products, mg/ml $C_{chol}$=HPLC detected concentration of cholesterol, mg/ml Relative content of different phospholipid derivatives was calculated using formula:

$$D\ \% = 100 * C_D/(C_{HSPC} + C_{PEG-DSPE})$$

where $C_D$=HPLC detected concentration of a degradation product, mg/ml $C_{HSPC}$=HPLC detected concentration of HSPC, mg/ml $C_{PEG-DSPE}$=HPLC detected concentration of PEG-DSPE, mg/ml Characteristics of the analytes and calibration curves are summarized in the following table (Table 46):

TABLE 46

Analyte and calibration curve characteristics

| Channel | Component | Ret. Time, min | Cal. Type | Number of points | Concentration range, μg/ml | Coeff of Determination | C0 (Offset) | C1 (Slope) |
|---|---|---|---|---|---|---|---|---|
| CAD | lyso-PC | 1.05 | Lin, AddZero | 5 | 5-60 | 0.999 | 0.014 | 0.031 |
| CAD | Palmitic Acid | 1.23 | Lin, AddZero | 5 | 5-60 | 0.999 | 0.030 | 0.035 |
| CAD | 7-HO-Cholesterol | 1.81 | Lin, AddZero | 5 | 5-60 | 0.991 | 0.078 | 0.028 |
| CAD | Stearic Acid | 2.16 | Lin, AddZero | 5 | 5-60 | 0.993 | 0.071 | 0.038 |
| UV230 nm | 7-Ketocholesterol | 2.05 | Lin, AddZero | 5 | 5-60 | 0.999 | −0.057 | 0.116 |
| CAD | Cholesterol | 4.78 | Lin, AddZero | 5 | 25-400 | 0.990 | 0.620 | 0.027 |
| CAD | PEG-DSPE | 5.34 | Lin, AddZero | 5 | 25-300 | 0.993 | 0.416 | 0.036 |
| CAD | HSPC | 6.33 | Lin, AddZero | 5 | 50-600 | 0.996 | 0.593 | 0.029 |

*Note that closely positioned peaks of stearic acid and 7-ketocholesterol were resolved using 7-ketocholestrol-specific UV detection at 230 nm.

Example 51. Liposome Preparations (Lots Ls-293-to-Ls-302) with Elevated AKG-28 and AKG-38 Drug Loads (DL Ratio); Preparation, Properties, and Storage Stability The potential for loading of AKG-28 or AKG-38 at elevated drug-to-lipid ratios, and retain the high efficiency of loading was evaluated. HSPC, cholesterol and PEG-DSPE were combined at the mass ratio of 5:3:1 (molar ratio 45:54.9:2.62, based on molecular weights of HSPC, cholesterol and PEG-DSPE of 786, 386.7, and 2700, respectively)

on the scale of 2.5 g HSPC. $DiIC_{18}(3)$-DS was added at 0.15 mol % of HSPC as an ethanolic solution; the lipids were dissolved in ethanol, dispersed in 0.5 M ammonium sulfate solution at about 60 mM phospholipid and the final 9.1 vol % of ethanol, and extruded through polycarbonate membrane filters essentially as described in Example 30, to give extruded lot L-94. A portion of L-94 material (Xz 122.9 nm, PdI 0.018) was extruded through the stack of 2×80 nm pore size PCTE membrane filters to give extruded lot L-95 (Xz 102.6 nm, PdI 0.0193), and a portion of L-95 was further extruded 4 times though a stack of two 50-nm PCTE membrane filters to give extruded lot L-96 (Xz 80.1 nm, PdI 0.0378). The extruded liposomes were passed through a 0.2-μm syringe filter, and the extraliposomal ammonium sulfate was removed by TFF against water to residual conductivity of less than 200 μS/cm (5.7-8.3 volume exchanges). The phospholipid concentration in the post-TFF liposomes was determined by the blue phosphomolybdate method, and the aliquots of liposomes were incubated with AKG-38 (8 mg/ml) or AKG-28 (6 mg/ml) at the given drug-to lipid (DL0) ratios (see TABLE 3) in the presence of 45 mg/ml dextrose and, in the case of AKG 38, 10 mM NaCl, with stirring on a 65° C. water bath for 20 min, followed by chilling in ice-water. The liposomes were adjusted to 0.1 M NaCl, stored at 2-8° C. overnight, subjected to TFF buffer exchange/unencapsulated drug removal by TFF using polysulfone hollow fiber cartridges (MWCO 500 KDa) (7-8 volume exchanges (Vex)), concentrated by continuing diafiltration without the buffer feed, sterilized by filtration though a 0.2-μm PES syringe filter, and adjusted with the respective exchange/excipient buffer, HBS-7 or His-6.5 (10 mM Histidine-HCl in 0.144 M NaCl, pH 6.5) to the final drug concentration of 18 mg/ml AKG-38, or 10 mg/ml AKG-28. However, as observations indicated that the pH 6.5 was unfavorable for the stability of liposome lipids against degradation (Example 65), the samples containing His-6.5 were re-adjusted by addition of 1 M Hepes-Na (final 20 mM) to pH 7.41-7.52 (target pH 7.5) The liposomes had the following characteristics:

Surprisingly, both AKG-28 and AKG-38 were efficiently (>95%) loaded into the 100-nm and 80-nm extruded liposomes at the increased DL0 ratios of about 600 g AKG-38/mol PhL and about 330 g AKG-28/mol PhL, respectively.

Example 52. HPLC Analysis of AKG-28, AKG-38, and $DiIC_{18}(3)$-DS in the PK Plasma Samples A bioanalytical assay was developed for measuring both AKG-28 and AKG-38 drugs, as well as the lipophilic $DiIC_{18}(3)$-DS liposome tracer using HPLC. The pharmacokinetic properties of AKG-28 and AKG 38 liposomes was determined by measuring the drug and liposomal phospholipid in mouse plasma using HPLC. The drug concentration was measured directly, and the phospholipid concentration in plasma was determined using the non-exchangeable fluorescent lipid label $DiIC_{is}(3)$-DS (AAT Bioquest, Cat No. 22052). Drug and $DiIC_{18}(3)$-DS were extracted from mouse plasma using 0.1% trifluoroacetic acid in isopropanol at a ratio of 1:3 (v:v). The plasma was diluted with PBS when necessary. The plasma/0.1% trifluoroacetic acid in isopropanol mixture was vortexed at high speed for 20 s followed by centrifugation at 13.4 RCF for 10 min, and the supernatant was transferred to an HPLC autosampler vial and stored protected from light at 23° C. until analysis by HPLC no more than 24 h after extraction. Standards were prepared from the liposome test articles and extracted using the same procedure as was used for mouse plasma. Liposome test articles were analyzed for phospholipid using a blue phosphomolybdate spectrophotometric assay and served as reference standards for calibration of the $DiIC_{18}(3)$-DS peak vs. phospholipid concentration. HPLC analysis of AKG-28, AKG-38 and the fluorescent lipid label $DiIC_{18}(3)$-DS in mouse plasma was conducted on a Thermo Vanquish system using a C8 reverse phase column (Phenomenex Kinetex C18 column, 50 mm×4.6 mm inner diameter, particle size of 5 μm, with 100 Å pores, Cat. No 00B-4608-E0) preceded by a C8 guard column (Phenomenex SecurityGuard 4×3 mm inner diameter, Cat. No. AJ0-4290). A sample injection volume of 2 μl was used, and the column was eluted with a mobile phase consisting of: A) 0.01% trifluoroacetic acid, B) 0.01% trifluoroacetic acid in acetonitrile, and C) 0.01% trifluoroacetic acid in isopropanol, at a flow rate of 1.0 mL/min using the gradient elution program listed below.

TABLE 47

Liposomal AKG-38 and AKG-28 formulation characteristics at various D/L ratios.

| Lot ID | Drug | pH | Xz nm | PDI | D/L ratio, g/mol PhL Pre-load | Post-load | EE % | Drug conc-n, mg/ml | Volume, ml |
|---|---|---|---|---|---|---|---|---|---|
| Ls-293-7.0 | AKG-38 | 7.05 | 123.2 | 0.0089 | 451.1 | 439.8 ± 9.2 | 97.5 | 17.7 | 5.35 |
| Ls-293 | | 7.43 | 122.1 | 0.0342 | 451.1 | 442.0 ± 9.5 | 98.0 | 17.8 | 5.86 |
| Ls-294 | | 7.45 | 121.7 | 0.0144 | 600.8 | 584.2 ± 13.1 | 97.2 | 17.8 | 6.07 |
| Ls-295 | | 7.52 | 105.3 | 0.0302 | 450.9 | 441.0 ± 9.3 | 97.8 | 17.8 | 7.15 |
| Ls-296 | | 7.41 | 104.7 | 0.0503 | 602.3 | 574.6 ± 7.4 | 95.4 | 17.8 | 7.56 |
| Ls-297 | | 7.49 | 83.4 | 0.0876 | 452.2 | 440.7 ± 9.3 | 97.5 | 17.81 | 3.76 |
| Ls-298-7.0 | AKG-28 | 7.05 | 121.8 | 0.0535 | 250.5 | 256.6 ± 5.0 | 102.4 | 9.8 | 5.49 |
| Ls-298 | | 7.40 | 122.1 | 0.0257 | 250.5 | 249.8 ± 7.5 | 99.7 | 9.9 | 5.27 |
| Ls-299 | | 7.44 | 122.4 | 0.0120 | 327.0 | 326.0 ± 8.4 | 99.7 | 9.9 | 4.21 |
| Ls-300 | | 7.44 | 104.5 | 0.0362 | 249.0 | 245.7 ± 4.8 | 98.7 | 9.9 | 7.10 |
| Ls-301 | | 7.50 | 104.5 | 0.0255 | 330.5 | 326.1 ± 7.0 | 98.7 | 9.9 | 7.40 |
| Ls-302 | | 7.43 | 82.5 | 0.0578 | 286.8 | 267.6 ± 4.8 | 93.3 | 9.91 | 3.08 |

TABLE 48

| HPLC gradient elution protocol for drug and fluorescent lipid ($DiIC_{18}$(3)-DS) | | | |
|---|---|---|---|
| Minutes | % A | % B | % C |
| 0 | 95 | 5 | 0 |
| 3 | 71 | 29 | 0 |
| 8 | 0 | 29 | 71 |
| 10 | 0 | 29 | 71 |
| 11 | 95 | 5 | 0 |
| 15 | 95 | 5 | 0 |

AKG-28 and AKG-38 were detected by absorbance at 305 nm with a retention time of 2.7 and 3.6 min respectively and $DiIC_{18}$(3)-DS was detected by fluorescence using an excitation of 550 nm and emission of 570 nm with a retention time of 9.2 min.

Example 53. Blood Plasma Pharmacokinetics of Liposomes Ls-293-Ls-302 in Mice

The potential for new liposome formulations of AKG-28 and AKG-38 with high drug-to-lipid loading (Example 51) to retain long circulating pharmacokinetic properties in mice despite further exhaustion of the ammonium gradient was evaluated. Liposomes prepared according to Example 51 were injected i.v. into female CD-1 mice at the dose of 50 mg/kg AKG-38 liposomes or 30 mg/kg AKG-28 liposomes in duplicate. Blood was sampled into Li-heparinized Microvettes (Sarstedt) at 5 min (0.083 hour), 1, 3, 6, 24, and 48 hours post injection. centrifuged, and plasma was analyzed for AKG-28 by direct HPLC assay and liposome phospholipid by indirect ($DiIC_{18}$(3)-DS label) HPLC assay as described in Example 52. The results are in the tables below:

TABLE 49

Plasma pharmacokinetics of liposomal AKG-38, lots Ls-293-Ls-297 (Example 51) in CD-1 mice.

| | Lot ID | | | | | |
|---|---|---|---|---|---|---|
| Time, hours | Ls-293-7 | Ls-293 | Ls-294 | Ls-295 | Ls-296 | Ls-297 |
| | AKG-38, mg/ml | | | | | |
| 0.083 | 1.451 | 1.896 | 1.375 | 1.650 | 1.462 | 1.385 |
| 1 | 1.517 | 1.234 | 1.376 | 1.192 | 1.249 | 1.103 |
| 3 | 0.908 | 1.276 | 0.831 | 0.948 | 1.008 | 0.968 |
| 6 | 0.859 | 0.948 | 0.822 | 0.754 | 0.696 | 0.748 |
| 24 | 0.284 | 0.383 | 0.210 | 0.179 | 0.287 | 0.183 |
| 48 | 0.0360 | 0.0514 | 0.0224 | 0.0225 | 0.0108 | 0.0076 |
| $C_0$, mg/ml | 1.423 | 1.599 | 1.347 | 1.361 | 1.485 | 1.417 |
| k, 1/hr | 0.0750 | 0.0695 | 0.0839 | 0.0855 | 0.0963 | 0.1044 |
| $R^2$ | 0.9888 | 0.9836 | 0.9927 | 0.9955 | 0.9662 | 0.9856 |
| $T_{1/2}$, hr | 9.2 | 10.0 | 8.3 | 8.1 | 7.2 | 6.6 |
| | Lipid, μM PhL | | | | | |
| 0.083 | 3367.4 | 4473.9 | 2353.9 | 3738.4 | 2506.4 | 3141.9 |
| 1 | 3828.0 | 2871.4 | 2360.3 | 2831.7 | 2220.2 | 2469.7 |
| 3 | 2387.3 | 2987.5 | 1428.6 | 2290.0 | 1835.1 | 2234.1 |
| 6 | 2163.2 | 2348.6 | 1465.8 | 1838.9 | 1309.6 | 1975.2 |
| 24 | 1015.7 | 1294.7 | 509.0 | 673.8 | 755.7 | 766.9 |
| 48 | 216.6 | 345.8 | 83.3 | 220.4 | 69.2 | 163.0 |
| $C_0$, μM PhL | 3368.1 | 3550.5 | 2235.3 | 2940.4 | 2445.5 | 2844.5 |
| k, 1/hr | 0.05607 | 0.04757 | 0.06740 | 0.05581 | 0.06973 | 0.05870 |
| $R^2$ | 0.9826 | 0.9716 | 0.9879 | 0.9806 | 0.9619 | 0.9946 |
| $T_{1/2}$, hr | 12.4 | 14.6 | 10.3 | 12.4 | 9.9 | 11.8 |
| $T_{1/2}$, hr, drug release | 36.6 | 31.6 | 41.9 | 23.3 | 26.1 | 15.2 |

TABLE 50

Plasma pharmacokinetics of liposomal AKG-28, lots Ls-298-Ls-302 (Example 51) in CD-1 mice.

| | Lot ID | | | | | |
|---|---|---|---|---|---|---|
| Time, hours | Ls-298-7 | Ls-298 | Ls-299 | Ls-300 | Ls-301 | Ls-302 |
| | AKG-28, mg/ml | | | | | |
| 0.083 | 0.879 | 0.637 | 0.790 | 0.678 | 0.851 | 0.381 |
| 1 | 0.687 | 0.579 | 0.760 | 0.777 | 0.567 | 0.461 |
| 3 | 0.612 | 0.438 | 0.593 | 0.502 | 0.504 | 0.315 |
| 6 | 0.473 | 0.329 | 0.475 | 0.470 | 0.426 | 0.309 |
| 24 | 0.144 | 0.112 | 0.210 | 0.137 | 0.157 | 0.0891 |
| 48 | 0.0479 | 0.0280 | 0.0817 | 0.0262 | 0.0322 | 0.0034 |
| $C_0$, mg/ml | 0.733 | 0.561 | 0.715 | 0.708 | 0.673 | 0.425 |
| k, 1/hr | 0.0592 | 0.0637 | 0.0466 | 0.0687 | 0.0631 | 0.0646 |
| R^2 | 0.9847 | 0.9914 | 0.9857 | 0.9945 | 0.9877 | 0.9715 |
| $T_{1/2}$, hr | 11.7 | 10.9 | 14.9 | 10.1 | 11.0 | 10.7 |

TABLE 50-continued

Plasma pharmacokinetics of liposomal AKG-28, lots Ls-298-Ls-302 (Example 51) in CD-1 mice.

| Time, hours | Lot ID Ls-298-7 | Ls-298 | Ls-299 | Ls-300 | Ls-301 | Ls-302 |
|---|---|---|---|---|---|---|
| | Lipid, μM PhL | | | | | |
| 0.083 | 3480.0 | 2937.0 | 2794.1 | 3284.1 | 3234.1 | 1797.6 |
| 1 | 2696.5 | 2598.3 | 2505.9 | 3805.1 | 2159.8 | 1871.0 |
| 3 | 2335.4 | 1970.9 | 2067.8 | 2573.6 | 1910.8 | 1525.4 |
| 6 | 2061.6 | 1485.0 | 1631.3 | 2392.0 | 1418.1 | 1391.6 |
| 24 | 517.8 | 459.7 | 796.5 | 674.6 | 506.3 | 456.1 |
| 48 | 185.5 | 106.5 | 263.6 | 123.7 | 122.6 | 138.8 |
| $C_0$, μM PhL | 2914.8 | 2560.0 | 2493.5 | 3538.0 | 2446.5 | 1854.5 |
| k, 1/hr | 0.06032 | 0.06763 | 0.04728 | 0.06970 | 0.06343 | 0.05482 |
| $R^2$ | 0.9800 | 0.9924 | 0.9904 | 0.9957 | 0.9837 | 0.9970 |
| $T_{1/2}$, hr | 11.5 | 10.2 | 14.7 | 9.9 | 10.9 | 12.6 |
| $T_{1/2}$, hr, drug release | ND | ND | ND | ND | ND | 70.7 |

ND—not detectable.

The concentration data were fit to a monoexponential equation using Excel spreadsheet LOGEST function. Drug release half-lives were calculated by the formula:

$$T_{1/2\,release} = T_{1/2\,drug} * T_{1/2\,lipid}/(T_{1/2\,lipid} - T_{1/2\,drug})$$

The blood levels for both drug and lipid component of the liposomes fit well to a monoexponential (single compartment) model as expected for the long-circulating liposomes with relatively strong drug retention in vivo. For both drugs, plasma half-life the lipid matrix was in the range of 9.9-14.7 hours. Drug release half-time for AKG-38 liposomes was noticeably lower than for AKG-28, likely due to the divalent character of AKG-28 ionic interactions with the trapping agent counterion (sulphate) inside the liposomes, as opposed to AKG-38 that forms a monovalent cation. In fact, the rate of in vivo drug release of AKG-38 from the liposomes of about 100 nm or about 120 nm at both lower (about 250 g/mol PhL) and higher (about 330 g/mol PhL) drug/lipid ratio was too slow to be reliably determined in our experimental setting. For AKG-38, drug release half-life was higher in the formulations with larger liposome size, and in the formulations with lower DL ratio (~450 vs. ~600 g/mol PhL), however the difference was less prominent in the liposomes with average size (Xz) of around 120 nm. Liposomes of the smaller size (around 80 nm) showed markedly increased drug release rate in vivo. Contrary to expectations, the liposomes with higher DL ratios, about 600 g/mol P for AKG-38 and about 330 g/mol P for AKG-28, in the liposome average size (Xz) range of about 100-125 nm showed blood PK characteristics very close to that of the liposomes with the lower DL ratios of about 450 g/mol PhL (AKG-38) and about 250 d/mol PhL (AKG-28).

Example 54. Preparation and Properties of AKG-28 Liposomes at Various Drug Loading and Post-Loading Processing Conditions In this Example, we evaluated different strategies for reducing the phospholipid degradation by altering the drug loading or post-loading processing steps. Extruded liposomes of HSPC, Cholesterol (Chol), and PEG-DSPE (45:55:2.25 molar ratio) (extruded lot L-97, Xz 117.3 nm, PDI 0.0453) were prepared on the scale of 3 mmol HSPC essentially as described in Example 30, except the amount of $DiIC_{18}(3)$-DS was 0.05 mol % relative to HSPC (Lot L-97). The extruded liposomes were passed through 0.2-μm syringe filter, and extraliposomal ammonium sulfate was removed by TFF against water to residual conductivity of 115 μS/cm (6.0 volume exchanges). The phospholipid concentration in the post-TFF liposomes was determined by the blue phosphomolybdate method, the aliquots of liposomes were mixed with 20 mg/ml aqueous stock solution of AKG-28 (pH 5.14) at DL0 ratio of 250 g/mol PhL in the presence of dextrose, incubated with stirring on a 65° C. water bath for 20 min, followed by chilling in ice-water, and processed further, under the following conditions (LM means drug-liposome loading mixture):

- Lot Ls-307-1-A: LM, 6 mg/ml drug, 45 mg/ml dextrose, post-loading NaCl addition 0.1 M, TFF buffer exchange (as per Example 2A): 20 mM Hepes-Na, 144 mM NaCl buffer pH 7.5 (HBS-20-7.5) (10 Vex);
- Ls-307-1-B: same as Ls-307-1-A, except the exchange/excipient buffer was 10 mM Na-phosphate, 144 mM NaCl, pH 7.5 (PBS-10-7.5);
- Ls-307-1-C; same as Ls-307-1-A, except the exchange/excipient buffer was 10 mM Hepes-Na, 144 mM NaCl, pH 7.0 (HBS-7);
- Ls-307-2: LM, 6 mg/ml drug, 45 mg/ml dextrose, no post-loading NaCl addition, no post-loading buffer exchange, 1M Hepes-Na added to the final 20 mM Hepes, pH 7.5.
- Ls-308: same as Ls-307-1-A, except 1 M Hepes-Na (pH 7.63, produces pH 7.50 at 20 mM dilution) was added to the LM 5 mi before the end of 65° C. incubation.
- Ls-309: same as Ls-307-1-C, except LM contained 3 mg/ml drug and 140 mg/mi dextrose.
- Ls-310: same as Ls-309, except LM contained 5.4 mg/mi of the drug.

The liposomes were concentrated by diafiltration to approximately 8 mg/m of the drug and sterile-filtered (0.2-um PES) into sterile glass borosilicate vials with round stoppers (Gerresheimer). The drug concentration (by UV spectrophotometry), liposome particle size, and pH were determined as described herein, and the liposomes were incubated at 37° C. for two weeks. The lipid integrity and degradation products were quantified by HPLC (see Example 50). The results are in the following table:

TABLE 51

Liposomal AKG-28 formulation characteristics (Ls-307 to Ls-310) and 2-week stability

| Lot ID | DL ratio g/mol PhL | EE, % | AKG-28 mg/ml | Liposome size Xz nm | Liposome size PDI | Pre-incubation pH | Pre-incubation Lipid degradation, % Chol | Pre-incubation Lipid degradation, % HSPC | 2 weeks at 37° C. pH | 2 weeks at 37° C. Lipid degradation, % Chol | 2 weeks at 37° C. Lipid degradation, % HSPC |
|---|---|---|---|---|---|---|---|---|---|---|---|
| Ls-307-1-A | 245.0 | 97.3 | 7.95 | 119.1 | 0.0050 | 7.48 | 0.00 | 0.00 | 7.40 | 0.33 | 0.38 |
| Ls-307-1-B | 245.6 | 97.6 | 8.15 | 117.6 | 0.0152 | 7.36 | 0.00 | 0.04 | 7.16 | 0.00 | 0.82 |
| Ls-307-1-C | 244.0 | 96.9 | 7.87 | 119.2 | 0.0163 | 6.92 | 0.00 | 0.22 | 6.46 | 56.55 | 3.91 |
| Ls-307-2 | 245.5 | 97.3 | 8.00 | 119.1 | 0.0418 | 7.46 | 0.00 | 0.00 | 6.63 | 45.93 | 0 |
| Ls-308 | 240.5 | 97.4 | 8.03 | 119.2 | 0.0198 | 7.48 | 0.00 | 0.00 | 7.34 | 8.17 | 0.96 |
| Ls-309 | 247.2 | 97.7 | 8.66 | 116.2 | 0.0316 | 6.89 | 0.00 | 0.39 | 6.36 | 57.02 | 5.13 |
| Ls-310 | 245.5 | 97.1 | 8.59 | 119.7 | 0.0083 | 6.93 | 0.00 | 0.18 | 6.32 | 60.63 | 2.75 |

EE—encapsulation efficiency.

Under the accelerated stability study conditions (37° C., Arrhenius factor to 4° C. is 9.85) considerable degradation of the lipids was detected in the samples at pH 7.0 or lower, and in unpurified, buffered LM (lot L-307-2). Cholesterol degradation products were identified by peak elution times on HPLC and by UV spectroscopy as 7-hydroxycholesterol and 7-ketocholesterol; HSPC degradation products included lyso-PC, stearic acid, and palmitic acid. Surprisingly, however, in the unpurified, buffered LM, without the buffer exchange step, despite high degradation of cholesterol, degradation of HSPC was undetectable.

Example 55. Preparation and Properties of AKG-38 Liposomes at Various Drug Loading and Post-Loading Processing Conditions Different drug loading and processing steps were evaluated for the potential of reducing phospholipid degradation during storage. Extruded liposomes were prepared, purified of extraliposomal trapping agent, and analyzed as in Example 54. Aliquots of the liposomes were mixed with 20 mg/ml aqueous stock solution of AKG-38 (pH 4.99) at DL0 ratio of 450 g/mol PhL in the presence of dextrose, incubated with stirring on a 65° C. water bath for 20 min, followed by chilling in ice-water, and processed further, under the following conditions (LM means drug-liposome loading mixture):

Lot Ls-303-1-A: LM, 8 mg/ml drug, 45 mg/ml dextrose, post-loading NaCl addition 0.1 M, TFF buffer exchange (as per Example 51): 20 mM Hepes-Na, 144 mM NaCl buffer pH 7.5 (HBS-20-7.5) (10 Vex);

Ls-303-1-B: same as Ls-307-1-A, except the exchange/excipient buffer was 10 mM Na-phosphate, 144 mM NaCl, pH 7.5 (PBS-10-7.5);

Ls-303-1-C; same as Ls-307-1-A, except the exchange/excipient buffer was 10 mM Hepes-Na, 144 mM NaCl, pH 7.0 (HBS-7);

Ls-303-2: LM, 8 mg/ml drug, 45 mg/ml dextrose, no post-loading NaCl addition, no post-loading buffer exchange, 1M Hepes-Na added to the final 20 mM Hepes, pH 7.5.

Ls-304: same as Ls-307-1-A, except 1 M Hepes-Na (pH 7.63, produces pH 7.50 at 20 mM dilution) was added to the LM 5 min before the end of 65° C. incubation.

Ls-305: same as Ls-307-1-C, except LM contained 3 mg/ml drug and 140 mg/ml dextrose.

Ls-306: same as Ls-309, except LM contained 7.4 mg/ml of the drug.

The liposomes were concentrated by diafiltration to approximately 15 mg/ml of the drug and sterile-filtered (0.2-um PES) into sterile glass borosilicate vials with round stoppers (Gerresheimer). The drug concentration (by UV spectrophotometry), liposome particle size, and pH were determined as described herein, and the liposomes were incubated at 37° C. for two weeks. The lipid integrity and degradation products were quantified by HPLC (see Example 50). The results are in the following table:

TABLE 52

Liposomal AKG-38 formulation characteristics (Ls-303 to Ls-306) and 2-week stability

| Lot ID | DL ratio g/mol PhL | EE, % | AKG-38 mg/ml | Liposome size Xz nm | Liposome size PDI | Pre-incubation pH | Pre-incubation Lipid degradation, % Chol | Pre-incubation Lipid degradation, % HSPC | 2 weeks at 37° C. pH | 2 weeks at 37° C. Lipid degradation, % Chol | 2 weeks at 37° C. Lipid degradation, % HSPC |
|---|---|---|---|---|---|---|---|---|---|---|---|
| Ls-303-1-A | 442.6 | 96.4 | 15.63 | 118.5 | 0.0309 | 7.49 | 0.00 | 0.00 | 7.40 | 0.00 | 0.81 |
| Ls-303-1-B | 445.9 | 97.1 | 15.30 | 117.8 | 0.0092 | 7.32 | 0.00 | 0.00 | 7.15 | 0.00 | 1.46 |
| Ls-303-1-C | 452.6 | 98.5 | 15.10 | 120.2 | 0.0185 | 6.90 | 0.00 | 0.67 | 6.64 | 0.00 | 8.76 |
| Ls-303-2 | 455.3 | 100.5 | 15.00 | 117.9 | 0.0443 | 7.39 | 0.00 | 0.00 | 7.33 | 20.11 | 0 |
| Ls-304 | 438.2 | 95.8 | 15.40 | 118.5 | 0.0065 | 7.47 | 0.00 | 0.00 | 7.38 | 0.00 | 2.29 |
| Ls-305 | 449.8 | 99.5 | 14.91 | 116.9 | 0.0308 | 6.85 | 0.00 | 5.00 | 6.50 | 0.00 | 10.22 |
| Ls-306 | 459.9 | 100.6 | 15.02 | 120.2 | 0.0246 | 6.88 | 0.00 | 1.90 | 6.63 | 0.00 | 6.66 |

Degradation of the liposome lipids was detectable after 2-week storage at 37° C. (accelerated stability study), although at a lower rate compared with similarly prepared AKG-28 liposomes (Example 54). Significant degradation of cholesterol was observed in one of the liposome lots; however, unexpectedly, degradation of HSPC in the same lot (drug-loaded liposomes without post-loading buffer exchange) was the lowest.

Example 56. AKG-28 and AKG-38 Liposomes with Increased DL Ratio: Preparation, Lipid Stability and Cholesterol Stabilization with a Chelator In this Example, the potential for reducing observed cholesterol oxidation degradation products during storage using heavy metal chelators was evaluated. Extruded liposomes of HSPC, Cholesterol (Chol), and PEG-DSPE (45:55:2.25 molar ratio)(extruded lot L-99, Xz 117.9 nm, PdI 0.0078) were prepared as in Example 54 on the scale of 5.9 mmol HSPC. The extruded liposomes were passed through 0.2-μm syringe filter, and the extraliposomal ammonium sulfate was removed by TFF against water to residual conductivity of 138 μS/cm (6.1 volume exchanges). The phospholipid concentration in the post-TFF liposomes was determined by the blue phosphomolybdate method, and the aliquots of liposomes were incubated with AKG-38 (8 mg/ml) or AKG-28 (6 mg/ml) at the given drug-to lipid (DL0) ratio (see Table 53 below) in the presence of 45 mg/ml dextrose and, in the case of AKG 38, 10 mM NaCl, with stirring on a 65° C. water bath for 20 min, followed by chilling in ice-water. The liposomes were adjusted to 0.1 M NaCl, stored at 2-8° C. overnight, and each lot was divided into 6 portions. To portions 3 and 6, a chelator, 100 mM deferoxamine mesylate (Desferal, DFO) was added to a final concentration of 1 mM, and all portions were subjected to TFF buffer exchange/unencapsulated drug removal by TFF on a polysulfone hollow fiber cartridge (MWCO 500 KDa) (8-11.2 volume exchanges (Vex)), using either HBS-20-7.5 (portions 1-3) or PBS-20-7.5 (20 mM Na-phosphate, 144 mM NaCl, pH 7.5; portions 4-6) buffer. TFF-purified liposomes were concentrated by continuing diafiltration without the buffer feed, sterilized by filtration though a 0.2-μm PES syringe filter, and adjusted with the respective exchange/excipient buffer to the drug concentration of 15 mg/ml AKG-38 or 8 mg/ml AKG-28. To portions 3 and 6, sterile 100 mM DFO stock was added to the final 0.1 mM DFO, and to portions 2 and 4, DFO stock was added to the final 0.5 mM DFO. The drug concentration (by UV spectrophotometry), liposome particle size, and pH were determined as described herein. Phospholipid concentration in Hepes-buffered samples was determined by blue phosphomolybdate (Mo) assay, and in the phosphate-buffered samples by the fluorometry of the $DiIC_{18}(3)$-DS lipid label in 70% acidified isopropanol, using Mo-assayed Hepes-buffered samples as standards. The liposomes were aseptically aliquoted into sterile glass borosilicate vials with sterile round stoppers (Gerresheimer), and the vials were incubated at 37° C. At 1, 2, and 3 months of incubation, the liposomes were sampled and analyzed for pH, particle size, and for the drug and lipid degradation. The lipid and drug degradation products were identified and quantified by HPLC as described in Example 50. The following results were obtained:

TABLE 53

Impact of pH, DL0, and DFO on the pH and lipid degradation of AKG-38 liposomes

| AKG-38 liposomes | | | | | | | 1 month | | |
|---|---|---|---|---|---|---|---|---|---|
| Lot ID | DL0 ratio | DL encapsulated | DFO in LM | Excipient buffer | | Initial | | Lipid degradation, % | |
| Ls-. . . | g/mol P | g/mol P | post load | Buffer | DFO | pH | pH | Chol | HSPC |
| 311-1 | 450 | 450.6 ± 3.1 | None | HBS-20-7.5 | None | 7.49 | 7.25 | 19.86 | 6.39 |
| 311-2 | 450 | 452.4 ± 5.2 | None | HBS-20-7.5 | 0.5 mM | 7.46 | 7.28 | 0 | 5.76 |
| 311-3 | 450 | 456.6 ± 3.1 | 1 mM | HBS-20-7.5 | 0.1 mM | 7.47 | 7.30 | 0 | 5.28 |
| 311-4 | 450 | 451.8 ± 6.3 | None | PBS-20-7.5 | None | 7.39 | 7.15 | 0 | 6.09 |
| 311-5 | 450 | 453.5 ± 9.9 | None | PBS-20-7.5 | 0.5 mM | 7.39 | 7.13 | 0 | 5.61 |
| 311-6 | 450 | 447.9 ± 9.6 | 1 mM | PBS-20-7.5 | 0.1 mM | 7.39 | 7.13 | 0 | 7.08 |
| 312-1 | 600 | 599.9 ± 5.6 | None | HBS-20-7.5 | None | 7.47 | 6.59 | 48.49 | 5.10 |
| 312-2 | 600 | 601.4 ± 6.3 | None | HBS-20-7.5 | 0.5 mM | 7.48 | 7.01 | 0 | 11.72 |
| 312-3 | 600 | 587.6 ± 6.3 | 1 mM | HBS-20-7.5 | 0.1 mM | 7.44 | 7.37 | 0 | 3.17 |
| 312-4 | 600 | 613.3 ± 14.0 | None | PBS-20-7.5 | None | 7.40 | 7.26 | 0 | 5.32 |
| 312-5 | 600 | 613.3 ± 16.2 | None | PBS-20-7.5 | 0.5 mM | 7.36 | 7.25 | 0 | 3.67 |
| 312-6 | 600 | 606.0 ± 13.3 | 1 mM | PBS-20-7.5 | 0.1 mM | 7.44 | 7.25 | 0 | 4.00 |

| AKG-38 liposomes | | 2 months | | | 3 months | | |
|---|---|---|---|---|---|---|---|
| Lot ID | DL0 ratio | | Lipid degradation, % | | | Lipid degradation, % | |
| Ls-. . . | g/mol P | pH | Chol | HSPC | pH | Chol | HSPC |
| 311-1 | 450 | 7.15 | 34.43 | 5.2 | 6.90 | 40.59 | 10.75 |
| 311-2 | 450 | 7.25 | 0 | 8.85 | 7.12 | 0 | 13.51 |
| 311-3 | 450 | 7.27 | 0 | 9.42 | 7.19 | 0 | 15.29 |
| 311-4 | 450 | 7.01 | 30.43 | 9.92 | 6.84 | 33.21 | 18.6 |
| 311-5 | 450 | 7.07 | 0 | 8.63 | 6.94 | 0 | 13.87 |
| 311-6 | 450 | 7.11 | 0 | 9.54 | 7.00 | 0 | 14.96 |
| 312-1 | 600 | 6.52 | 50.43 | 4.77 | 6.41 | 49.90 | 11.19 |
| 312-2 | 600 | nd | nd | nd | nd | nd | nd |
| 312-3 | 600 | 7.31 | 0 | 7.92 | 7.25 | 0 | 15.23 |
| 312-4 | 600 | 7.16 | 29.13 | 8.79 | 6.87 | 43.04 | 21.79 |
| 312-5 | 600 | 7.20 | 0 | 6.96 | 7.10 | 0 | 13.25 |
| 312-6 | 600 | 7.20 | 0 | 7.91 | 7.13 | 0 | 15.51 |

TABLE 54

Impact of pH, DL0, and DFO on the pH and lipid degradation of AKG-28 liposomes

| AKG-28 liposomes | | | | | | | 1 month | | |
|---|---|---|---|---|---|---|---|---|---|
| Lot ID | target DL0 | DL encapsulated | DFO in LM | Excipient buffer | | Initial | | Lipid degradation, % | |
| Ls- . . . | g/mol P | g/mol P | post load | Buffer | DFO | pH | pH | Chol | HSPC |
| 313-1 | 250 | 257.5 ± 3.4 | None | HBS-20-7.5 | None | 7.50 | 7.20 | 41.09 | 2.46 |
| 313-2 | 250 | 257.4 ± 2.7 | None | HBS-20-7.5 | 0.5 mM | 7.50 | 7.34 | 0 | 3.91 |
| 313-3 | 250 | 258.8 ± 2.9 | 1 mM | HBS-20-7.5 | 0.1 mM | 7.50 | 7.34 | 0 | 4.17 |
| 313-4 | 250 | 257.1 ± 6.2 | None | PBS-20-7.5 | None | 7.50 | 7.01 | 42.12 | 2.24 |
| 313-5 | 250 | 261.8 ± 5.7 | None | PBS-20-7.5 | 0.5 mM | 7.41 | 7.14 | 0 | 4.50 |
| 313-6 | 250 | 261.1 ± 6.0 | 1 mM | PBS-20-7.5 | 0.1 mM | 7.40 | 7.14 | 0 | 5.23 |
| 314-1 | 330 | 338.3 ± 4.8 | None | HBS-20-7.5 | None | 7.48 | 6.99 | 52.12 | 3.53 |
| 314-2 | 330 | 337.9 ± 6.4 | None | HBS-20-7.5 | 0.5 mM | 7.48 | 7.25 | 0 | 7.25 |
| 314-3 | 330 | 341.4 ± 3.7 | 1 mM | HBS-20-7.5 | 0.1 mM | 7.48 | 7.36 | 0 | 2.28 |
| 314-4 | 330 | 350.2 ± 21.1 | None | PBS-20-7.5 | None | 7.41 | 7.12 | 40.92 | 2.18 |
| 314-5 | 330 | 350.1 ± 21.1 | None | PBS-20-7.5 | 0.5 mM | 7.41 | 7.24 | 0 | 2.00 |
| 314-6 | 330 | 346.2 ± 22.8 | 1 mM | PBS-20-7.5 | 0.1 mM | 7.41 | 7.25 | 0 | 3.43 |

| AKG-28 liposomes | | 2 months | | | 3 months | | |
|---|---|---|---|---|---|---|---|
| Lot ID | target DL0 | | Lipid degradation, % | | | Lipid degradation, % | |
| Ls- . . . | g/mol P | pH | Chol | HSPC | pH | Chol | HSPC |
| 313-1 | 250 | 7.17 | 39.26 | 3.40 | 7.07 | 39.42 | 3.57 |
| 313-2 | 250 | 7.27 | 0 | 4.85 | 7.21 | 0 | 8.52 |
| 313-3 | 250 | 7.27 | 0 | 6.66 | 7.20 | 0 | 11.78 |
| 313-4 | 250 | 7.02 | 34.60 | 3.22 | 6.83 | 38.81 | 3.31 |
| 313-5 | 250 | 7.07 | 0 | 6.85 | 6.97 | 0 | 11.30 |
| 313-6 | 250 | 7.10 | 0 | 7.89 | 7.02 | 0 | 13.35 |
| 314-1 | 330 | nd | nd | nd | nd | nd | nd |
| 314-2 | 330 | nd | nd | nd | nd | nd | nd |
| 314-3 | 330 | 7.33 | 0 | 5.93 | 7.28 | 6.98 | 10.07 |
| 314-4 | 330 | 7.00 | 46.96 | 3.36 | 6.80 | 50.87 | 4.48 |
| 314-5 | 330 | 7.14 | 0 | 5.94 | 7.06 | 0 | 9.35 |
| 314-6 | 330 | 7.15 | 0 | 7.84 | 7.06 | 0 | 13.42 |

Initial levels of lipid degradation products were undetectable. The appearance of cholesterol degradation products, 7-hydroxy- and 7-ketocholesterol, suggested the oxidative degradation, while HSPC degradation proceeded hydrolytically at the ester bond(s). Addition of a chelator deferoxamine to the liposome excipient buffer completely prevented degradation of cholesterol, even at 3 months 37° C. storage (equivalent to about 29 months of refrigerated storage at 4° C.). Although DFO is known to inhibit metal-catalyzed oxidation of unsaturated fatty acids, this extraordinary capacity of DFO to inhibit oxidative degradation of cholesterol in the liposomes containing AKG-28 and AKG-38 oxazolidinone drugs was surprising. Oxidative degradation of cholesterol is not a frequent observation in pharmaceutical liposomes loaded with weakly basic lipophilic drugs. As the cholesterol degradation has not been observed in the liposomes of identical composition but lacking the drug, we hypothesize, without being bound by the theory, that the degradation is likely related to the catalysis of cholesterol oxidation by these encapsulated drugs, alone or in a complex with traces of heavy metals commonly present in pharmaceutical formulations and excipients. This stabilizing effect of DFO was observed equally in the liposomal preparations buffered with Hepes or phosphate. Also, the high encapsulation efficiency of the liposomes with increased DL0 ratios (AKG-28, 330 g/mol PhL, AKG-38, 600 g/mol PhL) was high, and effectively quantitative, despite the higher concentration of drug initially added to the preparation.

Example 57. Addition of Chelators to Drug Stocks Prior to Loading does not Protect Against Lipid Degradation in Liposomal Formulations of AKG-28 (Ls 315-318) and AKG-38 (Ls 319-322)

The potential for reducing cholesterol oxidation products by including chelators in the original drug stocks prior to loading was evaluated. Liposomes loaded with AKG-28 at DL0 250 g/mol PhL or with AKG-38 at DL0 450 g/mol PhL were prepared essentially as in Example 56, except in some lots, 1 mM of the chelators DFO, EDTA), or DTPA were added to the 20 mg/ml drug stock solution before addition to the liposomes. After the loading, the liposomes were subjected to TFF buffer exchange for HBS-20-7.5 and stored without additional chelator. The liposomes were filter-sterilized, analyzed, dispensed into sterile glass vials, incubated at 37° C., and sampled as described in Example 56. The results of sample analysis and liposome characteristics are in the following table:

TABLE 55

Stability of AKG-28 and AKG-38 liposomes loaded with chelator-containing drug stocks

| Lot ID | Drug | DL encapsulated g/mol P | Chelator in drug stock solution pre-load | Initial pH | 2 weeks pH | 2 weeks Lipid degradation, % Chol | 2 weeks Lipid degradation, % HSPC | 1 month pH | 1 month Lipid degradation, % Chol | 1 month Lipid degradation, % HSPC |
|---|---|---|---|---|---|---|---|---|---|---|
| Ls-315 | AKG-28 | 248.2 ± 3.1 | None | 7.47 | 7.32 | 22.31 | 1.37 | 7.14 | 46.01 | 2.26 |
| Ls-316 | AKG-28 | 250.2 ± 3.3 | DFO 1 mM | 7.47 | 7.37 | 0 | 3.36 | 7.32 | 0 | 4.13 |
| Ls-317 | AKG-28 | 252.8 ± 2.6 | EDTA 1 mM | 7.47 | 7.35 | 0 | 4.25 | 7.33 | 0 | 5.81 |
| Ls-318 | AKG-28 | 250.2 ± 2.3 | DTPA 1 mM | 7.48 | 7.37 | 0 | 4.73 | 7.32 | 0 | 5.65 |
| Ls-319 | AKG-38 | 440.1 ± 4.3 | None | 7.45 | 7.32 | 16.4 | 3.87 | 7.18 | 38.72 | 2.81 |
| Ls-320 | AKG-38 | 445.4 ± 5.0 | DFO 1 mM | 7.44 | 7.32 | 0 | 5.2 | 7.27 | 0 | 6.03 |
| Ls-321 | AKG-38 | 442.6 ± 4.2 | EDTA 1 mM | 7.44 | 7.32 | 0 | 5.28 | 7.27 | 0 | 6.86 |

| Lot ID | 2 months pH | 2 months Lipid degradation, % Chol | 2 months Lipid degradation, % HSPC | 3 months pH | 3 months Lipid degradation, % Chol | 3 months Lipid degradation, % HSPC |
|---|---|---|---|---|---|---|
| Ls-315 | 7.14 | 40.26 | 2.86 | 7.02 | 38.8 | 4.59 |
| Ls-316 | 7.22 | 18.47 | 7.12 | 6.37 | 55.18 | 7.15 |
| Ls-317 | 7.15 | 28.00 | 9.3 | 7.02 | 30.02 | 15.55 |
| Ls-318 | 7.17 | 16.20 | 9.37 | 7.12 | 25.95 | 12.3 |
| Ls-319 | 7.13 | 34.94 | 3.53 | 6.98 | 38.94 | 9.13 |
| Ls-320 | 7.15 | 28.16 | 9.83 | 6.97 | 32.77 | 18.98 |
| Ls-321 | 7.20 | 15.48 | 11.25 | 7.02 | 30.34 | 18.22 |

Although the addition of any of the three chelators to the drug stock solution before mixing with the liposomes delayed the formation of cholesterol degradation products, the degradation was not prevented over the whole 3-month period of observation. Therefore, addition of a chelator to the liposome storage medium is preferred.

Example 58. Stability of Ls-AKG28 Preparations in the Presence of a Chelator

The potential for either DFO or EDTA chelators in the final liposomal drug product to reduce the presence of cholesterol oxidation products generated during storage was evaluated. Lots Ls-323, Ls-324. Extruded liposomes of HSPC, Cholesterol (Chol), and PEG-DSPE (45:55:2.25 molar ratio) (extruded lot L-100, Xz 121.4 nm, PdI 0.0131) were prepared essentially as in Example 54 on the scale of 10 mmol HSPC, except that fluorescent lipid label $DiIC_{18}$ (3)-DS was not added. The hydrated lipid dispersion in 0.5 M ammonium sulfate-9.1 vol % ethanol at about 60 mM phospholipid was divided into two portions, and each was passed 4 times through the stack of 2×100 nm+1×200 nm PCTE membranes at 70° C. and 280 psi using Lipex 100 ml thermobarrel extruder. The two portions were combined and further passed via the same membrane stack 6 more times to give extruded lot L-100, Xz 121.4 nm, PdI 0.0131. The extruded liposomes were kept at 2-8° C. overnight, passed through 0.2-µm syringe filter, and the extraliposomal ammonium sulfate was removed by TFF against water to residual conductivity of 152 µS/cm (5.9 volume exchanges). The phospholipid concentration in the post-TFF extruded liposomes (54.7 mM) was determined by the blue phosphomolybdate method. The aliquots of these liposomes were incubated with AKG-28 (6 mg/ml) at the DL0 ratio of 250 g/mol PhL (lot Ls-323) or 320 g/mol PhL (lot Ls-324) on the scale of 1.61 g or 0.59 g of the drug, respectively, in the presence of 45 mg/ml dextrose, with stirring, on a 85° C. water bath until the loading mixture reached 64° C. (4 min), continued on a 65° C. water for another 23 min, followed by chilling in ice-water for 10 min. The liposomes were adjusted to 0.1 M NaCl with 3 M NaCl stock solution and concentrated by TFF diafiltration on a polysulfone hollow fiber cartridge (MWCO 500 KDa) to 13-14 mg/ml of AKG-28. A portion of each concentrated lot was subjected to TFF buffer exchange/unencapsulated drug removal by TFF on the same cartridge (6.9-7.9 Vex), using HBS-20-7.5 buffer. TFF-purified and unpurified drug-loaded liposomes were adjusted with HBS-20-7.5 buffer to the drug concentration of 12.5 mg/ml (Lot-Ls-323) or 13.4 mg/ml (Ls-324) and sterilized by passage through 0.2-µm PES syringe filter. DL ratio of encapsulated drug was determined from the drug and phospholipid assay in post-TFF portions and found to be 246.0±2.3 g/mol PhL (Ls-323; EE 98.4%), and 315.6±4.8 g/mol PhL (Ls-324; EE 95.6%).

Another portion of post-TFF extruded liposomes of lot L-100 was mixed with 38.5 mg/ml AKG-28 aqueous stock solution (pH 5.13) to the final 12.8 mg/ml of AKG-28 on the scale of 0.365 g of the drug and at the DL0 ratio of 320 g/mol PhL (lot Ls-326), in the absence of dextrose. The loading mixture (LM) was stirred on a 65° C. water bath for 23 min, followed by chilling in ice-water for 10 min, and 3 M NaCl was added to the final 60 mM. The added NaCl concentration was chosen to provide post-loading tonicity of the LM within the isotonic osmolality range of 270-310 mOsm/L. Osmolality of the NaCl-adjusted LM, determined using Wescor Vapro 5520 dew point osmometer, was 291±3 mOsm/kg. Aliquots of post-incubation LM purified from non-encapsulated drug by SEC on Sepharose CL-4B showed encapsulated DL ratio of 320.4±3.5 g/mol PhL (EE 97.0%). Post-incubation LM (pH 5.7) was divided into two parts; part 1 was adjusted to pH 6.49 with 1 N NaOH (Ls-326LM), and part 2 was adjusted to 20 mM Hepes, using 1 M Hepes-Na pH 7.5 (Ls-326LMH; post-adjustment pH 7.16). Each part was 0.2-µm sterile-filtered and further divided into three portions: portion 1 served as a no-chelator control, portion 2 was adjusted with sterile 100 mM deferoxamine mesylate to 0.5 mM deferoxamine (DFO), and portion 3 was adjusted to 0.5 mM EDTA-Na with sterile 100 mM EDTA-Na, pH 6.0. Three aliquots of each of Ls-323 (TFF-purified/buffer exchanged) and Ls-323LM (unpurified post-incubation loading mixture) were processed in the same way to contain 0.5 mM DFO, 0.5 mM EDTA, or no chelator. The drug concentration (by UV spectrophotometry), liposome particle size, and pH were determined as described herein. Phospholipid was determined by blue phosphomolybdate (Mo) assay. The liposomes were aseptically aliquoted into sterile glass borosilicate vials with sterile round stoppers (Gerresheimer), and the vials were incubated at 37° C. At 2 weeks, 1 month, 6 weeks, and 10 weeks of incubation the liposomes were sampled and analyzed for pH, particle size, and for the drug and lipid integrity. The lipid integrity and degradation products were identified and quantified by HPLC as described in Example 54. The following results were obtained:

TABLE 56

Impact of chelators in final liposomal drug preparation on storage stability.

| AKG-28 liposomes | | | | | 2 weeks | | | 1 month | | | 10 weeks | | |
|---|---|---|---|---|---|---|---|---|---|---|---|---|---|
| | DL0 ratio | Drug | | Initial | | Lipid degradation, % | | | Lipid degradation, % | | | Lipid degradation, % | |
| Lot ID | g/mol P | mg/ml | Chelator* | pH | pH | Chol | HSPC | pH | Chol | HSPC | pH | Chol | HSPC |
| Ls-323 | 250 | 12.5 | None | 7.50 | 7.36 | 7.46 | 0.00 | 7.06 | 41.98 | 0.52 | 5.06 | 74.62 | 4.06 |
| Ls-323 | 250 | 12.5 | DFO | 7.50 | 7.39 | 0.00 | 0.29 | 7.35 | 0.00 | 1.38 | 7.16 | 0.00 | 6.42 |
| Ls-323 | 250 | 12.5 | EDTA | 7.50 | 7.37 | 0.00 | 0.41 | 7.27 | 0.00 | 1.83 | 7.07 | 0.00 | 6.62 |
| Ls-323LM | 250 | 13.4 | None | 6.07 | 4.76 | 37.03 | 0.47 | 4.13 | 39.63 | 5.06 | 3.44 | 47.51 | 82.97 |
| Ls-323LM | 250 | 13.4 | DFO | 6.07 | 5.73 | 0.00 | 0.11 | 5.43 | 0.00 | 1.42 | 4.78 | 0.00 | 13.70 |
| Ls-323LM | 250 | 13.4 | EDTA | 6.07 | 5.83 | 0.00 | 0.05 | 5.48 | 0.00 | 0.94 | 4.72 | 0.00 | 12.74 |
| Ls-326 | 323 | 12.2 | EDTA | 6.49 | 6.51 | 0.00 | 0.00 | 6.47 | 0.00 | 0.00 | 6.40 | 0.00 | 0.00 |
| Ls-326 | 323 | 12.2 | DFO | 6.49 | 6.53 | 0.00 | 0.00 | 6.49 | 0.00 | 0.00 | 6.36 | 0.00 | 0.16 |
| Ls-326 | 323 | 12.2 | None | 6.49 | 6.37 | 25.41 | 0.00 | 4.99 | 59.31 | 1.13 | 3.93 | 70.62 | 14.38 |
| Ls-326H | 323 | 12.0 | None | 7.16 | 7.16 | 0.00 | 0.00 | 7.12 | 21.34 | 0.00 | 6.21 | 67.86 | 0.00 |
| Ls-326H | 323 | 12.0 | DFO | 7.16 | 7.16 | 0.00 | 0.00 | 7.15 | 0.00 | 0.00 | 7.08 | 0.00 | 0.95 |
| Ls-326H | 323 | 12.0 | EDTA | 7.16 | 7.15 | 0.00 | 0.00 | 7.15 | 0.00 | 0.00 | 7.12 | 0.00 | 1.01 |

*EDTA or DFO were added at a final concentration of 0.5 mM

Without chelators, oxidative degradation of cholesterol was observed already after two weeks of incubation in TFF-purified/buffer exchanged samples as well as in the unpurified LM at initial pH below pH 7.0. Eventually, significant degradation of cholesterol (47.5-74.6% at 10 weeks) was observed in all samples without a chelator. In contrast, in the samples containing 0.5 mM chelator, DFO or EDTA, cholesterol degradation was undetectable even after 10 weeks of incubation. Also, in Ls-326 samples, loaded without an osmotic agent, dextrose, and adjusted with NaCl to isotonicity, hydrolytic degradation of HSPC in the presence of a chelator was remarkably low (0-1.01% after 10 weeks incubation). Samples with cholesterol degradation also showed the drop in pH that correlated with the extent of degradation.

Example 59. Effect of Various Loading Conditions and Liposome External Medium Composition on the Properties and Storage Stability of AKG-28 Liposomes—(Lots Ls-338-340)

The impact of various loading conditions and external medium compositions on storage stability of liposomal AKG-28 formulations was evaluated. Lots Ls-338, Ls-339. Extruded liposomes of HSPC, Cholesterol (Chol), and PEG-DSPE (45:55:2.25 molar ratio)(extruded lot L-102, Xz 117.8 nm, PdI 0.0118) were prepared essentially as described in Example 54 on the scale of 5.9 mmol HSPC, except the number of passages through the PCTE membrane stack was 10. The extruded liposomes were kept at 2-8° C. overnight and passed through 0.2-μm syringe filter. Extraliposomal ammonium sulfate was removed by TFF against water to residual conductivity of 542 μS/cm (4.2 volume exchanges). The phospholipid concentration in the post-TFF extruded liposomes (57.2 mM) was determined by the blue phosphomolybdate method. The aliquots of these liposomes were mixed with AKG-28 (6 mg/ml, added as 40 mg/ml stock solution, pH 5.17) at the DL0 ratio of 259 g/mol PhL (lot Ls-338) or 345 g/mol PhL (lot Ls-339) on the scale of 100 mg of the drug, in the presence of 45 mg/ml dextrose, and incubated with stirring on a 66° C. water bath for 20 min, followed by chilling in ice-water for 10 min. The liposomes were adjusted to 0.1 M NaCl with 3 M NaCl stock solution and subjected to TFF buffer exchange/unencapsulated drug removal by TFF on a polysulfone hollow fiber cartridge (MWCO 500 KDa) (8.0-9.4 Vex), using HBS-20-7.5 buffer. The liposome retentate was concentrated by diafiltration on the same cartridge without buffer feed. TFF-purified concentrated liposomes were adjusted with HBS-20-7.5 buffer to the drug concentration of 9 mg/ml and sterilized by passage through 0.2-μm PES syringe filter. DL ratio of encapsulated drug determined from the drug and phospholipid assay in post-TFF portions was 253.7±5.3 g/mol PhL for Ls-338 (EE 99.9/6), and 329.9±6.3 g/mol PhL for Ls-339 (EE 95.8%).

Another portion of post-TFF extruded liposomes of lot L-102 was mixed with 40 mg/ml AKG-28 aqueous stock solution to the final 12 mg/ml of AKG-28 on the scale of 0.400 g of the drug at the DL0 ratio of 345 g/mol PhL in the absence of dextrose (Lot Ls-340). The loading mixture (LM) was stirred on a 66° C. water bath for 20 min, followed by chilling in ice-water for 10 min, and 3 M NaCl was added to the final NaCl increase of 50 mM. The added NaCl concentration was selected to account for further osmolality increase due to the added buffer. Osmolality of the LM after the drug loading but before NaCl and pH adjustments was 133±6 mOsm/kg. Aliquots of post-incubation LM purified from non-encapsulated drug by SEC on Sepharose CL-4B showed encapsulated DL ratio of 321.7±5.8 g/mol PhL (EE 95.0%). Post-incubation, NaCl-adjusted LM (pH 5.7) was divided into several lots and further processed as follows:

Lot 340S: purified/buffer exchanged by TFF into 0.85% NaCl (8.3 Vex), and after the exchange adjusted to 20 M Hepes-Na, pH 7.5 and 9 mg/ml of the drug.

Lot 340H: purified/buffer exchanged by TFF into HBS-20-7.5 buffer (8.3 Vex) and adjusted to 9 m g/ml of the drug with the same buffer.

Lot 340P: purified/buffer exchanged by TFF into PBS-20-7.5 buffer (8.2 Vex) and adjusted to 9 m g/ml of the drug with the same buffer.

Lot 340LMH: without buffer exchange/purification, adjusted to 20 mM Hepes-Na using 1 M Hepes-Na stock solution, and brought to pH 7.48 with additional NaOH and to 10 mg/ml of the drug with small amount of HBS-20-7.5 buffer.

Lot 340LMP: without buffer exchange/purification, adjusted to 20 mM Na-phosphate using 1 M Na-phosphate, pH 7.5, and brought to pH 7.51 with additional NaOH and to 10 mg/ml of the drug with small amount of PBS-20-7.5 buffer.

Each lot was 0.2-μm sterile-filtered. Then Ls-338 and Ls-339 were divided into three portions: portion 1 served as a no-chelator control, portion 1 was adjusted with sterile 100 mM deferoxamine mesylate to 0.5 mM deferoxamine (DFO), portion 2 was adjusted to 0.5 mM EDTA-Na with sterile 100 mM EDTA-Na, pH 6.0, and portion 3 served as a no-chelator control. Each of Ls-340 series lots was divided into two portions, adjusted to 0.5 mM DFO or 0.5 mM EDTA in the same way. The drug concentration (by UV spectrophotometry), liposome particle size, and pH were determined as described herein. Phospholipid was determined by blue phosphomolybdate (Mo) assay, and in the phosphate-buffered samples—by the fluorometry of the $DiIC_{18}$(3)-DS lipid label in 70% acidified isopropanol, using Mo-assayed Hepes-buffered samples as standards. The liposomes were aseptically aliquoted into sterile glass borosilicate vials with sterile round stoppers (Gerresheimer), and the vials were incubated at 37° C. At 2, 4, and 6 weeks of incubation the liposomes were sampled and analyzed for pH, particle size, and for the drug and lipid integrity. The lipid integrity and degradation products were identified and quantified by HPLC (Example 50). The following results were obtained (Table 57):

At the initial point, lipid degradation products were undetectable. In the absence of a chelator, significant oxidative degradation of cholesterol was observed already at the 2 weeks point, consistent with previous observations. EDTA provided partial protection, slowing down cholesterol degradation, while DFO protection from cholesterol degradation over 6 weeks incubation was complete. The samples where no buffer exchange was performed after the drug loading showed lower rates of phospholipid hydrolysis. After 6 weeks of incubation the average phospholipid degradation in the four non-exchanged, chelator-stabilized samples was 0.52±0.08%, and 0.91±0.55% in the ten buffer-exchanged, chelator-stabilized samples. There was no increase in lipid instability between the similarly processed lots loaded at the drug concentration of 6 mg/ml (Ls-339) or 12 mg/ml (Ls-340H); in fact, the loading at higher drug concentration in the loading mixture favored lower phospholipid degradation (sample 79, 0.9% vs. sample 74, 1.11%, and sample 80, 0.72%, vs. sample 75, 1.05%).

Example 60. Blood Pharmacokinetics of Liposomes Ls-338, Ls-339, Ls-340 in Mice The potential for chelator and stabilized liposome formulations of AKG-28 prepared at different DL ratio to retain their long circulating pharmacokinetic properties was evaluated. DFO-stabilized samples of the liposome lots Ls-338 (sample 71), Ls-339 (sample 74), and Ls-340S (sample 77) of Example 59 were injected i.v. into female CD-1 mice (22-25 g) at the dose of 50 mg/kg AKG-28, in triplicate. Blood was sampled into Li-heparinized Microvettes at 5 min (0.083 hour), 1, 3, 6, 24, and 48 hours post injection. centrifuged, and plasma was analyzed for AKG-28 by direct HPLC assay and liposome phospholipid by indirect ($DiIC_{18}$ (3)-DS label) HPLC assay as described in Example 52. Pharmacokinetic parameters were determined from plasma concentrations of the drug and the liposome phospholipid using PK Solutions software (Summit Research) as described in Example 39, except the initial concentration (Co) was determined instead of C. as appropriate to i.v. bolus administration. The plasma concentration versus time profiles for the drug, liposome lipid, and DL ratio in plasma

TABLE 57A

| Sample code | Lot ID | DL ratio g/mol P | Post-load processing: TFF | Post-load processing: Buffer pH 7.5 to 20 mM | Post-load processing: Chelator to 0.5 mM | pH | Lipid degradation, %: 2 weeks Chol | 2 weeks PC | 4 weeks Chol | 4 weeks PC | 6 weeks Chol | 6 weeks PC |
|---|---|---|---|---|---|---|---|---|---|---|---|---|
| 71 | Ls-338 | 253.7 ± 5.3 | HBS-20-7.5 | | DFO | 7.51 | 0.00 | 0.40 | 0.00 | 0.48 | 0.00 | 2.33 |
| 72 | Ls-338 | 253.7 ± 5.3 | HBS-20-7.5 | | EDTA | 7.51 | 4.05 | 0.00 | 10.29 | 0.00 | 10.35 | 0.86 |
| 73 | Ls-338 | 253.7 ± 5.3 | HBS-20-7.5 | | None | 7.51 | 21.19 | 0.33 | 24.58 | 0.54 | 27.32 | 1.07 |
| 74 | Ls-339 | 329.9 ± 6.3 | HBS-20-7.5 | | DFO | 7.49 | 0.00 | 0.00 | 0.00 | 0.84 | 0.00 | 1.11 |
| 75 | Ls-339 | 329.9 ± 6.3 | HBS-20-7.5 | | EDTA | 7.49 | 7.38 | 0.00 | 9.97 | 0.00 | 13.09 | 1.05 |
| 76 | Ls-339 | 329.9 ± 6.3 | HBS-20-7.5 | | None | 7.49 | 24.46 | 0.00 | 33.36 | 0.29 | 38.92 | 0.89 |
| 77 | Ls-340S | 321.7 ± 5.8 | 0.85% NaCl | Hepes | DFO | 7.47 | 0.00 | 0.00 | 0.00 | 0.00 | 0.00 | 0.67 |
| 78 | Ls-340S | 321.7 ± 5.8 | 0.85% NaCl | Hepes | EDTA | 7.47 | 2.99 | 0.00 | 6.55 | 0.00 | 7.93 | 0.58 |
| 79 | Ls-340H | 320.7 ± 7.2 | HBS-20-7.5 | | DFO | 7.47 | 0.00 | 0.00 | 0.00 | 0.29 | 0.00 | 0.69 |
| 80 | Ls-340H | 320.7 ± 7.2 | HBS-20-7.5 | | EDTA | 7.47 | 4.77 | 0.00 | 7.49 | 0.18 | 8.18 | 0.72 |
| 81 | Ls-340P | 325.1 ± 7.4 | PBS-20-7.5 | | DFO | 7.38 | 0.00 | 0.00 | 0.00 | 0.00 | 0.00 | 0.70 |
| 82 | Ls-340P | 325.1 ± 7.4 | PBS-20-7.5 | | EDTA | 7.38 | 15.63 | 0.00 | 16.90 | 0.00 | 18.91 | 0.34 |
| 83 | Ls-340LMH | 344.5 ± 7.9* | None | Hepes | DFO | 7.37 | 0.00 | 0.00 | 0.00 | 0.00 | 0.00 | 0.42 |
| 84 | Ls-340LMH | 344.5 ± 7.9* | None | Hepes | EDTA | 7.37 | 0.00 | 0.00 | 0.00 | 0.17 | 0.00 | 0.54 |
| 85 | Ls-340LMP | 344.5 ± 7.9* | None | Phosphate | DFO | 7.34 | 0.00 | 0.00 | 0.00 | 0.20 | 0.00 | 0.53 |
| 86 | Ls-340LMP | 344.5 ± 7.9* | None | Phosphate | EDTA | 7.34 | 0.00 | 0.00 | 0.00 | 0.00 | 0.00 | 0.60 |

Figure 20A:
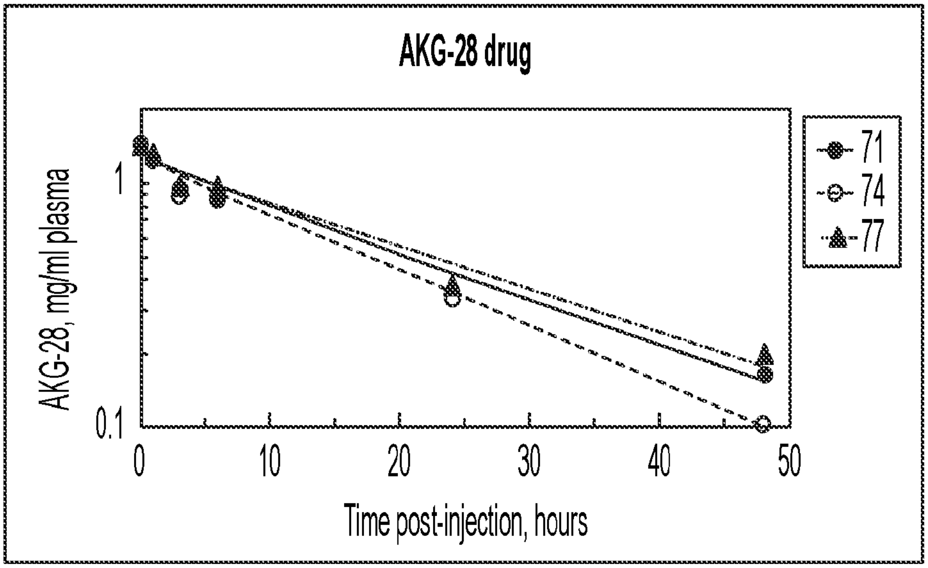
FIG. 20A, FIG. 20B, and FIG. 20C are graphs showing the plasma concentration versus time profiles of AKG-28 drug, liposome lipid (using nonexchangeable DiIC18(3)-DS label), and plasma drug-to-lipid ratio for liposomal AKG-28 lots Ls-338 (sample 71), Ls-339 (sample 74), and Ls-340S (sample 76) after single intravenous injection in CD-1 mice. The liposome characteristics are given in Example 59. The datapoints are the mean of three animals.
Figure 20B:
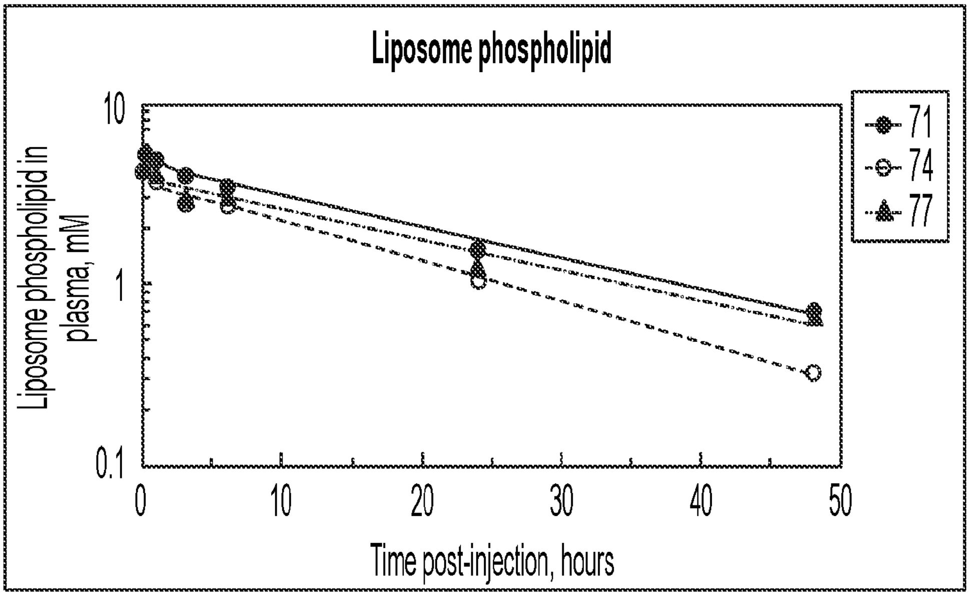
Figure 20C:
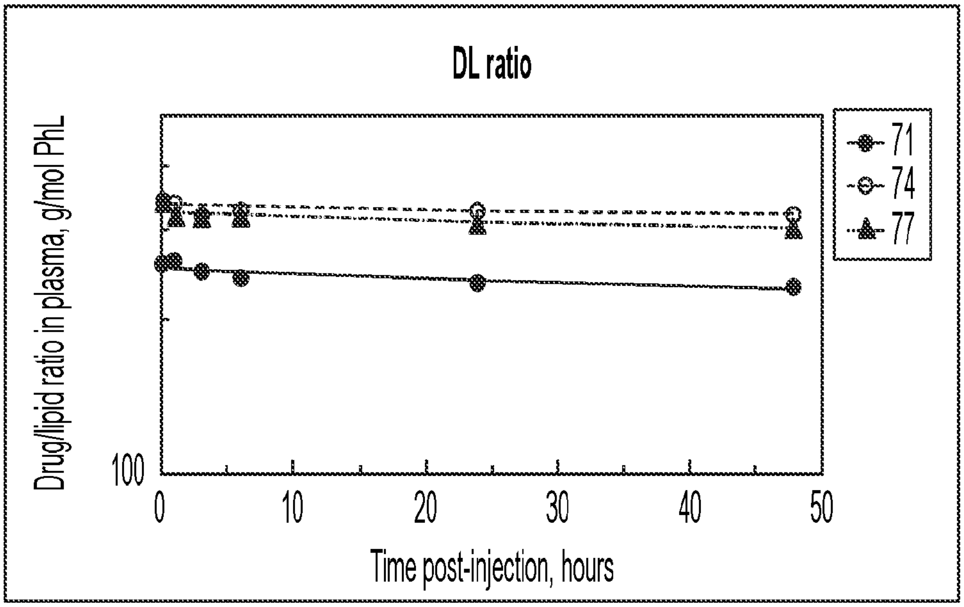

*Includes encapsulated and non-encapsulated drug that has not been removed.

after administration of the liposomes are presented on FIG. 20A, FIG. 20B, and FIG. 20C, respectively. The summary of plasma pharmacokinetic parameters is presented in Table 58. A solution of 5 mg/ml AKG-28 in HBS-7 buffer was used for the free drug pharmacokinetic study. AKG-28 solution was injected at 20 mg/kg, and plasma samples obtained in a similar manner at 5 min, 30 min, 1 hour, 3 hours, and 6 hours post-injection. Plasma samples were analyzed for AKG-28 by HPLC using the method of Example 52, except here the AKG-28 was detected by fluorescence using excitation of 305 nm and emission of 410 nm. Standards were prepared from a 2 mg/mi stock solution of unencapsulated AKG-28. The drug concentrations vs. time, expressed as % injected dose (% ID), are in Table 59.

TABLE 58

PK of liposomal AKG-28 formulations prepared at different DLO.

| Sample code | 71 | 74 | 77 |
|---|---|---|---|
| AKG-28 drug | | | |
| Lot ID | Ls-338 | Ls-339 | Ls-340S |
| DL ratio, g/mol PhL | 253.7 ± 5.3 | 329.9 ± 6.3 | 321.7 ± 5.8 |
| Dose, mg/kg | 50 | 50 | 50 |
| $C_0$, mg/L | 1212 | 1293 | 1209 |
| $C_{last}$, mg/L | 165.2 | 104.3 | 199.0 |
| $T_{last}$, hr | 48 | 48 | 48 |
| $AUC_{0\text{-}last}$, hr*mg/L | 23,702 | 22,709 | 25,687 |
| $AUC_{0\text{-}last}$/Dose, [hr*mg/L]/[mg/kg] | 474.0 | 454.2 | 513.7 |
| $AUC_{0\text{-}inf}$, hr*mg/L | 27,540 | 24,700 | 30,621 |
| CL, mL/hr/kg | 1.82 | 2.02 | 1.63 |
| $V_d$, mL/kg | 42.2 | 38.6 | 40.5 |
| $T_{1/2}$, hr | 16.1 | 13.2 | 17.2 |
| Monoexponential fit, $R^2$ | 0.9800 | 0.9889 | 0.9642 |
| Liposome phospholipid | | | |
| Dose, mmol/kg | 0.1971 | 0.1516 | 0.1554 |
| $C_0$, mmol/L | 4.734 | 3.753 | 3.821 |
| $C_{last}$, mmol/L | 0.709 | 0.323 | 0.654 |
| $T_{last}$, hr | 48 | 48 | 48 |
| $AUC_{0\text{-}last}$, hr*mmol/L | 98.31 | 69.28 | 81.31 |
| $AUC_{0\text{-}last}$/Dose, [hr*mmol/L]/[mmol/kg] | 498.8 | 457.0 | 523.2 |
| $AUC_{0\text{-}inf}$, hr*mmol/L | 115.66 | 75.54 | 98.15 |
| CL, mL/hr/kg | 1.70 | 2.01 | 1.58 |
| $V_d$, mL/kg | 41.7 | 38.9 | 40.7 |
| $T_{1/2}$, hr | 16.9 | 13.4 | 17.8 |
| Monoexponential fit, $R^2$ | 0.9868 | 0.9925 | 0.9669 |
| $T_{1/2}$, hr, drug release | 325.3 | 908.3 | 471.9 |

TABLE 59

PK of free (unencapsulated) AKG-28.
AKG-28 solution

| time, hours | % of injected dose |
|---|---|
| 0.0833 | 0.557 |
| 0.5 | 0.191 |
| 1 | 0.182 |
| 3 | 0.049 |
| 6 | 0.029 |

The liposomes prepared at DL0 ratio of about 330 g/mol PhL retained excellent plasma stability and long-circulating pharmacokinetic properties of the liposomes prepared at the lower DL0 ratio of 250 g/mol PhL. AUC values for the liposomal drug component, normalized to the injected dose of the drug, were in the range of 454-513 hour-mg/L per mg/kg, that compares well to the value of 474 hour-mg/L per mg/kg for the liposomes with DL0 of 250 g/mol PhL in this study and 396 hour-mg/L per mg/kg in the previous study (Example 39). Plasma concentration data for both drug and liposome lipid showed good fit to monoexponential model with the coefficients of determination ($R^2$) in the range of 0.964-0.993 All liposomes were long-circulating (plasma half-life 13.4-17.8 hours). Drug release half-lives were calculated by the formula:

$$T_{1/2\,release} = T_{1/2\,drug} * T_{1/2\,lipid} / (T_{1/2\,lipid} - T_{1/2\,drug})$$

and evidenced very slow release (half-release time 325-960 hours). AUC values and drug release rates for the liposomes loaded at DL0=250 g/mol PhL and DL0=330 g/mol PhL were similar. Free drug was cleared from plasma very quickly.

Example 61. AKG-28 Recrystallization

The potential for recrystallization to reduce the levels of potential impurities in the active AKG-28 drug substance was evaluated. To reduce the level of potential impurities in the liposome formulation of AKG-28 without post-load buffer exchange step, a portion of AKG-28 was recrystallized from the aqueous ethanol by the following procedure. 2 g of AKG-28 were dissolved in 10 ml of WFI-equivalent water, and the solution was filtered through a 0.2-μm PES filter under positive pressure. With stirring, 100% ethanol (Sigma E7023) was slowly added to the solution at ambient temperature. After about 8.5 ml crystallization began. Addition of ethanol continued until 25 ml was added, to about 70 vol % of ethanol. The mixture was stirred for 1 hour and left in refrigerator overnight. The precipitate was filtered out on a Buchner funnel, rinsed with 100% ethanol, and dried in air, followed by drying in vacuum overnight. The yield of recrystallized AKG-28 was 1.742 g (96.3%). The loss of drug in the mother liquor, determined by UV spectrophotometry in water at 302 nm, 59.0 mg (2.95%), and in the ethanol rinse, 2.5 mg (0.13%). The recrystallized drug dissolved in water at 20 mg/ml produced pH 4.53, while the solution of the starting material was significantly more acidic. The chloride content was determined in the recrystallized batch (AKG-28R) and in the analytical reference batch without recrystallization using QuantiChrom colorimetric chloride assay kit (BioAssay Systems). The chloride content agreed with 1.94 equivalents of chloride per mole of the drug on the anhydrous basis, or with 2.01 equivalent of chloride per mole of drug on the basis of a monohydrate. Endotoxin level in AKG-28R was less than 0.04 EU/mg, determined using Endosafe PTS system (Charles River) with 0.01-1 EU/ml cartridges. Storage stability studies of the ethanol-recrystallized AKG-28 dihydrochloride in the range of 4-40° C. and 60-75% RH after several months showed constant water content of 3.2-3.3% (by Karl Fisher titration method) consistent with the monohydrate state (calculated water content 3.48%).

Example 62. Impact of Pre-Loading NaC and pH on Encapsulation Efficiency for Liposomal AKG-28 (Ls-345-355 Lots)

The effect of ionic strength adjustment and the drug sock solution pH on the loading efficiency of AKG-28R was studied. Portions of the AKG-28R aqueous stock solution at 42.7 mg/ml were titrated with 1 N NaOH to various pH endpoints in the range of 5.7-7.0. At pH>7.0 gelation of the drug solution was observed. A 40 mg/ml stock solution of AKG-28 without recrystallization was also used. Extruded liposomes of the lot L-102 (Example 59) were purified from extraliposomal ammonium sulfate using TFF exchange for WFI equivalent water (5.8 Vex; residual conductivity 415 μS/cm, phospholipid 58.4 mM). Aliquots of post-TFF extruded liposomes were mixed with the calculated volumes of the drug stocks, 3 M NaCl, and water to achieve DL0 ratio of about 330 g/mol PhL, drug concentration of about 12 mg/ml, and the desired pre-loading concentration of NaCl (an ionic strength agent). The mixtures were incubated on a 65° C. water bath with stirring for 20 min. and quenched in ice-water for 10 min. To the lots Ls-348 and Ls-349 (see below), 3 M NaCl was added to the concentration of 60 mM after the loading. Before and after the 65° C. incubation, the loading mixture pH was measured using double-junction glass microelectrode. Aliquots of the loading mixtures were purified from unencapsulated drug on a Sepharose CL-4B columns, analyzed for the drug by UV spectrophotometry assay at 302 nm, for the phospholipid by the blue phosphomolybdate assay, encapsulated DL ratio was calculated and divided by the DL ratio of pre-column samples to obtain encapsulation efficiency. The results are presented in Table 60.

TABLE 60

Loading conditions and encapsulation efficiency for Ls-AKG28 lots Ls-345-355.

| | | Loading conditions | | | | | Encapsulation results | |
|---|---|---|---|---|---|---|---|---|
| Lot ID | Drug lot | drug mg/ml | NaCl added mM | pH Drug stock | Pre-load | Post-load | Encapsulated DL ratio g/mol P | EE, % |
| Ls-346 | AKG-28R | 11.3 | 188 | 5.29 | 5.55 | 6.05 | 333.1 ± 3.3 | 97.8 |
| Ls-347 | AKG-28R | 10.7 | 357 | 5.29 | 5.63 | 6.26 | 341.2 ± 6.5 | 99.5 |
| Ls-348 | AKG-28 | 11.8 | 0 | 5.17 | 5.37 | 5.74 | 316.5 ± 3.1 | 90.7 |
| Ls-349 | AKG-28R | 11.8 | 20 | 5.29 | 5.44 | 5.87 | 323.6 ± 9.3 | 93.8 |
| Ls-350 | AKG-28R | 12.0 | 80 | 5.29 | 5.49 | 5.95 | 342.6 ± 7.3 | 98.8 |
| Ls-351 | AKG-28R | 12.0 | 80 | 5.70 | 5.78 | 6.44 | 336.5 ± 4.3 | 98.2 |
| Ls-352 | AKG-28R | 12.0 | 80 | 6.15 | 6.21 | 6.91 | 348.5 ± 10.7 | 99.6 |
| Ls-353 | AKG-28R | 12.0 | 80 | 6.51 | 6.60 | 7.17 | 340.9 ± 3.9 | 98.0 |
| Ls-354 | AKG-28R | 12.0 | 80 | 6.83 | 7.01 | 7.42 | 343.0 ± 7.2 | 100.6 |
| Ls-355 | AKG-28R | 12.0 | 80 | 6.96 | ~7.6 (unstable | 7.55 | 332.6 ± 4.8 | 97.7 |

Contrary to expectations, increased ionic strength of the loading mixture by addition of NaCl before the 65° C. incubation step not only did not decrease the loading efficiency, but instead, clearly increased it. The samples loaded with none or low NaCl (0-20 mM) showed 90-95% encapsulation efficiency, whereas the samples loaded at 80 mM NaCl or higher, up to 357 mM, showed more that 95% EE, and typically more than 97%., and, at 80 mM NaCl, in the range of the drug stock solution pH between 5.29 and 7.01, more than 98%. Minimization of the residual unencapsulated drug in the post-loading mixture is especially important for the liposomal formulations that do not go through unencapsulated drug removal step. Importantly, the possibility of adjusting the drug stock pH to achieve the post-loading pH close to the stability optimum of 7.5 without the loss of EE allows to preserve the liposome excipient buffer capacity for better stability of the formulation pH during storage. At the higher range of pH close to 7.0 the loading mixture gelated at ambient temperature, making the handling of the loading mixture less convenient.

Example 63. Ammonium in Post-Load External Medium of Selected LMs

The impact of formulation processing on extraliposomal ammonium content in liposomal AKG-28 preparations was evaluated. We observed that liposome preparations keeping certain levels of extraliposomal ammonium ions generated during the loading step, such as the levels close to the gram-equivalent concentration of the drug in the loading mixture, show reduced degradation of phospholipids. during storage. Such levels of ammonium displaced from the liposomes by the encapsulated weakly basic drug molecules during the drug loading step are generated in the post-loading mixtures that do not undergo post-loading buffer exchange/unencapsulated drug removal. Alternatively, the necessary levels of ammonium (or substituted ammonium) salt may be added to the liposomes after post-loading buffer exchange/unencapsulated drug removal step or included into the exchange/excipient buffer. To determine the levels of extraliposomal ammonia in the non-exchanged loading mixtures of the liposome lots prepared according to Examples herein, the extraliposomal medium of post-load liposome loading mixtures was separated from the liposomes using microcentrifuge ultrafiltration device (Nanosep Omega 300, Pall Corp.) with MWCO 300 KDa (30 min, 12000×g). Concentration of ammonium in the diafiltrates was determined using Amplite colorimetric ammonia/ammonium quantitation kit (AAT Bioquest, USA). The results are in the table 61 below.

TABLE 61

Ammonia concentrations in the external medium of post-loaded liposomes

| | Loading conditions | | | Post-load TFF | pH | | | |
|---|---|---|---|---|---|---|---|---|
| | DL0 | Drug | Dextrose | exchange | adjustment | Chelator | Ammonium, mM | |
| Sample | g/mol P | mg/ml | mg/ml | (buffer) | (buffer) | (0.5 mM) | found | estimated |
| Blank | | | | | | | <0.5 | 0 |
| Ls-323 | 250 | 6.0 | 45 | HBS-20-7.5 | no | none | <0.5 | 0 |
| Ls-323 | 250 | 6.0 | 45 | none | pH 6.07 | none | 21.3 ± 1.2 | ~22 |
| Ls-324 | 320 | 6.0 | 45 | HBS-20-7.5 | no | none | <0.5 | 0 |
| Ls-324 | 320 | 6.0 | 45 | none | pH 5.93 | none | 19.4 ± 0.3 | ~22 |
| Ls-326 | 320 | 12.8 | 0 | none | pH 6.49 | none | 55.5 ± 0.6 | ~50 |
| Ls-326 | 320 | 12.8 | 0 | none | pH 7.16 (Hepes 20 mM) | none | 48.4 ± 0.3 | ~50 |
| Ls-338 | 259 | 6.0 | 45 | HBS-20-7.5 | no | DFO | <0.5 | 0 |
| Ls-339 | 345 | 6.0 | 45 | HBS-20-7.5 | no | DFO | <0.5 | 0 |
| Ls-340H | 345 | 12.0 | 0 | HBS-20-7.5 | no | DFO | <0.5 | 0 |
| Ls-340LMH | 345 | 12.0 | 0 | none | pH 7.5 (Hepes 20 mM) | DFO | 34.1 ± 1.0 | ~38 |

Estimates of ammonium concentration in the liposome loading mixture were made as follows:

$$[NH_4^+] = C_{drug}/499.4 * 2\ eq/\text{mol} * EE * DF,$$

where $C_{drug}$—drug concentration in the loading mixture during the 65° C. incubation step 499.4—AKG-28 mol. weight (dihydrochloride)

2 eq/mol—valency of the drug cation

EE—encapsulation efficiency (100%=1.0)

DF—dilution factor, introduced by post-load processing

The concentration of ammonium in the extraliposomal medium of the preparations without post-loading buffer exchange step was pronounced and agreed with the estimates of extraliposomal ammonium generated through equivalent transmembrane exchange of intraliposomal ammonium ions for the ionized molecules of the drug that enter the liposome during the drug loading. In the preparations subject to post-load buffer exchange, ammonium concentration was below 0.5 mM (1-2.5% of the pre-buffer exchange ammonium level).

Example 64. Effect of Storage on the Liposome Size in Accelerated Stability Study The impact of storage on liposome size over time was evaluated. The liposome size expressed as z-average diameter (Xz, nm) and polydispersity index (PDI) were determined in the stored liposome samples of Examples 51, 54, 57, 58, and 59 by dynamic light scattering using the cumulants method on a Malvern Zetasizer Pro in a backscatter mode. Aliquots of 2-4 μL of the liposomes were mixed with 1-1.2 ml of HBS-7 (0.2-μm filtered), and the measurements were performed in an auto mode at 25° C. with appropriate refraction index and viscosity parameters. Additionally, a set of eleven pre-incubation samples of Example 59 was measured twice, and the difference between the results of the first and second measurement was used as indication of the variability of the measurements. The Xz data were expressed as percentage change relative to corresponding pre-incubation samples. Remarkably, all liposomes in the above Examples were stable with regard to particle size, the changes in Xz being essentially within the variability of the measurements (Table 62). The maximum change of 4.91% and 4.31% over 3 months 37° C. storage was observed in the lots Ls-312-1 (Example 56) and Ls-321 (Example 57), respectively. PDI of all samples remained below 0.1, with the only exception of Ls-302 (Example 51) where the initial PDI 0.0578 increased to 0.1107 over 1 month of 37° C. incubation, giving evidence for some aggregation of the liposomes.

TABLE 62

Relative change of the particle size in the liposome samples in the accelerated (37° C.) stability study.

| Lots ID | | No. of | Stability | Xz change, % | | |
|---|---|---|---|---|---|---|
| Ls-. . . | Example | samples | Timepoint | Maximum | Average | SD |
| 293-302 | 51 | 12 | 1 month | 1.66 | 0.31 | 0.82 |
| 303-310 | 54, 55 | 14 | 2 weeks | 2.66 | 0.23 | 1.44 |
| 313-322 | 56, 57 | 28 | 3 months | 4.91 | 2.06 | 1.30 |
| 323-326 | 58 | 12 | 10 weeks | 2.77 | −0.27 | 1.64 |
| 338-340 | 159 | 16 | 1 month | 2.13 | 0.25 | 1.20 |
| Method variability | | 11 | n/a | 3.37 | 1.36 | 1.51 |

SD—standard deviation

Example 65. Effect of Storage Buffer pH on the Cholesterol Stability in Ls-AKG28 and Ls-AKG38 Liposomes The impact of storage buffer pH on cholesterol oxidation during storage for both liposomal AKG-28 and liposomal AKG-38 was evaluated. Liposomes Ls-AKG28 (Lot Ls-281) were prepared at descried in Example 26. Liposomes Ls-AKG38 (Lot Ls-280) on the scale of 1471 mg of the drug (as free base) were prepared using essentially the same procedure (Example 26) except that the AKG-38 stock solution was prepared as in Example 25, and combined with the extruded, post-TFF liposomes at the DL0 450 g/mol PhL in the presence of 44.5 mg/ml dextrose, 10 mM NaCl, and 8 mg/ml of the drug. Post-65° C. incubation loading mixture, adjusted to 0.1 M NaCl had pH 6.77. After concentration and TFF buffer exchange for HBS-7, Ls-280 liposomes had 18.04±0.15 mg/ml AKG-38, DL ratio 426.3±5.2 g/mol PhL, Xz 117.0 nm, and PDI 0.0250. A portion of the liposome loading mixtures after the 65° C. incubation, ice-water quenching, and NaCl adjustment step from Ls-280 and Ls-281 lots was subjected to TFF buffer exchange with pre-concentration, using 8.0-8.2 volume exchanges of 10 mM L-Histidine-HCl, 144 mM NaCl buffer, pH 6.5 (His-6.5). HBS-7 portion and His-6.5 portion of each of the buffer-exchanged lots was further divided into parts, and the pH of each part was adjusted with NaOH, or HCl, as appropriate, according to the following table:

TABLE 63

| Lot ID | TFF exchange buffer | pH adjusted to |
|---|---|---|
| Ls-280-1; Ls-281-1 | His-6.5 | 6.0 (adjusted with HCl) |
| Ls-280-2; Ls-281-2 | His-6.5 | 6.5 (no adjustment) |
| Ls-280-3; Ls-281-3 | HBS-7 | 7.0 (no adjustment) |
| Ls-280-4; Ls-281-4 | HBS-7 | 7.5 (adjusted with NaOH) |

Figure 19A:
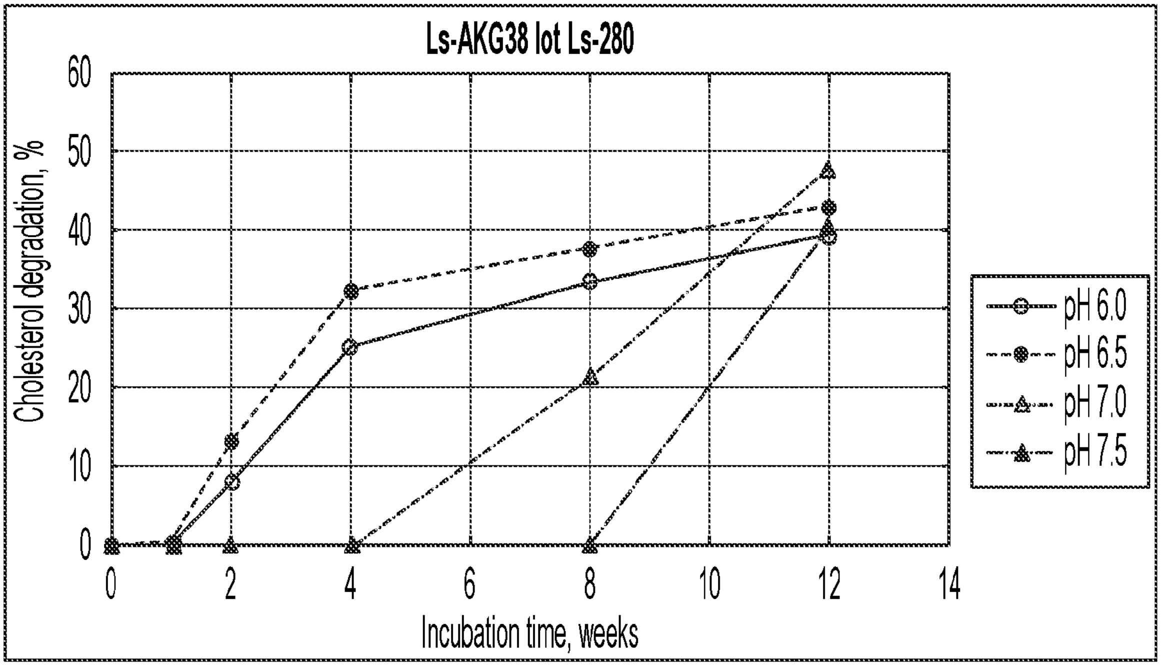
FIG. 19A is a graph showing data for cholesterol degradation of AKG-38 liposome compositions for 12 weeks at room temperature.
Figure 19B:
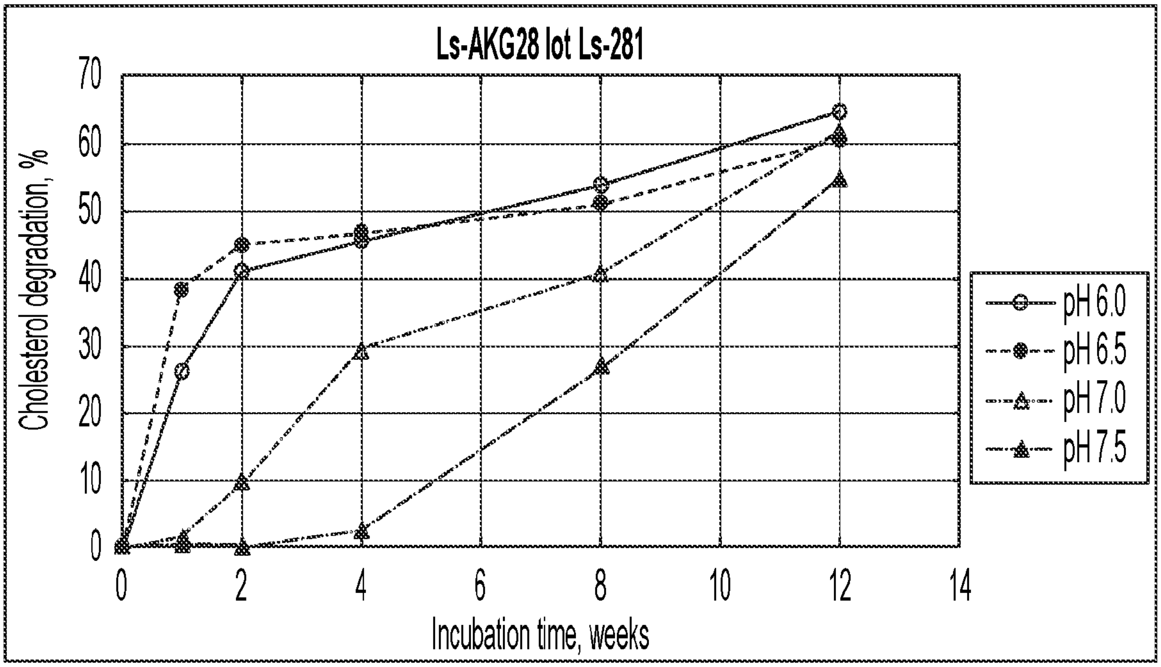
FIG. 19B is a graph showing data for cholesterol degradation of AKG-28 liposome compositions for 12 weeks at room temperature.

The liposomes were 0.2-μm filter-sterilized, the drug concentrations were determined by UV spectrophotometry and adjusted to 10.0 mg/ml with the sterile exchange buffer of the same composition and pH (for pH-adjusted samples, similarly pH-adjusted exchange buffers were used). The concentration-adjusted liposomes were aseptically aliquoted into sterile glass borosilicate vials with sterile round stoppers (Gerresheimer) and incubated at ambient temperature (20-25° C.). At 1, 2, 4, 8, and 12 weeks of incubation the liposomes were analyzed for lipid integrity by HPLC (Example 50). The liposomes showed an unusual feature of lipid instability, namely, a noticeable degradation of cholesterol (FIG. 19A, FIG. 19B). After 12-week period, in the AKG-38 liposomal formulation, the intact cholesterol content decreased to about to 50-60% of its pre-incubation value, and in the AKG-28 liposomal formulation this effect was even more pronounced, with 35-45% cholesterol remaining intact. The new peak with retention time of about 1.77 min was detected, that increased concomitantly with the decrease in the intact cholesterol peak. This component was further identified as 7-hydroxycholesterol (RT 1.81 min). Cholesterol degradation was dependent on the liposome storage buffer pH: At pH 6.0-6.5 the onset of cholesterol degradation was the fastest, and in the range of studied pH values, the slowest onset of degradation was observed at the highest pH 7.5. While the convention in the field of liposomes is that the maximum lipid stability requires pH around 6.5, in the case of Ls-AKG28 and Ls-AKG38 the lipid stability at pH 6.0-6.5 was the lowest, and better stability was observed at pH>7.0, such as pH 7.5.

Example 66. Recrystallization of AKG-38

This example describes a method for recrystallization of AKG-38 to remove undesirable impurities. 1.00 g of (5R)-3-{3-Fluoro-4-[6-(2-(2-dimethylaminoethyl)-2H-tetrazol-5-yl)-3-pyridinyl]phenyl}-5-(methylacetamido)-1,3-oxazolidin-2-one (AKG-38 free base) was dissolved in 12.5 ml of 100% ethanol (Sigma E7023) with stirring in a closed glass vial on an 80° C. water bath. The hot solution was stirred with 0.1 g of Celite 545 for 20 min and filtered. The filtrate was chilled to room temperature, then on an ice bath, and kept in refrigerator for 1 hour. The crystalline precipitate was filtered out on a Buchner funnel, rinsed with 2 ml of chilled 100% ethanol, and dried in air, followed by drying in vacuum. The yield of recrystallized AKG-38 was 0.75 g (75%).

Example 67. Storage Stability of AKG-38 Liposomes in the Presence of a Chelator

This example describes the effect of a chelator deferoxamine at various concentrations on the storage stability of AKG-38 liposomes.

Liposome preparation. (Lot ID Ls-371) HSPC (Lipoid AG) 18.89 g (24.0 mmol), cholesterol (Dishman, High purity) 11.34 g (29.3 mmol), PEG-DSPE (Lipoid AG) 3.37 g (1.20 mmol), making the HSPC/Cholesterol/PEGDSPE molar ratio of 45/55/2.25 were combined with 40 ml of absolute ethanol (Sigma, E-7023) and heated with stirring on a 68-69° C. bath until all lipids dissolved. In a separate container 373 g (360 ml) of 0.5 M aqueous ammonium sulfate (0.2-micron filtered) was preheated on a 70° C. bath and poured with stirring into the hot lipid ethanolic solution. The obtained suspension was stirred on a 70° C. bath for 35 min. and passed five times (four extruder fills per passage) at 400-420 psi through the stack of two 47-mm 100-nm pore size and one 200-nm pore size polycarbonate track-etched membranes (Whatman Nucleopore) interlayed with 37 mm polyester drain discs using Lipex 100-ml thermobarrel liposome extruder (Northern Lipids, Inc.) heated with circulating 70° C. water. The liposomes had Xz 118.5 nm, PDI 0.0214 by DLS. The liposomes were kept overnight in a refrigerator (2-8° C.) and filtered through 0.2-μm polyethersulfone (PES) filter under positive pressure. The filtered liposomes phospholipid concentration was 56.76±0.67 mM. Extraliposomal trapping agent (ammonium sulfate) was removed by TFF buffer exchange for WFI quality endotoxin-free water on a KrosFlo TFF system using polysulfone hollow fiber cartridge with MW cut-off 500 KDa (Spectrum Laboratories) until residual conductivity of the diafiltrate dropped to 446 μS/cm (4.6 volume exchanges). Residual conductivity of the retentate was 355 μS/cm, the phospholipid concentration (blue phosphomolybdate method) was 58.04±5.08 mM.

AKG-38 recrystallized from ethanol (8.12 g, 17.34 mmol)) was mixed with 0.9 equivalents of 1 N HCl (15.6 ml) and made up with WFI quality water to obtain 39.9 mg/ml aqueous stock solution, pH 5.61. Pycnometry of the pre-filtration solution at ambient temperature (21° C.) gave the density value of 1.010. The solution was passed through 0.2-μm filter, and 202.7 g (200.7 ml) of the filtrate was combined with 56.1 g WFI quality water, 13.35 ml of 3 M NaCl stock solution, and 229.9 g of the post-TFF liposome suspension, to form the loading mixture having 16 mg/ml AKG-38, DL0 ratio 600 g/mol PhL, and 80 mM NaCl, pH 5.75. The mixture was divided into two equal portions of 251.6 g, each portion in a thin-walled glass 300-ml Erlenmeyer flask was pre-heated with stirring on the 85° C. bath until the temperature reached 64.5° C. (2.5 min), the flask was transferred into 65° C. bath, incubated with stirring for 20 min, chilled in ice-water bath with stirring for 10 min (chilling time to reach <10° C. was 5 min) and transferred to ambient conditions. Post-loading pH 6.63 (portion 1), pH 6.61 (portion 2). Each portion was purified by TFF using polysulfone hollow fiber cartridge with molecular weight cutoff 500 KD. The liposomes were pre-concentrated by diafiltration to about 22 mg/ml of AKG-38 and purified from any extraliposomal drug by TFF exchange into 144 mM NaCl, 2 mM Hepes pH 7.50 buffer (HBS-2-7.5) for the total of 8.0 volume exchanges. The permeate was collected and weighed; the concentration of AKG-38 in the permeate (nonencapsulated drug removed from the loading mixture) was and in the last few ml of the permeate (residual non-encapsulated drug) was determined by direct UV spectrophotometry using NanoDrop 2000 microspectrophotometer (1 mm path) at the drug spectral maximum of 298 nm with 400 nm background correction. The encapsulation efficiency, estimated from the amount of unencapsulated drug in the permeate divided by the total drug in the loading mixture taken into the TFF purification step, was 97.2% for the portion 1, and 97.1% for the portion 2. The residual unencapsulated drug estimated from the amount of drug in the permeate after 8 volume exchanges was about 0.006 mg/ml (~0.04%). The liposome average size Xz by DLS was 118.2±2.3 nm in portion 1, and 118.7±2.6 nm in portion 2 (N=3). To each portion, the calculated amount of 1 M HEPES-Na buffer stock pH 7.63 (pH 7.50 when diluted to 20 mM in 144 mM NaCl) was added to increase the HEPES concentration by 18 mM, to the final 20 mM of HEPES. As the encapsulation efficiency, post-loading pH, and particle size in both portions were practically identical, the portions were combined to give 361.8 of the liposomes with the drug concentration of 21.75±0.08 mg/ml (by UV spectroscopy in 70% IPA-0.1 N HC). A calculated amount of 20 mM HEPES, 144 mM NaCl, pH 7.50 (HBS-20-7.5) buffer was added to bring the drug concentration to 20.2 mg/ml. A 12-ml aliquot of the combined liposomes was set aside for the storage stability study. To the rest, stock solution of 100 mM deferoxamine mesylate pH 6.0 (DFO)(Excella USP grade) was added to the final 0.5 mM of DFO. The combined purified liposomes were aseptically passed through 0.2-μm PES high-flow sterile filter and analyzed for the particle size by DLS, and for the drug and phospholipid concentration by spectrophotometry. The potency was finally adjusted to 20.0 mg/ml of AKG-38 with sterile full excipient buffer (20 mM HEPES, 144 mM NaCl, 0.5 mM DFO, pH 7.50). The liposomes had the following characteristics: phospholipid 34.08±0.55 mM; AKG-38 (UV) 19.99 f 0.08 mg/ml, DL ratio 586.6±3.9 g/mol phospholipid, pH 7.49, osmolality (Wescor Vapro dew point osmometer) 300.3±6.4 mOs, Xz 117.6±0.9 nm, PDI 0.0130.

The stability aliquot (12 ml) was further divided into three portions, adjusted to 20 mg/ml AKG-38 with HBS-20-7.5 buffer and to no DFO, 0.1 mM DFO, or 0.5 mM DFO with 100 mM DFO stock solution. Each portion was filter-sterilized and aseptically dispensed into two sterile 2-ml glass vials with gray butyl stoppers. The remaining amount was kept as a “time zero” incubation timepoint. The vials were incubated at 37° C., 0.25-ml analytical samples were aseptically withdrawn twice a month for three months, alternating between vial 1 and vial 2 (0.1 mM DFO variant was sampled once a month). The samples were analyzed for pH and lipid (cholesterol and HSPC) degradation.

Figure 21:
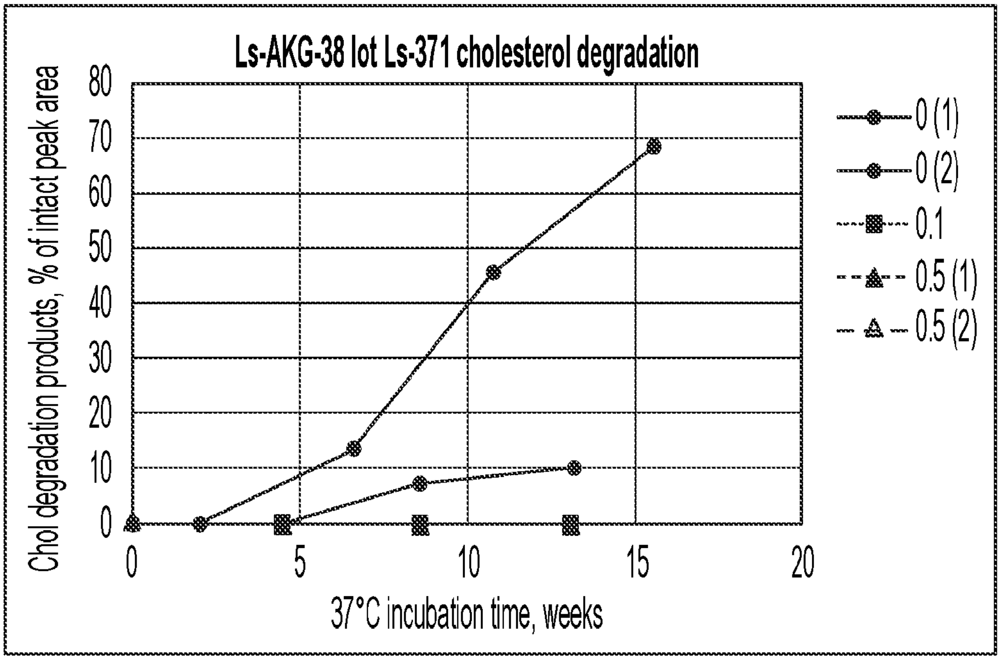
FIG. 21 is a graph showing the data for cholesterol degradation of AKG-38 liposome composition lot Ls-371 (Example 67) upon storage at 37° C. in the presence of various concentration of deferoxamine.
Figure 22:
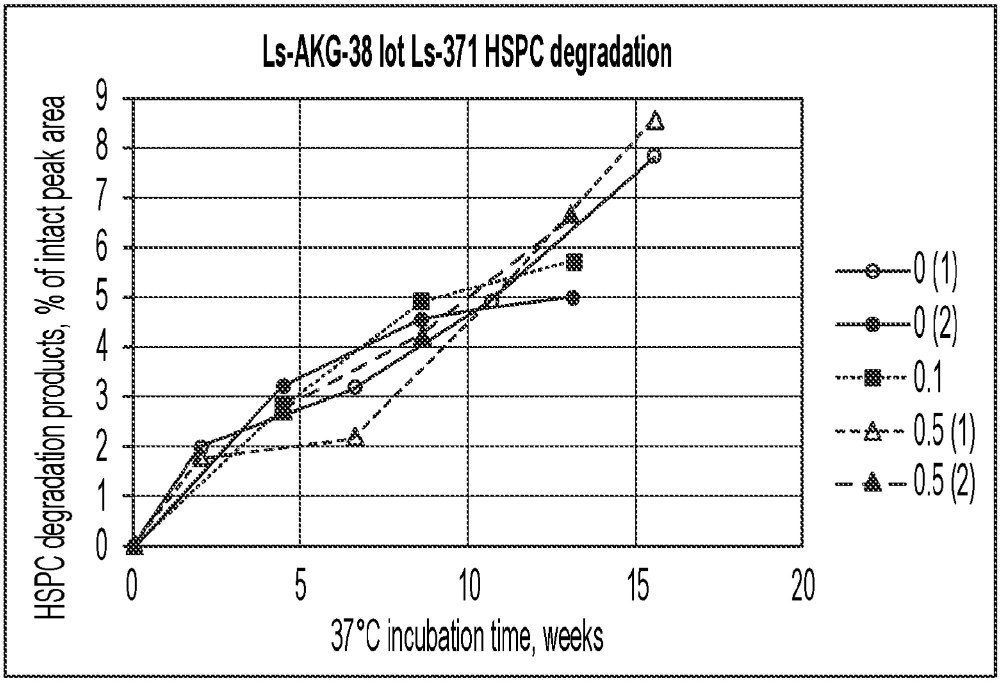
FIG. 22 is a graph showing the data for HSPC degradation of AKG-38 liposome composition lot Ls-371 (Example 67) upon storage at 37° C. in the presence of various concentration of deferoxamine.
Figure 23:
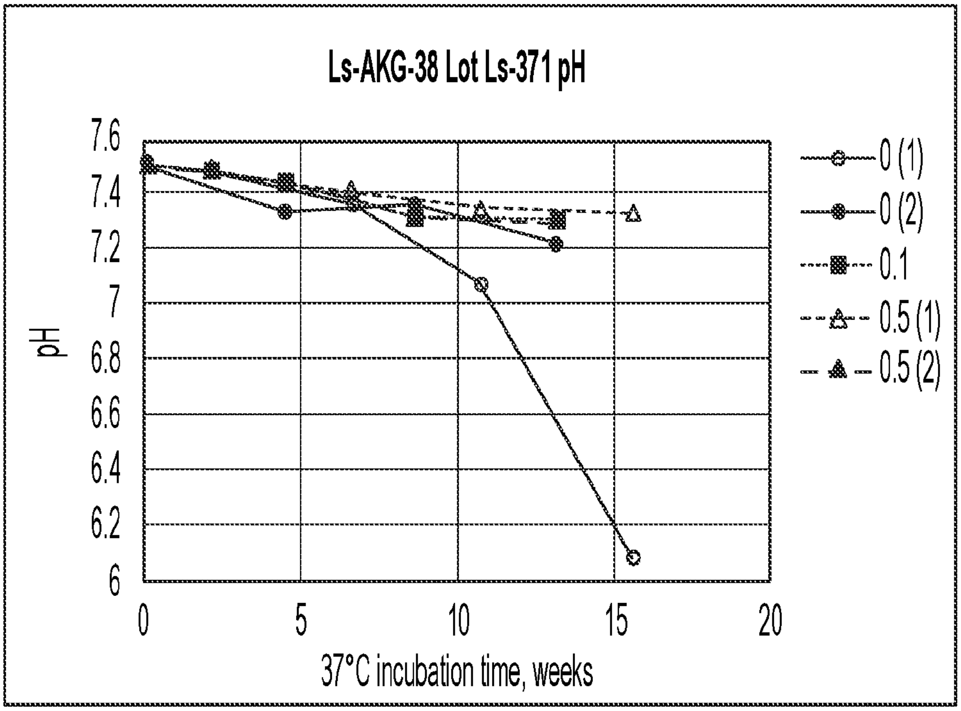
FIG. 23 is a graph showing the changes of pH in the AKG-38 liposome composition lot Ls-371 (Example 67) upon storage at 37° C. in the presence of various concentration of deferoxamine.

The results are presented on FIG. 21, FIG. 22, and FIG. 23. The numbers 0, 0.1, and 0.5 on the chart legend refer to DFO concentration in the sample (mM). Analytical aliquots were withdrawn from the storage vials twice a month, alternating between vial 1 and vial 2 for both no-DFO and 0.5 mM DFO variants. The results are plotted for each vial separately.

Accelerated degradation study was conducted at 37° C. Accepting the Arrhenius factor between 37 C and 4 C (refrigerated storage) equal to 9, the last timepoint (15.6 weeks) is equivalent to 2.7 years of refrigerated storage.

Cholesterol degradation in the samples at 0.1 mM and 0.5 mM DFO was undetectable. In the absence of DFO, significant cholesterol degradation was observed in both samples, after a lag period of 2-4 weeks. This, the stabilizing role of DFO in the liposomal formulation of AKG-38 was confirmed at both 0.1 mM and 0.5 mM DFO concentration. PC degradation products (lyso-PC and stearic acid) gradually accumulated in all samples in a linear fashion. Linear approximation of the combined (vial 1 and vial 2) HSPC degradation data using Excel LINEST function suggested that HSPC degradation rates have only minor dependence on the presence of DFO (Table 64). The expected PC degradation rate upon refrigerated (4° C.) storage was about 0.24%/month.

TABLE 64

| DFO, mM | PC degradation products accumulation rate at 37° C., %/week, mean ± SE | Predicted rate at 4° C., %/month, | $R^2$ |
|---|---|---|---|
| 0 | 0.415 ± 0.051 | 0.20 | 0.918 |
| 0.1 | 0.444 ± 0.076 | 0.21 | 0.944 |
| 0.5 | 0.501 ± 0.046 | 0.24 | 0.950 |

Gradual decrease of pH was observed in all samples (FIG. 23). The most prominent drop in pH was in the samples without DFO. At 0.5 mM DFO and 37° C. the pH dropped at the rate of 0.013±0.0022 units per week ($R^2$=0.853), giving rise to the estimate of 0.00625 units/month at 4° C.

Example 68. Storage Stability of AKG-38 Compound in the Liposome Formulation

This example describes the chemical stability of AKG-38 compound encapsulated in the liposome formulation during storage in the presence of deferoxamine under accelerated degradation conditions (37° C.). Liposomes (Lot ID Ls-378) on the scale of 1.7 g AKG-38 were prepared according to the procedure of Example 67, except that the lipids additionally included a fluorescent lipid label DiIC18(3)-DS in the amount of 0.05 mol % relative to HSPC. The loading mixture had pre-loading pH 5.89, post-loading pH 6.74. The drug was encapsulated into the liposomes with encapsulation efficiency of 96.4±1.6%. The final formulation contained 0.5 mM deferoxamine and had the following characteristics: AKG-38 19.9±0.15 mg/ml; phospholipid 35.76±0.52 mM; DL ratio 556.6±9.1 g/mol PhL; particle size (average of three runs) Xz 117.8±0.7 nm, PDI 0.0275; pH 7.50. Filter-sterilized liposomes were aseptically dispensed into sterile glass vials with gray butyl rubber stoppers in triplicate and stored at 37° C. Analytical samples were aseptically withdrawn at given intervals and analyzed for pH, particle size (Xz, PDI; three parallel instrument runs), lipid (cholesterol and HSPC) degradation. The samples at 6 weeks and 3 months 37° C. storage time were analyzed for the drug and impurity peaks by HPLC with UV detection at 305 nm (AKG-38 UV absorbance maximum). The results are shown in Table 65 (N—number of parallel instrument runs.). Amounts of HSPC degradation products are shown as % relative to the intact HSPC lipid peak area on HPLC. Degradation products of cholesterol were not detectable at any storage time point. AKG-38 purity was expressed as % area of the main HPLC peak (intact AKG-38) relative to all detected peaks. The AKG-38 concentration refers to the concentration of the intact drug. Over the 3 months period at 37° C. the AKG-38 purity decreased by 0.92 percentage points from about 98.99% to about 98.07%, and the overall intact drug concentration had only a minor change from about 19.9 mg/ml to about 19.1 mg/ml (4.2% decrease). These data indicate that during the storage period of 3 months at 37° C. AKG-38 in the Ls-378 liposome formulation was chemically stable. Three-month storage at 37° C. is equivalent to about 27 months of refrigerated (4° C.) storage according to Arrhenius law assuming rate increase factor of 2-fold per each 10° C.

TABLE 65

| Storage of AKG-38 liposomes lot Ls-378 at 37° C. N-number of parallel instrument runs. | | | |
|---|---|---|---|
| Storage time at 37° C. | 0 | 6 weeks | 3 months |
| pH | 7.50 | 7.27 ± 0.06 | 7.19 ± 0.02 |
| Cholesterol degradation products, % | not detectable | not detectable | not detectable |
| HSPC degradation products, % | not detectable | 2.74 ± 0.52 | 11.29 ± 0.35 |
| AKG-38 purity, % | 98.99 | 98.50 | 98.07 |
| AKG-38 concentration. mg/mL | 19.9 ± 0.2 | 19.7 ± 0.62 | 19.06 ± 0.03 |
| Z-average particle size, nm (N = 3) | 117.8 ± 0.7 | 120.6 ± 1.4 | 119.0 ± 1.4 |
| PDI | 0.0275 | 0.0258 | 0.0185 |

Example 69. Storage Stability of AKG-28 Compound in the Liposome Formulation

This example describes the chemical stability of AKG-28 compound encapsulated in the liposome formulation during storage in the presence of deferoxamine under accelerated degradation conditions (37° C.). Liposomes (Lot ID Ls-376 were prepared essentially as described in Examples 67 and 68 on the scale of 220 mg. AKG-28 (ethanol-recrystallized) was prepared as a 40 mg/ml stock solution in water without pH adjustment. The drug loading was performed at the DL ratio of 340 g/mol PhL (280 g/mol PhL on the AKG-28 pure anhydrous free base (FB) basis) and the drug concentration of 12 mg/mL in the loading mixture. The loading mixture had pre-loading pH 6.11, post-loading pH 6.78. The drug was encapsulated into the liposomes with encapsulation efficiency of 98.6±1.9%. The final formulation contained 0.5 mM deferoxamine and had the following characteristics: AKG-28 8.70±0.07 mg/ml (on the FB basis); phospholipid 31.5±0.5 mM; DL ratio (FB) 276.2±5.1 g/mol PhL; particle size (average of three runs) Xz 118.7±0.8 nm, PDI 0.016; pH 7.52. The storage stability study at 37° C. was performed as described in Example 68 (with HPLC detection for the drug at 254 nm). The results are shown in Table 66.

TABLE 66

| Storage of AKG-28 liposomes lot Ls-376 at 37° C. N-number of parallel instrument runs. | | | |
|---|---|---|---|
| Storage time at 37° C. | 0 | 6 weeks | 3 months |
| pH | 7.52 | 7.40 ± 0.03 | 7.36 ± 0.03 |
| Cholesterol degradation products, % | not detectable | not detectable | not detectable |
| HSPC degradation products, % | not detectable | 2.95 ± 0.24 | 6.58 ± 0.13 |
| AKG-28 purity, % | 99.12 | 99.00 | 98.82 |
| AKG-28 concentration. mg/mL (FB) | 8.69 ± 0.0 | 9.12 ± 0.72 | 8.47 ± 0.13 |
| Z-average particle size, nm (N = 3) | 118.7 ± 0.8 | 118.2 ± 1.7 | 118.3 ± 0.6 |
| PDI | 0.0162 | 0.0279 | 0.0345 |

Over the 3 months period at 37° C. the AKG-28 purity decreased by 0.3 percentage points from about 99.1% to about 98.8%, and the overall intact drug concentration had only a minor change from about 8.7 mg/ml to about 8.5 mg/ml (2.3% decrease) which is close to the analytical uncertainty. These data indicate that during the storage period of 3 months at 37° C. AKG-28 in the Ls-376 liposome formulation was chemically stable.

Example 70. Effect of Storage on the Blood Pharmacokinetics of AKG-28 and AKG-38 Liposomes in Mice Blood pharmacokinetics of the drug in AKG-28 liposomes (Lot Ls-376, Example 69) and AKG-38 liposomes (Lot Ls-378, Example 68) before and after 3 months storage as 37° C. was studied in CD-1 mice as described in Examples 39 and 60. The results (Table 67) show slight increase of the drug AUC and half-life and slight decrease of the drug clearance and volume of distribution indicating that long circulating properties and/or in vivo drug retention properties of the liposomes were not compromised during storage.

TABLE 67

Effect of storage on the pharmacokinetic properties of AKG-28 and AKG-38 liposomes in mice.

| | Lot ID | | | | | |
|---|---|---|---|---|---|---|
| | Ls-378 | | | Ls-376 | | |
| | Encapsulated drug | | | | | |
| | AKG-38 | | | AKG-28 | | |
| | Storage time, months | | | | | |
| | 0 | 3 | Change, % | 0 | 3 | Change, % |
| Injected dose, mg/kg | 90 | 90 | | 50 | 50 | |
| $AUC_{0\text{-}last}$ (obs area) µg-hr/ml | 30097 | 34814 | 15.7 | 20611 | 22417 | 8.8 |
| $AUC_{inf}$ (expo) µg-hr/ml | 28316 | 34887 | 23.2 | 20830 | 23319 | 11.9 |
| AUC/dose | 314.6 | 387.6 | 23.2 | 412.2 | 448.3 | 8.8 |
| Vd (area) mL/kg | 41.71 | 39.29 | −5.8 | 38.12 | 38.08 | −0.1 |
| CL (area) mL/hr/kg | 2.89 | 2.46 | −14.9 | 2.29 | 2.07 | −9.6 |
| $T_{1/2}$ (from Vd and CL), hr | 9.99 | 11.08 | 10.9 | 11.52 | 12.75 | 10.7 |

Example 71. Storage of AKG-28 Liposomes at Various Concentrations of Deferoxamine The impact of various concentrations of deferoxamine (DFO), and post-loading liposome processing conditions on the storage stability of liposomal AKG-28 formulations was evaluated. Extruded liposomes of HSPC, Cholesterol (Chol), PEG-DSPE, and DiIC18(3)-DS (45:55:2.25:0.0225 molar ratio) (extruded lot L-105, Xz 119.2 nm, PdI 0.0391) were prepared essentially as described in Example 30 on the scale of 11 mmol HSPC, except the number of passages through the PCTE membrane stack was seven at the working pressure of 350 psi. The extruded liposomes were kept at 2-8° C. overnight and passed through 0.2-µm syringe filter. Extraliposomal ammonium sulfate was removed by TFF against water to residual conductivity of 428 µS/cm (5.9 volume exchanges). The phospholipid concentration in the post-TFF extruded liposomes (63.6 mM) was determined by the blue phosphomolybdate method. The aliquot of these liposomes was mixed with AKG-28 (recrystallized from ethanol; 11 mg/ml, added as 40 mg/ml stock solution) at the DL0 ratio of 340 g/mol PhL (280 g/mol PhL on the anhydrous free base (FB) basis) on the scale of 1.1 g of the drug, in the presence of 80 m NaCl, and incubated with stirring on a 65° C. water bath for 20 min, followed by chilling in ice-water for 10 min. The loading mixture had pre-incubation (pre-loading) pH 6.11, and post-incubation (post-loading) pH 6.83. The liposomes were subjected to TFF buffer exchange/unencapsulated drug removal by TFF on a polysulfone hollow fiber cartridge (MWCO 500 KDa)(9.9 Vex), using either non-buffered 0.85% NaCl (lot Ls-357S) or HBS-20-7.5 buffer (Lot Ls-357H). The liposome retentate was concentrated by diafiltration on the same cartridge without buffer feed. After TFF purification, liposomes of the lot Ls-357S were adjusted to 20 mM of HEPES-Na buffer pH 7.5 by adding 1 M HEPES-Na buffer stock, pH 7.63. TFF-purified concentrated liposomes were adjusted with HBS-20-7.5 buffer to the drug concentration of 10.4 mg/ml of AKG-28 as a dihydrochloride monohydrate (8.5 mg/ml as anhydrous free base) and sterilized by passage through 0.2-µm PES syringe filter. DL ratio of encapsulated drug determined from the drug and phospholipid assay in post-TFF portions was 344.3±3.6 g/mol PhL for Ls-357H, and 336.2±3.9 g/mol PhL for Ls-357s (practically quantitative loading). Each lot was further split into three portions, and 100 mM sterile solution of deferoxamine mesylate (DFO) was added to either 0.1 mM, or 0.5 mM; in the first portion, no deferoxamine was added.

The liposomes were aseptically dispensed into sterile glass vials and put on a 37° C. storage stability study as described in Example 68, with aliquots taken twice a month at equal intervals. The liposomes were analyzed for pH and lipid degradation (Table 68).

TABLE 68

Stability of AKG-28 liposomes in the presence of various concentrations of DFO.

| Storage | Ls-357H | | | Ls-357S | | |
|---|---|---|---|---|---|---|
| time months | No DFO | 0.1 mM DFO | 0.5 mm DFO | No DFO | 0.1 mM DFO | 0.5 mm DFO |
| Cholesterol degradation products, % of intact cholesterol peak area | | | | | | |
| 0.5 | 0 | 0 | 0 | 0 ± 0 | 0 | 0 |
| 1.0 | 0 | 0 | 0 | 0 ± 0 | 0 | 0 |
| 1.5 | 0 | 0 | 0 | 0 ± 0 | 0 | 0 |
| 2.0 | 0 | 0 | 0 | 0 ± 0 | 0 | 0 |
| 2.5 | 0.47 ± 0.54 | 0 | 0 | 0 ± 0 | 0 | 0 |
| 3.0 | 20.7 ± 4.33 | 0 | 0 | 0.9 ± 1.27 | 0 | 0 |
| 3.5 | 27.9 ± 3.37 | 0 | 0 | 14.7 ± 1.95 | 0 | 0 |
| 4.0 | 64.1 ± 3.68 | 0 | 0 | 34.7 ± 4.43 | 0 | 0 |

TABLE 68-continued

Stability of AKG-28 liposomes in the presence of various concentrations of DFO.

| Storage time months | Ls-357H No DFO | Ls-357H 0.1 mM DFO | Ls-357H 0.5 mm DFO | Ls-357S No DFO | Ls-357S 0.1 mM DFO | Ls-357S 0.5 mm DFO |
|---|---|---|---|---|---|---|
| HSPC degradation products, % of intact HSPC peak area | | | | | | |
| 0.5 | 2.48 ± 0.11 | 2.25 ± 0.21 | 2.05 ± 0.06 | 0.94 ± 0.00 | 0.97 ± 0.10 | 0.85 ± 0.11 |
| 1.0 | 4.52 ± 0.24 | 4.25 ± 0.13 | 3.38 ± 0.13 | 1.80 ± 0.02 | 1.77 ± 0.12 | 1.72 ± 0.09 |
| 1.5 | 6.72 ± 0.19 | 6.13 ± 0.10 | 4.66 ± 0.09 | 2.51 ± 0.07 | 2.60 ± 0.08 | 2.35 ± 0.14 |
| 2.0 | 7.24 ± 0.42 | 6.06 ± 0.54 | 4.70 ± 0.29 | 2.26 ± 0.38 | 2.40 ± 0.20 | 2.33 ± 0.32 |
| 2.5 | 11.3 ± 0.27 | 9.27 ± 0.51 | 6.22 ± 0.32 | 3.25 ± 0.36 | 3.28 ± 0.24 | 3.01 ± 0.30 |
| 3.0 | 11.6 ± 0.56 | 11.1 ± 1.37 | 7.23 ± 0.21 | 3.72 ± 0.46 | 3.53 ± 0.21 | 3.78 ± 0.18 |
| 3.5 | 12.6 ± 0.49 | 12.7 ± 0.75 | 8.01 ± 0.44 | 4.43 ± 0.05 | 4.70 ± 0.11 | 4.53 ± 0.63 |
| 4.0 | 12.6 ± 2.53 | 15.5 ± 0.97 | 12.2 ± 1.40 | 5.35 ± 0.10 | 7.43 ± 0.18 | 7.56 ± 0.27 |
| pH | | | | | | |
| 0.5 | 7.40 ± 0.01 | 7.40 ± 0.00 | 7.41 ± 0.00 | 7.53 ± 0.00 | 7.52 ± 0.00 | 7.52 ± 0.01 |
| 1.0 | 7.37 ± 0.00 | 7.37 ± 0.00 | 7.38 ± 0.02 | 7.51 ± 0.00 | 7.53 ± 0.00 | 7.50 ± 0.02 |
| 1.5 | 7.33 ± 0.00 | 7.35 ± 0.00 | 7.38 ± 0.02 | 7.51 ± 0.04 | 7.52 ± 0.01 | 7.51 ± 0.00 |
| 2.0 | 7.32 ± 0.01 | 7.33 ± 0.01 | 7.37 ± 0.00 | 7.52 ± 0.00 | 7.52 ± 0.00 | 7.49 ± 0.03 |
| 2.5 | 7.30 ± 0.01 | 7.31 ± 0.00 | 7.33 ± 0.02 | 7.49 ± 0.02 | 7.51 ± 0.01 | 7.50 ± 0.00 |
| 3.0 | 7.18 ± 0.02 | 7.25 ± 0.01 | 7.21 ± 0.09 | 7.45 ± 0.02 | 7.44 ± 0.00 | 7.41 ± 0.01 |
| 3.5 | 7.11 ± 0.03 | 7.26 ± 0.02 | 7.27 ± 0.03 | 7.43 ± 0.00 | 7.46 ± 0.02 | 7.43 ± 0.00 |
| 4.0 | 6.18 ± 0.07 | 7.25 ± 0.00 | 7.27 ± 0.01 | 7.34 ± 0.03 | 7.48 ± 0.01 | 7.44 ± 0.00 |

Addition of DFO at 0.1 mM and 0.5 mM was equally protective against cholesterol degradation in AKG-28 liposomes during the whole period of observation (4 months) which according to the Arrhenius law, assuming the factor of two per 10 degrees Celsius, is approximately equivalent to 36 months (3 years) of refrigerated (4° C.) storage. In the samples without a chelator (DFO) cholesterol degradation was observed. HSPC degradation in the Ls-537S samples obtained by post-loading exchange into unbuffered physiological saline (0.85% NaCl) was about two times slower than in the samples obtained by post-loading exchange into saline buffered at pH 7.5 with HEPES.

The drug chemical degradation was studied in the samples containing 0.5 mM DFO using the method of Example 68 (using 254 nm HPLC UV detection for the drug) with the following results (Table 69):

TABLE 69

Chemical purity of AKG-28 during the storage of AKG-28 liposomes at 37 C. (as % of the intact drug by HPLC).

| Storage time, months | Ls-357H | Ls-357S |
|---|---|---|
| 0 | 99.939 ± 0.002 | 99.931 ± 0.002 |
| 1 | 99.795 ± 0.013 | 99.742 ± 0.008 |
| 2 | 99.701 ± 0.006 | 99.604 ± 0.010 |
| 2.5 | 99.638 ± 0.005 | 99.553 ± 0.007 |
| 3 | 99.604 ± 0.006 | 99.503 ± 0.008 |
| Change 0-3 months | −0.335 ± 0.008 | −0.428 ± 0.010 |

The drug was quite stable upon storage in the liposomes of both post-loading purification variants. Three-month decrease in AKG-28 purity was 0.33-0.43 percentage points.

Example 72. Lipid Stability in the AKG-28 Liposomes Prepared Under Different Post-Load Purification Conditions: Relation to the Amounts of Extraliposomal Ammonium Extruded liposomes of HSPC, Cholesterol (Chol), PEG-DSPE, (45:55:2.25 molar ratio) (extruded lot L-111, Xz 118.5 nm, PdI 0.0317) were prepared essentially as described in Example 30 (but the lipid label DiIC18(3)-DS was not used) on the scale of 10.3 mmol HSPC, except the PCTE filter stack included 3×100 nm and 1×200 nm filters, and the liposomes were passed through the filter stack 4 times at the working pressure of 460 psi and 70° C. The extruded liposomes were kept at 2-8° C. overnight and passed through 0.2-μm syringe filter. Extraliposomal ammonium sulfate was removed by TFF against water to residual conductivity of 408 μS/cm (4.7 volume exchanges). The phospholipid concentration in the post-TFF extruded liposomes (53.1 mM) was determined by the blue phosphomolybdate method. The liposomes were mixed with AKG-28 (recrystallized from ethanol) to the final 12 mg/ml (added as 40 mg/ml stock solution) at the DL0 ratio of 340 g/mol PhL (280 g/mol PhL on the anhydrous free base (FB) basis) on the scale of 3.37 g of the drug, in the presence of 80 m NaCl. The loading mixture was pre-heated to 65° C. with stirring in a 85° C. water bath and further incubated with stirring on a 65° C. water bath for 20 min, followed by chilling in ice-water to <10° C. and incubating at this temperature for 10 min. The loading mixture had pre-incubation (pre-loading) pH 6.13, and post-incubation (post-loading) pH 6.91. The liposomes were subjected to TFF buffer exchange/unencapsulated drug removal by TFF on a polysulfone hollow fiber cartridge (MWCO 500 KDa)(8 volume exchanges), using either non-buffered 0.85% (146 mM) NaCl (lot 389-0), or 144 mM NaCl buffered with 1 mM (lot 389-1), 2 mM (lot 389-2), or 20 mM (lot 389-20) HEPES-Na, pH 7.50. After TFF purification, the liposome compositions, where needed, were adjusted to 20 mM of HEPES-Na buffer pH 7.5 by adding 1 M HEPES-Na buffer stock, pH 7.63, and all were adjusted to 0.5 M DFO by adding 100 mM DFO stock solution. TFF-purified concentrated liposomes were further adjusted with HBS-20-7.5 buffer with 0.5 mM DFO to the drug concentration of 8.34 mg/mi of AKG-28 counting on an anhydrous free base (FB) content and sterilized by passage through 0.2-μm PES syringe filter. The loading efficiency calculated from the amount of unencapsulated AKG-28 removed during the TFF purification step was 98.9-99.1%%, DL ratio 323.9 g/mol PhL (276.6 g/mol PhL on a FB basis). The liposomes were aseptically dispensed into sterile glass vials and put on a 37° C. storage stability study; aliquots were withdrawn at approximately 2 weeks intervals and analyzed for pH and lipid integrity as described in Example 68. The liposomes were also analyzed for the ammonium content by the method of Example 63, except that in addition to extraliposomal ammonium, the total ammonium concentration in the liposome composition was measured after the lysis of the liposomes with C12E10 detergent (67 mg/ml) at 65° C. for 2 min. The results are shown in Table 70.

TABLE 70

Lipid stability and ammonium assay in the AKG-28 liposomes prepared under various post-loading buffer exchange conditions.

| HEPES in exchange buffer, mM: | 0 | 1 | 2 | 20 |
|---|---|---|---|---|
| Days at 37° C. | HSPC degradation, % | | | |
| 0 | 0.00 | 0.00 | 0.00 | 0.00 |
| 16 | 0.60 ± 0.18 | 0.70 ± 0.17 | 0.84 ± 0.17 | 0.90 ± 0.45 |
| 33 | 1.52 ± 0.14 | 2.23 ± 0.46 | 2.25 ± 0.34 | 2.77 ± 0.25 |
| 47 | 2.67 ± 0.59 | 3.15 ± 0.49 | 3.29 ± 0.25 | 4.16 ± 0.75 |
| 62 | 3.17 ± 0.39 | 4.42 ± 0.40 | 4.95 ± 0.41 | 5.10 ± 0.44 |
| 77 | 4.50 ± 0.17 | 6.13 ± 0.41 | 6.40 ± 0.07 | 7.05 ± 0.33 |
| 95 | 5.49 ± 0.14 | 7.34 ± 0.02 | 7.99 ± 0.32 | 8.98 ± 0.13 |
| Degradation rate, %/day | 0.0559 | 0.0750 | 0.0806 | 0.0895 |
| $R^2$ | 0.9937 | 0.9938 | 0.9943 | 0.9943 |
| | $[NH4^+]$, mM | | | |
| Total | 22.93 ± 0.70 | 22.48 ± 0.92 | 21.74 ± 0.72 | 21.76 ± 0.49 |
| Extraliposomal | 1.70 ± 0.20 | 0.80 ± 0.03 | 0.83 ± 0.21 | 0.61 ± 0.02 |
| Extraliposomal as % of total | 7.4 ± 0.9 | 3.5 ± 0.2 | 3.8 ± 1.0 | 2.8 ± 0.1 |

Stability of the phospholipid against degradation upon storage was noticeably higher in the compositions with after-load purification using unbuffered saline. We unexpectedly found that this better phospholipid stability correlates with the higher extraliposomal concentration of ammonium ion in the liposome composition. The composition prepared with the after-load buffer exchange for unbuffered saline showed 1.3-1.6 times lower average degradation rate of HSPC than those made with pH 7.5-buffered post-load buffer exchange media, and at the same time, it had the amount of extraliposomal ammonium (ie., ammonium in the liposome external medium) of 1.7 mM (7.4% of the total), twice as high as the amount of extraliposomal ammonium in the compositions prepared with the pH 7.5-buffered post-load exchange saline buffers (0.6-0.8 mM, 2.8-3.8% of the total). Thus, the concentration of ammonia in the liposome outer medium (extraliposomal concentration) of over 1 mM is associated with better storage stability of the phospholipid.

Example 73. Encapsulation of AKG-28 into the Liposomes with Increased Cholesterol Content at Various Drug-to-Lipid Ratios Extruded liposomes of HSPC, Cholesterol (Chol), PEG-DSPE, (45:55:2.25 molar ratio) (extruded lot L-115, Xz 112.5 nm, PdI 0.0186) were prepared essentially as described in Example 30 (but the lipid label DiIC18(3)-DS was not used) on the scale of 15 mmol HSPC, except the PCTE filter stack included (from the bottom to the top) 1×80 nm, 3×100 nm, and 2×200 nm filters, and the liposomes were passed through the filter stack two times at the working pressure of 700 psi at 70° C. The extruded liposomes were kept at 2-8° C. overnight and passed through 0.2-μm syringe filter. Extraliposomal ammonium sulfate was removed by TFF against water to residual conductivity of 426 μS/cm (4.7 volume exchanges). The phospholipid concentration in the post-TFF extruded liposomes (55.1 mM) was determined by the blue phosphomolybdate method. The liposomes were mixed with AKG-28 (recrystallized from ethanol) (added as 39.8 mg/ml stock solution) at the DL0 ratios of 100-800 g/mol PhL (85.4-683.2 g/mol PhL on the anhydrous free base (FB) basis) on the scale of 3.7-9.6 mg of the drug in the final volume of 0.8 ml, in the presence of 80 m NaCl. The loading mixture was incubated with stirring on a 65° C. water bath for 20 min, followed by chilling in ice-water to <10° C. for 10 min. The loading mixtures had pre-incubation (pre-loading) pH 6.1-6.18, and post-incubation (post-loading) pH 6.34-7.26. Unencapsulated AKG-28 was removed by chromatography on Sepharose CL-4B in PD-10 gravity-fed columns (eluent HBS-7 buffer), the liposomes were collected in the void volume fraction and analyzed for AKG-28 (using UV spectrophotometry at 302 nm in 50% isopropanol-0.1 M HCl) and phospholipid (using blue phosphomolybdate method). Drug-to lipid (DL) ratios for the encapsulated drug were calculated and compared to the initial drug-to lipid ratios (DL0) in the liposome loading mixtures. The results are shown in Table 71. Efficient (>90%) encapsulation was observed in the DL0 range of 100-500 g/mol, yielding the liposomes with DL ratio of about 99-470 g/mol PhL (85-400 g/mol PhL as FB). At the higher DL0 ratios the encapsulation efficiency decreased, as the liposomes reached the limit of the encapsulated DL ratio of about 530-540 g/mol PhL (456-458 g/mol PhL as FB).

TABLE 71

| DL0 | DL (encapsulated) | | Encapsulation |
|---|---|---|---|
| g/mol PhL | g/mol PhL | g/mol PhL (FB) | efficiency % |
| 100 | 99.4 ± 3.3 | 84.8 ± 2.8 | 99.4 ± 3.3 |
| 200 | 192.6 ± 6.8 | 164.5 ± 5.8 | 96.3 ± 3.5 |
| 300 | 292.3 ± 5.3 | 249.6 ± 4.6 | 97.4 ± 1.8 |
| 400 | 393.0 ± 14.6 | 335.6 ± 12.5 | 98.3 ± 3.7 |
| 500 | 473.3 ± 3.3 | 404.2 ± 2.8 | 94.7 ± 0.7 |
| 600 | 516.2 ± 5.3 | 440.9 ± 4.5 | 86.0 ± 1.0 |
| 700 | 533.9 ± 4.9 | 455.9 ± 4.2 | 76.3 ± 0.9 |
| 800 | 536.6 ± 7.8 | 458.2 ± 6.7 | 67.1 ± 1.5 |

Example 74. Exemplary Liposome Products

AKG-28 Liposome Injection Product

AKG-28 liposome injection product is formulated using a dihydrochloride monohydrate salt of AKG-28, an antibacterial agent, into a liposomal dispersion for intravenous use. The chemical name of AKG-28 dihydrochloride monohydrate salt is (5R)-3-{3-Fluoro-4-[6-(2-(2-dimethylamino-ethyl)-2H-tetrazol-5-yl)-3-pyridinyl]phenyl}-5-(methyl-amino)-1,3-oxazolidin-2-one dihydrochloride hydrochloride monohydrate. The molecular structure is:

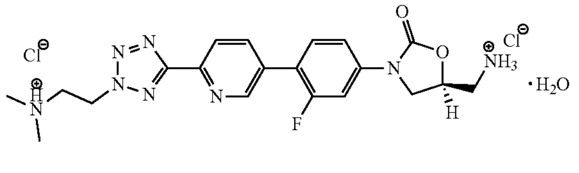

The conversion factor for the concentration of AKG-28 dihydrochloride monohydrate into the concentration of AKG-28 free base is 0.824.

The liposome injection product is a sterile, white to slightly off-white opaque isotonic liquid liposomal dispersion packaged in 10-ml glass vials. Each 10 mL single-dose vial contains 85 mg (8.5 mg/mL) AKG-28 free base (2-oxazolidinone, 5-(aminomethyl)-3-[4-[6-[2-[2-(dimethylamino) ethyl]-2H-tetrazol-5-yl]-3-pyridinyl]-3-fluorophenyl]-(5S)—). The liposome is a unilamellar lipid bilayer vesicle, approximately 115 nm in diameter (Z-average), which encapsulates an aqueous space containing AKG-28 in an insoluble gelated or precipitated state as the sulfate salt. The vesicle is composed of hydrogenated soy phosphatidyl choline (HSPC) 22.6 mg/mL, cholesterol (Chol) 13.6 mg/mL, and methoxy-terminated polyethylene glycol (MW 2000)-distearoylphosphatidyl ethanolamine (MPEG-2000-DSPE) 4 mg/mL, and suspended in a saline buffer (20 mM HEPES, 141 mM NaCl, 0.5 mM deferoxamine, pH 7.5) Each mL also contains 4.8 mg/mL of 2-[4-(2-hydroxyethyl) piperazin-1-yl]ethanesulfonic acid (HEPES) as a buffer, 0.33 mg/mL deferoxamine mesylate as a chelator, and 8.2 mg/mL sodium chloride as an isotonicity reagent in water for injection. Sodium hydroxide and/or hydrochloric acid are added quantum satis to pH 7.5. The mole ratio of lipids within the liposome is 45:55:2.25 (HSPC:Chol:MPEG-DSPE). AKG-28 is encapsulated by ammonium sulfate gradient method at the AKG-28(free base)-phospholipid ratio of 280 g/mol.

AKG-28 liposome injection is an anti-bacterial agent useful for the treatment of patients with mycobacterial infections such as *Mycobacterium tuberculosis*. In some embodiments, AKG-28 liposome injection is an anti-bacterial agent useful for the treatment of patients with mycobacterial infections such as multi-drug resistant (MDR) or extremely drug resistant (XDR) *Mycobacterium tuberculosis*.

AKG-38 Liposome Injection Product

AKG-38 liposome injection product is formulated using a free base of AKG-38, an antibacterial agent, into a liposomal dispersion for intravenous use. The chemical name of AKG-38 is (5R)-3-{3-Fluoro-4-[6-(2-(2-dimethylaminoethyl)-2H-tetrazol-5-yl)-3-pyridinyl]phenyl}-5-(methylacetamido)-1,3-oxazolidin-2-one. The molecular structure is:

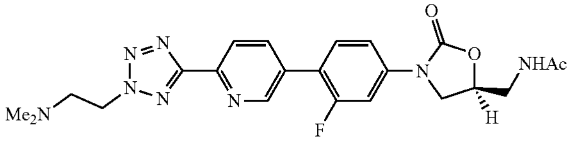 [SMILES: CC(=O)NC[C@H]1CN(c2ccc(-c3ccc(-c4nnn(CCN(C)C)n4)nc3)c(F)c2)C(=O)O1]

AKG-38 liposome injection product is a sterile, white to slightly off-white opaque isotonic liposomal dispersion packaged in 10-ml glass vials. Each 10 mL single-dose vial contains 160 mg AKG-38 free base at a concentration of 16 mg/mL. The liposome is a unilamellar lipid bilayer vesicle, approximately 115 nm in diameter, which encapsulates an aqueous space containing AKG-38 in an insoluble gelated or precipitated state as the sulfate salt. The vesicle is composed of hydrogenated soy phosphatidyl choline (HSPC) 20 mg/mL, cholesterol (Chol) 12 mg/mL, and methoxy-terminated polyethylene glycol (MW 2000)-distearoylphosphatidyl ethanolamine (MPEG-2000-DSPE) 3.5 mg/mL, and suspended in a saline buffer (20 mM HEPES, 141 mM NaCl, 0.5 mM deferoxamine, pH 7.5) Each mL also contains 4.8 mg/mL of 2-[4-(2-hydroxyethyl) piperazin-1-yl]ethanesulfonic acid (HEPES) as a buffer, 0.33 mg/mL deferoxamine mesylate as a chelator, and 8.2 mg/mL sodium chloride as an isotonicity reagent in water for injection. Sodium hydroxide and/or hydrochloric acid are added quantum satis to pH 7.5. The mole ratio of lipids within the liposome is 45:55:2.25 (HSPC:Chol:MPEG-DSPE). AKG-38 is encapsulated by ammonium sulfate gradient method at the AKG-38 (free base)-phospholipid ratio of 600 g/mol.

AKG-38 liposome injection is an anti-bacterial agent useful for the treatment of patients with Gram positive bacterial infections, including treatment of methicillin-resistant *Staphylococcus aureus* (MRSA) bacterial infections. AKG-38 liposome injection is an anti-bacterial agent useful for the treatment of patients with mycobacterial infections such as *Mycobacterium tuberculosis*. In some embodiments, AKG-38 liposome injection is an anti-bacterial agent useful for the treatment of patients with mycobacterial infections such as multi-drug resistant (MDR) or extremely drug resistant (XDR) *Mycobacterium tuberculosis*.

Disclosed herein are compounds, compositions and methods related to the treatment of bacterial infections. As used herein, the term "compound" and "drug" are used interchangeably. Some aspects of the disclosure relate to novel aminoalkyl derivatives of oxazolidinones. Some aspects of the disclosure relate to the process for the synthesis of the novel aminoalkyl derivatives of oxazolidinone compounds. Other aspects relate to compositions comprising aminoalkyl derivatives of oxazolidinone compounds in liposomes. Other aspects of the disclosure relate to the use of aminoalkyl derivatives of oxazolidinone compounds or liposome compositions comprising aminoalkyl derivatives of oxazolidinone compounds in the treatment of bacterial infections. In some embodiments, the compounds and compositions described herein can be used to treat infections from mycobacteria and gram-positive bacteria. In some embodiments, the bacterial infection is *Mycobacterium tuberculosis*. In some embodiments, the compounds and compositions described herein inhibits growth of mycobacteria and gram-positive bacteria. These include, but are not limited to, *Mycobacterium tuberculosis, Mycobacterium avium* complex, *Mycobacterium leprae, Mycobacterium gordonae, Mycobacterium abscessus, Mycobacterium* mucogenicum, streptococci, vancomycin-resistant enterococci (VRE), methicillin-resistant *Staphylococcus aureus* (MRSA),

*Staphylococcus pneumoniae, Enterococcus faecium, Streptococcus agalactiae, Streptococcus pneumoniae, Streptococcus pyogenes*, the *viridans* group streptococci, *Listeria monocytogenes, Nocardia*, and *Corynebacterium*.

In some embodiments, the aminoalkyl derivatives of oxazolidinone compounds described herein are selectively active against *Mycobacterium tuberculosis*, when compared to mammalian cells, such as human kidney or hepatocyte cells. In some embodiments, the aminoalkyl derivatives of oxazolidinone compounds described herein exhibit an unexpectedly high selectivity of at least 1000-fold towards *Mycobacterium tuberculosis* compared to mammalian cells, such as kidney or hepatocyte mammalian cells. In some embodiments, the aminoalkyl derivatives of oxazolidinone compounds described herein exhibit an unexpectedly high selectivity of at least 100-fold. In some embodiments, the aminoalkyl derivatives of oxazolidinone compounds described herein exhibit an unexpectedly high selectivity of from 100 to 6,500 folds, 100 to 6,000 folds, 100 to 5,500 folds, 100 to 5,000 folds, 100 to 4,500 folds, 100 to 4,000 folds, 100 to 3,500 folds, 100 to 3,000 folds, 100 to 2,500 folds, 100 to 2,000 folds, 100 to 1,500 folds, 100 to 1,000 folds, 500 to 6,500 folds, 500 to 6,000 folds, 500 to 5,500 folds, 500 to 5,000 folds, 500 to 4,500 folds, 500 to 4,000 folds, 500 to 3,500 folds, 500 to 3,000 folds, 500 to 2,500 folds, 500 to 2,000 folds, 500 to 1,500 folds, 500 to 1,000 folds, 1,000 to 6,500 folds, 1,000 to 6,000 folds, 1,000 to 5,500 folds, 1,000 to 5,000 folds, 1,000 to 4,500 folds, 1,000 to 4,000 folds, 1,000 to 3,500 folds, 1,000 to 3,000 folds, 1,000 to 2,500 folds, 1,000 to 2,000 folds, 1,000 to 1,500 folds towards *Mycobacterium tuberculosis* compared to mammalian cells, such as kidney or hepatocyte mammalian cells.

In some embodiments, the compounds and compositions described herein may promote selective uptake in *Mycobacterium*-residing macrophages in the liver, spleen, or lungs, helping to provide potent intracellular killing. Macrophages are responsible for the clearance of foreign particles via phagocytosis, including both foreign infectious agent like *Mycobacterium*, as well as laboratory-derived nanoparticles such as liposomes. This results in the opportunity for both to be co-localized in the same biological reservoir, effectively concentrating the active agent at an important depot for the disease.

Compositions and methods for the treatment of tuberculosis, as well as other mycobacterial and gram positive bacterial infections are disclosed.

One aspect of the disclosure provides a compound of Formula (I) or pharmaceutically acceptable salts thereof:

Formula (I)

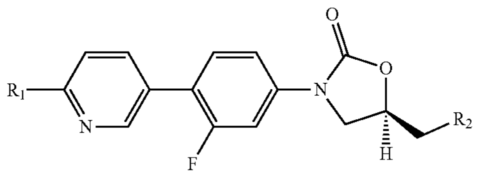

wherein $R_2$ is an amine ($NH_2$) or an acetamide ($NHCOCH_3$), and wherein $R_1$ is a tetrazole ring substituted at position 2' with an aminoalkyl.

In some embodiments, the aminoalkyl is a dimethylaminoalkyl. In some embodiments, the aminoalkyl derivatives of oxazolidinone compounds include either an amine or acetamide group at the $R_2$ positions of the oxazolidinone ring and a dimethylaminoethyl group on the tetrazole ring.

In some embodiments, a compound of Formula 1a is provided:

Formula 1a

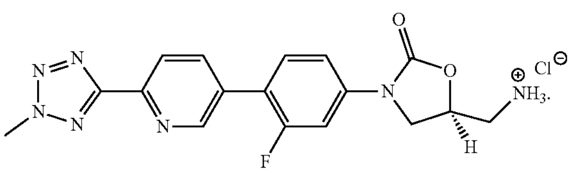

In some embodiments, a compound of Formula 1b is provided:

Formula 1b

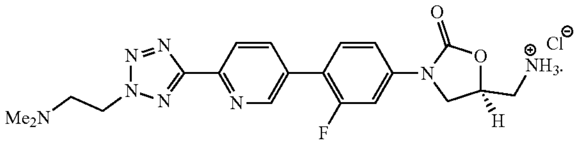

In some embodiments, the compound of the Formula 1b is crystallized from aqueous ethanol. In some embodiments the compound of the Formula 1b is the form of a dihydrochloride or dihydrochloride monohydrate.

In some embodiments, a compound of Formula 1c or pharmaceutically acceptable salts thereof is provided:

Formula 1c

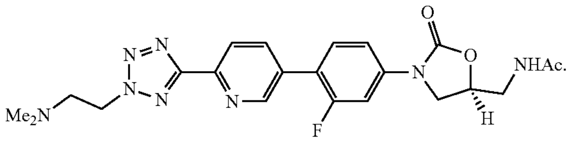

In some embodiments, a compound of Formula 1d or pharmaceutically acceptable salts thereof is provided:

Formula 1d

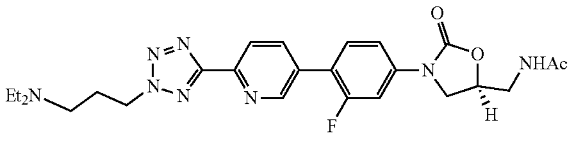

In some embodiments, a compound of Formula 1e is provided:

Formula 1e

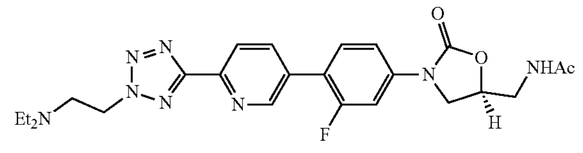

In some embodiments, the compound has a Selectivity Index (SI) index for Erd/HepG2 and H37Rv/HepG2 ranges from 100 to 1700.

In some embodiments, the compound has a SI index for Erd/HepG2 and H37Rv/HepG2 ranges from 200 to 1700.

In some embodiments, the compound has a SI index for Erd/HepG2 and H37Rv/HepG2 ranges from 300 to 1700.

Another aspect of the disclosure provides a liposomal composition comprising liposome vesicles, the liposome vesicles comprising a compound of Formula (I) or pharmaceutically acceptable salts thereof therein Formula (I)

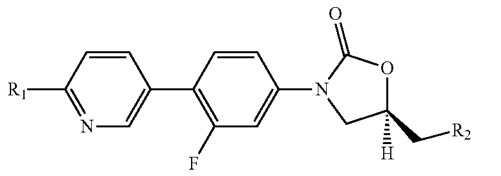

wherein $R_2$ is an amine ($NH_2$) or an acetamide ($NHCOCH_3$), and wherein $R_1$ is a tetrazole ring substituted at position 2' with an aminoalkyl.

In some embodiments, the aminoalkyl is a dimethylaminoalkyl. In some embodiments, the aminoalkyl derivatives of oxazolidinone compounds include either an amine or acetamide group at the $R_2$ positions of the oxazolidinone ring and a dimethylaminoethyl group on the tetrazole ring.

In some embodiments, a liposomal composition is provided comprising liposome vesicles, the liposome vesicles comprising a compound of Formula 1a:

Formula 1a

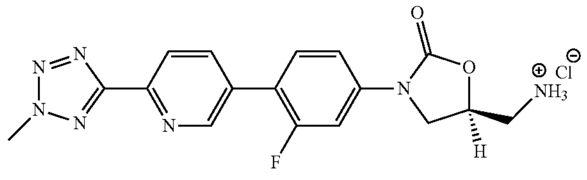

In some embodiments, a liposomal composition is provided comprising liposomes vesicles, the liposome vesicles comprising a compound of Formula 1b:

Formula 1b

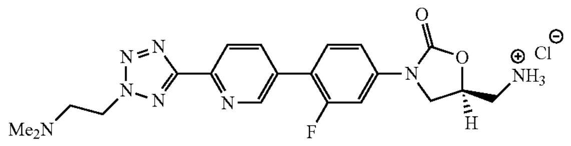

In some embodiments, the compound of the Formula 1b is crystallized from aqueous ethanol. In some embodiments the compound of the Formula 1b is the form of a dihydrochloride or dihydrochloride monohydrate.

In some embodiments, a liposomal composition is provided comprising liposomes vesicles, the liposome vesicles comprising a compound of Formula 1c or a pharmaceutically acceptable salt thereof:

Formula 1c

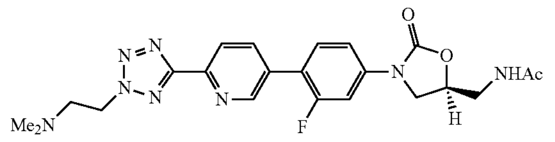

In some embodiments, a liposomal composition is provided comprising liposomes vesicles, the liposome vesicles comprising a compound of Formula 1d:

Formula 1d

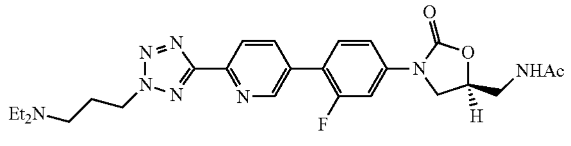

In some embodiments, a liposomal composition is provided comprising liposomes vesicles, the liposome vesicles comprising a compound of Formula 1e:

Formula 1e

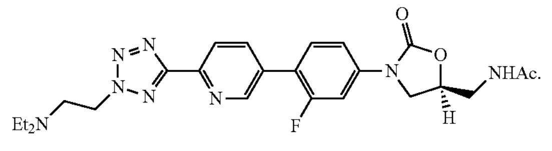

Aspects of the disclosure relate to compounds that are aminoalkyl derivatives of oxazolidinones (see FIG. 6). In some embodiments, the compounds having the following chemical Formula (I) and pharmaceutically acceptable salts thereof:

Formula (I)

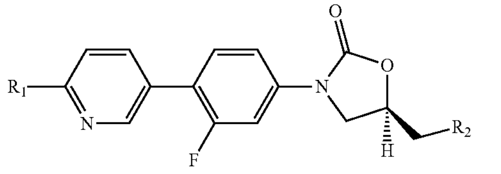

wherein $R_2$ is an amine ($NH_2$) or an acetamide ($NHCOCH_3$), and wherein $R_1$ is a tetrazole ring substituted at position 2' with an aminoalkyl.

In other embodiments, the compounds having the following chemical Formula (I) and pharmaceutically acceptable salts thereof:

Formula (I)

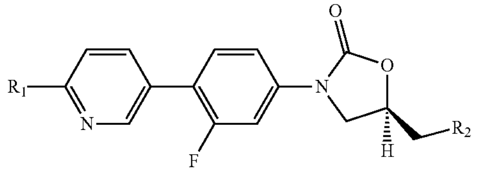

wherein $R_2$ is an amine ($NH_2$) or an acetamide ($NHCOCH_3$), and wherein $R_1$ is a tetrazole ring substituted at 1' with an aminoalkyl group.

In some embodiments, the aminoalkyl is a dimethylaminoalkyl. In some embodiments, the aminoalkyl derivatives of oxazolidinone compounds include either an amine or acetamide group at the $R_2$ positions of the oxazolidinone ring and a dimethylaminoethyl group on the tetrazole ring.

The present disclosure shows a very specific structure-activity relationship (SAR) for the aminoalkyl derivatives of oxazolidinone compounds described herein that included either an amine or acetamide group at the $R_2$ positions of the oxazolidinone ring and a dimethylaminoethyl group on the tetrazole ring. These compounds are (1) highly selective against *Mycobacterium tuberculosis* when compared to activity in mammalian cells (for example human kidney or hepatocyte cells), (2) highly active against *Mycobacterium tuberculosis*, and (3) efficiently loaded into liposomes.

In some embodiments, the aminoalkyl derivatives of oxazolidinones described herein load in liposomes with 85% or better efficiency using gradient-based drug loading methods. In some embodiments, the loading efficiency of these derivatives is 90% or more. In some embodiments, the loading of these derivatives is 95% or more, or even quantitative. In some embodiments, methods for loading the aminoalkyl derivatives of oxazolidinones in liposomes are described. In some embodiments, the loading methods employs transmembrane gradients and trapping agents to efficiently load, and subsequently stabilize, weakly basic amphipathic drugs in the liposomal interior aqueous space. The gradients can include (1) simple pH gradients formed, for example, using citric acid solutions, (2) ammonium ion gradients employing citrate or sulfate ammonium salts, (3) alkyl, dialkyl, or trialkylammonium salts, (4) gradients of transition metals ($Cu^{2+}$, $Mn^{2+}$, $Zn^{2+}$, $Mg^{2+}$), or even (5) transmembrane gradients of drug solubility. See U.S. Pat. Nos. 5,316,771, 5,800,833, 8,147,867, 7,744,921, 8,349,360, 6,110,491, U.S. Patent Application Publication No. 20180369143A1 and International Patent Application Publication No. WO199001405, which are incorporated herein by reference in their entireties. See also Allen et al. (1995) Int J Cancer 62:199-204. Without being bound by the theory, the cation contained in the liposome interior plays a role in establishing a pH gradient across the membrane that helps drive the accumulation of weakly basic drugs into the liposome interior, or directly exchanges with the drug molecule. This results in some embodiments, in a quantitative loading of the drug below the total capacity of the gradient. The counterion can play an important role in stabilizing the formulation to premature leakage in the circulation or during storage by forming stable complexes with the drugs in the liposome interior (see Drummond et al. (2008) J. Pharm Sci 97, 4696-4740).

Compositions and methods for the treatment of tuberculosis, as well as other mycobacterial and gram positive bacterial infections are disclosed. These compositions contain a highly potent and selective oxazolidinone encapsulated with high efficiency to maximize dosing potential of low toxicity drugs, and are stable in the presence of plasma. The compositions are long circulating and retain their encapsulated drug while in the circulation following intravenous dosing to allow for efficient accumulation at the site of the bacterial or mycobacterial infection. The compositions are storage-stable with regard to component degradation. The high doses that can be achieved when combined with the long circulating properties and highly stable retention of the drug allow for a reduced frequency of administration when compared to daily or twice daily administrations of other drugs typically utilized to treat these infections.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

INCORPORATION BY REFERENCE

All publications, patents and patent applications referenced in this specification are incorporated herein by reference in their entirety for all purposes to the same extent as if each individual publication, patent or patent application were specifically indicated to be so incorporated by reference.

What is claimed is:

1. A stabilized injectable AKG-38 liposomal pharmaceutical composition comprising compound AKG-38

(AKG-38)

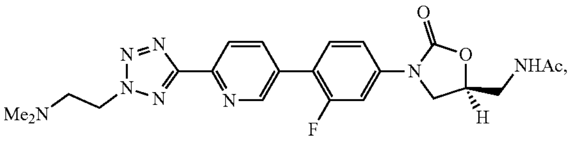

or a pharmaceutically acceptable salt thereof, encapsulated in liposomes comprising hydrogenated soy phosphatidylcholine (HSPC), cholesterol, and methoxy-terminated polyethylene glycol (MW 2000)-distearoylphosphatidyl ethanolamine (PEG (2000)-DSPE) in a 45:55:2.25 molar ratio, wherein the liposomes are suspended in a cholesterol-stabilizing aqueous solution comprising 0.1 mM-1 mM of an extra-liposomal heavy metal chelator at a pH of 6.7-8.0, wherein the heavy metal chelator is selected from the group consisting of: deferoxamine (desferrioxamine) (DFO), ethylenediamine tetraacetic acid (EDTA), diethylenetriamine pentaacetic acid (DTPA), nitrilotriacetic acid (NTA), ethyleneglycol-O, O'-bis(2-aminoethyl)-N, N,N', N'-tetraacetic acid (EGTA), N-(2-hydroxyethyl) ethylenediamine-N, N', N'-triacetic acid (HEDTA), and 1,4,7,10-tetraazacyclododecane-1,4,7,10-tetraacetic acid (DOTA).

2. The composition of claim 1, wherein the composition comprises a sulfate or hydrosulfate salt of the AKG-38 compound encapsulated in the liposomes.

3. The composition of claim 1, wherein the cholesterol-stabilizing aqueous solution comprises less than 0.1 mM of extra-liposomal ammonia or ammonium ion.

4. The composition of claim 1, wherein the cholesterol-stabilizing aqueous solution comprises 0.1 mM-0.5 mM of the extra-liposomal heavy metal chelator.

5. The composition of claim 1, wherein the AKG-38 is encapsulated in the liposomes at a ratio equivalent to 430-650 g AKG-38 (free base)/mol phospholipid.

6. The composition of claim 1, wherein the liposomes are unilamellar lipid bilayer vesicles encapsulating a sulfate salt of the AKG-38 compound.

7. The composition of claim 1, wherein the liposomes are approximately 90-130 nm diameter (Z average).

8. The composition of claim 1, wherein the AKG-38 is encapsulated as a sulfate salt in the liposomes at a ratio equivalent to 450 g AKG-38 (free base)/mol phospholipid; and wherein the composition comprises a total amount of AKG-38 equivalent to 12-25 mg AKG-38 (free base)/mL.

9. The composition of claim 1, wherein the liposomes are unilamellar lipid bilayer vesicles encapsulating a sulfate salt of the AKG-38 compound;

the cholesterol stabilizing aqueous solution comprises 0.1 mM-0.5 mM of the extra-liposomal heavy metal chelator;

the cholesterol stabilizing aqueous solution comprises less than 0.1 mM of extra-liposomal ammonia or ammonium ion;

the AKG-38 compound is encapsulated in the liposomes at a ratio equivalent to 430-650 g AKG-38 (free base)/mol phospholipid;

the liposomes are approximately 90-130 nm diameter (Z average); and the composition comprises a total amount of AKG-38 equivalent to 12-25 mg AKG-38 (free base)/mL.

10. The composition of claim 9, wherein the heavy metal chelator is deferoxamine (desferrioxamine) (DFO).

11. A stabilized injectable AKG-38 liposomal pharmaceutical composition comprising compound AKG-38

(AKG-38)

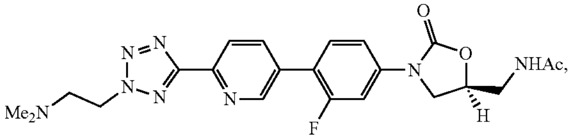

or a pharmaceutically acceptable salt thereof, encapsulated in liposomes having a diameter of 90-130 nm (Z average) and consisting of hydrogenated soy phosphatidylcholine (HSPC), cholesterol, and methoxy-terminated polyethylene glycol (MW 2000)-distearoylphosphatidyl ethanolamine (PEG (2000)-DSPE), wherein the liposomes are suspended in an aqueous solution comprising 0.1 mM-1 mM of extra-liposomal deferoxamine (DFO) or ethylenediaminetetraacetic acid (EDTA) chelator at a pH of 6.7-8.0.

12. The composition of claim 11, wherein the composition comprises a sulfate or hydrosulfate salt of the AKG-38 compound encapsulated in the liposomes.

13. The composition of claim 12, wherein the composition comprises a total amount of AKG-38 equivalent to 12-25 mg AKG-38 free base/mL of the composition.

14. The composition of claim 13, wherein the liposomes comprise a total of 22.6 mg/mL hydrogenated soy phosphatidyl choline (HSPC), 13.6 mg/mL cholesterol and 4 mg/mL methoxy-terminated polyethylene glycol (MW 2000)-distearoylphosphatidyl ethanolamine (MPEG-2000-DSPE).

15. The composition of claim 14, wherein the aqueous solution contains 4.8 mg/mL of 2-[4-(2-hydroxyethyl) piperazin-1-yl] ethanesulfonic acid (HEPES) as a buffer, 0.33 mg/mL deferoxamine mesylate as the chelator, and 8.2 mg/mL sodium chloride as an isotonicity reagent in water.

16. The composition of claim 15, wherein the aqueous solution comprises less than 0.1 mM of extra-liposomal ammonia or ammonium ion.

17. The composition of claim 16, wherein the composition is a dispersion of the AKG-38 liposomes in an aqueous medium comprising the deferoxamine (DFO) chelator.

18. The composition of claim 17, wherein the aqueous medium comprises 0.1-0.5 mM of the DFO chelator.

19. A stabilized injectable AKG-38 liposomal pharmaceutical composition comprising compound AKG-38:

(AKG-38)

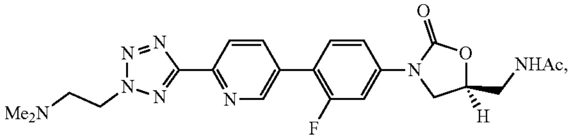

or a pharmaceutically acceptable salt thereof, encapsulated in liposomes consisting of hydrogenated soy phosphatidylcholine (HSPC), cholesterol, and methoxy-terminated polyethylene glycol (MW 2000)-distearoylphosphatidyl ethanolamine (PEG (2000)-DSPE) in a molar ratio of 45:55:2.25, wherein the liposomes are suspended in an extra-liposomal aqueous solution comprising 0.1 mM-1 mM of deferoxamine (DFO) chelator and less than 0.1 mM of ammonia or ammonium ion at a pH of 6.7-8.0 to stabilize the cholesterol in the liposomes.

20. The composition of claim 19, wherein the liposomes are unilamellar lipid bilayer vesicles encapsulating a sulfate salt of the AKG-38 compound;

the aqueous solution comprises 0.1 mM-0.5 mM of the extra-liposomal DFO chelator;

the aqueous solution comprises less than 0.1 mM of extra-liposomal ammonia or ammonium ion;

the AKG-38 compound is encapsulated in the liposomes at a ratio equivalent to 430-650 g AKG-38 (free base)/mol phospholipid;

the liposomes are approximately 90-130 nm diameter (Z average); and the composition comprises a total amount of AKG-38 equivalent to 12-25 mg AKG-38 (free base)/mL.

21. An injectable AKG-38 liposome composition, comprising a pharmaceutically acceptable sulfate salt of AKG-38 compound, (AKG-38)

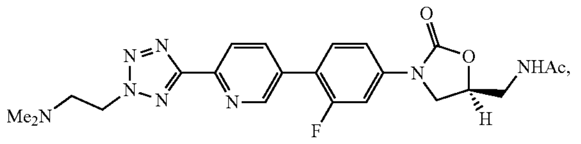

encapsulated in liposomes suspended in a cholesterol-stabilizing extra-liposomal aqueous solution comprising a heavy metal chelator, the composition obtained by a process comprising the steps of:

a. dissolving hydrogenated soy phosphatidylcholine (HSPC), cholesterol, and methoxy-terminated polyethylene glycol (MW 2000)-distearoylphosphatidyl ethanolamine (PEG (2000)-DSPE) in ethanol to obtain a lipid solution;

b. combining the lipid solution of step (a) with an ammonium sulfate trapping agent solution to obtain a lipid suspension;

c. extruding the lipid suspension of step (b) through membranes having defined pore sizes;

d. purifying liposomes from extra-liposomal trapping agent in the extruded lipid suspension to obtain a purified extruded liposome preparation;

e. contacting the liposomes with the AKG-38 compound in an aqueous medium to effect encapsulation of the AKG-38 compound into AKG-38 liposomes;

f. optionally removing unencapsulated AKG-38 compound from the aqueous medium; and g. providing the AKG-38 liposomes in an aqueous medium comprising the chelator.

* * * * *